United States Patent
Tang et al.

(10) Patent No.: US 10,987,354 B2
(45) Date of Patent: Apr. 27, 2021

(54) INHIBITORS OF INFLUENZA VIRUS REPLICATION AND USES THEREOF

(71) Applicants: SUNSHINE LAKE PHARMA CO., LTD., Guangdong (CN); NORTH & SOUTH BROTHER PHARMACY INVESTMENT COMPANY LIMITED, Wanchai (HK)

(72) Inventors: Changhua Tang, Dongguan (CN); Qingyun Ren, Dongguan (CN); Junjun Yin, Dongguan (CN); Kai Yi, Dongguan (CN); Yibo Lei, Dongguan (CN); Yejun Wang, Guangdong (CN); Yingjun Zhang, Guangdong (CN)

(73) Assignee: SUNSHINE LAKE PHARMA CO., LTD., Guangdong (CN)

( * ) Notice: Subject to any disclaimer, the term of this patent is extended or adjusted under 35 U.S.C. 154(b) by 0 days.

(21) Appl. No.: 16/467,969

(22) PCT Filed: Dec. 14, 2017

(86) PCT No.: PCT/CN2017/116154
§ 371 (c)(1),
(2) Date: Jun. 9, 2019

(87) PCT Pub. No.: WO2018/108125
PCT Pub. Date: Jun. 21, 2018

(65) Prior Publication Data
US 2020/0085822 A1    Mar. 19, 2020

(30) Foreign Application Priority Data
Dec. 15, 2016    (CN) .......................... 201611158754.5

(51) Int. Cl.
| A61K 31/506 | (2006.01) |
| C07D 487/04 | (2006.01) |
| C07D 519/00 | (2006.01) |
| A61P 31/16 | (2006.01) |

(52) U.S. Cl.
CPC ............ *A61K 31/506* (2013.01); *A61P 31/16* (2018.01); *C07D 487/04* (2013.01); *C07D 519/00* (2013.01)

(58) Field of Classification Search
CPC ...... A61K 31/519; A61K 31/13; A61K 45/06; A61K 2300/00; A61K 31/506; A61K 31/7056; C07D 471/04; C07D 495/04; C07D 519/00; C07D 487/04
USPC ........................................................ 514/234
See application file for complete search history.

(56) References Cited

U.S. PATENT DOCUMENTS

| 8,829,007 B2 | 9/2014 | Charifson et al. |
| 8,871,774 B2 | 10/2014 | Charifson et al. |
| 9,051,319 B2 | 6/2015 | Charifson et al. |
| 9,345,708 B2 | 5/2016 | Charifson et al. |
| 9,394,302 B2 | 7/2016 | Charifson et al. |
| 9,518,056 B2 | 12/2016 | Charifson et al. |
| 9,908,878 B2 | 3/2018 | Charifson et al. |
| 9,932,346 B2 | 4/2018 | Jonckers et al. |
| 10,023,569 B2 | 7/2018 | Tanoury et al. |
| 2012/0171245 A1 | 7/2012 | Charifson et al. |
| 2013/0345218 A1 | 12/2013 | Charifson et al. |
| 2014/0005197 A1 | 1/2014 | Charifson et al. |
| 2017/0226102 A1 | 8/2017 | Jonckers et al. |
| 2018/0065962 A1 | 3/2018 | Farmer et al. |
| 2018/0155342 A1 | 6/2018 | Charifson et al. |
| 2018/0258074 A1 | 9/2018 | Jonckers et al. |
| 2018/0318301 A1 | 11/2018 | Simone et al. |
| 2018/0346463 A1 | 12/2018 | Zhang et al. |
| 2019/0023713 A1 | 1/2019 | Guillemont et al. |
| 2019/0047989 A1 | 2/2019 | Jonckers et al. |

FOREIGN PATENT DOCUMENTS

| WO | 2013184985 | * 12/2013 |
| WO | 2013184985 A1 | 12/2013 |
| WO | 2017133657 A1 | 8/2017 |
| WO | 2017133658 A1 | 8/2017 |
| WO | 2017133664 A1 | 8/2017 |
| WO | 2017133665 A1 | 8/2017 |
| WO | 2017133667 A1 | 8/2017 |
| WO | 2017133669 A1 | 8/2017 |
| WO | 2017133670 A1 | 8/2017 |
| WO | 2017198122 A1 | 11/2017 |
| WO | 2018033082 A1 | 2/2018 |
| WO | 2018041091 A1 | 3/2018 |
| WO | 2018041263 A1 | 3/2018 |

OTHER PUBLICATIONS

B Testa et al., Prodrug Design in 5 Encyclopedia of Pharmaceutical Technology, 3008-3014 (J. Swarbrick ed., 3rd ed., 2007).*
Michael J. Boyd. etc, Bioorganic & Medicinal Chemistry Letters 25 (2015) 1990-1994.
Michael P. Clark. etc, Journal of Medicinal Chemistry(2014),57(15),6668-6678.
Luc J. Farmer. etc, ACS Medicinal Chemistry Letters (2017), 8(2), 256-260.
Upul K. Bandarage. etc, ACS Medicinal Chemistry Letters (2017), 8(2), 261-265.
Jianglin Liang. etc, Organic Process Research & Development (2016), 20(5), 965-969.

* cited by examiner

Primary Examiner — Tracy Vivlemore
Assistant Examiner — Ebenezer O Sackey
(74) Attorney, Agent, or Firm — Kam Wah Law

(57) ABSTRACT

The invention provides a class of compounds as inhibitors of influenza virus replication, preparation methods thereof, pharmaceutical compositions containing these compounds, and uses of these compounds and pharmaceutical compositions thereof in the treatment of influenza.

24 Claims, No Drawings

INHIBITORS OF INFLUENZA VIRUS REPLICATION AND USES THEREOF

CROSS REFERENCE TO RELATED APPLICATIONS

This is a U.S. national stage application of the International Patent Application No. PCT/CN2017/116154, filed Dec. 14, 2017, which claims priority to Chinese Patent Application No. 201611158754.5, filed Dec. 15, 2016, both of which are incorporated herein by reference in their entirety.

FIELD

The invention relates to medicine field, and specifically, it relates to a novel class of compounds as inhibitors of influenza virus replication, preparation methods thereof, pharmaceutical compositions containing these compounds, and uses of these compounds and pharmaceutical compositions thereof in the treatment of influenza. More specifically, the compounds of the invention can be used as inhibitors of influenza virus RNA polymerase.

BACKGROUND

Influenza (the following referred to as flu) is an acute respiratory infectious disease and harmful to human health, which is caused by the influenza virus and characterized by high prevalence, widespread, rapid propagation. Influenza virus can cause serious symptoms in the elderly and children with weaker immune systems, and immunocompromised patients, such as pneumonia or cardiopulmonary failure. Influenza virus was first discovered by Wilson Smith, a British, who called influenza virus as H1N1. The H denotes hemagglutinin; the N denotes neuraminidase, and the numbers represent different types. Influenza virus has caused the global pandemic for many times since the discovery, and the outbreak of influenza virus happens every decade or so, which causes enormous losses in worldwide. Influenza spreads around the world in a yearly outbreak, resulting in about 250,000 to 500,000 deaths, and about three to five million cases of severe illness, and a total of about 5% to 15% of people in worldwide are infected. Every time a pandemic was due to the emergence of new strains in humans. Usually, these new strains are caused by the spread of existing influenza virus from other animal species to humans.

Influenza viruses are RNA viruses belong to the family of orthomyxoviridae, which belong to the genus of influenza virus. According to the differences of the virion nucleoprotein (NP) and matrix protein (M) antigenic characteristics and genetic characteristics, influenza viruses are divided into three types: A, B and C. The three types of influenza viruses have similar biochemical and biological characteristics. The virus particle is 80-120 nanometers in diameter and usually roughly spherical, although filamentous forms can occur. Virus is constituted with three layers, and the inner layer is the viral nucleocapsid containing nucleoprotein (NP), P protein and RNA. NP is a soluble antigen (S antigen) with type specificity and antigenic stability. P protein (P1, P2, P3) may be polymerase required for RNA transcription and replication. The middle is a viral envelope consisting of a lipoid layer and a layer of membrane protein (MP), MP has antigenic stability and type specificity. Outer layer is a radial tuber consisting of two different glycoprotein projections, i.e., hemagglutinin (H) and neuraminidase (N). H is a tool for viral absorbtion on sensitive cell surface which can cause agglutination of erythrocyte, N is a tool for breaking away from cell surface after the completing of virus replication, which is capable of hydrolyzing mucus protein and N-acetylneuraminic acid that locates at the end of cell surface specific glycoprotein receptor. H and N both have variation characteristics, and only have the strain specific antigen, the antibody of which has a protective effect.

Influenzavirus A has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A virus is the most virulent human pathogen among the three influenza types and cause the severest disease, and can be transmitted to other species and may then cause human influenza pandemic. The influenza A virus can be subdivided into different serotypes based on the antibody response to these viruses. The serotypes that have been confirmed in humans, ordered by the number of known human pandemic deaths, are: H1N1, which caused Spanish Flu in 1918; H2N2, which caused Asian Flu in 1957; H3N2, which caused Hong Kong Flu in 1968; H5N1, which caused pandemic threats in the influenza season of 2007-2008; H7N7, which has unusual zoonotic potential; H1N2, endemic in humans and pigs; H9N2; H7N2; H7N3; and H10N7.

Influenzavirus B has one species, influenza B virus, which causes local epidemic influenza and can not cause the global influenza pandemic. The only animals known to be susceptible to influenza B infection are humans and the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

Influenzavirus C has one species, influenza C virus, which exsits in sporadic form, and usually only causes mild disease in children. Influenzavirus C usually can not cause influenza pandemic, and infect humans and pigs.

Unusually for a virus, its genome is not a single piece of nucleic acid; instead, it contains seven or eight pieces of segmented negative-sense RNA. The genome of influenza A viruses encodes 11 proteins: hemagglutinin (H), neuraminidase (N), nucleoprotein (NP), M1, M2, NS1, NS2 (NEP), PA, PB1 (polymerase basic 1), PB1-F2 and PB2. Hemagglutinin (H) and neuraminidase (N) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins are targets for antiviral drugs. Furthermore, they are antigens to which antibodies can be raised. Influenza A viruses are classified into subtypes based on antibody responses to H and N. These different types of HA and NA form the basis of the H and N distinctions in, for example, H5N1.

Vaccination and usage of antiviral drugs are important tools for responsing to influenza pandemic. Due to the high mutation rate of the flu virus antigen, the vaccine can't be produced in large scale before influenza pandemic. The two classes of antiviral drugs used against influenza are M2 protein inhibitors (amantadine and rimantadine) and neuraminidase inhibitors (oseltamivir, zanamivir, peramivir and laninamivir). However, the influenza viruses have developed drug resistance to all these drugs. Therefore, continuing demand for new anti-influenza treatment agent is existing.

Favipiravir, a new antiviral agent, having a new mechanism has been lanched, which plays antiviral action by inhibiting influenza virus RNA polymerase to target the inhibition of viral gene replication, but the therapeutic effect and the drug resistance of influenza viruses still need to be proved. Therefore, other compounds as anti-influenza agents of this mechanism still need to be researched.

SUMMARY

The invention discloses a novel class of compounds used as inhibitors of influenza virus RNA polymerase. These compounds and compositons thereof can be used in the manufacture of a medicament for preventing, managing, treating or lessening virus infection in patients.

In one aspect, provided herein is a compound having Formula (I) or a stereoisomer, a tautomer, an N-oxide, a solvate, a metabolite, a pharmaceutically acceptable salt or a prodrug thereof,

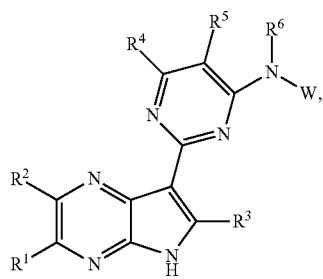

(I)

wherein $R^1$, $R^2$, $R^3$, $R^4$, $R^5$, $R^6$ and W are as defined herein.

In some embodiments, each of $R^1$, $R^2$ and $R^3$ is independently H, D, F, Cl, Br, CN, $NO_2$, —C(=O)$R^a$, —C(=O)$OR^6$, —C(=O)$NR^cR^d$, $OR^b$, —$NR^cR^d$, $R^bO$—$C_{1-4}$ alkylene, $R^dR^cN$—$C_{1-4}$ alkylene, $C_{1-6}$ alkyl, $C_{2-6}$ alkenyl or $C_{2-6}$ alkynyl; or, $R^1$ and $R^2$, together with the carbon atoms to which they are attached, form a $C_{3-6}$ carbocyclic ring, 5- to 6-membered heterocyclic ring, $C_{6-10}$ aromatic ring or 5- to 6-membered heteroaromatic ring, and wherein each of $C_{1-6}$ alkyl, $C_{2-6}$ alkenyl, $C_{2-6}$ alkynyl, $C_{3-6}$ carbocyclic ring, 5- to 6-membered heterocyclic ring, $C_{6-10}$ aromatic ring and 5- to 6-membered heteroaromatic ring is independently unsubstituted or substituted with 1, 2, 3 or 4 substituents independently selected from D, F, Cl, Br, CN, $OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

$R^4$ is $OR^b$, —$NR^cR^d$, $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl or (5- to 16-membered heteroaryl)-$C_{1-4}$ alkylene, and wherein each of $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl and (5- to 16-membered heteroaryl)-$C_{1-4}$ alkylene is independently unsubstituted or substituted with 1, 2, 3, 4 or 5 R';

$R^5$ is H, D, F, Cl, Br, CN, $NO_2$, —C(=O)$R^a$, —C(=O)$OR^b$, —C(=O)$NR^cR^d$, $OR^b$, —$NR^cR^d$, $R^bO$—$C_{1-4}$ alkylene, $R^dR^cN$—$C_{1-4}$ alkylene, $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ alkylene, 5- to 10-membered heteroaryl and (5- to 10-membered heteroaryl)-$C_{1-4}$ alkylene is independently unsubstituted or substituted with 1, 2, 3, 4 or 5 R';

or, $R^4$ and $R^5$, together with the carbon atoms to which they are attached, form a $C_{3-12}$ carbocyclic ring, 3- to 12-membered heterocyclic ring, $C_{6-10}$ aromatic ring or 5- to 10-membered heteroaromatic ring, and wherein each of $C_{3-12}$ carbocyclic ring, 3- to 12-membered heterocyclic ring, $C_{6-10}$ aromatic ring and 5- to 10-membered heteroaromatic ring is independently unsubstituted or substituted with 1, 2, 3, 4 or 5 R';

each R' is independently D, F, Cl, Br, CN, $NO_2$, $OR^b$, —$NR^cR^d$, $R^bO$—$C_{1-4}$ alkylene, $R^dR^cN$—$C_{1-4}$ alkylene, $R^a$—C(=O)—O—$C_{1-4}$ alkylene-O—$C_{1-4}$ alkylene, $R^bO$—C(=O)—O—$C_{1-4}$ alkylene —O—$C_{1-4}$ alkylene, —C(=O)$R^a$, —C(=O)$OR^b$, —C(=O)$NR^cR^d$, $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3 or 4 substituents independently selected from D, F, Cl, Br, CN, $NO_2$, $OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

$R^6$ is H, D or $C_{1-6}$ alkyl, and wherein $C_{1-6}$ alkyl is optionally substituted with 1, 2, 3 or 4 substituents independently selected from D, F, Cl, Br, CN, $NO_2$ or $OR^b$;

W is $C_{1-8}$ alkyl, $C_{3-12}$ carbocyclyl or 3- to 12-membered heterocyclyl, and wherein each of $C_{1-8}$ alkyl, $C_{3-12}$ carbocyclyl and 3- to 12-membered heterocyclyl is independently unsubstituted or substituted with 1, 2, 3 or 4 $R^w$;

each $R^w$ is independently D, F, Cl, Br, CN, $NO_2$, oxo (=O), —C(=O)$R^a$, —C(=O)$OR^b$, —C(=O)—O—$C_{1-4}$ alkylene-O—C(=O)—$OR^b$, —C(=O)$NR^cR^d$, —$NR^eC$(=O)$R^a$, —$NR^eC$(=O)$NR^cR^d$, —S(=O)$_2R^f$, —S(=O)$_2NR^eC$(=O)$R^a$, —S(=O)$_2NR^cR^d$, $(R^bO)_2P$(=O)—$O_{0-2}$ alkylene, $OR^b$, $R^bO$—$C_{1-2}$ alkylene, $R^dR^cN$—$C_{1-2}$ alkylene, $C_{1-6}$ alkyl, 5- to 6-membered heteroaryl or 5- to 6-membered heterocyclyl, and wherein each of $C_{1-6}$ alkyl, 5- to 6-membered heteroaryl and 5- to 6-membered heterocyclyl is independently unsubstituted or substituted with 1, 2, 3 or 4 substituents independently selected from D, F, Cl, Br, CN, $N_3$, oxo (=O), $NO_2$, $OR^b$, $C_{1-6}$ alkyl or $C_{1-6}$ haloalkyl;

each $R^a$, $R^b$, $R^c$, $R^d$, $R^e$ and $R^f$ is independently H, D, hydroxy, $C_{1-6}$ haloalkyl, $C_{1-6}$ alkyl, n-heptyl, $C_{1-6}$ alkoxy, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-6}$ alkyl, n-heptyl, $C_{1-6}$ alkoxy, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino;

or, $R^c$ and $R^d$, together with the nitrogen atom to which they are attached, form 3- to 8-membered heterocyclyl or 5- to 8-membered heteroaryl, and wherein each of 3- to 8-membered heterocyclyl and 5- to 8-membered heteroaryl is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino.

In other embodiments, the invention relates to the compound having Formula (II), or a stereoisomer, a tautomer, an N-oxide, a solvate, a metabolite, a pharmaceutically acceptable salt or a prodrug thereof,

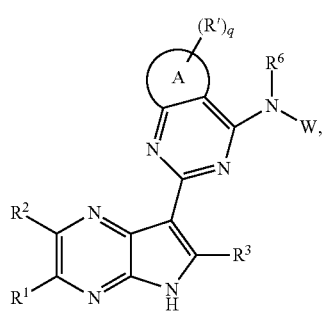

(II)

wherein A, $R^1$, $R^2$, $R^3$, $R^6$, R', q and W are as defined herein.

In other embodiments, A is a $C_{3-12}$ carbocyclic ring, 3- to 12-membered heterocyclic ring, $C_{6-10}$ aromatic ring or 5- to 10-membered heteroaromatic ring; and q is 0, 1, 2, 3, 4 or 5.

In other embodiments, each of $R^1$, $R^2$ and $R^3$ is independently H, D, F, Cl, Br, CN, $NO_2$, —C(=O)$R^a$, —C(=O)$OR^b$, —C(=O)$NR^cR^d$, $OR^b$, —$NR^cR^d$, methyl, ethyl, n-propyl or i-propyl; or, $R^1$ and $R^2$, together with the carbon atoms to which they are attached, form a $C_{5-6}$ carbocyclic ring, 5- to 6-membered heterocyclic ring, benzene ring or 5- to 6-membered heteroaromatic ring, and wherein each of methyl, ethyl, n-propyl, i-propyl, $C_{5-6}$ carbocyclic ring, 5- to 6-membered heterocyclic ring, benzene ring and 5- to 6-membered heteroaromatic ring is independently unsubstituted or substituted with 1, 2, 3 or 4 substituents independently selected from D, F, Cl, Br, CN, $OR^b$, —$NR^cR^d$ or $C_{1-3}$ haloalkyl.

In other embodiments, $R^4$ is $OR^b$, —$NR^cR^d$, $C_{2-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 8-membered heterocyclyl, (5- to 8-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{2-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 8-membered heterocyclyl, (5- to 8-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3, 4 or 5 R';

$R^5$ is H, D, F, Cl, Br, CN, $NO_2$, —C(=O)$R^a$, —C(=O)$OR^b$, —C(=O)$NR^cR^d$, $OR^b$, —$NR^cR^d$, $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with 1, 2, 3, 4 or 5 R';

or, $R^4$ and $R^5$, together with the carbon atoms to which they are attached, form a $C_{3-6}$ carbocyclic ring, 3- to 6-membered heterocyclic ring, $C_{6-10}$ aromatic ring or 5- to 6-membered heteroaromatic ring, and wherein each of $C_{3-6}$ carbocyclic ring, 3- to 6-membered heterocyclic ring, $C_{6-10}$ aromatic ring and 5- to 6-membered heteroaromatic ring is independently unsubstituted or substituted with 1, 2, 3, 4 or 5 R'.

In other embodiments, each R' is independently D, F, Cl, Br, CN, $NO_2$, $OR^b$, —$NR^cR^d$, $R^a$—C(=O)—O—$C_{1-2}$ alkylene-O—$C_{1-2}$ alkylene, $R^bO$—C(=O)—O—$C_{1-2}$ alkylene-O—$C_{1-2}$ alkylene, —C(=O)$R^a$, —C(=O)$OR^b$, —C(=O)$NR^cR^d$, $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene and 5- to 10-membered heteroaryl, and wherein each of $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene and 5- to 10-membered heteroaryl is independently unsubstituted or substituted with 1, 2, 3 or 4 substituents independently selected from D, F, Cl, Br, CN, $NO_2$, $OR^b$, —$NR^cR^d$, methyl, ethyl, n-propyl or i-propyl;

In other embodiments, each R' is independently D, F, Cl, Br, CN, $NO_2$, $OR^b$, —$NR^cR^d$,

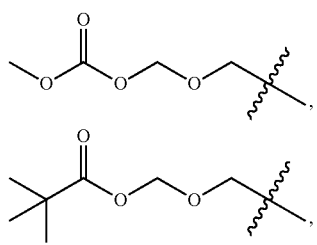

—C(=O)$R^a$, —C(=O)$OR^b$, —C(=O)$NR^cR^d$, methyl, ethyl, n-propyl, i-propyl, n-butyl, i-butyl, t-butyl, trifluoromethyl, difluoromethyl, monofluoromethyl, 2,2-difluoroethyl, 1,2-difluoroethyl, trifluoroethyl, 1-fluoroethyl, 2-fluoroethyl, cyclopropyl, tetrahydrofuranyl, tetrahydrothienyl, tetrahydropyranyl, tetrahydrothiapyranyl, piperidyl, morpholinyl, thiomorpholinyl, piperazinyl, phenyl, phenyl-$C_{1-2}$ alkylene, furyl, benzofuranyl, pyrrolyl, pyridinyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl or pyrimidinyl, and wherein methyl, ethyl, n-propyl, i-propyl, n-butyl, i-butyl, t-butyl, difluoromethyl, monofluoromethyl, 2,2-difluoroethyl, 1,2-difluoroethyl, trifluoroethyl, 1-fluoroethyl, 2-fluoroethyl, cyclopropyl, tetrahydrofuranyl, tetrahydrothienyl, tetrahydropyranyl, tetrahydrothiapyranyl, piperidyl, morpholinyl, thiomorpholinyl, piperazinyl, phenyl, phenyl-$C_{1-2}$ alkylene, furyl, benzofuranyl, pyrrolyl, pyridinyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl and pyrimidinyl is independently unsubstituted or substituted with 1, 2, 3 or 4 substituents independently selected from D, F, Cl, Br, CN, $NO_2$, OH, —$NH_2$, methyl, ethyl, n-propyl or i-propyl.

In other embodiments, $R^6$ is H, D, $CF_3$, methyl, ethyl, n-propyl or i-propyl.

In other embodiments, W is $C_{1-6}$ alkyl, $C_{5-8}$ carbocyclyl or 5- to 8-membered heterocyclyl, and wherein each of $C_{1-6}$ alkyl, $C_{5-8}$ carbocyclyl and 5- to 8-membered heterocyclyl is independently unsubstituted or substituted with 1, 2, 3 or 4 $R^w$.

In other embodiments, $R^w$ is D, F, Cl, Br, CN, $NO_2$, oxo (=O), —C(=O)$OCH_3$, —C(=O)$OCH_2CH_3$, —C(=O)$OCH_2CH_2CH_3$, —C(=O)$O(CH_2)_6CH_3$, —C(=O)OH,

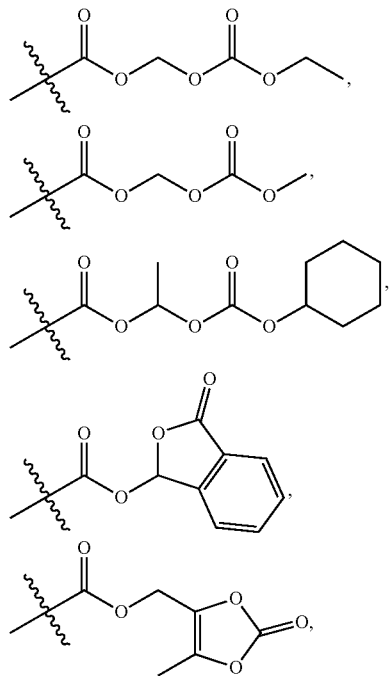

—C(=O)$NR^cR^d$, —NHC(=O)$R^a$, —NHC(=O)$NR^cR^d$, —S(=O)$_2R^f$, —S(=O)$_2NHC(=O)R^a$, —S(=O)$_2NR^cR^d$, ($R^bO)_2P(=O)$—$C_{0-2}$ alkylene, $OR^b$, methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl, pyrimidyl or 5- to 6-membered heterocyclyl, and wherein each of methyl, ethyl, n-propyl, i-propyl, furyl, pyrrolyl, pyridyl, pyrazolyl, imdazolyl, triazolyl, tetrazolyl, oxazolyl, oxadiazolyl, 1,3, 5-triazinyl, thiazolyl, thienyl, pyrazinyl, pyridazinyl, pyrimidyl and 5- to 6-membered heterocyclyl is independently unsubstituted or substituted with 1, 2, 3 or 4 substituents independently selected from D, F, Cl, Br, CN, $N_3$, oxo (=O), $NO_2$, —$OCH_3$, $C_{1-3}$ alkyl or $C_{1-3}$ haloalkyl.

In other embodiments, each $R^a$, $R^b$, $R^c$, $R^d$, $R^e$ and $R^f$ is independently H, D, hydroxy, trifluoromethyl, methyl, ethyl, i-propyl, n-propyl, n-butyl, t-butyl, n-pentyl, n-hexyl, n-heptyl, methoxy, ethoxy, $C_{3-6}$ carbocyclyl, 5- to 6-membered heterocyclyl, phenyl, 5- to 10-membered heteroaryl or (5- to 10-membered heteroaryl)-$C_{1-4}$ alkylene, and wherein each of methyl, ethyl, i-propyl, n-propyl, n-butyl, t-butyl, n-pentyl, n-hexyl, n-heptyl, methoxy, ethoxy, $C_{3-6}$ carbocyclyl, 5- to 6-membered heterocyclyl, phenyl, 5- to 10-membered heteroaryl and (5- to 10-membered heteroaryl)-$C_{1-4}$ alkylene is independently unsubstituted or substituted with 1, 2, 3 or 4 substituents independently selected from D, F, Cl, CN, OH, $NH_2$, $C_{1-3}$ alkyl, $C_{1-3}$ haloalkyl or methoxy;

or, $R^c$ and $R^d$, together with the nitrogen atom to which they are attached, form 5- to 6-membered heterocyclyl or 5- to 6-membered heteroaryl, and wherein each of 5- to 6-membered heterocyclyl or 5- to 6-membered heteroaryl is independently unsubstituted or substituted with 1, 2, 3 or 4 substituents independently selected from D, F, Cl, CN, OH, $NH_2$, $C_{1-3}$ alkyl, $C_{1-3}$ haloalkyl or methoxy.

In other embodiments, A is a $C_{3-6}$ carbocyclic ring, 3- to 6-membered heterocyclic ring, $C_{6-10}$ aromatic ring or 5- to 6-membered heteroaromatic ring.

In other embodiments, $R^4$ is $OR^b$, —$NR^cR^d$, ethynyl, propinyl, $C_{3-6}$ carbocyclyl, pyrrolidinyl, pyrazolidinyl, imidazolidinyl, tetrahydrofuryl, tetrahydrothienyl, tetrahydropyranyl, tetrahydrothiopyranyl, tetrahydroisoquinolyl, piperidinyl, morpholinyl, thiomorpholinyl, piperazinyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thiadiazolyl, thienyl, benzothienyl, pyrazinyl, pyridazinyl, pyrimidinyl, indolyl, purinyl, quinolyl, isoquinolyl, phenoxathiinyl,

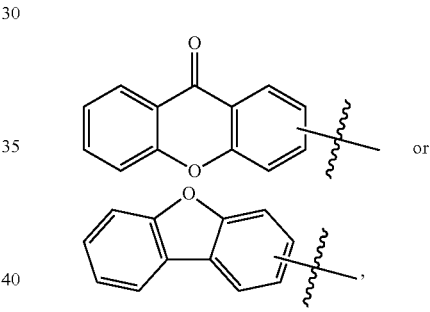 or and wherein each of ethynyl, propinyl, $C_{3-6}$ carbocyclyl, pyrrolidinyl, pyrazolidinyl, imidazolidinyl, tetrahydrofuryl, tetrahydrothienyl, tetrahydropyranyl, tetrahydrothiopyranyl, tetrahydroisoquinolyl, piperidinyl, morpholinyl, thiomorpholinyl, piperazinyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thiadiazolyl, thienyl, benzothienyl, pyrazinyl, pyridazinyl, pyrimidinyl, indolyl, purinyl, quinolyl, isoquinolyl, phenoxathiinyl,

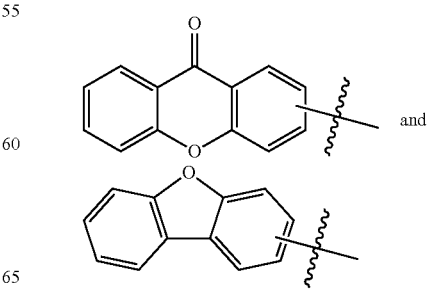 and is independently unsubstituted or substituted with 1, 2, 3, 4 or 5 R';

$R^5$ is H, D, F, Cl, Br, CN, $NO_2$, methyl, ethyl or i-propyl;

or, $R^4$ and $R^5$, together with the carbon atoms to which they are attached, form a $C_{3-6}$ carbocyclic ring, 3- to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline, and wherein each of $C_{3-6}$ carbocyclic ring, 3- to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline and isoquinoline is independently unsubstituted or substituted with 1, 2, 3, 4 or 5 R'.

In other embodiments, A is a $C_{3-6}$ carbocyclic ring, 3- to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline.

In other embodiments, W is one of the following sub-formulae:

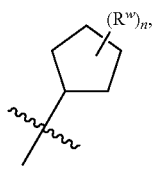

(W-1)

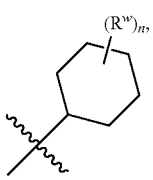

(W-2)

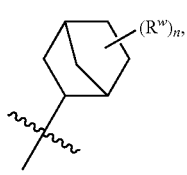

(W-3)

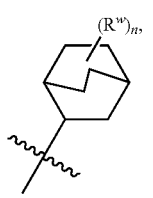

(W-4)

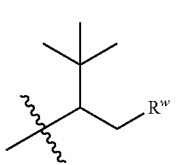

(W-5)

or

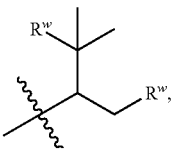

(W-6)

wherein n and $R^w$ are as defined herein.

In other embodiments, n is 0, 1, 2, 3 or 4.

In other embodiments, the invention relates to the compound having Formula (III) or a stereoisomer, a tautomer, an N-oxide, a solvate, a metabolite, a pharmaceutically acceptable salt or a prodrug thereof,

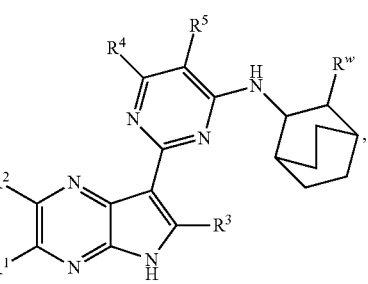

(III)

wherein $R^1$, $R^2$, $R^3$, $R^4$, $R^5$ and $R^w$ are as defined herein.

In other embodiments, the invention relates to the compound having Formula (IV) or a stereoisomer, a tautomer, an N-oxide, a solvate, a metabolite, a pharmaceutically acceptable salt or a prodrug thereof,

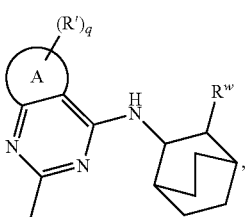

(IV)

wherein A, $R^1$, $R^2$, $R^3$, R', q and $R^w$ are as defined herein.

In other embodiments, the invention relates to the compound having Formula (V) or a stereoisomer, a tautomer, an N-oxide, a solvate, a metabolite, a pharmaceutically acceptable salt or a prodrug thereof,

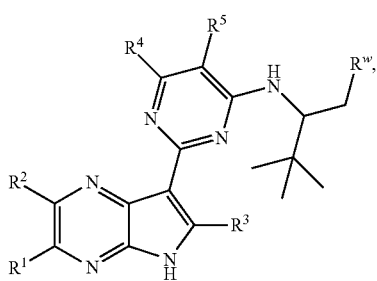

(V)

wherein $R^1$, $R^2$, $R^3$, $R^4$, $R^5$ and $R^w$ are as defined herein.

In other embodiments, the invention relates to the compound having Formula (VI) or a stereoisomer, a tautomer, an N-oxide, a solvate, a metabolite, a pharmaceutically acceptable salt or a prodrug thereof,

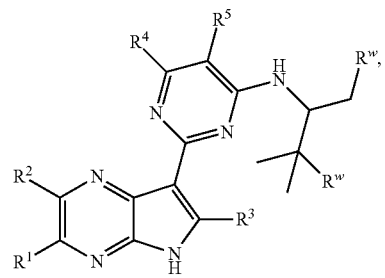

(VI)

wherein A, $R^1$, $R^2$, $R^3$, R', q and $R^w$ are as defined herein.

In other embodiments, the invention relates to the compound having Formula (VII) or a stereoisomer, a tautomer, an N-oxide, a solvate, a metabolite, a pharmaceutically acceptable salt or a prodrug thereof,

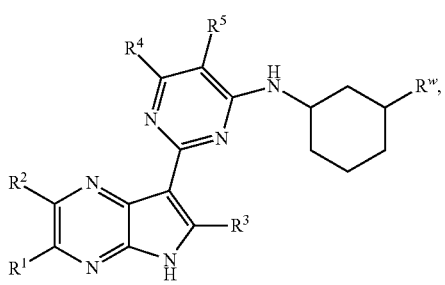

(VII)

wherein $R^1$, $R^2$, $R^3$, $R^4$, $R^5$ and $R^w$ are as defined herein.

In other embodiments, the invention relates to the compound having Formula (VIII) or a stereoisomer, a tautomer, an N-oxide, a solvate, a metabolite, a pharmaceutically acceptable salt or a prodrug thereof,

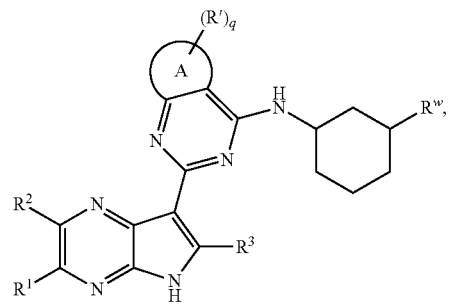

(VIII)

wherein A, $R^1$, $R^2$, $R^3$, R', q and $R^w$ are as defined herein.

In other embodiments, the invention relates to the compound having Formula (IX) or a stereoisomer, a tautomer, an N-oxide, a solvate, a metabolite, a pharmaceutically acceptable salt or a prodrug thereof, (IX)

wherein $R^1$, $R^2$, $R^3$, $R^4$, $R^5$ and $R^w$ are as defined herein.

In other embodiments, the invention relates to the compound having Formula (X) or a stereoisomer, a tautomer, an N-oxide, a solvate, a metabolite, a pharmaceutically acceptable salt or a prodrug thereof,

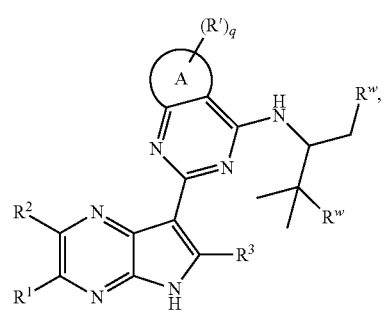

(X)

wherein A, $R^1$, $R^2$, $R^3$, R', q and $R^w$ are as defined herein.

In other embodiments, the invention relates to the compound having Formula (XI) or a stereoisomer, a tautomer, an N-oxide, a solvate, a metabolite, a pharmaceutically acceptable salt or a prodrug thereof, (XI)

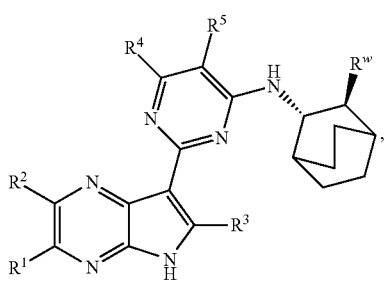

wherein $R^1$, $R^2$, $R^3$, $R^4$, $R^5$ and $R^w$ are as defined herein.

In other embodiments, the invention relates to the compound having Formula (XII) or a stereoisomer, a tautomer, an N-oxide, a solvate, a metabolite, a pharmaceutically acceptable salt or a prodrug thereof, (XII)

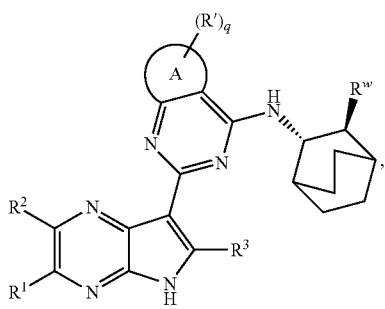

wherein A, $R^1$, $R^2$, $R^3$, R', q and $R^w$ are as defined herein.

In other embodiments, the invention relates to the compound having Formula (XIII) or a stereoisomer, a tautomer, an N-oxide, a solvate, a metabolite, a pharmaceutically acceptable salt or a prodrug thereof, (XIII)

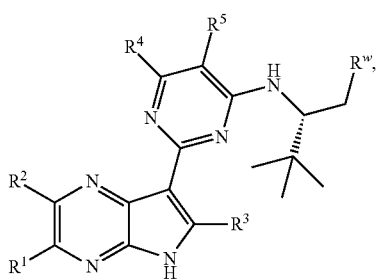

wherein $R^1$, $R^2$, $R^3$, $R^4$, $R^5$ and $R^w$ are as defined herein.

In other embodiments, the invention relates to the compound having Formula (XIV) or a stereoisomer, a tautomer, an N-oxide, a solvate, a metabolite, a pharmaceutically acceptable salt or a prodrug thereof, (XIV)

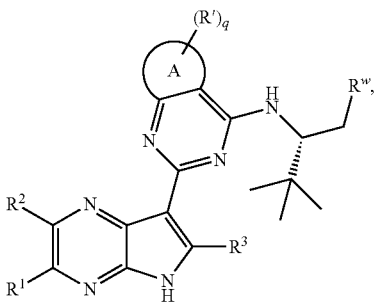

wherein A, $R^1$, $R^2$, $R^3$, R', q and $R^w$ are as defined herein.

In other aspect, provided herein is a pharmaceutical composition comprising an effective amount of the compound disclosed herein.

In certain embodiments, the pharmaceutical composition provided herein further comprises a pharmaceutically acceptable carrier, adjuvant, vehicle or a combination thereof.

In certain embodiments, the pharmaceutical composition provided herein further comprises one or more therapeutic agents.

In other embodiments, the therapeutic agent disclosed herein is an anti-influenza virus agent or anti-influenza virus vaccine.

In other embodiments, the pharmaceutical composition is in the form of a liquid, solid, semi-solid, gel or spray.

In other embodiments, the pharmaceutical composition, wherein the therapeutic agent is amantadine, rimantadine, oseltamivir, zanamivir, peramivir, laninamivir, laninamivir octanoate hydrate, favipiravir, arbidol, ribavirin, stachyflin, ingavirin, fludase, CAS no. 1422050-75-6, JNJ-872, S-033188, an influenza vaccine (FluMist Quadrivalent®, Fluarix® Quadrivalent, Fluzone® Quadrivalent, Flucelvax® or FluBlok®) or a combination thereof.

In another aspect, provided herein is use of the compound or the pharmaceutical composition disclosed herein in the manufacture of a medicament for preventing, managing, treating or lessening a disorder or disease caused by virus infection in a subject.

In certain embodiments, the virus infection disclosed herein is influenza virus infection.

In another aspect, provided herein is use of the compound or the pharmaceutical composition disclosed herein in the manufacture of a medicament for inhibiting influenza virus RNA polymerase.

In another aspect, provided herein is the compound or the pharmaceutical composition disclosed herein for use in preventing, managing, treating or lessening a disorder or disease caused by virus infection in a subject.

In certain embodiments, the virus infection is influenza virus infection.

In another aspect, provided herein is the compound or the pharmaceutical composition disclosed herein for use in inhibiting influenza virus RNA polymerase.

In another aspect, provided herein is a method of preventing, managing, treating or lessening a disorder or disease caused by a virus infection in a subject, comprising administering to the subject a therapeutically effective amount of the compound or the pharmaceutical composition disclosed herein.

In certain embodiments, the virus infection is influenza virus infection.

In another aspect, provided herein is a method of inhibiting influenza virus RNA polymerase in a subject, comprising administering to the subject a therapeutically effective amount of the compound or the pharmaceutical composition disclosed herein.

Unless otherwise stated, all stereoisomers, geometric isomers, tautomers, solvates, hydrates, metabolites, salts and pharmaceutically acceptable prodrugs of the compounds disclosed herein are within the scope of the invention.

In one embodiment, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith.

In another embodiment, the compounds of the invention also include the salts forms thereof, and these salts are not necessarily pharmaceutically acceptable salts, and which may be useful as intermediates for preparing and/or purifying compounds of the invention and/or for separating enantiomers of compounds of the invention.

Furthermore, the compounds disclosed herein, including their salts, can also be obtained in the form of their hydrates, or include other solvents used for their crystallization. The compounds of the present invention may be formed into solvates with pharmaceutically acceptable solvents (including water) inherently or by designing; therefore, it is intended that the invention embrace both solvated and unsolvated forms.

In another embodiment, the compounds disclosed herein may contain several asymmetric centers and therefore exist in the form of racemic mixture generally described. Furthermore, it is intended that all racemic mixture, parts of the racemic mixture, and enantiomer and diastereomers purified by separation form part of the present invention.

The compounds disclosed herein may exist in the form of possible isomers, including rotamers, atropisomers, tautomer or a mixture thereof. It is intended that mixtures of isomers, including rotamers, atropisomers, tautomers, parts of the mixtures of isomers, rotamers, atropisomers, tautomers, and the isomers, including rotamers, atropisomers, tautomer purified by separation form part of the present invention.

In another aspect, the compounds of the invention include isotopically enriched compounds as defined herein, for example those into which radioactive isotopes, such as $^3$H, $^{14}$C and $^{18}$F, or those into which non-radioactive isotopes, such as $^2$H and $^{13}$C are present.

In other aspect, provided herein is a method of preparing, separating or purifying the compound of Formula (I).

The foregoing merely summarizes certain aspects disclosed herein and is not intended to be limiting in nature. These aspects and other aspects and embodiments are described more fully below.

DETAILED DESCRIPTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application shall prevail.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless otherwise defined, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes disclosed herein, the chemical elements are identified in accordance with the Periodic Table of the Elements, CAS version, and the Handbook of Chemistry and Physics, 75 thEd. 1994. Additionally, general principles of organic chemistry are described in Sorrell et al., "Organic Chemistry", University Science Books, Sausalito: 1999, and "March's Advanced Organic Chemistry", by Michael B. Smith and Jerry March, John Wiley & Sons, New York: 2007, all of which are incorporated herein by reference in their entireties.

As used herein, the term "subject" refers to an animal. Typically the animal is a mammal. The subject also refers to primates (e.g., humans), cows, sheep, goats, horses, dogs, cats, rabbits, rats, mice, fish, birds and the like. In certain embodiments, the subject is a primate. In other embodiments, the subject is a human.

The term "subject" can be used interchangeablely with "patient" in the invention. The term "subject" and "patient" refer to animals (eg., birds such as chicken, quail or turkey, or mammals), specially mammals including non-primates (eg., cattle, pigs, horses, sheep, rabbits, guinea pigs, rats, dogs, cats and mice) and primates (eg., monkeys, chimpanzees and humans), more specially humans. In some embodiments, the subject is a non-human animal, such as livestock (eg., horses, cattle, pigs or sheep) or pet (eg., dogs, cats, guinea pigs or rabbits). In other embodiments, the "patient" refers to a human.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^2$H, $^3$H, $^{13}$C, $^{14}$C, $^{15}$N, $^{16}$O, $^{17}$O, $^{31}$P, $^{32}$P, $^{36}$S, $^{18}$F and $^{37}$Cl, respectively.

The compounds disclosed herein containing isotopes described above or other atom isotopes and pharmaceutical salts thereof are included within the scope of the present invention. Certain isotopically-labeled compounds of the present invention, for example those into which radioactive isotopes such as $^3$H or $^{14}$C are incorporated, are useful in drug and/or substrate tissue distribution assays. Because of easy preparation and detection, isotopes such as tritiated, i.e., $^3$H, and carbon-14, i.e., $^{14}$C are preferred. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. Therefore, the heavier isotopes may be preferred in somewhere.

Stereochemical definitions and conventions used herein generally follow the definition as described in S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A specific stereoisomer may be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

The compounds disclosed herein may contain asymmetric or chiral centers, and therefore exist in different stereoisomeric forms. It is intended that all stereoisomeric forms of the compounds disclosed herein, including but not limited to, diastereomers, enantiomers, atropisomers and geometric (conformational) isomers as well as mixtures thereof such as racemic mixtures, form part of the present invention.

Unless otherwise specified, the Formula described herein also contain all the isomers thereof (such as, enantiomers, diastereomers, atropisomers and geometric (conformational) isomers; such as all (R)- and (S)-isomers, (Z) and (E) isomers around the double bond, (Z) and (E) conformational isomers. Therefore, single stereochemical isomers as well as enantiomeric, diastereomeric, or geometric mixtures of the present compounds are within the scope disclosed herein.

The term "tautomer" or "tautomeric form" refers to structural isomers of different energies which are interconvertible via a low energy barrier. If tautomerization is possible (e.g., in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

An "N-oxide" refers to one or more than one nitrogen atoms oxidised to form an N-oxide or N-oxides, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g., a peroxycarboxylic acid) (See, Advanced Organic Chemistiy, by Jerry March, 4th Edition, Wiley Interscience, pages). More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The term "solvate" refers to an association or complex of one or more solvent molecules and a compound disclosed herein. Some non-limiting examples of solvents that form solvates include water, isopropanol, ethanol, methanol, dimethylsulfoxide, ethyl acetate, acetic acid and ethanolamine. The term "hydrate" refers to the complex where the solvent molecule is water.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphanic acid salt, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oilsoluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, *Journal of Medicinal Chemistry,* 2008, 51, 2328-2345, all of which are incorporated herein by reference in their entireties.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. If the compound contains a double bond, the substituent may be cis-(Z)- or trans-(E)-configuration.

Therefore, as the invention described, the compounds disclosed herein may exist in the form of any possible isomer, such as rotational isomer, atropisomer, tautomer, or a mixture thereof, i.e., substantially pure geometric (cis- or trans-) isomer, diastereoisomer, optical isomer (enantiomer), racemate or a mixture thereof.

Any resulting mixtures of stereoisomers can be separated on the basis of the physicochemical differences of the constituents, into the pure or substantially pure geometric isomers, optical isomers, diastereoisomers, racemate, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent.

Preferred enantiomers can also be prepared by asymmetric syntheses. See, for example, Jacques, et al., Enantiomers, Racemates and Resolutions (Wiley Interscience, New York, 1981); Principles of Asymmetric Synthesis (2nd Ed. Robert E. Gawley, Jeffrey Aubé, Elsevier, Oxford, UK, 2012); Eliel, E. L. Stereochemistry of Carbon Compounds (McGraw-Hill, N.Y., 1962); Wilen, S. H. Tables of Resolving Agents and Optical Resolutions p. 268 (E. L. Eliel, Ed., Univ. of Notre Dame Press, Notre Dame, Ind. 1972).

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". The term "optional" or "optionally" refers to that a subsequently described event or circumstance may but need not occur, and that the description includes instances where the event or circumstance occurs and instances in which it does not. In general, whenever the term "optionally" is or is not before the term "substituted", the term "substituted" refers to the unreplacement or replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substitutents can be, but are not limited to, D, F, Cl, Br, CN, $N_3$, OH, $NH_2$, $NO_2$, oxo (=O), —C(=O)$R^a$, —C(=O)O$R^b$, —C(=O)N$R^cR^d$, —N$R^c$C(=O)$R^a$, —S(=O)$_2R^f$, —S(=O)$_2$N$R^c$C(=O)$R^a$, —S(=O)$_2$N$R^cR^d$, $(R^bO)_2$P(=O)—O—$C_{0-2}$ alkylene, O$R^b$, —N$R^cR^d$, $R^b$O—$C_{1-4}$ alkylene, $R^dR^c$N—$C_{1-4}$ alkylene, $R^a$—C(=O)—O—$C_{1-4}$ alkylene-O—$C_{1-4}$ alkylene, $R^b$O—C(=O)—O—$C_{1-4}$ alkylene-O—$C_{1-4}$ alkylene, —C(=O)—O—$C_{1-4}$ alkylene-O—C(=O)—O$R^b$, $C_{1-12}$ alkyl, $C_{1-6}$ haloalkyl, $C_{1-6}$ alkoxy, $C_{1-6}$ alkylamino, $C_{2-6}$ alkenyl, $C_{2-6}$ alkynyl, $C_{3-12}$ cycloalkyl, $C_{3-12}$ cycloalkyl-$C_{1-4}$ alkylene, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl or (5- to 16-membered heteroaryl)-$C_{1-4}$ alkylene, and wherein each $R^a$, $R^b$, $R^c$, $R^d$, $R^e$ and $R^f$ are as defined herein.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same group.

At various places in the present specification, substituents of compounds disclosed herein are disclosed in groups or in ranges. It is specifically intended that the invention includes each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms. Unless otherwise specified, the alkyl group contains 1-20 carbon atoms. In some embodiments, the alkyl group contains 1-12 carbon atoms. In other embodiments, the alkyl group contains 1-10 carbon atoms. In other embodiments, the alkyl group contains 1-9 carbon atoms. In other embodiments, the alkyl group contains 1-8 carbon atoms. In other embodiments, the alkyl group contains 1-6 carbon atoms. In still other embodiments, the alkyl group contains 1-4 carbon atoms. In yet other embodiments, the alkyl group contains 1-3 carbon atoms.

Some non-limiting examples of the alkyl group include, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), n-heptyl and n-octyl, etc. Wherein the alkyl group can be independently unsubstituted or substituted with one or more substituents described herein.

The term "alkyl" or the prefix "alk-" is inclusive of both straight chain and branched saturated carbon chain.

The term "alkylene" refers to a saturated divalent hydrocarbon group derived from a straight or branched chain saturated hydrocarbon by the removal of two hydrogen atoms. Unless otherwise specified, the alkylene group contains 1-10 carbon atoms. In other embodiments, the alkylene group contains 1-6 carbon atoms. In still other embodiments, the alkylene group contains 1-4 carbon atoms. In yet other embodiments, the alkylene group contains 1-2 carbon atoms. And alkylene group is exemplified by methylene (—CH$_2$—), ethylene (—CH$_2$CH$_2$—), isopropylene (—CH(CH$_3$)CH$_2$—), and the like, wherein the alkylene group is independently unsubstituted or substituted with one or more substitutents disclosed herein.

The term "alkenyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "F" and "Z" orientations. Specific examples of the alkenyl group include, but are not limited to, vinyl (—CH═CH$_2$), allyl (—CH$_2$CH═CH$_2$), and the like.

The term "alkynyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp triple bond, wherein the alkynyl radical may be optionally substituted independently with one or more substituents described herein. Specific examples of the alkenyl group include, but are not limited to, ethynyl (—C≡CH), propargyl (—CH$_2$C≡CH), 1-propinyl (—C≡C—CH$_3$), and the like.

The term "alkoxy" refers to an alkyl group, as previously defined, attached to the parent molecular moiety via an oxygen atom. Unless otherwise specified, the alkyl group contains 1-20 carbon atoms. In other embodiments, the alkyl group contains 1-10 carbon atoms. In other embodiments, the alkyl group contains 1-8 carbon atoms. In still other embodiments, the alkyl group contains 1-6 carbon atoms. In yet other embodiments, the alkyl group contains 1-4 carbon atoms and in still yet other embodiments, the alkyl group contains 1-3 carbon atoms.

Some non-limiting examples of alkoxy group include, methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —C(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like. Wherein the alkoxy group is independently unsubstituted or substituted with one or more substitutents disclosed herein.

The terms "haloalkyl", "haloalkenyl" or "haloalkoxy" refer to alkyl, alkenyl or alkoxy, as the case may be, substituted with one or more halogen atoms. In some embodiments, the haloalkyl group contains 1-10 carbon atoms. In other embodiments, the haloalkyl group contains 1-8 carbon atoms. In other embodiments, the haloalkyl group contains 1-6 carbon atoms. In still other embodiments, the haloalkyl group contains 1-4 carbon atoms. In yet other embodiments, the haloalkyl group contains 1-3 carbon atoms. Some non-limiting examples of the haloalkyl group and haloalkoxy group include trifluoromethyl, monofluoroethyl, trifluoromethoxy, and the like.

The terms "carbocycle", "carbocyclyl", "carbocyclic" and "carbocyclic ring" used interchangeably herein refer to a non-aromatic carboncyclic ring system having 3 to 14 ring carbon atoms, which is saturated or contains one or more units of unsaturation, but there is no aromatic ring existing in the ring system. In some embodiments, the number of carbon atom is 3 to 12; in other embodiments, the number of carbon atom is 3 to 10; in other embodiments, the number of carbon atom is 3 to 8; in other embodiments, the number of carbon atom is 3 to 6; in other embodiments, the number of carbon atom is 5 to 6; in other embodiments, the number of carbon atom is 5 to 8; in other embodiments, the number of carbon atom is 6 to 8. The "carbocyclyl" includes a monocyclic, bicyclic, or polycyclic fused ring, spiro ring or bridged ring system. The bicyclic carbocyclyl groups include bridged bicyclic carbocyclyl, fused bicyclic carbocyclyl and spiro bicyclic carbocyclyl group, and fused bicyclic system contains two rings which share two adjacent ring atoms. Bridged bicyclic group contains two rings which share 2, 3, 4 or 5 adjacent ring atoms. Spiro bicyclic system contains two rings which share one ring atom. Some non-limiting examples of the cycloaliphatic group include cycloalkyl, cycloalkenyl and cycloalkynyl. Further examples of carbocyclyl groups include cyclopropyl, cyclobutyl, cyclopentyl, 1-cyclopent-1-enyl, 1-cyclopent-2- enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Bridged bicyclic carbocyclyl group includes, but are not limited to, bicyclo[2.2.2]octyl, bicyclo[2.2.1]heptyl, bicyclo[3.3.1]nonyl, bicyclo[3.2.3]nonyl, and the like.

The term "cycloalkyl" refers to a saturated ring having 3 to 12 ring carbon atoms as a monocyclic, bicyclic, or tricyclic ring system, which has one or more attachments attaching to the rest of the molecule. In some embodiments, the cycloalkyl group contains 3 to 10 ring carbon atoms. In other embodiments, the cycloalkyl group contains 3 to 8 ring carbon atoms. In still other embodiments, the cycloalkyl group contains 3 to 6 ring carbon atoms. In yet other embodiments, the cycloalkyl group contains 5 to 6 ring carbon atoms. Examples of cycloalkyl group include, but are not limited to, cyclopropyl, cyclobutyl, cyclopentyl, and the like. The cycloalkyl radical is independently unsubstituted or substituted with one or more substituents described herein.

The term "heterocycle", "heterocyclyl", or "heterocyclic ring" as used interchangeably herein refers to a saturated or partially unsaturated non-aromatic monocyclic, bicyclic or tricyclic ring containing 3-12 ring atoms of which at least one ring atom is selected from nitrogen, sulfur and oxygen, wherein the heterocyclyl system is non-aromatic, and there is no aromatic ring existing in the heterocyclyl system, and of which may has one or more attachments attached to the rest of the molecule. The term "heterocyclyl" includes a monocyclic, bicyclic, or polycyclic fused, spiro, bridged heterocyclic ring system. Biheterocyclyl radical includes bridged biheterocyclyl, fused biheterocyclyl and spiro biheterocyclyl. Unless otherwise specified, the heterocyclyl group may be carbon or nitrogen linked, and a —CH$_2$— group can be optionally replaced by a —C(=O)— group. In which, the sulfur can be optionally oxygenized to S-oxide; and the nitrogen can be optionally oxygenized to N-oxide. In some embodiments, the heterocyclyl group is a 3- to 8-membered heterocyclyl group; in other embodiments, the heterocyclyl group is a 3- to 6-membered heterocyclyl group; in other embodiments, the heterocyclyl group is a 5- to 7-membered heterocyclyl group; in other embodiments, the heterocyclyl group is a 5- to 8-membered heterocyclyl group; in other embodiments, the heterocyclyl group is a 6- to 8-membered heterocyclyl group; in other embodiments, the heterocyclyl group is a 5- to 6-membered heterocyclyl group; in other embodiments, the heterocyclyl group is a 4-membered heterocyclyl group; in other embodiments, the heterocyclyl group is a 5-membered heterocyclyl group; in other embodiments, the heterocyclyl group is a 6-membered heterocyclyl group; in other embodiments, the heterocyclyl group is a 7-membered heterocyclyl group; in other embodiments, the heterocyclyl group is a 8-membered heterocyclyl group.

Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, and the like. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, or

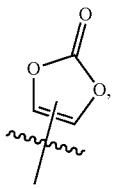

and the like. Some non-limiting examples of heterocyclyl wherein the ring sulfur atom is oxidized include sulfolanyl and 1,1-dioxo-thiomorpholinyl. Some non-limiting examples of bridged heterocyclyl group include, 2-oxabicyclo[2.2.2]octyl, 1-azabicyclo[2.2.2]octyl, 3-azabicyclo[3.2.1]octyl, and the like. The heterocyclyl group may be optionally substituted with one or more substituents disclosed herein.

The term "bridged" refers to a bond, an atom or an unbranched atom chain connecting two different parts of a molecule. The two atoms (usually but not always two tertiary carbon atoms) linked by the bridge denotes "bridgeheads".

The term "m-membered", where m is an integer typically describes the number of ring-forming atoms in a moiety where the number of ring-forming atoms is m. For example, piperidinyl is an example of a 6-membered heterocyclyl and 1,2,3,4-tetrahydro-naphthalene is an example of a 10-membered carbocyclyl group.

The term "heteroatom" refers to O, S, N, P and Si, including any oxidized form of N, S and P; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to fluorine (F), chlorine (Cl), bromine (Br), or iodine (I).

The term "azido" or "N$_3$" refers to an azide moiety. This radical may be attached, for example, to a methyl group to form azidomethane (methyl azide, MeN$_3$); or attached to a phenyl group to form phenyl azide (PhN$_3$).

The term "D" refers to deuteration, ie., $^2$H.

The term "aryl" used alone or as a great part of "arylalkyl", "arylalkoxy" or "aryloxyalkyl", refers to monocyclic, bicyclic and tricyclic carbocyclic ring systems having a total of 6 to 14 ring members, or 6 to 12 ring members, or 6 to 10 ring members, wherein at least one ring in the system is aromatic, wherein each ring in the system contains 3 to 7 ring members and that has a single point or multipoint of attachment to the rest of the molecule. The term "aryl" may be used interchangeably with the term "aryl ring" or "aromatic ring". Some non-limiting examples of the aryl group include phenyl, 2,3-dihydro-1H-indenyl, naphthyl and anthracene. The aryl group may be optionally unsubstituted or substituted with one or more substituents disclosed herein.

The term "heteroaryl" used alone or as a great part of "heteroarylalkyl" or "heteroarylalkoxy", refers to monocyclic, bicyclic and tricyclic ring systems having a total of five to sixteen ring members, wherein at least one ring in the system is aromatic, and in which at least one ring member is selected from heteroatom, and wherein each ring in the system contains 5 to 11 ring members and that has a single point or multipoint of attachment to the rest of the molecule. When there exists a —CH$_2$— group in the heteroaryl group, the —CH$_2$— group can be optionally replaced by a —C(=O)— group. The terms "heteroaryl" and "heteroaromatic ring" or "heteroaromatic compound" can be used interchangeably herein. In one embodiment, the heteroaryl group is a 5- to 14-membered heteroaryl comprising 1, 2, 3 or 4 heteroatoms independently selected from O, S and N. In another embodiment, the heteroaryl group is a 5- to 12-membered heteroaryl comprising 1, 2, 3 or 4 heteroatoms independently selected from O, S and N. In another embodiment, the heteroaryl group is a 5- to 10-membered heteroaryl comprising 1, 2, 3 or 4 heteroatoms independently selected from O, S and N. In another embodiment, the heteroaryl group is a 5- to 8-membered heteroaryl comprising 1, 2, 3 or 4 heteroatoms independently selected from O, S and N. In another embodiment, the heteroaryl group is a 5- to 7-membered heteroaryl comprising 1, 2, 3 or 4 heteroatoms independently selected from O, S and N. In another embodiment, the heteroaryl group is a 5- to 6-membered heteroaryl comprising 1, 2, 3 or 4 heteroatoms independently selected from O, S and N. In another embodiment, the heteroaryl group is a 5-membered heteroaryl comprising 1, 2, 3 or 4 heteroatoms independently selected from O, S and N. In another embodiment, the heteroaryl group is a 6-membered heteroaryl comprising 1, 2, 3 or 4 heteroatoms independently selected from O, S and N.

In another embodiment, some non-limiting examples of heteroaryl group include the following mono-cyclic groups, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl and 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiadiazolyl, 1,3,4-thiadiazolyl, 1,2,5-thiadiazolyl, pyrazinyl or 1,3,5-triazinyl, and the following bicycles, but are not limited to: indolinyl, 1,2,3,4-tetrahydroisoquinolyl, benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), phenoxathiinyl,

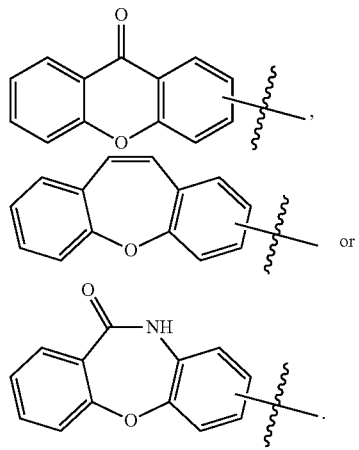

The heteroaryl group is optionally substituted with one or more substituents disclosed herein.

The terms "carboxy" or "carboxyl", whether used alone or with other terms, such as "carboxyalkyl", refer to —CO$_2$H.

The term "carbonyl", whether used alone or with other terms, such as "aminocarbonyl", "acyloxy", denotes —(C=O)—.

The term "alkylamino" refers to "N-alkylamino" and "N,N-dialkylamino", wherein amino groups are independently substituted with one alkyl radical or two alkyl radicals, respectively. In some embodiments, the alkylamino group is a lower alkylamino group having one or two C$_{1-6}$ alkyl groups attached to nitrogen atom. In other embodiments, the alkylamino group is a lower alkylamino group having 1 to 3 carbon atoms. Suitable alkylamino radical may be monoalkylamino or dialkylamino Examples of the alkylamino radical include, but are not limited to, N-methylamino, N-ethylamino, N,N-dimethylamino, N,N-diethylamino, and the like.

The term "arylamino" refers to an amino group substituted with one or two aryl groups. Some non-limiting examples of such group include N-phenylamino. In some embodiments, the aryl group of the arylamino may be further substituted.

The term "aminoalkyl" refers to a C$_{1-10}$ linear or branched-chain alkyl group substituted with one or more amino groups. In some embodiments, the aminoalkyl is a C$_{1-6}$ lower aminoalkyl derived from an alkyl group substituted with one or more amino groups. Some non-limiting examples of the aminoalkyl group include aminomethyl, aminoethyl, aminopropyl, aminobutyl and aminohexyl.

As described herein, a bond drawn from a substituent to the center of one ring within a ring system represents substitution of substituents at any substitutable position on the rings, and wherein the ring system includes mono-, bi- or polycyclic ring system. For example, formula a represents substitution of substituents at any substitutable position on the cyclic ring system, i.e., formula b-1 to formula b-8:

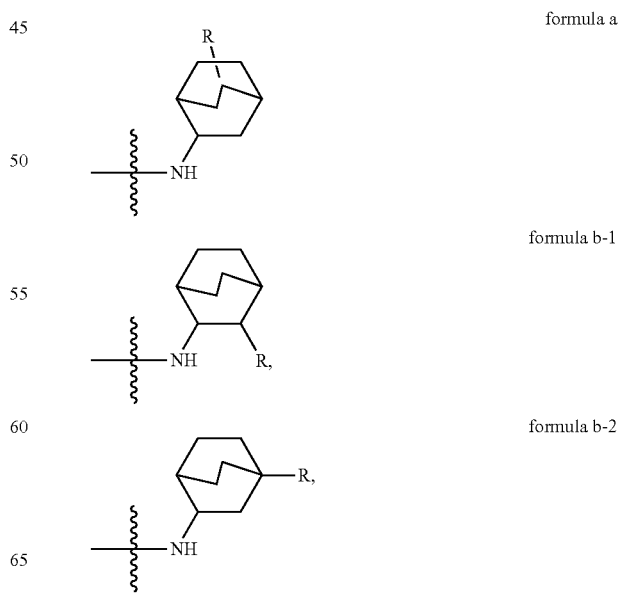

formula b-3
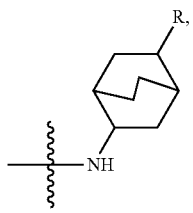

formula b-4
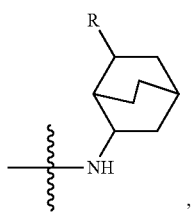

formula b-5
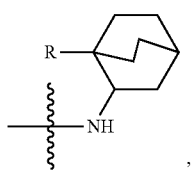

formula b-6
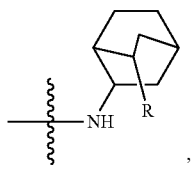

formula b-7
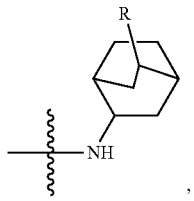

formula b-8
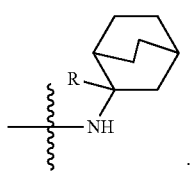

As described herein, a bond drawn from a substituent to the center of one ring within a ring system represents the bond can attach to the rest of the molecule at any attachable position on the rings. For example, formula c represents substitution of substituents which can attach to the rest of the molecule at any substitutable position on the rings, i.e., formula d-1 and formula d-2.

formula c
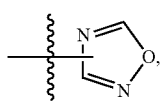

formula d-1
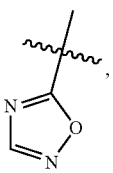

formula d-2
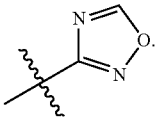

As described herein, when there exists two or more substituents represented by the same letter, number or symbol in one structural formula, the substituents are independent from each other. For example, in formula e, each $R^W$ is as defined herein, and each $R^W$ is independent of each other, which can be the same or different of each other.

formula e
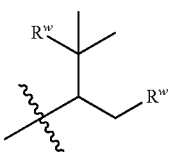

The term "unsaturated" refers to a moiety having one or more units of unsaturation.

The term "comprising" or "comprise" is meant to be open ended, including the indicated component but not excluding other elements.

As described herein, the term "pharmaceutically acceptable carrier" includes any solvents, dispersion media, coating agents, surfactants, antioxidants, preservatives (e.g., antibacterial agents, antifungal agents), isotonic agents, salt, drug stabilizers, binders, excipients, dispersants, lubricants, sweetening agents, flavoring agents, coloring agents, or a combination thereof, all of which are well know to the skilled in the art. (e.g., Remington's Pharmaceutical Sciences, 18th Ed. Mack Printing Company, 1990, pp. 1289-1329, all of which are incorporated herein by reference). Except any conventional carrier is incompatible with the active ingredient, the pharmaceutically acceptable carriers are effectively used in the treatment or pharmaceutical compositions.

As used herein, the term "inhibition of the replication of influenza viruses" includes both the reduction in the amount of virus replication (e.g., the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

As used herein, an "effective amount" refers to an amount sufficient to elicit the desired biological response. In the present invention, the desired biological response is to inhibit the replication of influenza virus, to reduce the amount of influenza viruses or to reduce or ameliorate the severity, duration, progression, or onset of a influenza virus infection, prevent the advancement of an influenza virus infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other anti viral agents, e.g., when co-administered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between approximately 0.01 to 100 mg/kg body weight/day for therapeutic or prophylactic treatment.

As used herein, the terms "treat", "treatment" and "treating" refer to both therapeutic and prophylactic treatments. For example, therapeutic treatments include the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the invention). In specific embodiments, the therapeutic treatment includes the amelioration of at least one measurable physical parameter of an influenza virus mediated condition. In other embodiments, the therapeutic treatment includes the inhibition of the progression of an influenza virus mediated condition, either physically by, e.g., stabilization of a discernible symptom, physiologically by, e.g., stabilization of a physical parameter, or both. In other embodiments, the therapeutic treatment includes the reduction or stabilization of influenza viruses mediated infections. Antiviral drugs can be used in the community setting to treat people who already have influenza to reduce the severity of symptoms and reduce the number of days that they are sick.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, p-toluenesulfonyl (Ts), t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

DESCRIPTION OF COMPOUNDS OF THE INVENTION

The invention discloses a novel class of compounds used as inhibitors of influenza virus RNA polymerase. These compounds and compositons thereof can be used in the manufacture of a medicament for preventing, managing, treating or lessening virus infection in patients.

In one aspect, provided herein is a compound having Formula (I) or a stereoisomer, a tautomer, an N-oxide, a solvate, a metabolite, a pharmaceutically acceptable salt or a prodrug thereof,

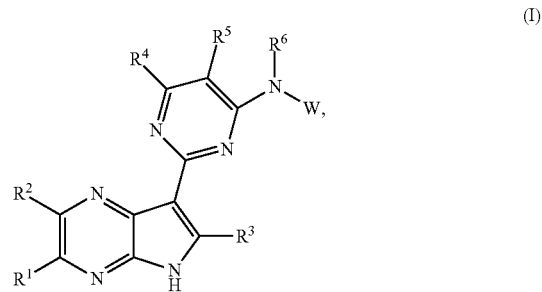

wherein $R^1$, $R^2$, $R^3$, $R^4$, $R^5$, $R^6$ and W are as defined herein.

In some embodiments, each of $R^1$, $R^2$ and $R^3$ is independently H, D, F, Cl, Br, CN, $NO_2$, —C(=O)$R^a$, —C(=O)O$R^b$, —C(=O)N$R^cR^d$, O$R^b$, —N$R^cR^d$, $R^b$O—$C_{1-4}$ alkylene, $R^dR^cN$—$C_{1-4}$ alkylene, $C_{1-6}$ alkyl, $C_{2-6}$ alkenyl or $C_{2-6}$ alkynyl; or, $R^1$ and $R^2$, together with the carbon atoms to which they are attached, form a $C_{3-6}$ carbocyclic ring, 5- to 6-membered heterocyclic ring, $C_{6-10}$ aromatic ring or 5- to 6-membered heteroaromatic ring, and wherein each of $C_{1-6}$ alkyl, $C_{2-6}$ alkenyl, $C_{2-6}$ alkynyl, $C_{3-6}$ carbocyclic ring, 5- to 6-membered heterocyclic ring, $C_{6-10}$ aromatic ring and 5- to 6-membered heteroaromatic ring is independently unsubstituted or substituted with 1, 2, 3 or 4 substituents independently selected from D, F, Cl, Br, CN, O$R^b$, —N$R^cR^d$, $C_{1-6}$ alkyl, $C_{1-6}$ haloalkyl, $R^b$O—$C_{1-4}$ alkylene or $R^dR^cN$—$C_{1-4}$ alkylene;

$R^4$ is O$R^b$, —N$R^cR^d$, $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl or (5- to 16-membered heteroaryl)-$C_{1-4}$ alkylene, and wherein each of $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl and (5- to 16-membered heteroaryl)-$C_{1-4}$ alkylene is independently unsubstituted or substituted with 1, 2, 3, 4 or 5 R';

$R^5$ is H, D, F, Cl, Br, CN, $NO_2$, —C(=O)$R^a$, —C(=O)O$R^b$, —C(=O)N$R^cR^d$, O$R^b$, —N$R^cR^d$, $R^b$O—$C_{1-4}$ alkylene, $R^dR^cN$—$C_{1-4}$ alkylene, $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ alkylene, 5- to 10-membered heteroaryl and (5- to 10-membered heteroaryl)-$C_{1-4}$ alkylene is independently unsubstituted or substituted with 1, 2, 3, 4 or 5 R';

or, $R^4$ and $R^5$, together with the carbon atoms to which they are attached, form a $C_{3-12}$ carbocyclic ring, 3- to 12-membered heterocyclic ring, $C_{6-10}$ aromatic ring or 5- to 10-membered heteroaromatic ring, and wherein each of $C_{3-12}$ carbocyclic ring, 3- to 12-membered heterocyclic ring, $C_{6-10}$ aromatic ring and 5- to 10-membered heteroaromatic ring is independently unsubstituted or substituted with 1, 2, 3, 4 or 5 R';

each R' is independently D, F, Cl, Br, CN, $NO_2$, $OR^b$, —$NR^cR^d$, $R^bO$—$C_{1-4}$ alkylene, $R^dR^cN$—$C_{1-4}$ alkylene, $R^a$—C(=O)—O—$C_{1-4}$ alkylene-O—$C_{1-4}$ alkylene, $R^bO$—C(=O)—O—$C_{1-4}$ alkylene-O—$C_{1-4}$ alkylene, —C(=O)$R^a$, —C(=O)$OR^b$, —C(=O)$NR^cR^d$, $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-12}$ alkyl, $C_{1-6}$ haloalkyl, $C_{3-6}$ cycloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3 or 4 substituents independently selected from D, F, Cl, Br, CN, $NO_2$, $OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

$R^6$ is H, D or $C_{1-6}$ alkyl, and wherein $C_{1-6}$ alkyl is optionally substituted with 1, 2, 3 or 4 substituents independently selected from D, F, Cl, Br, CN, $NO_2$ or $OR^b$;

W is $C_{1-8}$ alkyl, $C_{3-12}$ carbocyclyl or 3- to 12-membered heterocyclyl, and wherein each of $C_{1-8}$ alkyl, $C_{3-12}$ carbocyclyl and 3- to 12-membered heterocyclyl is independently unsubstituted or substituted with 1, 2, 3 or 4 $R^w$;

each $R^w$ is independently D, F, Cl, Br, CN, $NO_2$, oxo (=O), —C(=O)$R^a$, —C(=O)$OR^b$, —C(=O)—O—$C_{1-4}$ alkylene-O—C(=O)—$OR^b$, —C(=O)$NR^cR^d$, —$NR^cC$(=O)$R^a$, —$NR^cC$(=O)$NR^cR^d$, —$S$(=O)$_2R^f$, —$S$(=O)$_2NR^cC$(=O)$R^a$, —$S$(=O)$_2NR^cR^d$, $(R^bO)_2P$(=O)—$C_{0-2}$ alkylene, $OR^b$, $R^bO$—$C_{1-2}$ alkylene, $R^dR^cN$—$C_{1-2}$ alkylene, $C_{1-6}$ alkyl, 5- to 6-membered heteroaryl or 5- to 6-membered heterocyclyl, and wherein each of $C_{1-6}$ alkyl, 5- to 6-membered heteroaryl and 5- to 6-membered heterocyclyl is independently unsubstituted or substituted with 1, 2, 3 or 4 substituents independently selected from D, F, Cl, Br, CN, $N_3$, oxo (=O), $NO_2$, $OR^b$, $C_{1-6}$ alkyl or $C_{1-6}$ haloalkyl;

each $R^a$, $R^b$, $R^c$, $R^d$, $R^e$ and $R^f$ is independently H, D, hydroxy, $C_{1-6}$ haloalkyl, $C_{1-6}$ alkyl, n-heptyl, $C_{1-6}$ alkoxy, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-6}$ alkyl, n-heptyl, $C_{1-6}$ alkoxy, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino;

or, $R^c$ and $R^d$, together with the nitrogen atom to which they are attached, form 3- to 8-membered heterocyclyl or 5- to 8-membered heteroaryl, and wherein each of 3- to 8-membered heterocyclyl and 5- to 8-membered heteroaryl is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino.

In other embodiments, the invention relates to the compound having Formula (II), or a stereoisomer, a tautomer, an N-oxide, a solvate, a metabolite, a pharmaceutically acceptable salt or a prodrug thereof,

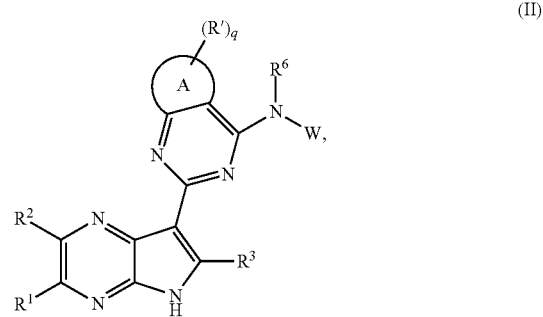

(II)

wherein A, $R^1$, $R^2$, $R^3$, $R^6$, R', q and W are as defined herein.

In other embodiments, A is a $C_{3-12}$ carbocyclic ring, 3- to 12-membered heterocyclic ring, $C_{6-10}$ aromatic ring or 5- to 10-membered heteroaromatic ring; and q is 0, 1, 2, 3, 4 or 5.

In other embodiments, each of $R^1$, $R^2$ and $R^3$ is independently H, D, F, Cl, Br, CN, $NO_2$, —C(=O)$R^a$, —C(=O)$OR^b$, —C(=O)$NR^cR^d$, $OR^b$, —$NR^cR^d$, methyl, ethyl, n-propyl or i-propyl; or, $R^1$ and $R^2$, together with the carbon atoms to which they are attached, form a $C_{5-6}$ carbocyclic ring, 5- to 6-membered heterocyclic ring, benzene ring or 5- to 6-membered heteroaromatic ring, and wherein each of methyl, ethyl, n-propyl, i-propyl, $C_{5-6}$ carbocyclic ring, 5- to 6-membered heterocyclic ring, benzene ring and 5- to 6-membered heteroaromatic ring is independently unsubstituted or substituted with 1, 2, 3 or 4 substituents independently selected from D, F, Cl, Br, CN, $OR^b$, —$NR^cR^d$ or $C_{1-3}$ haloalkyl.

In other embodiments, $R^4$ is $OR^b$, —$NR^cR^d$, $C_{2-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 8-membered heterocyclyl, (5- to 8-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{2-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 8-membered heterocyclyl, (5- to 8-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3, 4 or 5 R';

$R^5$ is H, D, F, Cl, Br, CN, $NO_2$, —C(=O)$R^a$, —C(=O)$OR^b$, —C(=O)$NR^cR^d$, $OR^b$, —$NR^cR^d$, $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with 1, 2, 3, 4 or 5 R';

or, $R^4$ and $R^5$, together with the carbon atoms to which they are attached, form a $C_{3-6}$ carbocyclic ring, 3- to 6-membered heterocyclic ring, $C_{6-10}$ aromatic ring or 5- to 6-membered heteroaromatic ring, and wherein each of $C_{3-6}$ carbocyclic ring, 3- to 6-membered heterocyclic ring, $C_{6-10}$ aromatic ring and 5- to 6-membered heteroaromatic ring is independently unsubstituted or substituted with 1, 2, 3, 4 or 5 R'.

In other embodiments, $R^4$ is $OR^b$, $-NR^cR^d$, $C_{2-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of $C_{2-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with 1, 2, 3, 4 or 5 R';

In other embodiments, each R' is independently D, F, Cl, Br, CN, $NO_2$, $OR^b$, $-NR^cR^d$, $R^a-C(=O)-O-C_{1-2}$ alkylene-$O-C_{1-2}$ alkylene, $R^bO-C(=O)-O-C_{1-2}$ alkylene-$O-C_{1-2}$ alkylene, $-C(=O)R^a$, $-C(=O)OR^b$, $-C(=O)NR^cR^d$, $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene and 5- to 10-membered heteroaryl, and wherein each of $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene and 5- to 10-membered heteroaryl is independently unsubstituted or substituted with 1, 2, 3 or 4 substituents independently selected from D, F, Cl, Br, CN, $NO_2$, $OR^b$, $-NR^cR^d$, methyl, ethyl, n-propyl or i-propyl.

In other embodiments, each R' is independently D, F, Cl, Br, CN, $NO_2$, $OR^b$, $-NR^cR^d$,

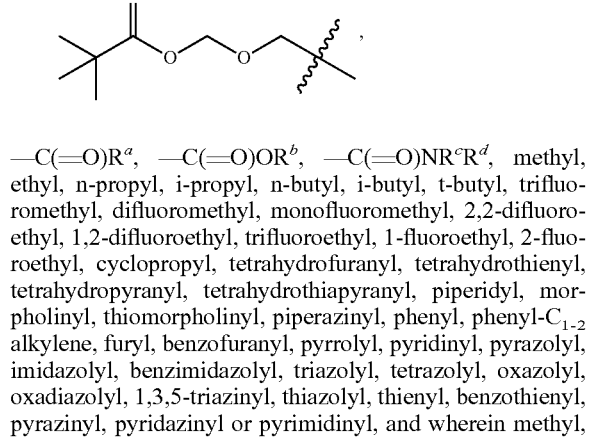

$-C(=O)R^a$, $-C(=O)OR^b$, $-C(=O)NR^cR^d$, methyl, ethyl, n-propyl, i-propyl, n-butyl, i-butyl, t-butyl, trifluoromethyl, difluoromethyl, monofluoromethyl, 2,2-difluoroethyl, 1,2-difluoroethyl, trifluoroethyl, 1-fluoroethyl, 2-fluoroethyl, cyclopropyl, tetrahydrofuranyl, tetrahydrothienyl, tetrahydropyranyl, tetrahydrothiapyranyl, piperidyl, morpholinyl, thiomorpholinyl, piperazinyl, phenyl, phenyl-$C_{1-2}$ alkylene, furyl, benzofuranyl, pyrrolyl, pyridinyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl or pyrimidinyl, and wherein methyl, ethyl, n-propyl, i-propyl, n-butyl, i-butyl, t-butyl, difluoromethyl, monofluoromethyl, 2,2-difluoroethyl, 1,2-difluoroethyl, trifluoroethyl, 1-fluoroethyl, 2-fluoroethyl, cyclopropyl, tetrahydrofuranyl, tetrahydrothienyl, tetrahydropyranyl, tetrahydrothiapyranyl, piperidyl, morpholinyl, thiomorpholinyl, piperazinyl, phenyl, phenyl-$C_{1-2}$ alkylene, furyl, benzofuranyl, pyrrolyl, pyridinyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl and pyrimidinyl is independently unsubstituted or substituted with 1, 2, 3 or 4 substituents independently selected from D, F, Cl, Br, CN, $NO_2$, OH, $-NH_2$, methyl, ethyl, n-propyl or i-propyl.

In other embodiments, $R^6$ is H, D, $CF_3$, methyl, ethyl, n-propyl or i-propyl.

In other embodiments, W is $C_{1-6}$ alkyl, $C_{5-8}$ carbocyclyl or 5- to 8-membered heterocyclyl, and wherein each of $C_{1-6}$ alkyl, $C_{5-8}$ carbocyclyl and 5- to 8-membered heterocyclyl is independently unsubstituted or substituted with 1, 2, 3 or 4 $R^w$.

In other embodiments, $R^w$ is D, F, Cl, Br, CN, $NO_2$, oxo (=O), $-C(=O)OCH_3$, $-C(=O)OCH_2CH_3$, $-C(=O)OCH_2CH_2CH_2CH_3$, $-C(=O)O(CH_2)_6CH_3$, $-C(=O)OH$,

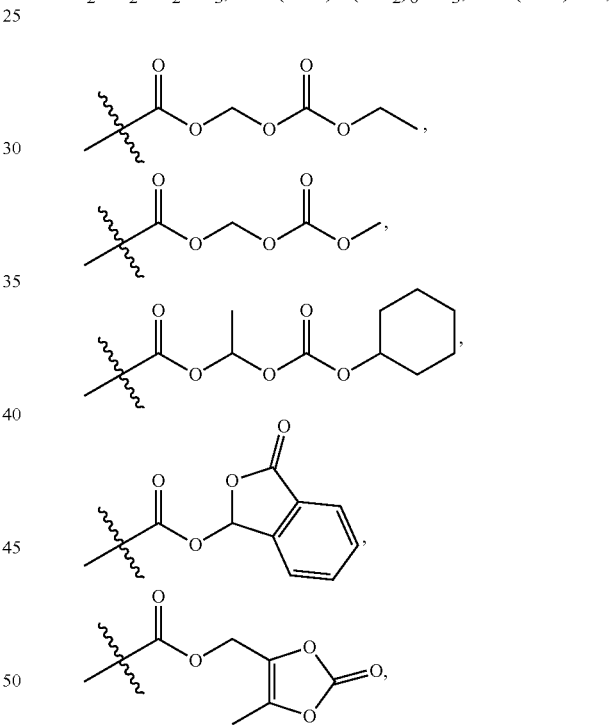

$-C(=O)NR^cR^d$, $-NHC(=O)R^a$, $-NHC(=O)NR^cR^d$, $-S(=O)_2R^f$, $-S(=O)_2NHC(=O)R^a$, $-S(=O)_2NR^cR^d$, $(R^bO)_2P(=O)-C_{0-2}$ alkylene, $OR^b$, methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl, pyrimidyl or 5- to 6-membered heterocyclyl, and wherein each of methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl, pyrimidyl and 5- to 6-membered heterocyclyl is independently unsubstituted or substituted with 1, 2, 3 or 4 substituents independently selected from D, F, Cl, Br, CN, $N_3$, oxo (=O), $NO_2$, $-OCH_3$, $C_{1-3}$ alkyl or $C_{1-3}$ haloalkyl.

In other embodiments, each $R^a$, $R^b$, $R^c$, $R^d$, $R^e$ and $R^f$ is independently H, D, hydroxy, trifluoromethyl, methyl, ethyl, i-propyl, n-propyl, n-butyl, t-butyl, n-pentyl, n-hexyl, n-heptyl, methoxy, ethoxy, $C_{3-6}$ carbocyclyl, 5- to 6-membered heterocyclyl, phenyl, 5- to 10-membered heteroaryl or (5- to 10-membered heteroaryl)-$C_{1-4}$ alkylene, and wherein each of methyl, ethyl, i-propyl, n-propyl, n-butyl, t-butyl, n-pentyl, n-hexyl, n-heptyl, methoxy, ethoxy, $C_{3-6}$ carbocyclyl, 5- to 6-membered heterocyclyl, phenyl, 5- to 10-membered heteroaryl and (5- to 10-membered heteroaryl)-$C_{1-4}$ alkylene is independently unsubstituted or substituted with 1, 2, 3 or 4 substituents independently selected from D, F, Cl, CN, OH, $NH_2$, $C_{1-3}$ alkyl, $C_{1-3}$ haloalkyl or methoxy;

or, $R^c$ and $R^d$, together with the nitrogen atom to which they are attached, form 5- to 6-membered heterocyclyl or 5- to 6-membered heteroaryl, and wherein each of 5- to 6-membered heterocyclyl and 5- to 6-membered heteroaryl is independently unsubstituted or substituted with 1, 2, 3 or 4 substituents independently selected from D, F, Cl, CN, OH, $NH_2$, $C_{1-3}$ alkyl, $C_{1-3}$ haloalkyl, $C_{1-3}$ alkoxy or methoxy.

In other embodiments, A is a $C_{3-6}$ carbocyclic ring, 3- to 6-membered heterocyclic ring, $C_{6-10}$ aromatic ring or 5- to 6-membered heteroaromatic ring.

In other embodiments, $R^4$ is $OR^b$, —$NR^cR^d$, ethynyl, propinyl, $C_{3-6}$ carbocyclyl, pyrrolidinyl, pyrazolidinyl, imidazolidinyl, tetrahydrofuryl, tetrahydrothienyl, tetrahydropyranyl, tetrahydrothiopyranyl, tetrahydroisoquinolyl, piperidinyl, morpholinyl, thiomorpholinyl, piperazinyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thiadiazolyl, thienyl, benzothienyl, pyrazinyl, pyridazinyl, pyrimidinyl, indolyl, purinyl, quinolyl, isoquinolyl, phenoxathiinyl,

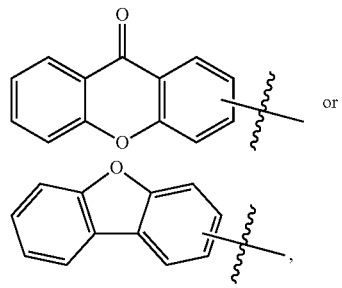

and wherein each of ethynyl, propinyl, $C_{3-6}$ carbocyclyl, pyrrolidinyl, pyrazolidinyl, imidazolidinyl, tetrahydrofuryl, tetrahydrothienyl, tetrahydropyranyl, tetrahydrothiopyranyl, tetrahydroisoquinolyl, piperidinyl, morpholinyl, thiomorpholinyl, piperazinyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thiadiazolyl, thienyl, benzothienyl, pyrazinyl, pyridazinyl, pyrimidinyl, indolyl, purinyl, quinolyl, isoquinolyl, phenoxathiinyl, is

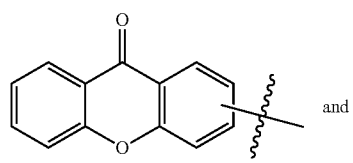

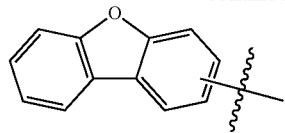

independently unsubstituted or substituted with 1, 2, 3, 4 or 5 R';

$R^5$ is H, D, F, Cl, Br, CN, $NO_2$, methyl, ethyl or i-propyl;

or, $R^4$ and $R^5$, together with the carbon atoms to which they are attached, form a $C_{3-6}$ carbocyclic ring, 3- to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline, and wherein each of $C_{3-6}$ carbocyclic ring, 3- to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline and isoquinoline is independently unsubstituted or substituted with 1, 2, 3, 4 or 5 R'.

In other embodiments, A is a $C_{3-6}$ carbocyclic ring, 3- to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline.

In other embodiments, W is one of the following subformulae:

(W-1)

(W-2)

(W-3)

(W-4)

-continued

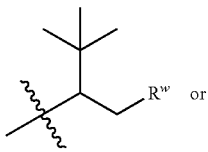 (W-5)

or

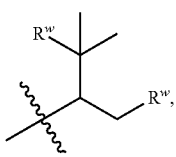 (W-6)

wherein n and R$^w$ are as defined herein.

In other embodiments, n is 0, 1, 2, 3 or 4.

In other embodiments, the invention relates to the compound having Formula (III) or a stereoisomer, a tautomer, an N-oxide, a solvate, a metabolite, a pharmaceutically acceptable salt or a prodrug thereof,

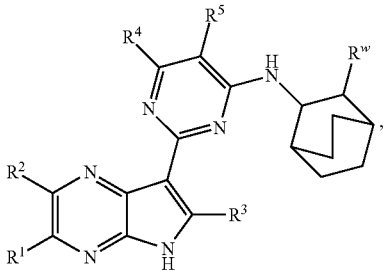 (III)

wherein R$^1$, R$^2$, R$^3$, R$^4$, R$^5$ and R$^w$ are as defined herein.

In other embodiments, the invention relates to the compound having Formula (IV) or a stereoisomer, a tautomer, an N-oxide, a solvate, a metabolite, a pharmaceutically acceptable salt or a prodrug thereof,

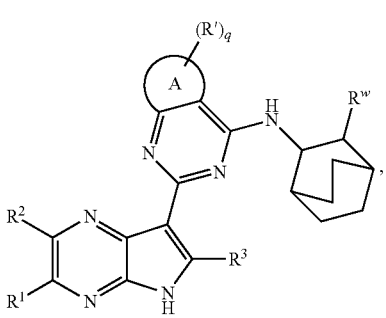 (IV)

wherein A, R$^1$, R$^2$, R$^3$, R', q and R$^w$ are as defined herein.

In other embodiments, the invention relates to the compound having Formula (V) or a stereoisomer, a tautomer, an N-oxide, a solvate, a metabolite, a pharmaceutically acceptable salt or a prodrug thereof,

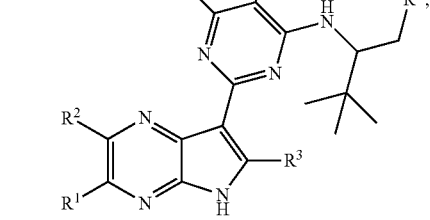 (V)

wherein R$^1$, R$^2$, R$^3$, R$^4$, R$^5$ and R$^w$ are as defined herein.

In other embodiments, the invention relates to the compound having Formula (VI) or a stereoisomer, a tautomer, an N-oxide, a solvate, a metabolite, a pharmaceutically acceptable salt or a prodrug thereof,

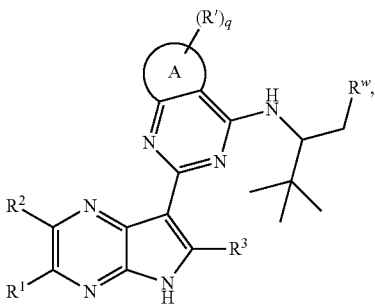 (VI)

wherein A, R$^1$, R$^2$, R$^3$, R', q and R$^w$ are as defined herein.

In other embodiments, the invention relates to the compound having Formula (VII) or a stereoisomer, a tautomer, an N-oxide, a solvate, a metabolite, a pharmaceutically acceptable salt or a prodrug thereof,

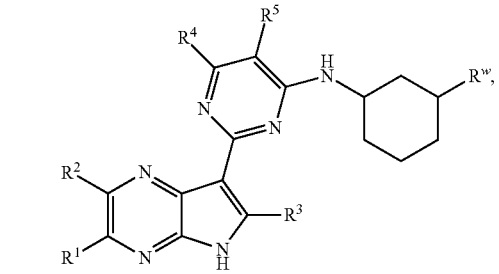 (VII)

wherein R$^1$, R$^2$, R$^3$, R$^4$, R$^5$ and R$^w$ are as defined herein.

In other embodiments, the invention relates to the compound having Formula (VIII) or a stereoisomer, a tautomer, an N-oxide, a solvate, a metabolite, a pharmaceutically acceptable salt or a prodrug thereof,

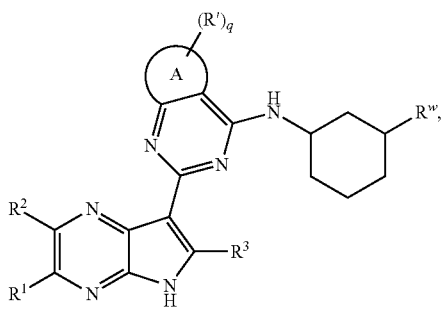

(VIII)

wherein A, $R^1$, $R^2$, $R^3$, R', q and $R^w$ are as defined herein.

In other embodiments, the invention relates to the compound having Formula (IX) or a stereoisomer, a tautomer, an N-oxide, a solvate, a metabolite, a pharmaceutically acceptable salt or a prodrug thereof,

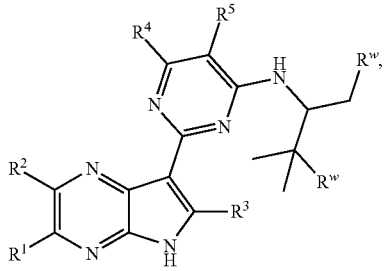

(IX)

wherein $R^1$, $R^2$, $R^3$, $R^4$, $R^5$ and $R^w$ are as defined herein.

In other embodiments, the invention relates to the compound having Formula (X) or a stereoisomer, a tautomer, an N-oxide, a solvate, a metabolite, a pharmaceutically acceptable salt or a prodrug thereof,

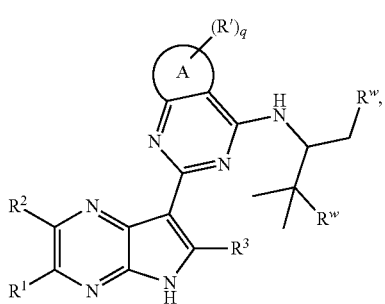

(X)

wherein A, $R^1$, $R^2$, $R^3$, R', q and $R^w$ are as defined herein.

In other embodiments, the invention relates to the compound having Formula (XI) or a stereoisomer, a tautomer, an N-oxide, a solvate, a metabolite, a pharmaceutically acceptable salt or a prodrug thereof,

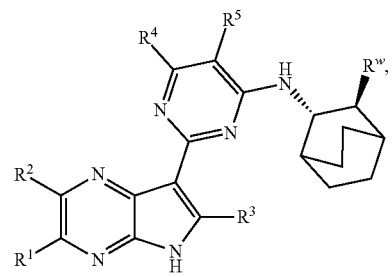

(XI)

wherein $R^1$, $R^2$, $R^3$, $R^4$, $R^5$ and $R^w$ are as defined herein.

In other embodiments, the invention relates to the compound having Formula (XII) or a stereoisomer, a tautomer, an N-oxide, a solvate, a metabolite, a pharmaceutically acceptable salt or a prodrug thereof,

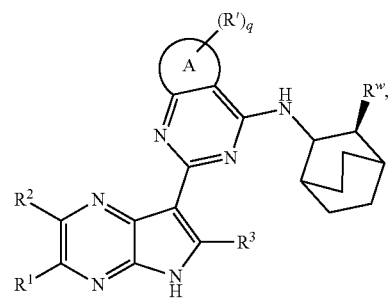

(XII)

wherein A, $R^1$, $R^2$, $R^3$, R', q and $R^w$ are as defined herein.

In other embodiments, the invention relates to the compound having Formula (XIII) or a stereoisomer, a tautomer, an N-oxide, a solvate, a metabolite, a pharmaceutically acceptable salt or a prodrug thereof,

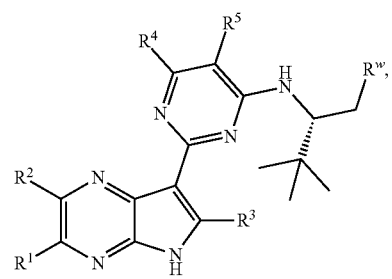

(XIII)

wherein $R^1$, $R^2$, $R^3$, $R^4$, $R^5$ and $R^w$ are as defined herein.

In other embodiments, the invention relates to the compound having Formula (XIV) or a stereoisomer, a tautomer, an N-oxide, a solvate, a metabolite, a pharmaceutically acceptable salt or a prodrug thereof,

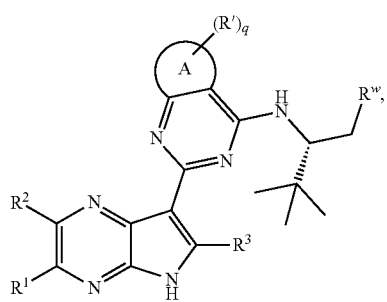
(XIV)
wherein A, R$^1$, R$^2$, R$^3$, R', q and R$^w$ are as defined herein.
In other embodiments, the invention relates to one of the following compounds, or a stereoisomer, a tautomer, an N-oxide, a solvate, a metabolite, a pharmaceutically acceptable salt or a prodrug thereof, but is not limited to,
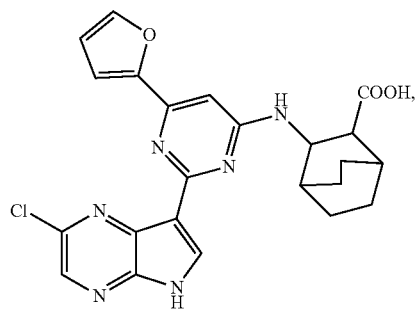
(1)
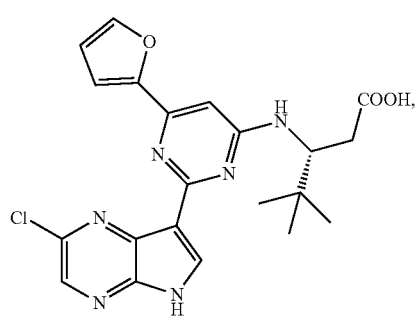
(2)
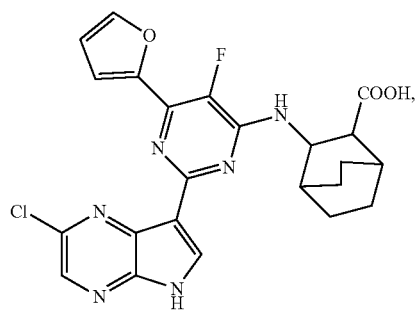
(3)
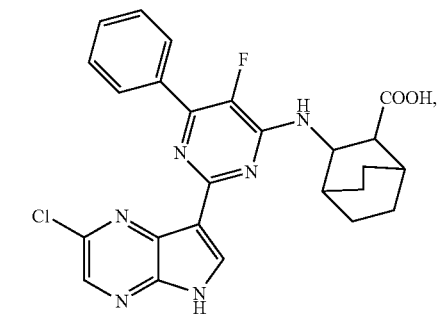
(4)
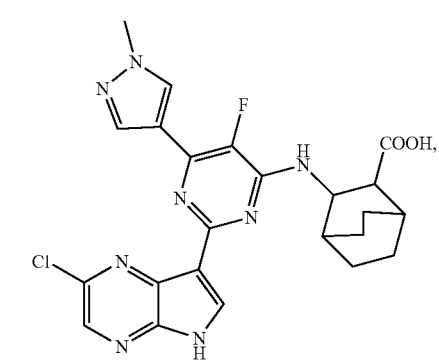
(5)
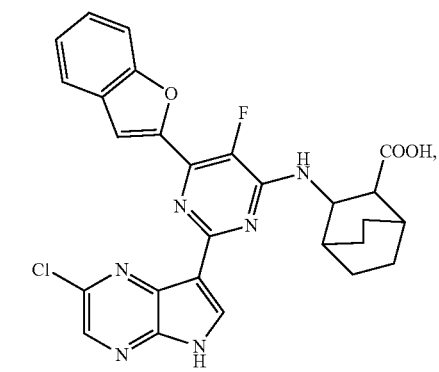
(6)
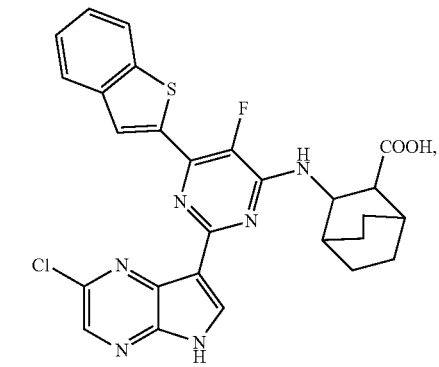
(7)

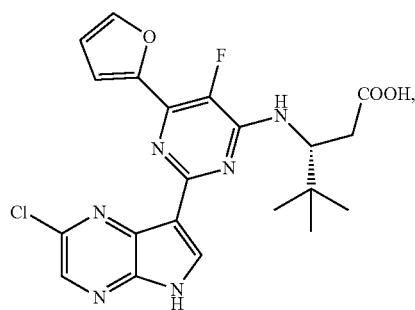
(8)
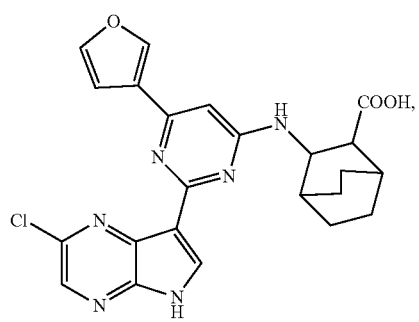
(9)
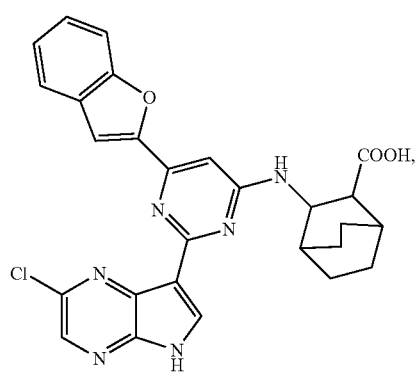
(10)
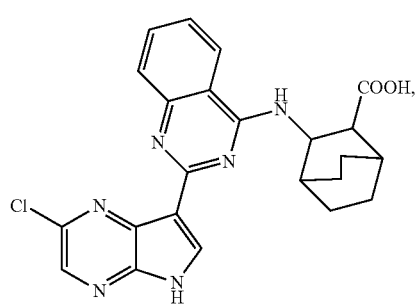
(11)
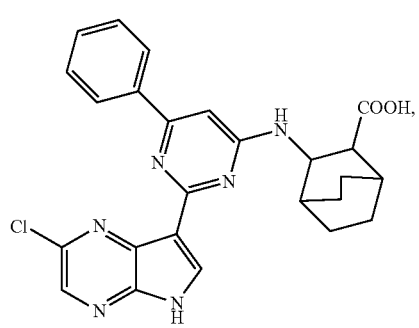
(12)
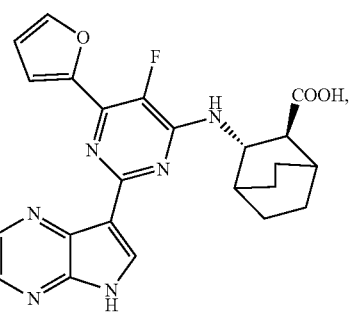
(13)
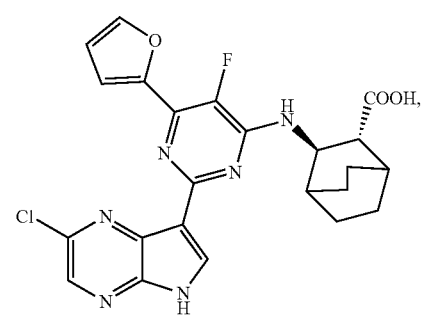
(14)
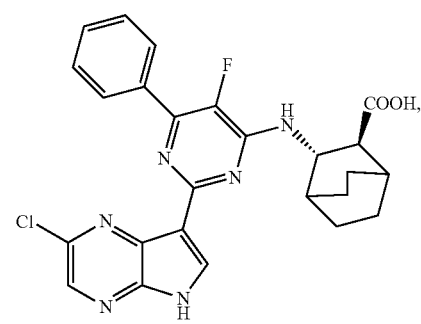
(15)
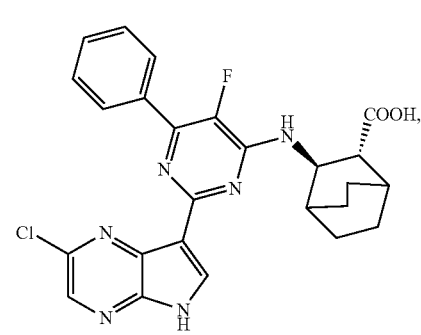
(16)
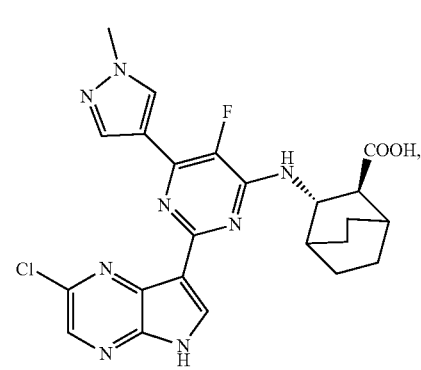
(17)

-continued
(18)
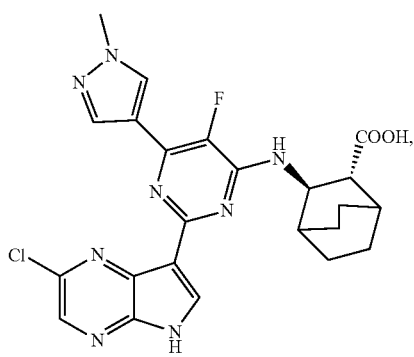
(19)
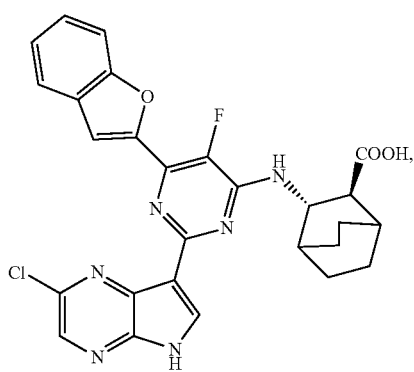
(20)
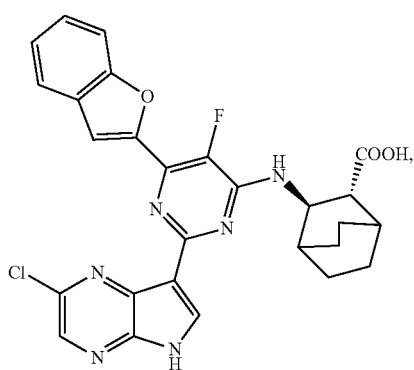
(21)
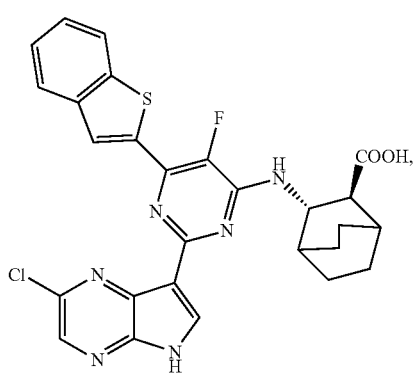
-continued
(22)
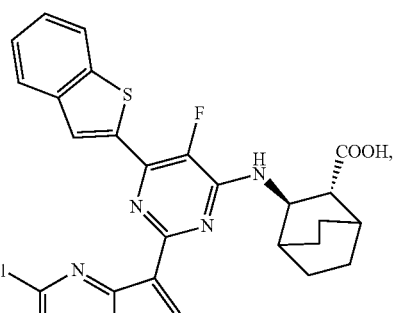
(23)
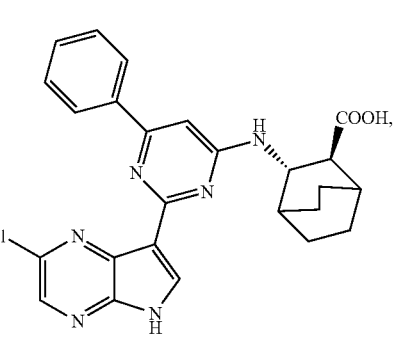
(24)
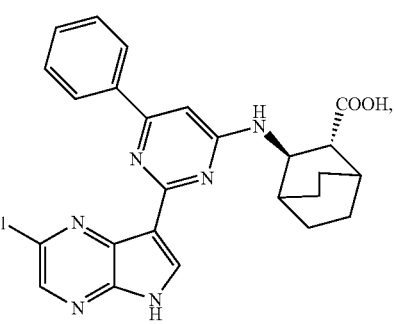
(25)
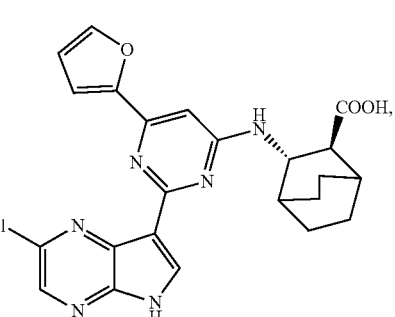
(26)
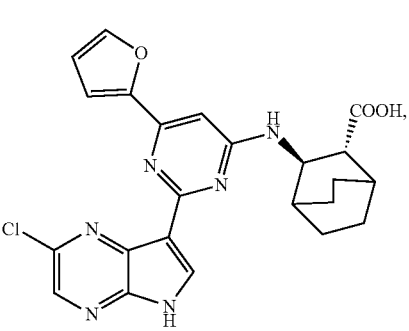

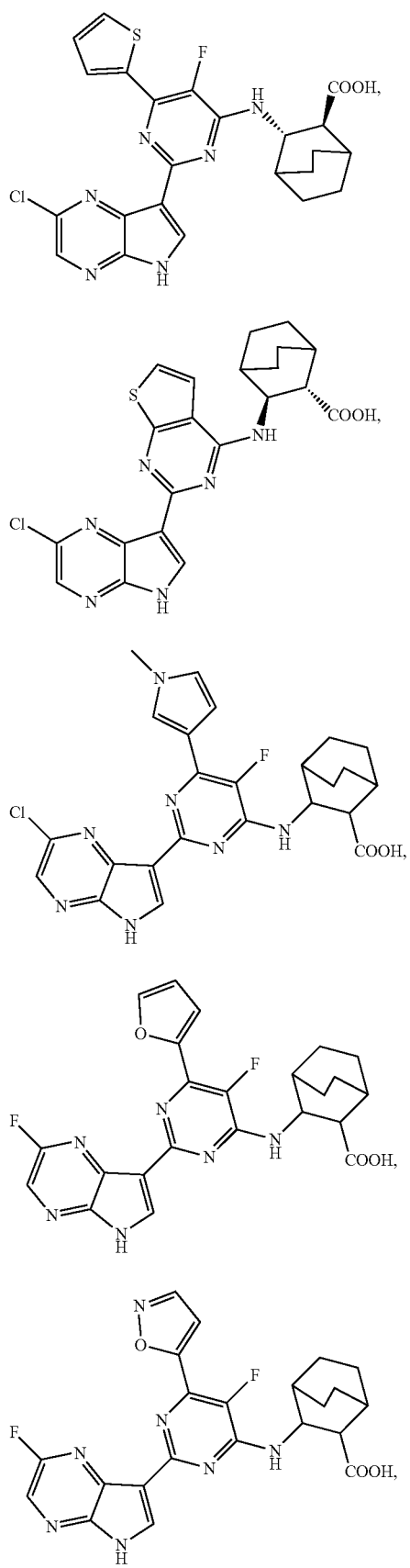
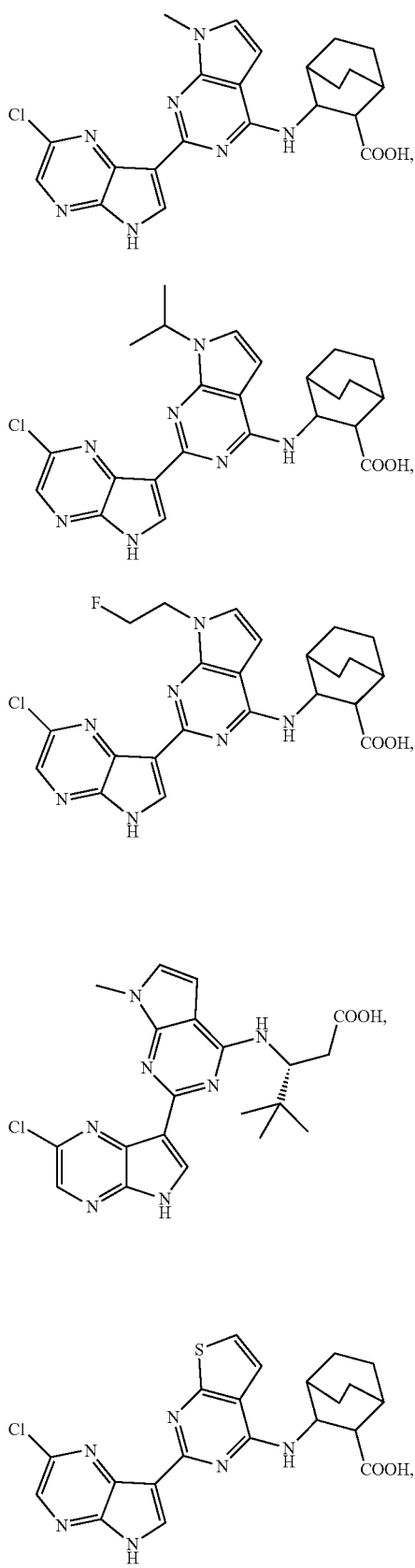

(37)
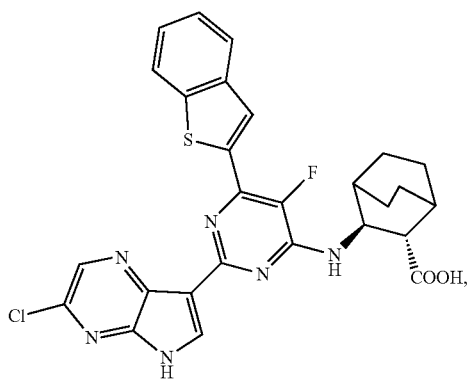
(38)
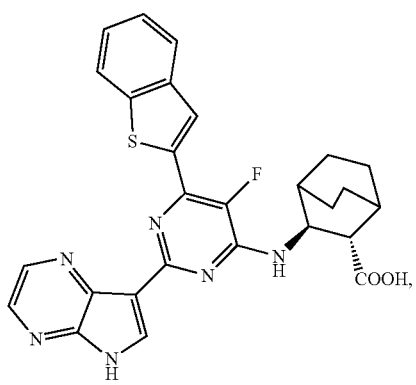
(39)
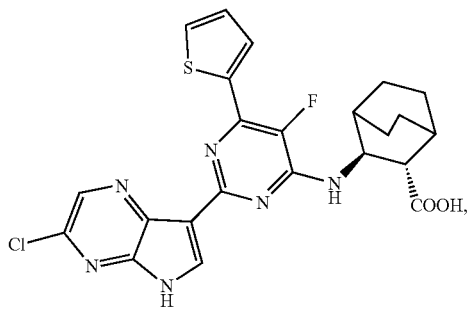
(40)
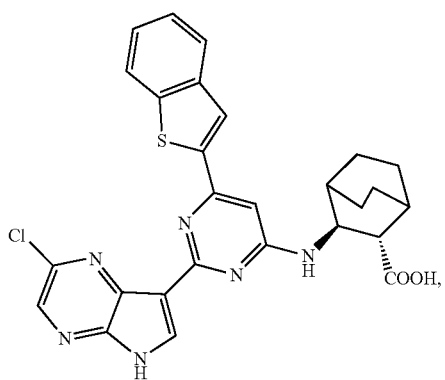
(41)
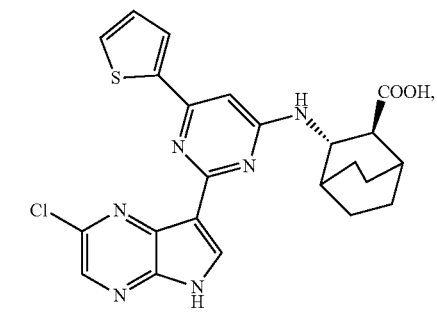
(42)
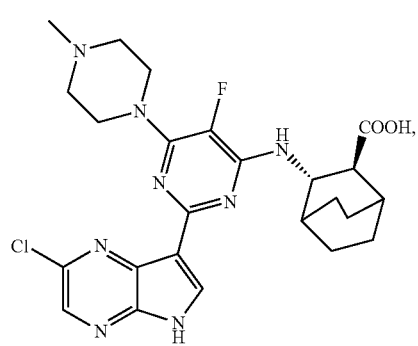
(43)
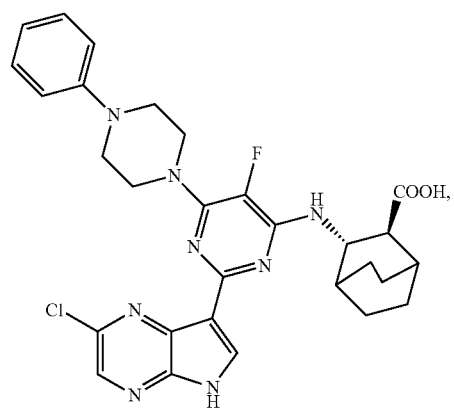
(44)
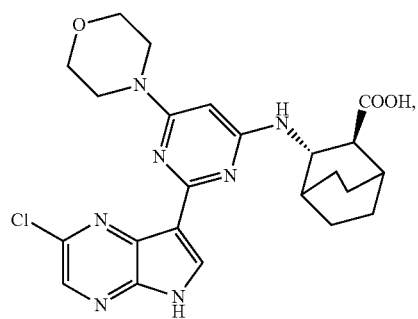

-continued
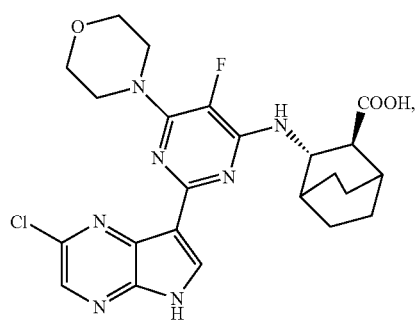
(45)
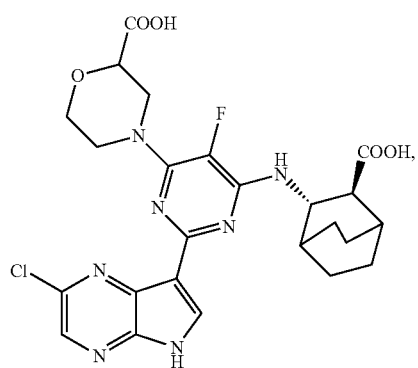
(46)
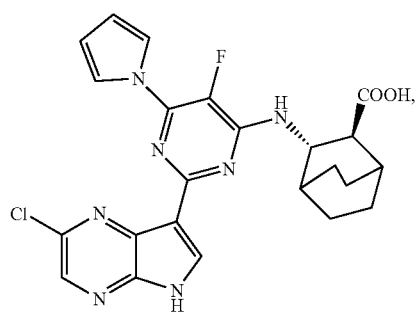
(47)
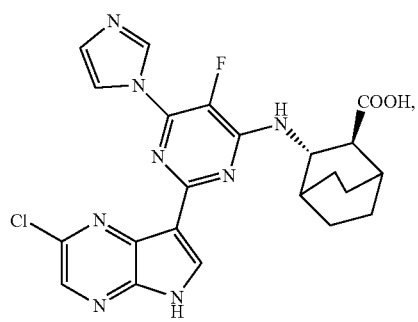
(48)
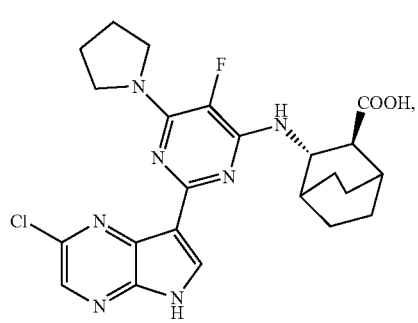
(49)
-continued
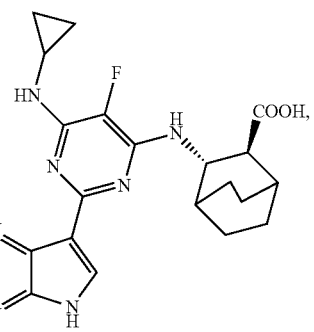
(50)
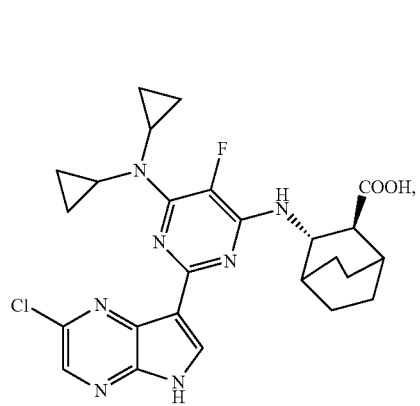
(51)
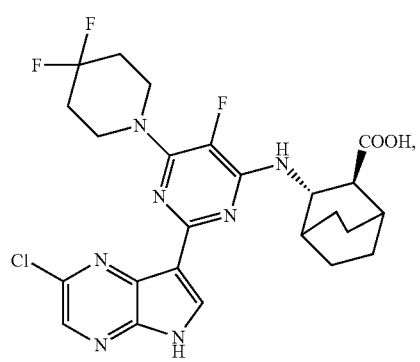
(52)
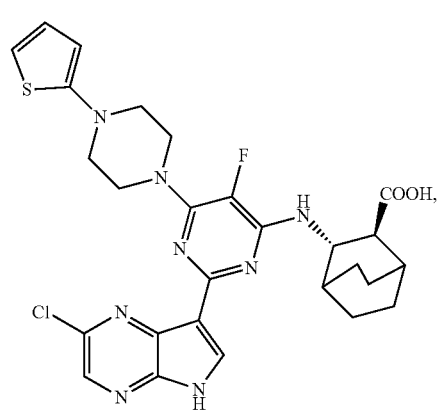
(53)

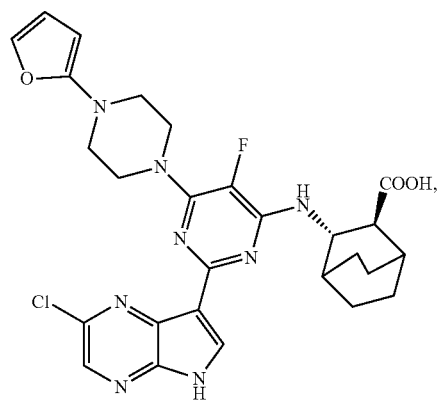
(54)
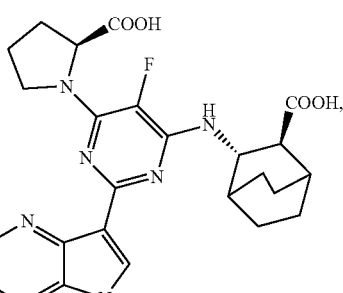
(55)
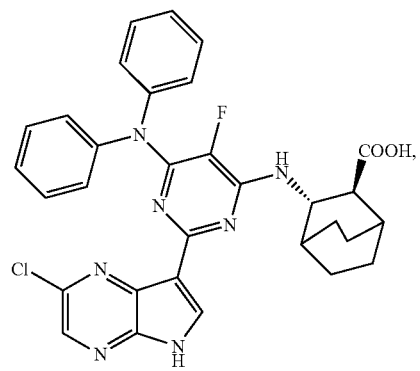
(56)
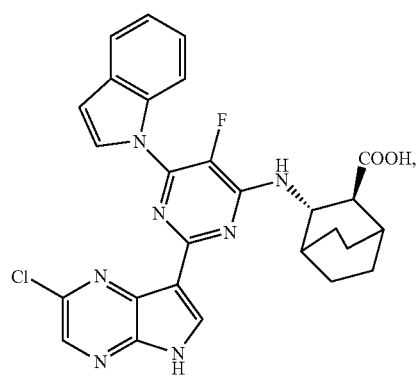
(57)
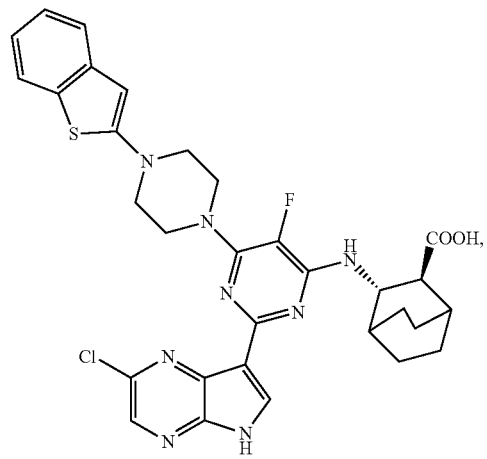
(58)
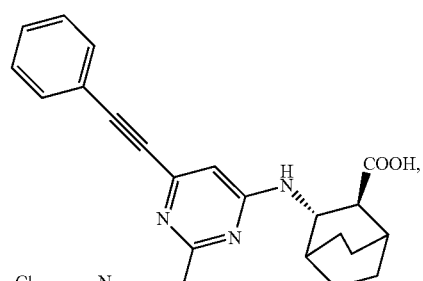
(59)
(60)
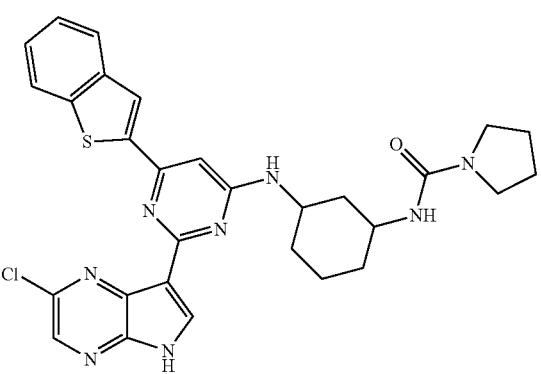
(61)

55
-continued
(62)
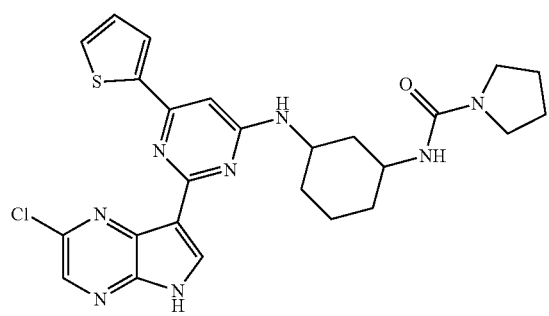
(63)
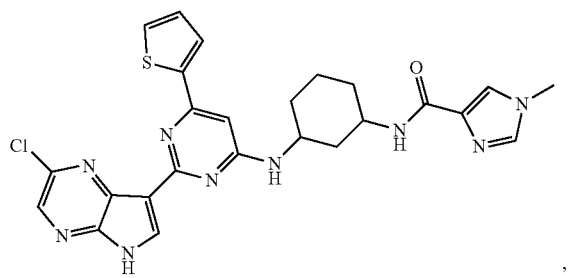
(64)
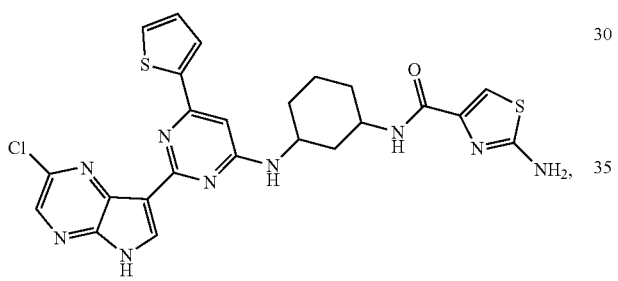
(65)
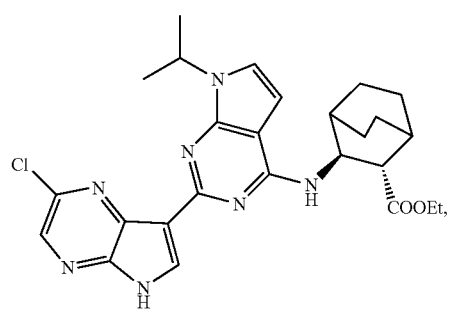
(66)
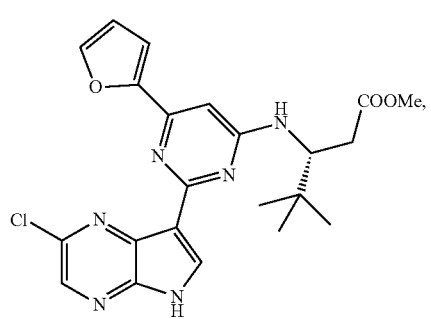
56
-continued
(67)
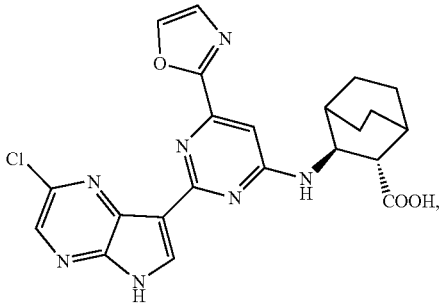
(68)
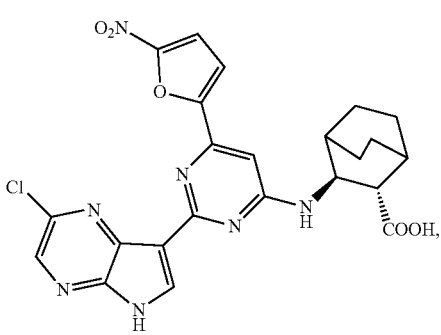
(69)
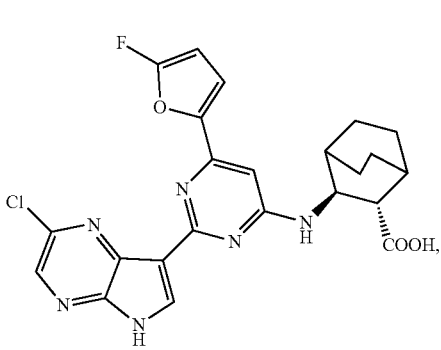
(70)
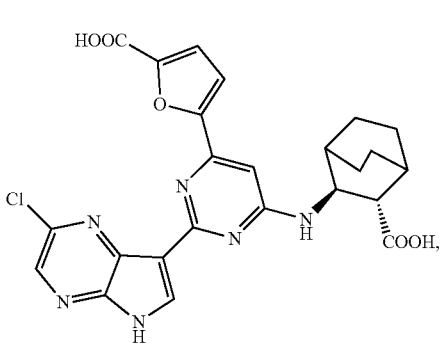
(71)
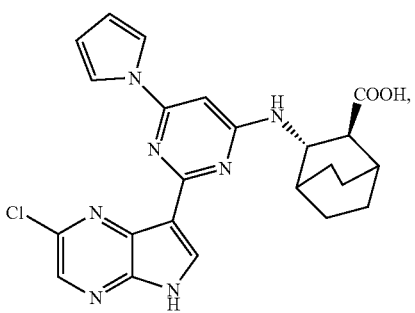

(72), (73), (74), (75), (76), (77), (78), (79), (80), (81)

(82)
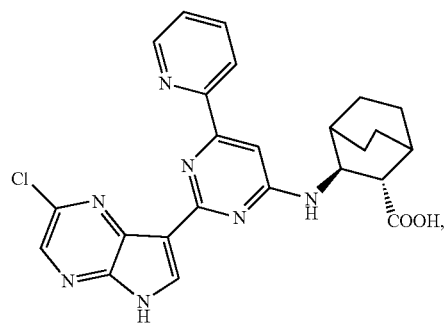
(83)
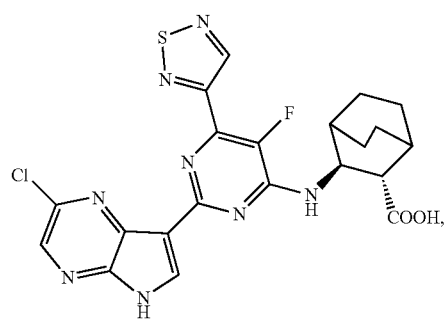
(84)
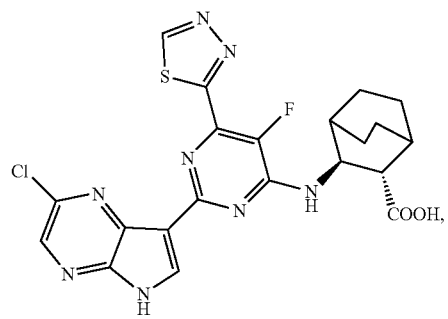
(85)
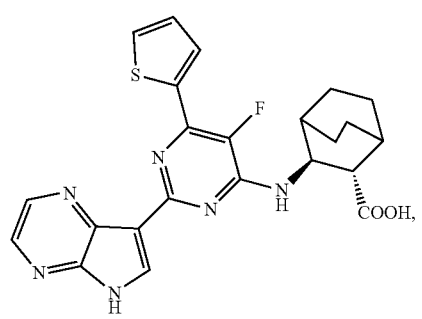
(86)
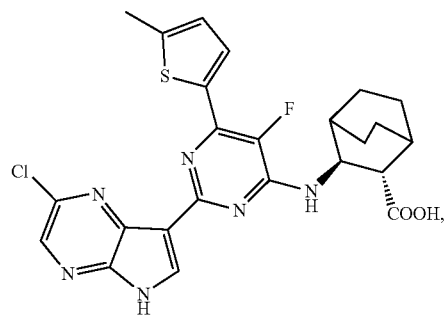
(87)
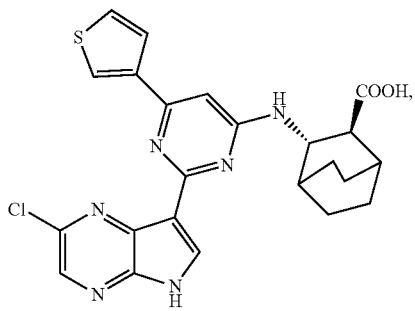
(88)
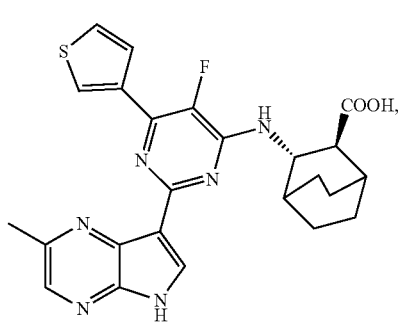
(89)
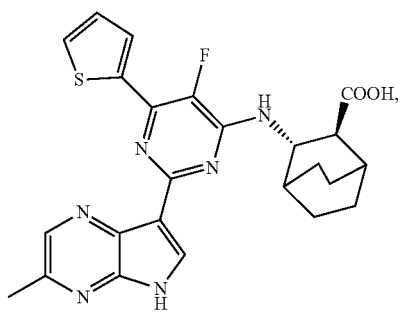
(90)
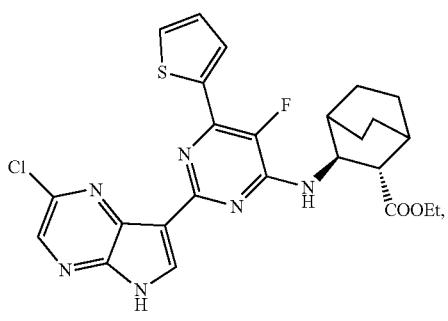
(91)
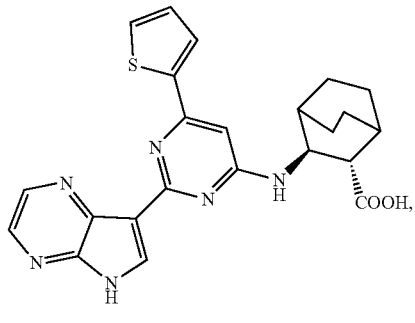

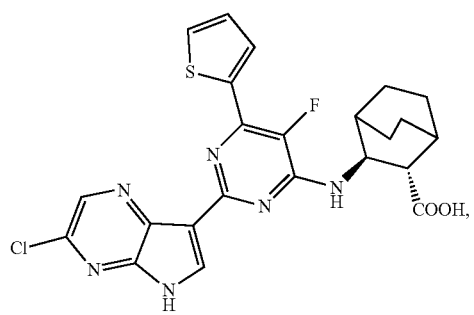
(92)
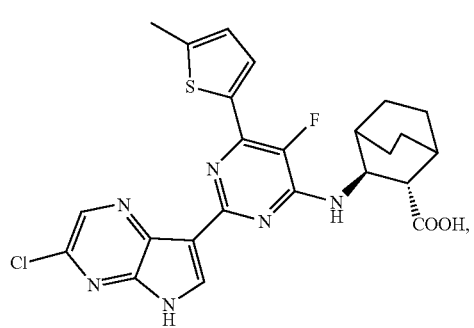
(93)
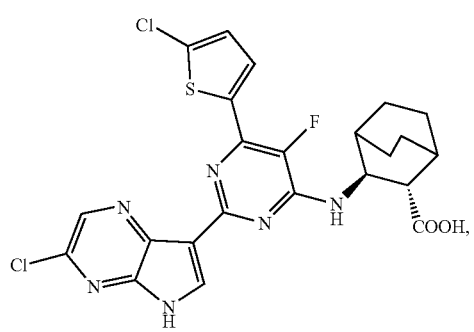
(94)
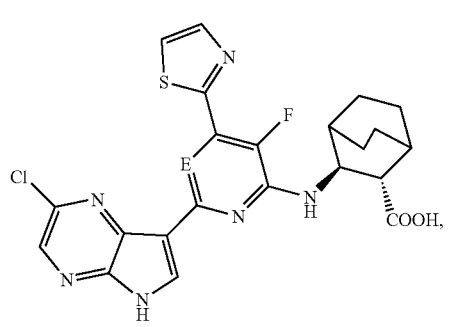
(95)
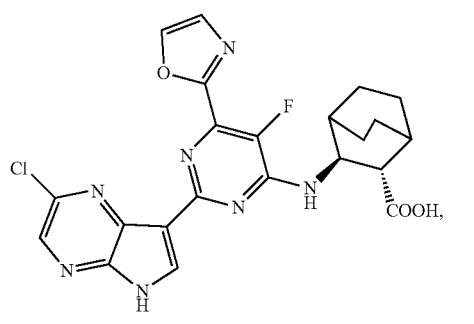
(96)
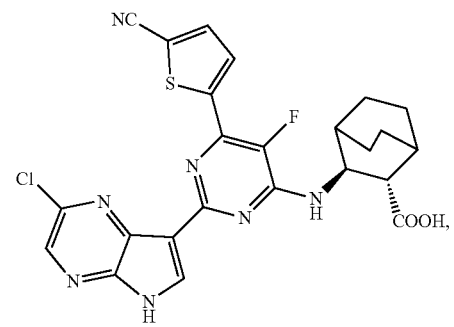
(97)
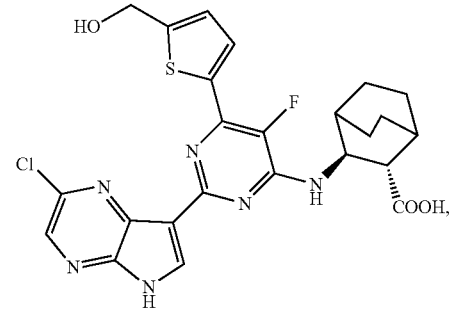
(98)
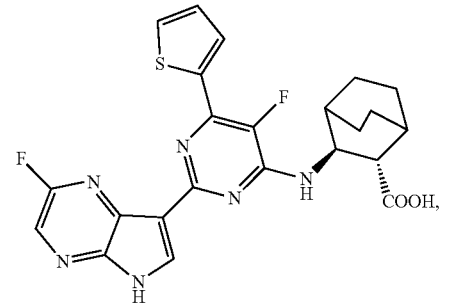
(99)
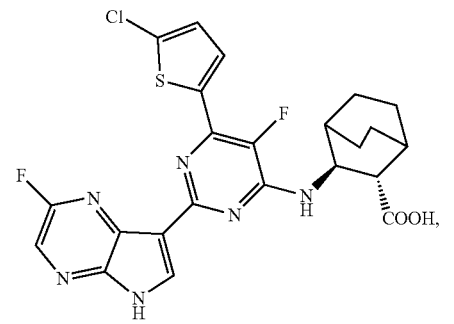
(100)
(101)

(102)
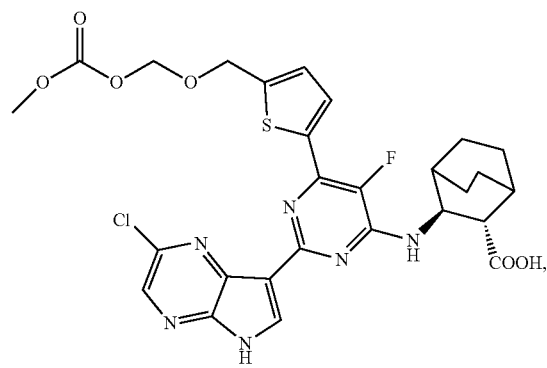
(103)
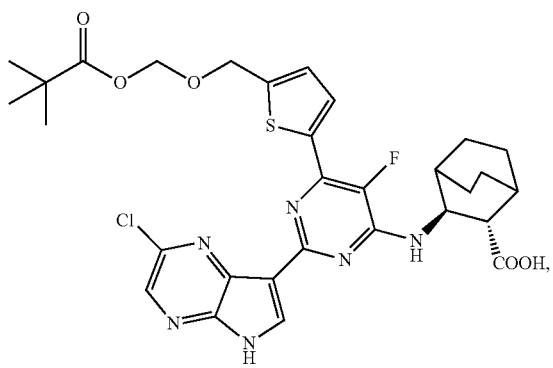
(104)
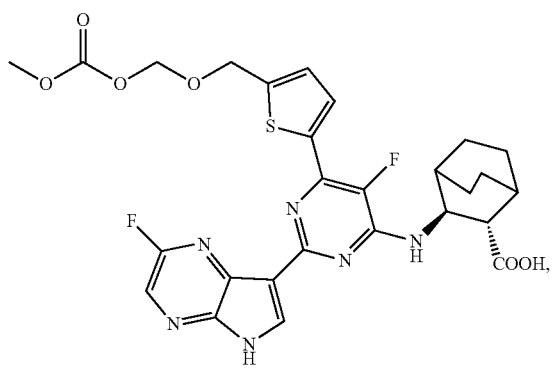
(105)
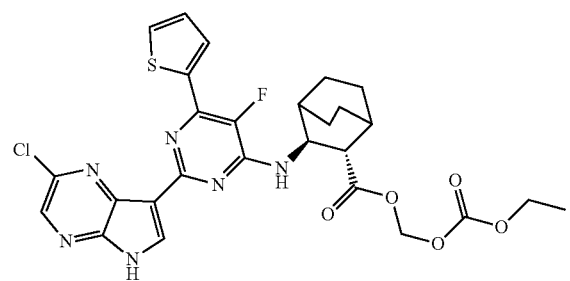
(106)
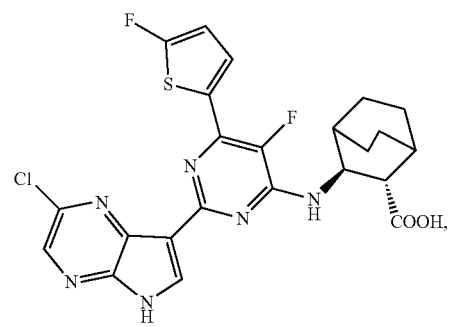
(107)
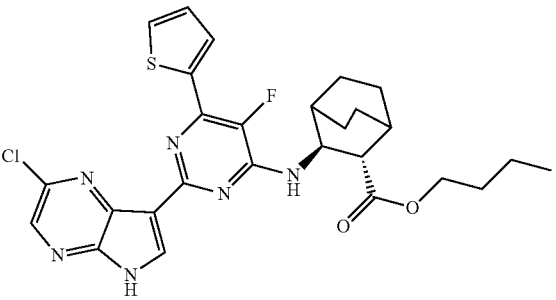
(108)
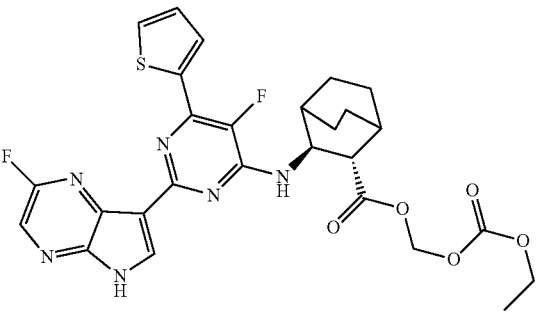
(109)
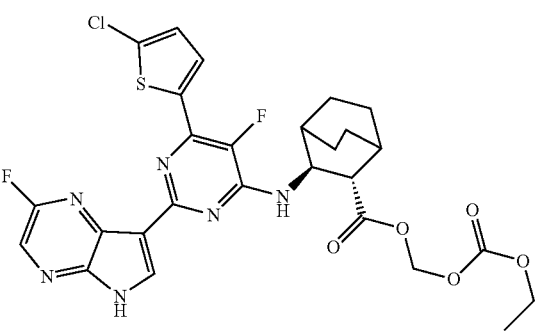

-continued
(110)
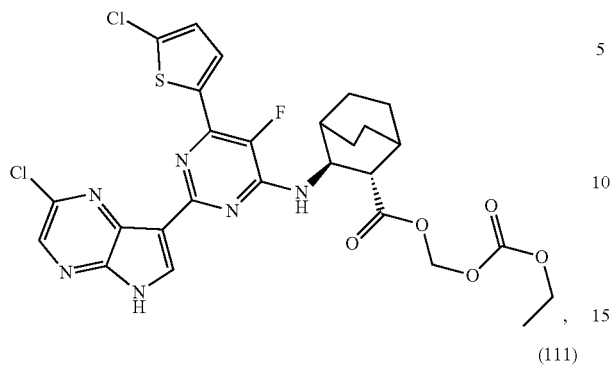
(111)
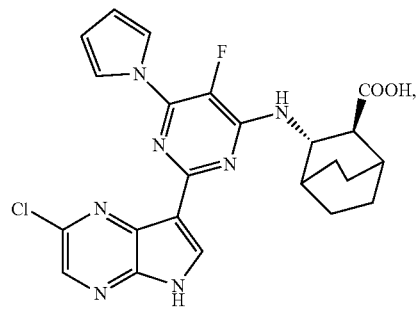
(112)
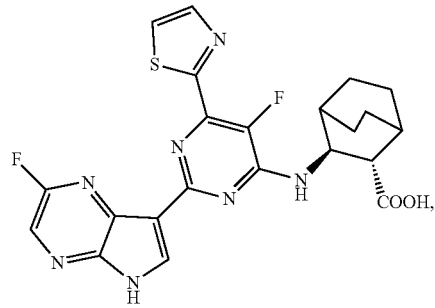
(113)
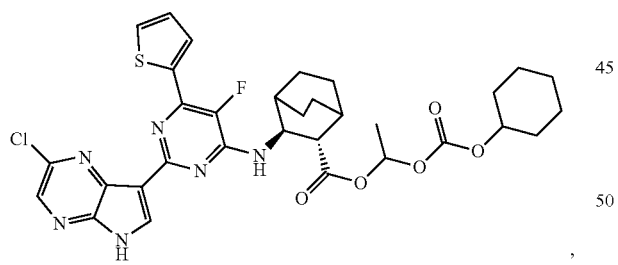
(114)
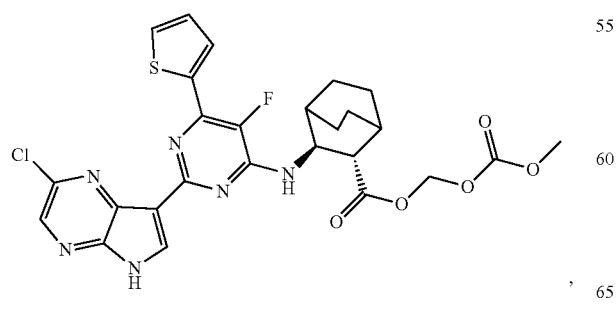
-continued
(115)
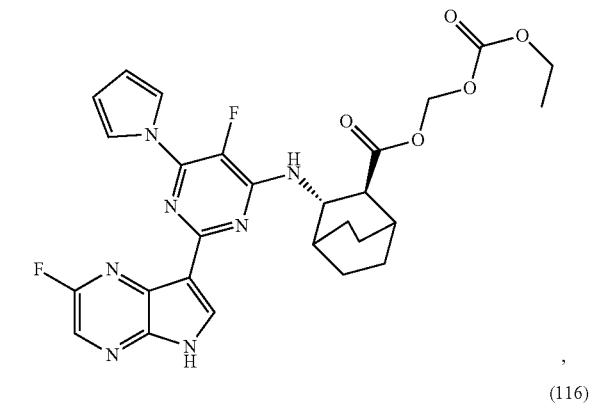
(116)
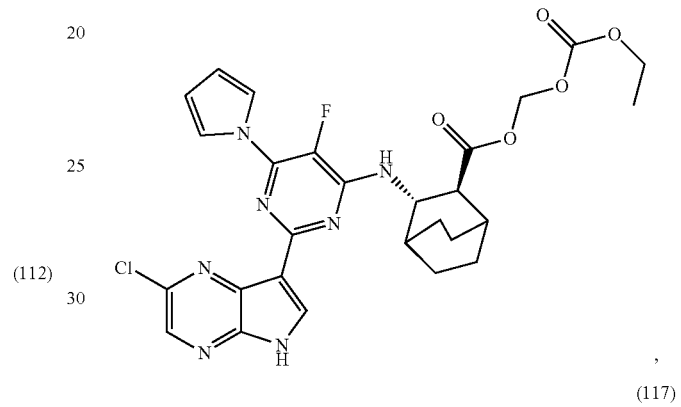
(117)
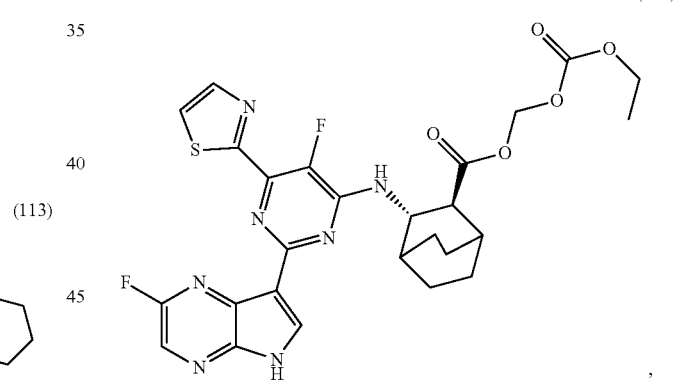
(118)
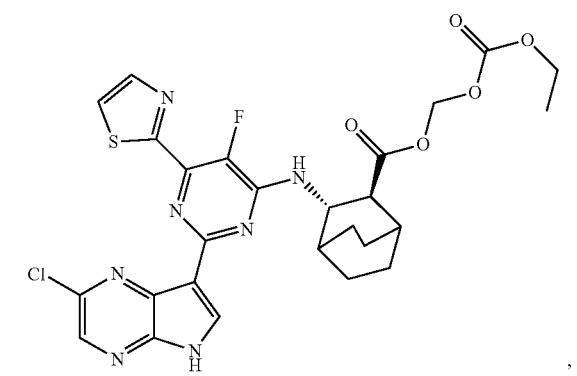

(119) 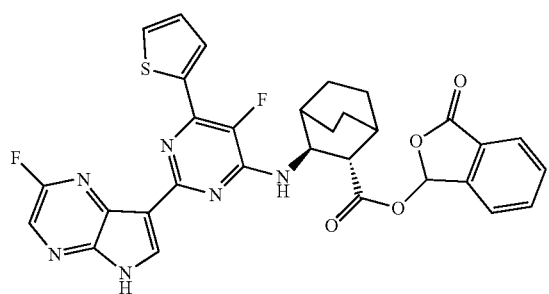
,
(120) 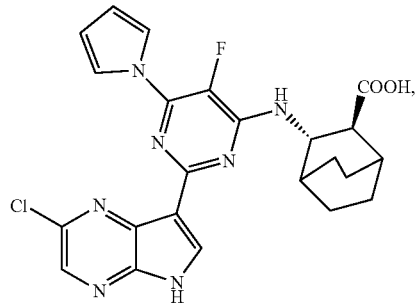
,
(121) 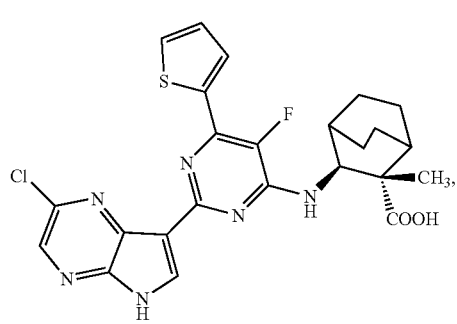
,
(122) 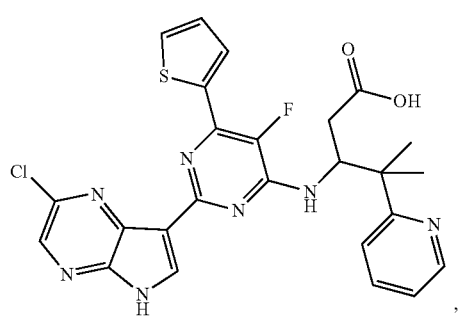
,
(123) 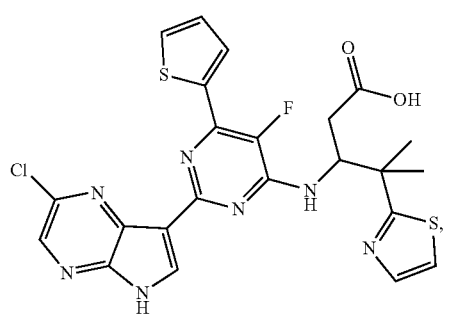
,
(124) 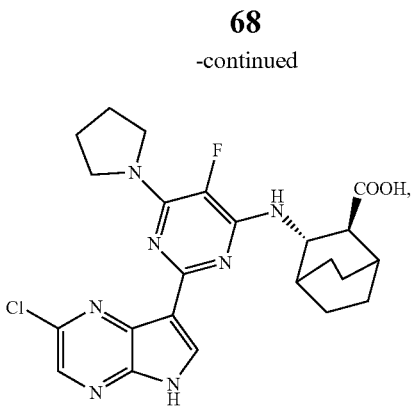
,
(125) 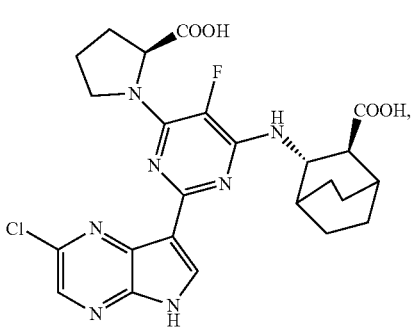
,
(126) 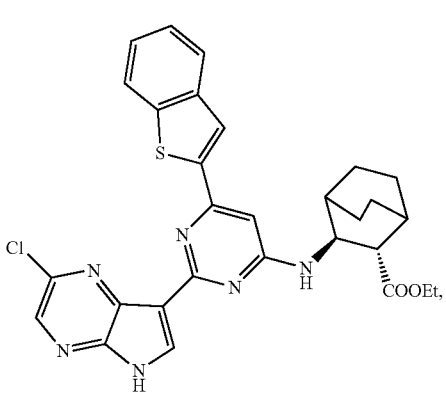
,
(127) 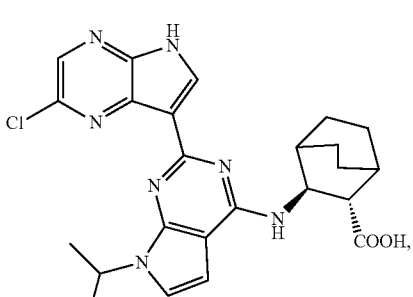
,
(128) 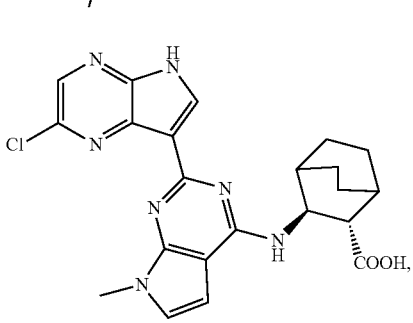
, (129)
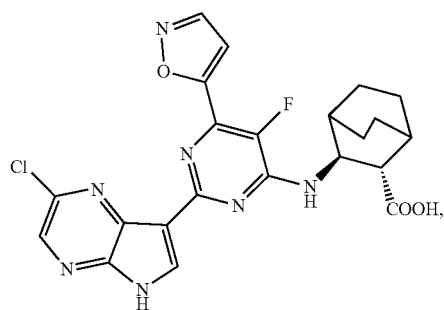
(130)
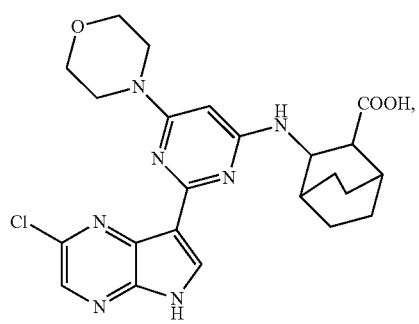
(131)
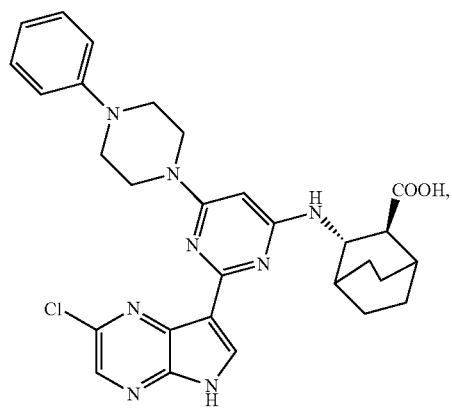
(132)
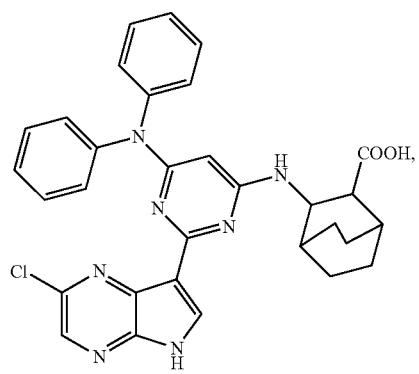
(133)
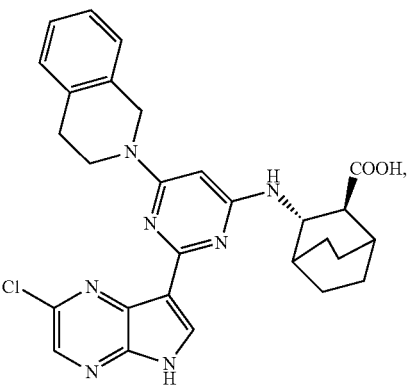
(134)
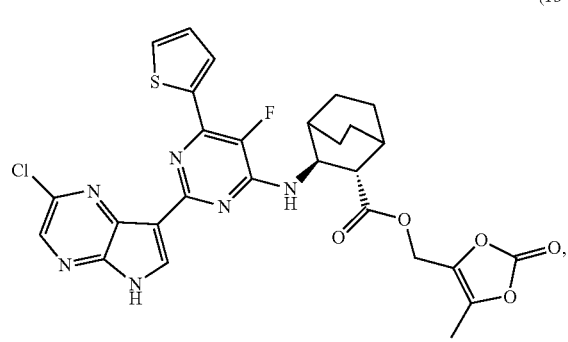
(135)
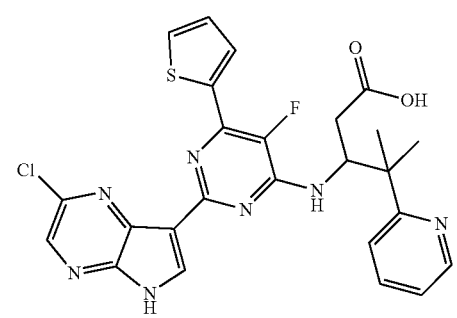
(136)
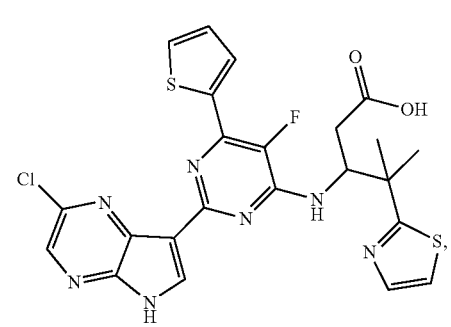

-continued (137) 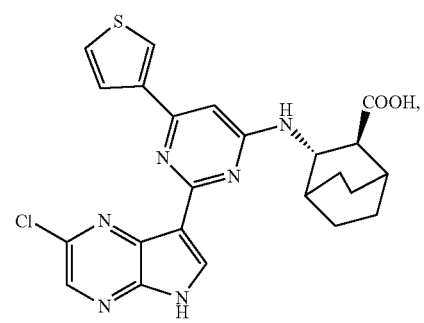

(138) 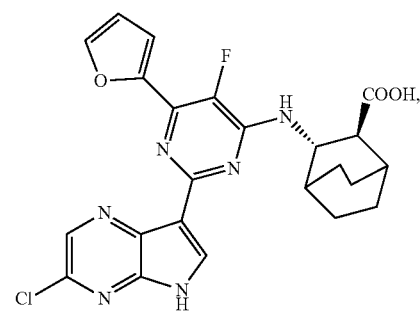

(139) 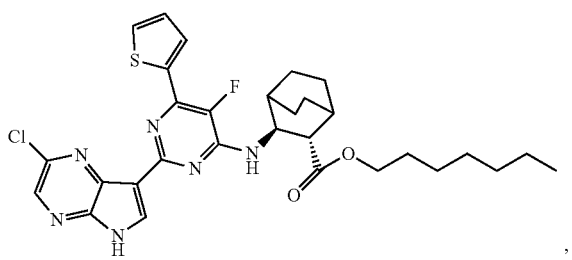

(140) 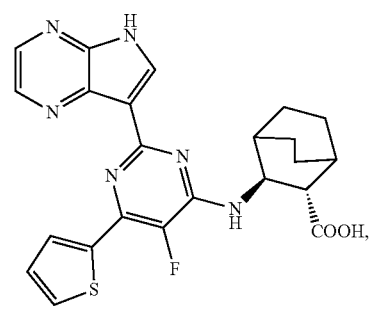

, (141) 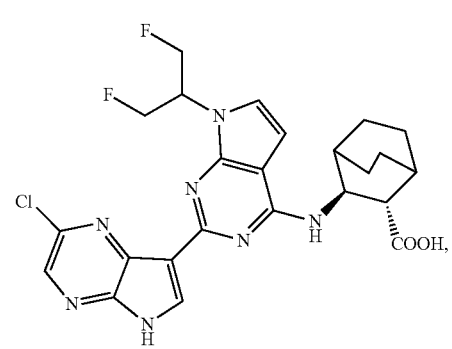

-continued (142) 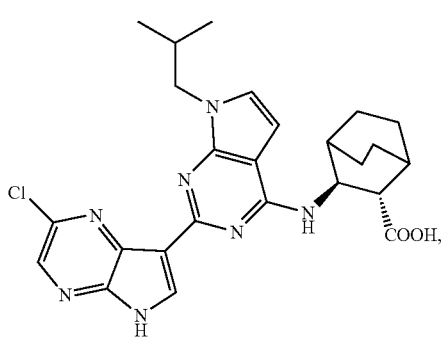

(143) 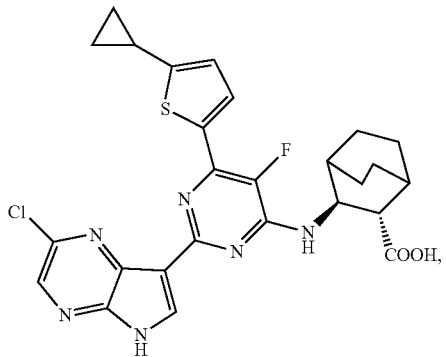

(144) 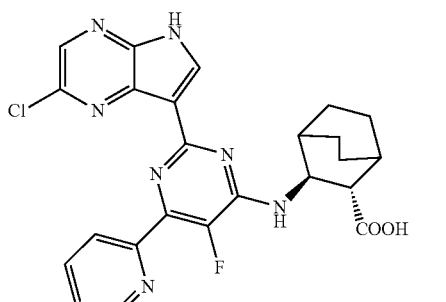

or (145) 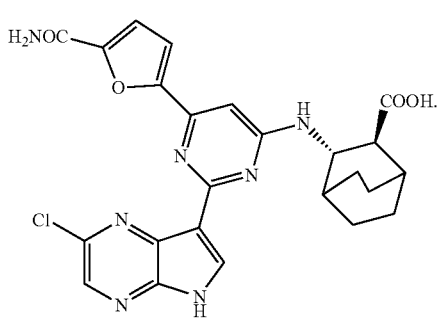

In another aspect, provided herein is a pharmaceutical composition comprising an effective amount of the compound disclosed herein.

In certain embodiments, the pharmaceutical composition provided herein further comprises a pharmaceutically acceptable carrier, adjuvant, vehicle or a combination thereof.

In certain embodiments, the pharmaceutical composition provided herein further comprises one or more therapeutic agents.

In other embodiments, the therapeutic agent disclosed herein is anti-influenza virus agent or anti-influenza virus vaccine.

In other embodiments, the pharmaceutical composition is in the form of a liquid, solid, semi-solid, gel or spray.

In other embodiments, the pharmaceutical composition, wherein the therapeutic agent is amantadine, rimantadine, oseltamivir, zanamivir, peramivir, laninamivir, laninamivir octanoate hydrate, favipiravir, arbidol, ribavirin, stachyflin, ingavirin, fludase, CAS no.1422050-75-6, JNJ-872, S-033188, an influenza vaccine (FluMist Quadrivalent®, Fluarix® Quadrivalent, Fluzone® Quadrivalent, Flucelvax® or FluBlok®) or a combination thereof.

In another aspect, provided herein is use of the compound or the pharmaceutical composition disclosed herein in the manufacture of a medicament for preventing, managing, treating or lessening a disorder or disease caused by a virus infection in a subject.

In certain embodiments, the virus infection disclosed herein is influenza virus infection.

In another aspect, provided herein is use of the compound or the pharmaceutical composition disclosed herein in the manufacture of a medicament for inhibiting influenza virus RNA polymerase.

In one embodiment, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith.

The compound of the invention also embraces the salts thereof, and the salts are not necessarily pharmaceutically acceptable salts, and which may be useful as intermediates for preparing and/or purifying compounds of the invention and/or for separating enantiomers of compounds of the invention.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "*Remington's Pharmaceutical Sciences*", 20th ed., Mack Publishing Company, Easton, Pa., (1985); and in "*Handbook of Pharmaceutical Salts: Properties, Selection, and Use*" by Stahl and Wermuth (Wiley-VCH, Weinheim, Germany, 2002).

Furthermore, the compounds disclosed herein, including their salts, can also be obtained in the form of their hydrates, or include other solvents used for their crystallization. The compounds of the present invention may be formed to solvates with pharmaceutically acceptable solvents (including water) inherently or by design; therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^{2}H$, $^{3}H$, $^{11}C$, $^{13}C$, $^{14}C$, $^{15}N$, $^{18}F$, $^{31}P$, $^{32}P$, $^{36}S$, $^{37}Cl$, $^{125}I$, respectively.

In another aspect, the compounds of the invention include isotopically enriched compounds as defined herein, for example those into which radioactive isotopes, such as 3H, $^{14}C$ and $^{18}F$, or those into which non-radioactive isotopes, such as $^{2}H$ and $^{13}C$ are present. Such isotopically enriched compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g., $D_2O$, acetone-$d_6$, DMSO-$d_6$.

Pharmaceutical Composition of the Compound of the Invention and Preparations and Administration The invention provides a pharmaceutical composition containing a therapeutic effective amount of the compound of the invention or a steroisomer thereof, a racemic mixture or non-racemic mixture of the steroisomer thereof, a pharmaceutically acceptable salt or solvate thereof. In one embodiment, the pharmaceutical composition further comprises at least one pharmaceutically acceptable carrier, diluent, adjuvant or vehicle, and optionally other treating and/or preventing ingredients. In one embodiment, the pharmaceutical composition comprises an effective amount of at least one pharmaceutically acceptable carrier, diluent, adjuvant or vehicle.

A pharmaceutically acceptable carrier may contain inert ingredients which do not unduely inhibit the biological activity of the compound(s) described herein. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed.

As described above, the pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington: The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as Tween 80, phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, methyl cellulose, hydroxypropyl methyl cellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, abherent, coating agents, sweetening, flavoring and perfuming agents, preservatives and antioxidants can also be present in the composition, according to the judgment of the formulator.

The pharmaceutically acceptable compositions can be administered to humans and other animals orally, rectally, parenterally, intracisternally, intravaginally, intraperitoneally, topically (as by powders, ointments or drops), bucally, as an oral or nasal spray, or the like, depending on the severity of the infection being treated.

Liquid formulations for oral administration include, but are not limited to, pharmaceutically acceptable emulsions, micro-emulsion, solution, suspension, syrup and elixir. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Addition to inert diluents, the oral compositions can also contain adjuvants such as wetting agents, emulsifiers or suspending agent, sweeteners, flavorings and fragrances.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is soften desirable to slow the absorption of the compound from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

The solid dosage forms for oral administration include capsules, tablets, pills, powders and granules. In such solid dosage forms, the active compounds are mixed with at least one pharmaceutically acceptable inert excipients or carrier, such as sodium citrate or calcium phosphate and/or (a) fillers or swelling agents such as starch, lactose, sucrose, glucose, mannitol and silicic acid; (b) adhesives such as carboxymethylcellulose, alginates, gelatin, polyethylene pyrrole ketone, sucrose and gum arabic; (c) moisturizing agents such as glycerol; (d) disintegrating agents such as agar, calcium carbonate, potato starch or tapioca starch, alginic acid, certain silicates and sodium carbonate; (e) blocker solution, such as paraffin; (f) absorption promoter such as quaternary ammonium compounds; (g) wetting agents such as cetyl alcohol and glycerol monostearate; (h) absorbents such as kaolin and bentonite, (i) lubricants such as talc, calcium stearate, magnesium stearate, solid polyethylene glycol, laurylsodium sulfate, and mixtures thereof. In the case of capsules, tablets and pills, the pharmaceutical compositions may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, controlled release coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the pharmaceutical compositions may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Use of the Compounds and Pharmaceutical Compositions

The compounds and pharmaceutical compositions provided herein can be used in the manufacture of medicaments for preventing, treating or lessening a disorder or disease caused by virus infection in a patient. In some embodiments, the virus infection is influenza virus infection.

Also provided herein are the uses of the compounds and pharmaceutical compositions described above in the manufacture of medicaments which are inhibitors of influenza virus RNA polymerase.

Provided herein is a method of treating, preventing or delaying the infections caused by viruses, and wherein the method comprises administering to the patent a therapeutically effective amount of the compound or the pharmaceutical composition described herein to a patient in need of treatment. Wherein the virus is an influenza virus, and the compounds or pharmaceutical compositions thereof can be co-administered with other therapies or therapeutic agents. The co-administration can be performed simultaneously, sequentially, or in a certain time interval.

Doses of the compound or pharmaceutical composition needed for implementing functions such as treating, preventing or delaying usually depend on the particular compound to be administered, patient, specific disease or disorder and severity thereof, route and frequency of administration and so on, and need to be determined by the attending doctor in accordance with specific conditions. For example, when the compound or pharmaceutical composition of the present invention is administrated intravenously, the administration may be once a week or even longer intervals.

As described above, the present invention provides a novel class of compounds, and wherein the compounds can be used as inhibitors of the influenza virus RNA polymerase. The compounds of the invention are suitable for preparing medicaments as various dosage forms, which can be used for treating seasonal flu, avian flu, swine flu as well as tamiflu-resistant influenza virus mutants.

Besides being useful for human treatment, these compounds are also useful for veterinary treatment of animals such as companion animals, exotic animals and farm animals. In other embodiments, the animals disclosed herein include horses, dogs, and cats. As used herein, the compounds disclosed herein include the pharmaceutically acceptable derivatives thereof.

General Synthetic Procedures

In the present specification, if the chemical name of the compound doesn't match the corresponding structure, the compound is characterized by the corresponding structure.

For the purpose of describing the invention, the following examples are listed. It should be understood that, the invention is not limited to these examples, and the present invention only provide the method to practice the invention.

Generally, the compounds disclosed herein may be prepared by methods described herein, wherein the substituents are as defined for Formula (I), except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjing Fuchen Chemical Reagent Factory, Wuhan XinHuayuan technology development co., LTD., Qingdao Tenglong Reagent Chemical Ltd., Qingdao Ocean Chemical Factory, Beijin Ouhe Technology Co., Ltd., Shanghai Topbiochem Technology Co., Ltd, and Accela ChemBio Co., Ltd.

Anhydrous THF, 1,4-dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, N,N-dimethylacetamide and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

$^1$H NMR spectra were recorded with a Bruker 400 MHz or 600 MHz spectrometer using $CDCl_3$, DMSO-$d_6$, $CD_3OD$ or acetone-$d_6$ as solutions (reported in ppm), and using TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants, when given, are reported in Hertz (Hz).

Low-resolution mass spectral (MS) data were determined on an Agilent 6120 Quadrupole HPLC-MS spectrometer equipped with an Agilent Zorbax SB-C18 (2.1×30 mm, 3.5 µm). The flow rate was 0.6 mL/min; the mobile phases consisted of a combination of A (0.1% formic acid in $CH_3CN$) and B (0.1% formic acid in $H_2O$) in gradient mode (5% to 95%), and an ESI source was used, the peak of HPLC was recorded with UV-Vis detection at 210/254 nm.

Purification of compound by preparative chromatography was implemented on Agilent 1260 Series preparative high performance liquid chromatography (Pre-HPLC) or Calesep Pump 250 Series preparative high performance liquid chromatography (Pre-HPLC) with UV detection at 210/254 nm (NOVASEP, 50/80 mm DAC).

The following abbreviations are used throughout the specification:
AcOH, HAc, HOAc, $CH_3COOH$ acetic acid
AcOK, KOAc, $CH_3COOK$ potassium acetate
BnOH phenylcarbinol
$Bu_4NF$ tetrabutylammonium fluoride
BOC, Boc tert-butoxycarbonyl
$(Boc)_2O$ di-tert-butyl dicarbonate ester
n-BuOH n-butyl alcohol
$CHCl_3$ chloroform
$CDCl_3$ chloroform-d
$CD_3OD$ methyl alcohol-$d_4$
DCM, $CH_2Cl_2$ dichloromethane
$CH_3CN$, MeCN acetonitrile
$CH_3Cl$ chloromethane
$CH_3I$ iodomethane
$CH_3SO_2Cl$, MsCl methylsufonyl chloride
Cbz benzyloxycarbonyl
DIAD diisopropyl azodicarboxylate
DIEA, DIPEA, $iPr_2Net$ N,N-diisopropylethylamine
DMF N,N-dimethylformamide, dimethylformamide
DMF-DMA N,N-dimethylformamide dimethyl acetal
DME dimethyl ether
DMAP 4-dimethylaminopyridine
DMSO dimethylsulfoxide
DMSO-$d_6$ dimethyl sulfoxide-$d_6$
DPPA diphenylphosphoryl azide
$EC_{50}$ half effective concentration
EA, EtOAc ethyl acetate
$Et_3N$, TEA triethylamine
$Et_2O$ ethyl ether
EtOH ethyl alcohol
$Et_3SiH$ triethyl silicane
g gram
h hour, hours
$H_2$ hydrogen
$H_2O$ water
HCl hydrogen chloride
$H_2O_2$ hydrogen peroxide
$H_3PO_4$ phosphoric acid
$H_2SO_4$ sulfuric acid
$HNO_3$ nitric acid
HCOOK potassium formate
$HCOONH_4$ ammonium formate
$HBF_4$ fluoroboric acid
HPLC high performance liquid chromatography
HPTLC high performance thin layer chromatography
HRMS high-resolution mass spectrometry
$I_2$ iodine
Fe iron
2-MeTHF 2-methyltetrahydrofuran
LDA Lithium diisopropylamide
LiOH lithium hydroxide
$MgSO_4$ magnesium sulfate
$CH_3OH$, MeOH methanol
MeI, $CH_3I$ iodomethane
mL, ml milliliter
min minute, minutes
$N_2$ nitrogen NH₃ ammonia
NMP N-methylprrolidone
NaHCO₃ sodium bicarbonate
NaBH₄ sodium borohydride
NaBH₃CN sodium cyanoborohydride
NaOMe, NaOCH₃, CH₃ONa sodium methoxide
NaOH sodium hydroxide
NaCl sodium chloride
NaH₂PO₄ sodium dihydrogen phosphate
NaH sodium hydride
NaI sodium iodide
Na₂SO₄ sodium sulfate
Na₂S₂O₃ sodium thiosulfate
NBS N-bromosuccinimide
NFSI N-fluorobenzenesulfonimide
NIS N-iodosuccinimide
NCS N-chlorosuccinimide
NH₄Cl ammonium chloride
NH₂OH.HCl hydroxylamine hydrochloride
psi pound per square inch
Pd/C palladium on activated carbon
Pd(OAc)₂ palladium diacetate
Pd(OH)₂ palladium hydroxide
Pd(PPh₃)₄ tetrakis(triphenylphosphine)palladium
Pd(PPh₃)₂Cl₂, PdCl₂(PPh₃)₂ bis(triphenylphosphine)palladium(II) chloride
Pd(dppf)Cl₂, PdCl₂(dppf) [1,1'-bis(diphenylphosphino)ferrocene]dichloropalladium(II)
Pd(dppf)Cl₂CH₂Cl₂ 1,1'-bis(diphenylphosphino)ferrocene-palladium(II)dichloride dichloromethane complex
Pd₂(dba)₃ tris(dibenzylideneacetone)dipalladium
P(t-Bu)₃ tri-tert-butylphosphine
Pd(dtbpf)Cl₂, PdCl₂(dtbpf) 1,1'-bis (di-t-butylphosphino) ferrocene palladium dichloride
PE petroleum ether (60-90° C.)
POCl₃ phosphorus oxychloride
Ph₃CCl triphenylchloromethane
K₂CO₃ potassium carbonate
K₃PO₄ potassium phosphate
KOH potassium hydroxide
RT, rt, r.t. room temperature
Rt retention time
SOCl₂ thionyl chloride
SI therapeutic index
t-BuOK potassium tert-butoxide
THF tetrahydrofuran
TFA trifluoroacetic acid
TBAI tetrabutylammonium iodide
TBAF tetrabutylammonium fluoride
TBS tris(hydroxymethyl)aminomethane saline buffer
TsCl tosyl chloride
Ts Tosyl
ZnCl₂-TMEDA dichloro(N,N,N',N'-tetramethylethane-1,2-diamine)zinc(II)
X-Phos 2-(dicyclohexylphosphino)-2',4',6'-tri-i-propyl-1,1'-biphenyl
xantphos 9,9-dimethyl-4,5-bis(diphenylphosphino)xanthene
Vss apparent volume of distribution
Zn zinc
μL microliter The following schemes list the synthetic steps of the compounds of the invention, wherein each A, R¹, R², R⁴, R⁵ R', R'" and q is as defined herein; X is Br or Cl, R'' is C₃₋₈ alkyl,

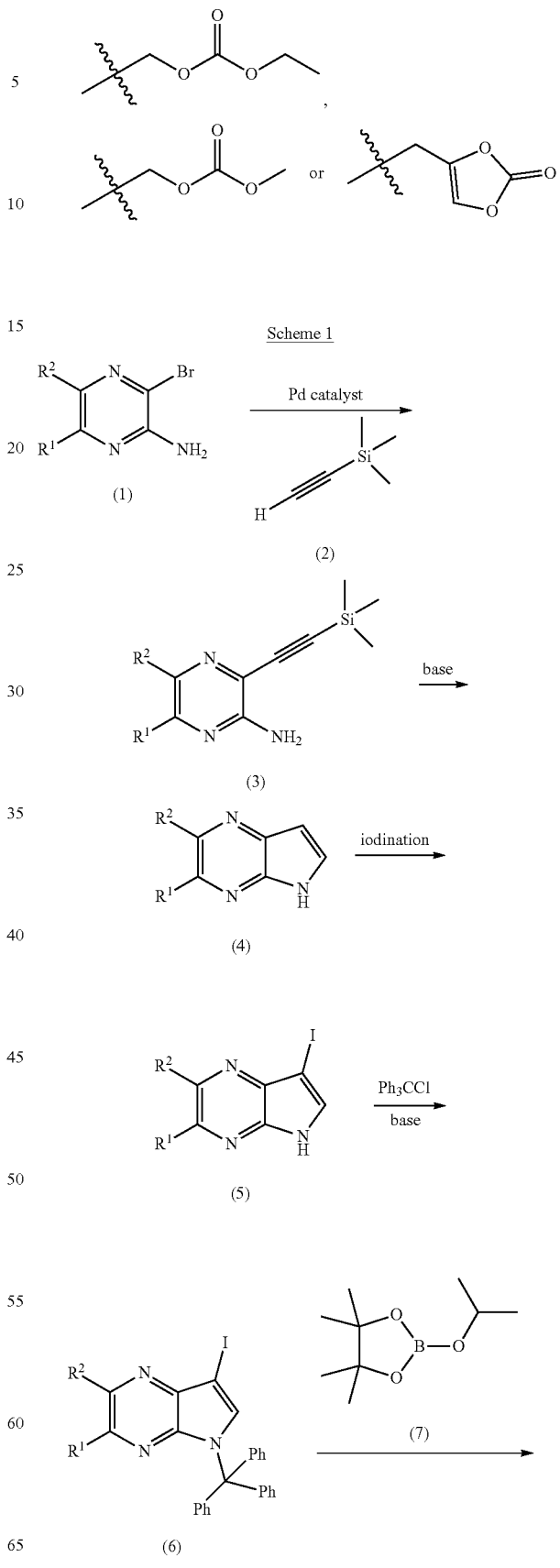

Scheme 3

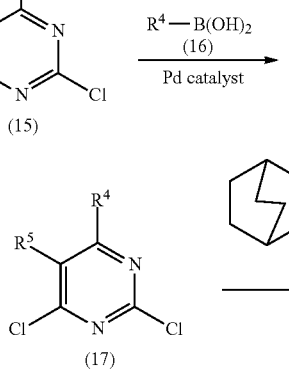

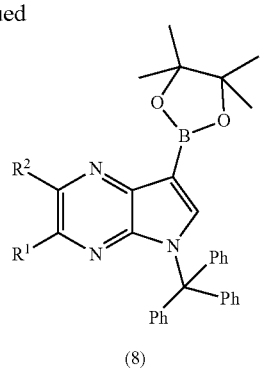

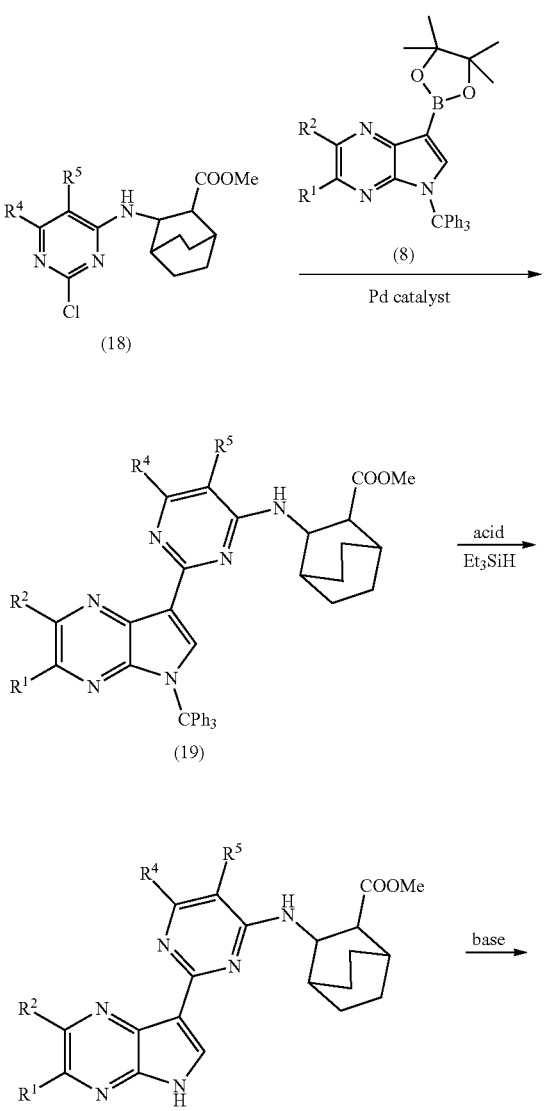

The intermediate having Formula (8) can be prepared by the process illustrated in scheme 1. Compound (1) can react with compound (2) in the presence of a Pd catalyst to give compound Compound (3) can undergo cyclization reaction in the presence of a base to give compound (4). Then, compound (4) can undergo iodination to give compound (5). At last, compound can react with Ph₃CCl under an alkaline condition to give compound Lastly, compound (6) can react with compound (7) undergoing coupling reaction to give compound (8).

Scheme 2

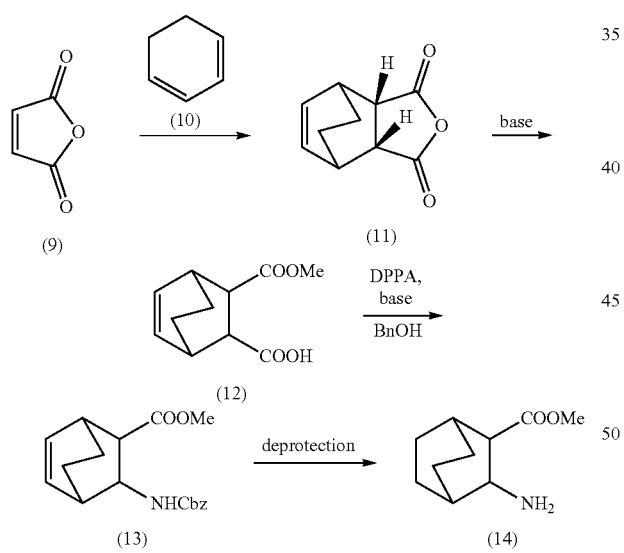

The intermediate having Formula (14) can be prepared by the process illustrated in scheme 2. Firstly, compound (9) can react with compound (10) in the absence of light to give compound (11). Then, compound (11) can undergo ring-opening reaction in the presence of a base such as sodium methoxide to give compound (12). Compound (12) with DPPA and benzyl alcohol can undergo rearrangement reaction under an alkaline condition to give compound (13). Lastly, the amino-protecting group of compound (13) can be removed under a reduction condition to give intermediate (14).

-continued

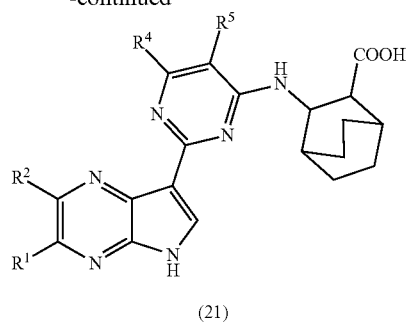

(21)

Compounds having Formula (20) and Formula (21) can be prepared by the process illustrated in scheme 3. Firstly, compound (15) with boric acid compound (16) can undergo suzuki coupling reaction to give compound (17). Then, compound (17) can react with compound (14) under an alkaline condition to give compound (18). Compound (18) with compound (8) can undergo Suzuki coupling reaction in the presence of a Pd catalyst to give compound (19). The amino-protecting group of compound (19) can be removed in the presence of an acid and Et₃SiH to give compound (20). Lastly, the carboxy-protecting group of compound (20) can be removed in the presence of a base to give compound (21).

Scheme 4

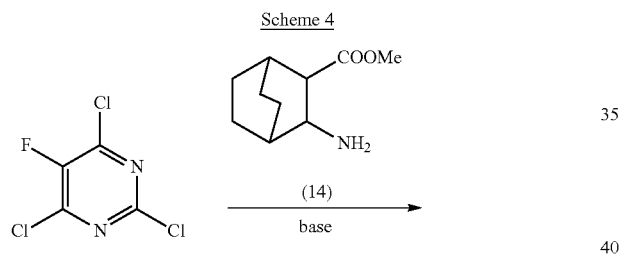

(22)

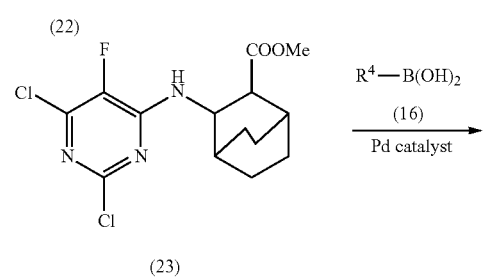

(23)

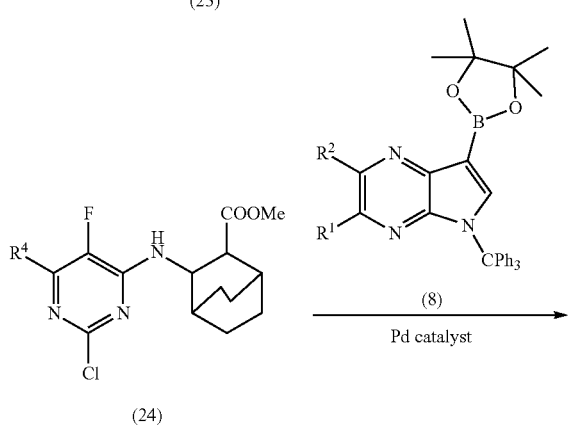

(24)

-continued

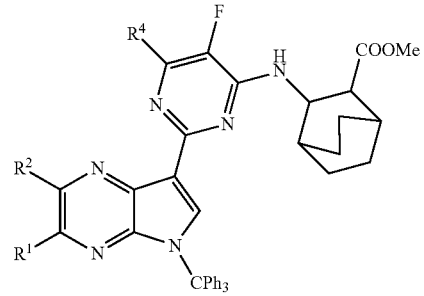

(25)

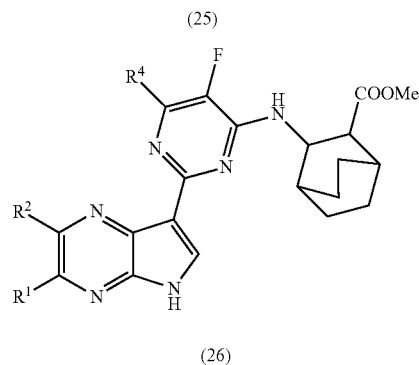

(26)

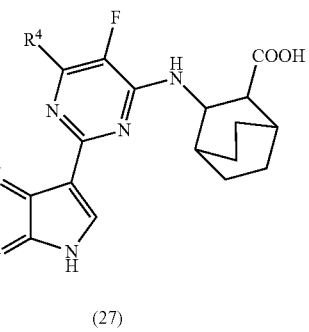

(27)

Compounds having Formula (26) and Formula (27) can be prepared by the process illustrated in scheme 4. Firstly, compound (22) can react with compound (14) under an alkaline condition to give compound (23). Then, compound (23) with boric acid compound (16) can undergo suzuki coupling reaction to give compound (24). Compound (24) with compound (8) can undergo Suzuki coupling reaction in the presence of a Pd catalyst to give compound (25). The amino-protecting group of compound (25) can be removed in the presence of an acid and Et₃SiH to give compound (26). Lastly, the carboxy-protecting group of compound (26) can be removed in the presence of a base to give compound (27).

Scheme 5

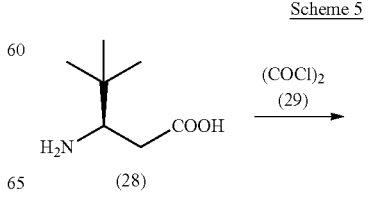

(28)

-continued

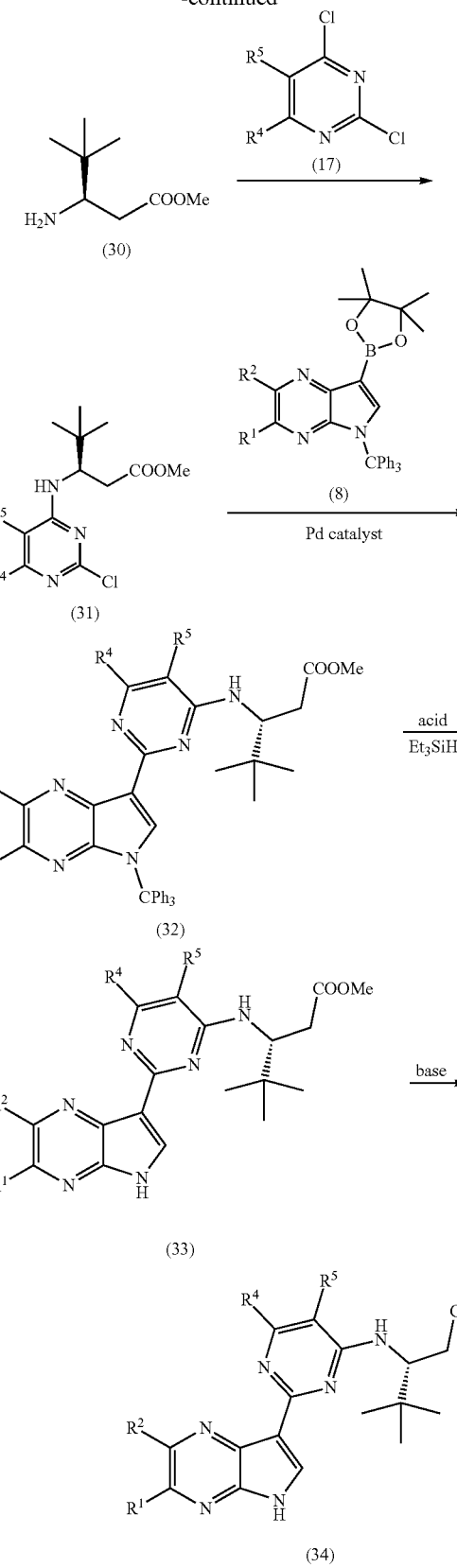

compound (28) can react with methanol in the presence of compound (29) to give compound (30). Then, compound (30) with compound (17) can undergo condensation reaction to give compound (31). Compound (31) with compound (8) can undergo Suzuki coupling reaction in the presence of a Pd catalyst to give compound (32). The amino-protecting group of compound (32) can be removed in the presence of an acid and $Et_3SiH$ to give compound (33). Lastly, the carboxy-protecting group of compound (33) can be removed in the presence of a base to give compound (34).

Scheme 6

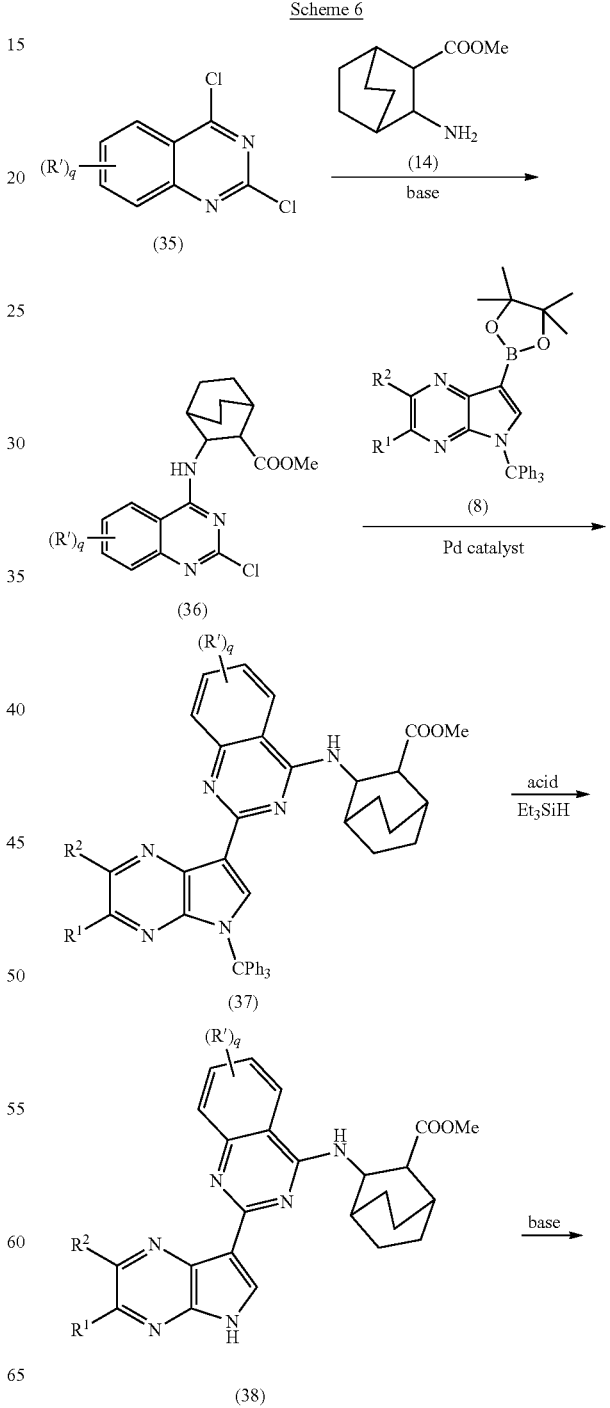

Compounds having Formula (33) and Formula (34) can be prepared by the process illustrated in scheme 5. Firstly,

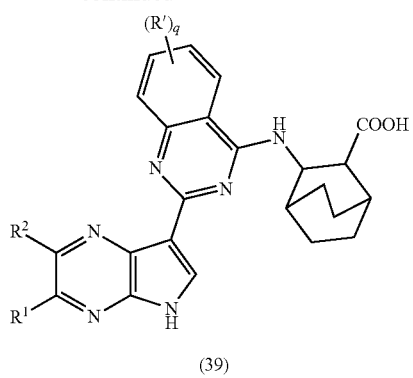

(39)

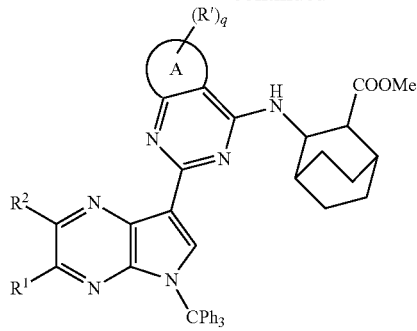

(42)

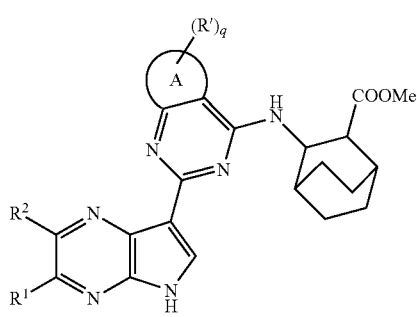

(43)

Compounds having Formula (38) and Formula (39) can be prepared by the process illustrated in scheme 6. Firstly, compound (35) can react with compound (14) under an alkaline condition to give compound (36). Compound (36) with compound (8) can undergo Suzuki coupling reaction in the presence of a Pd catalyst to give compound (37). The amino-protecting group of compound (37) can be removed in the presence of an acid and Et$_3$SiH to give compound (38). Lastly, the carboxy-protecting group of compound (33) can be removed in the presence of a base to give compound (39).

Scheme 7

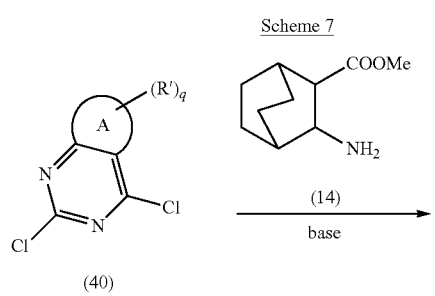

(40)

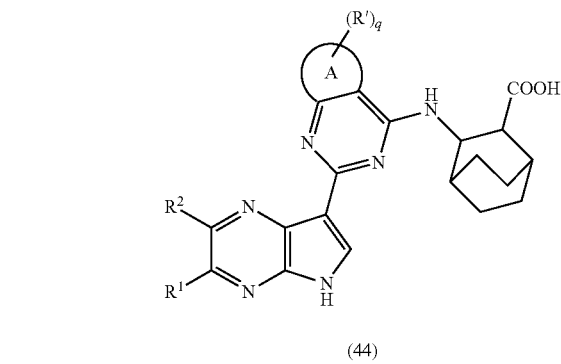

(44)

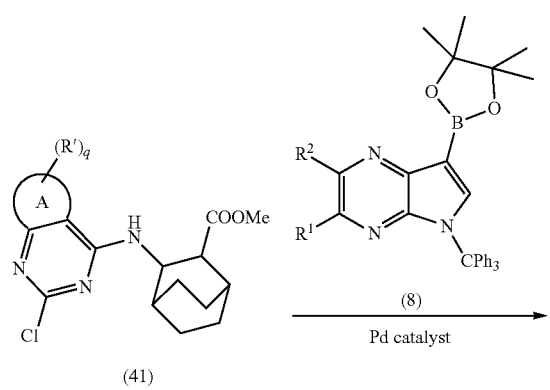

(41)

Compounds having Formula (43) and Formula (44) can be prepared by the process illustrated in scheme 7. Compound (40) with compound (14) can undergo coupling reaction under an alkaline condition to give compound (41). Compound (41) with intermediate (8) can undergo Suzuki coupling reaction in the presence of a Pd catalyst to give compound (42). Compound (42) can undergo deprotection reaction to remove the amino-protecting group in the presence of an acid and Et$_3$SiH to give compound (43). Lastly, compound (43) can react to give compound (44) under an alkaline condition.

Scheme 8

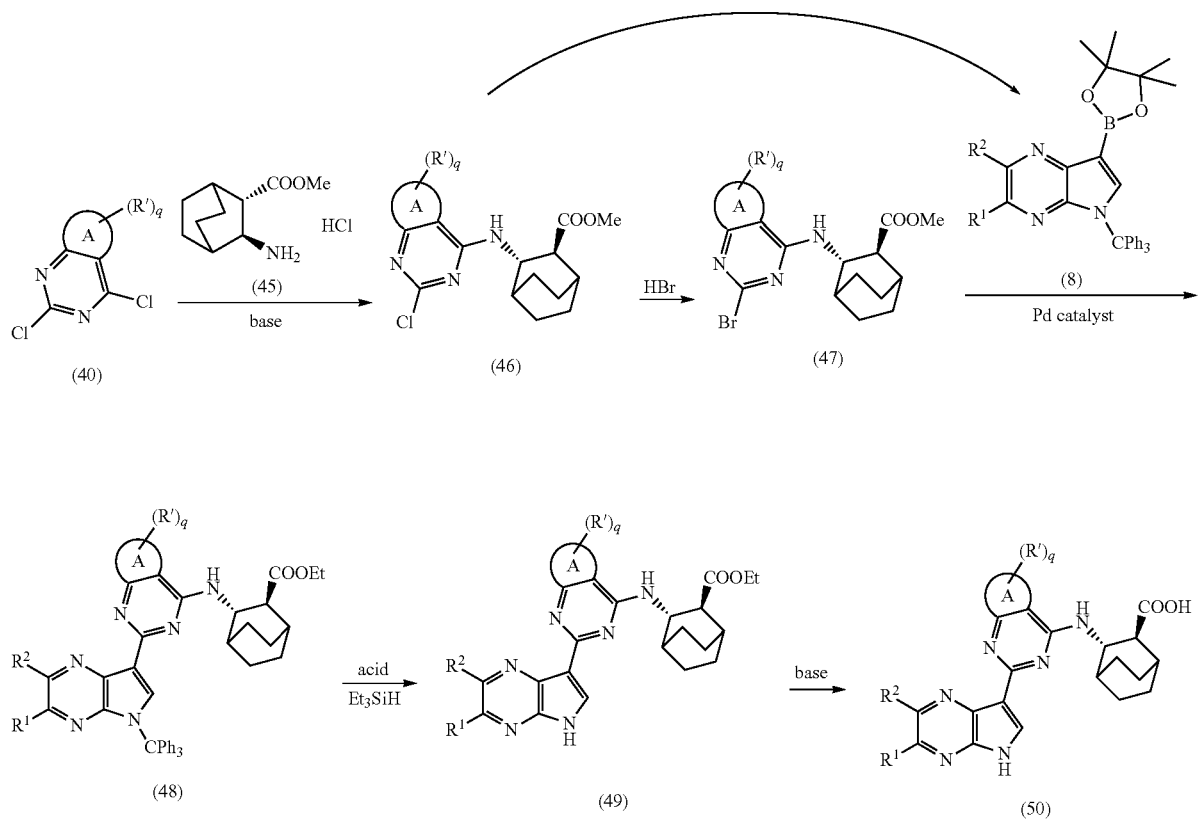

Compounds having Formula (49) and Formula (50) can be prepared by the process illustrated in scheme 8. Compound (40) with compound (45) can undergo coupling reaction under an alkaline condition to give compound (46). Compound (46) with intermediate (8) can undergo Suzuki coupling reaction in the presence of a Pd catalyst to give compound (48); or, firstly, Compound (46) can react with HBr to give compound (47), then compound (47) with intermediate (8) can undergo Suzuki coupling reaction in the presence of a Pd catalyst to give compound (48). Compound (48) can undergo deprotection reaction to remove the amino-protecting group in the presence of an acid and $Et_3SiH$ to give compound (49). Lastly, compound (49) can react to give compound (50) under an alkaline condition.

Scheme 9

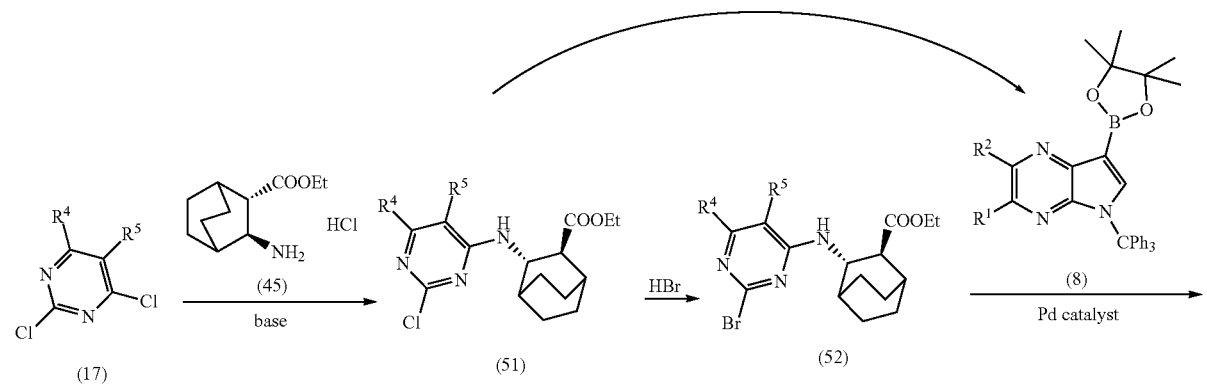

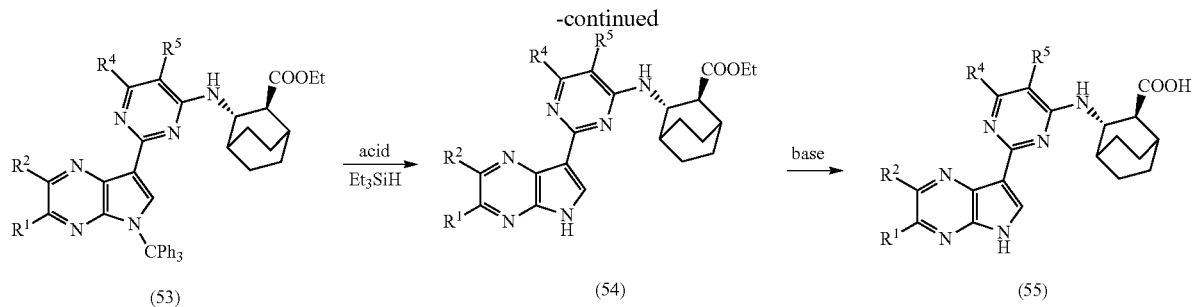

Compounds having Formula (54) and Formula (55) can be prepared by the process illustrated in scheme 9. Compound (17) with compound (45) can undergo coupling reaction under an alkaline condition to give compound (51). Compound (51) with intermediate (8) can undergo Suzuki coupling reaction in the presence of a Pd catalyst to give compound (53); or, firstly, Compound (51) can react with HBr to give compound (52), then compound (52) with intermediate (8) can undergo Suzuki coupling reaction in the presence of a Pd catalyst to give compound (53). Compound (53) can undergo deprotection reaction to remove the amino-protecting group in the presence of an acid and $Et_3SiH$ to give compound (54). Lastly, compound (54) can react to give compound (55) under an alkaline condition.

Compounds having Formula (59) and Formula (60) can be prepared by the process illustrated in scheme 10. Firstly, compound (40) can react with compound (30) to give compound (56). Then, Compound (56) with compound (8) can undergo Suzuki coupling reaction in the presence of a Pd catalyst to give compound (58); or, firstly, Compound (56) can react with hydrobromic acid to give compound (57), then compound (57) with compound (8) can undergo Suzuki coupling reaction in the presence of a Pd catalyst to give compound (58). Then, compound (58) can undergo deprotection reaction to remove the amino-protecting group in the presence of an acid and $Et_3SiH$ to give compound (59). Lastly, the carboxy-protecting group of compound (59) can be removed to give compound (60) under an alkaline condition.

Scheme 10

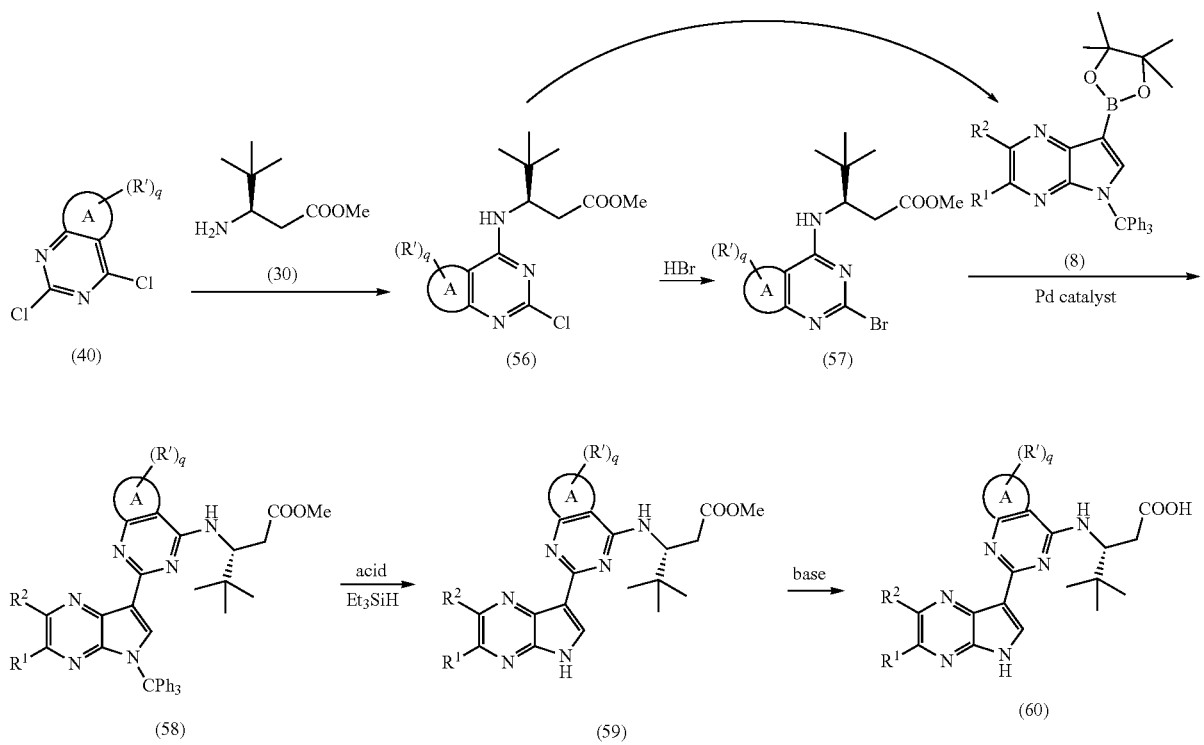

Scheme 11

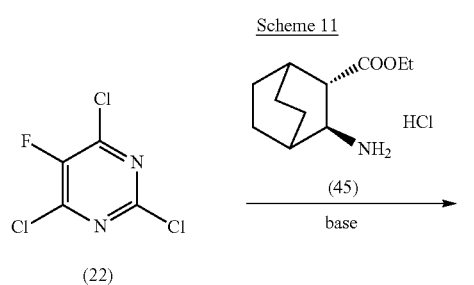

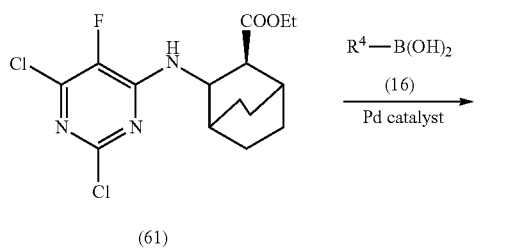

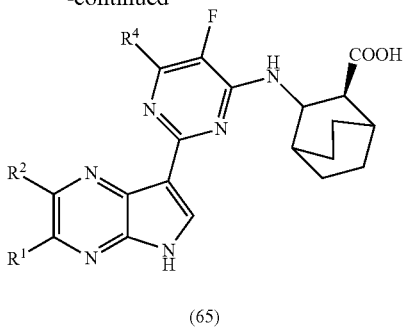

Compounds having Formula (64) and Formula (65) can be prepared by the process illustrated in scheme 11. Firstly, compound (22) can react with compound (45) under an alkaline condition to give compound (61). Then, Compound (61) with a boric acid derivative (16) can undergo Suzuki coupling reaction to give compound (62). Then, Compound (62) with compound (8) can undergo Suzuki coupling reaction in the presence of a Pd catalyst to give compound (63). Then, compound (63) can undergo deprotection reaction to remove the amino-protecting group in the presence of an acid and $Et_3SiH$ to give compound (64). Lastly, compound (64) can undergo deprotection reaction to remove the carboxy-protecting group in the presence of a base to give compound (65).

Scheme 12

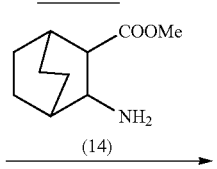

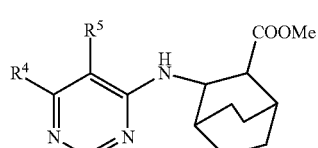

Intermediate having Formula (18) can be prepared by the process illustrated in scheme 12. Firstly, compound (15) can react with compound (14) under an alkaline condition to give compound (66). Then, compound (66) can react with a boric acid derivative (16) undergoing Suzuki coupling reaction to give intermediate (18).

Scheme 13

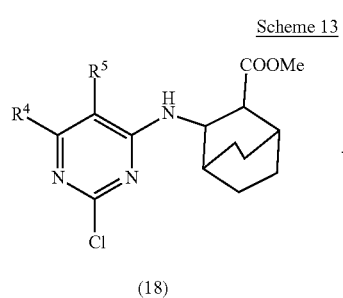

(18)

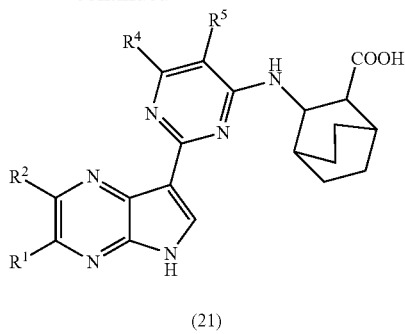

(21)

Compounds having Formula (20) and Formula (21) can be prepared by the process illustrated in scheme 13. Firstly, compound (18) can react with HBr to give compound (67). Then, Compound (67) with compound (8) can undergo Suzuki coupling reaction in the presence of a Pd catalyst to give compound (19). Then, compound (19) can undergo deprotection reaction to remove the amino-protecting group in the presence of an acid and Et$_3$SiH to give compound (20). Lastly, compound (20) can undergo deprotection reaction to remove the carboxy-protecting group in the presence of a base to give compound (21).

Scheme 14

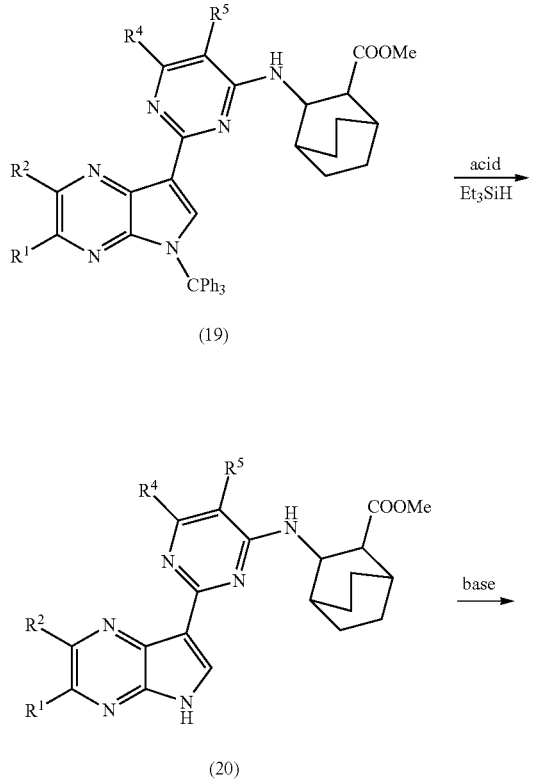

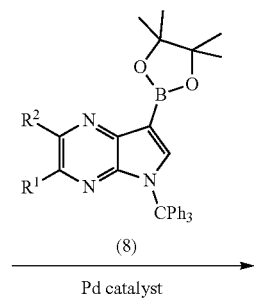

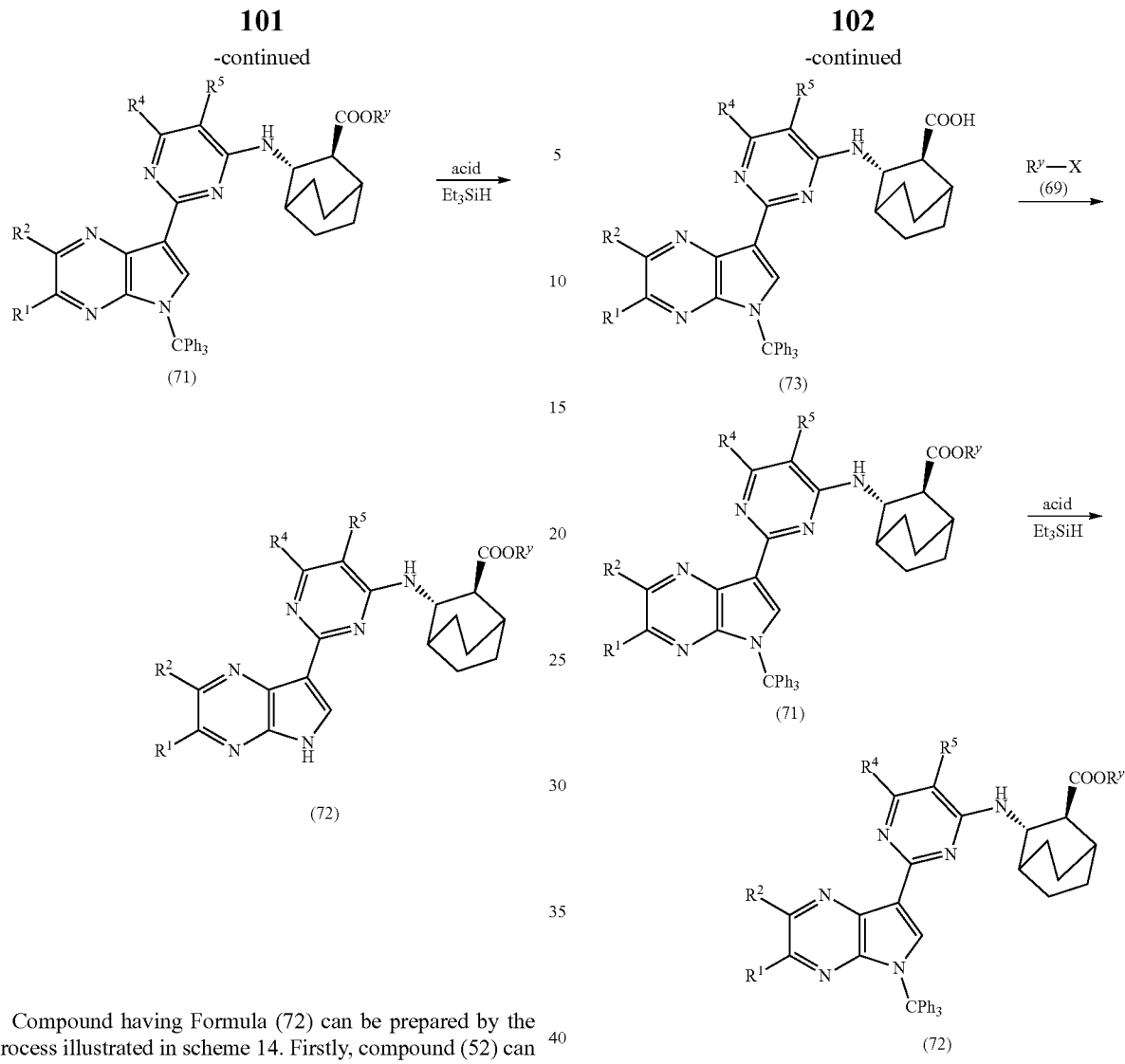

Compound having Formula (72) can be prepared by the process illustrated in scheme 14. Firstly, compound (52) can undergo deprotection reaction to remove the carboxy-protecting group in the presence of a base to give compound (68). Then, compound (68) can react with compound (69) to give compound (70). Nextly, compound (70) with compound (8) can undergo Suzuki coupling reaction in the presence of a Pd catalyst to give compound (71). Lastly, compound (71) can undergo deprotection reaction to remove the amino-protecting group in the presence of an acid and Et$_3$SiH to give compound (72).

Compound having Formula (72) can also be prepared by the process illustrated in scheme 15. Firstly, compound (53) can undergo deprotection reaction to remove the carboxy-protecting group in the presence of a base to give compound (73). Then, compound (73) can react with compound (69) to give compound (71). Lastly, compound (71) can undergo deprotection reaction to remove the amino-protecting group in the presence of an acid and Et$_3$SiH to give compound (72).

Scheme 15

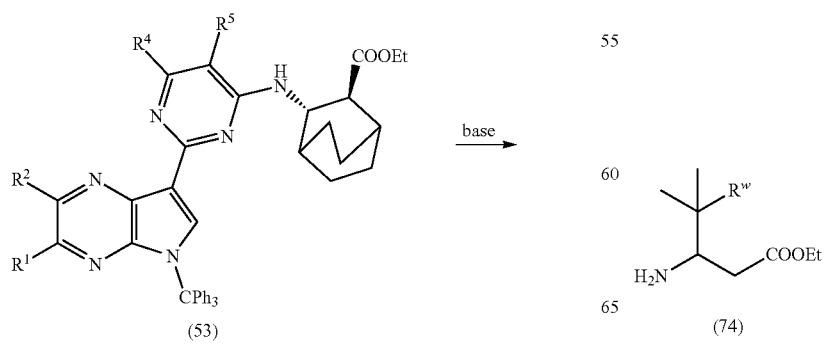

Scheme 16

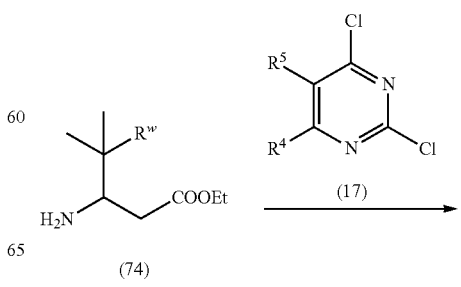

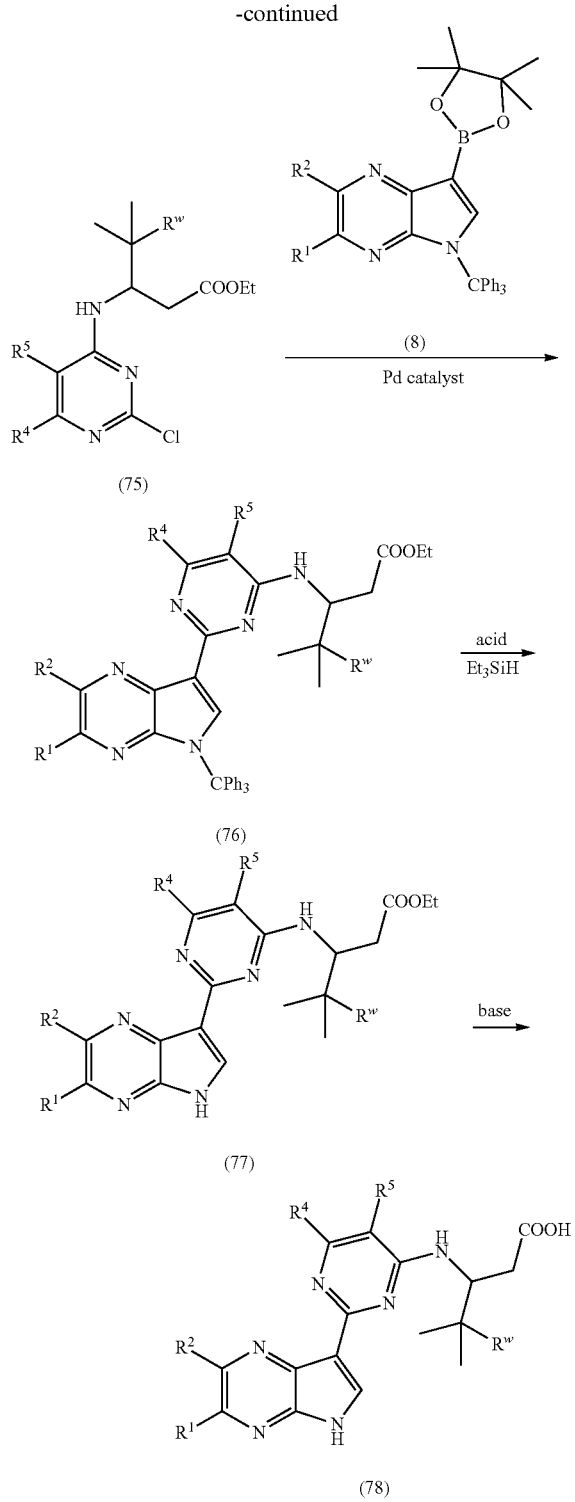

(75)

(76)

(77)

(78)

Compound having Formula (78) can be prepared by the process illustrated in scheme 16. Firstly, compound (74) with compound (17) can undergo condensation reaction to give compound (75). Then, compound (75) with compound (8) can undergo Suzuki coupling reaction in the presence of a Pd catalyst to give compound (76). Compound (76) can undergo deprotection reaction to remove the amino-protecting group in the presence of an acid and Et₃SiH to give compound (77). Lastly, compound (77) can undergo deprotection reaction to remove the carboxy-protecting group in the presence of a base to give compound (78).

DESCRIPTION OF THE PREFERRED EMBODIMENTS

The following examples are used for illustrating the invention, but can not be construed to limit the scope of the invention.

Preparation Examples

Using parts of the compounds of the invention as examples, the preparations of the compounds of the present invention have been described in detail in the following examples.

Example 1: (+/−)-trans-3-((2-(2-chloro-5H-pyrrolo[2,3-b]pyrazin-7-yl)-6-(furan-2-yl) pyrimidin-4-yl)amino)bicyclo[2.2.2]octane-2-carboxylic Acid

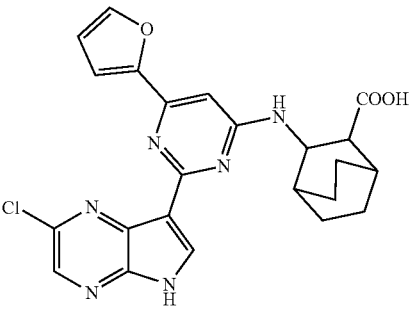 [SMILES: O=C(O)C1C2CCC(CC2)C1Nc1cc(-c2ccco2)nc(-c2c[nH]c3ncc(Cl)nc23)n1]

Step 1: meso-endo-tetrahydro-4,7-ethanoisobenzofuran-1,3-dione

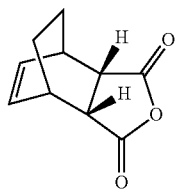

To a 2000 mL dried flask were added maleic anhydride (100 g, 1.02 mol) and chloroform (1000.0 mL) in turn, then the mixture was cooled to 0° C., and 1,3-cyclohexadiene (112.5 mL, 1.12 mol) was added dropwise. After the addition, the mixture was warmed to rt, and stirred overnight in the absence of light. After the reaction was completed, the mixture was concentrated in vacuo to remove the solvent. To the residue was added methanol (700.0 mL), and the resulting mixture was heated to 50° C. and stirred for 10 min, then cooled to 0° C. and stirred for 30 min. The mixture was filtered by suction, and the filter cake was dried in vacuo at 45° C. to give the title compound as a white solid (147 g, 81%).

MS (ESI, pos. ion) m/z: 179.1 [M+H]⁺;

$^1$H NMR (400 MHz, DMSO-d$_6$) δ (ppm): 6.28 (dd, J=4.2, 3.4 Hz, 2H), 3.29 (s, 2H), 3.04 (s, 2H), 1.61 (d, J=7.9 Hz, 2H), 1.22 (d, J=7.6 Hz, 2H).

Step 2: (+/−)-trans-3-(methoxycarbonyl)bicyclo[2.2.2]oct-5-ene-2-carboxylic Acid

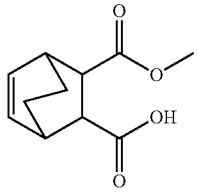

To a dried flask was added meso-endo-tetrahydro-4,7-ethanoisobenzofuran-1,3-dione (33.50 g, 188.01 mmol), then a solution of sodium methoxide in methanol (5 M, 300.8 mL) was added dropwise at 0° C. After the addition, the mixture was warmed to rt and stirred for 4 days, then concentrated in vacuo to remove part of the methanol (about 120 mL). The residue was added slowly into 0° C. aqueous hydrochloric acid solution (277 mL, 18% wt), and there was a white solid precipitated out. The mixture was concentrated in vacuo to remove methanol, and the residue was stirred at 0° C. for 30 min, then filtered by suction. The filter cake was washed with water three times and dried in vacuo to give the title compound as a white solid (37.19 g, 94%).

MS (ESI, neg. ion) m/z: 209.0 [M−H]$^-$;

$^1$H NMR (600 MHz, DMSO-d$_6$) δ (ppm): 12.28 (s, 1H), 6.34 (s, 1H), 6.17 (s, 1H), 3.65 (s, 3H), 2.94 (s, 1H), 2.91 (d, J=4.4 Hz, 1H), 2.86 (d, J=2.4 Hz, 1H), 2.72 (s, 1H), 1.48-1.58 (m, 1H), 1.34-1.44 (m, 1H), 1.26-1.16 (m, 1H), 1.09-0.99 (m, 1H).

Step 3: (+/−)-trans-methyl 3-(((benzyloxy)carbonyl)amino)bicyclo[2.2.2]oct-5-ene-2-carboxylate

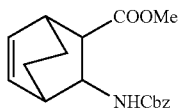

A solution of (+/−)-trans-methyl 3-(methoxycarbonyl)bicyclo[2.2.2]oct-5-ene-2-carboxylic acid (6.0 g, 29 mmol) in toluene (50 mL) was degassed and filled with nitrogen for three times, then diphenyl azidophosphate (7.0 mL, 32 mmol) and triethylamine (4.0 mL, 29 mmol) were added in turn by syringe. The mixture was heated to 90° C. and stirred for 2 hours, then phenylcarbinol (3.0 mL, 29 mmol) was added dropwise by syringe. The mixture was stirred for further 3 days maintaining at this temperature. The reaction mixture was cooled to rt, and ethyl acetate (60 mL) was added to dilute the mixture. The resulting mixture was washed with saturated aqueous sodium bicarbonate (60 mL×2) and saturated brine (50 mL) in turn, and the organic layer was dried over anhydrous sodium sulfate, filtered, then the filtrate was concentrated in vacuo. The residue was purified by silica gel column chromatography (PE/EtOAc (v/v)=8/1) to give the title compound as a yellow oil (8.25 g, 92%).

MS (ESI, pos. ion) m/z: 316.1 [M+H]$^+$.

Step 4: (+/−)-trans-methyl 3-aminobicyclo[2.2.2]octane-2-carboxylate

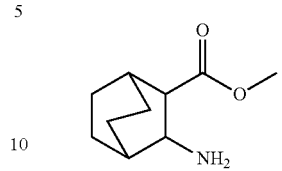

To an autoclave were added (+/−)-trans-methyl 3-(((benzyloxy)carbonyl)amino) bicyclo[2.2.2]oct-5-ene-2-carboxylate (8.21 g, 26.0 mmol), tetrahydrofuran (20 mL) and methanol (20 mL) in turn. To the solution was added Pd/C (10% wt of Pd, 1.40 g), and the mixture was stirred at rt overnight under a hydrogen pressure of 40 psi. The reaction mixture was filtered through a celite pad to remove the catalyst, then the filter cake was washed with methanol (20 mL) and ethyl acetate (20 mL) in turn. The combined filtrates were concentrated in vacuo to give colourless oil, which was purified by silica-gel column chromatography (DCM/MeOH (v/v)=20/1-10/1) to give the title compound as colourless oil (3.95 g, 83%).

MS (ESI, neg. ion) m/z: 184.2 [M−H]$^-$;

$^1$H NMR (400 MHz, CDCl$_3$) δ (ppm): 3.68 (s, 3H), 3.31 (d, J=6.7 Hz, 1H), 2.11 (d, J=6.7 Hz, 1H), 1.98-1.91 (m, 1H), 1.83-1.71 (m, 1H), 1.60-1.33 (m, 10H).

Step 5: 5-chloro-3-((trimethylsilyl)ethynyl)pyrazin-2-amine

3-Bromo-5-chloropyrazin-2-amine (200 mg, 0.96 mmol), triethylamine (290 mg, 2.88 mmol), cuprous iodide (5 mg, 0.33 mmol) and palladium(II)bis(triphenylphosphine)dichloride (13 mg, 0.02 mmol) were dissolved in tetrahydrofuran (5 mL). The mixture was stirred at rt, then trimethylsilylacetylene (0.15 mL, 1.06 mmol) was added dropwise to the mixture. After the addition, the reaction mixture was warmed to 55° C. and stirred for 1 h. The reaction mixture was cooled to rt, and diluted with ethyl acetate (50 mL). The mixture was filtered. The filtrate was concentrated in vacuo, and the residue was purified by silica gel column chromatography (PE/EtOAc (v/v)=30/1) to give the title compound as a light yellow solid (208 mg, 96%).

MS (ESI, pos. ion) m/z: 227.00 [M+H]$^+$;

$^1$H NMR (400 MHz, CDCl$_3$) δ (ppm): 7.98 (s, 1H), 5.11 (s, 2H), 0.31 (s, 9H).

Step 6: 2-chloro-5H-pyrrolo[2,3-b]pyrazine

A solution of 5-chloro-3-((trimethylsilyl)ethynyl)pyrazin-2-amine (100 mg, 0.44 mmol) in THF (8 mL) was stirred at rt, then potassium tert-butoxide (59 mg, 0.53 mmol) was added. The mixture was stirred in a sealed-tub at 120° C. for 1 h. The reaction mixture was cooled to rt, and diluted with ethyl acetate (80 mL). The mixture was filtered. The filtrate was concentrated in vacuo, and the residue was purified by silica gel column chromatography (PE/EtOAc (v/v)=3/1) to give the title compound as a light yellow solid (40 mg, 59%).

$^1$H NMR (400 MHz, DMSO-d$_6$) δ (ppm): 8.29 (s, 1H), 7.98 (d, J=3.5 Hz, 1H), 6.62 (d, J=3.5 Hz, 1H), 5.75 (s, 1H).

Step 7: 2-chloro-7-iodo-5H-pyrrolo[2,3-b]pyrazine

To a solution of 2-chloro-5H-pyrrolo[2,3-b]pyrazine (80 mg, 1.82 mmol) in 2-methyltetrahydrofuran (10 mL) was added NIS (451 mg, 2.00 mmol), and the reaction mixture was stirred at rt overnight. Saturated aqueous sodium thiosulfate (50 mL) was added to quench the reaction, and the resulting mixture was partitioned. The aqueous layer was extracted with EtOAc (50 mL×2). The combined organic layers were washed with saturated brine (80 mL), dried over anhydrous $Na_2SO_4$, filtered, and the filtrate was concentrated in vacuo. The residue was purified by silica gel chromatograph (PE/EtOAc (v/v)=20/1-4/1) to give the title compound as a yellow solid (456 mg, 89%).

MS (ESI, pos. ion) m/z: 280.00 $[M+H]^+$;
$^1$H NMR (600 MHz, DMSO-$d_6$) δ (ppm): 12.81 (s, 1H), 8.36 (s, 1H), 8.21 (d, J=2.7 Hz, 1H).

Step 8: 2-chloro-7-iodo-5-trityl-5H-pyrrolo[2,3-b]pyrazine

A solution of 2-chloro-7-iodo-5H-pyrrolo[2,3-b]pyrazine (1.76 g, 6.30 mmol), $K_2CO_3$ (1.74 g, 12.60 mmol) and triphenylchloromethane (1.93 g, 6.93 mmol) in DMF (10 mL) was stirred at rt overnight. The reaction mixture was added into water (100 mL), and the resulting mixture was extracted with EtOAc (100 mL×3). The combined organic layers were washed with saturated brine (180 mL), dried over anhydrous $Na_2SO_4$, filtered, and the filtrate was concentrated in vacuo. The residue was purified by silica gel chromatograph (PE/EtOAc (v/v)=20/1) to give the title compound as a light yellow solid (2.96 g, 90%).

$^1$H NMR (400 MHz, $CDCl_3$) δ (ppm): 7.92 (s, 1H), 7.65 (s, 1H), 7.35-7.30 (m, 10H), 7.17 (dd, J=6.5, 3.0 Hz, 5H).

Step 9: 2-chloro-7-(4,4,5,5-tetramethyl-1,3,2-dioxaborolan-2-yl)-5-trityl-5H-pyrrolo[2,3-b]pyrazine A solution of 2-chloro-7-iodo-5-trityl-5H-pyrrolo[2,3-b]pyrazine (500 mg, 0.96 mmol) and isopropoxyboronic acid pinacol ester (231 mg, 1.25 mmol) in THF (10 mL) was cooled to −27° C. under nitrogen protection, then isopropylmagnesium chloride solution (2 M, 0.70 mL) was added dropwise. After the addition, the mixture was stirred at −27° C. for 1.5 h. The reaction was stopped, and the reaction mixture was added into saturated aqueous sodium bicarbonate (100 mL). The resulting mixture was extracted with ethyl acetate (100 mL×3). The combined organic layers were concentrated in vacuo, and the residue was purified by silica gel column chromatography (PE/EtOAc (v/v)=10/1) to give the title compound as a yellow solid (210 mg, 42%).

Step 10: 2,4-dichloro-6-(furan-2-yl)pyrimidine

To a solution of 2,4,6-trichloropyrimidine (100 mg, 0.55 mmol) in tetrahydrofuran (4 mL) was added tetrakis(triphenylphosphine)palladium (43 mg, 0.05 mmol), furan-2-ylboronic acid (61 mg, 0.55 mol) and aqueous sodium bicarbonate solution (1 M, 1.64 mL, 1.64 mmol). The mixture was stirred at 80° C. overnight. To the reaction mixture was added water (50 mL), and the resulting mixture was extracted with ethyl acetate (50 mL×3). The combined organic layers were washed with saturated brine (100 mL), dried over anhydrous sodium sulfate and filtered. The filtrate was concentrated in vacuo and the residue was purified by silica gel column chromatography (PE) to give the title compound as a green solid (42 mg, 36%).

MS (ESI, pos.ion) m/z: 215.0 $[M+H]^+$;
$^1$H NMR (400 MHz, $CDCl_3$) δ (ppm): 7.67 (d, J=0.7 Hz, 1H), 7.58 (s, 1H), 7.43 (d, J=3.4 Hz, 1H), 6.65 (dd, J=3.4, 1.6 Hz, 1H).

Step 11: (+/−)-trans-methyl 3-((2-chloro-6-(furan-2-yl)pyrimidin-4-yl)amino)bicyclo[2.2.2]octane-2-carboxylate (+/−)-trans-Methyl 3-aminobicyclo[2.2.2]octane-2-carboxylate (429 mg, 2.34 mmol) and 2,4-dichloro-6-(furan-2-yl)pyrimidine (420 mg, 1.95 mmol) were dissolved in DMF (6 mL), then potassium carbonate (809 mg, 5.86 mmol) was added. The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (383 mg, 54%).

MS (ESI, pos.ion) m/z: 362.1 $[M+H]^+$;
$^1$H NMR (400 MHz, $CDCl_3$) δ (ppm): 7.56 (s, 1H), 7.22 (s, 1H), 6.93 (s, 1H), 6.55 (d, J=1.6 Hz, 1H), 5.47 (d, J=5.5 Hz, 1H), 4.44 (s, 1H), 3.70 (s, 3H), 2.44-2.33 (m, 1H), 1.96 (d, J=2.5 Hz, 1H), 1.88 (s, 1H), 1.84-1.58 (m, 8H).

Step 12: (+/−)-trans-methyl 3-((2-(2-chloro-5-trityl-5H-pyrrolo[2,3-b]pyrazin-7-yl)-6-(furan-2-yl)pyrimidin-4-yl)amino)bicyclo[2.2.2]octane-2-carboxylate To 1,4-dioxane (8 mL) were added 2-chloro-7-(4,4,5,5-tetramethyl-1,3,2-dioxaborolan-2-yl)-5-trityl-5H-pyrrolo[2,3-b]pyrazine (313 mg, 0.30 mmol, 50%), $K_2CO_3$ (115 mg, 0.83 mmol), $PdCl_2(dppf)$ (20 mg, 0.03 mmol) and (+/−)-trans-methyl 3-((2-chloro-6-(furan-2-yl)pyrimidin-4-yl)amino)bicyclo[2.2.2]octane-2-carboxylate (100 mg, 0.28 mmol), then $H_2O$ (1 mL) was added. The mixture was exchanged with nitrogen by bubbling emptying for 10 min. The mixture was sealed in a sealed tub, and stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (121 mg, 61%).

Step 13: (+/−)-trans-methyl 3-((2-(2-chloro-5H-pyrrolo[2,3-b]pyrazin-7-yl)-6-(furan-2-yl) pyrimidin-4-yl)amino)bicyclo[2.2.2]octane-2-carboxylate To a solution of (+/−)-trans-methyl 3-((2-(2-chloro-5-trityl-5H-pyrrolo[2,3-b]pyrazin-7-yl)-6-(furan-2-yl)pyrimidin-4-yl)amino)bicyclo[2.2.2]octane-2-carboxylate (120 mg, 0.17 mmol) in dichloromethane (8 mL) were added triethyl silicane (200 mg, 1.72 mmol) and trifluoroacetic acid (200 mg, 1.75 mmol). The mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (46 mg, 57%).

Step 14: (+/−)-trans-3-((2-(2-chloro-5H-pyrrolo[2,3-b]pyrazin-7-yl)-6-(furan-2-yl)pyrimidin-4-yl)amino) bicyclo[2.2.2]octane-2-carboxylic Acid To a solution of (+/−)-trans-methyl 3-((2-(2-chloro-5H-pyrrolo[2,3-b]pyrazin-7-yl)-6-(furan-2-yl)pyrimidin-4-yl)

amino)bicyclo[2.2.2]octane-2-carboxylate (46 mg, 0.10 mmol) in THF/MeOH (v/v=5 mL/3 mL) was added a solution of NaOH (81 mg, 1.94 mmol) in water (1 mL). The mixture was stirred at rt overnight. The reaction mixture was diluted with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (26 mg, 58%).

MS (ESI, pos.ion) m/z: 465.0 [M+H]$^+$;
HRMS (ESI, pos. ion) m/z: 465.1452 [M+H]$^+$, ($C_{23}H_{22}ClN_6O_3$)[M+H]$^+$ theoretical value: 465.1442;
$^1$H NMR (600 MHz, DMSO-$d_6$) δ (ppm): 12.73 (s, 1H), 8.60 (s, 1H), 8.36 (s, 1H), 7.87 (s, 1H), 7.46 (d, J=6.5 Hz, 1H), 7.22 (s, 1H), 6.70 (s, 1H), 6.64 (s, 1H), 4.57 (s, 1H), 2.10 (s, 1H), 1.97 (s, 1H), 1.74-1.35 (m, 8H), 1.24 (s, 2H).

Example 2: (R)-3-((2-(2-chloro-5H-pyrrolo[2,3-b]pyrazin-7-yl)-6-(furan-2-yl)pyrimidin-4-yl)amino)-4,4-dimethylpentanoic Acid

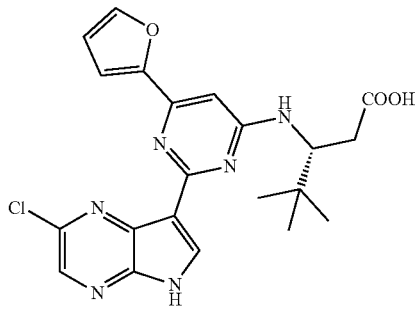 [SMILES: CC(C)(C)[C@@H](CC(=O)O)Nc1cc(-c2ccco2)nc(-c2c[nH]c3ncc(Cl)nc23)n1]

Step 1: (R)-methyl 3-amino-4,4-dimethylpentanoate

To a 0° C. solution of (R)-3-amino-4,4-dimethylpentanoic acid (1.01 g, 6.96 mmol) in methanol (60 mL) was added dropwise slowly oxalyl chloride (0.9 mL, 10 mmol). The mixture was stirred at this temperature for 1 h, then heated to 65° C. and stirred for 2 h. The reaction mixture was concentrated in vacuo, and the residue was washed with toluene (30 mL×3) and filtered by suction to give the title compound as a white solid (1.11 g, 99%).
MS (ESI, pos.ion) m/z: 160.3 [M+H]$^+$.

Step 2: (R)-methyl 3-((2-chloro-6-(furan-2-yl)pyrimidin-4-yl)amino)-4,4-dimethylpentanoate To a solution of (R)-methyl 3-amino-4,4-dimethylpentanoate (243 mg, 1.67 mmol) and 2,4-dichloro-6-(furan-2-yl)pyrimidine (300 mg, 1.40 mmol) in DMF (6 mL) was added potassium carbonate (385 mg, 2.80 mmol). The mixture was stirred at rt overnight. To the reaction mixture was added water (40 mL), and the resulting mixture was extracted with ethyl acetate (40 mL×3). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=5/1) to give the title compound as a white solid (103 mg, 22%).
MS (ESI, pos.ion) m/z: 339.2 [M+H]$^+$.

Step 3: (R)-methyl 3-((2-(2-chloro-5-trityl-5H-pyrrolo[2,3-b]pyrazin-7-yl)-6-(furan-2-yl)pyrimidin-4-yl)amino)-4,4-dimethylpentanoate To a solution of 2-chloro-7-(4,4,5,5-tetramethyl-1,3,2-dioxaborolan-2-yl)-5-trityl-5H-pyrrolo[2,3-b]pyrazine (189 mg, 0.18 mmol, 50%), $K_2CO_3$ (115 mg, 0.83 mmol), Pd(dppf)Cl$_2$ (13 mg, 0.02 mmol) and (R)-methyl 3-((2-chloro-6-(furan-2-yl) pyrimidin-4-yl)amino)-4,4-dimethylpentanoate (56 mg, 0.17 mmol) in 1,4-dioxane (8 mL) was added $H_2O$ (1 mL). The mixture was exchanged with nitrogen by bubbling emptying for 10 min. The mixture was sealed in a sealed tub, and stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (23 mg, 20%).

Step 4: (R)-methyl 3-((2-(2-chloro-5H-pyrrolo[2,3-b]pyrazin-7-yl)-6-(furan-2-yl)pyrimidin-4-yl)amino)-4,4-dimethylpentanoate To a solution of (R)-methyl 3-((2-(2-chloro-5-trityl-5H-pyrrolo[2,3-b]pyrazin-7-yl)-6-(furan-2-yl)pyrimidin-4-yl)amino)-4,4-dimethylpentanoate (53 mg, 0.08 mmol) in DCM (8 mL) were added Et$_3$SiH (86 mg, 0.76 mmol) and TFA (88 mg, 0.76 mmol). The mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (48 mg, 64%).

Step 5: (R)-3-((2-(2-chloro-5H-pyrrolo[2,3-b]pyrazin-7-yl)-6-(furan-2-yl)pyrimidin-4-yl)amino)-4,4-dimethylpentanoic Acid To a solution of (R)-methyl 3-((2-(2-chloro-5H-pyrrolo[2,3-b]pyrazin-7-yl)-6-(furan-2-yl)pyrimidin-4-yl)amino)-4,4-dimethylpentanoate (22 mg, 0.05 mmol) in THF/MeOH (v/v=5 mL/5 mL) was added a solution of NaOH (21 mg, 0.48 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (15 mg, 70%).

MS (ESI, pos.ion) m/z: 441.1 [M+H]$^+$;
HRMS (ESI, pos. ion) m/z: 441.1448 [M+H]$^+$, ($C_{21}H_{22}ClN_6O_3$)[M+H]$^+$ theoretical value: 441.1442;
$^1$H NMR (600 MHz, DMSO-$d_6$) δ (ppm): 12.71 (s, 1H), 8.58 (s, 1H), 8.37 (s, 1H), 7.87 (s, 1H), 7.31 (d, J=8.3 Hz, 1H), 7.20 (s, 1H), 6.69 (s, 1H), 6.66 (s, 1H), 5.33 (t, J=4.6 Hz, 1H), 2.02-1.99 (m, 3H), 1.02 (s, 9H).

Example 3: (+/−)-trans-3-((2-(2-chloro-5H-pyrrolo[2,3-b]pyrazin-7-yl)-5-fluoro-6-(furan-2-yl)pyrimidin-4-yl)amino)bicyclo[2.2.2]octane-2-carboxylic Acid

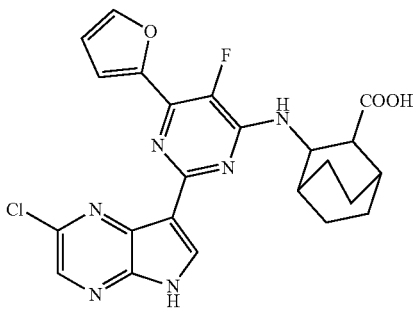 [SMILES: O=C(O)C1C2CCC(CC2)C1Nc1nc(-c2c[nH]c3ncc(Cl)nc23)nc(-c2ccco2)c1F]

Step 1: (+/−)-trans-methyl 3-((2,6-dichloro-5-fluoropyrimidin-4-yl)amino)bicyclo[2.2.2]octane-2-carboxylate A suspension of 2,4,6-trichloro-5-fluoropyrimidine (2.21 g, 8.78 mmol), (+/−)-trans-methyl 3-aminobicyclo[2.2.2]octane-2-carboxylate (1.75 g, 8.78 mmol) and K₂CO₃ (2.43 g, 17.60 mmol) in DMF (5 mL) was stirred at rt overnight. To the reaction mixture was added water (70 mL) to quench the reaction, and the resulting mixture was extracted with ethyl acetate (50 mL×3). The combined organic layers were washed with saturated brine (100 mL×3), dried over anhydrous sodium sulfate and filtered. The filtrate was concentrated in vacuo and the residue was purified by silica gel column chromatography (PE/EtOAc (v/v)=5/1) to give the title compound as a white solid (2.71 g, 89%).

MS (ESI, pos. ion) m/z: 348.00 [M+H]⁺.

Step 2: (+/−)-trans-methyl 3-((2-chloro-5-fluoro-6-(furan-2-yl)pyrimidin-4-yl)amino)bicyclo[2.2.2]octane-2-carboxylate To a solution of furan-2-boric acid (0.22 g, 1.00 mmol), K₂CO₃ (0.63 g, 4.00 mmol), Pd(dppf)Cl₂ (0.12 g, 0.10 mmol), (+/−)-trans-methyl 3-((2,6-dichloro-5-fluoropyrimidin-4-yl)amino)bicyclo[2.2.2]octane-2-carboxylate (500 mg, 1.44 mmol) in 1,4-dioxane (8 mL) was added H₂O (0.5 mL). The mixture was exchanged with nitrogen by bubbling emptying for 10 min. The mixture was sealed in a sealed tub, and stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (423 mg, 66%).

MS (ESI, pos. ion) m/z: 380.10 [M+H]⁺;

¹H NMR (400 MHz, CDCl₃) δ (ppm): 7.66 (s, 1H), 7.19-7.14 (m, 1H), 6.59 (dd, J=3.4, 1.7 Hz, 1H), 5.33 (s, 1H), 4.51 (s, 1H), 3.78 (s, 3H), 2.43 (d, J=5.7 Hz, 1H), 2.02 (d, J=2.1 Hz, 1H), 1.91 (s, 1H), 1.84 (t, J=11.7 Hz, 1H), 1.69 (dd, J=18.2, 10.0 Hz, 5H), 1.46 (t, J=10.7 Hz, 1H), 1.28 (s, 1H).

Step 3: (+/−)-trans-t-butyl 3-((2-(2-chloro-5-trityl-5H-pyrrolo[2,3-b]pyrazin-7-yl)-5-fluoro-6-(furan-2-yl)pyrimidin-4-yl)amino)bicyclo[2.2.2]octane-2-carboxylate To a solution of 2-chloro-7-(4,4,5,5-tetramethyl-1,3,2-dioxaborolan-2-yl)-5-trityl-5H-pyrrolo[2,3-b]pyrazine (1.38 g, 1.32 mmol, 50%), K₂CO₃ (110 mg, 0.77 mmol), PdCl₂(dppf) (75 mg, 0.10 mmol) and (+/−)-trans-methyl 3-((2-chloro-5-fluoro-6-(furan-2-yl) pyrimidin-4-yl)amino)bicyclo[2.2.2]octane-2-carboxylate (385 mg, 1.01 mmol) in 1,4-dioxane (8 mL) was added H₂O (0.5 mL). The mixture was exchanged with nitrogen by bubbling emptying for 10 min. The mixture was sealed in a sealed tub, and stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as light yellow oil (499 mg, 67%).

Step 4: (+/−)-trans-methyl 3-((2-(2-chloro-5H-pyrrolo[2,3-b]pyrazin-7-yl)-5-fluoro-6-(furan-2-yl)pyrimidin-4-yl)amino)bicyclo[2.2.2]octane-2-carboxylate To a solution of (+/−)-trans-t-butyl 3-((2-(2-chloro-5-trityl-5H-pyrrolo[2,3-b]pyrazin-7-yl)-5-fluoro-6-(furan-2-yl)pyrimidin-4-yl)amino)bicyclo[2.2.2]octane-2-carboxylate (499 mg, 0.68 mmol) in DCM (15 mL) were added Et₃SiH (1.3 mL, 8.10 mmol) and TFA (1.0 mL, 8.10 mmol). The mixture was stirred at rt overnight. The reaction was stopped, and the reaction mixture was added into saturated aqueous sodium bicarbonate (20 mL). The resulting mixture was extracted with dichloromethane (20 mL×3). The combined organic layers were washed with saturated brine (50 mL), dried over anhydrous sodium sulfate, and filtered. The filtrate was concentrated in vacuo to give the title compound as black oil (46 mg, 57%), which was used for the next step without further purification.

MS (ESI, pos. ion) m/z: 497.10 [M+H]⁺.

Step 5: (+/−)-trans-3-((2-(2-chloro-5H-pyrrolo[2,3-b]pyrazin-7-yl)-5-fluoro-6-(furan-2-yl) pyrimidin-4-yl)amino)bicyclo[2.2.2]octane-2-carboxylic Acid To a solution of (+/−)-trans-methyl 3-((2-(2-chloro-5H-pyrrolo[2,3-b]pyrazin-7-yl)-5-fluoro-6-(furan-2-yl)pyrimidin-4-yl) amino)bicyclo[2.2.2]octane-2-carboxylate (635 mg, 1.28 mmol) in THF/MeOH/H₂O (v/v/v=6 mL/6 mL/6 mL) was added NaOH (0.52 g, 12.78 mmol). The mixture was stirred at rt overnight, then diluted with saturated brine (40 mL). The resulting mixture was acidified with diluted hydrochloric acid (1 M) to pH about 6. The resulting mixture was extracted with ethyl acetate (40 mL×3). The combined organic layers were washed with saturated brine (80 mL), dried over anhydrous sodium sulfate and filtered. The filtrate was concentrated in vacuo to remove the solvent and the residue was purified by silica gel column chromatography (DCM/MeOH (v/v)=15/1) to give the title compound as a light yellow solid (3 mg, yield of step 4 and step 5: 1.2%).

MS (ESI, pos.ion) m/z: 483.2 [M+H]⁺;

HRMS (ESI, pos. ion) m/z: 483.1224 [M+H]⁺, (C₂₃H₂₁ClN₆O₃)[M+H]⁺ theoretical value: 483.1348;

¹H NMR (600 MHz, DMSO-d₆) δ (ppm): 12.74 (s, 1H), 8.54 (s, 1H), 8.36 (s, 1H), 7.99 (s, 1H), 7.61 (s, 1H), 6.76 (s, 1H), 5.32 (s, 1H), 4.67 (s, 1H), 2.85 (d, J=6.8 Hz, 1H), 2.11 (s, 1H), 1.74 (s, 2H), 1.57-1.40 (m, 4H), 1.35 (s, 1H), 1.17 (s, 2H), 0.85 (s, 2H).

Example 4: (+/−)-trans-3-((2-(2-chloro-5H-pyrrolo[2,3-b]pyrazin-7-yl)-5-fluoro-6-phenyl pyrimidin-4-yl)amino)bicyclo[2.2.2]octane-2-carboxylic Acid

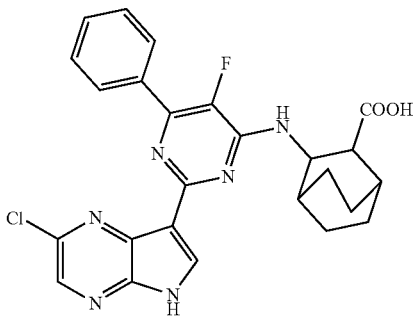 [SMILES: O=C(O)C1C2CCC(CC2)C1Nc1nc(-c2c[nH]c3ncc(Cl)nc23)nc(-c2ccccc2)c1F]

Step 1: (+/−)-trans-methyl 3-((2-chloro-5-fluoro-6-phenylpyrimidin-4-yl)amino)bicyclo[2.2.2]octane-2-carboxylate To acetonitrile (100 mL) were added (+/−)-trans-methyl 3-((2,6-dichloro-5-fluoropyrimidin-4-yl)amino)bicyclo[2.2.2]octane-2-carboxylate (2.00 g, 5.74 mmol), phenylboronic acid (0.70 g, 5.74 mmol), potassium acetate (1.70 g, 17.2 mmol) and Pd(dppf)Cl$_2$ (0.50 g, 0.57 mmol), then to the mixture was added water (5 mL). The resulting mixture was stirred at 80° C. for 12 h under nitrogen protection. The mixture was filtered to remove the solid impuries, and the filtrate was concentrated to remove the solvent. The residue was purified by silica gel column chromatography (PE/EtOAc (v/v)=20/1) to give the title compound as a yellow solid (430 mg, 19.2%).
MS (ESI, pos. ion) m/z: 390.1 [M+H]$^+$.

Step 2: (+/−)-trans-methyl 3-((2-(2-chloro-5-trityl-5H-pyrrolo[2,3-b]pyrazin-7-yl)-5-fluoro-6-phenylpyrimidin-4-yl)amino)bicyclo[2.2.2]octane-2-carboxylate 2-Chloro-7-(4,4,5,5-tetramethyl-1,3,2-dioxaborolan-2-yl)-5-trityl-5H-pyrrolo[2,3-b]pyrazine (293 mg, 0.28 mmol, 50%), K$_2$CO$_3$ (110 mg, 0.77 mmol), Pd(dppf)Cl$_2$ (20 mg, 0.03 mmol) and (+/−)-trans-methyl 3-((2-chloro-5-fluoro-6-phenylpyrimidin-4-yl)amino)bicyclo[2.2.2]octane-2-carboxylate (100 mg, 0.26 mmol) was added into a mixture of 1,4-dioxane (8 mL) and H$_2$O (1 mL). The mixture was exchanged with nitrogen by bubbling emptying for 10 min. The mixture was sealed in a sealed tub, and stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (96 mg, 50%).

Step 3: (+/−)-trans-methyl 3-((2-(2-chloro-5H-pyrrolo[2,3-b]pyrazin-7-yl)-5-fluoro-6-phenylpyrimidin-4-yl)amino)bicyclo[2.2.2]octane-2-carboxylate To a solution of (+/−)-trans-methyl 3-((2-(2-chloro-5-trityl-5H-pyrrolo[2,3-b]pyrazin-7-yl)-5-fluoro-6-phenylpyrimidin-4-yl) amino)bicyclo[2.2.2]octane-2-carboxylate (97 mg, 0.13 mmol) in DCM (5 mL) was added Et$_3$SiH (150 mg, 1.30 mmol) and TFA (150 mg, 1.30 mmol). The mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (33 mg, 50%).
MS (ESI, pos. ion) m/z: 508.20 [M+H]$^+$.

Step 4: (+/−)-trans-3-((2-(2-chloro-5H-pyrrolo[2,3-b]pyrazin-7-yl)-5-fluoro-6-phenyl pyrimidin-4-yl)amino)bicyclo[2.2.2]octane-2-carboxylic Acid To a solution of (+/−)-trans-methyl 3-((2-(2-chloro-5H-pyrrolo[2,3-b]pyrazin-7-yl)-5-fluoro-6-phenylpyrimidin-4-yl)amino)bicyclo[2.2.2]octane-2-carboxylate (36 mg, 0.07 mmol) in THF/MeOH (v/v=5 mL/5 mL) was added a solution of NaOH (31 mg, 0.71 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (16 mg, 46%).
MS (ESI, pos.ion) m/z: 493.3 [M+H]$^+$;
HRMS (ESI, pos. ion) m/z: 493.1556 [M+H]$^+$, (C$_{25}$H$_{23}$ClN$_6$O$_3$)[M+H]$^+$ theoretical value: 493.1555;
$^1$H NMR (600 MHz, DMSO-d$_6$) δ (ppm): 13.03 (s, 1H), 8.63 (s, 1H), 8.43 (d, J=3.9 Hz, 2H), 8.41 (s, 1H), 7.74 (d, J=6.3 Hz, 1H), 7.49 (d, J=6.7 Hz, 3H), 4.70 (s, 1H), 2.87 (d, J=6.8 Hz, 1H), 1.98 (d, J=15.0 Hz, 2H), 1.85-1.31 (m, 9H).

Example 5: (+/−)-trans-3-((2-(2-chloro-5H-pyrrolo[2,3-b]pyrazin-7-yl)-5-fluoro-6-(1-methyl-1H-pyrazol-4-yl)pyrimidin-4-yl)amino)bicyclo[2.2.2]octane-2-carboxylic Acid

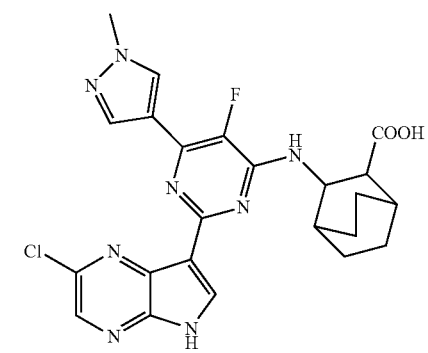 [SMILES: Cn1cc(-c2nc(-c3c[nH]c4ncc(Cl)nc34)nc(NC3C4CCC(CC4)C3C(=O)O)c2F)cn1]

Step 1: (+/−)-trans-methyl 3-((2-chloro-6-(1-methyl-1H-pyrazol-4-yl)pyrimidin-4-yl)amino)bicyclo[2.2.2]octane-2-carboxylate To a solution of (1-methyl-1H-pyrazol-4-yl)boronic acid (180 mg, 1.44 mmol), K$_2$CO$_3$ (595 mg, 4.31 mmol), Pd(dppf)Cl$_2$ (110 mg, 0.14 mmol), (+/−)-trans-methyl 3-((2,6-dichloropyrimidin-4-yl)amino)bicyclo[2.2.2]octane-2-carboxylate (500 mg, 1.44 mmol) in 1,4-dioxane (8 mL) was added H$_2$O (1 mL). The mixture was exchanged with nitrogen by bubbling emptying for 10 min. The mixture was sealed in a sealed tub, and stirred for 3 h at 115° C. The mixture was filtered to remove the solid impurities, and the filtrate was concentrated to remove the solvent. The residue was purified by silica gel column chromatography (PE/EtOAc (v/v)=10/1-5/1) to give the title compound as a white solid (190 mg, 34%).

MS (ESI, pos. ion) m/z: 394.05 [M+H]$^+$;

$^1$H NMR (400 MHz, CDCl$_3$) δ (ppm): 8.09-7.99 (m, 2H), 5.25 (s, 1H), 4.49 (s, 1H), 3.98 (s, 3H), 3.78 (s, 3H), 2.42 (d, J=5.7 Hz, 1H), 2.01 (d, J=2.1 Hz, 1H), 1.91 (s, 1H), 1.67 (s, 8H).

Step 2: (+/−)-trans-methyl 3-((2-(2-chloro-5-trityl-5H-pyrrolo[2,3-b]pyrazin-7-yl)-5-fluoro-6-(1-methyl-1H-pyrazol-4-yl)pyrimidin-4-yl)amino)bicyclo[2.2.2]octane-2-carboxylate To a solution of 2-chloro-7-(4,4,5,5-tetramethyl-1,3,2-dioxaborolan-2-yl)-5-trityl-5H-pyrrolo[2,3-b]pyrazine (355 mg, 0.34 mmol, 50%), K$_2$CO$_3$ (130 mg, 0.91 mmol), PdCl$_2$(dppf) (18 mg, 0.03 mmol) and (+/−)-trans-methyl 3-((2-chloro-6-(1-methyl-1H-pyrazol-4-yl)pyrimidin-4-yl)amino)bicyclo[2.2.2]octane-2-carboxylate (120 mg, 0.30 mmol) in 1,4-dioxane (8 mL) was added H$_2$O (1 mL). The mixture was exchanged with nitrogen by bubbling emptying for 10 min. The mixture was sealed in a sealed tub, and stirred for 3 h at 115° C. The mixture was filtered to remove the solid impurities, and the filtrate was concentrated to remove the solvent. The residue was purified by silica gel column chromatography (PE/EtOAc (v/v)=10/1-5/1) to give the title compound as a white solid (106 mg, 46%).

Step 3: (+/−)-trans-methyl 3-((2-(2-chloro-5H-pyrrolo[2,3-b]pyrazin-7-yl)-5-fluoro-6-(1-methyl-1H-pyrazol-4-yl)pyrimidin-4-yl)amino)bicyclo[2.2.2]octane-2-carboxylate To a solution of (+/−)-trans-methyl 3-((2-(2-chloro-5-trityl-5H-pyrrolo[2,3-b]pyrazin-7-yl)-5-fluoro-6-(1-methyl-1H-pyrazol-4-yl)pyrimidin-4-yl) amino)bicyclo[2.2.2]octane-2-carboxylate (111 mg, 0.15 mmol) in DCM (5 mL) were added Et$_3$SiH (200 mg, 1.47 mmol) and TFA (200 mg, 1.47 mmol). The mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (43 mg, 57%).

MS (ESI, pos. ion) m/z: 511.25 [M+H]$^+$.

Step 4: (+/−)-trans-3-((2-(2-chloro-5H-pyrrolo[2,3-b]pyrazin-7-yl)-5-fluoro-6-(1-methyl-1H-pyrazol-4-yl)pyrimidin-4-yl)amino)bicyclo[2.2.2]octane-2-carboxylic Acid To a solution of (+/−)-trans-methyl 3-((2-(2-chloro-5H-pyrrolo[2,3-b]pyrazin-yl)-5-fluoro-6-(1-methyl-1H-pyrazol-4-yl)pyrimidin-4-yl) amino)bicyclo[2.2.2]octane-2-carboxylate (30 mg, 0.06 mmol) in THF/MeOH (v/v=5 mL/5 mL) was added a solution of NaOH (21 mg, 0.57 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered The filtrate was concentrated in vacuo to remove the solvent and the residue was purified by silica gel column chromatography (DCM/MeOH (v/v)=10/1-5/1) to give the title compound as a white solid (18 mg, 64%).

MS (ESI, pos.ion) m/z: 497.1 [M+H]$^+$;

HRMS (ESI, pos. ion) m/z: 497.1612 [M+H]$^+$, (C$_{23}$H$_{23}$ClN$_8$O$_2$)[M+H]$^+$ theoretical value: 497.1617;

$^1$H NMR (600 MHz, DMSO-d$_6$) δ (ppm): 12.72 (s, 1H), 8.59 (s, 1H), 8.36 (s, 1H), 8.34 (s, 1H), 8.11 (s, 1H), 7.43 (d, J=6.3 Hz, 1H), 4.65 (t, J=6.5 Hz, 1H), 3.96 (s, 3H), 2.84 (d, J=7.1 Hz, 1H), 2.11 (s, 1H), 1.73 (d, J=8.5 Hz, 2H), 1.61-1.31 (m, 6H), 1.23 (s, 2H);

$^{13}$C NMR (101 MHz, DMSO-d$_6$) δ (ppm): 176.10, 155.97, 155.79, 142.64, 141.03, 139.18, 139.08, 138.32, 136.02, 135.85, 135.02, 131.96, 130.11, 116.84, 114.39, 60.21, 51.19, 48.02, 28.81, 28.59, 25.93, 24.20, 21.69, 19.56.

Example 6: (+/−)-trans-3-((6-(benzofuran-2-yl)-2-(2-chloro-5H-pyrrolo[2,3-b]pyrazin-7-yl)-5-fluoropyrimidin-4-yl)amino)bicyclo[2.2.2]octane-2-carboxylic Acid

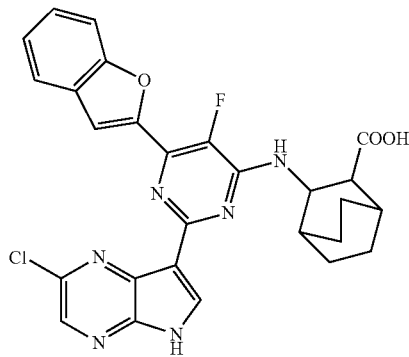 [SMILES: O=C(O)C1C2CCC(CC2)C1Nc1nc(-c2c[nH]c3ncc(Cl)nc23)nc(-c2cc3ccccc3o2)c1F]

Step 1: (+/−)-trans-methyl 3-((6-(benzofuran-2-yl)-2-chloropyrimidin-4-yl)amino)bicyclo[2.2.2]octane-2-carboxylate To a solution of benzofuran-2-boric acid (50 mg, 0.29 mmol), K$_2$CO$_3$ (0.63 g, 4.00 mmol), Pd(dppf)Cl$_2$ (0.12 g, 0.10 mmol), (+/−)-trans-methyl 3-((2,6-dichloro-5-fluoropyrimidin-4-yl) amino)bicyclo[2.2.2]octane-2-carboxylate (100 mg, 0.29 mmol) in 1,4-dioxane (8 mL) was added H$_2$O (1 mL). The mixture was exchanged with nitrogen by bubbling emptying for 10 min. The mixture was sealed in a sealed tub, and stirred for 3 h at 115° C. The mixture was filtered to remove the solid impurities, and the filtrate was concentrated to remove the solvent. The residue was purified by silica gel column chromatography (PE/EtOAc (v/v)=10/1-5/1) to give the title compound as a white solid (33 mg, 27%).

MS (ESI, pos. ion) m/z: 430.20 [M+H]$^+$.

Step 2: (+/−)-trans-methyl 3-((6-(benzofuran-2-yl)-2-(2-chloro-5-trityl-5H-pyrrolo[2,3-b]pyrazin-7-yl)-5-fluoropyrimidin-4-yl)amino)bicyclo[2.2.2]octane-2-carboxylate To a solution of 2-chloro-7-(4,4,5,5-tetramethyl-1,3,2-dioxaborolan-2-yl)-5-trityl-5H-pyrrolo[2,3-b]pyrazine (262 mg, 0.25 mmol, 50%), $K_2CO_3$ (90 mg, 0.67 mmol), $PdCl_2$(dppf) (18 mg, 0.02 mmol) and (+/−)-trans-methyl 3-((6-(benzofuran-2-yl)-2-chloro-5-fluoropyrimidin-4-yl)amino)bicyclo[2.2.2]octane-2-carboxylate (96 mg, 0.22 mmol) in 1,4-dioxane (8 mL) was added $H_2O$ (1 mL). The mixture was exchanged with nitrogen by bubbling emptying for 10 min. The mixture was sealed in a sealed tub, and stirred for 3 h at 115° C. The mixture was filtered to remove the solid impurities, and the filtrate was concentrated to remove the solvent. The residue was purified by silica gel column chromatography (PE/EtOAc (v/v)=10/1-5/1) to give the title compound as a white solid (103 mg, 58%).

Step 3: (+/−)-trans-methyl 3-((6-(benzofuran-2-yl)-2-(2-chloro-5H-pyrrolo[2,3-b]pyrazin-7-yl)-5-fluoropyrimidin-4-yl)amino)bicyclo[2.2.2]octane-2-carboxylate To a solution of (+/−)-trans-methyl 3-((6-(benzofuran-2-yl)-2-(2-chloro-5-trityl-5H-pyrrolo[2,3-b]pyrazin-7-yl)-5-fluoropyrimidin-4-yl)amino)bicyclo[2.2.2]octane-2-carboxylate (111 mg, 0.15 mmol) in DCM (5 mL) were added $Et_3SiH$ (200 mg, 1.47 mmol) and TFA (200 mg, 1.47 mmol). The mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (43 mg, 56%).

MS (ESI, pos. ion) m/z: 548.10 [M+H]$^+$.

Step 4: (+/−)-trans-3-((6-(benzofuran-2-yl)-2-(2-chloro-5H-pyrrolo[2,3-b]pyrazin-7-yl)-5-fluoropyrimidin-4-yl)amino)bicyclo[2.2.2]octane-2-carboxylic Acid To a solution of (+/−)-trans-methyl 3-((6-(benzofuran-2-yl)-2-(2-chloro-5H-pyrrolo[2,3-b]pyrazin-7-yl)-5-fluoropyrimidin-4-yl)amino)bicyclo[2.2.2]octane-2-carboxylate (30 mg, 0.05 mmol) in THF/MeOH (v/v=5 mL/5 mL) was added a solution of NaOH (21 mg, 0.53 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (16 mg, 56%).

MS (ESI, pos.ion) 533.2 [M+H]$^+$;
HRMS (ESI, pos. ion) m/z: 533.1509 [M+H]$^+$, ($C_{27}H_{23}ClN_6O_3$)[M+H]$^+$ theoretical value: 533.1504;

$^1$H NMR (600 MHz, DMSO-d$_6$) δ (ppm): 12.79 (s, 1H), 8.62 (s, 1H), 8.38 (s, 1H), 7.83 (d, J=7.7 Hz, 1H), 7.73 (dd, J=8.1, 4.1 Hz, 3H), 7.46 (t, J=7.6 Hz, 1H), 7.36 (t, J=7.4 Hz, 1H), 4.72 (s, 1H), 2.90 (d, J=7.2 Hz, 1H), 2.15 (s, 1H), 2.02 (s, 2H), 1.85-1.32 (m, 8H);

$^{13}$C NMR (101 MHz, DMSO-d$_6$) δ (ppm): 176.02, 156.27, 155.16, 152.85, 152.74, 150.62, 142.74, 141.04, 139.07, 137.02, 136.07, 135.98, 135.27, 128.17, 126.58, 124.03, 122.62, 114.08, 112.09, 110.25, 110.17, 51.48, 47.88, 28.78, 28.50, 25.91, 24.21, 21.70, 19.61.

Example 7: (+/−)-trans-3-((6-(benzo[b]thiophen-2-yl)-2-(2-chloro-5H-pyrrolo[2,3-b]pyrazin-7-yl)-5-fluoropyrimidin-4-yl)amino)bicyclo[2.2.2]octane-2-carboxylic Acid

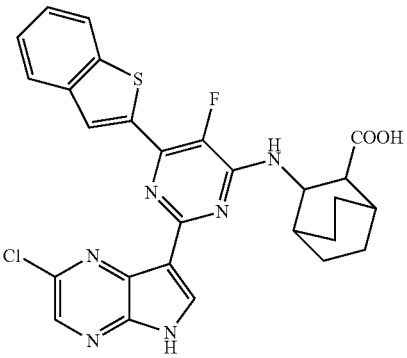 [SMILES: O=C(O)C1C2CCC(CC2)C1Nc1nc(-c2c[nH]c3ncc(Cl)nc23)nc(-c2cc3ccccc3s2)c1F]

Step 1: (+/−)-trans-methyl 3-((6-(benzo[b]thiophen-2-yl)-2-chloro-5-fluoropyrimidin-4-yl)amino)bicyclo[2.2.2]octane-2-carboxylate To a solution of benzofuran-2-boric acid (255 mg, 1.44 mmol), $K_2CO_3$ (595 mg, 4.31 mmol), Pd(dppf)Cl$_2$ (110 mg, 0.14 mmol), (+/−)-trans-methyl 3-((2,6-dichloro-5-fluoropyrimidin-4-yl)amino)bicyclo[2.2.2]octane-2-carboxylate (500 mg, 1.44 mmol) in 1,4-dioxane (8 mL) was added $H_2O$ (1 mL). The mixture was exchanged with nitrogen by bubbling emptying for 10 min. The mixture was sealed in a sealed tub, and stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (423 mg, 66%).

MS (ESI, pos. ion) m/z: 446.20 [M+H]$^+$;
$^1$H NMR (400 MHz, CDCl$_3$) δ (ppm): 8.09 (s, 1H), 7.93-7.84 (m, 2H), 7.43-7.38 (m, 2H), 5.40 (d, J=4.2 Hz, 1H), 4.53 (s, 1H), 3.80 (s, 3H), 2.45 (d, J=5.7 Hz, 1H), 2.03 (s, 1H), 1.94 (s, 1H), 1.90-1.64 (m, 8H).

Step 2: (+/−)-trans-methyl 3-((6-(benzo[b]thiophen-2-yl)-2-(2-chloro-5-trityl-5H-pyrrolo[2,3-b]pyrazin-7-yl)-5-fluoropyrimidin-4-yl)amino)bicyclo[2.2.2]octane-2-carboxylate To a solution of 2-chloro-7-(4,4,5,5-tetramethyl-1,3,2-dioxaborolan-2-yl)-5-trityl-5H-pyrrolo[2,3-b]pyrazine (262 mg, 0.30 mmol, 50%), $K_2CO_3$ (90 mg, 0.81 mmol), $PdCl_2$(dppf) (18 mg, 0.03 mmol) and (+/−)-trans-methyl 3-((6-(benzo[b]thiophen-2-yl)-2-chloro-5-fluoropyrimidin-4-yl)

amino)bicyclo[2.2.2]octane-2-carboxylate (120 mg, 0.27 mmol) in 1,4-dioxane (8 mL) was added H₂O (1 mL). The mixture was exchanged with nitrogen by bubbling emptying for 10 min. The mixture was sealed in a sealed tub, and stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (166 mg, 77%).

Step 3: (+/−)-trans-methyl 3-((6-(benzo[b]thiophen-2-yl)-2-(2-chloro-5H-pyrrolo[2,3-b]pyrazin-7-yl)-5-fluoropyrimidin-4-yl)amino)bicyclo[2.2.2]octane-2-carboxylate To a solution of (+/−)-trans-methyl 3-((6-(benzo[b]thiophen-2-yl)-2-(2-chloro-5-trityl-5H-pyrrolo[2,3-b]pyrazin-7-yl)-5-fluoropyrimidin-4-yl)amino)bicyclo[2.2.2]octane-2-carboxylate (166 mg, 0.21 mmol) in dichloromethane (5 mL) were added triethyl silicane (250 mg, 2.06 mmol) and trifluoroacetic acid (236 mg, 2.06 mmol). The mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (43 mg, 37%).

MS (ESI, pos. ion) m/z: 564.20 [M+H]⁺.

Step 4: (+/−)-trans-3-((6-(benzo[b]thiophen-2-yl)-2-(2-chloro-5H-pyrrolo[2,3-b]pyrazin-7-yl)-5-fluoro-pyrimidin-4-yl)amino)bicyclo[2.2.2]octane-2-carboxylic Acid To a solution of (+/−)-trans-methyl 3-((6-(benzo[b]thiophen-2-yl)-2-(2-chloro-5H-pyrrolo[2,3-b]pyrazin-7-yl)-5-fluoropyrimidin-4-yl)amino)bicyclo[2.2.2]octane-2-carboxylate (43 mg, 0.07 mmol) in THF/MeOH (v/v=5 mL/5 mL) was added a solution of NaOH (30 mg, 0.74 mmol) in water (1 mL). The mixture was stirred at rt overnight, then diluted with water (10 mL). The resulting mixture was acidfied with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (20 mg, 49%).

MS (ESI, pos.ion) m/z: 549.2 [M+H]⁺;

HRMS (ESI, pos. ion) m/z: 549.1269 [M+H]⁺, (C₂₇H₂₃ClN₆O₂S)[M+H]⁺ theoretical value: 549.1276;

¹H NMR (600 MHz, DMSO-d₆) δ (ppm): 12.81 (s, 1H), 8.56 (s, 1H), 8.39 (s, 1H), 8.22 (s, 1H), 8.10-8.00 (m, 2H), 7.76 (d, J=6.4 Hz, 1H), 7.49-7.42 (m, 2H), 4.71 (s, 1H), 2.89 (d, J=6.9 Hz, 1H), 2.14 (s, 1H), 2.02 (s, 2H), 1.76 (d, J=8.4 Hz, 2H), 1.65-1.31 (m, 6H).

Example 7a: (2S,3S)-3-((6-(benzo[b]thiophen-2-yl)-2-(2-chloro-5H-pyrrolo[2,3-b]pyrazin-7-yl)-5-fluoropyrimidin-4-yl)amino)bicyclo[2.2.2]octane-2-carboxylic Acid

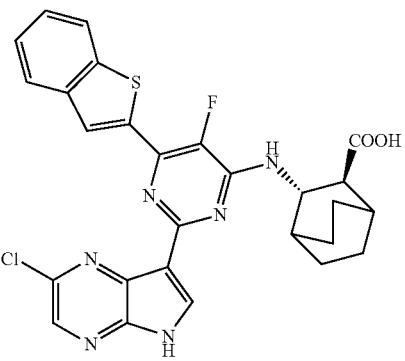 [SMILES: O=C(O)[C@H]1C2CCC(CC2)[C@@H]1Nc1nc(-c2c[nH]c3ncc(Cl)nc23)nc(-c2cc3ccccc3s2)c1F]

Step 1: (2S,3S)-ethyl 3-aminobicyclo[2.2.2]octane-2-carboxylate hydrochloride

The title compound was prepared according to the synthetic method disclosed in patent application WO 2015073491.

Step 2: (2S,3S)-ethyl 3-((2,6-dichloro-5-fluoropyrimidin-4-yl)amino)bicyclo[2.2.2]octane-2-carboxylate A suspension of 2,4,6-trichloro-5-fluoropyrimidine (2.34 g, 11.70 mmol), (2S,3S)-ethyl 3-aminobicyclo[2.2.2]octane-2-carboxylate hydrochloride (2.48 g, 10.60 mmol) and K₂CO₃ (4.40 g, 31.80 mmol) in DMF (5 mL) was stirred at rt overnight. H₂O (100 mL) was added to quenched the reaction, and the resulting mixture was extracted with EtOAc (80 mL×3). The combined organic phases were washed with saturated brine (150 mL×3), dried over anhydrous Na₂SO₄, filtered, and the filtrate was concentrated in vacuo. The residue was purified by silica gel chromatograph (PE/EtOAc (v/v)=5/1) to give the tilted compound as a white solid (2.22 g, 58%).

MS (ESI, pos. ion) m/z: 349.15 [M+H]⁺.

Step 3: (2S,3S)-methyl 3-((6-(benzo[b]thiophen-2-yl)-2-chloro-5-fluoropyrimidin-4-yl)amino)bicyclo[2.2.2]octane-2-carboxylate The title compound was prepared by the synthetic method described in step 1 of example 7, using benzo[b]thiophen-2-ylboronic acid (770 mg, 4.30 mmol), K₂CO₃ (1.80 g, 13.00 mmol), Pd(dppf)Cl₂ (110 mg, 0.43 mmol), (2S,3S)-ethyl 3-((2,6-dichloro-5-fluoropyrimidin-4-yl) amino)bicyclo[2.2.2]octane-2-carboxylate (1.50 g, 4.30 mmol) as reagents and a mixture of tetrahydrofuran (8 mL) and H₂O (1 mL) as mixed solvent. The title compound was a white solid (840 mg, 42%).

MS (ESI, pos. ion) m/z: 461.25 [M+H]⁺;

¹H NMR (400 MHz, CDCl₃) δ (ppm): 8.07 (s, 1H), 7.89 (d, J=7.1 Hz, 1H), 7.87-7.85 (m, 1H), 7.43-7.39 (m, 2H), 5.42 (d, J=4.6 Hz, 1H), 4.57 (d, J=5.5 Hz, 1H), 4.28-4.24 (m, 2H), 2.43 (d, J=5.8 Hz, 1H), 2.05 (d, J=2.5 Hz, 1H), 1.94 (d, J=2.6 Hz, 1H), 1.76-1.64 (m, 8H), 1.30-1.27 (m, 3H).

Step 4: (2S,3S)-ethyl 3-((6-(benzo[b]thiophen-2-yl)-2-(2-chloro-5-trityl-5H-pyrrolo[2,3-b]pyrazin-7-yl)-5-fluoropyrimidin-4-yl)amino)bicyclo[2.2.2]octane-2-carboxylate The title compound was prepared by the synthetic method described in step 2 of example 7, using 2-chloro-7-(4,4,5,5-tetramethyl-1,3,2-dioxaborolan-2-yl)-5-trityl-5H-pyrrolo[2,3-b]pyrazine (1.04 g, 1.20 mmol, 60%), K₂CO₃ (460 mg, 3.28 mmol), PdCl₂(dppf) (90 mg, 0.11 mmol) and (2S,3S)-methyl 3-((6-(benzo[b]thiophen-2-yl)-2-chloro-5-fluoropyrimidin-4-yl)amino)bicyclo[2.2.2]octane-2-carboxylate (503 mg, 1.10 mmol) as reagents and a mixture of 1,4-dioxane (8 mL) and H₂O (1 mL) as mixed solvent. The title compound was a white solid (692 mg, 77%).

Step 5: (2S,3S)-ethyl 3-((6-(benzo[b]thiophen-2-yl)-2-(2-chloro-5H-pyrrolo[2,3-b]pyrazin-7-yl)-5-fluoropyrimidin-4-yl)amino)bicyclo[2.2.2]octane-2-carboxylate The title compound was prepared by the synthetic method described in step 3 of example 7, using (2S,3S)-ethyl 3-((6-(benzo[b]thiophen-2-yl)-2-(2-chloro-5-trityl-5H-pyrrolo[2,3-b]pyrazin-7-yl)-5-fluoropyrimidin-4-yl)amino)bicyclo[2.2.2]octane-2-carboxylate (691 mg, 0.84 mmol), Et₃SiH (1.35 mL, 8.43 mmol) and TFA (0.70 mL, 8.43 mmol) as reagents and DCM (5 mL) as solvent. The title compound was a white solid (59 mg, 12%).

MS (ESI, pos. ion) m/z: 578.0 [M+H]⁺.

Step 6: (2S,3S)-3-((6-(benzo[b]thiophen-2-yl)-2-(2-chloro-5H-pyrrolo[2,3-b]pyrazin-7-yl)-5-fluoropyrimidin-4-yl)amino)bicyclo[2.2.2]octane-2-carboxylic Acid The title compound was prepared by the synthetic method described in step 4 of example 7, using (2S,3S)-ethyl 3-((6-(benzo[b]thiophen-2-yl)-2-(2-chloro-5H-pyrrolo[2,3-b]pyrazin-7-yl)-5-fluoropyrimidin-4-yl)amino)bicyclo[2.2.2]octane-2-carboxylate (58 mg, 0.10 mmol), and a solution of NaOH (30 mg, 0.74 mmol) in water (1 mL) as reagents, and THF/MeOH (v/v=5 mL/5 mL) as solvent. The title compound was a white solid (29 mg, 54%).

MS (ESI, pos. ion) m/z: 549.1 [M+H]⁺;
¹H NMR (600 MHz, DMSO-d₆) δ (ppm): 12.82 (s, 1H), 8.57 (s, 1H), 8.39 (s, 1H), 8.22 (s, 1H), 8.07 (s, 1H), 8.03 (s, 1H), 7.76 (s, 1H), 7.47 (s, 2H), 4.71 (s, 1H), 2.89 (d, J=5.8 Hz, 1H), 2.14 (s, 1H), 2.02 (s, 2H), 1.77 (s, 2H), 1.58-1.35 (m, 6H).

Example 8: (R)-3-((2-(2-chloro-5H-pyrrolo[2,3-b]pyrazin-7-yl)-5-fluoro-6-(furan-2-yl)pyrimidin-4-yl)amino)-4,4-dimethylpentanoic Acid

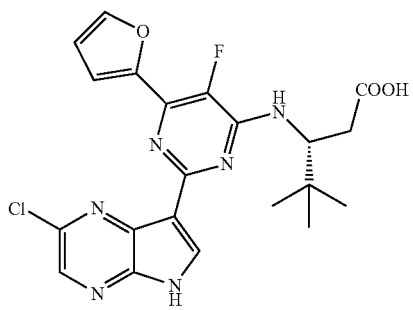 [SMILES: CC(C)(C)[C@@H](CC(=O)O)Nc1nc(-c2c[nH]c3ncc(Cl)nc23)nc(-c2ccco2)c1F]

Step 1) (R)-methyl 3-amino-4,4-dimethylpentanoate

To a 0° C. solution of (R)-methyl 3-amino-4,4-dimethylpentanoic acid (1.01 g, 6.96 mmol) in methanol (60 mL) was added dropwise slowly oxalyl chloride (0.9 mL, 10 mmol). The mixture was stirred at this temperature for 1 h, then heated to 65° C. and stirred for 2 h. The reaction solution was concentrated to dry, and the residue was washed with toluene (30 mL×3) and filtered by suction to give the title compound as a white solid (1.11 g, 99%).

MS (ESI, pos. ion) m/z: 160.3 [M+H]⁺.

Step 2: (R)-methyl 3-((2,6-dichloro-5-fluoropyrimidin-4-yl)amino)-4,4-dimethylpentanoate To a solution of 2,4,6-trichloro-5-fluoropyrimidine (0.71 g, 3.80 mmol) and (R)-methyl 3-amino-4,4-dimethylpentanoate (1.13 g, 4.20 mmol) in DMF (20 mL) was added potassium carbonate (1.63 g, 12.00 mmol), and the mixture was stirred at rt overnight. To the reaction mixture was added water (40 mL), and the resulting mixture was extracted with ethyl acetate (50 mL×3). The combined organic layers were washed with saturated brine (150 mL), dried over anhydrous sodium sulfate and filtered. The filtrate was concentrated in vacuo to dry and the residue was purified by silica gel column chromatography (PE/EA (v/v) =10/1) to give the title compound as a light yellow solid (0.98 g, 79%).

MS (ESI, pos.ion) m/z: 324.20 [M+H]⁺.

Step 3: (R)-methyl 3-((2-chloro-5-fluoro-6-(furan-2-yl)pyrimidin-4-yl)amino)-4,4-dimethylpentanoate To a sealed-tube were added (R)-methyl 3-((2,6-dichloro-5-fluoropyrimidin-4-yl)amino)-4,4-dimethylpentanoate (0.93 g, 2.90 mmol), furan-2-boric acid (0.33 g, 2.90 mmol), Pd(dppf)Cl₂ (0.23 g, 0.29 mmol) and K₂CO₃ (1.25 g, 8.60 mmol), then solvents THF (20 mL) and water (1 mL) were added. The air in the mixture was exchanged with nitrogen by bubbling for 10 min and the tub was sealed. The mixture was stirred at 100° C. for 3 h. After the reaction was completed, the mixture was filtered to remove the solid impurity, and the filtrate was concentrated to remove the solvent. The residue was purified by silica gel column chromatography (PE/EA (v/v)=10/1) to give the title compound as light yellow oil (390 mg, 38%).

MS (ESI, pos. ion) m/z: 356.10[M+H]⁺;
¹H NMR (400 MHz, CDCl₃) δ (ppm): 7.66 (s, 1H), 7.19-7.13 (m, 1H), 6.60-6.57 (m, 1H), 5.64 (d, J=9.3 Hz, 1H), 3.65 (s, 3H), 3.56 (s, 1H), 2.76-2.44 (m, 3H), 1.01 (s, 9H).

Step 4: (R)-methyl 3-((2-(2-chloro-5-trityl-5H-pyrrolo[2,3-b]pyrazin-7-yl)-5-fluoro-6-(furan-2-yl)pyrimidin-4-yl)amino)-4,4-dimethylpentanoate To a solution of 2-chloro-7-(4,4,5,5-tetramethyl-1,3,2-dioxaborolan-2-yl)-5-trityl-5H-pyrrolo[2,3-b]pyrazine (376 mg, 0.36 mmol, 50%), K₂CO₃ (90 mg, 0.97 mmol), Pd(dppf)Cl₂ (18 mg, 0.03 mmol) and (R)-methyl 3-((2-chloro-5-fluoro-6-(furan-2-yl)pyrimidin-4-yl)amino)-4,4-dimethylpentanoate (120 mg, 0.32 mmol) in 1,4-dioxane (8 mL) was added H₂O (1 mL). The air in the mixture was exchanged with nitrogen by bubbling emptying for 10 min. The mixture was sealed in a sealed tub, and stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (191 mg, 83%).

Step 5: (R)-methyl 3-((2-(2-chloro-5H-pyrrolo[2,3-b]pyrazin-7-yl)-5-fluoro-6-(furan-2-yl)pyrimidin-4-yl)amino)-4,4-dimethylpentanoate To a solution of (R)-methyl 3-((2-(2-chloro-5-trityl-5H-pyrrolo[2,3-b]pyrazin-7-yl)-5-fluoro-6-(furan-2-yl)pyrimidin-4-yl)amino)-4,4-dimethylpentanoate (191 mg, 0.27 mmol) in DCM (5 mL) were added Et₃SiH (0.50 mL, 2.67 mmol) and TFA (0.20 mL, 2.67 mmol). The mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (41 mg, 32%).

MS (ESI, pos. ion) m/z: 474.10 [M+H]⁺.

Step 6: (R)-3-((2-(2-chloro-5H-pyrrolo[2,3-b]pyrazin-7-yl)-5-fluoro-6-(furan-2-yl)pyrimidin-4-yl)amino)-4,4-dimethylpentanoic Acid To a solution of (R)-methyl 3-((2-(2-chloro-5H-pyrrolo[2,3-b]pyrazin-7-yl)-5-fluoro-6-(furan-2-yl)pyrimidin-4-yl)amino)-4,4-dimethylpentanoate (41 mg, 0.09 mmol) in THF/MeOH (v/v=5 mL/5 mL) was added a solution of NaOH (31 mg, 0.87 mmol) in water (1 mL). The mixture was stirred at rt overnight, then diluted with water (20 mL). The resulting mixture was acidified with hydrochloric acid (1 M) to pH about 6. The resulting mixture was extracted with ethyl acetate (30 mL×3). The combined organic layers were washed with saturated brine (80 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (13 mg, 33%).

MS (ESI, pos.ion) m/z: 459.2 [M+H]⁺;

HRMS (ESI, pos. ion) m/z: 459.1354 [M+H]⁺, (C₂₃H₂₁ClN₆O₃)[M+H]⁺ theoretical value: 459.1348;

¹H NMR (600 MHz, DMSO-d₆) δ (ppm): 12.72 (s, 1H), 8.54 (s, 1H), 8.37 (s, 1H), 7.98 (s, 1H), 7.43 (d, J=8.8 Hz, 1H), 7.25 (s, 1H), 6.76 (s, 1H), 4.89 (d, J=4.3 Hz, 1H), 2.61 (s, 2H), 1.04 (s, 9H);

¹³C NMR (151 MHz, DMSO-d₆) δ (ppm): 173.83, 155.62, 153.59, 148.71, 145.65, 142.60, 140.96, 139.03, 135.91, 135.48, 134.74, 131.82, 114.28, 112.57, 100.54, 55.40, 36.19, 35.44, 27.07.

Example 9: (+/−)-trans-3-((2-(2-chloro-5H-pyrrolo[2,3-b]pyrazin-7-yl)-6-(furan-3-yl) pyrimidin-4-yl)amino)bicyclo[2.2.2]octane-2-carboxylic Acid

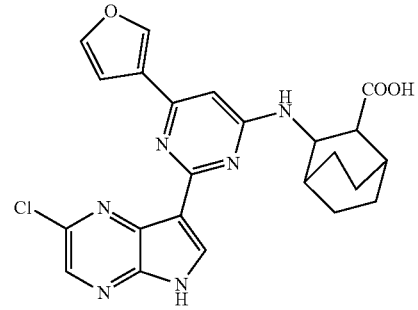 [SMILES: O=C(O)C1C2CCC(CC2)C1Nc1cc(-c2ccoc2)nc(-c2c[nH]c3ncc(Cl)nc23)n1]

Step 1: 2,4-dichloro-6-(furan-3-yl)pyrimidine

To a solution of 2,4,6-trichloropyrimidine (500 mg, 2.73 mmol) in glycol dimethyl ether (32 mL) were added tetrakis(triphenylphosphine)palladium(0) (317 mg, 0.27 mmol), furan-3-ylboronic acid (308 mg, 2.75 mmol) and sodium carbonate solution (1M, 8.18 mL, 8.18 mmol). The reaction mixture was stirred at 80° C. for 6 h, then water (30 mL) was added to diluted the reaction mixture. The mixture was extracted with ethyl acetate (30 mL×3). The combined organic layers were washed with saturated brine (30 mL), dried over anhydrous sodium sulfate and filtered. The filtrate was concentrated in vacuo to dry, and the residue was purified by silica gel column chromatography (PE) to give the title compound as a white solid (42 mg, 31%).

¹H NMR (400 MHz, CDCl₃) δ (ppm): 8.26 (s, 1H), 7.57 (s, 1H), 7.36 (s, 1H), 6.89 (s, 1H).

Step 2: (+/−)-trans-methyl 3-((2-chloro-6-(furan-3-yl)pyrimidin-4-yl)amino)bicyclo[2.2.2]octane-2-carboxylate (+/−)-trans-Methyl 3-aminobicyclo[2.2.2]octane-2-carboxylate (324 mg, 1.77 mmol) and 2,4-dichloro-6-(furan-3-yl)pyrimidine (317 mg, 1.47 mmol) were dissolved in DMF (6 mL), then potassium carbonate (611 mg, 4.42 mmol) was added. The mixture was stirred at rt overnight. The reaction mixture was diluted with water (40 mL), and the resulting mixture was extracted with EtOAc (40 mL×3). The combined organic layers were washed with saturated brine (50 mL), dried over anhydrous Na₂SO₄, and filtered. The filtrate was concentrated in vacuo, and the residue was purified by silica gel column chromatography (PE/EtOAc (v/v)=20/1) to give the title compound as a white solid (353 mg, 66%).

MS (ESI, pos.ion) m/z: 362.1 [M+H]⁺.

Step 3: (+/−)-trans-methyl 3-((2-(2-chloro-5-trityl-5H-pyrrolo[2,3-b]pyrazin-7-yl)-6-(furan-3-yl)pyrimidin-4-yl)amino)bicyclo[2.2.2]octane-2-carboxylate To a solution of 2-chloro-7-(4,4,5,5-tetramethyl-1,3,2-dioxaborolan-2-yl)-5-trityl-5H-pyrrolo[2,3-b]pyrazine (1.16 g, 1.11 mmol, 50%), K₂CO₃ (77 mg, 0.55 mmol), Pd(dtbpf)Cl₂ (37 mg, 0.06 mmol) and (+/−)-trans-methyl 3-((2-chloro-6-(furan-3-yl)pyrimidin-4-yl)amino)bicyclo[2.2.2]octane-2-carboxylate (100 mg, 0.28 mmol) in 1,4-dioxane (8 mL) was added H₂O (0.5 mL). The air in the mixture was exchanged with nitrogen by bubbling emptying for 10 min. The mixture was sealed in a sealed tub, and stirred for 3 h at 115° C. The mixture was filtered to remove the solid impurities, and the filtrate was concentrated to remove the solvent. The residue was purified by silica gel column chromatography (PE/EtOAc (v/v)=10/1) to give the title compound as light yellow oil (98 mg, 48.08%).

Step 4: (+/−)-trans-methyl 3-((2-(2-chloro-5H-pyr-rolo[2,3-b]pyrazin-7-yl)-6-(furan-3-yl)pyrimidin-4-yl)amino)bicyclo[2.2.2]octane-2-carboxylate To a solution of (+/−)-trans-methyl 3-((2-(2-chloro-5-trityl-5H-pyrrolo[2,3-b]pyrazin-7-yl)-6-(furan-3-yl)pyrimidin-4-yl)amino)bicyclo[2.2.2]octane-2-carboxylate (98 mg, 0.14 mmol) in DCM (5 mL) were added Et₃SiH (0.26 mL, 1.63 mmol) and TFA (0.12 mL, 1.63 mmol). The mixture was stirred at rt overnight. The reaction was stopped, and the reaction mixture was added into saturated aqueous sodium bicarbonate (20 mL). The resulting mixture was extracted with dichloromethane (20 mL×3). The combined organic layers were washed with saturated brine (50 mL), dried over anhydrous sodium sulfate, and filtered. The filtrate was concentrated in vacuo to give the title compound as black oil (46 mg, 57%), which was used for the next step without further purification.

MS (ESI, pos. ion) m/z: 479.10 [M+H]⁺.

Step 5: (+/−)-trans-3-((2-(2-chloro-5H-pyrrolo[2,3-b]pyrazin-7-yl)-6-(furan-3-yl)pyrimidin-4-yl)amino)bicyclo[2.2.2]octane-2-carboxylic Acid To a solution of (+/−)-trans-methyl 3-((2-(2-chloro-5H-pyrrolo[2,3-b]pyrazin-7-yl)-6-(furan-3-yl)pyrimidin-4-yl)amino)bicyclo[2.2.2]octane-2-carboxylate (200 mg, 0.42 mmol) in THF/MeOH/H₂O (v/v/v=5 mL/5 mL/5 mL) was added a solution of NaOH (0.17 g, 4.20 mmol) in water. The mixture was stirred at rt overnight. To the reaction mixture was added saturated brine (10 mL), and the mixture was acidified with hydrochloric acid (1 M) to pH about 6. The resulting mixture was extracted with 2-MeTHF (15 mL×3). The combined organic layers were washed with saturated brine, dried over anhydrous sodium sulfate, and filtered. The filtrate was concentrated in vacuo to remove the solvent, and the residue was purified by preparative thin-layer chromatography (DCM/MeOH (v/v)=15/1) to give the title compound as a light yellow solid (16 mg, yield of two steps: 8%).

MS (ESI, pos.ion) m/z: 465.0 [M+H]⁺;

HRMS (ESI, pos. ion) m/z: 465.1435 [M+H]⁺, (C₂₃H₂₂ClN₆O₃)[M+H]⁺ theoretical value: 465.1442;

¹H NMR (600 MHz, DMSO-d₆) δ (ppm): 12.72 (s, 1H), 8.62 (s, 1H), 8.36 (s, 1H), 7.81 (s, 1H), 7.36 (s, 1H), 7.00 (s, 1H), 6.50 (s, 1H), 4.56 (s, 1H), 2.02 (m, 3H), 1.81-1.34 (m, 7H).

Example 10: (+/−)-trans-3-((6-(benzofuran-2-yl)-2-(2-chloro-5H-pyrrolo[2,3-b]pyrazin-7-yl)pyrimidin-4-yl)amino)bicyclo[2.2.2]octane-2-carboxylic Acid

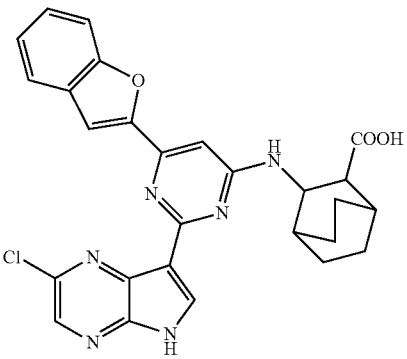 [SMILES: O=C(O)C1C2CCC(CC2)C1Nc1cc(-c2cc3ccccc3o2)nc(-c2c[nH]c3ncc(Cl)nc23)n1]

Step 1: 2,4-dichloro-6-(benzofuran-2-yl)pyrimidine

To a solution of 2,4,6-trichloropyrimidine (1.25 g, 6.79 mmol) in tetrahydrofuran (8 mL) were added tetrakis(triphenylphosphine)palladium (720 mg, 0.62 mmol), benzofuran-2-ylboronic acid (1.00 g, 6.17 mmol) and sodium carbonate (1.56 g, 18.52 mmol). The mixture was stirred at 80° C. overnight under nitrogen protection. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a green solid (552 mg, 34%).

MS (ESI, pos.ion) 266.95 [M+H]⁺;
¹H NMR (400 MHz, CDCl₃) δ (ppm): 7.80 (d, J=4.2 Hz, 2H), 7.73 (d, J=7.8 Hz, 1H), 7.59 (d, J=8.4 Hz, 1H), 7.48 (t, J=7.7 Hz, 1H), 7.35 (t, J=7.5 Hz, 1H).

Step 2: (+/−)-trans-methyl 3-((6-(benzofuran-2-yl)-2-chloropyrimidin-4-yl)amino)bicyclo[2.2.2]octane-2-carboxylate (+/−)-trans-Methyl 3-aminobicyclo[2.2.2]octane-2-carboxylate (250 mg, 1.25 mmol) and 2,4-dichloro-6-(benzofuran-2-yl)pyrimidine (300 mg, 1.13 mmol) were dissolved in DMF (6 mL), then potassium carbonate (312 mg, 2.26 mmol) was added. The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (350 mg, 75%).

MS (ESI, pos.ion) m/z: 412.20 [M+H]⁺.

Step 3: (+/−)-trans-methyl 3-((6-(benzofuran-2-yl)-2-(2-chloro-5-trityl-5H-pyrrolo[2,3-b]pyrazin-7-yl)pyrimidin-4-yl)amino)bicyclo[2.2.2]octane-2-carboxylate To a solution of 2-chloro-7-(4,4,5,5-tetramethyl-1,3,2-dioxaborolan-2-yl)-5-trityl-5H-pyrrolo[2,3-b]pyrazine (282 mg, 0.27 mmol, 50%), K₂CO₃ (115 mg, 0.73 mmol), Pd(dppf)Cl₂ (20 mg, 0.03 mmol) and (+/−)-trans-methyl 3-((6-(benzofuran-2-yl)-2-chloropyrimidin-4-yl) amino)bicyclo[2.2.2]octane-2-carboxylate (100 mg, 0.24 mmol) in 1,4-dioxane (8 mL) was added H₂O (1 mL). The air in the mixture was exchanged with nitrogen by bubbling for 10 min. The mixture was sealed in a sealed tub, and stirred for 3 h at 115° C. The mixture was filtered to remove the solid impurities, and the filtrate was concentrated to remove the solvent. The residue was purified by silica gel column chromatography (PE/EtOAc (v/v)=10/−5/1) to give the title compound as a white solid (110 mg, 59%).

Step 4: (+/−)-trans-methyl 3-((6-(benzofuran-2-yl)-2-(2-chloro-5H-pyrrolo[2,3-b]pyrazin-7-yl)pyrimidin-4-yl)amino)bicyclo[2.2.2]octane-2-carboxylate To a solution of (+/−)-trans-methyl 3-((6-(benzofuran-2-yl)-2-(2-chloro-5-trityl-5H-pyrrolo[2,3-b]pyrazin-7-yl)pyrimidin-4-yl)amino)bicyclo[2.2.2]octane-2-carboxylate (111 mg, 0.14 mmol) in DCM (5 mL) were added Et₃SiH (200 mg, 1.44 mmol) and TFA (200 mg, 1.44 mmol). The mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (60 mg, 79%).

Step 5: (+/−)-trans-3-((6-(benzofuran-2-yl)-2-(2-chloro-5H-pyrrolo[2,3-b]pyrazin-7-yl) pyrimidin-4-yl)amino)bicyclo[2.2.2]octane-2-carboxylic Acid To a solution of (+/−)-trans-methyl 3-((6-(benzofuran-2-yl)-2-(2-chloro-5H-pyrrolo[2,3-b]pyrazin-7-yl)pyrimidin-4-yl)amino)bicyclo[2.2.2]octane-2-carboxylate (22 mg, 0.04 mmol) in THF/MeOH (v/v=5 mL/5 mL) was added a solution of NaOH (21 mg, 0.41 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (16 mg, 77%).

MS (ESI, pos.ion) 515.1 [M+H]⁺;

HRMS (ESI, pos. ion) m/z: 515.1602 [M+H]⁺, (C₂₇H₂₄ClN₆O₃)[M+H]⁺ theoretical value: 515.1598;

¹H NMR (600 MHz, DMSO-d₆) δ (ppm): 12.78 (s, 1H), 8.67 (s, 1H), 8.38 (s, 1H), 7.79 (d, J=7.7 Hz, 1H), 7.68 (s, 2H), 7.62 (d, J=6.6 Hz, 1H), 7.43 (t, J=7.7 Hz, 1H), 7.33 (t, J=7.5 Hz, 1H), 6.90 (s, 1H), 4.60 (s, 1H), 2.12 (s, 1H), 1.98 (s, 2H), 1.85-1.33 (m, 8H).

Example 11: (+/−)-trans-3-((2-(2-chloro-5H-pyrrolo[2,3-b]pyrazin-7-yl)quinazolin-4-yl)amino)bicyclo[2.2.2]octane-2-carboxylic Acid

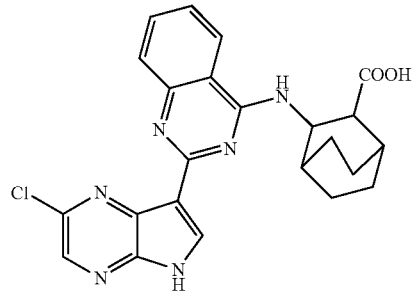 [SMILES: O=C(O)C1C2CCC(CC2)C1Nc1nc(-c2c[nH]c3ncc(Cl)nc23)nc2ccccc12]

Step 1: (+/−)-trans-methyl 3-((2-chloroquinazolin-4-yl)amino)bicyclo[2.2.2]octane-2-carboxylate A suspension of 2,4-dichloroquinazoline (542 mg, 2.72 mmol), (+/−)-trans-methyl 3-aminobicyclo[2.2.2]octane-2-carboxylate (598 mg, 3.27 mmol) and DIPEA (2.5 mL, 27.23 mmol) in THF (10 mL) was stirred at rt overnight. H₂O (100 mL) was added to quench the reaction, and the resulting mixture was extracted with EtOAc (50 mL×3). The combined organic layers were washed with saturated brine (80 mL), dried over anhydrous Na₂SO₄, filtered, and the filtrate was concentrated in vacuo. The residue was purified by silica gel chromatograph (PE/EtOAc (v/v)=5/1-2/1) to give the title compound as a white solid (635 mg, 67%).

MS (ESI, pos. ion) m/z: 346.05 [M+H]⁺.

Step 2: (+/−)-trans-methyl 3-((2-(2-chloro-5-trityl-5H-pyrrolo[2,3-b]pyrazin-7-yl)quinazolin-4-yl)amino)bicyclo[2.2.2]octane-2-carboxylate To a solution of 2-chloro-7-(4,4,5,5-tetramethyl-1,3,2-dioxaborolan-2-yl)-5-trityl-5H-pyrrolo[2,3-b]pyrazine (303 mg, 0.29 mmol, 50%), K₂CO₃ (120 mg, 0.86 mmol), PdCl₂(dppf) (21 mg, 0.03 mmol) and (+/−)-trans-methyl 3-((2-chloroquinazolin-4-yl)amino)bicyclo[2.2.2]octane-2-carboxylate (99 mg, 0.29 mmol) in 1,4-dioxane (8 mL) was added H₂O (1 mL). The mixture was exchanged with nitrogen by bubbling for 10 min. The mixture was sealed in a sealed tub, and stirred for 1.5 h at 110° C. The mixture was filtered and the filtrate was concentrated to remove the solvent. The residue was purified by silica gel chromatograph (PE/EtOAc (v/v)=10/1-5/1) to give the title compound as a white solid (45 mg, 22%).

¹H NMR (400 MHz, CDCl₃) δ (ppm): 8.59 (s, 1H), 7.95 (s, 2H), 7.76-7.68 (m, 2H), 7.44-7.38 (m, 1H), 7.31 (d, J=5.1 Hz, 10H), 7.26-7.24 (m, 5H), 4.80 (s, 1H), 3.57 (s, 3H), 2.07 (d, J=9.3 Hz, 5H), 1.74-1.63 (m, 7H).

Step 3: (+/−)-trans-methyl 3-((2-(2-chloro-5H-pyrrolo[2,3-b]pyrazin-7-yl)quinazolin-4-yl)amino)bicyclo[2.2.2]octane-2-carboxylate To a solution of (+/−)-trans-methyl 3-((2-(2-chloro-5-trityl-5H-pyrrolo[2,3-b]pyrazin-7-yl)quinazolin-4-yl) amino)bicyclo[2.2.2]octane-2-carboxylate (297 mg, 0.48 mmol) in dichloromethane (5 mL) were added trifluoroacetic acid (0.60 mL, 8.08 mmol) and triethyl silicane (0.39 mL, 2.43 mmol). The mixture was stirred at rt overnight. The reaction was stopped, and the reaction mixture was added into saturated aqueous sodium bicarbonate (100 mL). The resulting mixture was extracted with dichloromethane (50 mL×3). The combined organic layers were washed with saturated brine (120 mL), dried over anhydrous sodium sulfate, and filtered. The filtrate was concentrated in vacuo, and the residue was purified by silica gel column chromatography (DCM/MeOH (v/v)=10/1) to give the title compound as a white solid (23 mg, 61%).

MS (ESI, pos. ion) m/z: 463.05 [M+H]$^+$.

Step 4: (+/−)-trans-3-((2-(2-chloro-5H-pyrrolo[2,3-b]pyrazin-7-yl)quinazolin-4-yl)amino)bicyclo[2.2.2]octane-2-carboxylic Acid To a solution of (+/−)-trans-methyl 3-((2-(2-chloro-5H-pyrrolo[2,3-b]pyrazin-7-yl) quinazolin-4-yl)amino)bicyclo[2.2.2]octane-2-carboxylate (23 mg, 0.05 mmol) in THF/MeOH (v/v=3 mL/3 mL) was added a solution of NaOH (21 mg, 0.52 mmol) in water (0.5 mL). The mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (11 mg, 49%).

MS (ESI, pos. ion) m/z: 450.25 [M+H]$^+$;
HRMS (ESI, pos. ion) m/z: 449.1491[M+H]$^+$, (C$_{23}$H$_{22}$ClN$_6$O$_2$)[M+H]$^+$ theoretical value: 449.1493;
$^1$H NMR (600 MHz, DMSO-d$_6$) δ (ppm): 12.75 (s, 1H), 8.63 (s, 1H), 8.38 (s, 1H), 7.84 (s, 1H), 7.74 (d, J=8.4 Hz, 1H), 7.49-7.42 (m, 1H), 6.88 (s, 1H), 6.65 (s, 1H), 5.33 (s, 1H), 4.88 (s, 1H), 2.19 (s, 2H), 2.11-1.95 (m, 3H), 1.92-1.41 (m, 6H).

Example 12: (+/−)-trans-3-((2-(2-chloro-5H-pyrrolo[2,3-b]pyrazin-7-yl)-6-phenyl pyrimidin-4-yl)amino)bicyclo[2.2.2]octane-2-carboxylic Acid

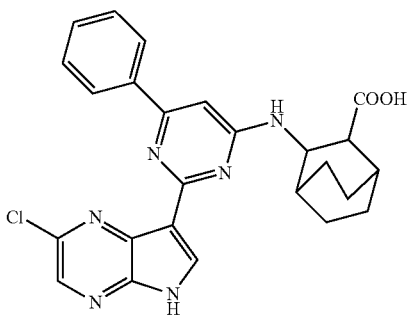 [SMILES: O=C(O)C1C2CCC(CC2)C1Nc1cc(-c2ccccc2)nc(-c2c[nH]c3ncc(Cl)nc23)n1]

Step 1: 2,4-dichloro-6-phenylpyrimidine

To a solution of 2,4,6-trichloropyrimidine (0.29 mL, 2.5 mmol) in THF (5 mL) were added palladium acetate (8 mg, 0.035 mmol), triphenylphosphine (18 mg, 0.065 mmol), benzeneboronic acid (0.20 g, 1.6 mmol) and aqueous sodium carbonate solution (1 M, 3.3 mL, 3.3 mmol). The mixture was stirred at 60° C. for 6 h under nitrogen protection. After the reaction was completed, the mixture was cooled to rt, and concentrated in vacuo. To the residue was added H$_2$O (10 mL), and the mixture was extracted with ethyl acetate (10 mL×3). The combined organic layers were washed with saturated brine (10 mL), dried over anhydrous sodium sulfate, filtered and concentrated. The residue was purified by silica gel column chromatography (PE) to give the title compound as a white solid (0.225 g, 61%).

MS (ESI, pos. ion) m/z: 225.0 [M+H]$^+$;
$^1$H NMR (400 MHz, CDCl$_3$) δ (ppm): 8.15-8.04 (m, 2H), 7.70 (s, 1H), 7.63-7.50 (m, 3H).

Step 2: (+/−)-trans-methyl 3-((2-chloro-6-phenylpyrimidin-4-yl)amino)bicyclo[2.2.2]octane-2-carboxylate To a solution of 2,4-dichloro-6-phenylpyrimidine (1.52 g, 6.7 mmol) and methyl (+/−)-trans-3-aminobicyclo[2.2.2]octane-2-carboxylate (1.84 g, 10.0 mmol) in N,N-dimethylformamide (10 mL) was added potassium carbonate (0.92 g, 6.7 mmol). The mixture was stirred at rt overnight. After the reaction was completed, the mixture was diluted with H$_2$O (50 mL). The mixture was extracted with ethyl acetate (40 mL×3). The combined organic layers were washed with saturated brine (50 mL), dried over anhydrous sodium sulfate, filtered and concentrated. The residue was purified by silica gel column chromatography (PE/EtOAc (v/v)=20/1-10/1) to give the title compound as a white solid (1.65 g, 66%).

MS (ESI, pos.ion) m/z: 372.2 [M+H]$^+$;
$^1$H NMR (400 MHz, CDCl$_3$) δ (ppm): 8.04-7.91 (m, 2H), 7.51-7.41 (m, 3H), 6.78 (s, 1H), 5.41 (s, 1H), 4.32 (s, 1H), 3.73 (s, 3H), 2.38 (d, J=5.1 Hz, 1H), 2.07 (s, 1H), 1.86 (m, 1H), 1.73 (m, 1H), 1.70-1.60 (m, 4H), 1.57 (m, 2H), 1.51-1.41 (m, 1H).

Step 3: (+/−)-trans-methyl 3-((2-(2-chloro-5-trityl-5H-pyrrolo[2,3-b]pyrazin-7-yl)-6-phenylpyrimidin-4-yl)amino)bicyclo[2.2.2]octane-2-carboxylate 2-chloro-7-(4,4,5,5-tetramethyl-1,3,2-dioxaborolan-2-yl)-5-trityl-5H-pyrrolo[2,3-b]pyrazine (616 mg, 0.59 mmol, 50%), K$_2$CO$_3$ (230 mg, 1.61 mmol), PdCl$_2$(dppf) (40 mg, 0.05 mmol) and (+/−)-trans-methyl 3-((2-chloro-6-phenylpyrimidin-4-yl)amino) bicyclo[2.2.2]octane-2-carboxylate (200 mg, 0.54 mmol) were mixed in a mixed solvent of 1.4-dioxane (8 mL) and H$_2$O (1 mL). The air in the mixture was exchanged with nitrogen by bubbling for 10 min. Then the mixture was sealed in a sealed tub, and stirred for 1.5 h at 110° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (163 mg, 41%).

Step 4: (+/−)-trans-methyl 3-((2-(2-chloro-5H-pyrrolo[2,3-b]pyrazin-7-yl)-6-phenylpyrimidin-4-yl)amino)bicyclo[2.2.2]octane-2-carboxylate To a solution of (+/−)-trans-methyl 3-((2-(2-chloro-5-trityl-5H-pyrrolo[2,3-b]pyrazin-7-yl)-6-phenylpyrimidin-4-yl)amino)bicyclo[2.2.2]octane-2-carboxylate (25 mg, 0.03 mmol) in dichloromethane (3 mL) were added trifluoroacetic acid ((0.26 mL, 3.42 mmol)) and triethyl silicane ((0.20 mL, 1.03 mmol). The mixture was stirred at rt overnight. The reaction was stopped, and the reaction mixture was added into saturated aqueous sodium bicarbonate (50 mL). The resulting mixture was extracted with dichloromethane (50 mL×3). The combined organic layers were washed with saturated brine (120 mL), dired over anhydrous sodium sulfate, and filtered. The filtrate was concentrated in vacuo, and the residue was purified by silica gel column chromatography (DCM/MeOH (v/v)=10/1) to give the title compound as a white solid (13 mg, 78%).

MS (ESI, pos. ion) m/z: 490.10 [M+H]$^+$.

Step 5: (+/−)-trans-3-((2-(2-chloro-5H-pyrrolo[2,3-b]pyrazin-7-yl)-6-phenylpyrimidin-4-yl)amino)bicyclo[2.2.2]octane-2-carboxylic Acid To a solution of (+/−)-trans-methyl 3-((2-(2-chloro-5H-pyrrolo[2,3-b]pyrazin-7-yl)-6-phenylpyrimidin-4-yl)amino)bicyclo[2.2.2]octane-2-carboxylate (13 mg, 0.03 mmol) in THF/MeOH (v/v=3 mL/3 mL) was added a solution of NaOH (12 mg, 0.27 mmol) in water (0.5 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1) to give the title compound as a white solid (8 mg, 63%).

MS (ESI, pos. ion) m/z: 476.10 [M+H]$^+$;
HRMS (ESI, pos. ion) m/z: 475.1649[M+H]$^+$, ($C_{25}H_{24}ClN_6O_2$)[M+H]$^+$ theoretical value: 475.1644;
$^1$H NMR (600 MHz, DMSO-$d_6$) δ (ppm): 12.75 (s, 1H), 8.65 (s, 1H), 8.38 (s, 1H), 8.18 (s, 2H), 7.57-7.48 (m, 3H), 7.44 (s, 1H), 6.82 (s, 1H), 4.58 (s, 1H), 2.10 (s, 1H), 1.97 (m, 3H), 1.82-1.33 (m, 9H).

Example 13: (2S,3S)-3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylic Acid

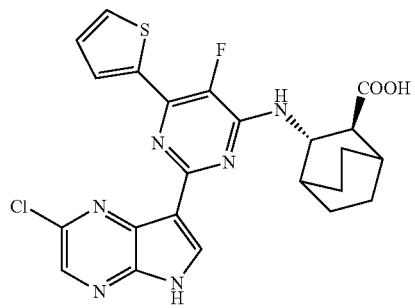 [SMILES: O=C(O)[C@H]1C2CCC(CC2)[C@@H]1Nc1nc(-c2c[nH]c3ncc(Cl)nc23)nc(-c2cccs2)c1F]

Step 1: (2S,3S)-ethyl 3-aminobicyclo[2.2.2]octane-2-carboxylate hydrochloride

The title compound was prepared according to the synthetic method disclosed in patent application WO 2015073491.

Step 2: 2,4-dichloro-5-fluoro-6-(thiophen-2-yl)pyrimidine

To a solution of thiophene (300 mg, 3.57 mmol) in anydrous tetrahydrofuran (20 mL) was added n-butyllithium (1.4 mL, 3.57 mmol, 2.5 mol/L) at −15° C., and the mixture was stirred for 1 h at −15° C. Then to the mixture was added ZnCl$_2$-TMEDA (300 mg, 1.18 mmol), and the resulting mixture was stirred for 1 h. Then palladium dichloride (65 mg, 0.36 mmol), triphenylphosphine (188 mg, 0.71 mmol) and 5-fluoro-2,4,6-trichloropyrimidine (790 mg, 3.92 mmol) were added into the mixture in turn. The resulting mixture was heated to 55° C. under nitrogen protection, and then stirred at this temperature overnight. To the reaction mixture was added water (50 mL), and the resulting mixture was extracted with ethyl acetate (50 mL×3).

The combined organic layers were washed with saturated brine (50 mL), dried over anhydrous sodium sulfate and filtered. The filtrate was concentrated in vacuo and the residue was purified by silica gel column chromatography (PE) to give the title compound as a white solid (366 mg, 41%).

MS (ESI, pos. ion) m/z: 250.9 [M+H]$^+$.

Step 3: (2S,3S)-ethyl 3-((2-chloro-5-fluoro-6-(thiophen-2-yl)pyrimidin-4-yl)amino)bicyclo[2.2.2]octane-2-carboxylate A suspension of 2,4-dichloro-5-fluoro-6-(thiophen-2-yl)pyrimidine (366 mg, 1.47 mmol), (2S,3S)-ethyl 3-aminobicyclo[2.2.2]octane-2-carboxylate hydrochloride (411 mg, 1.76 mmol) and K$_2$CO$_3$ (406 mg, 2.94 mmol) in DMF ((5 mL) was stirred at rt overnight. H$_2$O (100 mL) was added to quench the reaction, and the resulting mixture was extracted with EtOAc (80 mL×3). The combined organic layers were washed with brine (180 mL×3), dried over anhydrous Na$_2$SO$_4$, filtered, and the filtrate was concentrated in vacuo. The residue was purified by silica gel chromatograph (PE/EtOAc (v/v)=5/1) to give the tilte compound as a white solid (388 mg, 64%).

MS (ESI, pos. ion) m/z: 410.20[M+H]$^+$;
$^1$H NMR (400 MHz, CDCl$_3$) δ (ppm): 7.84 (s, 1H), 7.57 (d, J=4.8 Hz, 1H), 7.18 (t, J=4.2 Hz, 1H), 5.34 (s, 1H), 4.53 (s, 1H), 4.24 (m, 2H), 2.41 (d, J=5.5 Hz, 1H), 2.05 (d, J=10.7 Hz, 2H), 1.93-1.77 (m, 3H), 1.69 (d, J=9.2 Hz, 5H), 1.29 (t, J=5.2 Hz, 3H).

Step 4: (2S,3S)-ethyl 3-((2-(2-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate 2-Chloro-7-(4,4,5,5-tetramethyl-1,3,2-dioxaborolan-2-yl)-5-trityl-5H-pyrrolo[2,3-b]pyrazine (417 mg, 0.40 mmol, 50%), K$_2$CO$_3$ (152 mg, 1.10 mmol), PdCl$_2$(dppf) (30 mg, 0.04 mmol) and (2S,3S)-ethyl 3-((2-chloro-5-fluoro-6-(thiophen-2-yl)pyrimidin-4-yl) amino)bicyclo[2.2.2]octane-2-carboxylate (150 mg, 0.37 mmol) were mixed in a mixed solvent of 1,4-dioxane (8 mL) and H$_2$O (1 mL). The air in the mixture was exchanged with nitrogen by bubbling for 10 min. The mixture was sealed in a sealed tub, and stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (282 mg, 100%).

Step 5: (2S,3S)-ethyl 3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate (282 mg, 0.37 mmol) in DCM (5 mL) were added Et₃SiH (200 mg, 3.67 mmol) and TFA (200 mg, 3.67 mmol). The mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (120 mL), dried over anhydrous sodium sulfate, and filtered. The filtrate was concentrated in vacuo, and the residue was purified by silica gel column chromatography (DCM/MeOH (v/v)=10/1) to give the title compound as a white solid (75 mg, 39%).

MS (ESI, pos. ion) m/z: 528.05 [M+H]⁺.

Step 6: (2S,3S)-3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate (75 mg, 0.14 mmol) in THF/MeOH (v/v=5 mL/5 mL) was added a solution of NaOH (60 mg, 1.42 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (18 mg, 25%).

MS (ESI, pos. ion) m/z: 499.1 [M+H]⁺;
HRMS (ESI, pos. ion) m/z: 499.1107[M+H]⁺, (C₂₃H₂₁ClFN₆O₂S)[M+H]⁺ theoretical value: 499.1119;
¹H NMR (600 MHz, DMSO-d₆) δ (ppm): 12.76 (s, 1H), 8.52 (s, 1H), 8.38 (s, 1H), 7.89 (s, 1H), 7.86 (d, J=4.8 Hz, 1H), 7.64 (d, J=6.4 Hz, 1H), 7.32-7.26 (m, 1H), 4.67 (s, 1H), 2.85 (d, J=6.3 Hz, 1H), 2.10 (s, 1H), 2.00 (s, 2H), 1.78-1.37 (m, 8H).

Example 14: (2S,3S)-3-((2-(2-chloro-5H-pyrrolo[2,3-b]pyrazin-7-yl)thieno[2,3-d]pyrimidin-4-yl)amino)bicyclo[2.2.2]octane-2-carboxylic Acid

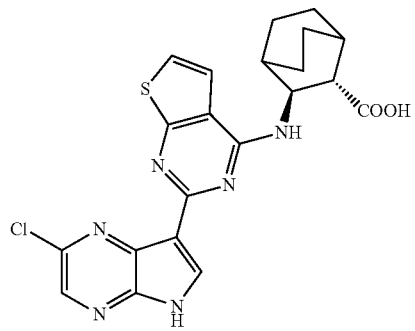 [SMILES: O=C(O)[C@H]1C2CCC(CC2)[C@@H]1Nc1nc(-c2c[nH]c3ncc(Cl)nc23)nc2sccc12]

Step 1: (2S,3S)-ethyl 3-aminobicyclo[2.2.2]octane-2-carboxylate hydrochloride

The title compound was prepared according to the synthetic method disclosed in patent application WO 2015073491.

Step 2: (2S,3S)-ethyl 3-((2-chlorothieno[2,3-d]pyrimidin-4-yl)amino)bicyclo[2.2.2]octane-2-carboxylate To a solution of 2,4-dichlorothieno[2,3-d]pyrimidine (1.01 g, 4.93 mmol), (2S,3S)-ethyl 3-aminobicyclo[2.2.2]octane-2-carboxylate hydrochloride (1.15 g, 4.93 mmol) in DMF (20 mL) was added K₂CO₃ (1.36 g, 9.84 mmol). The mixture was stirred at rt overnight. H₂O (50 mL) was added to quench the reaction, and the resulting mixture was extracted with EtOAc (50 mL×3). The combined organic layers were washed with saturated brine (150 mL×3), dried over anhydrous Na₂SO₄, filtered, and the filtrate was concentrated in vacuo. The residue was purified by silica gel chromatograph (PE/EtOAc (v/v)=5/1) to give the tilte compound as a light yellow solid (1.25 g, 69%).

MS (ESI, pos. ion) m/z: 366.00 [M+H]⁺;
¹H NMR (600 MHz, CDCl₃) δ (ppm): 7.26 (d, J=6.0 Hz, 1H), 7.16 (d, J=5.8 Hz, 1H), 4.64 (t, J=5.3 Hz, 1H), 4.25 (q, J=7.1 Hz, 2H), 2.45 (d, J=5.7 Hz, 1H), 2.03 (d, J=2.4 Hz, 1H), 1.96 (d, J=2.7 Hz, 1H), 1.89-1.82 (m, 1H), 1.75-1.63 (m, 6H), 1.46 (m, 1H), 1.28 (t, J=7.1 Hz, 4H).

Step 3: (2S,3S)-ethyl 3-((2-(2-chloro-5-trityl-5H-pyrrolo[2,3-b]pyrazin-7-yl)thieno[2,3-d]pyrimidin-4-yl)amino)bicyclo[2.2.2]octane-2-carboxylate 2-Chloro-7-(4,4,5,5-tetramethyl-1,3,2-dioxaborolan-2-yl)-5-trityl-5H-pyrrolo[2,3-b]pyrazine (1.15 g, 1.10 mmol, 50%), K₂CO₃ (395 mg, 2.86 mmol), Pd(OAc)₂ (38 mg, 0.17 mmol), X-Phos (159 mg, 0.40 mmol) and (2S,3S)-ethyl 3-((2-chlorothieno[2,3-d]pyrimidin-4-yl) amino)bicyclo [2.2.2]octane-2-carboxylate (300 mg, 0.82 mmol) were mixed in a mixed solvent of 1,4-dioxane (10 mL) and H₂O (0.5 mL). The air in the mixture was exchanged with nitrogen by bubbling for 10 min. The mixture was sealed in a sealed tub, and stirred overnight at 115° C. The mixture was filtered to remove the solid impuries, and the filtrate was concentrated to remove the solvent. The residue was purified by silica gel column chromatography (PE/EtOAc (v/v)=10/1) to give the title compound as light yellow oil (258 mg, 44%).

¹H NMR (400 MHz, DMSO-d₆) δ (ppm): 8.47 (s, 1H), 8.12 (s, 1H), 7.66 (d, J=6.2 Hz, 1H), 7.50 (d, J=5.9 Hz, 1H), 7.38-7.31 (m, 9H), 7.21 (d, J=7.5 Hz, 6H), 4.70 (s, 1H), 4.03 (m, 2H), 3.44 (s, 1H), 3.31 (s, 1H), 2.77 (m, 1H), 1.88 (s, 1H), 1.71 (m, 2H), 1.51 m, 3H), 1.41 (m, 3H), 1.17 (t, J=7.1 Hz, 4H).

Step 4: (2S,3S)-ethyl 3-((2-(2-chloro-5H-pyrrolo[2,3-b]pyrazin-7-yl)thieno[2,3-d]pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)thieno[2,3-d]pyrimidin-4-yl)amino)bicyclo[2.2.2]octane-2-carboxylate (258 mg, 0.36 mmol) in DCM (8 mL) were added Et₃SiH (0.70 mL, 1.63 mmol) and TFA (0.12 ml, 1.63 mmol). The mixture was stirred at rt overnight. The reaction was stopped, and the reaction mixture was added into saturated aqueous sodium bicarbonate (20 mL). The resulting mixture was extracted with dichloromethane (20 mL×3). The combined organic layers were washed with saturated brine (50 mL), dried over anhydrous sodium sulfate, and filtered. The filtrate was concentrated in vacuo, and the residue was purified by silica gel column chromatography (PE/EtOAc (v/v)=3/1) to give the title compound as light yellow oil (48 mg, 9%).

MS (ESI, pos. ion) m/z: 483.15 [M+H]$^+$.

Step 5: (2S,3S)-3-((2-(2-chloro-5H-pyrrolo[2,3-b]pyrazin-7-yl)thieno[2,3-d]pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl) thieno[2,3-d]pyrimidin-4-yl)amino)bicyclo[2.2.2]octane-2-carboxylate (48 mg, 0.01 mmol) in THF/MeOH/H$_2$O (v/v/v=2 mL/2 mL/2 mL) was added a solution of NaOH (0.52 g, 12.78 mmol) in water (1 mL). The mixture was stirred at rt overnight, then diluted with saturated brine (20 mL). The resulting mixture was acidified with hydrochloric acid (1 M) to pH about 6. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by preparative thin-layer chromatography (DCM/MeOH (v/v)=15/1) to give the title compound as a light yellow solid (12 mg, 26%).

MS (ESI, pos. ion) m/z: 455.0 [M+H]$^+$;
$^1$H NMR (400 MHz, DMSO-d$_6$) δ (ppm): 12.77 (s, 1H), 8.60 (s, 1H), 8.37 (s, 1H), 7.73 (d, J=6.0 Hz, 1H), 7.65 (d, J=6.4 Hz, 1H), 7.49 (d, J=5.9 Hz, 1H), 4.80 (s, 1H), 2.77 (d, J=7.0 Hz, 1H), 2.13 (s, 1H), 2.03-1.96 (m, 2H), 1.76 (m, 2H), 1.58 (m, 3H), 1.49-1.35 (m, 3H).

Example 15: (2S,3S)-3-((6-(benzo[b]thiophen-2-yl)-2-(2-chloro-5H-pyrrolo[2,3-b]pyrazin-7-yl)pyrimidin-4-yl)amino)bicyclo[2.2.2]octane-2-carboxylic Acid

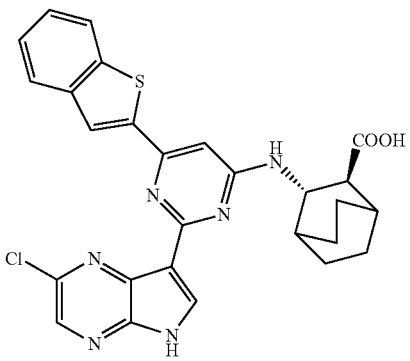 [SMILES: O=C(O)[C@H]1C2CCC(CC2)[C@@H]1Nc1cc(-c2cc3ccccc3s2)nc(-c2c[nH]c3ncc(Cl)nc23)n1]

Step 1: (2S,3S)-ethyl 3-aminobicyclo[2.2.2]octane-2-carboxylate hydrochloride

The title compound was prepared according to the synthetic method disclosed in patent application WO 2015073491.

Step 2: 4-(benzo[b]thiophen-2-yl)-2,6-dichloropyrimidine

A suspension of benzo[b]thiophen-2-ylboronic acid (485 mg, 2.73 mmol), bis(triphenylphosphine)palladium(II) chloride (383 mg, 0.54 mmol), 2,4,6-trichloropyrimidine (0.50 g, 2.73 mmol) and sodium carbonate (867 mg, 8.18 mmol) in a mixture of THF (15 mL) and water (5 mL) were refluxed for 4 hours under nitrogen protection. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a light yellow solid (500 mg, 65%).

MS (ESI, pos.ion) m/z: 281.0 [M+H]$^+$.

Step 3: (2S,3S)-ethyl 3-((6-(benzo[b]thiophen-2-yl)-2-chloropyrimidin-4-yl)amino)bicyclo[2.2.2]octane-2-carboxylate (2S,3S)-ethyl 3-aminobicyclo[2.2.2]octane-2-carboxylate hydrochloride (498 mg, 2.13 mmol) and 4-(benzo[b]thiophen-2-yl)-2,6-dichloropyrimidine (500 mg, 1.77 mmol) were dissolved in DMF (10 mL), then potassium carbonate (740 mg, 5.33 mmol) was added. The mixture was heated and stirred at 80° C. overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a light yellow solid (520 mg, 66%).

Step 4: (2S,3S)-ethyl 3-((6-(benzo[b]thiophen-2-yl)-2-(2-chloro-5-trityl-5H-pyrrolo[2,3-b]pyrazin-7-yl)pyrimidin-4-yl)amino)bicyclo[2.2.2]octane-2-carboxylate To a mixed solvent of 1,4-dioxane (10 mL) and H$_2$O (0.5 mL) was added 2-chloro-7-(4,4,5,5-tetramethyl-1,3,2-dioxaborolan-2-yl)-5-trityl-5H-pyrrolo[2,3-b]pyrazine (326 mg, 0.40 mmol, 60%), K$_2$CO$_3$(187 mg, 1.35 mmol), PdCl$_2$(dppf) (26 mg, 0.03 mmol) and (2S,3S)-ethyl 3-((6-(benzo[b]thiophen-2-yl)-2-chloropyrimidin-4-yl) amino)bicyclo[2.2.2]octane-2-carboxylate (150 mg, 0.33 mmol). The air in the mixture was exchanged with nitrogen by bubbling for 10 min. The mixture in the sealed tub was stirred for 1.5 h at 110° C. The mixture was filtered to remove the solid impuries, and the solvent was removed. The residue was purified by silica gel column chromatography (PE/EtOAc (v/v)=10/1-5/1) to give the title compound as a white solid (83 mg, 30%).

Step 5: (2S,3S)-ethyl 3-((6-(benzo[b]thiophen-2-yl)-2-(2-chloro-5H-pyrrolo[2,3-b]pyrazin-7-yl)pyrimidin-4-yl) amino)bicyclo[2.2.2]octane-2-carboxylate To a solution of (2S,3S)-ethyl 3-((6-(benzo[b]thiophen-2-yl)-2-(2-chloro-5-trityl-5H-pyrrolo[2,3-b]pyrazin-7-yl) pyrimidin-4-yl) amino)bicyclo[2.2.2]octane-2-carboxylate (150 mg, 0.18 mmol) in DCM (5 mL) were added triethyl silicane (0.38 mL, 4.95 mmol) and trifluoacetic acid (0.80 mL, 4.95 mmol), and the mixture was stirred at rt overnight. The reaction was stopped, and the reaction mixture was added into saturated aqueous sodium bicarbonate (100 mL). The resulting mixture was extracted with dichloromethane (50 mL×3). The combined organic layers were washed with saturated brine (120 mL), dried over anhydrous sodium sulfate, and filtered. The filtrate was concentrated in vacuo, and the residue was purified by silica gel column chromatography (DCM/MeOH (v/v)=10/1) to give the title compound as a yellow solid (53 mg, 50%).

MS (ESI, pos. ion) m/z: 559.2 [M+H]$^+$.

Step 6: (2S,3S)-3-((6-(benzo[b]thiophen-2-yl)-2-(2-chloro-5H-pyrrolo[2,3-b]pyrazin-7-yl)pyrimidin-4-yl)amino)bicyclo[2.2.2]octane-2-carboxylic Acid To a solution of (2S,3S)-ethyl 3-((6-(benzo[b]thiophen-2-yl)-2-(2-chloro-5H-pyrrolo[2,3-b]pyrazin-7-yl)pyrimidin-4-yl) amino)bicyclo[2.2.2]octane-2-carboxylate (53 mg, 0.09 mmol) in THF/MeOH (v/v=5 mL/5 mL) was added a solution of NaOH (37 mg, 0.94 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (25 mg, 49%).

MS (ESI, pos.ion) m/z: 531.2 [M+H]$^+$;
HRMS (ESI, pos. ion) m/z: 531.1361 [M+H]$^+$, (C$_{27}$H$_{24}$ClN$_6$O$_2$S)[M+H]$^+$ theoretical value: 531.1370;
$^1$H NMR (400 MHz, DMSO-d$_6$) δ (ppm): 13.32 (s, 1H), 8.82 (s, 1H), 8.50 (d, J=9.8 Hz, 1H), 8.24 (s, 1H), 8.09 (s, 1H), 7.99 (s, 1H), 7.48 (d, J=3.7 Hz, 2H), 6.95 (s, 1H), 4.65 (s, 1H), 2.56 (s, 1H), 2.04 (m, 2H), 1.76 (m, 3H), 1.60-1.42 (m, 5H).

Example 16: (2S,3S)-3-((2-(2-chloro-5H-pyrrolo[2,3-b]pyrazin-7-yl)-6-(thiophen-2-yl)pyrimidin-4-yl)amino)bicyclo[2.2.2]octane-2-carboxylic Acid

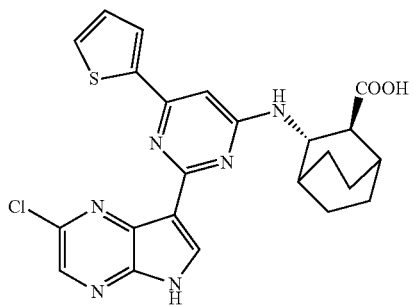 [SMILES: O=C(O)[C@H]1C2CCC(CC2)[C@@H]1Nc1cc(-c2cccs2)nc(-c2c[nH]c3ncc(Cl)nc23)n1]

Step 1: (2S,3S)-ethyl 3-aminobicyclo[2.2.2]octane-2-carboxylate hydrochloride

The title compound was prepared by the synthetic method disclosed in patent application WO 2015073491.

Step 2: 2,4-dichloro-6-(thiophen-2-yl)pyrimidine

To a solution of thiophene (500 mg, 5.94 mmol) in anydrous tetrahydrofuran (20 mL) was added n-butyllithium (2.4 mL, 6.0 mmol, 2.5 mol/L) at −15° C., and the mixture was stirred for 1 h at −15° C. Then to the mixture was added dichloro(N,N,N',N'-tetramethylethylenediamine) zinc(II) (495 mg, 1.96 mmol), and the resulting mixture was stirred for 1 h. Then palladium dichloride (105 mg, 0.59 mmol), triphenylphosphine (658 mg, 1.19 mmol) and 2,4,6-trichloropyrimidine (1.09 g, 5.94 mmol) were added to the mixture in turn. The resulting mixture was heated to 55° C. under nitrogen protection, and then stirred at this temperature overnight. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a white solid (616 mg, 45%).

MS (ESI, pos.ion) m/z: 230.2 [M+H]$^+$;
$^1$H NMR (400 MHz, CDCl$_3$) δ (ppm): 7.86 (d, J=3.7 Hz, 1H), 7.66 (d, J=4.9 Hz, 1H), 7.51 (s, 1H), 7.24-7.17 (m, 1H).

Step 3: (2S,3S)-ethyl 3-((2-chloro-6-(thiophen-2-yl)pyrimidin-4-yl)amino)bicyclo[2.2.2]octane-2-carboxylate (2S,3S)-Ethyl 3-aminobicyclo[2.2.2]octane-2-carboxylate hydrochloride (362 mg, 1.55 mmol) and 2,4-dichloro-6-(thiophen-2-yl)pyrimidine (300 mg, 1.29 mmol) were dissolved in DMF (6 mL), then potassium carbonate (538 mg, 3.89 mmol) was added. The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (330 mg, 64%).

MS (ESI, pos.ion) m/z: 392.2 [M+H]+.

Step 4: (2S,3S)-ethyl 3-((2-bromo-6-(thiophen-2-yl)pyrimidin-4-yl)amino)bicyclo[2.2.2]octane-2-carboxylate To a reaction flask were added (2S,3S)-ethyl 3-((2-chloro-6-(thiophen-2-yl) pyrimidin-4-yl)amino)bicyclo[2.2.2]octane-2-carboxylate (100 mg, 0.26 mmol) and a solution of hydrobromic acid in acetic acid (5 mL, 30.00 mmol, 33%), and the reaction mixture was stirred at rt for 1 h. The reaction mixture was cooled to 0° C., and to the reaction mixture was added water (30 mL), and the resulting mixture was extracted with ethyl acetate (20 mL×3). The combined organic layers were washed with saturated brine (30 mL), dried over anhydrous sodium sulfate and filtered. The filtrate was concentrated in vacuo to give the title compound as a light yellow solid (108 mg, 97%).

MS (ESI, pos.ion) 436.1[M+H]$^+$.

Step 5: (2S,3S)-ethyl 3-((2-(2-chloro-5-trityl-5H-pyrrolo[2,3-b]pyrazin-7-yl)-6-(thiophen-2-yl)pyrimidin-4-yl)amino)bicyclo[2.2.2]octane-2-carboxylate To a mixed solvent of 1,4-dioxane (10 mL) and H$_2$O ((0.5 mL) were added 2-chloro-7-(4,4,5,5-tetramethyl-1,3,2-dioxaborolan-2-yl)-5-trityl-5H-pyrrolo[2,3-b]pyrazine (258 mg, 0.29 mmol, 60%), K$_2$CO$_3$(136 mg, 0.99 mmol), Pd(dppf)Cl$_2$ (26 mg, 0.03 mmol) and (2S,3S)-ethyl 3-((2-bromo-6-(thiophen-2-yl)pyrimidin-4-yl)amino)bicyclo[2.2.2]octane-2-carboxylate (108 mg, 0.24 mmol). The air in the mixture was exchanged with nitrogen by bubbling for 10 min. The mixture in the sealed tub was stirred for 1.5 h at 110° C. The mixture was filtered to remove the solid impurities, and the filtrate was concentrated to remove the solvent. The residue was purified by silica gel column chromatography (PE/EtOAc (v/v)=10/1-5/1) to give the title compound as a white solid (53 mg, 28%).

Step 6: (2S,3S)-ethyl 3-((2-(2-chloro-5H-pyrrolo[2,3-b]pyrazin-7-yl)-6-(thiophen-2-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-6-(thiophen-2-yl)pyrimidin-4-yl)amino)bicyclo[2.2.2]octane-2-carboxylate (53 mg, 0.07 mmol) in dichloromethane (5 mL) were added trifluoroacetic acid ((0.80 mL, 4.95 mmol) and triethyl silicane (0.38 mL, 4.95 mmol), and the mixture was stirred at rt overnight. The reaction was stopped, and the reaction mixture was added into saturated aqueous sodium carbonate (100 mL), and the resulting mixture was extracted with dichloromethane (50 mL×3). The combined organic layers were washed with saturated brine (100 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (20 mg, 55%).

MS (ESI, pos.ion) m/z: 509.2 [M+H]$^+$.

Step 7: (2S,3S)-3-((2-(2-chloro-5H-pyrrolo[2,3-b]pyrazin-7-yl)-6-(thiophen-2-yl)pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-6-(thiophen-2-yl)pyrimidin-4-yl)amino)bicyclo[2.2.2]octane-2-carboxylate (20 mg, 0.04 mmol) in THF/MeOH (v/v=5 mL/3 mL) was added a solution of NaOH (15 mg, 0.40 mmol) in water (1 mL). The mixture was stirred at rt overnight. The reaction mixture was diluted with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (13 mg, 68%).

MS (ESI, pos. ion) m/z: 481.1 [M+H]$^+$;

HRMS (ESI, pos. ion) m/z: 481.1183 [M+H]$^+$, (C$_{23}$H$_{22}$ClN$_6$O$_2$S)[M+H]$^+$ theoretical value: 481.1213;

$^1$H NMR (400 MHz, DMSO-d$_6$) δ (ppm): 13.43 (s, 1H), 8.83 (s, 1H), 8.55 (s, 1H), 7.95 (s, 1H), 7.37 (s, 1H), 6.85 (s, 1H), 4.63 (s, 1H), 2.00 (s, 2H), 1.85 (d, J=12.0 Hz, 3H), 1.69 (s, 1H), 1.58 (s, 3H), 1.45 (d, J=11.5 Hz, 2H).

Example 17: (R)-3-((2-(2-chloro-5H-pyrrolo[2,3-b]pyrazin-7-yl)-7-methyl-7H-pyrrolo[2,3-d]pyrimidin-4-yl)amino)-4,4-dimethylpentanoic Acid

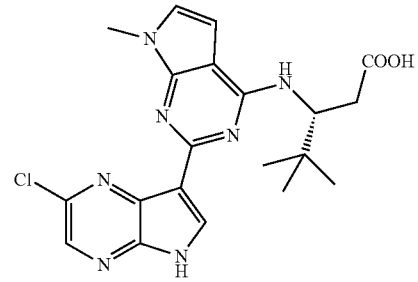 [SMILES: Cn1ccc2c(N[C@H](CC(=O)O)C(C)(C)C)nc(-c3c[nH]c4ncc(Cl)nc34)nc21]

Step 1: 2,4-dichloro-7-methyl-7H-pyrrolo[2,3-d]pyrimidine

A 0° C. solution of 2,4-dichloro-7H-pyrrolo[2,3-d]pyrimidine (1.00 g, 5.32 mmol) in THF (8 mL) was stirred at 0° C. for 5 min. Then sodium hydride (255 mg, 6.38 mmol) was added. The resulting mixture was stirred for 15 min, then iodomethane (8.50 g, 53.20 mmol) was added. The reaction mixture was warmed to rt and stirred overnight. To the reaction mixture was added water (60 mL) to quench the reaction, and the resulting mixture was extracted with ethyl acetate (50 mL×3). The combined organic layers were washed with saturated brine (80 mL), dried over anhydrous sodium sulfate and filtered. The filtrate was concentrated and the residue was purified by silica gel column chromatography (PE/EtOAc (v/v)=10/1) to give the title compound as a white solid (1.00 g, 93%).

MS (ESI, pos. ion) m/z: 202.0[M+H]$^+$.

Step 2: (R)-methyl 3-((2-chloro-7-methyl-7H-pyrrolo[2,3-d]pyrimidin-4-yl)amino)-4,4-dimethylpentanoate To a solution of 2,4-dichloro-7-methyl-7H-pyrrolo[2,3-d]pyrimidine (1.06 g, 5.25 mmol) in DMF (10 mL) were added (R)-methyl 3-amino-4,4-dimethylpentanoate (913 mg, 5.73 mmol) and K$_2$CO$_3$ (1.45 g, 10.50 mmol). The mixture was stirred at 70° overnight. After the reaction was completed, to the reaction mixture was added water (50 mL), and the resulting mixture was extracted with ethyl acetate (60 mL×3). The combined organic layers were washed with saturated brine (150 mL×3), dried over anydrous sodium sulfate and filtered. The solvent in the filtrate was removed and the residue was purified by silica gel column chromatography (PE/EtOAc (v/v)=10/1) to give the title compound as a light yellow solid (315 mg, 18%).

MS (ESI, pos. ion) m/z: 325.2 [M+H]$^+$;

$^1$H NMR (400 MHz, CDCl$_3$) δ (ppm): 6.88 (s, 1H), 5.45 (s, 1H), 4.74 (s, 1H), 3.76 (s, 3H), 3.60 (s, 3H), 2.74 (dd, J=14.8, 4.0 Hz, 1H), 2.47 (dd, J=14.8, 8.8 Hz, 1H), 1.71 (s, 1H), 1.01 (s, 9H).

Step 3: (R)-methyl 3-((2-bromo-7-methyl-7H-pyrrolo[2,3-d]pyrimidin-4-yl)amino)-4,4-dimethylpentanoate To a solution of hydrobromic acid in acetic acid (1M, 10 mL) was added (R)-methyl 3-((2-chloro-7-methyl-7H-pyrrolo[2,3-d]pyrimidin-4-yl)amino)-4,4-dimethylpentanoate (0.37 g, 1.14 mmol). The mixture was stirred at rt for 2 h. The reaction mixture was added slowly into ice-water (100 mL), and the resulting mixture was extracted with EtOAc (100 mL×3). The combined organic layers were washed with saturated aqueous sodium bicarbonate (300 mL×3), dried over anhydrous Na$_2$SO$_4$, and filtered. The solvent in the filtrate was removed to give the title compound as light yellow oil (325 mg, 77%).

MS (ESI, pos. ion) m/z: 369.2 [M+H]$^+$.

Step 4: (R)-methyl 3-((2-(2-chloro-5-trityl-5H-pyrrolo[2,3-b]pyrazin-7-yl)-7-methyl-7H-pyrrolo[2,3-d]pyrimidin-4-yl) amino)-4,4-dimethylpentanoate To a mixed solvent of 1,4-dioxane (10 mL) and H$_2$O (0.5 mL) were added 2-chloro-7-(4,4,5,5-tetramethyl-1,3,2-dioxaborolan-2-yl)-5-trityl-5H-pyrrolo[2,3-b]pyrazine (0.39 g, 0.45 mmol, 60%), K$_2$CO$_3$ (197 mg, 1.42 mmol), Pd(dppf)Cl$_2$ (60 mg, 0.08 mmol) and (R)-methyl 3-((2-bromo-7-methyl-7H-pyrrolo[2,3-d]pyrimidin-4-yl)amino)-4,4-dimethylpentanoate (150 mg, 0.41 mmol). The air in the mixture was exchanged with nitrogen by bubbling for 10 min. The mixture in the sealed tub was stirred for 4 h at 115° C. The mixture was filtered to remove the solid impurity, and the filtrate was concentrated to remove the solvent. The residue was purified by silica gel column chromatography (PE/EtOAc (v/v)=10/1) to give the title compound as light yellow oil (140 mg, 50%).

Step 5: (R)-methyl 3-((2-(2-chloro-5H-pyrrolo[2,3-b]pyrazin-7-yl)-7-methyl-7H-pyrrolo[2,3-d]pyrimidin-4-yl)amino)-4,4-dimethylpentanoate To a solution of (R)-methyl 3-((2-(2-chloro-5-trityl-5H-pyrrolo[2,3-b]pyrazin-7-yl)-7-methyl-7H-pyrrolo[2,3-d]pyrimidin-4-yl)amino)-4,4-dimethylpentanoate (140 mg, 0.20 mmol) in DCM (8 mL) were added Et$_3$SiH (0.40 mL, 2.52 mmol) and TFA (0.19 mL, 2.70 mmol). The mixture was stirred at rt overnight. The reaction was stopped, and the reaction mixture was added into saturated aqueous sodium bicarbonate (30 mL). The resulting mixture was extracted with dichloromethane (30 mL×3). The combined organic layers were washed with saturated brine (80 mL), dried over anhydrous sodium sulfate, and filtered. The filtrate was concentrated in vacuo, and the residue was purified by silica gel column chromatography (DCM/EtOAc (v/v)=1/1) to give the title compound as light yellow oil (71 mg, 79%).

MS (ESI, pos. ion) m/z: 442.20 [M+H]$^+$.

Step 6: (R)-3-((2-(2-chloro-5H-pyrrolo[2,3-b]pyrazin-7-yl)-7-methyl-7H-pyrrolo[2,3-d]pyrimidin-4-yl)amino)-4,4-dimethylpentanoic Acid To a solution of (R)-methyl 3-((2-(2-chloro-5H-pyrrolo[2,3-b]pyrazin-7-yl)-7-methyl-7H-pyrrolo[2,3-d]pyrimidin-4-yl)amino)-4,4-dimethylpentanoate (71 mg, 0.16 mmol) in THF/MeOH/H$_2$O (v/v/v=2 mL/2 mL/2 mL) was added a solution of NaOH (64 mg, 1.60 mmol) in water (1 mL). The mixture was stirred at rt overnight, then saturated brine (20 mL) was added. The resulting mixture was acidified with diluted hydrochloric acid (1 M) to pH about 6. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by preparative thin-layer chromatography (DCM/MeOH (v/v)=15/1) to give the title compound as a light yellow solid (22 mg, 32%).

MS (ESI, pos.ion) m/z: 428.15 [M+H]$^+$;
HRMS (ESI, pos. ion) m/z: 428.1613[M+H]$^+$, (C$_{20}$H$_{23}$ClN$_7$O$_2$)[M+H]$^+$ theoretical value: 428.1602;
$^1$H NMR (400 MHz, DMSO-d$_6$) δ (ppm): 12.60 (s, 1H), 8.50 (s, 1H), 8.34 (s, 1H), 7.08 (s, 1H), 7.06 (d, J=3.0 Hz, 1H), 6.68 (d, J=3.3 Hz, 1H), 5.06 (s, 1H), 3.75 (s, 3H), 2.63 (m, 1H), 2.48-2.41 (m, 1H), 1.03 (s, 9H).

Example 18: (2S,3S)-3-((6-(benzo[b]thiophen-2-yl)-5-fluoro-2-(5H-pyrrolo[2,3-b]pyrazin-7-yl)pyrimidin-4-yl)amino)bicyclo[2.2.2]octane-2-carboxylic Acid

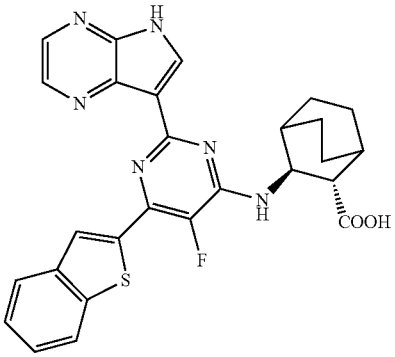 [SMILES: O=C(O)[C@H]1C2CCC(CC2)[C@@H]1Nc1nc(-c2c[nH]c3nccnc23)nc(-c2cc3ccccc3s2)c1F]

Step 1: 7-iodo-5H-pyrrolo[2,3-b]pyrazine

To a solution of 5H-pyrrolo[2,3-b]pyrazine (500 mg, 4.20 mmol) in 2-methyltetrahydrofuran (8 mL) was added NIS (1.13 g, 5.04 mmol), and the reaction mixture was stirred at rt overnight. Saturated aqueous sodium thiosulfate (50 mL) was added to quench the reaction, and the resulting mixture was partitioned. The aqueous layer was extracted with EtOAc (50 mL×2). The combined organic phases were washed with saturated brine (80 mL), dried over anhydrous sodium sulfate, filtered, and the filtrate was concentrated in vacuo. The residue was purified by silica gel chromatograph (PE/EtOAc (v/v)=20/1-4/1) to give the title compound as a yellow solid (965 mg, 94%).

MS (ESI, pos. ion) m/z: 246.0 [M+H]$^+$;
$^1$H NMR (600 MHz, DMSO-d$_6$) δ (ppm): 12.51 (s, 1H), 8.46 (d, J=2.5 Hz, 1H), 8.29 (d, J=2.5 Hz, 1H), 8.11 (d, J=2.5 Hz, 1H).

Step 2: 7-iodo-5-trityl-5H-pyrrolo[2,3-b]pyrazine

To a stirred 0° C. solution of 7-iodo-5H-pyrrolo[2,3-b]pyrazine (937 mg, 3.82 mmol) in DMF (8 mL) was added slowly NaH (185 mg, 4.59 mmol, 60%), then triphenylchloromethane (1.18 g, 4.21 mmol) was added. The resulting mixture was warmed to rt and stirred overnight. The reaction was stopped, and the reaction mixture was added into water (100 mL). The resulting mixture was extracted with ethyl acetate (100 mL×3). The combined organic layers were washed with saturated brine (120 mL×3), dried over anhydrous sodium sulfate, and filtered. The filtrate was concentrated in vacuo, and the residue was purified by silica gel column chromatography (PE/EA (v/v)=20/1) to give the title compound as a light yellow solid (1.55 g, 83%).

¹H NMR (400 MHz, CDCl₃) δ (ppm): 8.40 (d, J=2.5 Hz, 1H), 7.98 (d, J=2.5 Hz, 1H), 7.65 (s, 1H), 7.34-7.29 (m, 10H), 7.20-7.17 (m, 5H).

Step 3: 7-(4,4,5,5-tetramethyl-1,3,2-dioxaborolan-2-yl)-5-trityl-5H-pyrrolo[2,3-b]pyrazine A solution of 7-iodo-5-trityl-5H-pyrrolo[2,3-b]pyrazine (500 mg, 1.03 mmol) and isopropoxyboronic acid pinacol ester (250 mg, 1.33 mmol) in THF (10 mL) was cooled to −27° C. under nitrogen protection, then isopropylmagnesium chloride solution (2 M, 0.70 mL) was added dropwise. After the addition, the mixture was stirred at −27° C. for 1.5 h. The reaction was stopped, and the reaction mixture was added into saturated aqueous sodium bicarbonate (100 mL). The resulting mixture was extracted with ethyl acetate (100 mL×3). The combined organic layers were concentrated in vacuo, and the residue was purified by silica gel column chromatography (PE/EtOAc (v/v)=10/1) to give the title compound as a yellow solid (383 mg, 77%).
MS (ESI, pos. ion) m/z: 488.3 [M+H]⁺.

Step 4: (2S,3S)-ethyl 3-aminobicyclo[2.2.2]octane-2-carboxylate hydrochloride

The title compound was prepared according to the synthetic method disclosed in patent application WO 2015073491.

Step 5: (2S,3S)-ethyl 3-((2,6-dichloro-5-fluoropyrimidin-4-yl)amino)bicyclo[2.2.2]octane-2-carboxylate A suspension of 2,4,6-trichloro-5-fluoropyrimidine (2.34 g, 11.70 mmol), (2S,3S)-ethyl 3-aminobicyclo[2.2.2]octane-2-carboxylate hydrochloride (2.48 g, 10.60 mmol) and K₂CO₃ (2.95 g, 21.30 mmol) in DMF (5 mL) was stirred at rt overnight. To the reaction mixture was added water (60 mL) to quench the reaction, and the resulting mixture was extracted with ethyl acetate (50 mL×3). The combined organic layers were washed with saturated brine (80 mL×3), dried over anhydrous sodium sulfate and filtered. The filtrate was concentrated in vacuo and the residue was purified by silica gel column chromatography (PE/EtOAc (v/v)=5/1) to give the title compound as a white solid (2.22 g, 58%).
MS (ESI, pos. ion) m/z: 349.15 [M+H]⁺.

Step 6: (2S,3S)-ethyl 3-((6-(benzo[b]thiophen-2-yl)-2-chloro-5-fluoropyrimidin-4-yl)amino)bicyclo[2.2.2]octane-2-carboxylate The title compound was prepared according to the method described in step 1 of example 7, using benzo[b]thiophen-2-ylboronic acid (770 mg, 4.30 mmol), K₂CO₃ (1.80 g, 13.00 mmol), Pd(dppf)Cl₂ (110 mg, 0.43 mmol), (2S,3S)-ethyl 3-((2,6-dichloro-5-fluoropyrimidin-4-yl)amino) bicyclo[2.2.2]octane-2-carboxylate (1.50 g, 4.30 mmol), and solvent comprising tetrahydrofuran (8 mL) and H₂O (1 mL). The title compound prepared was a white solid (840 mg, 42%).
MS (ESI, pos. ion) m/z: 461.25 [M+H]⁺;
¹H NMR (400 MHz, CDCl₃) δ (ppm): 8.07 (s, 1H), 7.89 (d, J=7.1 Hz, 1H), 7.87-7.85 (m, 1H), 7.43-7.39 (m, 2H), 5.42 (d, J=4.6 Hz, 1H), 4.57 (d, J=5.5 Hz, 1H), 4.28-4.24 (m, 2H), 2.43 (d, J=5.8 Hz, 1H), 2.05 (d, J=2.5 Hz, 1H), 1.94 (d, J=2.6 Hz, 1H), 1.76-1.64 (m, 8H), 1.30-1.27 (m, 3H).

Step 7: (2S,3S)-ethyl 3-((6-(benzo[b]thiophen-2-yl)-5-fluoro-2-(5-trityl-5H-pyrrolo[2,3-b]pyrazin-7-yl)pyrimidin-4-yl)amino)bicyclo[2.2.2]octane-2-carboxylate To a mixed solvent of 1,4-dioxane (8 mL) and H₂O (1 mL) were added 7-(4,4,5,5-tetramethyl-1,3,2-dioxaborolan-2-yl)-5-trityl-5H-pyrrolo[2,3-b]pyrazine (225 mg, 0.46 mmol, 60%), K₂CO₃ (175 mg, 1.25 mmol), Pd(dppf)Cl₂ (34 mg, 0.04 mmol) and (2S,3S)-ethyl 3-((6-(benzo[b]thiophen-2-yl)-2-chloro-5-fluoropyrimidin-4-yl) amino) bicyclo [2.2.2]octane-2-carboxylate (210 mg, 0.42 mmol). The air in the mixture was exchanged with nitrogen by bubbling for 10 min. The mixture in the sealed tub was stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (161 mg, 49%).

Step 8: (2S,3S)-ethyl 3-((6-(benzo[b]thiophen-2-yl)-5-fluoro-2-(5H-pyrrolo[2,3-b]pyrazin-7-yl)pyrimidin-4-yl)amino)bicyclo[2.2.2]octane-2-carboxylate To a solution of (2S,3S)-ethyl 3-((6-(benzo[b]thiophen-2-yl)-5-fluoro-2-(5-trityl-5H-pyrrolo[2,3-b]pyrazin-7-yl) pyrimidin-4-yl) amino)bicyclo[2.2.2]octane-2-carboxylate (66 mg, 0.08 mmol) in DCM (5 mL) were added Et₃SiH (0.14 mL, 0.84 mmol) and trifluoacetic acid (0.07 mL, 0.84 mmol), and the mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (43 mg, 94%).
MS (ESI, pos. ion) m/z: 543.3 [M+H]⁺.

Step 9: (2S,3S)-3-((6-(benzo[b]thiophen-2-yl)-5-fluoro-2-(5H-pyrrolo[2,3-b]pyrazin-7-yl)pyrimidin-4-yl)amino)bicyclo[2.2.2]octane-2-carboxylic Acid To a solution of (2S,3S)-ethyl 3-((6-(benzo[b]thiophen-2-yl)-5-fluoro-2-(5H-pyrrolo[2,3-b]pyrazin-7-yl)pyrimidin-4-yl)amino)bicyclo[2.2.2]octane-2-carboxylate (43 mg, 0.08 mmol) in THF/MeOH (v/v=5 mL/5 mL) was added a solution of NaOH (31 mg, 0.77 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (16 mg, 40%).
MS (ESI, pos.ion) 515.2 [M+H]⁺;
HRMS (ESI, pos. ion) m/z: 515.1663[M+H]⁺, ($C_{27}H_{24}FN_6O_2S$)[M+H]⁺ theoretical value: 515.1665);
¹H NMR (600 MHz, DMSO-d₆) δ (ppm): 12.48 (s, 1H), 8.59 (s, 1H), 8.46 (s, 1H), 8.31 (s, 1H), 8.20 (s, 1H), 8.08 (d, J=4.9 Hz, 1H), 8.03 (d, J=4.9 Hz, 1H), 7.71 (d, J=6.1 Hz, 1H), 7.46 (d, J=3.5 Hz, 2H), 4.68 (s, 1H), 2.88 (d, J=6.7 Hz, 1H), 2.13 (s, 1H), 2.01 (s, 1H), 1.99 (s, 1H), 1.94-1.40 (m, 8H).

Example 19: (2S,3S)-ethyl 3-((2-(2-chloro-5H-pyrrolo[2,3-b]pyrazin-7-yl)-7-isopropyl-7H-pyrrolo[2,3-d]pyrimidin-4-yl)amino)bicyclo[2.2.2]octane-2-carboxylate

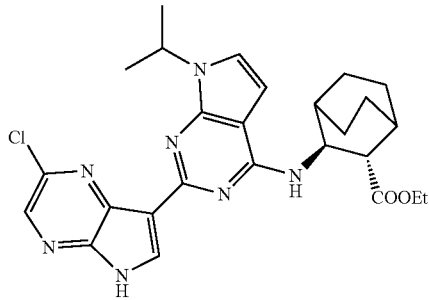 [SMILES: CCOC(=O)[C@H]1C2CCC(CC2)[C@@H]1Nc1nc(-c2c[nH]c3ncc(Cl)nc23)nc2c1ccn2C(C)C]

Step 1: (2S,3S)-ethyl 3-aminobicyclo[2.2.2]octane-2-carboxylate hydrochloride

The title compound was prepared by the synthetic method disclosed in patent application WO 2015073491.

Step 2: 2,4-dichloro-7-isopropyl-7H-pyrrolo[2,3-d]pyrimidine

To a solution of 2,4-dichloro-7H-pyrrolo[2,3-d]pyrimidine (500 mg, 2.66 mmol) in DMF (5 mL) was added NaH (130 mg, 3.19 mmol, 60%) at 0° C., and the mixture was stirred at this temperature for 30 min. Then 2-iodopropane (904 mg, 5.32 mmol) was added to the mixture, and the resulting mixture was stirred at rt overnight. Water (50 mL) was added to quench the reaction, and the resulting mixture was extracted with EtOAc (50 mL×2). The combined organic phases were washed with saturated brine (80 mL), dried over anhydrous $Na_2SO_4$, filtered, and the filtrate was concentrated in vacuo. The residue was purified by silica gel chromatograph (PE/EtOAc (v/v)=10/1) to give the title compound as a yellow solid (460 mg, 75%).
MS (ESI, pos. ion) m/z: 232.0 [M+H]$^+$.

Step 3: (2S,3S)-ethyl 3-((2-chloro-7-isopropyl-7H-pyrrolo[2,3-d]pyrimidin-4-yl) amino)bicyclo[2.2.2]octane-2-carboxylate (2S,3S)-Ethyl 3-aminobicyclo[2.2.2]octane-2-carboxylate hydrochloric acid (1.26 g, 5.40 mmol) and 2,4-dichloro-7-isopropyl-7H-pyrrolo[2,3-d]pyrimidine (1.10 g, 5.40 mmol) were dissolved in tetrahydrofuran (5 mL), then potassium carbonate (1.87 g, 13.50 mmol) was added. The mixture was stirred at rt overnight. The reaction was stopped, and water (50 mL) was added to quench the reaction, and the resulting mixture was extracted with EtOAc (50 mL×2). The combined organic phases were washed with saturated brine (80 mL), dried over anhydrous $Na_2SO_4$, filtered, and the filtrate was concentrated in vacuo. The residue was purified by silica gel chromatograph (PE/EtOAc (v/v)=10/1) to give the title compound as a yellow solid (979 mg, 50%).

Step 4: (2S,3S)-ethyl 3-((2-bromo-7-isopropyl-7H-pyrrolo[2,3-d]pyrimidin-4-yl)amino)bicyclo[2.2.2]octane-2-carboxylate To a solution of hydrobromic acid in acetic acid (380 mg, 1.54 mmol, 33%) was added (2S,3S)-ethyl 3-((2-chloro-7-isopropyl-7H-pyrrolo[2,3-d]pyrimidin-4-yl)amino)bicycle [2.2.2]octane-2-carboxylate (500 mg, 1.28 mmol), and the resulting mixture was stirred at rt for 2 h. Then the mixture was added slowly into ice-water (40 mL). The mixture was extracted with ethyl acetate (30 mL×3). The combined organic layers were washed with saturated aqueous sodium bicarbonate (30 mL×3), dried over anydrous sodium sulfate, and filtered. The filtrate was concentrated in vacuo to give the title compound as a white solid (463 mg, 83%).
MS (ESI, pos. ion) m/z: 435.0 [M+H]$^+$.

Step 5: (2S,3S)-ethyl 3-((2-(2-chloro-5-trityl-5H-pyrrolo[2,3-b]pyrazin-7-yl)-7-isopropyl-7H-pyrrolo [2,3-d]pyrimidin-4-yl) amino)bicyclo[2.2.2]octane-2-carboxylate To 1,4-dioxane (12 mL) were added (2S,3S)-ethyl 3-((2-bromo-7-isopropyl-7H-pyrrolo[2,3-d]pyrimidin-4-yl) amino)bicyclo[2.2.2]octane-2-carboxylate (150 mg, 0.34 mmol), $K_2CO_3$ (143 mg, 1.03 mmol), $PdCl_2$(dppf) (30 mg, 0.03 mmol) and 2-chloro-7-(4,4,5,5-tetramethyl-1,3,2-dioxaborolan-2-yl)-5-trityl-5H-pyrrolo[2,3-b]pyrazine (330 mg, 0.38 mmol), then $H_2O$ (1 mL) was added. The air in the resulting mixture was exchanged with nitrogen by bubbling for 10 min, then the mixture in the tube was sealed and stirred at 115° C. for 3 h. The mixture was filtered to remove the solid impuries, and the filtrate was concentrated to remove the solvent. The residue was purified by silica gel column chromatography (PE/EtOAc (v/v)=10/1-5/1) to give the title compound as a white solid (166 mg, 64%).
$^1$H NMR (400 MHz, CDCl$_3$) δ (ppm): 8.46 (s, 1H), 7.92 (s, 1H), 7.33-7.28 (m, 10H), 7.27-7.23 (m, 5H), 7.03 (d, J=3.6 Hz, 1H), 6.44 (s, 1H), 5.18-5.12 (m, 1H), 4.75 (t, J=7.4 Hz, 1H), 4.10-4.01 (m, 2H), 2.37 (d, J=7.2 Hz, 1H), 2.05 (s, 2H), 1.77-1.62 (m, 9H), 1.54 (m, 6H), 1.17 (t, J=7.1 Hz, 3H).

Step 6: (2S,3S)-ethyl 3-((2-(2-chloro-5H-pyrrolo[2,3-b]pyrazin-7-yl)-7-isopropyl-7H-pyrrolo[2,3-d]pyrimidin-4-yl) amino)bicyclo[2.2.2]octane-2-carboxylate To a solution of (2S,3S)-ethyl 3-((2-(2-chloro-5-trityl-5H-pyrrolo[2,3-b]pyrazin-7-yl)-7-isopropyl-7H-pyrrolo[2,3-d]pyrimidin-4-yl)amino)bicyclo[2.2.2]octane-2-carboxylate (166 mg, 0.22 mmol) in dichloromethane (5 mL) were added Et$_3$SiH (0.37 mL, 2.20 mmol) and TFA (0.18 mL, 2.20 mmol), and the mixture was stirred at rt for 8 h. The reaction mixture was added into saturated aqueous sodium bicarbonate (50 mL). The resulting mixture was extracted with dichloromethane (60 mL×3). The combined organic layers were washed with saturated brine (120 mL), dried over anhydrous sodium sulfate, and filtered. The filtrate was concentrated in vacuo, and the residue was purified by silica gel column chromatography (DCM/MeOH (v/v)=10/1) to give the title compound as a white solid (100 mg, 89%).
MS (ESI, pos. ion) m/z: 508.3 [M+H]$^+$;
HRMS (ESI, pos. ion) m/z: 508.2239, (C$_{26}$H$_{31}$ClN$_7$O$_2$) [M+H]$^+$ theoretical value: 508.2228;
$^1$H NMR (400 MHz, CDCl$_3$) δ (ppm): 9.99 (s, 1H), 8.53 (s, 1H), 8.25 (s, 1H), 7.06 (d, J=3.6 Hz, 1H), 6.48 (s, 1H), 5.23 (dt, J=13.1, 6.5 Hz, 1H), 4.86 (s, 1H), 4.20-3.98 (m, 2H), 2.51 (s, 1H), 2.07 (s, 2H), 1.91 (d, J=12.0 Hz, 2H), 1.81-1.61 (m, 5H), 1.56 (dd, J=6.7, 2.0 Hz, 6H), 1.29 (d, J=10.0 Hz, 2H), 1.15 (t, J=7.1 Hz, 3H).

Example 20: (2S,3S)-3-((2-(2-chloro-5H-pyrrolo[2,3-b]pyrazin-7-yl)-7-isopropyl-7H-pyrrolo[2,3-d]pyrimidin-4-yl)amino)bicyclo[2.2.2]octane-2-carboxylic Acid

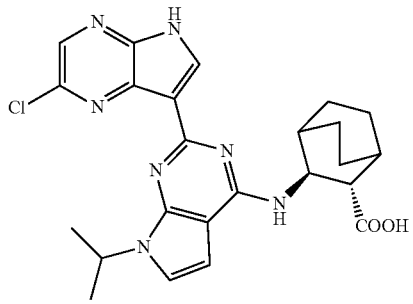 [SMILES: CC(C)n1ccc2c(N[C@H]3C4CCC(CC4)[C@@H]3C(=O)O)nc(-c3c[nH]c4ncc(Cl)nc34)nc21]

To a solution of (2S,3S)-ethyl 3-((2-(2-chloro-5H-pyrrolo[2,3-b]pyrazin-7-yl)-7-(thiophen2,3-yl)pyrimidin-4-yl)amino)bicyclo[2.2.2]octane-2-carboxylate (100 mg, 0.19 mmol) in THF/MeOH (v/v=5 mL/5 mL) was added a solution of NaOH (88 mg, 1.91 mmol) in water (1 mL), and the mixture was stirred at rt overnight. The reaction mixture was quenched with water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (61 mg, 67%).

MS (ESI, pos. ion) m/z: 480.1 [M+H]$^+$;

HRMS (ESI, pos. ion) m/z: 480.1920 [M+H]$^+$, ($C_{24}H_{27}ClN_7O_2$)[M+H]$^+$ theoretical value: 480.1915;

$^1$H NMR (600 MHz, DMSO-$d_6$) δ (ppm): 12.57 (s, 1H), 8.50 (s, 1H), 8.34 (s, 1H), 7.23 (s, 1H), 7.19 (s, 1H), 6.64 (s, 1H), 5.08-4.95 (m, 1H), 4.74 (s, 1H), 2.69 (d, J=6.4 Hz, 1H), 2.16 (s, 1H), 1.99 (s, 1H), 1.94-1.54 (m, 6H), 1.49 (t, J=6.3 Hz, 6H), 1.43-1.30 (m, 2H);

$^{13}$C NMR (151 MHz, DMSO-$d_6$) δ (ppm): 176.22, 155.96, 153.85, 149.84, 142.29, 140.99, 136.16, 135.55, 134.12, 120.89, 116.13, 101.68, 98.95, 55.37, 48.89, 45.69, 28.93, 26.17, 24.26, 23.12, 23.05, 21.65, 19.60, 19.01.

Example 21: (2S,3S)-3-((2-(2-chloro-5H-pyrrolo[2,3-b]pyrazin-7-yl)-7-methyl-7H-pyrrolo[2,3-d]pyrimidin-4-yl)amino)bicyclo[2.2.2]octane-2-carboxylic Acid

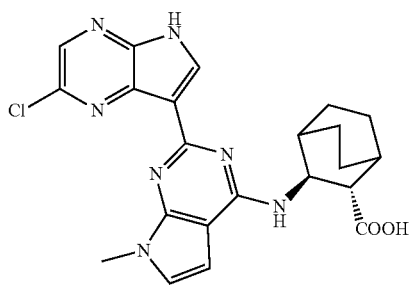 [SMILES: Cn1ccc2c(N[C@H]3C4CCC(CC4)[C@@H]3C(=O)O)nc(-c3c[nH]c4ncc(Cl)nc34)nc21]

Step 1: (2S,3S)-ethyl 3-aminobicyclo[2.2.2]octane-2-carboxylate hydrochloride

The title compound was prepared by the synthetic method disclosed in patent application WO 2015073491.

Step 2: (2S,3S)-ethyl 3-((2-chloro-7-methyl-7H-pyrrolo[2,3-d]pyrimidin-4-yl)amino)bicyclo[2.2.2]octane-2-carboxylate (2S,3S)-Ethyl 3-aminobicyclo[2.2.2]octane-2-carboxylate hydrochloride (1.26 g, 5.40 mmol) and 2,4-dichloro-7-methyl-7H-pyrrolo[2,3-d]pyrimidine (1.10 g, 5.40 mmol) were dissolved in DMF (5 mL), then $K_2CO_3$ (1.50 g, 11.00 mmol) was added. The mixture was stirred at rt overnight. The reaction was stopped, and water (50 mL) was added to quench the reaction, and the resulting mixture was extracted with EtOAc (50 mL×2). The combined organic phases were washed with saturated brine (80 mL), dried over anhydrous $Na_2SO_4$, filtered, and the filtrate was concentrated in vacuo. The residue was purified by silica gel chromatograph (PE/EtOAc (v/v)=10/1) to give the title compound as a yellow solid (979 mg, 50%).

MS (ESI, pos.ion) m/z: 363.2 [M+H]$^+$;

$^1$H NMR (400 MHz, CDCl$_3$) δ (ppm): 6.87 (d, J=3.4 Hz, 1H), 6.41 (s, 1H), 5.32 (s, 1H), 4.63 (s, 1H), 4.21 (q, J=7.1 Hz, 2H), 3.76 (s, 3H), 2.39 (d, J=4.9 Hz, 1H), 1.96-1.52 (m, 10H), 1.26 (t, J=7.0 Hz, 3H).

Step 3: (2S,3S)-ethyl 3-((2-bromo-7-methyl-7H-pyrrolo[2,3-d]pyrimidin-4-yl)amino)bicyclo[2.2.2]octane-2-carboxylate To a solution of hydrobromic acid in acetic acid (360 mg, 1.20 mmol, 33%) was added (2S,3S)-ethyl 3-((2-chloro-7-methyl-7H-pyrrolo[2,3-d]pyrimidin-4-yl)amino)bicyclo[2.2.2]octane-2-carboxylate (435 mg, 1.20 mmol), and the resulting mixture was stirred at rt for 2 h. Then the mixture was added slowly into ice-water (30 mL). The mixture was extracted with ethyl acetate (30 mL×3). The combined organic layers were washed with saturated aqueous sodium bicarbonate (30 mL×3), dried over anydrous sodium sulfate, and filtered. The filtrate was concentrated in vacuo to give the title compound as a white solid (471 mg, 96%).

MS (ESI, pos. ion) m/z: 407.2 [M+H]$^+$.

Step 4: (2S,3S)-ethyl 3-((2-(2-chloro-5-trityl-5H-pyrrolo[2,3-b]pyrazin-7-yl)-7-methyl-7H-pyrrolo[2,3-d]pyrimidin-4-yl) amino)bicyclo[2.2.2]octane-2-carboxylate To a mixture of 1,4-dioxane (12 mL) and H$_2$O (1 mL) were added (2S,3S)-ethyl 3-((2-bromo-7-methyl-7H-pyrrolo[2,3-d]pyrimidin-4-yl)amino)bicyclo[2.2.2]octane-2-carboxylate (471 mg, 1.16 mmol), $K_2CO_3$ (480 mg, 3.47 mmol), PdCl$_2$(dppf) (90 mg, 0.12 mmol) and 2-chloro-7-(4,4,5,5-tetramethyl-1,3,2-dioxaborolan-2-yl)-5-trityl-5H-pyrrolo[2,3-b]pyrazine (1.11 g, 1.27 mmol). The air in the resulting mixture was exchanged with nitrogen by bubbling for 10 min, then the mixture in the tube was sealed and stirred at 115° C. for 3 h. The mixture was filtered to remove the solid impuries, and the solvent was removed. The residue was purified by silica gel column chromatography (PE/EtOAc (v/v)=10/1-5/1) to give the title compound as a white solid (705 mg, 84%).

$^1$H NMR (400 MHz, CDCl$_3$) δ (ppm): 8.49 (s, 1H), 7.93 (s, 1H), 7.31-7.29 (m, 10H), 7.24 (m, 5H), 6.90 (d, J=3.5 Hz, 1H), 6.42 (s, 1H), 4.74 (t, J=7.2 Hz, 1H), 4.07 (m, 2H), 3.88 (s, 3H), 2.36 (d, J=6.7 Hz, 1H), 2.04 (s, 2H), 1.94 (s, 2H), 1.70-1.49 (m, 7H), 1.15 (t, J=7.2 Hz, 3H).

Step 5: (2S,3S)-ethyl 3-((2-(2-chloro-5H-pyrrolo[2,3-b]pyrazin-7-yl)-7-methyl-7H-pyrrolo[2,3-d]pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-7-methyl-7H-pyrrolo[2,3-d]pyrimidin-4-yl)amino)bicyclo[2.2.2]octane-2-carboxylate (700 mg, 0.97 mmol) in DCM (5 mL) were added Et₃SiH (1.60 mL, 9.70 mmol) and TFA (0.80 mL, 9.70 mmol), and the mixture was stirred at rt for 8 h. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a yellow solid (220 mg, 47%).

MS (ESI, pos. ion) m/z: 480.1 [M+H]⁺.

Step 6: (2S,3S)-3-((2-(2-chloro-5H-pyrrolo[2,3-b]pyrazin-7-yl)-7-methyl-7H-pyrrolo[2,3-d]pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-7-methyl-7H-pyrrolo[2,3-d]pyrimidin-4-yl)amino)bicyclo[2.2.2]octane-2-carboxylate (220 mg, 0.44 mmol) in THF/MeOH (v/v=5 mL/5 mL) were added a solution of NaOH (180 mg, 4.44 mmol) in water (1 mL), and the mixture was stirred at rt overnight. The reaction mixture was quenched with water (10 mL), and the mixture was acidified with hydrochloric acid (1 M) to pH about 6 to 4. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (66 mg, 33%).

MS (ESI, pos. ion) m/z: 452.1 [M+H]⁺;
HRMS (ESI, pos. ion) m/z: 452.1618[M+H]⁺, (C₂₂H₂₃ClN₇O₂)[M+H]⁺ theoretical value: 452.1602;

¹H NMR (600 MHz, DMSO-d₆) δ (ppm): 12.58 (s, 1H), 8.51 (d, J=2.8 Hz, 1H), 8.34 (s, 1H), 7.19 (d, J=6.3 Hz, 1H), 7.10 (d, J=3.2 Hz, 1H), 6.62 (d, J=2.9 Hz, 1H), 4.74 (s, 1H), 3.77 (s, 3H), 2.68 (d, J=6.3 Hz, 1H), 2.16 (s, 1H), 2.01-1.33 (m, 10H).

Example 22: (2S,3S)-3-((2-(2-chloro-5H-pyrrolo[2,3-b]pyrazin-7-yl)-5-fluoro-6-(isoxazol-5-yl pyrimidin-4-yl)amino)bicyclo[2.2.2]octane-2-carboxylic Acid

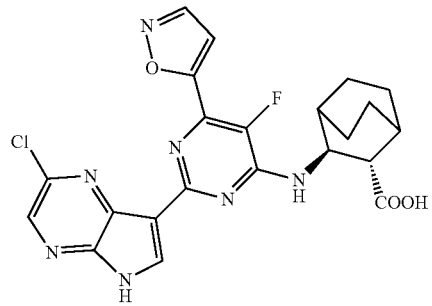 [SMILES: O=C(O)[C@H]1C2CCC(CC2)[C@@H]1Nc1nc(-c2c[nH]c3ncc(Cl)nc23)nc(-c2ccno2)c1F]

Step 1: (2S,3S)-ethyl 3-aminobicyclo[2.2.2]octane-2-carboxylate hydrochloride

The title compound can be prepared according to the synthetic method disclosed in patent application WO 2015073491.

Step 2: 1-(2,6-dichloro-5-fluoropyrimidin-4-yl)ethanone

To a solution of 2,4-dichloro-5-fluoropyrimidine (5.03 g, 30.10 mmol) in acetic acid (100 mL) was added aqueous sulfuric acid solution (160 mL, 240 mmol, 1.5 M). The mixture was cooled to 10° C. under nitrogen protection, then to the mixture was added slowly aqueous ammonium persulfate (60 mL, 60 mmol, 1 M) and aqueous ferrous sulfate solution (60 mL, 90 mmol, 1.5 M). After the addition, the mixture was stirred at 10° C. for 5 h. The mixture was filtered by suction, and the filter cake was washed with 0° C. water (50 mL) and dried to give the title compound as a white solid (1.40 g, 22%).
¹H NMR (400 MHz, CDCl₃) δ (ppm): 2.71 (s, 3H).

Step 3: (2S,3S)-ethyl 3-((6-acetyl-2-chloro-5-fluoropyrimidin-4-yl)amino) bicyclo[2.2.2]octane-2-carboxylate To a solution of 1-(2,6-dichloro-5-fluoropyrimidin-4-yl)ethanone (1.06 g, 5.25 mmol) in DMF (10 mL) were added (2S,3S)-ethyl 3-aminobicyclo[2.2.2]octane-2-carboxylate hydrochloride (1.90 g, 8.11 mmol) and DIPEA (4.70 mL, 26.90 mmol). The mixture was stirred at rt overnight. To the reaction mixture was added water (50 mL), and the resulting mixture was extracted with ethyl acetate (50 mL×3). The combined organic layers were washed with saturated brine (100 mL×3), dried over anhydrous sodium sulfate and filtered. The solvent in the filtrate was removed and the residue was purified by silica gel column chromatography (PE/EtOAc (v/v)=10/1) to give the title compound as a light yellow solid (1.37 g, 55%).
MS (ESI, pos. ion) m/z: 370.3 [M+H]⁺;
¹H NMR (400 MHz, CDCl₃) δ (ppm): 6.88 (s, 1H), 5.45 (s, 1H), 4.74 (s, 1H), 3.76 (s, 3H), 3.60 (s, 3H), 2.74 (dd, J=14.8, 4.0 Hz, 1H), 2.47 (dd, J=14.8, 8.8 Hz, 1H), 1.71 (s, 1H), 1.01 (s, 9H).

Step 4: (2S,3S)-ethyl 3-((6-acetyl-2-bromo-5-fluoropyrimidin-4-yl) amino)bicyclo[2.2.2]octane-2-carboxylate To a solution of hydrobromic acid in acetic acid (30 mL, 33%) was added (2S,3S)-ethyl 3-((6-acetyl-2-chloro-5-fluoropyrimidin-4-yl) amino)bicyclo[2.2.2]octane-2-carboxylate (0.91 g, 2.50 mmol), and the mixture was stirred at rt for 2 h. After the reaction was completed, the reaction mixture was added slowly into ice-water (100 mL), and the resulting mixture was extracted with EtOAc (100 mL×3). The combined organic layers were washed with saturated aqueous sodium bicarbonate (300 mL×3), dried over anhydrous Na$_2$SO$_4$, and filtered. The solvent in the filtrate was removed to give the title compound as light yellow oil (0.98 g, 96%).

MS (ESI, pos. ion) m/z: 414.10 [M+H]$^+$.

Step 5: (2S,3S)-ethyl 3-((2-bromo-6-((E)-3-(dimethylamino) acryloyl)-5-fluoropyrimidin-4-yl)amino) bicyclo[2.2.2]octane-2-carboxylate A solution of (2S,3S)-ethyl 3-((6-acetyl-2-bromo-5-fluoropyrimidin-4-yl)amino)bicyclo[2.2.2]octane-2-carboxylate (0.98 g, 2.40 mmol) in DMF-DMA (20 mL) was heated to 50° C. and stirred for 5 h, and then the mixture was cooled to rt and stirred overnight. To the reaction mixture was added water (50 mL), and the resulting mixture was extracted with ethyl acetate (50 mL×3). The combined organic layers were washed with saturated brine (100 mL×3), dried over anhydrous sodium sulfate and filtered. The filtrate was concentrated in vacuo and the residue was purified by silica gel column chromatography (PE/EtOAc (v/v)=1/1) to give the title compound as a yellow solid (0.87 g, 78%).

MS (ESI, pos. ion) m/z: 469.2 [M+H]$^+$;

$^1$H NMR (400 MHz, CDCl$_3$) δ (ppm): 7.83 (s, 1H), 5.86 (s, 1H), 4.51 (s, 1H), 4.24 (q, J=6.7 Hz, 2H), 3.19 (s, 3H), 2.97 (s, 3H), 2.38 (d, J=5.7 Hz, 1H), 2.03 (d, J=1.8 Hz, 1H), 1.89 (s, 1H), 1.81 (m, 1H), 1.62 (m, 8H), 1.28 (m, 3H).

Step 6: (2S,3S)-ethyl-3-((2-bromo-5-fluoro-6-(isoxazol-5-yl)pyrimidin-4-yl)amino) bicyclo[2.2.2]octane-2-carboxylate To a solution of (2S,3S)-ethyl 3-((2-bromo-6-((E)-3-(dimethylamino)acryloyl)-5-fluoropyrimidin-4-yl)amino)bicyclo[2.2.2]octane-2-carboxylate (0.87 g, 1.90 mmol) in anhydrous ethanol (15 mL) was added hydroxylamine hydrochloride (0.27 g, 3.80 mmol). The reaction mixture was stirred at 78° C. for 8 h under nitrogen protection. After the reaction was completed, the mixture was concentrated to remove the solvent, and the residue was dissolved in ethyl acetate (20 mL). Then water (30 mL) was added, and the resulting mixture was partitioned. The aqueous layer was extracted with ethyl acetate (20 mL×2). The combined organic phases were washed with saturated brine (50 mL), dried over anhydrous Na$_2$SO$_4$, filtered, and the filtrate was concentrated in vacuo. The residue was purified by silica gel chromatograph (PE/EtOAc (v/v)=5/1) to give the title compound as a white solid (0.44 g, 54%).

MS (ESI, pos. ion) m/z: 439.0 [M+H]$^+$;

$^1$H NMR (400 MHz, CDCl$_3$) δ (ppm): 8.40 (d, J=1.7 Hz, 1H), 6.99 (s, 1H), 4.57 (t, J=4.8 Hz, 1H), 4.25 (q, J=7.1 Hz, 2H), 2.43 (d, J=5.8 Hz, 1H), 1.93 (d, J=2.3 Hz, 1H), 1.82 (m, 1H), 1.74-1.64 (m, 7H), 1.48 (m, 1H), 1.28 (m, 4H).

Step 7: (2S,3S)-ethyl-3-((2-(2-chloro-5-trityl-5H-pyrrolo[2,3-b]pyrazin-7-yl)-5-fluoro-6-(isoxazol-5-yl)pyrimidin-4-yl)amino)bicyclo[2.2.2]octane-2-carboxylate To 1,4-dioxane (15 mL) were added 2-chloro-7-(4,4,5,5-tetramethyl-1,3,2-dioxaborolan-2-yl)-5-trityl-5H-pyrrolo[2,3-b]pyrazine(0.41 g, 0.51 mmol, 60%), K$_2$CO$_3$(190 mg, 1.40 mmol), Pd(AcO)$_2$ (21 mg, 0.09 mmol), X-Phos (90 mg, 0.18 mmol) and (2S,3S)-ethyl-3-((2-bromo-5-fluoro-6-(isoxazol-5-yl)pyrimidin-4-yl) amino)bicyclo[2.2.2]octane-2-carboxylate (150 mg, 0.41 mmol), then H$_2$O (0.5 mL) was added into the mixture. The mixture was heated to 105° C. and stirred for 4 h. The mixture was filtered to remove the solid impuries, and the filtrate was concentrated to remove the solvent. The residue was purified by silica gel column chromatography (PE/EtOAc (v/v)=10/1-5/1) to give the title compound as a yellow solid (337 mg, 98%).

Step 8: (2S,3S)-ethyl 3-((2-(2-chloro-5H-pyrrolo[2,3-b]pyrazin-7-yl)-5-fluoro-6-(isoxazol-5-yl) pyrimidin-4-yl)amino)bicyclo[2.2.2]octane-2-carboxylate To a solution of (2S,3S)-ethyl-3-((2-(2-chloro-5-trityl-5H-pyrrolo[2,3-b]pyrazin-7-yl)-5-fluoro-6-(isoxazol-5-yl) pyrimidin-4-yl)amino)bicyclo[2.2.2]octane-2-carboxylate (337 mg, 0.45 mmol) in dichloromethane (10 mL) were added Et$_3$SiH (0.86 mL, 5.40 mmol) and TFA (0.40 mL, 5.40 mmol), and the mixture was stirred at 30° C. overnight. The reaction was stopped, and the reaction mixture was added into saturated aqueous sodium bicarbonate (30 mL). The resulting mixture was extracted with dichloromethane (30 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=2/1) to give the title compound as a yellow solid (18 mg, 8%).

MS (ESI, pos. ion) m/z: 512.20 [M+H]$^+$.

Step 9: (2S,3S)-3-((2-(2-chloro-5H-pyrrolo[2,3-b]pyrazin-7-yl)-5-fluoro-6-(isoxazol-5-yl)pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-5-fluoro-6-(isoxazol-5-yl)pyrimidin-4-yl)amino)bicyclo[2.2.2]octane-2-carboxylate (18 mg, 0.04 mmol) in THF/MeOH/H$_2$O (v/v/v=1 mL/1 mL/0.5 mL) was added a solution of NaOH (15 mg, 0.38 mmol) in water (0.5 mL), and the mixture was stirred at rt overnight. After the reaction was completed, to the reaction mixture was added saturated brine (10 mL), and the mixture was acidified with hydrochloric acid (1 M) to pH about 6. The resulting mixture was extracted with 2-methyl tetrahydrofuran (10 mL×3). The combined organic layers were washed with saturated brine (30 mL), dried over anhydrous sodium sulfate, and filtered. The filtrate was concentrated in vacuo to remove the solvent, and the residue was purified by thin-layer preparative chromatography (DCM/MeOH (v/v)=15/1) to give the title compound as a light yellow solid (3 mg, 18%).

MS (ESI, pos. ion) m/z: 484.20 [M+H]$^+$.

HRMS (ESI, pos. ion) m/z: 484.1306, (C$_{22}$H$_{20}$ClN$_7$O$_3$) [M+H]$^+$ theoretical value: 484.1300;

$^1$H NMR (400 MHz, DMSO-d$_6$) δ (ppm): 12.86 (s, 1H), 9.18 (s, 1H), 8.63 (s, 1H), 8.38 (s, 1H), 7.85 (s, 1H), 7.24 (s, 1H), 4.70 (s, 1H), 3.18 (s, 1H), 2.87 (s, 1H), 2.12 (s, 1H), 1.75 (s, 3H), 1.62-1.38 (m, 6H).

Example 23: (2S,3S)-3-((2-(2-chloro-5H-pyrrolo[2,3-b]pyrazin-7-yl)-6-(phenylethynyl)pyrimidin-4-yl)amino)bicyclo[2.2.2]octane-2-carboxylic Acid

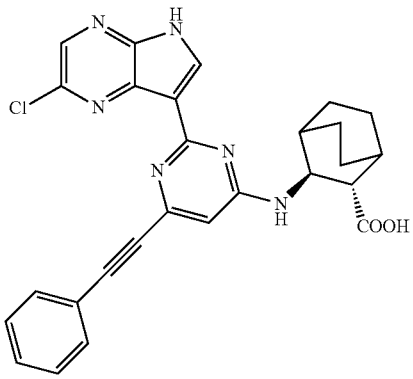 [SMILES: O=C(O)[C@H]1C2CCC(CC2)[C@@H]1Nc1cc(C#Cc2ccccc2)nc(-c2c[nH]c3ncc(Cl)nc23)n1]

Step 1: (2S,3S)-ethyl 3-aminobicyclo[2.2.2]octane-2-carboxylate hydrochloride

The title compound was prepared by the synthetic method disclosed in patent application WO 2015073491.

Step 2: 2,4-dichloro-6-(2-phenylethynyl)pyrimidine

To a solution of 2,4,6-trichloropyrimidine (101 mg, 0.55 mmol) in toluene (3 mL) were added phenylethynyltri-n-butyltin (259 mg, 0.66 mmol), arsenic triphenyl (67 mg, 0.22 mmol) and Pd(PPh$_3$)C$_2$ (40 mg, 0.06 mmol). The mixture was heated to 80° C. and stirred for 6 h. The mixture was concentrated in vacuo to remove the solvent and the residue was purified by silica gel column chromatography (PE) to give the title compound as a white solid (42 mg, 94%).

MS (ESI, pos.ion) m/z: 249.3 [M+H]$^+$;

$^1$H NMR (400 MHz, CDCl$_3$) δ (ppm): 8.40 (t, J=7.9 Hz, 2H), 8.29 (d, J=8.7 Hz, 1H), 7.88-7.74 (m, 2H).

Step 3: (2S,3S)-ethyl 3-((2-chloro-6-(phenylethynyl)pyrimidin-4-yl)amino)bicyclo[2.2.2]octane-2-carboxylate To a solution of (2S,3S)-ethyl 3-aminobicyclo[2.2.2]octane-2-carboxylate hydrochloride (568 mg, 2.43 mmol) and 2,4-dichloro-6-(2-phenylethynyl)pyrimidine (622 mg, 2.91 mmol) in DMF (5 mL) was added potassium carbonate (671 mg, 4.86 mmol), and the mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (624 mg, 63%).

MS (ESI, pos.ion) m/z: 410.2 [M+H]$^+$.

Step 4: (2S,3S)-ethyl 3-((2-(2-chloro-5-trityl-5H-pyrrolo[2,3-b]pyrazin-7-yl)-6-(phenylethynyl)pyrimidin-4-yl)amino)bicyclo[2.2.2]octane-2-carboxylate To 1,4-dioxane (8 mL) were added 2-chloro-7-(4,4,5,5-tetramethyl-1,3,2-dioxaborolan-2-yl)-5-trityl-5H-pyrrolo[2,3-b]pyrazine (468 mg, 0.54 mmol, 60%), K$_2$CO$_3$ (211 mg, 1.46 mmol), PdCl$_2$(dppf) (40 mg, 0.05 mmol) and (2S,3S)-ethyl 3-((2-chloro-6-(phenylethynyl) pyrimidin-4-yl)amino)bicyclo[2.2.2]octane-2-carboxylate (200 mg, 0.49 mmol), then H$_2$O (1 mL) was added into the mixture. The air in the mixture was exchanged with nitrogen by bubbling for 10 min. The mixture in the sealed tub was stirred for 3 h at 115° C. The mixture was filtered to remove the solid impuries, and the solvent was removed. The residue was purified by silica gel column chromatography (PE/EtOAc (v/v)=10/1-5/1) to give the title compound as a white solid (115 mg, 31%).

Step 5: (2S,3S)-ethyl 3-((2-(2-chloro-5H-pyrrolo[2,3-b]pyrazin-7-yl)-6-(phenylethynyl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-6-(phenylethynyl)pyrimidin-4-yl)amino)bicyclo[2.2.2]octane-2-carboxylate (115 mg, 0.15 mmol) in dichloromethane (5 mL) were added Et$_3$SiH (0.23 mL, 1.50 mmol) and TFA (0.11 mL, 1.50 mmol), and the mixture was stirred at 30° C. overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (55 mg, 70%).

MS (ESI, pos. ion) m/z: 527.3 [M+H]$^+$.

Step 6: (2S,3S)-3-((2-(2-chloro-5H-pyrrolo[2,3-b]pyrazin-7-yl)-6-(phenylethynyl)pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-6-(phenylethynyl)pyrimidin-4-yl)amino)bicyclo[2.2.2]octane-2-carboxylate (55 mg, 0.10 mmol) in THF/MeOH (v/v=5 mL/5 mL) was added a solution of NaOH (42 mg, 1.04 mmol) in water (1 mL), and the mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (11 mg, 21%).

MS (ESI, pos. ion) m/z: 499.4 [M+H]$^+$;

HRMS (ESI, pos. ion) m/z: 499.1645[M+H]$^+$, (C$_{27}$H$_{24}$ClN$_6$O$_2$)[M+H]$^+$ theoretical value: 499.1649;

$^1$H NMR (600 MHz, DMSO-d$_6$) δ (ppm): 13.07 (s, 1H), 8.65 (s, 1H), 8.47 (s, 1H), 7.73 (s, 1H), 7.67 (s, 2H), 7.51 (s, 4H), 5.76 (s, 1H), 4.38 (s, 1H), 2.02-1.79 (m, 6H), 1.54 (s, 3H).

Example 24: (2S,3S)-3-((2-(2-chloro-5H-pyrrolo[2,3-b]pyrazin-7-yl)-6-(oxazol-2-yl)pyrimidin-4-yl)amino)bicyclo[2.2.2]octane-2-carboxylic Acid

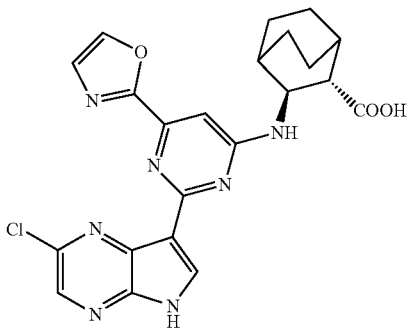 [SMILES: O=C(O)[C@H]1C2CCC(CC2)[C@@H]1Nc1cc(-c2ncco2)nc(-c2c[nH]c3ncc(Cl)nc23)n1]

Step 1: (2S,3S)-ethyl 3-aminobicyclo[2.2.2]octane-2-carboxylate hydrochloride The title compound was prepared by the synthetic method disclosed in patent application WO 2015073491.

Step 2: 2-(2,6-dichloropyrimidin-4-yl)oxazole

To a solution of 2.4.6-trichloropyrimidine (0.29 g, 1.60 mmol) in anhydrous DMF (10 mL) were added bis(triphenylphosphine)palladium(II) chloride (99 mg, 0.14 mmol) and 2-(tributylstannyl)oxazole (500 mg, 1.40 mmol). The mixture was stirred at 90° C. overnight under nitrogen protection. To the reaction mixture was added water (30 mL), and the resulting mixture was extracted with ethyl acetate (30 mL×3). The combined organic layers were washed with saturated brine (50 mL×3), dried over anhydrous sodium sulfate and filtered. The solvent in the filtrate was removed and the residue was purified by silica gel column chromatography (PE/EtOAc (v/v)=10/1) to give the title compound as a white solid (80 mg, 27%).

$^1$H NMR (400 MHz, CDCl$_3$) δ (ppm): 8.07 (s, 1H), 7.94 (s, 1H), 7.46 (s, 1H).

Step 3: (2S,3S)-ethyl 3-((2-chloro-6-(oxazol-2-yl)pyrimidin-4-yl)amino)bicyclo[2.2.2]octane-2-carboxylate To a solution of 2-(2,6-dichloropyrimidin-4-yl)oxazole (80 mg, 0.37 mmol) in DMF (5 mL) were added (2S,3S)-ethyl 3-aminobicyclo[2.2.2]octane-2-carboxylate hydrochloride (89 mg, 0.38 mmol) and potassium carbonate (95 mg, 0.69 mmol). The mixture was stirred at rt overnight. To the reaction mixture was added water (20 mL), and the resulting mixture was extracted with ethyl acetate (20 mL×3). The combined organic layers were washed with saturated brine (50 mL×3), dried over anhydrous sodium sulfate and filtered. The filtrate was concentrated in vacuo and the residue was purified by silica gel column chromatography (PE/EtOAc (v/v)=10/1) to give the title compound as a light yellow solid (100 mg, 72%).

MS (ESI, pos. ion) m/z: 377.20 [M+H]$^+$;

$^1$H NMR (400 MHz, CDCl$_3$) δ (ppm): 7.84 (s, 1H), 7.35 (s, 1H), 7.18 (s, 1H), 4.34 (s, 1H), 4.22 (q, 2H), 2.36 (d, J=5.5 Hz, 1H), 2.10 (s, 1H), 1.87 (s, 1H), 1.77 (m, 1H), 1.71-1.66 (m, 3H), 1.57 (s, 2H), 1.49 (m, 2H), 1.29-1.27 (m, 3H).

Step 4: (2S,3S)-ethyl 3-((2-bromo-6-(oxazol-2-yl)pyrimidin-4-yl) amino)bicyclo[2.2.2]octane-2-carboxylate (2S,3S)-Ethyl 3-((2-chloro-6-(oxazol-2-yl)pyrimidin-4-yl) amino) bicyclo[2.2.2]octane-2-carboxylate (0.87 g, 1.90 mmol) was dissolved in a solution of hydrobromic acid in acetic acid (33%, 5 mL), and the resulting mixture was stirred at rt for 2 h. After the reaction was completed, the reaction mixture was added slowly into ice-water (30 mL). The mixture was extracted with ethyl acetate (30 mL×3). The combined organic layers were washed with saturated aqueous sodium sulfate (90 mL×3), dried over anydrous sodium sulfate, and filtered. The filtrate was concentrated in vacuo to give the title compound as a light yellow solid (101 mg, 90%).

MS (ESI, pos. ion) m/z: 421.10 [M+H]$^+$.

Step 5: (2S,3S)-ethyl 3-((2-(2-chloro-5-trityl-5H-pyrrolo[2,3-b]pyrazin-7-yl)-6-(oxazol-2-yl)pyrimidin-4-yl)amino)bicyclo[2.2.2]octane-2-carboxylate To a mixture of 2-chloro-7-(4,4,5,5-tetramethyl-1,3,2-dioxaborolan-2-yl)-5-trityl-5H-pyrrolo[3,4-b]pyrazine (0.21 g, 0.26 mmol, 65%), K$_2$CO$_3$ (0.10 g, 0.72 mmol), Pd(dppf)Cl$_2$ (54 mg, 0.07 mmol) and (2S,3S)-ethyl 3-((2-bromo-6-(oxazol-2-yl)pyrimidin-4-yl)amino)bicyclo[2.2.2]octane-2-carboxylate (100 mg, 0.24 mmol) in 1,4-dioxane (10 mL) was added H$_2$O (0.3 mL). The mixture was heated to 105° C. and stirred for 4 h under nitrogen protection. After the reaction was completed, the mixture was filtered to remove the solid impuries, and the filtrate was concentrated to remove the solvent. The residue was purified by silica gel column chromatography (PE/EtOAc (v/v)=10/1) to give the title compound as a yellow solid (58 mg, 33%).

Step 6: (2S,3S)-ethyl 3-((2-(2-chloro-5H-pyrrolo[2,3-b]pyrazin-7-yl)-6-(oxazol-2-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-6-(oxazol-2-yl)pyrimidin-4-yl)amino)bicyclo[2.2.2]octane-2-carboxylate (58 mg, 0.08 mmol) in DCM (5 mL) were added Et$_3$SiH (0.16 mL, 1.00 mmol) and TFA (0.07 mL, 0.90 mmol), and the mixture was stirred at rt overnight. The reaction mixture was added into saturated aqueous sodium bicarbonate (30 mL). The resulting mixture was extracted with dichloromethane (30 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=1/1) to give the title compound as a light yellow solid (30 mg, 77%).

Step 7: (2S,3S)-3 (2-chloro-5H-pyrrolo[2,3-b]pyrazin-7-yl)-6-(oxazol-2-yl) pyrimidin-4-yl)amino) bicyclo[2.2.2]octane-2-carboxylic Acid To a solution of (2S,3S)-ethyl 3-((2-(2-chloro-5H-pyrrolo[2,3-b]pyrazin-7-yl)-6-(oxazol-2-yl)pyrimidin-4-yl)amino)bicyclo[2.2.2]octane-2-carboxylate (30 mg, 0.06 mmol) in THF/MeOH/H$_2$O (v/v/v=1 mL/1 mL/1 mL) was added NaOH (25 mg, 0.63 mmol) in portions. The mixture was stirred at rt overnight. To the reaction mixture was added saturated brine (10 mL), and the mixture was acidified with hydrochloric acid (1 M) to pH about 6. The resulting mixture was extracted with 2-methyltetrahydrofuran (30 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a light yellow solid (20 mg, 71%).

MS (ESI, pos. ion) m/z: 466.10 [M+H]$^+$;
HRMS (ESI, pos. ion) m/z: 466.1427, ($C_{22}H_{21}ClN_7O_3$) [M+H]$^+$ theoretical value: 466.1394;
$^1$H NMR (400 MHz, DMSO-$d_6$) δ (ppm): 8.67 (s, 1H), 8.35 (s, 1H), 8.24 (s, 1H), 7.70 (d, J=5.9 Hz, 1H), 7.47 (s, 1H), 7.01 (s, 1H), 4.67 (s, 1H), 2.23 (d, J=4.6 Hz, 1H), 2.06 (s, 1H), 1.99 (s, 1H), 1.89-1.80 (m, 1H), 1.78-1.58 (m, 4H), 1.50 (m, 3H).

Example 25: (2S,3S)-3-((6-(5-carbamoylfuran-2-yl)-2-(2-chloro-5H-pyrrolo[2,3-b]pyrazin-7-yl)pyrimidin-4-yl)amino)bicyclo[2.2.2]octane-2-carboxylic Acid

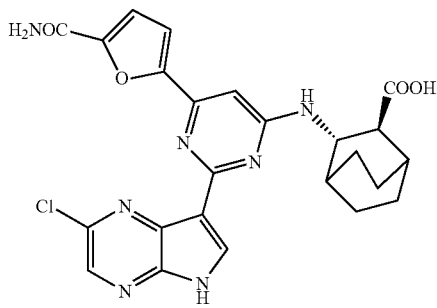 [SMILES: NC(=O)c1ccc(-c2cc(N[C@H]3C4CCC(CC4)[C@@H]3C(=O)O)nc(-c3c[nH]c4ncc(Cl)nc34)n2)o1]

Step 1: (2S,3S)-ethyl 3-aminobicyclo[2.2.2]octane-2-carboxylate hydrochloride

The title compound was prepared by the synthetic method disclosed in patent application WO 2015073491.

Step 2: 2,4-dichloro-6-(furan-2-yl)pyrimidine

The title compound was prepared by the synthetic method disclosed in step 10 of example 1.

Step 3: 2,4-dichloro-6-(5-bromofuran-2-yl)pyrimidine

To a solution of 2,4-dichloro-6-(furan-2-yl)pyrimidine (200 mg, 0.93 mmol) in DMF (8 mL) was added NBS (198 mg, 1.12 mmol) in portions. The mixture was stirred at rt for 2 h. The reaction mixture was added into water (50 mL), and the resulting mixture was extracted with ethyl acetate (50 mL×3). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1) to give the title compound as yellow powder (187 mg, 68%).

$^1$H NMR (400 MHz, CDCl$_3$) δ (ppm): 7.54 (s, 1H), 7.38 (d, J=3.6 Hz, 1H), 6.57 (d, J=3.6 Hz, 1H).

Step 4: (2S,3S)-ethyl 3-((6-(5-bromofuran-2-yl)-2-chloropyrimidin-4-yl)amino)bicyclo[2.2.2]octane-2-carboxylate A suspension of 2,4-dichloro-6-(5-bromofuran-2-yl)pyrimidine (188 mg, 0.64 mmol), (2S,3S)-ethyl 3-aminobicyclo[2.2.2]octane-2-carboxylate hydrochloride (180 mg, 0.77 mmol) and K$_3$CO$_3$ (265 mg, 1.92 mmol) in DMF (10 mL) was stirred at rt overnight. Water (100 mL) was added to quench the reaction, and the resulting mixture was extracted with EtOAc (50 mL×3). The combined organic phases were washed with saturated brine (80 mL), dried over anhydrous Na$_2$SO$_4$, filtered, and the filtrate was concentrated in vacuo. The residue was purified by silica gel chromatograph (PE/EtOAc (v/v)=5/1) to give the title compound as a white solid (210 mg, 75%).

MS (ESI, pos. ion) m/z: 442.2 [M+H]$^+$;
$^1$H NMR (400 MHz, CDCl$_3$) δ (ppm): 7.18 (d, J=3.3 Hz, 1H), 6.64 (s, 1H), 6.49 (d, J=3.4 Hz, 1H), 4.30 (s, 1H), 3.79 (s, 3H), 2.38 (d, J=4.9 Hz, 1H), 2.06 (s, 1H), 1.87 (d, J=2.4 Hz, 1H), 1.70-1.46 (m, 9H).

Step 5: (2S,3S)-ethyl 3-((2-chloro-6-(5-cyanofuran-2-yl)pyrimidin-4-yl)amino)bicyclo[2.2.2]octane-2-carboxylate To a reaction flask were added (2S,3S)-ethyl 3-((6-(5-bromofuran-2-yl)-2-chloropyrimidin-4-yl)amino)bicyclo[2.2.2]octane-2-carboxylate (633 mg, 1.39 mmol), tetrakis(triphenylphosphine)palladium(0) (322 mg, 0.28 mmol), cuprous cyanide (633 mg, 6.96 mmol), then DMF (15 mL) was added. The air in the mixture was exchanged with nitrogen by bubbling for 10 min, then the mixture was stirred at 150° C. for 8 h by microwave heating. After the reaction was completed, the reaction mixture was filtered through a celite pad, and the filter cake was washed with ethyl acetate (20 mL). The filtrate was concentrated in vacuo and the residue was purified by silica gel chromatograph (PE/EtOAc (v/v)=10/1) to give the title compound as light yellow oil (206 mg, 37%).

MS (ESI, pos. ion) m/z: 401.2 [M+H]$^+$.

Step 6: (2S,3S)-ethyl 3-((2-(2-chloro-5-trityl-5H-pyrrolo[2,3-b]pyrazin-7-yl)-6-(5-cyanofuran-2-yl)pyrimidin-4-yl) amino)bicyclo[2.2.2]octane-2-carboxylate To a mixed solvent of 1,4-dioxane (20 mL) and H$_2$O (0.5 mL) were added 2-chloro-7-(4,4,5,5-tetramethyl-1,3,2-dioxaborolan-2-yl)-5-trityl-5H-pyrrolo[2,3-b]pyrazine (491 mg, 0.57 mmol, 50%), K$_2$CO$_3$ (213 mg, 1.54 mmol), PdCl$_2$(dppf) (41 mg, 0.05 mmol) and (2S,3S)-ethyl 3-((2-chloro-6-(5-cyanofuran-2-yl)pyrimidin-4-yl) amino)bicyclo[2.2.2]octane-2-carboxylate (206 mg, 0.51 mmol). The air in the mixture was exchanged with nitrogen by bubbling for 10 min. The mixture in the sealed tub was stirred for 3 h at 110° C. The mixture was filtered to remove the solid impurity, and the filtrate was concentrated to remove the solvent. The residue was purified by silica gel column chromatography (PE/EtOAc (v/v)=10/1) to give the title compound as light yellow oil (131 mg, 34%).

Step 7: (2S,3S)-ethyl 3-((2-(2-chloro-5H-pyrrolo[2,3-b]pyrazin-7-yl)-6-(5-cyanofuran-2-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-6-(5-cyanofuran-2-yl)pyrimidin-4-yl)amino)bicyclo[2.2.2]octane-2-carboxylate (131 mg, 0.17 mmol) in dichloromethane (20 mL) were added Et$_3$SiH (0.28 mL, 1.73 mmol) and TFA (0.14 mL, 5.40 mmol), and the mixture was stirred at rt overnight. The reaction was stopped, and the reaction mixture was added into saturated aqueous sodium bicarbonate (30 mL). The resulting mixture was extracted with dichloromethane (30 mL×3). The combined organic layers were washed with saturated brine (100 mL), dried over anhydrous sodium sulfate, and filtered. The filtrate was concentrated in vacuo to remove the solvent, and the residue was purified by silica gel column chromatography (PE/EtOAc (v/v)=2/1) to give the title compound as light yellow oil (51 mg, 57%).

MS (ESI, pos. ion) m/z: 518.2 [M+H]$^+$.

Step 8: (2S,3S)-3-((6-(5-carbamoylfuran-2-yl)-2-(2-chloro-5H-pyrrolo[2,3-b]pyrazin-7-yl)pyrimidin-4-yl) amino)bicyclo[2.2.2]octane-2-carboxylic Acid To a solution of (2S,3S)-ethyl 3-((2-(2-chloro-5H-pyrrolo[2,3-b]pyrazin-7-yl)-6-(5-cyanofuran-2-yl)pyrimidin-4-yl)amino)bicyclo[2.2.2]octane-2-carboxylate (52 mg, 0.10 mmol) in THF/MeOH/H$_2$O (v/v/v=2 mL/2 mL/1 mL) was added a solution of NaOH (42 mg, 1.00 mmol) in water (1 mL), and the mixture was stirred at rt overnight. To the reaction mixture was added saturated brine (10 mL), and the mixture was acidified with hydrochloric acid (1 M) to pH about 6. The resulting mixture was extracted with 2-methyltetrahydrofuran (15 mL×3). The combined organic layers were washed with saturated brine (40 mL), dried over anhydrous sodium sulfate, and filtered. The filtrate was concentrated in vacuo to remove the solvent, and the residue was purified by preparative thin-layer chromatography (DCM/MeOH (v/v)=15/1) to give the title compound as a light yellow solid (29 mg, 57%).

MS (ESI, pos. ion) m/z: 508.6 [M+H]$^+$;
HRMS (ESI, pos. ion) m/z: 508.1497, (C$_{24}$H$_{22}$FN$_6$)O$_5$) [M+H]$^+$ theoretical value: 508.1500;
$^1$H NMR (400 MHz, DMSO-d$_6$) δ (ppm) 12.76 (s, 1H), 8.63 (d, J=2.3 Hz, 1H), 8.37 (s, 1H), 7.94 (s, 1H), 7.57 (d, J=6.6 Hz, 1H), 7.51 (s, 1H), 7.29 (s, 2H), 6.82 (s, 1H), 5.33 (t, J=4.9 Hz, 1H), 4.58 (s, 1H), 2.10 (s, 1H), 1.94 (m, 2H), 1.79-1.43 (m, 8H).

Example 26: (2S,3S)-3-((2-(2-chloro-5H-pyrrolo[2,3-b]pyrazin-7-yl)-6-(5-methylthiophen-2-yl) pyrimidin-4-yl)amino)bicyclo[2.2.2]octane-2-carboxylic Acid

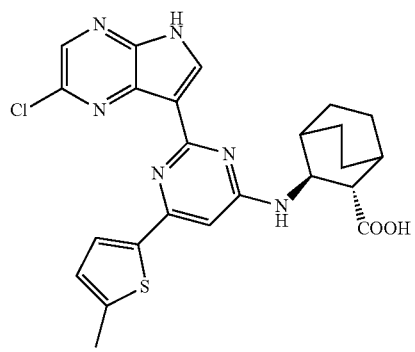 [SMILES: Cc1ccc(-c2cc(N[C@H]3C4CCC(CC4)[C@@H]3C(=O)O)nc(-c3c[nH]c4ncc(Cl)nc34)n2)s1]

Step 1: (2S,3S)-ethyl 3-aminobicyclo[2.2.2]octane-2-carboxylate hydrochloride

The title compound was prepared according to the synthetic method disclosed in patent application WO 2015073491.

Step 2: 2,4-dichloro-6-(5-methylthiophen-2-yl)pyrimidine

To a solution of 2-methylthiophene (500 mg, 5.09 mmol) in anydrous tetrahydrofuran (20 mL) was added n-butyllithium (2.00 mL, 5.10 mmol, 2.5 mol/L) at −15° C., and the mixture was stirred for 1 h at −15° C. Then to the mixture was added (N,N,N',N'-tetramethylethylenediamine)zinc(II) dichloride (425 mg, 1.68 mmol), and the resulting mixture was stirred for 1 h. Then palladium dichloride (91 mg, 0.51 mmol), triphenylphosphine (270 mg, 1.02 mmol) and 2,4,6-trichloropyrimidine (1.21 g, 5.60 mmol) were added into the mixture in turn. The resulting mixture was heated to 55° C. under nitrogen protection, and then stirred at this temperature overnight. To the reaction mixture was added water (50 mL), and the resulting mixture was extracted with ethyl acetate (50 mL×3). The combined organic layers were washed with saturated brine (100 mL), dried over anhydrous sodium sulfate and filtered. The filtrate was concentrated in vacuo and the residue was purified by silica gel column chromatography (PE) to give the title compound as a white solid (442 mg, 35%).

$^1$H NMR (400 MHz, CDCl$_3$) δ (ppm): 7.68 (d, J=3.8 Hz, 1H), 7.41 (s, 1H), 6.88 (dd, J=3.8, 0.9 Hz, 1H), 2.59 (s, 3H).

Step 3: (2S,3S)-ethyl 3-((2-chloro-6-(5-methylthiophen-2-yl)pyrimidin-4-yl)amino)bicyclo[2.2.2]octane-2-carboxylate To a solution of (2S,3S)-ethyl 3-aminobicyclo[2.2.2]octane-2-carboxylate hydrochloride (505 mg, 2.16 mmol) and 2,4-dichloro-6-(5-methylthiophen-2-yl)pyrimidine (442 mg, 1.80 mmol) in DMF (6 mL) was added potassium carbonate (500 mg, 3.61 mmol), and the mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (250 mg, 34%).

MS (ESI, pos.ion) m/z: 406.2 [M+H]$^+$;
$^1$H NMR (400 MHz, CDCl$_3$) δ (ppm): 7.55 (d, J=3.6 Hz, 1H), 6.83-6.77 (m, 1H), 6.60 (s, 1H), 5.38 (d, J=4.7 Hz, 1H), 4.21 (dd, J=7.1, 4.6 Hz, 2H), 2.55 (s, 3H), 2.39-2.32 (m, 1H), 2.08 (s, 1H), 1.89-1.84 (m, 1H), 1.67 (m, 6H), 1.60 (s, 3H), 1.25 (d, J=7.1 Hz, 3H).

Step 4: (2S,3S)-ethyl 3-((2-bromo-6-(5-methylthiophen-2-yl)pyrimidin-4-yl)amino)bicyclo[2.2.2]octane-2-carboxylate To a solution of hydrobromic acid in acetic acid ((235 mg, 1.25 mmol, 33%) were added (2S,2S)-ethyl 3-((2-chloro-6-(5-methylthiophen-2-yl)pyrimidin-4-yl)amino)bicyclo[2.2.2]octane-2-carboxylate (325 mg, 0.80 mmol), and the mixture was stirred at rt overnight. The reaction mixture was added into ice-water (30 mL), and the resulting mixture was extracted with EtOAc (30 mL×3). The combined organic layers were washed with saturated aqueous sodium bicarbonate (80 mL×3) and saturated brine (50 mL), dried over anhydrous Na$_2$SO$_4$, and filtered. The filtrate was concentrated in vacuo to give the title compound as a light yellow solid (310 mg, 86%).

MS (ESI, pos.ion) 452.5 [M+H]$^+$.

Step 5: (2S,3S)-ethyl 3-((2-(2-chloro-5-trityl-5H-pyrrolo[2,3-b]pyrazin-7-yl)-6-(5-methylthiophen-2-yl)pyrimidin-4-yl)amino)bicyclo[2.2.2]octane-2-carboxylate To a mixed solvent of 1,4-dioxane (8 mL) and H$_2$O (1 mL) were added 2-chloro-7-(4,4,5,5-tetramethyl-1,3,2-dioxaborolan-2-yl)-5-trityl-5H-pyrrolo[2,3-b]pyrazine (660 mg, 0.76 mmol, 60%), K$_2$CO$_3$ (290 mg, 2.07 mmol), PdCl$_2$(dppf) (60 mg, 0.07 mmol) and (2S,3S)-ethyl 3-((2-bromo-6-(5-methylthiophen-2-yl)pyrimidin-4-yl) amino)bicyclo[2.2.2]octane-2-carboxylate (310 mg, 0.69 mmol). The air in the mixture was exchanged with nitrogen by bubbling for 10 min. The mixture in the sealed tub was stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (260 mg, 49%).

$^1$H NMR (400 MHz, CDCl$_3$) δ(ppm): 8.53 (s, 1H), 7.94 (s, 1H), 7.54 (d, J=3.6 Hz, 1H), 7.38-7.30 (m, 10H), 7.22 (dd, J=6.3, 3.4 Hz, 5H), 6.79 (d, J=2.7 Hz, 1H), 6.55 (s, 1H), 4.31 (s, 1H), 4.16 (d, J=7.1 Hz, 2H), 2.55 (s, 3H), 2.43 (s, 1H), 1.93 (s, 1H), 1.89-1.64 (m, 6H), 1.60-1.36 (m, 4H), 1.23 (t, J=7.1 Hz, 3H).

Step 6: (2S,3S)-ethyl 3-((2-(2-chloro-5H-pyrrolo[2,3-b]pyrazin-7-yl)-6-(5-methylthiophen-2-yl)pyrimidin-4-yl) amino)bicyclo[2.2.2]octane-2-carboxylate To a solution of (2S,3S)-ethyl 3-((2-(2-chloro-5-trityl-5H-pyrrolo[2,3-b]pyrazin-7-yl)-6-(5-methylthiophen-2-yl)pyrimidin-4-yl)amino)bicyclo[2.2.2]octane-2-carboxylate (220 mg, 0.29 mmol) in DCM (5 mL) were added Et$_3$SiH (0.22 mL, 2.87 mmol) and TFA (0.46 mL, 5.40 mmol), and the mixture was stirred at rt overnight. The reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (141 mg, 94%).

MS (ESI, pos.ion) m/z: 523.2 [M+H]$^+$.

Step 7: (2S,3S)-3-((2-(2-chloro-5H-pyrrolo[2,3-b]pyrazin-7-yl)-6-(5-methylthiophen-2-yl)pyrimidin-4-yl) amino)bicyclo[2.2.2]octane-2-carboxylic Acid To a solution of (2S,3S)-ethyl 3-((2-(2-chloro-5H-pyrrolo[2,3-b]pyrazin-7-yl)-6-(5-methylthiophen-2-yl)pyrimidin-4-yl)amino)bicyclo[2.2.2]octane-2-carboxylate (180 mg, 0.34 mmol) in THF/MeOH (v/v=5 mL/5 mL) was added a solution of NaOH (140 mg, 3.44 mmol) in water (1 mL), and the mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (24 mg, 14%).

MS (ESI, pos. ion) m/z: 495.6 [M+H]$^+$;
HRMS (ESI, pos. ion) m/z: 495.1369, (C$_{24}$H$_{24}$ClN$_6$O$_2$S) [M+H]$^+$ theoretical value: 495.1370;
$^1$H NMR (600 MHz, DMSO-d$_6$) δ (ppm): 12.73 (s, 1H), 8.55 (s, 1H), 8.37 (s, 1H), 7.59 (s, 1H), 7.39 (s, 1H), 6.91 (s, 1H), 6.59 (s, 1H), 4.56 (s, 1H), 2.09 (s, 1H), 1.97 (s, 2H), 1.55 (m, 9H), 1.24 (s, 3H).

Example 27: (2S,3S)-3-((2-(2-chloro-5H-pyrrolo[2,3-b]pyrazin-7-yl)-6-(5-cyclopropylthiophen-2-yl)-5-fluoropyrimidin-4-yl)amino)bicyclo[2.2.2]octane-2-carboxylic Acid

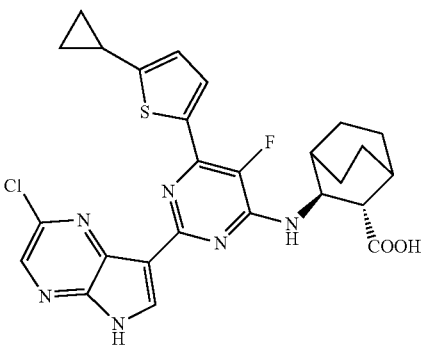 [SMILES: O=C(O)[C@H]1C2CCC(CC2)[C@@H]1Nc1nc(-c2c[nH]c3ncc(Cl)nc23)nc(-c2ccc(C3CC3)s2)c1F]

Step 1: (2S,3S)-ethyl 3-aminobicyclo[2.2.2]octane-2-carboxylate hydrochloride

The title compound was prepared by the synthetic method disclosed in patent application WO 2015073491.

Step 2: 2,4-dichloro-5-fluoro-6-(thiophen-2-yl)pyrimidine

The title compound was prepared by the synthetic method according to step 2 of example 13.

Step 3: (2S,3S)-ethyl 3-((2-chloro-5-fluoro-6-(thiophen-2-yl)pyrimidin-4-yl)amino)bicyclo[2.2.2]octane-2-carboxylate The title compound was prepared by the synthetic method according to step 3 of example 13.

Step 4: (2S,3S)-ethyl 3-((6-(5-bromothiophen-2-yl)-2-chloro-5-fluoropyrimidin-4-yl)amino)bicyclo[2.2.2]octane-2-carboxylate To a solution of (2S,3S)-ethyl 3-((2-chloro-5-fluoro-6-(thiophen-2-yl)pyrimidin-4-yl)amino)bicyclo[2.2.2]octane-2-carboxylate (1.59 g, 3.88 mmol) in DMF (20 mL) was added NBS (0.84 g, 4.70 mmol), and the mixture was stirred at rt for 12 h. To the reaction mixture was added water (30 mL), and the resulting mixture was extracted with ethyl acetate (40 mL×3). The combined organic layers were washed with saturated brine (100 mL×3), dried over anhydrous sodium sulfate and filtered. The filtrate was concentrated in vacuo and the residue was purified by silica gel column chromatography (PE/EtOAc (v/v)=10/1) to give the title compound as a light yellow solid (1.09 g, 57%).

MS (ESI, pos. ion) m/z: 488.0 [M+H]$^+$.

Step 5: (2S,3S)-ethyl 3-((2-chloro-6-(5-cyclopropyl-thiophen-2-yl)-5-fluoropyrimidin-4-yl)amino)bicyclo[2.2.2]octane-2-carboxylate To a mixed solvent of toluene (20 mL) and H$_2$O (1 mL) were added (2S,3S)-ethyl 3-((6-(5-bromothiophen-2-yl)-2-chloro-5-fluoropyrimidin-4-yl) amino)bicyclo[2.2.2]octane-2-carboxylate (950 mg, 1.94 mmol), cesium carbonate (45 mg, 0.20 mmol), Pd(OAc)$_2$ (45 mg, 0.20 mmol), n-butyldi-1-adamantylphosphine (143 mg, 0.39 mmol) and cyclopropylboronic acid (205 mg, 2.39 mmol). The mixture was stirred at 90° C. for 2 h. The reaction mixture was filtered through a celite pad. The filter cake was washed with ethyl acetate (30 mL×2). The combined filtrates was concentrated in vacuo, and the residue was purified by silica gel column chromatography (PE/EtOAc (v/v)=10/1) to give the title compound as a light yellow solid (842 mg, 96%).

$^1$H NMR (400 MHz, CDCl$_3$) δ (ppm): 7.61 (dd, J=3.8, 1.5 Hz, 1H), 6.84 (d, J=3.8 Hz, 1H), 4.51 (t, J=5.1 Hz, 1H), 4.23 (qd, J=7.1, 1.0 Hz, 2H), 2.40 (d, J=5.8 Hz, 1H), 2.03 (d, J=2.3 Hz, 1H), 1.91 (d, J=2.4 Hz, 1H), 1.84 (m, 1H), 1.75-1.63 (m, 6H), 1.28 (t, J=7.1 Hz, 3H), 1.12-1.07 (m, 2H), 0.86-0.81 (m, 2H).

Step 6: (2S,3S)-ethyl 3-((2-bromo-6-(5-cyclopropyl-thiophen-2-yl)-5-fluoropyrimidin-4-yl)amino)bicyclo[2.2.2]octane-2-carboxylate To a solution of hydrobromic acid in acetic acid (33%, 10 mL) was added (2S,3S)-ethyl 3-((2-chloro-6-(5-cyclopropylthiophen-2-yl)-5-fluoropyrimidin-4-yl)amino) bicyclo[2.2.2]octane-2-carboxylate (0.84 g, 1.90 mmol), and the resulting mixture was stirred at rt for 3 h. After the reaction was completed, the reaction mixture was added slowly into ice-water (100 mL). The mixture was extracted with ethyl acetate (100 mL×3). The combined organic layers were washed with saturated aqueous sodium sulfate (100 mL×3), dried over anydous sodium sulfate, and filtered. The filtrate was concentrated in vacuo to give the title compound as a light yellow solid (0.98 g, 90%), which was used directly in the next step without further purification.

MS (ESI, pos. ion) m/z: 494.0 [M+H]$^+$.

Step 7: (2S,3S)-ethyl 3-((2-(2-chloro-5-trityl-5H-pyrrolo[2,3-b]pyrazin-7-yl)-6-(5-cyclopropylthiophen-2-yl)-5-fluoropyrimidin-4-yl)amino)bicyclo[2.2.2]octane-2-carboxylate To 1,4-dioxane (20 mL) were added 2-chloro-7-(4,4,5,5-tetramethyl-1,3,2-dioxaborolan-2-yl)-5-trityl-5H-pyrrolo[2,3-b]pyrazine (65%, 1.81 g, 2.25 mmol), K$_2$CO$_3$(0.83 g, 6.00 mmol), PdCl$_2$(dppf) (0.45 g, 0.60 mmol) and (2S,3S)-ethyl 3-((2-bromo-6-(5-cyclopropylthiophen-2-yl)-5-fluoropyrimidin-4-yl)amino)bicyclo[2.2.2]octane-2-carboxylate (0.98 g, 2.00 mmol), then H$_2$O (1 mL) was added into the mixture. The air in the mixture was exchanged with nitrogen by bubbling for 10 min. The mixture in the sealed tub was stirred for 4 h at 115° C. The mixture was filtered to remove the solid impuries, and the filtrate was concentrated to remove the solvent. The residue was purified by silica gel column chromatography (PE/EtOAc (v/v)=10/1) to give the title compound as a yellow solid (1.07 g, 67%).

Step 8: (2S,3S)-ethyl 3-((2-(2-chloro-5H-pyrrolo[2,3-b]pyrazin-7-yl)-6-(5-cyclopropylthiophen-2-yl)-5-fluoropyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-6-(5-cyclopropylthiophen-2-yl)-5-fluoropyrimidin-4-yl) amino)bicyclo[2.2.2]octane-2-carboxylate (1.07 g, 1.32 mmol) in dichloromethane (20 mL) were added Et$_3$SiH (2.55 mL, 16.00 mmol) and TFA (1.20 mL, 5.40 mmol), and the mixture was stirred at rt for 2 days. The reaction mixture was added into saturated aqueous sodium bicarbonate (50 mL). The resulting mixture was extracted with dichloromethane (50 mL×3). The combined organic layers were washed with saturated brine (100 mL), dried over anhydrous sodium sulfate, and filtered. The filtrate was concentrated in vacuo, and the residue was purified by silica gel column chromatography (PE/EtOAc (v/v)=2/1) to give the title compound as a white solid (120 mg, 16%).

Step 9: (2S,3S)-3-((2-(2-chloro-5H-pyrrolo[2,3-b]pyrazin-7-yl)-6-(5-cyclopropylthiophen-2-yl)-5-fluoropyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-6-(5-cyclopropylthiophen-2-yl)-5-fluoropyrimidin-4-yl)amino)bicyclo[2.2.2]octane-2-carboxylate (0.12 g, 0.21 mmol) in THF/MeOH/H$_2$O (v/v/v=2 mL/2 mL/2 mL) was added NaOH (86 mg, 2.15 mmol), and the mixture was stirred at rt overnight. To the reaction mixture was added saturated brine (10 mL), and the mixture was acidified with hydrochloric acid (1 M) to pH about 6. The resulting mixture was extracted with ethyl acetate (30 mL×3). The combined organic layers were washed with saturated brine (50 mL), dried over anhydrous sodium sulfate, and filtered. The filtrate was concentrated in vacuo to remove the solvent, and the residue was purified by preparative thin-layer chromatography (DCM/MeOH (v/v)=20/1) to give the title compound as a light yellow solid (62 mg, 54%).

MS (ESI, pos. ion) m/z: 539.0 [M+H]$^+$;
HRMS (ESI, pos. ion) m/z: 539.1448, (C$_{26}$H$_{25}$ClN$_6$O$_2$S) [M+H]$^+$ theoretical value: 539.1432;
$^1$H NMR (400 MHz, DMSO-d$_6$) δ (ppm): 12.76 (s, 1H), 8.50 (d, J=2.9 Hz, 1H), 8.37 (s, 1H), 7.66 (d, J=3.0 Hz, 1H), 7.58 (d, J=6.1 Hz, 1H), 6.97 (d, J=3.6 Hz, 1H), 4.66 (t, J=6.2 Hz, 1H), 2.84 (d, J=7.0 Hz, 1H), 2.23 (m, 1H), 2.10 (s, 1H), 1.74 (m, 2H), 1.59-1.48 (m, 3H), 1.44-1.31 (m, 2H).

Example 28: (2S,3S)-3-((2-(2-chloro-5H-pyrrolo[2,3-b]pyrazin-7-yl)-6-(5-fluorothiophen-2-yl) pyrimidin-4-yl)amino)bicyclo[2.2.2]octane-2-carboxylic Acid

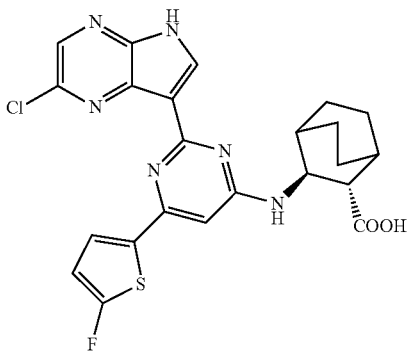 [SMILES: O=C(O)[C@H]1C2CCC(CC2)[C@@H]1Nc1cc(-c2ccc(F)s2)nc(-c2c[nH]c3ncc(Cl)nc23)n1]

Step 1: (2S,3S)-ethyl 3-aminobicyclo[2.2.2]octane-2-carboxylate hydrochloride The title compound was prepared by the synthetic method disclosed in patent application WO 2015073491.

Step 2: 2-fluorothiophene

To a −15° C. solution of thiophene (500 mg, 5.94 mmol) in anhydrous tetrahydrofuran (8 mL) under nitrogen protection was added n-butyllithium (2.60 mL, 6.54 mmol, 2.5 mol/L), and the mixture was stirred for 1 h maintaining at this temperature. Then the reaction mixture was cooled to −78° C. and stirred for 5 min, and NFSI (2.07 g, 6.54 mmol) was added. The resulting mixture was warmed naturally to rt in 6 hours, then fraction was collected by using distillation method to give the title compound as colorless oil (607 mg, 41%), which was used directly in the next step.

Step 3: 2,4-dichloro-6-(5-flurothiophen-2-yl)pyrimidine

To a solution of 2-fluorothiophene (3.76 g, 36.80 mmol) in anydrous tetrahydrofuran (20 mL) was added n-butyllithium (15.0 mL, 36.80 mmol, 2.5 mol/L) at −15° C., and the mixture was stirred for 1 h at −15° C. Then to the mixture was added dichloro(N,N,N',N'-tetramethylethylenediamine)zinc(II) (3.07 g, 12.11 mmol), and the resulting mixture was stirred for 1 h. Then palladium dichloride (653 mg, 3.68 mmol), triphenylphosphine (1.93 g, 7.36 mmol) and 2,4,6-trichloropyrimidine (7.43 g, 40.50 mmol) were added to the mixture in turn. The resulting mixture was heated to 55° C. under nitrogen protection, and then stirred at this temperature overnight. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a white solid (2.41 g, 26%).

MS (ESI, pos.ion) m/z: 249.0 [M+H]$^+$.

Step 4: (2S,3S)-ethyl 3-((2-chloro-6-(5-fluorothiophen-2-yl)pyrimidin-4-yl)amino)bicyclo[2.2.2]octane-2-carboxylate To a solution of (2S,3S)-ethyl 3-aminobicyclo[2.2.2]octane-2-carboxylate hydrochloride (631 mg, 2.70 mmol) and 2,4-dichloro-6-(5-fluorofuran-3-yl)pyrimidine (559 mg, 2.24 mmol) in DMF (30 mL) was added potassium carbonate (620 mg, 4.49 mmol), and the mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (559 mg, 61%).

MS (ESI, pos.ion) m/z: 410.0 [M+H]$^+$.

Step 5: (2S,3S)-ethyl 3-((2-bromo-6-(5-fluorothiophen-2-yl)pyrimidin-4-yl)amino)bicyclo[2.2.2]octane-2-carboxylate To a solution of hydrobromic acid (880 mg, 3.51 mmol) in acetic acid (6 mL) was added (2S,2S)-ethyl 3-((2-chloro-6-(5-fluorohiophen-2-yl)pyrimidin-4-yl)amino)bicyclo[2.2.2]octane-2-carboxylate (1.20 g, 2.93 mmol), and the mixture was stirred at rt overnight. The reaction mixture was added into ice-water (40 mL), and the resulting mixture was extracted with EtOAc (40 mL×3). The combined organic layers were washed with saturated aqueous sodium bicarbonate (50 mL×3) and saturated brine (30 mL), dried over anhydrous Na$_2$SO$_4$, and filtered. The filtrate was concentrated in vacuo to give the title compound as a light yellow solid (1.12 g, 84%).

MS (ESI, pos.ion) m/z: 454.0 [M+H]$^+$.

Step 6: (2S,3S)-ethyl 3-((2-(2-chloro-5-trityl-5H-pyrrolo[2,3-b]pyrazin-7-yl)-6-(5-fluorothiophen-2-yl)pyrimidin-4-yl)amino)bicyclo[2.2.2]octane-2-carboxylate To a mixed solvent of 1,4-dioxane (8 mL) and H$_2$O (1 mL) were added 2-chloro-7-(4,4,5,5-tetramethyl-1,3,2-dioxaborolan-2-yl)-5-trityl-5H-pyrrolo[2,3-b]pyrazine (2.36 g, 2.71 mmol, 60%), K$_2$CO$_3$ (1.02 g, 7.39 mmol), PdCl$_2$(dppf) (190 mg, 0.25 mmol) and (2S,3S)-ethyl 3-((2-bromo-6-(5-fluorothiophen-2-yl)pyrimidin-4-yl)amino)bicyclo[2.2.2]octane-2-carboxylate (1.12 g, 2.46 mmol). The air in the mixture was exchanged with nitrogen by bubbling for 10 min. The mixture in the sealed tub was stirred for 3 h at 115° C. The mixture was filtered to remove the solid impuries, and the solvent was removed. The residue was purified by silica gel column chromatography (PE/EtOAc (v/v)=10/1-5/1) to give the title compound as a white solid (1.18 g, 62%).

Step 7: (2S,3S)-ethyl 3-((2-(2-chloro-5H-pyrrolo[2,3-b]pyrazin-7-yl)-6-(5-fluorothiophen-2-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-6-(5-fluorothiophen-2-yl)pyrimidin-4-yl)amino)bicyclo[2.2.2]octane-2-carboxylate (1.18 g, 1.53 mmol) in dichloromethane (5 mL) were added Et$_3$SiH (2.40 mL, 15.30 mmol) and TFA (1.20 mL, 5.40 mmol), and the mixture was stirred at rt overnight. The reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (780 mg, 97%).

MS (ESI, pos. ion) m/z: 527.7 [M+H]$^+$.

Step 8: (2S,3S)-3-((2-(2-chloro-5H-pyrrolo[2,3-b]pyrazin-7-yl)-6-(5-fluorothiophen-2-yl)pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-6-(5-fluorothiophen-2-yl)pyrimidin-4-yl)amino)bicyclo[2.2.2]octane-2-carboxylate (780 mg, 1.48 mmol) in THF/MeOH (v/v=5 mL/5 mL) were added a solution of NaOH (592 mg, 14.80 mmol) in water (1 mL), and the mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (565 mg, 77%).

MS (ESI, pos. ion) m/z: 499.10 [M+H]$^+$;

HRMS (ESI, pos. ion) m/z: 499.1121, ($C_{23}H_{21}FClN_6O_2S$) [M+H]$^+$ theoretical value: 499.1119;

$^1$H NMR (600 MHz, DMSO-d$_6$) δ (ppm): 13.17 (s, 1H), 8.54 (s, 1H), 8.49 (s, 1H), 8.33 (s, 1H), 7.38 (s, 1H), 6.82 (d, J=3.0 Hz, 1H), 6.52 (s, 1H), 4.47 (s, 1H), 2.43 (s, 1H), 1.93 (m, 2H), 1.87-1.28 (m, 9H).

Example 29: (2S,3S)-3-((2-(2-chloro-5H-pyrrolo[2,3-b]pyrazin-7-yl)-6-(5-chlorothiophen-2-yl)-5-fluoropyrimidin-4-yl)amino)bicyclo[2.2.2]octane-2-carboxylic Acid

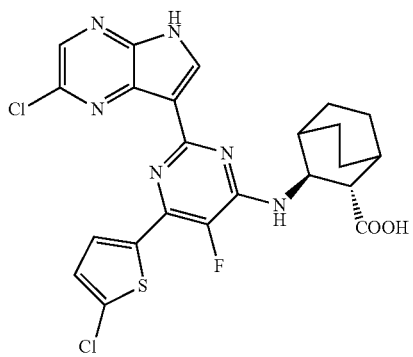 [SMILES: O=C(O)[C@H]1C2CCC(CC2)[C@@H]1Nc1nc(-c2c[nH]c3ncc(Cl)nc23)nc(-c2ccc(Cl)s2)c1F]

Step 1: (2S,3S)-ethyl 3-aminobicyclo[2.2.2]octane-2-carboxylate hydrochloride The title compound was prepared by the synthetic method disclosed in patent application WO 2015073491.

Step 2: (2S,3S)-ethyl 3-((2-(2-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate To a mixed solvent of 1,4-dioxane (8 mL) and H$_2$O (1 mL) were added 2-chloro-7-(4,4,5,5-tetramethyl-1,3,2-dioxaborolan-2-yl)-5-trityl-5H-pyrrolo[2,3-b]pyrazine (280 mg, 0.54 mmol), K$_2$CO$_3$ (202 mg, 1.46 mmol), PdCl$_2$(dppf) (40 mg, 0.05 mmol) and (2S,3S)-ethyl 3-((2-chloro-5-fluoro-6-(thiophen-2-yl)pyrimidin-4-yl)amino)bicyclo[2.2.2]octane-2-carboxylate (200 mg, 0.49 mmol). The air in the mixture was exchanged with nitrogen by bubbling for 10 min. The mixture in the sealed tub was stirred for 3 h at 115° C. The mixture was filtered to remove the solid impuries, and the solvent was removed. The residue was purified by silica gel column chromatography (PE/EtOAc (v/v)=10/1-5/1) to give the title compound as a white solid (101 mg, 27%).

Step 3: (2S,3S)-ethyl 3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate (183 mg, 0.24 mmol) in dichloromethane (5 mL) were added Et$_3$SiH (0.40 mL, 2.38 mmol) and TFA (0.20 mL, 5.40 mmol), and the mixture was stirred at rt overnight. The reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (89 mg, 71%).

MS (ESI, pos. ion) m/z: 527.1 [M+H]$^+$.

Step 4: (2S,3S)-ethyl 3-((2-(2-chloro-5H-pyrrolo[2,3-b]pyrazin-7-yl)-6-(5-chlorothiophen-2-yl)-5-fluoropyrimidin-4-yl) amino)bicyclo[2.2.2]octane-2-carboxylate To a solution of (2S,3S)-ethyl 3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate (75 mg, 0.14 mmol) in DMF(5 mL) was added NCS (0.86 mL, 5.40 mmol), and the mixture was stirred at 100° C. for 3 h under nitrogen protection. To the reaction mixture was added water (30 mL), and the mixture was extracted with EtOAc (30 mL×3). The combined organic layers were washed with saturated brine (80 mL), dried over anhydrous sodium sulfate, and filtered. The filtrate was concentrated in vacuo to remove the solvent, and the residue was purified by silica gel column chromatography (PE/EA (v/v)=10/1-3/1) to give the title compound as a yellow solid (513 mg, 92%).

Step 5: (2S,3S)-3-((2-(2-chloro-5H-pyrrolo[2,3-b]pyrazin-7-yl)-6-(5-chlorothiophen-2-yl)-5-fluoropyrimidin-4-yl) amino)bicyclo[2.2.2]octane-2-carboxylic Acid To a solution of (2S,3S)-ethyl 3-((2-(2-chloro-5H-pyrrolo[2,3-b]pyrazin-7-yl)-6-(5-chlorothiophen-2-yl)-5-fluoropyrimidin-4-yl) amino)bicyclo[2.2.2]octane-2-carboxylate (513 mg, 0.91 mmol) in THF/MeOH (v/v=5 mL/5 mL) were added a solution of NaOH (366 mg, 9.14 mmol) in water (1 mL), and the mixture was stirred at rt overnight. To the reaction mixture was added water (20 mL), and the mixture was acidified with hydrochloric acid (1 M) to pH about 6. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (101 mg, 21%).

MS (ESI, pos. ion) m/z: 533.0 [M+H]$^+$;
HRMS (ESI, pos. ion) m/z: 533.0743, ($C_{23}H_{20}FCl_2N_6O_2S$) [M+H]$^+$ theoretical value: 533.0730;
$^1$H NMR (600 MHz, DMSO-d$_6$) δ (ppm): 12.78 (s, 1H), 8.52 (d, J=2.4 Hz, 1H), 8.36 (s, 1H), 7.69 (m, 2H), 7.27 (d, J=3.7 Hz, 1H), 4.67 (s, 1H), 2.85 (d, J=6.7 Hz, 1H), 2.09 (s, 1H), 2.00 (s, 2H), 1.74 (d, J=10.2 Hz, 2H), 1.62-1.41 (m, 5H), 1.21 (d, J=5.9 Hz, 1H).

Example 30: (2S,3S)-3-((2-(2-chloro-5H-pyrrolo[2,3-b]pyrazin-7-yl)-5-fluoro-6-(1H-pyrrol-2-yl)pyrimidin-4-yl)amino)bicyclo[2.2.2]octane-2-carboxylic Acid

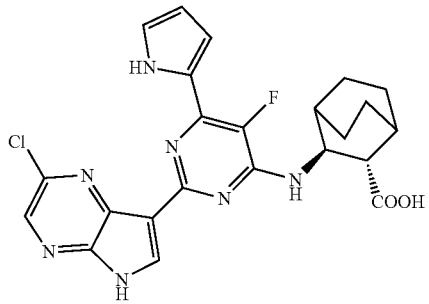 [SMILES: O=C(O)[C@H]1C2CCC(CC2)[C@@H]1Nc1nc(-c2c[nH]c3ncc(Cl)nc23)nc(-c2ccc[nH]2)c1F]

Step 1: tert-butyl 2-(2-chloro-6-(((2S,3S)-3-(ethoxycarbonyl)bicyclo[2.2.2]octan-2-yl)amino)-5-fluoropyrimidin-4-yl)-1H-pyrrole-1-carboxylate To a mixture of 1,4-dioxane (3 mL) and H$_2$O (0.1 mL) were added (2S,3S)-ethyl 3-((2,6-dichloro-5-fluoropyrimidin-4-yl)amino)bicyclo[2.2.2]octane-2-carboxylate (50 mg, 0.14 mmol), K$_2$CO$_3$ (58 mg, 0.42 mmol), Pd(dppf)Cl$_2$ (21 mg, 0.03 mmol) and (1-(tert-butoxycarbonyl)-1H-pyrrol-2-yl)boronic acid (30 mg, 0.14 mmol). The air in the mixture was exchanged with nitrogen by bubbling for 10 min, then the mixture in the tub was sealed and stirred at 115° C. for 4 h. The mixture was filtered to remove the solid impurity, and the filtrate was concentrated to remove the solvent. The residue was purified by silica gel column chromatography (PE/EtOAc (v/v)=10/1) to give the title compound as light yellow oil (20 mg, 29%).

MS (ESI, pos. ion) m/z: 493.1 [M+H]$^+$;
$^1$H NMR (400 MHz, CDCl$_3$) δ (ppm): 7.42 (dd, J=3.2, 1.7 Hz, 1H), 6.60 (dd, J=3.2, 1.5 Hz, 1H), 6.29 (t, J=3.3 Hz, 1H), 4.53 (t, J=5.6 Hz, 1H), 4.24 (q, J=7.1 Hz, 2H), 2.39 (d, J=5.8 Hz, 1H), 2.03 (d, J=2.2 Hz, 1H), 1.91 (d, J=2.1 Hz, 1H), 1.84 (m, 1H), 1.74-1.63 (m, 6H), 1.47 (s, 9H), 1.27 (t, J=2.1 Hz, 3H).

Step 2: (2S,3S)-ethyl 3-((2-bromo-5-fluoro-6-(1H-pyrrol-2-yl)pyrimidin-4-yl)amino)bicyclo[2.2.2]octane-2-carboxylate To a solution of hydrobromic acid in acetic acid (33%, 4 mL) was added tert-butyl 2-(2-chloro-6-(((2S,3S)-3-(ethoxycarbonyl)bicyclo[2.2.2]octan-2-yl)amino)-5-fluoropyrimidin-4-yl)-1H-pyrrole-1-carboxylate (0.12 g, 0.24 mmol), and the mixture was stirred at rt for 2 h. The reaction mixture was added into ice-water, and the resulting mixture was extracted with dichloromethane (80 mL×3). The combined organic layers were washed with saturated aqueous sodium bicarbonate (100 mL×3), dried over anhydrous sodium sulfate, and filtered. The filtrate was concentrated in vacuo to remove the solvent and give the title compound as light yellow oil (100 mg, 94%).

MS (ESI, pos. ion) m/z: 369.2 [M+H]$^+$.

Step 3: (2S,3S)-ethyl 3-((2-(2-chloro-5-trityl-5H-pyrrolo[2,3-b]pyrazin-7-yl)-5-fluoro-6-(1H-pyrrol-2-yl)pyrimidin-4-yl)amino)bicyclo[2.2.2]octane-2-carboxylate To a mixed solvent of 1,4-dioxane (20 mL) and H$_2$O (1 mL) were added 2-chloro-7-(4,4,5,5-tetramethyl-1,3,2-dioxaborolan-2-yl)-5-trityl-5H-pyrrolo[2,3-b]pyrazine (985 g, 1.23 mmol, 65%), K$_2$CO$_3$ (465 mg, 3.36 mmol), Pd(dppf)Cl$_2$ (251 mg, 0.34 mmol) and (2S,3S)-ethyl 3-((2-bromo-5-fluoro-6-(1H-pyrrol-2-yl)pyrimidin-4-yl)amino)bicyclo[2.2.2]octane-2-carboxylate (486 mg, 1.11 mmol). The air in the mixture was exchanged with nitrogen by bubbling for 10 min. The mixture in the sealed tub was stirred for 4 h at 115° C. The mixture was filtered to remove the solid impurity, and the filtrate was concentrated to remove the solvent. The residue was purified by silica gel column chromatography (PE/EtOAc (v/v)=10/1) to give the title compound as light yellow oil (588 mg, 45%).

Step 4: (2S,3S)-ethyl 3-((2-(2-chloro-5H-pyrrolo[2,3-b]pyrazin-7-yl)-5-fluoro-6-(1H-pyrrol-2-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-5-fluoro-6-(1H-pyrrol-2-yl)pyrimidin-4-yl) amino)bicyclo[2.2.2]octane-2-carboxylate (588 mg, 0.78 mmol) in dichloromethane (20 mL) was added Et$_3$SiH (1.50 mL, 9.39 mmol) and TFA (0.70 mL, 9.40 mmol), and the mixture was stirred at rt overnight. The reaction was stopped, and the reaction mixture was added into saturated aqueous sodium bicarbonate (30 mL). The resulting mixture was extracted with dichloromethane (30 mL×3). The combined organic layers were washed with saturated brine (80 mL), dried over anhydrous sodium sulfate, and filtered. The filtrate was concentrated in vacuo to remove the solvent, and the residue was purified by silica gel column chromatography (PE/EtOAc (v/v)=2/1) to give the title compound as light yellow oil (82 mg, 21%).

MS (ESI, pos. ion) m/z: 510.1 [M+H]$^+$.

Step 5: (2S,3S)-3-((2-(2-chloro-5H-pyrrolo[2,3-b]pyrazin-7-yl)-5-fluoro-6-(1H-pyrrol-2-yl)pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-5-fluoro-6-(1H-pyrrol-2-yl)pyrimidin-4-yl)amino)bicyclo[2.2.2]octane-2-carboxylate (83 mg, 0.16 mmol) in THF/MeOH/H$_2$O (v/v/v=2 mL/2 mL/2 mL)

was added NaOH (66 mg, 1.65 mmol), and the mixture was stirred at rt overnight. To the reaction mixture was added saturated brine (10 mL), and the mixture was acidified with hydrochloric acid (1 M) to pH about 6. The resulting mixture was extracted with ethyl acetate (30 mL×3). The combined organic layers were washed with saturated brine (50 mL), dried over anhydrous sodium sulfate, and filtered. The filtrate was concentrated in vacuo to remove the solvent, and the residue was purified by preparative thin-layer chromatography (DCM/MeOH (v/v)=20/1) to give the title compound as a light yellow solid (60 mg, 77%).

MS (ESI, pos. ion) m/z: 482.60 [M+H]$^+$.

HRMS (ESI, pos. ion) m/z: 482.1509, ($C_{23}H_{22}ClN_7O_2$) [M+H]$^+$ theoretical value: 482.1508;

$^1$H NMR (400 MHz, DMSO-$d_6$) δ (ppm): 12.85 (s, 1H), 11.57 (s, 1H), 9.00 (s, 1H), 8.34 (s, 1H), 7.37 (d, J=6.4 Hz, 1H), 7.07 (s, 1H), 6.78 (s, 1H), 6.28 (d, J=3.1 Hz, 1H), 4.68 (s, 1H), 2.86 (d, J=7.0 Hz, 1H), 2.17 (s, 1H), 1.99 (s, 1H), 1.80-1.68 (m, 2H), 1.48 (m, 5H).

Example 31: (2S,3S)-3-((2-(2-chloro-5H-pyrrolo[2,3-b]pyrazin-7-yl)-5-fluoro-6-(1,2,3-thiadiazol-5-yl)pyrimidin-4-yl)amino)bicyclo[2.2.2]octane-2-carboxylic Acid

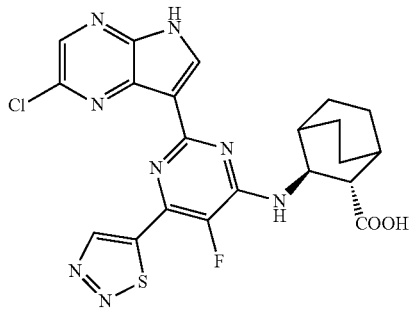 [SMILES: O=C(O)[C@H]1C2CCC(CC2)[C@@H]1Nc1nc(-c2c[nH]c3ncc(Cl)nc23)nc(-c2cnns2)c1F]

Step 1:
1-(2,6-dichloro-5-fluoropyrimidin-4-yl)ethanone

To a 2 L three-neck flask were added 2,4-dichloro-5-fluoropyrimidine (10.0 g, 59.9 mmol) and acetic acid (100 mL) in turn. The solid in the mixture was dissolved until the mixture was clear by ultraphonic, then sulfuric acid (320 mL, 480 mmol, 1.5 mol/L) was added into the mixture. The resulting mixture was cooled to 10° C. and stirred under nitrogen protection, then acetaldehyde (34 mL, 604 mmol) was added by syring. The mixture was stirred for 5 min, then ammonium persulfate solution (120 mL, 120 mmol, 1 mol/L) and ferrous sulfate heptahydrate solution (120 mL, 120 mmol, 1 mol/L) were syringed into reaction the mixture at a similar dripping speed in one hour. The reaction was stopped, and the mixture was filtered to give the title compound as a white solid (1.36 g, 11%).

$^1$H NMR (400 MHz, CDCl$_3$) δ (ppm): 2.72 (s, 3H).

Step 2: (E)-methyl 2-(1-(2,6-dichloro-5-fluoropyrimidin-4-yl)ethylidene)hydrazinecarboxylate A suspension of 1-(2,6-dichloro-5-fluoropyrimidin-4-yl)ethanone (200 mg, 0.96 mmol), methyl carbazate (95 mg, 1.06 mmol) and p-toluenesulfonic acid (18 mg, 0.11 mmol) in toluene (10 mL) was heated to 110° C. and stirred for 2 hours under nitrogen protection. The reaction mixture was concentrated in vacuo and the residue was purified by silica gel column chromatography (PE/EA (v/v)=5/1) to give the title compound as a white solid (151 mg, 56%).

MS (ESI, pos.ion) m/z: 281.3 [M+H]$^+$;
$^1$H NMR (400 MHz, CDCl$_3$) δ (ppm): 8.27 (s, 1H), 3.94 (s, 3H), 2.32 (s, 3H).

Step 3: 542, 6-dichloro-5-fluoropyrimidin-4-yl)-1,2,3-thiadiazole

To thionyl chloride (8 mL) was added (E)-methyl 2-(1-(2,6-dichloro-5-fluoropyrimidin-4-yl)ethylidene)hydrazinecarboxylate (112 mg, 0.40 mmol) at 0° C. After the addition, the mixture was warmed to rt and stirred for 5 h. The reaction mixture was concentrated in vacuo to remove the excess thionyl chloride and the residue was purified by silica gel column chromatography (PE/EA (v/v)=5/1) to give the title compound as a white solid (26 mg, 26%).

$^1$H NMR (400 MHz, CDCl$_3$) δ(ppm) 9.52 (s, 1H).

Step 4: (2S,3S)-ethyl 3-((2-chloro-5-fluoro-6-(1,2,3-thiadiazol-5-yl)pyrimidin-4-yl)amino)bicyclo[2.2.2]octane-2-carboxylate To a solution of (2S,3S)-ethyl 3-aminobicyclo[2.2.2]octane-2-carboxylate hydrochloride (159 mg, 0.68 mmol) and 5-(2,6-dichloro-5-fluoropyrimidin-4-yl)-1,2,3-thiadiazole (142 mg, 0.57 mmol) in THF (8 mL) was added DIPEA (730 mg, 5.66 mmol), and the mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (215 mg, 92%).

MS (ESI, pos.ion) 412.5 [M+H]$^+$;
$^1$H NMR (400 MHz, CDCl$_3$) δ(ppm) 9.31 (s, 1H), 5.58 (d, J=3.8 Hz, 1H), 4.61 (t, J=5.0 Hz, 1H), 4.25 (q, J=7.1 Hz, 2H), 2.45 (d, J=5.8 Hz, 1H), 2.07 (s, 1H), 1.96 (d, J=2.4 Hz, 1H), 1.88-1.60 (m, 8H), 1.29 (d, J=7.2 Hz, 3H).

Step 5: (2S,3S)-ethyl 3-((2-bromo-5-fluoro-6-(1,2,3-thiadiazol-5-yl)pyrimidin-4-yl)amino)bicyclo[2.2.2]octane-2-carboxylate To a solution of hydrobromic acid (370 mg, 0.63 mmol) in acetic acid (6 mL) was added (2S,3S)-ethyl 3-((2-chloro-5-fluoro-6-(1,2,3-thiadiazol-5-yl)pyrimidin-4-yl)amino)bicyclo[2.2.2]octane-2-carboxylate (215 mg, 0.52 mmol), and the mixture was stirred at rt overnight. The reaction mixture was added into ice-water (40 mL), and the resulting mixture was extracted with EtOAc (30 mL×3). The combined organic layers were washed with saturated aqueous sodium bicarbonate (50 mL×3) and saturated brine (30 mL), dried over anhydrous Na$_2$SO$_4$, and filtered. The filtrate was concentrated in vacuo to give the title compound as a light yellow solid (229 mg, 96%).

MS (ESI, pos.ion) m/z: 458.5 [M+H]$^+$.

Step 6: (2S,3S)-ethyl 3-((2-(2-chloro-5-trityl-5H-pyrrolo[2,3-b]pyrazin-7-yl)-5-fluoro-6-(1,2,3-thiadiazol-5-yl)pyrimidin-4-yl) amino)bicyclo[2.2.2]octane-2-carboxylate To a mixed solvent of 1,4-dioxane (8 mL) and H$_2$O (1 mL) were added 2-chloro-7-(4,4,5,5-tetramethyl-1,3,2-dioxaborolan-2-yl)-5-trityl-5H-pyrrolo[2,3-b]pyrazine (480 mg, 0.55 mmol, 60%), K₂CO₃ (210 mg, 1.51 mmol), PdCl₂ (dppf) (40 mg, 0.05 mmol) and (2 S,3S)-ethyl 3-((2-bromo-5-fluoro-6-(1,2,3-thiadiazol-5-yl)pyrimidin-4-yl) amino)bicyclo[2.2.2]octane-2-carboxylate (229 mg, 0.50 mmol). The air in the mixture was exchanged with nitrogen by bubbling for 10 min. The mixture in the sealed tub was stirred for 3 h at 115° C. The mixture was filtered to remove the solid impurities, and the solvent was removed. The residue was purified by silica gel column chromatography (PE/EtOAc (v/v)=10/1-5/1) to give the title compound as a white solid (186 mg, 48%).

¹H NMR (400 MHz, CDCl₃) δ (ppm): 9.58 (s, 1H), 8.45 (s, 1H), 7.96 (s, 1H), 7.34-7.29 (m, 10H), 7.23 (m, 5H), 5.33 (d, J=5.8 Hz, 1H), 4.65 (t, J=7.1 Hz, 1H), 4.10 (m, 2H), 3.72 (d, J=4.8 Hz, 1H), 2.38 (d, J=6.7 Hz, 1H), 2.09 (s, 1H), 2.06 (s, 1H), 1.76-1.64 (m, 8H), 1.18 (t, J=7.1 Hz, 3H).

Step 7: (2S,3S)-ethyl 3-((2-(2-chloro-5H-pyrrolo[2,3-b]pyrazin-7-yl)-5-fluoro-6-(1,2,3-thiadiazol-5-yl) pyrimidin-4-yl) amino)bicyclo[2.2.2]octane-2-carboxylate To a solution of (2S,3S)-ethyl 3-((2-(2-chloro-5-trityl-5H-pyrrolo[2,3-b]pyrazin-7-yl)-5-fluoro-6-(1,2,3-thiadiazol-5-yl)pyrimidin-4-yl)amino)bicyclo[2.2.2]octane-2-carboxylate (375 mg, 0.49 mmol) in dichloromethane (5 mL) were added Et₃SiH (0.78 mL, 4.89 mmol) and TFA (0.39 mL, 5.40 mmol), and the mixture was stirred at rt overnight. The reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (201 mg, 78%).

MS (ESI, pos. ion) m/z: 529.0 [M+H]⁺.

Step 8: (2S,3S)-3-((2-(2-chloro-5H-pyrrolo[2,3-b]pyrazin-7-yl)-5-fluoro-6-(1,2,3-thiadiazol-5-yl)pyrimidin-4-yl) amino)bicyclo[2.2.2]octane-2-carboxylic Acid To a solution of (2S,3S)-ethyl 3-((2-(2-chloro-5H-pyrrolo[2,3-b]pyrazin-7-yl)-5-fluoro-6-(1,2,3-thiadiazol-5-yl)pyrimidin-4-yl)amino)bicyclo[2.2.2]octane-2-carboxylate (150 mg, 0.28 mmol) in THF (5 mL) was added concentrated hydrochloric acid (290 mg, 2.84 mmol, 33%), and the mixture was stirred at 55° C. overnight. To the reaction mixture was added water (20 mL), and the mixture was adjusted with saturated NaHCO₃ (3 M) to pH about 6. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH/Et₃N (v/v/v)=10/1-5/1) to give the title compound as a white solid (35 mg, 25%).

MS (ESI, pos. ion) m/z: 501.5 [M+H]⁺;
HRMS (ESI, pos. ion) m/z: 501.1016, (C₂₁H₁₉FClN₈O₂S)[M+H]⁺ theoretical value: 501.1024;
¹H NMR (600 MHz, DMSO-d₆) δ (ppm): 9.85 (s, 1H), 8.65 (s, 1H), 8.37 (s, 1H), 7.84 (d, J=6.1 Hz, 1H), 4.73 (s, 1H), 2.88 (d, J=7.2 Hz, 1H), 2.14 (s, 1H), 2.01 (s, 2H), 1.76-1.37 (m, 8H).

Example 32: (2S,3S)-3-((2-(2-chloro-5H-pyrrolo[2,3-b]pyrazin-7-yl)-5-fluoro-6-(pyridin-2-yl) pyrimidin-4-yl)amino)bicyclo[2.2.2]octane-2-carboxylic Acid

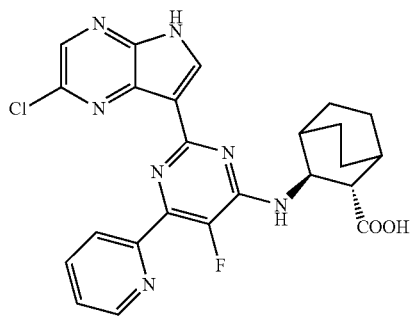 [SMILES: O=C(O)[C@H]1C2CCC(CC2)[C@@H]1Nc1nc(-c2c[nH]c3ncc(Cl)nc23)nc(-c2ccccn2)c1F]

Step 1: (2S,3S)-ethyl 3-((2-chloro-5-fluoro-6-(pyridin-2-yl)pyrimidin-4-yl)amino)bicyclo[2.2.2]octane-2-carboxylate To a mixture of tetrahydrofuran (8 mL) and H₂O (1 mL) were added pyridin-2-ylboronic acid (200 mg, 1.63 mmol), K₂CO₃ (675 mg, 4.88 mmol), PdCl₂ (dPPf) (122 mg, 0.16 mmol) and (2S,3S)-ethyl-3-((2,6-dichloro-5-fluoropyrimidin-4-yl)amino) bicyclo[2.2.2]octane-2-carboxylate (650 mg, 1.79 mmol). The air in the mixture was exchanged with nitrogen by bubbling for 10 min. The mixture in sealed tub was stirred for 3 h at 100° C. The mixture was filtered to remove the solid impuries, and the solvent was removed. The residue was purified by silica gel column chromatography (PE/EtOAc (v/v)=10/1-5/1) to give the title compound as a white solid (98 mg, 15%).

MS (ESI, pos. ion) m/z: 405.5 [M+H]⁺.

Step 2: (2S,3S)-ethyl 3-((2-bromo-5-fluoro-6-(pyridin-2-yl)pyrimidin-4-yl)amino)bicyclo[2.2.2]octane-2-carboxylate To a solution of hydrobromic acid (440 mg, 0.41 mmol) in acetic acid (6 mL) was added (2S,3S)-ethyl 3-((2-chloro-5-fluoro-6-(pyridin-2-yl)pyrimidin-4-yl)amino) bicyclo[2.2.2]octane-2-carboxylate (140 mg, 0.35 mmol), and the mixture was stirred at rt overnight. The reaction mixture was added into ice-water (40 mL), and the resulting mixture was extracted with EtOAc (30 mL×3). The combined organic layers were washed with saturated aqueous sodium bicarbonate (80 mL) and saturated brine (80 mL), dried over anhydrous Na₂SO₄, and filtered. The filtrate was concentrated in vacuo to give the title compound as a light yellow solid (141 mg, 91%).

MS (ESI, pos.ion) m/z: 449.0 [M+H]⁺.

Step 3: (2S,3S)-ethyl 3-((2-(2-chloro-5-trityl-5H-pyrrolo[2,3-b]pyrazin-7-yl)-5-fluoro-6-(pyridin-2-yl) pyrimidin-4-yl) amino)bicyclo[2.2.2]octane-2-carboxylate To a mixed solvent of 1,4-dioxane (8 mL) and H₂O (1 mL) were added 2-chloro-7-(4,4,5,5-tetramethyl-1,3,2-dioxaborolan-2-yl)-5-trityl-5H-pyrrolo[2,3-b]pyrazine (310 mg, 0.36 mmol, 60%), K₂CO₃ (135 mg, 0.97 mmol), PdCl₂ (dppf) (25 mg, 0.03 mmol) and (2S,3S)-ethyl 3-((2-bromo- 5-fluoro-6-(pyridin-2-yl)pyrimidin-4-yl) amino)bicyclo[2.2.2]octane-2-carboxylate (140 mg, 0.32 mmol). The air in the mixture was exchanged with nitrogen by bubbling for 10 min. The mixture in the sealed tub was stirred for 3 h at 115° C. The mixture was filtered to remove the solid impurities, and the solvent was removed. The residue was purified by silica gel column chromatography (PE/EtOAc (v/v)=10/1-5/1) to give the title compound as a white solid (164 mg, 68%).

Step 4: (2S,3S)-ethyl 3-((2-(2-chloro-5H-pyrrolo[2,3-b]pyrazin-7-yl)-5-fluoro-6-(pyridin-2-yl)pyrimidin-4-yl)amino)bicyclo[2.2.2]octane-2-carboxylate To a solution of (2S,3S)-ethyl 3-((-2-(2-chloro-5-trityl-5H-pyrrolo[2,3-b]pyrazin-7-yl)-5-_fluoro-6-(pyridin-2-yl)pyrimidin-4-yl)amino)bicyclo[2.2.2]octane-2-carboxylate (164 mg, 0.21 mmol) in dichloromethane (6 mL) were added Et₃SiH (2.50 mg, 2.14 mmol) and TFA (0.14 mL, 5.40 mmol), and the mixture was stirred at rt overnight. The reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (96 mg, 86%).

MS (ESI, pos. ion) m/z: 522.1 [M+H]⁺.

Step 5: (2S,3S)-3-((2-(2-chloro-5H-pyrrolo[2,3-b]pyrazin-7-yl)-5-fluoro-6-(pyridin-2-yl)pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-5-fluoro-6-(pyridin-2-yl)pyrimidin-4-yl)amino)bicyclo[2.2.2]octane-2-carboxylate (92 mg, 0.18 mmol) in THF/MeOH/H₂O (v/v=5 mL/5 mL) was added a solution of NaOH (70 mg, 1.76 mmol) in water (1 mL), and the mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (58 mg, 67%).

MS (ESI, pos. ion) m/z: 494.1 [M+H]⁺;
HRMS (ESI, pos. ion) m/z: 494.1496, (C₂₄H₂₂FClN₇O₂) [M+H]⁺ theoretical value: 494.1508;
¹H NMR (600 MHz, DMSO-d₆) δ (ppm): 8.74 (s, 1H), 8.57 (s, 1H), 8.37 (s, 1H), 8.26 (s, 1H), 8.02 (s, 1H), 7.61 (s, 1H), 7.52 (s, 1H), 4.69 (s, 1H), 2.85 (s, 1H), 2.12 (s, 1H), 1.99 (s, 2H), 1.77-1.30 (m, 8H).

Example 33: (2S,3S)-3-((2-(2-chloro-5H-pyrrolo[2,3-b]pyrazin-7-yl)-5-fluoro-6-(5-methylthiophen-2-yl)pyrimidin-4-yl)amino)bicyclo[2.2.2]octane-2-carboxylic Acid

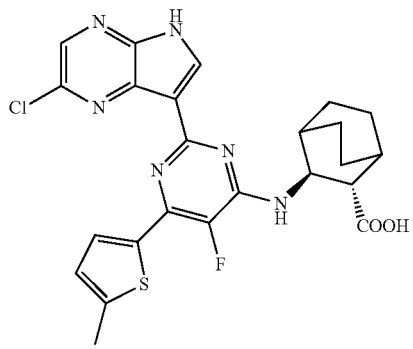 [SMILES: Cc1ccc(-c2nc(-c3c[nH]c4ncc(Cl)nc34)nc(N[C@H]3C4CCC(CC4)[C@@H]3C(=O)O)c2F)s1]

Step 1: (2S,3S)-ethyl 3-aminobicyclo[2.2.2]octane-2-carboxylate hydrochloride

The title compound was prepared by the synthetic method disclosed in patent application WO 2015073491.

Step 2: 2,4-dichloro-5-fluoro-6-(5-methylthiophen-2-yl)pyrimidine

To a solution of 2-methylthiophene (1.00 g, 10.00 mmol) in anydrous tetrahydrofuran (20 mL) was added n-butyllithium (4.10 mL, 10.0 mmol, 2.5 mol/L) at −15° C., and the mixture was stirred for 1 h at −15° C. Then to the mixture was added dichloro(N,N,N',N'-tetramethylethylenediamine)zinc(II) (850 mg, 3.40 mmol), and the resulting mixture was stirred for 1 h maintaining at this temperature. Then palladium dichloride (180 mg, 1.0 mmol), triphenylphosphine (530 mg, 2.0 mmol) and 2,4,6-trichloro-5-fluoropyrimidine (2.30 g, 11.0 mmol) were added to the mixture in turn. The resulting mixture was heated to 55° C. under nitrogen protection, and then stirred at this temperature overnight. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a white solid (587 mg, 22%).

MS (ESI, pos.ion) m/z: 262.9 [M+H]⁺;
¹H NMR (400 MHz, CDCl₃) δ (ppm) 7.86 (dd, J=3.7, 1.6 Hz, 1H), 6.93 (d, J=3.7 Hz, 1H), 2.61 (s, 3H).

Step 3: (2S,3S)-ethyl 3-((2-chloro-5-fluoro-6-(5-methylthiophen-2-yl)pyrimidin-4-yl) amino)bicyclo[2.2.2]octane-2-carboxylate To a solution of (2S,3S)-ethyl 3-aminobicyclo[2.2.2]octane-2-carboxylate hydrochloride (627 mg, 2.68 mmol) and 2,4-dichloro-5-fluoro-6-(5-methylthiophen-2-yl) pyrimidine (587 mg, 2.23 mmol) in DMF (6 mL) was added potassium carbonate (620 mg, 4.46 mmol), and the mixture was stirred at rt overnight. The reaction mixture was diluted with water (40 mL), and the resulting mixture was extracted with EtOAc (40 mL×3). The combined organic layers were washed with saturated brine (50 mL), dried over anhydrous Na₂SO₄, and filtered. The filtrate was concentrated in vacuo. And the residue was purified by silica gel column chromatography (PE/EA (v/v)=5/1) to give the title compound as a white solid (528 mg, 56%).

MS (ESI, pos.ion) m/z: 410.2 [M+H]⁺;

¹H NMR (400 MHz, CDCl₃) δ (ppm): 7.64 (d, J=2.7 Hz, 1H), 6.84 (d, J=3.6 Hz, 1H), 5.27 (d, J=4.5 Hz, 1H), 4.52 (s, 1H), 4.27-4.20 (m, 2H), 2.56 (s, 3H), 2.40 (d, J=5.8 Hz, 1H), 2.03 (d, J=2.3 Hz, 1H), 1.91 (d, J=2.4 Hz, 1H), 1.85-1.59 (m, 7H), 1.45 (m, 1H), 1.29 (m, 3H).

Step 4: (2S,3S)-ethyl 3-((2-bromo-5-fluoro-6-(5-methylthiophen-2-yl)pyrimidin-4-yl)amino)bicyclo[2.2.2]octane-2-carboxylate To a solution of hydrobromic acid in acetic acid ((528 mg, 1.25 mmol) was added (2S,3S)-ethyl 3-((2-chloro-5-fluoro-6-(5-methylthiophen-2-yl)pyrimidin-4-yl)amino) bicyclo[2.2.2]octane-2-carboxylate (280 mg, 0.54 mmol), and the mixture was stirred at rt for 4 h. The reaction was stopped, and the mixture was added into ice-water (30 mL). The resulting mixture was extracted with EtOAc (30 mL×3). The combined organic layers were washed with saturated aqueous sodium bicarbonate (80 mL) and saturated brine (50 mL), dried over anhydrous Na₂SO₄, and filtered. The filtrate was concentrated in vacuo to give the title compound as a light yellow solid (521 mg, 89%).

Step 5: (2S,3S)-ethyl 3-((2-(2-chloro-5-trityl-5H-pyrrolo[2,3-b]pyrazin-7-yl)-5-fluoro-6-(5-methylthiophen-2-yl)pyrimidin-4-yl) amino)bicyclo[2.2.2]octane-2-carboxylate To a mixed solvent of 1,4-dioxane (8 mL) and H₂O (1 mL) were added 2-chloro-7-(4,4,5,5-tetramethyl-1,3,2-dioxaborolan-2-yl)-5-trityl-5H-pyrrolo[2,3-b]pyrazine (1.08 mg, 1.25 mmol, 60%), K₂CO₃ (470 mg, 3.41 mmol), PdCl₂(dppf) (86 mg, 0.09 mmol) and (2S,3S)-ethyl 3-((2-bromo-5-fluoro-6-(5-methylthiophen-2-yl)pyrimidin-4-yl)amino)bicyclo[2.2.2]octane-2-carboxylate (532 mg, 1.14 mmol). The air in the mixture was exchanged with nitrogen by bubbling for 10 min. The mixture in the sealed tub was stirred for 3 h at 115° C. The mixture was filtered to remove the solid impuries, and the solvent was removed. The residue was purified by silica gel column chromatography (PE/EtOAc (v/v)=10/1-5/1) to give the title compound as a white solid (599 mg, 67%).

¹H NMR (400 MHz, CDCl₃) δ(ppm) 8.42 (s, 1H), 7.94 (s, 1H), 7.71 (d, J=3.0 Hz, 1H), 7.37-7.30 (m, 10H), 7.22 (m, 5H), 6.85 (d, J=3.2 Hz, 1H), 5.04 (d, J=5.6 Hz, 1H), 4.61 (t, J=7.0 Hz, 1H), 4.06 (m, 2H), 2.58 (s, 3H), 2.33 (d, J=7.2 Hz, 1H), 2.07 (s, 3H), 1.69 (m, 5H), 1.56-1.38 (m, 5H), 1.17 (t, J=7.1 Hz, 3H).

Step 6: (2S,3S)-ethyl 3-((2-(2-chloro-5H-pyrrolo[2,3-b]pyrazin-7-yl)-5-fluoro-6-(5-methylthiophen-2-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-5-fluoro-6-(5-methylthiophen-2-yl)pyrimidin-4-yl)amino)bicyclo[2.2.2]octane-2-carboxylate (599 mg, 0.76 mmol) in dichloromethane (5 mL) were added Et₃SiH (1.30 mL, 7.65 mmol) and TFA (0.60 mL, 5.40 mmol), and the mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (385 mg, 93%).

MS (ESI, pos. ion) m/z: 541.2 [M+H]⁺.

Step 7: (2S,3S)-3-((2-(2-chloro-5H-pyrrolo[2,3-b]pyrazin-7-yl)-5-fluoro-6-(5-methylthiophen-2-yl)pyrimidin-4-yl) amino)bicyclo[2.2.2]octane-2-carboxylic Acid To a solution of (2S,3S)-ethyl 3-((2-(2-chloro-5H-pyrrolo[2,3-b]pyrazin-7-yl)-5-fluoro-6-(5-methylthiophen-2-yl)pyrimidin-4-yl) amino)bicyclo[2.2.2]octane-2-carboxylate (385 mg, 0.71 mmol) in THF/MeOH (v/v=5 mL/5 mL) was added a solution of NaOH (285 mg, 7.12 mmol) in water (1 mL), and the mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (201 mg, 55%).

MS (ESI, pos. ion) m/z: 513.6 [M+H]⁺;

HRMS (ESI, pos. ion) m/z: 513.1285, (C₂₄H₂₃FClN₆O₂S)[M+H]⁺ theoretical value: 513.1276;

¹H NMR (600 MHz, DMSO-d₆) δ (ppm): 12.76 (s, 1H), 8.50 (s, 1H), 8.37 (s, 1H), 7.70 (d, J=3.1 Hz, 1H), 7.57 (d, J=6.3 Hz, 1H), 6.97 (d, J=3.0 Hz, 1H), 4.66 (t, J=6.6 Hz, 1H), 2.85 (d, J=7.1 Hz, 1H), 2.54 (s, 3H), 2.11 (s, 1H), 1.99 (s, 2H), 1.83-1.64 (m, 2H), 1.64-1.21 (m, 6H);

¹³C NMR (600 MHz, DMSO-d₆) δ (ppm) 176.08, 155.77, 155.69, 152.50, 152.39, 144.26, 144.21, 142.71, 141.01, 140.66, 140.53, 140.45, 138.07, 135.97, 135.91, 135.84, 134.92, 130.03, 129.93, 127.48, 114.07, 51.35, 48.00, 28.79, 28.57, 25.91, 24.21, 21.68, 19.56, 15.63.

Example 34: (2S,3S)-ethyl 3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate

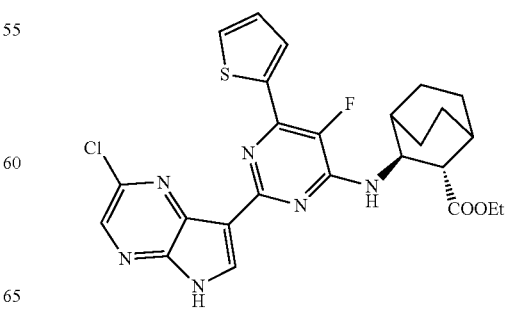

Step 1: (2S,3S)-ethyl 3-aminobicyclo[2.2.2]octane-2-carboxylate hydrochloride The title compound was prepared by the synthetic method disclosed in patent application WO 2015073491.

Step 2: 2,4-dichloro-5-fluoro-6-(thiophen-2-yl)pyrimidine

To a solution of thiophene (300 mg, 3.57 mmol) in anydrous tetrahydrofuran (20 mL) was added n-butyllithium (1.4 mL, 3.57 mmol, 2.5 mol/L) at −15° C., and the mixture was stirred for 1 h at −15° C. Then to the mixture was added (N,N,N',N'-tetramethylethylenediamine)zinc(II) dichloride (300 mg, 1.18 mmol), and the resulting mixture was warmed to rt and stirred for 1 h. Then palladium dichloride (65 mg, 0.36 mmol), triphenylphosphine (188 mg, 0.71 mmol) and 5-fluoro-2,4,6-trichloropyrimidine (790 mg, 3.92 mmol) were added to the mixture in turn. The resulting mixture was heated to 55° C. under nitrogen protection, and then stirred at this temperature overnight. To the reaction mixture was added water (50 mL), and the resulting mixture was extracted with ethyl acetate (50 mL×3). The combined organic layers were washed with saturated brine (100 mL), dried over anhydrous sodium sulfate and filtered. The filtrate was concentrated in vacuo and the residue was purified by silica gel column chromatography (PE) to give the title compound as a white solid (366 mg, 41%).

MS (ESI, pos.ion) m/z: 272.0 [M+Na]$^+$.

Step 3: (2S,3S)-ethyl 3-((2-chloro-5-fluoro-6-(thiophen-2-yl)pyrimidin-4-yl)amino)bicyclo[2.2.2]octane-2-carboxylate To a solution of (2S,3S)-ethyl 3-aminobicyclo[2.2.3]octane-2-carboxylate hydrochloride (411 mg, 1.76 mmol) and 2,4-dichloro-5-fluoro-6-(thiophen-2-yl)pyrimidine (366 mg, 1.47 mmol) in DMF (6 mL) was added potassium carbonate (406 mg, 2.94 mmol), and the mixture was stirred at rt overnight. The reaction mixture was diluted with water (40 mL), and the resulting mixture was extracted with EtOAc (40 mL×3). The combined organic layers were washed with saturated brine (50 mL), dried over anhydrous Na$_2$SO$_4$, and filtered. The filtrate was concentrated in vacuo. And the residue was purified by silica gel column chromatography (PE/EA (v/v)=5/1) to give the title compound as a white solid (388 mg, 64%).

MS (ESI, pos.ion) m/z: 410.2 [M+H]$^+$;
$^1$H NMR (400 MHz, CDCl$_3$) δ (ppm): 7.84 (s, 1H), 7.57 (d, J=4.8 Hz, 1H), 7.18 (t, J=4.2 Hz, 1H), 5.34 (s, 1H), 4.53 (s, 1H), 4.24 (m, 2H), 2.41 (d, J=5.5 Hz, 1H), 2.05 (d, J=10.7 Hz, 2H), 1.93-1.77 (m, 3H), 1.69 (d, J=9.2 Hz, 5H), 1.29 (t, J=5.2 Hz, 3H).

Step 4: (2S,3S)-ethyl 3-((2-bromo-5-fluoro-6-(thiophen-2-yl)pyrimidin-4-yl)amino)bicyclo[2.2.2]octane-2-carboxylate To a solution of hydrobromic acid in acetic acid (33%, 20 mL) was added (2S,3S)-ethyl 3-((2-chloro-5-fluoro-6-(thiophen-2-yl)pyrimidin-4-yl)amino)bicyclo[2.2.2]octane-2-carboxylate (0.74 g, 1.80 mmol), and the resulting mixture was stirred at rt for 2.5 h. After the reaction was completed, the reaction mixture was added slowly into ice-water (100 mL). The mixture was extracted with ethyl acetate (100 mL×3). The combined organic layers were washed with saturated aqueous sodium sulfate (200 mL×3), dried over anydrous sodium sulfate, and filtered. The filtrate was concentrated in vacuo to give the title compound as light yellow oil (0.75 g, 91%).

MS (ESI, pos. ion) m/z: 454.1 [M+H]$^+$.

Step 5: (2S,3S)-ethyl 3-((2-(2-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate To a mixed solvent of 1,4-dioxane (20 mL) and H$_2$O (0.5 mL) were added 2-chloro-7-(4,4,5,5-tetramethyl-1,3,2-dioxaborolan-2-yl)-5-trityl-5H-pyrrolo[2,3-b]pyrazine (65%, 1.07 g, 1.10 mmol), K$_2$CO$_3$ (0.51 g, 3.70 mmol), PdCl$_2$(dppf) (0.28 g, 0.38 mmol) and (2S,3S)-ethyl 3-((2-bromo-5-fluoro-6-(thiophen-2-yl)pyrimidin-4-yl)amino)bicyclo[2.2.2]octane-2-carboxylate (0.55 g, 1.21 mmol). The air in the mixture was exchanged with nitrogen by bubbling for 10 min. The mixture in the sealed tub was stirred for 4 h at 115° C. The mixture was filtered to remove the solid impuries, and the filtrate was concentrated to remove the solvent. The residue was purified by silica gel column chromatography (PE/EtOAc (v/v)=10/1) to give the title compound as a yellow solid (713 mg, 77%).

Step 6: (2S,3S)-ethyl 3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate (0.71 g, 0.92 mmol) in dichloromethane (20 mL) were added Et$_3$SiH (1.80 mL, 11.30 mmol) and TFA (0.82 mL, 5.40 mmol), and the mixture was stirred at rt for 40 h. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=2/1) to give the title compound as a white solid (300 mg, 62%).

MS (ESI, pos. ion) m/z: 527.1 [M+H]$^+$;
HRMS (ESI, pos. ion) m/z: 527.1430, (C$_{25}$H$_{25}$FClN$_6$O$_2$S)[M+H]$^+$ theoretical value: 527.1432;
$^1$H NMR (400 MHz, DMSO-d$_6$) δ (ppm): 8.50 (s, 1H), 8.38 (s, 1H), 7.86 (d, J=4.6 Hz, 1H), 7.67 (d, J=6.4 Hz, 1H), 7.29 (s, 1H), 6.63 (d, J=3.0 Hz, 1H), 4.73 (s, 1H), 4.11-4.01 (m, 2H), 2.92 (d, J=6.5 Hz, 1H), 2.09 (s, 1H), 1.97 (s, 2H), 1.76 (m, 3H), 1.55 (s, 3H), 1.45-1.36 (m, 2H), 1.12 (t, J=6.9 Hz, 3H).

Example 35: (2S,3S)-3-((2-(3-chloro-5H-pyrrolo[2,3-b]pyrazin-7-yl)-5-fluoro-6-(5-methylthiophen-2-yl)pyrimidin-4-yl)amino)bicyclo[2.2.2]octane-2-carboxylic Acid

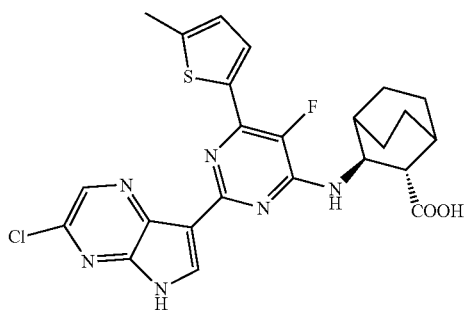 [SMILES: Cc1ccc(-c2nc(-c3c[nH]c4nc(Cl)cnc34)nc(N[C@H]3C4CCC(CC4)[C@@H]3C(=O)O)c2F)s1]

Step 1: 3-chloro-7-iodo-5H-pyrrolo[2,3-b]pyrazine

To a solution of 3-chloro-5H-pyrrolo[2,3-b]pyrazine (300 mg, 1.95 mmol) in 2-methyltetrahydrofuran (10 mL) was added NIS (543 mg, 2.34 mmol), and the reaction mixture was stirred at rt for 1 h. Saturated aqueous sodium thiosulfate (50 mL) was added to quench the reaction, and the resulting mixture was partitioned. The aqueous layer was extracted with EtOAc (50 mL×2). The combined organic phases were washed with saturated brine (80 mL), dried over anhydrous $Na_2SO_4$, filtered, and the filtrate was concentrated in vacuo to give the title compound as a yellow solid (546 mg, 100%).

MS (ESI, pos. ion) m/z: 280.2 [M+H]$^+$.

Step 2: 3-chloro-7-iodo-5-trityl-5H-pyrrolo[2,3-b]pyrazine

To a solution of 3-chloro-7-iodo-5H-pyrrolo[2,3-b]pyrazine (546 mg, 1.95 mmol) in DMF (10 mL) was added NaH (93 mg, 2.34 mmol) at 0° C., and the mixture was stirred for 15 min, then triphenylchloromethane (599 mg, 2.15 mmol) was added. The resulting mixture was warmed to rt and stirred for 1 h. To the reaction mixture was added water (30 mL), and the resulting mixture was extracted with ethyl acetate (30 mL×3). The combined organic layers were washed with saturated brine (60 mL), dried over anhydrous sodium sulfate and filtered. The filtrate was concentrated in vacuo and the residue was purified by silica gel column chromatography (PE/EtOAc (v/v)=5/1) to give the title compound as a light yellow solid (884 mg, 87%).

$^1$H NMR (400 MHz, CDCl$_3$) δ (ppm): 8.45 (s, 1H), 7.70 (s, 1H), 7.34 (dd, J=9.7, 7.2 Hz, 10H), 7.17 (d, J=6.9 Hz, 5H).

Step 3: 3-chloro-7-(4,4,5,5-tetramethyl-1,3,2-dioxaborolan-2-yl)-5-trityl-5H-pyrrolo[2,3-b]pyrazine A solution of 3-chloro-7-iodo-5-trityl-5H-pyrrolo[2,3-b]pyrazine (450 mg, 0.86 mmol) and isopropoxyboronic acid pinacol ester (208 mg, 1.12 mmol) in anhydrous THF (10 mL) was cooled to −27° C. and stirred for 10 min under nitrogen protection, then isopropylmagnesium chloride solution (2 M in THF, 0.52 mL) was added dropwise slowly. After the addition, the mixture was stirred at −27° C. for 1.5 h. The reaction mixture was added into saturated aqueous sodium bicarbonate (30 mL). The resulting mixture was extracted with dichloromethane (30 mL×3). The combined organic layers were dried over anhydrous sodium sulfate, and filtered. The filtrate was concentrated in vacuo to give the title compound as a yellow solid (450 mg, 100%), which was used for the next step without further purification.

Step 4: (2S,3S)-ethyl 3-((2-(3-chloro-5-trityl-5H-pyrrolo[2,3-b]pyrazin-7-yl)-5-fluoro-6-(5-methylthiophen-2-yl)pyrimidin-4-yl)amino)bicyclo[2.2.2]octane-2-carboxylate To a mixed solvent of 1,4-dioxane (10 mL) and H$_2$O (0.5 mL) were added 3-chloro-7-(4,4,5,5-tetramethyl-1,3,2-dioxaborolan-2-yl)-5-trityl-5H-pyrrolo[2,3-b]pyrazine (40%, 326 mg, 0.25 mmol), K$_2$CO$_3$ (93 mg, 0.67 mmol), PdCl$_2$(dppf) (51 mg, 0.07 mmol) and (2S,3S)-ethyl 3-((2-bromo-5-fluoro-6-(5-methylthiophen-2-yl)pyrimidin-4-yl)amino)bicyclo[2.2.2]octane-2-carboxylate (105 mg, 0.22 mmol). The air in the mixture was exchanged with nitrogen by bubbling for 10 min. The mixture in the sealed tub was stirred for 3 h at 115° C. by microwave heating. The mixture was filtered to remove the solid impuries, and the filtrate was concentrated to remove the solvent. The residue was purified by silica gel column chromatography (PE/EtOAc (v/v)=10/1) to give the title compound as a yellow solid (161 mg, 92%).

Step 5: (2S,3S)-ethyl 3-((2-(3-chloro-5H-pyrrolo[2,3-b]pyrazin-7-yl)-5-fluoro-6-(5-methylthiophen-2-yl)pyrimidin-4-yl)amino)bicyclo[2.2.2]octane-2-carboxylate To a solution of (2S,3S)-ethyl 3-((2-(3-chloro-5-trityl-5H-pyrrolo[2,3-b]pyrazin-7-yl)-5-fluoro-6-(5-methylthiophen-2-yl)pyrimidin-4-yl) amino)bicyclo[2.2.2]octane-2-carboxylate (161 mg, 0.21 mmol) in dichloromethane (6 mL) were added Et$_3$SiH (0.40 mL, 2.50 mmol) and TFA (0.19 mL, 5.40 mmol), and the mixture was stirred at rt overnight. The reaction was stopped, and the reaction mixture was added into saturated aqueous sodium bicarbonate (30 mL). The resulting mixture was extracted with dichloromethane (30 mL×3). The combined organic layers were washed with saturated brine (80 mL), dried over anhydrous sodium sulfate, and filtered. The filtrate was concentrated in vacuo to remove the solvent, and the residue was purified by silica gel column chromatography (PE/EtOAc (v/v)=2/1) to give the title compound as light yellow oil (93 mg, 84%).

MS (ESI, pos. ion) m/z: 510.1 [M+H]$^+$.

Step 6: (2S,3S)-3-((2-(3-chloro-5H-pyrrolo[2,3-b]pyrazin-7-yl)-5-fluoro-6-(5-methylthiophen-2-yl)pyrimidin-4-yl)amino)bicyclo[2.2.2]octane-2-carboxylic Acid To a solution of (2S,3S)-ethyl 3-((2-(3-chloro-5H-pyrrolo[2,3-b]pyrazin-7-yl)-5-fluoro-6-(5-methylthiophen-2-yl)pyrimidin-4-yl)amino)bicyclo[2.2.2]octane-2-carboxylate (93 mg, 0.17 mmol) in THF/MeOH/H$_2$O (v/v/v=2 mL/2 mL/2 mL) was added NaOH (69 mg, 1.73 mmol) in water (1 mL), and the mixture was stirred at rt overnight. To the reaction mixture was added saturated brine (20 mL), and the mixture was acidified with hydrochloric acid (1 M) to pH about 6. The resulting mixture was extracted with EtOAc (30 mL×3). The combined organic layers were washed with saturated brine (50 mL), dried over anhydrous sodium sulfate, and filtered. The filtrate was concentrated in vacuo to remove the solvent, and the residue was purified by thin-layer preparative column chromatography (DCM/MeOH (v/v)=20/1) to give the title compound as a light yellow solid (85 mg, 96%).

MS (ESI, pos. ion) m/z: 513.6 [M+H]⁺;

HRMS (ESI, pos. ion) m/z: 513.1265, ($C_{23}H_{22}ClN_7O_2$) [M+H]⁺ theoretical value: 513.1276;

¹H NMR (400 MHz, DMSO-$d_6$) δ (ppm): 12.78 (s, 1H), 8.60 (s, 1H), 8.41 (s, 1H), 7.69 (s, 1H), 7.58 (d, J=5.9 Hz, 1H), 6.97 (s, 1H), 4.62 (s, 1H), 2.84 (d, J=6.6 Hz, 1H), 2.53 (s, 3H), 2.07 (s, 1H), 1.98 (s, 1H), 1.86 (s, 1H), 1.73 (m, 2H), 1.53 (m, 2H), 1.44-1.33 (m, 2H);

¹³C NMR (101 MHz, DMSO-$d_6$) δ (ppm): 176.08, 155.78, 152.32, 144.21, 140.95, 140.72, 138.17, 138.05, 135.85, 135.69, 133.87, 130.00, 129.90, 127.45, 114.74, 51.35, 48.07, 28.83, 28.57, 25.92, 24.10, 21.67, 19.54, 15.63.

Example 36: (+/−)-trans-3-((2-(2-chloro-5H-pyrrolo[2,3-b]pyrazin-7-yl)-6-morpholino pyrimidin-4-yl)amino)bicyclo[2.2.2]octane-2-carboxylic Acid

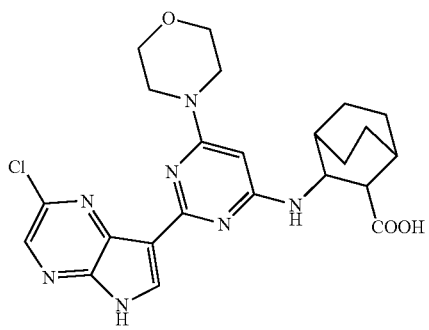 [SMILES: O=C(O)C1C2CCC(CC2)C1Nc1cc(N2CCOCC2)nc(-c2c[nH]c3ncc(Cl)nc23)n1]

Step 1: (+/−)-trans-methyl 3-((2,6-dichloropyrimidin-4-yl)amino)bicyclo[2.2.2]octane-2-carboxylate (+/−)-trans-Methyl 3-aminobicyclo[2.2.2]octane-2-carboxylate (2.40 g, 13.0 mmol), 2,4,6-trichloropyrimidine (1.80 g, 9.8 mmol) and DIPEA (4.00 g, 29.0 mmol) were dissolved in dichloromethane (20 mL). The mixture was stirred at rt overnight. To the reaction mixture was added water (50 mL), and the resulting mixture was extracted with dichloromethane (20 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=20/1) to give the title compound as a light yellow solid (2.06 g, 64%).

Step 2: (+/−)-trans-methyl 3-((2-chloro-6-morpholinopyrimidin-4-yl)amino)bicyclo[2.2.2]octane-2-carboxylate A mixture of (+/−)-trans-methyl 3-((2,6-dichloropyrimidin-4-yl)amino) bicyclo[2.2.2]octane-2-carboxylate (0.55 g, 1.50 mmol) and morphine (5.0 g, 60 mmol) was heated to 90° C. and stirred overnight. To the reaction mixture was added water (40 mL), and the resulting mixture was extracted with ethyl acetate (30 mL×3). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=15/1) to give the title compound as a white solid (0.45 g, 78%).

MS (ESI, pos.ion) m/z: 381.2 [M+H]⁺.

Step 3: (+/−)-trans-3-((2-bromo-6-morpholinopyrimidin-4-yl)amino)bicyclo[2.2.2]octane-2-carboxylic Acid To a reaction flask were added (+/−)-trans-methyl 3-((2-chloro-6-morpholinopyrimidin-4-yl)amino)bicyclo[2.2.2]octane-2-carboxylate (400 mg, 1.05 mmol), a solution of hydrobromic acid in acetic acid (5 mL, 30.00 mmol, 33%) and water (5 mL), and the mixture was stirred at rt overnight. The reaction mixture was cooled to rt and concentrated in vacuo to give the title compound as a light yellow solid (440 mg, 100%).

MS (ESI, pos.ion) m/z: 411.1 [M+H]⁺.

Step 4: (+/−)-trans-methyl 3-((2-bromo-6-morpholinopyrimidin-4-yl)amino)bicyclo[2.2.2]octane-2-carboxylate A solution of (+/−)-trans-3-((2-bromo-6-morpholinopyrimidin-4-yl)amino) bicyclo[2.2.2]octane-2-carboxylic acid (200 mg, 0.48 mmol) in anhydrous methanol (10 mL) was cooled to 0° C., and thionyl chloride (0.8 g, 7 mmol) was added dropwise slowly. After the addition, the mixture was refluxed overnight. The reaction mixture was concentrated in vacuo to give the title compound as a light yellow solid (100 mg, 48%).

MS (ESI, pos.ion) m/z: 425.2 [M+H]⁺.

Step 5: (+/−)-trans-methyl 3-((2-(2-chloro-5-trityl-5H-pyrrolo[2,3-b]pyrazin-7-yl)-6-morpholinopyrimidin-4-yl)amino)bicyclo[2.2.2]octane-2-carboxylate To a mixed solvent of 1,4-dioxane (10 mL) and $H_2O$ (0.5 mL) were added 2-chloro-7-(4,4,5,5-tetramethyl-1,3,2-dioxaborolan-2-yl)-5-trityl-5H-pyrrolo[2,3-b]pyrazine (258 mg, 0.29 mmol, 60%), $K_2CO_3$ (136 mg, 0.99 mmol), $PdCl_2$(dppf) (26 mg, 0.03 mmol) and (+/−)-trans-methyl 3-((2-bromo-6-morpholinopyrimidin-4-yl) amino)bicyclo[2.2.2]octane-2-carboxylate (100 mg, 0.24 mmol). The air in the mixture was exchanged with nitrogen by bubbling for 10 min. The mixture in the sealed tub was stirred for 1.5 h at 110° C. The mixture was filtered to remove the solid impuries, and the solvent was removed. The residue was purified by silica gel column chromatography (PE/EtOAc (v/v)=10/1-5/1) to give the title compound as a white solid (54 mg, 31%).

Step 6: (+/−)-trans-methyl 3-((2-(2-chloro-5H-pyrrolo[2,3-b]pyrazin-7-yl)-6-morpholinopyrimidin-4-yl) amino)bicyclo[2.2.2]octane-2-carboxylate To a solution of (+/−)-trans-methyl 3-((2-(2-chloro-5-trityl-5H-pyrrolo[2,3-b]pyrazin-7-yl)-6-morpholinopyrimidin-4-yl) amino)bicyclo[2.2.2]octane-2-carboxylate (54 mg, 0.07 mmol) in dichloromethane (5 mL) were added trifluoroacetic acid (0.80 mL, 4.95 mmol) and triethyl silicane (0.38 mL, 4.95 mmol), and the mixture was stirred at rt overnight. The reaction mixture was added into saturated aqueous sodium carbonate (100 mL), and the resulting mixture was extracted with dichloromethane (50 mL×3). The combined organic layers were washed with saturated brine (100 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (30 mg, 81%).

MS (ESI, pos.ion) m/z: 498.3 [M+H]$^+$.

Step 7: (+/−)-trans-3-((2-(2-chloro-5H-pyrrolo[2,3-b]pyrazin-7-yl)-6-morpholinopyrimidin-4-yl)amino) bicyclo[2.2.2]octane-2-carboxylic Acid To a solution of (+/−)-trans-methyl 3-((2-(2-chloro-5H-pyrrolo[2,3-b]pyrazin-7-yl)-6-morpholinopyrimidin-4-yl) amino)bicyclo[2.2.2]octane-2-carboxylate (30 mg, 0.06 mmol) in THF/MeOH (v/v=5 mL/3 mL) was added a solution of NaOH (24 mg, 0.60 mmol) in water (2 mL). The mixture was stirred at rt overnight. To the reaction mixture was added water (20 mL), and the mixture was acidified with hydrochloric acid (1 M) to pH about 6. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (15 mg, 51%).

MS (ESI, pos. ion) m/z: 484.3 [M+H]$^+$;

HRMS (ESI, pos. ion) m/z: 484.1864, ($C_{23}H_{27}ClN_7O_3$) [M+H]$^+$ theoretical value: 484.1864;

$^1$H NMR (400 MHz, DMSO-d$_6$) δ (ppm): 12.75 (s, 1H), 12.16 (s, 1H), 8.56 (s, 1H), 8.39 (s, 1H), 7.31 (s, 1H), 6.92 (s, 1H), 4.36 (s, 1H), 3.71 (d, J=3.7 Hz, 4H), 3.66 (d, J=4.1 Hz, 4H), 1.98 (d, J=6.9 Hz, 1H), 1.91 (s, 1H), 1.86 (s, 1H), 1.76 (s, 1H), 1.65 (s, 2H), 1.49 (m, 5H).

Example 37: (R)-methyl 3-((2-(2-chloro-5H-pyrrolo [2,3-b]pyrazin-7-yl)-6-(furan-2-yl)pyrimidin-4-yl) amino)-4,4-dimethylpentanoate

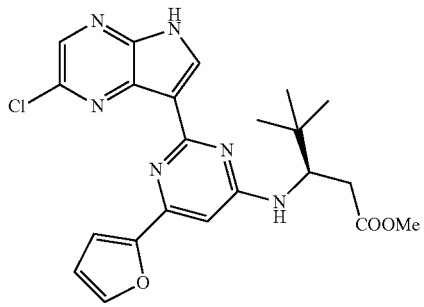 [SMILES: COC(=O)C[C@@H](Nc1cc(-c2ccco2)nc(-c2c[nH]c3ncc(Cl)nc23)n1)C(C)(C)C]

Step 1: (R)-methyl 3-amino-4,4-dimethylpentanoate

To a 0° C. solution of (R)-3-amino-4,4-dimethylpentanoic acid (1.01 g, 6.96 mmol) in methanol (60 mL) was added dropwise slowly oxalyl chloride (0.9 mL, 10 mmol). The mixture was stirred at this temperature for 1 h, then heated to 65° C. and stirred for further 2 h. The reaction mixture was concentrated in vacuo to dry and the residue was washed with toluene (30 mL×3), then the mixture was filtered by suction to give the title compound as a white solid (1.11 g, 99%).

MS (ESI, pos. ion) m/z: 160.3 [M+H]$^+$.

Step 2: (R)-methyl 3-((2-chloro-6-(furan-2-yl)pyrimidin-4-yl)amino)-4,4-dimethylpentanoate To a solution of (R)-methyl 3-amino-4,4-dimethylpentanoate (243 mg, 1.67 mmol) and 2,4-dichloro-6-(furan-2-yl)pyrimidine (300 mg, 1.40 mmol) in DMF (6 mL) was added potassium carbonate (385 mg, 2.80 mmol). The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (103 mg, 22%).

MS (ESI, pos.ion) m/z: 339.2 [M+H]$^+$.

Step 3: (R)-methyl 3-((2-(2-chloro-5-trityl-5H-pyrrolo[2,3-b]pyrazin-7-yl)-6-(furan-2-yl)pyrimidin-4-yl)amino)-4,4-dimethylpentanoate To a mixed solvent of 1,4-dioxane (8 mL) and H$_2$O (1 mL) were added 2-chloro-7-(4,4,5,5-tetramethyl-1,3,2-dioxaborolan-2-yl)-5-trityl-5H-pyrrolo[3,4-b]pyrazine (96 mg, 0.18 mmol), K$_2$CO$_3$ (115 mg, 0.83 mmol), PdCl$_2$(dppf) (13 mg, 0.02 mmol) and (R)-methyl 3-((2-chloro-6-(furan-2-yl)pyrimidin-4-yl)amino)-4,4-dimethylpentanoate (56 mg, 0.17 mmol). The air in the mixture was exchanged with nitrogen by bubbling for 10 min. The mixture in the sealed tub was stirred for 3 h at 115° C. The mixture was filtered to remove the solid impuries, and the filtrate was concentrated to remove the solvent. The residue was purified by silica gel column chromatography (PE/EtOAc (v/v)=10/1-5/1) to give the title compound as a white solid (23 mg, 20%).

Step 4: (R)-methyl 3-((2-(2-chloro-5H-pyrrolo[2,3-b]pyrazin-7-yl)-6-(furan-2-yl)pyrimidin-4-yl) amino)-4,4-dimethylpentanoate To a solution of (R)-methyl 3-((2-(2-chloro-5-trityl-5H-pyrrolo[2,3-b]pyrazin-7-yl)-6-(furan-2-yl)pyrimidin-4-yl) amino)-4,4-dimethylpentanoate (50 mg, 0.08 mmol) in dichloromethane (8 mL) were added Et$_3$SiH (0.76 mmol, 86 mg) and TFA (0.76 mmol, 88 mg), and the mixture was stirred at rt for 8 hours. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (20 mg, 61%).

MS (ESI, pos. ion) m/z: 455.2 [M+H]$^+$;

HRMS (ESI, pos. ion) m/z: 455.1620, ($C_{22}H_{24}ClN_6O_3$) [M+H]$^+$ theoretical value:455.1598;

$^1$H NMR (400 MHz, CDCl$_3$) δ (ppm): 9.52 (s, 1H), 8.53 (s, 1H), 8.28 (s, 1H), 7.59 (s, 1H), 7.32 (d, J=3.2 Hz, 1H), 6.78 (s, 1H), 6.59 (dd, J=3.3, 1.7 Hz, 1H), 5.37 (t, J=4.6 Hz, 1H), 3.60 (s, 3H), 2.78 (dd, J=15.2, 3.8 Hz, 1H), 2.50 (dd, J=14.9, 9.1 Hz, 1H), 2.08-2.00 (m, 1H), 1.07 (s, 9H).

Example 38: (2S,3S)-ethyl 3-((6-(benzo[b]thiophen-2-yl)-2-(2-chloro-5H-pyrrolo[2,3-b]pyrazin-7-yl)pyrimidin-4-yl)amino)bicyclo[2.2.2]octane-2-carboxylate

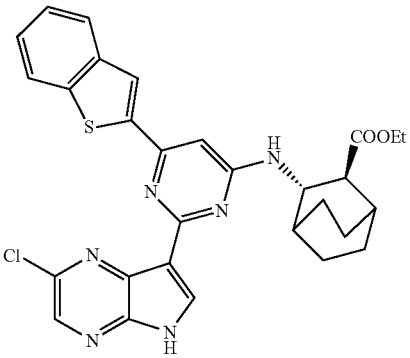 [SMILES: CCOC(=O)[C@H]1C2CCC(CC2)[C@@H]1Nc1cc(-c2cc3ccccc3s2)nc(-c2c[nH]c3ncc(Cl)nc23)n1]

Step 1: (2S,3S)-ethyl 3-aminobicyclo[2.2.2]octane-2-carboxylate hydrochloride The title compound was prepared by the synthetic method disclosed in patent application WO 2015073491.

Step 2: 4-(benzo[b]thiophen-2-yl)-2,6-dichloropyrimidine

A suspension of benzo[b]thiophen-2-ylboronic acid (485 mg, 2.73 mmol), bis(triphenylphosphine)palladium(II) chloride (383 mg, 0.54 mmol), 2,4,6-trichloropyrimidine (0.50 g, 2.73 mmol) and sodium carbonate (867 mg, 8.18 mmol) in a mixture of THF (15 mL) and water (5 mL) were refluxed for 4 hours under nitrogen protection. To the reaction mixture was added water (50 mL), and the resulting mixture was extracted with ethyl acetate (50 mL×3). The combined organic layers were washed with saturated brine (100 mL), dried over anhydrous sodium sulfate and filtered. The filtrate was concentrated in vacuo and the residue was purified by silica gel column chromatography (PE) to give the title compound as a light yellow solid (500 mg, 65%).

MS (ESI, pos.ion) m/z: 281.0 [M+H]$^+$.

Step 3: (2S,3S)-ethyl 3-((6-(benzo[b]thiophen-2-yl)-2-chloro-5-fluoropyrimidin-4-yl)amino)bicyclo[2.2.2]octane-2-carboxylate (2S,3S)-Ethyl 3-aminobicyclo[2.2.2]octane-2-carboxylate hydrochloride (460 mg, 2.13 mmol) and 4-(benzo[b]thiophen-2-yl)-2,6-dichloropyrimidine (500 mg, 1.77 mmol) were dissolved in DMF (10 mL), then potassium carbonate (740 mg, 5.33 mmol) was added. The mixture was stirred at 80° C. overnight. To the reaction mixture was added water (40 mL), and the resulting mixture was extracted with ethyl acetate (40 mL×3). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=5/1) to give the title compound as a light yellow solid (520 mg, 66%).

MS (ESI, pos.ion) m/z: 442.1 [M+H]$^+$.

Step 4: (2S,3S)-ethyl 3-((6-(benzo[b]thiophen-2-yl)-2-(2-chloro-5-trityl-5H-pyrrolo[2,3-b]pyrazin-7-yl)pyrimidin-4-yl)amino)bicyclo[2.2.2]octane-2-carboxylate To a mixed solvent of 1,4-dioxane (10 mL) and H$_2$O (0.5 mL) were added 2-chloro-7-(4,4,5,5-tetramethyl-1,3,2-dioxaborolan-2-yl)-5-trityl-5H-pyrrolo[2,3-b]pyrazine (326 mg, 0.40 mmol, 60%), K$_2$CO$_3$ (187 mg, 1.35 mmol), PdCl$_2$(dppf) (26 mg, 0.03 mmol) and (2S,3S)-ethyl 3-((6-(benzo[b]thiophen-2-yl)-2-chloropyrimidin-4-yl) amino) bicyclo[2.2.2]octane-2-carboxylate (150 mg, 0.33 mmol). The air in the mixture was exchanged with nitrogen by bubbling for 10 min. The mixture in the sealed tub was stirred for 1.5 h at 110° C. The mixture was filtered to remove the solid impuries, and the solvent was removed. The residue was purified by silica gel column chromatography (PE/EtOAc (v/v)=10/1-5/1) to give the title compound as a white solid (83 mg, 30%).

Step 5: (2S,3S)-ethyl 3-((6-(benzo[b]thiophen-2-yl)-2-(2-chloro-5H-pyrrolo[2,3-b]pyrazin-7-yl)pyrimidin-4-yl) amino)bicyclo[2.2.2]octane-2-carboxylate To a solution of (2S,3S)-ethyl 3-((6-(benzo[b]thiophen-2-yl)-2-(2-chloro-5-trityl-5H-pyrrolo[2,3-b]pyrazin-7-yl)pyrimidin-4-yl)amino)bicyclo[2.2.2]octane-2-carboxylate (45 mg, 0.06 mmol) in DCM (5 mL) were added trifluoacetic acid (0.80 mL, 4.95 mmol) and triethyl silicane (0.38 mL, 4.95 mmol, and the mixture was stirred at rt overnight. The reaction mixture was added into saturated aqueous sodium bicarbonate (100 mL), and the resulting mixture was extracted with dichloromethane (50 mL×3). The combined organic layers were washed with saturated brine (100 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (15 mg, 47%).

MS (ESI, pos. ion) m/z: 559.1 [M+H]$^+$;

HRMS (ESI, pos. ion) m/z: 559.1683, (C$_{26}$H$_{28}$ClN$_6$O$_2$S) [M+H]$^+$ theoretical value:559.1683;

$^1$H NMR (400 MHz, CDCl$_3$) δ (ppm): 10.30 (s, 1H), 8.62 (s, 1H), 8.25 (d, J=3.8 Hz, 1H), 8.02 (s, 1H), 7.89 (dd, J=5.8, 3.3 Hz, 1H), 7.85 (dd, J=5.8, 3.3 Hz, 1H), 7.38 (dd, J=6.0, 3.1 Hz, 2H), 7.28 (s, 1H), 6.78 (s, 1H), 4.40 (s, 1H), 4.25-4.13 (m, 2H), 2.49 (d, J=4.3 Hz, 1H), 2.10 (s, 1H), 2.06-2.01 (m, 1H), 1.96 (s, 1H), 1.85 (d, J=11.9 Hz, 2H), 1.75-1.61 (m, 5H), 1.23 (d, J=6.6 Hz, 3H).

Example 39: (2S,3S)-3-((2-(2-chloro-5H-pyrrolo[2,3-b]pyrazin-7-yl)-6-(4-phenylpiperazin-1-yl) pyrimidin-4-yl)amino)bicyclo[2.2.2]octane-2-carboxylic Acid

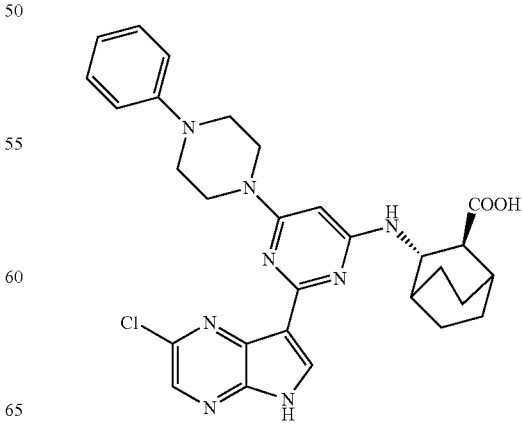

Step 1: (2S,3S)-ethyl 3-aminobicyclo[2.2.2]octane-2-carboxylate hydrochloride The title compound was prepared by the synthetic method disclosed in patent application WO 2015073491.

Step 2: (2S,3S)-ethyl 3-((2,6-dichloropyrimidin-4-yl)amino)bicyclo[2.2.2]octane-2-carboxylate (2S,3S)-Ethyl 3-aminobicyclo[2.2.2]octane-2-carboxylate hydrochloride (2.34 g, 10.0 mmol), 2,4,6-trichloropyrimidine (2.00 g, 11.00 mmol) and DIPEA (4.00 g, 29.0 mmol) were dissolved in dichloromethane (20 mL). The mixture was stirred at rt overnight. To the reaction mixture was added water (50 mL), and the resulting mixture was extracted with dichloromethane (20 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=20/1) to give the title compound as a light yellow solid (2.15 g, 62%).

Step 3: (2S,3S)-ethyl 3-((2-chloro-6-(4-phenylpiperazin-1-yl)pyrimidin-4-yl)amino)bicyclo[2.2.2]octane-2-carboxylate (2S,3S)-Ethyl 3-((2,6-dichloropyrimidin-4-yl)amino)bicyclo[2.2.2]octane-2-carboxylate (0.30 g, 0.87 mmol), 1-phenylpiperazine (0.68 g, 4.36 mmol) and DIPEA (0.34 g, 2.61 mmol) were dissolved in ethanol (5 mL), and then the mixture was heated to 90° C. and stirred overnight. To the reaction mixture was added water (40 mL), and the resulting mixture was extracted with ethyl acetate (30 mL×3). The combined organic layers were washed with saturated brine (60 mL), dried over anhydrous sodium sulfate and filtered. The filtrate was concentrated in vacuo and the residue was purified by silica gel column chromatography (PE/EtOAc (v/v)=15/1) to give the title compound as a white solid (0.36 g, 87%).

MS (ESI, pos.ion) m/z: 470.3 [M+H]$^+$.

Step 4: (2S,3S)-3-((2-chloro-6-(4-phenylpiperazin-1-yl)pyrimidin-4-yl)amino)bicyclo[2.2.2]octane-2-carboxylic Acid To a mixed solvent of water (1 mL), methanol (2 mL) and THF (2 mL) was added (2S,3S)-ethyl 3-((2-chloro-6-(4-phenylpiperazin-1-yl)pyrimidin-4-yl) amino)bicyclo[2.2.2]octane-2-carboxylate (100 mg, 0.21 mmol), then to the mixture was added sodium hydroxide (170 mg, 4.25 mmol). The resulting mixture was stirred at rt for 5 h. To the reaction mixture was added water (30 mL), and the resulting mixture was adjusted with HCl (1 M) to pH about 4 to 5. The mixture was extracted with ethyl acetate (20 mL×3). The combined organic layers were washed with saturated brine (50 mL), dried over anydrous sodium sulfate and filtered. The filtrate was concentrated in vacuo to give the title compound as a light yellow solid (94 mg, 99%).

MS (ESI, pos.ion) m/z: 442.2 [M+H]$^+$.

Step 5: (2S,3S)-3-((2-bromo-6-(4-phenylpiperazin-1-yl)pyrimidin-4-yl)amino)bicyclo[2.2.2]octane-2-carboxylic Acid To a solution of hydrobromic acid in acetic acid (235 mg, 10 mmol, 33%) were added (2S,3S)-3-((2-chloro-6-(4-phenylpiperazin-1-yl)pyrimidin-4-yl)amino)bicyclo[2.2.2]octane-2-carboxylic acid (200 mg, 0.48 mmol), and the mixture was stirred at rt overnight. To the reaction mixture was added water (30 mL), and the mixture was adjusted with saturated aqueous sodium hydroxide to pH about 4, and there was a large amount of solid precipitated out. The mixture was filtered, and the filter cake was washed with water (20 mL×2), dried in vacuo at 60° C. for 12 h to give the title compound as a white solid (100 mg, 96%).

MS (ESI, pos.ion) m/z:488.1 [M+H]$^+$.

Step 6: (2S,3S)-3 (2-chloro-5-trityl-5H-pyrrolo[2,3-b]pyrazin-7-yl)-6-(4-phenylpiperazin-1-yl)pyrimidin-4-yl) amino)bicyclo[2.2.2]octane-2-carboxylic Acid To a mixed solvent of 1,4-dioxane (5 mL) and H$_2$O (0.5 mL) were added 2-chloro-7-(4,4,5,5-tetramethyl-1,3,2-dioxaborolan-2-yl)-5-trityl-5H-pyrrolo[2,3-b]pyrazine (220 mg, 0.25 mmol, 60%), K$_2$CO$_3$ (142 mg, 1.03 mmol), PdCl$_2$(dppf) (30 mg, 0.04 mmol) and (2S,3S)-3-((2-bromo-6-(4-phenylpiperazin-1-yl)pyrimidin-4-yl) amino)bicyclo[2.2.2]octane-2-carboxylic acid (100 mg, 0.24 mmol). The air in the mixture was exchanged with nitrogen by bubbling for 10 min. The mixture in the sealed tub was stirred for 1.5 h at 110° C. After the reaction was completed, the mixture was filtered to remove the solid impuries, and the filtrate was concentrated in vacuo to give the title compound as a brownish red solid (165 mg, 100%).

Step 7: (2S,3S)-3 (2-chloro-5H-pyrrolo[2,3-b]pyrazin-7-yl)-6-(4-phenylpiperazin-1-yl)pyrimidin-4-yl) amino)bicyclo[2.2.2]octane-2-carboxylic Acid To a solution of (2S,3S)-3-((2-(2-chloro-5-trityl-5H-pyrrolo[2,3-b]pyrazin-7-yl)-6-(4-phenylpiperazin-1-yl)pyrimidin-4-yl) amino)bicyclo[2.2.2]octane-2-carboxylic acid (165 mg, 0.20 mmol) in dichloromethane (10 mL) were added trifluoroacetic acid (0.80 mL, 4.95 mmol) and triethyl silicane (0.38 mL, 4.95 mmol), and the mixture was stirred at rt overnight. The reaction mixture was added into saturated aqueous sodium bicarbonate (50 mL), and the resulting mixture was extracted with dichloromethane (50 mL×3). The combined organic layers were washed with saturated brine (100 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a light yellow solid (21 mg, 18%).

MS (ESI, pos. ion) m/z: 559.7 [M+H]$^+$;

HRMS (ESI, pos. ion) m/z: 559.2326, (C$_{29}$H$_{32}$ClN$_8$O$_2$) [M+H]$^+$ theoretical value: 559.2337;

$^1$H NMR (400 MHz, CD$_3$OD) δ (ppm): 8.44 (s, 1H), 8.23 (s, 1H), 7.61-7.48 (m, 1H), 7.26 (t, J=7.9 Hz, 2H), 7.01 (d, J=8.1 Hz, 2H), 6.87 (t, J=7.3 Hz, 1H), 6.71 (s, 1H), 4.60 (dd, J=13.6, 6.8 Hz, 1H), 3.90 (t, J=9.0 Hz, 4H), 3.27 (d, J=4.5 Hz, 4H), 2.56 (d, J=5.1 Hz, 1H), 2.06 (s, 1H), 1.92 (s, 2H), 1.77 (s, 2H), 1.71-1.62 (m, 3H), 1.54-1.47 (m, 2H).

Example 40: (+/−)-trans-3-((2-(2-chloro-5H-pyrrolo[2,3-b]pyrazin-7-yl)-6-(diphenylamino)pyrimidin-4-yl)amino)bicyclo[2.2.2]octane-2-carboxylic Acid

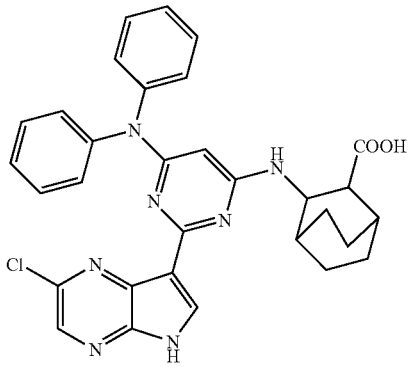 [SMILES: O=C(O)C1C2CCC(CC2)C1Nc1cc(N(c2ccccc2)c2ccccc2)nc(-c2c[nH]c3ncc(Cl)nc23)n1]

Step 1:
2,6-dichloro-N,N-diphenylpyrimidin-4-amine

To a solution of diphenylamine (1.00 g, 5.91 mmol) in THF (20 mL) was added dropwise slowly LDA (6.00 mL, 11.8 mmol, 2.0 mol/L) at 0° C. After the addition, the mixture was warmed to rt and stirred for 0.5 h, then cooled to 0° C. and 2,4,6-trichloropyrimidine (1.08 g, 5.91 mmol) was added dropwise slowly. After the addition, the mixture was stirred at 0° C. overnight. To the reaction mixture was added water (50 mL), and the resulting mixture was extracted with dichloromethane (20 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=50/1) to give the title compound as a light yellow solid (1.05 g, 56%).
MS (ESI, pos.ion) m/z:316.3 [M+H]$^+$.

Step 2: (+/−)-trans-methyl 3-((2-chloro-6-(diphenylamino)pyrimidin-4-yl)amino)bicyclo[2.2.2]octane-2-carboxylate A suspension of 2,6-dichloro-N,N-diphenylpyrimidin-4-amine (0.50 g, 1.60 mmol), (+/−)-trans-methyl 3-aminobicyclo[2.2.2]octane-2-carboxylate (0.41 g, 2.2 mmol), potassium carbonate (0.66 g, 4.7 mmol) in DMF (10 mL) was stirred at 80° C. overnight. To the reaction mixture was added water (40 mL), and the resulting mixture was extracted with ethyl acetate (30 mL×3). The combined organic layers were washed with saturated brine (60 mL), dried over anhydrous sodium sulfate and filtered. The filtrate was concentrated in vacuo and the residue was purified by silica gel column chromatography (PE/EtOAc (v/v)=20/1) to give the title compound as a light yellow solid (0.44 g, 60%).
MS (ESI, pos.ion) m/z: 463.1 [M+H]$^+$.

Step 3: (+/−)-trans-3-((2-chloro-6-(diphenylamino)pyrimidin-4-yl)amino)bicyclo[2.2.2]octane-2-carboxylic Acid To a mixed solvent of water (1 mL), methanol (2 mL) and THF (2 mL) was added (+/−)-trans-methyl 3-((2-chloro-6-(diphenylamino)pyrimidin-4-yl)amino)bicyclo[2.2.2]octane-2-carboxylate (280 mg, 0.60 mmol), then to the mixture was added sodium hydroxide (480 mg, 6.00 mmol). The resulting mixture was stirred at rt for 5 h. To the reaction mixture was added water (30 mL), and the resulting mixture was adjusted with HCl (1 M) to pH about 4. The mixture was extracted with ethyl acetate (20 mL×3). The combined organic layers were washed with saturated brine (50 mL), dried over anydrous sodium sulfate and filtered. The filtrate was concentrated in vacuo to give the title compound as a light yellow solid (265 mg, 97%).
MS (ESI, pos.ion) m/z:449.1 [M+H]$^+$.

Step 4: (+/−)-trans-3-((2-bromo-6-(diphenylamino)pyrimidin-4-yl)amino)bicyclo[2.2.2]octane-2-carboxylic Acid To a solution of hydrobromic acid in acetic acid (10 mL, 20 mmol, 33%) was added (+/−)-trans-3-((2-chloro-6-(diphenylamino)pyrimidin-4-yl)amino)bicyclo[2.2.2]octane-2-carboxylic acid (320 mg, 0.72 mmol), and the mixture was stirred at rt overnight. To the reaction mixture was added water (30 mL), and the mixture was adjusted with saturated aqueous sodium hydroxide to pH about 5. The mixture was filtered, and the filter cake was washed with water (20 mL), dried in vacuo at 60° C. for 12 h to give the title compound as a white solid (350 mg, 99%).
MS (ESI, pos.ion) m/z: 493.1 [M+H]$^+$.

Step 5: (+/−)-trans-methyl 3-((2-bromo-6-(diphenylamino)pyrimidin-4-yl)amino)bicyclo[2.2.2]octane-2-carboxylate (+/−)-trans-3-((2-Bromo-6-(diphenylamino)pyrimidin-4-yl)amino)bicyclo[2.2.2]octane-2-carboxylic acid (300 mg, 0.60 mmol) and iodomethane (172 mg, 1.20 mmol) were dissolved in DMF (10 mL), then potassium carbonate (252 mg, 1.80 mmol) was added. The mixture was stirred at rt overnight. To the reaction mixture was added water (30 mL), and the resulting mixture was extracted with ethyl acetate (20 mL×3). The combined organic layers were washed with saturated aqueous sodium chloride (50 mL), dried over anhydrous sodium sulfate and concentrated in vacuo to give the title compound as a light yellow solid (305 mg, 98%).
MS (ESI, pos.ion) m/z: 507.1 [M+H]$^+$.

Step 6: (+/−)-trans-methyl 3-((2-(2-chloro-5-trityl-5H-pyrrolo[2,3-b]pyrazin-7-yl)-6-(diphenylamino)pyrimidin-4-yl)amino)bicyclo[2.2.2]octane-2-carboxylate To a mixed solvent of 1,4-dioxane (5 mL) and H$_2$O (0.5 mL) was added 2-chloro-7-(4,4,5,5-tetramethyl-1,3,2-dioxaborolan-2-yl)-5-trityl-5H-pyrrolo[2,3-b]pyrazine (210 mg, 0.23 mmol, 60%), K$_2$CO$_3$ (110 mg, 0.78 mmol), PdCl$_2$(dppf) (28 mg, 0.04 mmol) and (+/−)-trans-methyl 3-((2-bromo-6-(diphenylamino)pyrimidin-4-yl)amino)bicyclo[2.2.2]octane-2-carboxylate (100 mg, 0.19 mmol). The air in the mixture was exchanged with nitrogen by bubbling for 10 min. The mixture in the sealed tub was stirred for 1.5 h at 110° C. The mixture was filtered to remove the solid impuries, and the solvent was removed. The residue was purified by silica gel column chromatography (PE/EtOAc (v/v)=10/1-5/1) to give the title compound as a white solid (150 mg, 92%).

Step 7: (+/−)-trans-(methyl 3-((2-(2-chloro-5H-pyrrolo[2,3-b]pyrazin-7-yl)-6-(diphenylamino) pyrimidin-4-yl)amino)bicyclo[2.2.2]octane-2-carboxylate To a solution of (+/−)-trans-methyl 3-((2-(2-chloro-5-trityl-5H-pyrrolo[2,3-b]pyrazin-7-yl)-6-(diphenylamino)pyrimidin-4-yl) amino)bicyclo[2.2.2]octane-2-carboxylate (150 mg, 0.18 mmol) in dichloromethane (10 mL) were added trifluoroacetic acid (0.80 mL, 4.95 mmol) and triethyl silicane (0.38 mL, 4.95 mmol), and the mixture was stirred at rt overnight. The reaction mixture was added into saturated aqueous sodium carbonate (100 mL), and the resulting mixture was extracted with dichloromethane (50 mL×3). The combined organic layers were washed with saturated brine (100 mL), dried over anhydrous sodium sulfate, and filtered. The filtrate was concentrated in vacuo to remove the solvent, and the residue was purified by silica gel column chromatography (DCM/MeOH (v/v)=20/1) to give the title compound as a light yellow solid (72 mg, 68%).

Step 8: (+/−)-trans-3-((2-(2-chloro-5H-pyrrolo[2,3-b]pyrazin-7-yl)-6-(diphenyl amino)pyrimidin-4-yl)amino)bicyclo[2.2.2]octane-2-carboxylic Acid To a solution of (+/−)-trans-methyl 3-((2-(2-chloro-5H-pyrrolo[2,3-b]pyrazin-7-yl)-6-(diphenylamino)pyrimidin-4-yl)amino)bicyclo[2.2.2]octane-2-carboxylate (72 mg, 0.12 mmol) in THF/MeOH (v/v=5 mL/3 mL) was added a solution of NaOH (50 mg, 1.20 mmol) in water (1 mL). The mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (30 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (40 mg, 56%).

MS (ESI, pos. ion) m/z: 566.2 [M+H]$^+$;
HRMS (ESI, pos. ion) m/z: 566.2077, ($C_{31}H_{29}ClN_7O_2$) [M+H]$^+$ theoretical value: 566.2071;
$^1$H NMR (400 MHz, DMSO-d$_6$) δ (ppm): 13.37 (s, 1H), 12.77-12.18 (m, 1H), 8.96 (s, 1H), 8.46 (s, 1H), 8.29 (s, 1H), 7.53 (s, 10H), 7.14 (s, 1H), 3.98 (s, 1H), 3.17 (s, 1H), 2.28 (d, J=5.7 Hz, 1H), 1.94 (s, 1H), 1.69 (s, 1H), 1.63 (d, J=7.1 Hz, 2H), 1.50 (s, 1H), 1.35-1.28 (m, 4H).

Example 41: (2S,3S)-3-((2-(2-chloro-5H-pyrrolo[2,3-b]pyrazin-7-yl)-6-(3,4-dihydroisoquinolin-2(1H)-yl)pyrimidin-4-yl)amino)bicyclo[2.2.2]octane-2-carboxylic Acid

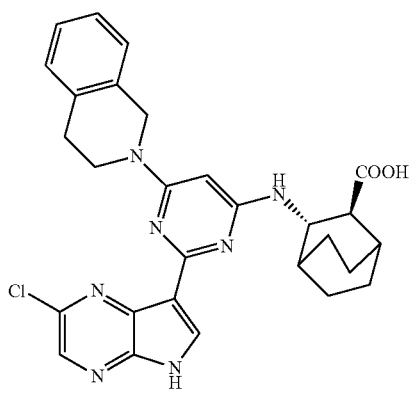 [SMILES: O=C(O)[C@H]1C2CCC(CC2)[C@@H]1Nc1cc(N2CCc3ccccc3C2)nc(-c2c[nH]c3ncc(Cl)nc23)n1]

Step 1: (2S,3S)-ethyl 3-((2-chloro-6-(3,4-dihydroisoquinolin-2(1H)-yl)pyrimidin-4-yl)amino)bicyclo[2.2.2]octane-2-carboxylate (2S,3S)-Ethyl 3-((2,6-dichloropyrimidin-4-yl)amino)bicyclo[2.2.2]octane-2-carboxylate (0.30 g, 0.87 mmol), tetrahydroisoquinoline (1.22 g, 8.72 mmol) and DIPEA (0.34 g, 2.61 mmol) were dissolved in ethanol (8 mL), and then the mixture was heated to 90° C. and stirred overnight. The reaction mixture was diluted with water (40 mL), and the resulting mixture was extracted with EtOAc (30 mL×3). The combined organic layers were washed with saturated brine (80 mL), dried over anhydrous Na$_2$SO$_4$, and filtered. The filtrate was concentrated in vacuo, and the residue was purified by silica gel column chromatography (PE/EA (v/v)=15/1) to give the title compound as a white solid (0.36 g, 93%).

MS (ESI, pos.ion) m/z:441.1 [M+H]$^+$.

Step 2: (2S,3S)-3-((2-chloro-6-(3,4-dihydroisoquinolin-2(1H)-yl)pyrimidin-4-yl)amino)bicyclo[2.2.2]octane-2-carboxylic Acid To a mixed solvent of water (2 mL), methanol (2 mL) and THF (2 mL) was added (2S,3S)-ethyl 3-((2-chloro-6-(3,4-dihydroisoquinolin-2(1H)-yl)pyrimidin-4-yl)amino)bicyclo[2.2.2]octane-2-carboxylate (360 mg, 0.81 mmol), then to the mixture was added sodium hydroxide (650 mg, 16.33 mmol). The resulting mixture was stirred at rt for 5 h. To the reaction mixture was added water 30 mL), and the resulting mixture was adjusted with HCl (1 M) to pH about 4 to 5. The mixture was extracted with ethyl acetate (20 mL×3). The combined organic layers were washed with saturated brine (50 mL), dried over anydrous sodium sulfate and filtered. The filtrate was concentrated in vacuo to give the title compound as a light yellow solid (330 mg, 97%).

MS (ESI, pos.ion) m/z: 413.1 [M+H]$^+$.

Step 3: (2S,3S)-3-((2-bromo-6-(3,4-dihydroisoquinolin-2(1H)-yl)pyrimidin-4-yl) amino)bicyclo[2.2.2]octane-2-carboxylic Acid To a solution of hydrobromic acid in acetic acid (10 mL, 20 mmol, 33%) was added (2S,3S)-3-((2-chloro-6-(3,4-dihydroisoquinolin-2(1H)-yl)pyrimidin-4-yl)amino)bicyclo[2.2.2]octane-2-carboxylic acid (330 mg, 0.80 mmol), and the mixture was stirred at rt overnight. To the reaction mixture was added water (30 mL), and the mixture was adjusted with saturated aqueous sodium hydroxide to pH about 5, and there was a large amount of solid precipitated out. The mixture was filtered, and the filter cake was washed with water (20 mL), dried in vacuo at 60° C. for 12 h to give the title compound as a white solid (360 mg, 98%).

MS (ESI, pos.ion) 457.5 [M+H]$^+$.

Step 4: (2S,3S)-methyl 3-((2-bromo-6-(3,4-dihydroisoquinolin-2(1H)-yl)pyrimidin-4-yl)amino)bicyclo[2.2.2]octane-2-carboxylate To a suspension of (2S,3S)-3-((2-bromo-6-(3,4-dihydroisoquinolin-2(1H)-yl)pyrimidin-4-yl) amino)bicyclo[2.2.2]octane-2-carboxylic acid (360 mg, 0.78 mmol), iodomethane (230 mg, 1.57 mmol) in DMF (10 mL) was added potassium carbonate (330 mg, 2.36 mmol). The mixture was stirred at rt overnight. To the reaction mixture was added water (30 mL), and the resulting mixture was extracted with ethyl acetate (20 mL×3). The combined organic layers were washed with saturated brine (50 mL), dried over anhydrous sodium sulfate and filtered. The filtrate was concentrated in vacuo to give the title compound as a light yellow solid (370 mg, 99%).

MS (ESI, pos.ion) m/z: 473.1 [M+H]$^+$.

Step 5: (2S,3S)-methyl 3-((2-(2-chloro-5-trityl-5H-pyrrolo[2,3-b]pyrazin-7-yl)-6-(3,4-dihydroisoquinolin-2(1H)-yl)pyrimidin-4-yl) amino)bicyclo[2.2.2]octane-2-carboxylate To 1,4-dioxane (5 mL) were added 2-chloro-7-(4,4,5,5-tetramethyl-1,3,2-dioxaborolan-2-yl)-5-trityl-5H-pyrrolo[2,3-b]pyrazine (381 mg, 0.38 mmol, 60%), K$_2$CO$_3$ (220 mg, 1.59 mmol), PdCl$_2$(dppf) (46 mg, 0.06 mmol) and (2S,3S)-methyl 3-((2-bromo-6-(3,4-dihydroisoquinolin-2(1H)-yl)pyrimidin-4-yl) amino)bicyclo[2.2.2]octane-2-carboxylate (150 mg, 0.31 mmol), then H$_2$O (0.5 mL) was added into the mixture. The air in the mixture was exchanged with nitrogen by bubbling for 10 min, then the mixture in the tub was sealed and was stirred for 1.5 h at 110° C. The mixture was filtered to remove the solid impurities, and the filtrate was concentrated to remove the solvent. The residue was purified by silica gel column chromatography (PE/EtOAc (v/v)=10/1-5/1) to give the title compound as a white solid (190 mg, 75%).

Step 6: (2S,3S)-methyl 3-((2-(2-chloro-5H-pyrrolo[2,3-b]pyrazin-7-yl)-6-(3,4-dihydroisoquinolin-2 (1H)-yl)pyrimidin-4-yl) amino)bicyclo[2.2.2]octane-2-carboxylate To a solution of (2S,3S)-methyl 3-((2-(2-chloro-5-trityl-5H-pyrrolo[2,3-b]pyrazin-7-yl)-6-(3,4-dihydroisoquinolin-2(1H)-yl)pyrimidin-4-yl) amino)bicyclo[2.2.2]octane-2-carboxylate (190 mg, 0.24 mmol) in dichloromethane (10 mL) was added trifluoroacetic acid (0.80 mL, 4.95 mmol) and triethyl silicane (0.38 mL, 4.95 mmol), and the mixture was stirred at rt overnight. The reaction mixture was added into saturated aqueous sodium carbonate (60 mL), and the resulting mixture was extracted with dichloromethane (50 mL×3). The combined organic layers were washed with saturated brine (100 mL), dried over anhydrous sodium sulfate, and filtered. The filtrate was concentrated in vacuo to remove the solvent, and the residue was purified by column chromatography (DCM/MeOH (v/v)=10/1) to give the title compound as a light yellow solid (110 mg, 83%).

MS (ESI, pos. ion) m/z: 544.2 [M+H]$^+$.

Step 7: (2S,3S)-3-((2-(2-chloro-5H-pyrrolo[2,3-b]pyrazin-7-yl)-6-(3,4-dihydroisoquinolin-2(1H)-yl)pyrimidin-4-yl)amino)bicyclo[2.2.2]octane-2-carboxylic Acid To a solution of (2S,3S)-methyl 3-((2-(2-chloro-5H-pyrrolo[2,3-b]pyrazin-7-yl)-6-(3,4-dihydroisoquinolin-2(1H)-yl)pyrimidin-4-yl) amino)bicyclo[2.2.2]octane-2-carboxylate (110 mg, 0.20 mmol) in THF/MeOH (v/v=5 mL/5 mL) were added a solution of NaOH (80 mg, 2.00 mmol) in water (1 mL), and the mixture was stirred at rt overnight. To the reaction mixture was added water (20 mL), and the mixture was acidified with hydrochloric acid (1 M) to pH about 6. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (50 mg, 51%).

MS (ESI, pos. ion) m/z: 530.7 [M+H]$^+$;
HRMS (ESI, pos. ion) m/z: 530.2078, (C$_{28}$H$_{29}$ClN$_7$O$_2$) [M+H]$^+$ theoretical value:530.2071;
$^1$H NMR (400 MHz, DMSO-d$_6$) δ (ppm): 12.85 (s, 1H), 12.24 (s, 1H), 8.69 (s, 1H), 8.43 (s, 1H), 7.21 (d, J=20.7 Hz, 4H), 6.92 (s, 1H), 5.00-4.88 (m, 2H), 4.47 (s, 1H), 4.03 (dd, J=14.2, 7.1 Hz, 3H), 2.90 (s, 2H), 1.99 (s, 1H), 1.96 (s, 1H), 1.90 (s, 1H), 1.71 (m, 3H), 1.60-1.48 (m, 3H), 1.41-1.34 (m, 2H).

Example 42: (2S,3S)-3-((5-fluoro-2-(3-methyl-5H-pyrrolo[2,3-b]pyrazin-7-yl)-6-(thiophen-2-yl)pyrimidin-4-yl)amino)bicyclo[2.2.2]octane-2-carboxylic Acid

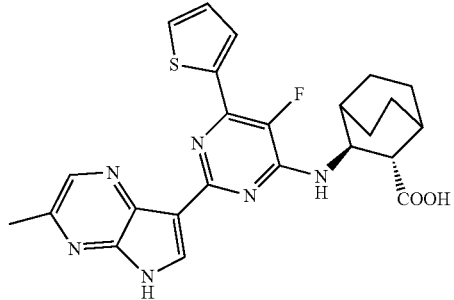 [SMILES: Cc1cnc2c(-c3nc(N[C@H]4C5CCC(CC5)[C@@H]4C(=O)O)c(F)c(-c4cccs4)n3)c[nH]c2n1]

Step 1: 3,5-dibromo-6-methylpyrazin-2-amine

To a solution of 6-methylpyrazin-2-amine (14.40 g, 132 mmol) and pyridine (26.0 g, 330 mmol) in DCM (300 mL) was added dropwise slowly bromine (53.00 g, 330 mmol). After the addition, the mixture was stirred at rt overnight. Water (150 mL) was added to quench the reaction, and the resulting mixture was partitioned. The organic phase was washed with saturated brine (100 mL), dried over anhydrous sodium sulfate, filtered, and the filtrate was concentrated in vacuo to give the title compound as a yellow solid (34.01 g, 96%).

MS (ESI, pos. ion) m/z: 267.9 [M+H]$^+$.

Step 2: 5-bromo-6-methyl-3-((trimethylsilyl)ethynyl)pyrazin-2-amine 3,5-Bibromo-6-methylpyrazin-2-amine (34.00 g, 127 mmol), triethylamine (39.3 g, 382 mmol), cuprous iodide (2.50 g, 12.7 mmol) and palladium(II)bis(triphenylphosphine) dichloride (9.0 g, 12.7 mmol) were dissolved in tetrahydrofuran (500 mL). The mixture was stirred at rt, then trimethylsilylacetylene (20.00 mL, 140 mmol) was added dropwise to the mixture. After the addition, the reaction mixture was stirred for 4 h. The reaction mixture was diluted with ethyl acetate (150 mL). The mixture was filtered. The filtrate was concentrated in vacuo, and the residue was purified by silica gel column chromatography (PE/EtOAc (v/v)=30/1) to give the title compound as a light yellow solid (28.0 g, 77%).

MS (ESI, pos. ion) m/z: 284.0 [M+H]$^+$.

Step 3: 5-bromo-3-ethynyl-6-methylpyrazin-2-amine

To methanol (100 mL) were added 5-bromo-6-methyl-3-((trimethylsilyl) ethynyl) pyrazin-2-amine (16.00 g, 56 mmol) and potassium carbonate (15.6 g, 112 mmol). The mixture was stirred at rt for 1 h. To the reaction mixture was added water (350 mL), and the mixture was filtered, and the filter cake was washed with water (50 mL), dried in vacuo at 60° C. for 24 h to give the title compound as a brown solid (10.2 g, 85%).

Step 4: 2-bromo-3-methyl-5H-pyrrolo[2,3-b]pyrazine

A solution of 5-bromo-3-ethynyl-6-methylpyrazin-2-amine (6.70 g, 32 mmol) in NMP (100 mL) was stirred at rt, then potassium tert-butoxide (11.0 g, 95 mmol) was added, and the resulting mixture was stirred at 80° C. overnight. The reaction was stopped, and the mixture was cooled to rt, diluted with ethyl acetate (80 mL). The mixture was filtered. The filtrate was concentrated in vacuo, and the residue was purified by column chromatography (PE/EtOAc (v/v)=3/1) to give the title compound as a light yellow solid (6.0 g, 90%).

MS (ESI, pos. ion) m/z: 212.0 [M+H]$^+$;
$^1$H NMR (400 MHz, CDCl$_3$) δ (ppm): 10.38 (s, 1H), 7.60-7.51 (m, 1H), 6.67 (dd, J=3.5, 1.8 Hz, 1H), 2.75 (s, 3H).

Step 5: 3-methyl-5H-pyrrolo[2,3-b]pyrazine

To anydrous ethanol (60 mL) were added 2-bromo-3-methyl-5H-pyrrolo[2,3-b]pyrazine (6.00 g, 28 mmol), ammonium formate (27.00 g, 428 mmol) and 10% Pd/C (6 g). The mixture was refluxed for 5 hours under nitrogen protection. The reaction mixture was filtered through a celite pad, concentrated in vacuo to remove the solvent, and the residue was purified by silica gel column chromatography (PE/EA (v/v)=4/1-2/1) to give the title compound as a yellow solid (3.10 g, 82%).

MS (ESI, pos. ion) m/z: 134.2 [M+H]$^+$.

Step 6: 7-iodo-3-methyl-5H-pyrrolo[2,3-b]pyrazine

To a solution of 3-methyl-5H-pyrrolo[2,3-b]pyrazine (3.10 g, 23 mmol) in DMF (30 mL) was added NIS (5.8 g, 26.00 mmol) in portions, and the reaction mixture was stirred at rt overnight. Saturated aqueous sodium thiosulfate (50 mL) was added to quench the reaction, and the resulting mixture was extracted with EtOAc (50 mL×2). The combined organic phases were washed with saturated brine (80 mL), dried over anhydrous Na$_2$SO$_4$, filtered, and the filtrate was concentrated in vacuo. The residue was purified by silica gel chromatograph (PE/EtOAc (v/v)=20/1-4/1) to give the title compound as a yellow solid (4.40 g, 73%).

MS (ESI, pos. ion) m/z: 259.9 [M+H]$^+$.

Step 7: 7-iodo-3-methyl-5-trityl-5H-pyrrolo[2,3-b]pyrazine

To a stirred 0° C. solution of 7-iodo-3-methyl-5H-pyrrolo[2,3-b]pyrazine (4.40 g, 17 mmol) in THF (80 mL) was added slowly NaH (1.40 g, 34 mmol, 60%) in portions, and the mixture was stirred at 0° C. for 30 min. Then triphenylchloromethane (7.10 g, 25.00 mmol) was added. The resulting mixture was warmed to rt and stirred overnight. To the reaction mixture was added water (100 mL), and the resulting mixture was extracted with ethyl acetate (100 mL×3). The combined organic layers were washed with saturated brine (120 mL×2), dried over anhydrous sodium sulfate and filtered. The filtrate was concentrated in vacuo and the residue was purified by silica gel column chromatography (PE/EA (v/v)=20/1) to give the title compound as a light yellow solid (8.20 g, 96%).

$^1$H NMR (400 MHz, CDCl$_3$) δ (ppm): 8.23 (s, 1H), 7.57 (m, 1H), 7.33-7.28 (m, 15H), 2.26 (s, 3H).

Step 8: 3-methyl-7-(4,4,5,5-tetramethyl-1,3,2-dioxaborolan-2-yl)-5-trityl-5H-pyrrolo[2,3-b]pyrazine A solution of 7-iodo-3-methyl-5-trityl-5H-pyrrolo[2,3-b]pyrazine (4.00 g, 7.98 mmol) and isopropoxyboronic acid pinacol ester (2.23 g, 5 mmol) in THF (80 mL) was cooled to −30° C. and stirred, then isopropylmagnesium chloride solution (2 M, 12 mL) was added dropwise. After the addition, the mixture was stirred at −30° C. for 1.5 h. The reaction mixture was added into saturated aqueous sodium bicarbonate (100 mL). The resulting mixture was extracted with ethyl acetate (100 mL×3). The combined organic layers were dried over anhydrous sodium sulfate and filtered. The filtrate was concentrated in vacuo, and the residue was purified by silica gel column chromatography (PE/EtOAc (v/v)=10/1) to give the title compound as a yellow solid (2.56 g, 64%).

MS (ESI, pos. ion) m/z: 502.4 [M+H]$^+$.

Step 9: (2S,3S)-ethyl 3-((5-fluoro-2-(3-methyl-5-trityl-5H-pyrrolo[2,3-b]pyrazin-7-yl)-6-(thiophen-2-yl)pyrimidin-4-yl)amino)bicyclo[2.2.2]octane-2-carboxylate To a mixed solvent of 1,4-dioxane (8 mL) and H$_2$O (1 mL) were added 3-methyl-7-(4,4,5,5-tetramethyl-1,3,2-dioxaborolan-2-yl)-5-trityl-5H-pyrrolo[2,3-b]pyrazine (310 mg, 0.61 mmol), K$_2$CO$_3$ (250 mg, 1.76 mmol), PdCl$_2$(dppf) (40 mg, 0.05 mmol) and (2S,3S)-ethyl 3-((2-bromo-5-fluoro-6-(thiophen-2-yl)pyrimidin-4-yl)amino)bicyclo[2.2.2]octane-2-carboxylate (200 mg, 0.44 mmol). The air in the mixture was exchanged with nitrogen by bubbling for 10 min. The mixture in the sealed tub was stirred for 3 h at 110° C. The mixture was filtered to remove the solid impuries, and the solvent was removed. The residue was purified by silica gel column chromatography (PE/EtOAc (v/v)=10/1-5/1) to give the title compound as a white solid (160 mg, 48%).

Step 10: (2S,3S)-ethyl 3-((5-fluoro-2-(3-methyl-5H-pyrrolo[2,3-b]pyrazin-7-yl)-6-(thiophen-2-yl)pyrimidin-4-yl)amino)bicyclo[2.2.2]octane-2-carboxylate To a solution of (2S,3S)-ethyl 3-((5-fluoro-2-(3-methyl-5-trityl-5H-pyrrolo[2,3-b]pyrazin-7-yl)-6-(thiophen-2-yl)pyrimidin-4-yl)amino)bicyclo[2.2.2]octane-2-carboxylate (160 mg, 0.21 mmol) in dichloromethane (5 mL) were added Et$_3$SiH (0.40 mL, 2.38 mmol) and TFA (0.20 mL, 5.40 mmol), and the mixture was stirred at rt overnight. The reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (94 mg, 86%).

MS (ESI, pos. ion) m/z: 507.1 [M+H]$^+$.

Step 11: (2S,3S)-3-((5-fluoro-2-(3-methyl-5H-pyrrolo[2,3-b]pyrazin-7-yl)-6-(thiophen-2-yl)pyrimidin-4-yl)amino)bicyclo[2.2.2]octane-2-carboxylic Acid To a solution of (2S,3S)-ethyl 3-((5-fluoro-2-(3-methyl-5H-pyrrolo[2,3-b]pyrazin-7-yl)-6-(thiophen-2-yl)pyrimidin-4-yl)amino)bicyclo[2.2.2]octane-2-carboxylate (94 mg, 0.14 mmol) in THF/MeOH (v/v=5 mL/5 mL) was added a solution of NaOH (60 mg, 1.42 mmol) in water (1 mL), and the mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (80 mg, 90%).

MS (ESI, pos. ion) m/z: 479.1 [M+H]$^+$;
HRMS (ESI, pos. ion) m/z: 479.1680, ($C_{24}H_{24}FN_7O_2S$) [M+H]$^+$ theoretical value:479.1665;
$^1$H NMR (600 MHz, DMSO-$d_6$) δ (ppm): 12.19 (s, 1H), 8.47 (s, 1H), 8.29 (d, J=2.4 Hz, 1H), 7.87 (s, 1H), 7.82 (d, J=4.9 Hz, 1H), 7.56 (d, J=6.1 Hz, 1H), 7.31-7.25 (m, 1H), 4.64 (s, 1H), 2.84 (d, J=6.9 Hz, 1H), 2.58 (s, 3H), 2.10 (s, 1H), 1.99 (s, 1H), 1.90 (s, 1H), 1.74 (s, 2H), 1.63-1.40 (m, 5H).

Example 43: (2S,3S)-3-((5-fluoro-2-(2-methyl-5H-pyrrolo[2,3-b]pyrazin-7-yl)-6-(thiophen-2-yl)pyrimidin-4-yl)amino)bicyclo[2.2.2]octane-2-carboxylic Acid

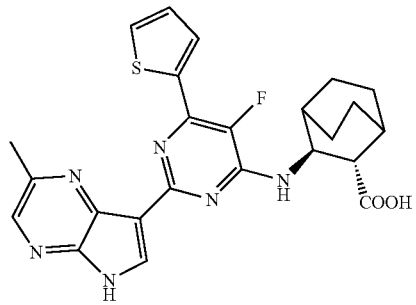 [SMILES: Cc1cnc2[nH]cc(-c3nc(N[C@H]4C5CCC(CC5)[C@@H]4C(=O)O)c(F)c(-c4cccs4)n3)c2n1]

Step 1: 3-bromo-5-methylpyrazine-2-amine

To a solution of 5-methylpyrazin-2-amine (5.00 g, 45.8 mmol) and pyridine (4.35 g, 55.0 mmol) in DCM (250 mL) was added bromine (8.80 g, 55.0 mmol). The mixture was stirred at rt overnight. To the reaction mixture was added water (150 mL), and the resulting mixture was partitioned. The organic layer was washed with saturated brine (100 mL), dried over anhydrous sodium sulfate and filtered. The filtrate was concentrated in vacuo to give the title compound as a yellow solid (7.64 g, 88%).

MS (ESI, pos. ion) m/z: 190.2 [M+H]$^+$;
$^1$H NMR (400 MHz, CDCl$_3$) δ (ppm): 7.83 (s, 1H), 4.93 (s, 2H), 2.41 (s, 3H).

Step 2: 5-methyl-3-((trimethylsilyl)ethynyl)pyrazin-2-amine

3-Bromo-5-methylpyrazin-2-amine (7.64 g, 40.6 mmol), triethylamine (12.3 g, 122 mmol), cuprous iodide (0.77 g, 4.06 mmol) and palladium(II)bis(triphenylphosphine) dichloride (2.85 g, 4.06 mmol) were dissolved in tetrahydrofuran (150 mL). The mixture was stirred at rt, then trimethylsilylacetylene (8.00 mL, 56.9 mmol) was added dropwise slowly to the mixture. The resulting mixture was continued to stir for 4 h. The reaction mixture was diluted with ethyl acetate (50 mL). The mixture was filtered. The filtrate was concentrated in vacuo, and the residue was purified by silica gel column chromatography (PE/EtOAc (v/v)=30/1) to give the title compound as a light yellow solid (7.0 g, 84%).

MS (ESI, pos. ion) m/z: 206.1 [M+H]$^+$.

Step 3: 3-ethynyl-5-methylpyrazine-2-amine

To methanol (70 mL) were added 5-methyl-3-((trimethylsilyl)ethynyl)pyrazin-2-amine (7.00 g, 34 mmol) and potassium carbonate (9.40 g, 68 mmol). The mixture was stirred at rt for 1 h. To the reaction mixture was added water (350 mL), and the mixture was filtered. The filter cake was washed with water (50 mL) one time, dried in vacuo at 60° C. for 24 h to give the title compound as a brown solid (4.0 g, 88%).

Step 4: 2-methyl-5H-pyrrolo[2,3-b]pyrazine

A solution of 3-ethynyl-5-methylpyrazine-2-amine (4.00 g, 30 mmol) in NMP (80 mL) was stirred at rt, then potassium tert-butoxide (10.0 g, 89 mmol) was added, and the resulting mixture was stirred at 80° C. overnight. The reaction mixture was cooled to rt, and diluted with ethyl acetate (80 mL). The mixture was filtered through a celite pad. The filtrate was concentrated in vacuo, and the residue was purified by silica gel column chromatography (PE/EtOAc (v/v)=3/1) to give the title compound as a light yellow solid (3.00 g, 75%).

MS (ESI, pos. ion) m/z: 134.1 [M+H]$^+$;
$^1$H NMR (400 MHz, CDCl$_3$) δ (ppm): 10.90 (s, 1H), 8.16 (s, 1H), 7.64-7.59 (m, 1H), 6.67 (dd, J=3.5, 1.8 Hz, 1H), 2.69 (s, 3H).

Step 5: 7-iodo-2-methyl-5H-pyrrolo[2,3-b]pyrazine

To a solution of 2-methyl-5H-pyrrolo[2,3-b]pyrazine (3.00 mg, 23 mmol) in DMF (30 mL) was added NIS (5.6 g, 25.00 mmol) in portions, and the reaction mixture was stirred at rt overnight. Saturated aqueous sodium thiosulfate (50 mL) was added to quench the reaction, and the resulting mixture was extracted with EtOAc (50 mL×2). The combined organic phases were washed with saturated brine (80 mL), dried over anhydrous sodium sulfate, filtered, and the filtrate was concentrated in vacuo. The residue was purified by silica gel chromatograph (PE/EtOAc (v/v)=20/1-4/1) to give the title compound as a yellow solid (2.40 g, 41%).

MS (ESI, pos. ion) m/z: 259.9 [M+H]$^+$.

Step 6: 7-iodo-2-methyl-5-trityl-5H-pyrrolo[2,3-b]pyrazine

To a 0° C. solution of 7-iodo-2-methyl-5H-pyrrolo[2,3-b]pyrazine (2.40 g, 9.30 mmol) in THF (40 mL) was added NaH (0.74 g, 19 mmol, 60%) in portions, and the mixture was stirred at 0° C. for 30 min. To the mixture was added triphenylchloromethane (3.90 g, 14.00 mmol), and the resulting mixture was stirred at rt overnight. To the reaction mixture was added water (100 mL), and the resulting mixture was extracted with ethyl acetate (100 mL×3). The combined organic layers were washed with saturated brine (120 mL×3), dried over anhydrous sodium sulfate and filtered. The filtrate was concentrated in vacuo and the residue was purified by silica gel column chromatography (PE/EtOAc (v/v)=20/1) to give the title compound as a light yellow solid (4.50 g, 97%).

Step 7: 2-methyl-7-(4,4,5,5-tetramethyl-1,3,2-dioxaborolan-2-yl)-5-trityl-5H-pyrrolo[2,3-b]pyrazine A solution of 7-iodo-2-methyl-5-trityl-5H-pyrrolo[2,3-b]pyrazine (4.50 g, 8.97 mmol) and isopropoxyboronic acid pinacol ester (3.34 g, 17.9 mmol) in THF (90 mL) was cooled to −30° C. and stirred, then isopropylmagnesium chloride solution (2 M, 13 mL) was added dropwise. After the addition, the mixture was stirred at −30° C. for 1.5 h. The reaction was stopped, and the reaction mixture was added into saturated aqueous sodium bicarbonate (100 mL). The resulting mixture was extracted with ethyl acetate (100 mL×3). The combined organic layers were concentrated in vacuo, and the residue was purified by silica gel column chromatography (PE/EtOAc (v/v)=10/1) to give the title compound as a yellow solid (3.20 g, 71%).

MS (ESI, pos. ion) m/z: 502.2 [M+H]$^+$.

Step 8: (2S,3S)-ethyl 3-((5-fluoro-2-(2-methyl-5-trityl-5H-pyrrolo[2,3-b]pyrazin-7-yl)-6-(thiophen-2-yl)pyrimidin-4-yl)amino)bicyclo[2.2.2]octane-2-carboxylate To a mixed solvent of 1,4-dioxane (8 mL) and H$_2$O (1 mL) were added 2-methyl-7-(4,4,5,5-tetramethyl-1,3,2-dioxaborolan-2-yl)-5-trityl-5H-pyrrolo[2,3-b]pyrazine (380 mg, 0.34 mmol, 45%), K$_2$CO$_3$ (160 mg, 1.14 mmol), PdCl$_2$(dppf) (40 mg, 0.05 mmol) and (2S,3S)-ethyl 3-((2-bromo-5-fluoro-6-(thiophen-2-yl)pyrimidin-4-yl)amino)bicyclo[2.2.2]octane-2-carboxylate (130 mg, 0.26 mmol). The air in the mixture was exchanged with nitrogen by bubbling for 10 min. The mixture in the sealed tub was stirred for 3 h at 110° C. The mixture was filtered to remove the solid impuries, and the solvent was removed. The residue was purified by silica gel column chromatography (PE/EtOAc (v/v)=10/1-5/1) to give the title compound as a white solid (150 mg, 70%).

Step 9: (2S,3S)-ethyl 3-((5-fluoro-2-(2-methyl-5H-pyrrolo[2,3-b]pyrazin-7-yl)-6-(thiophen-2-yl)pyrimidin-4-yl)amino)bicyclo[2.2.2]octane-2-carboxylate To a solution of (2S,3S)-ethyl 3-((5-fluoro-2-(2-methyl-5-trityl-5H-pyrrolo[2,3-b]pyrazin-7-yl)-6-(thiophen-2-yl)pyrimidin-4-yl)amino)bicyclo[2.2.2]octane-2-carboxylate (150 mg, 0.20 mmol) in dichloromethane (5 mL) were added Et$_3$SiH (0.40 mL, 2.38 mmol) and TFA (0.20 mL, 5.40 mmol), and the mixture was stirred at rt overnight. The reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (91 mg, 89%).

MS (ESI, pos. ion) m/z: 507.1 [M+H]$^+$.

Step 10: (2S,3S)-3-((5-fluoro-2-(2-methyl-5H-pyrrolo[2,3-b]pyrazin-7-yl)-6-(thiophen-2-yl) pyrimidin-4-yl)amino)bicyclo[2.2.2]octane-2-carboxylic Acid To a solution of (2S,3S)-ethyl 3-((5-fluoro-2-(2-methyl-5H-pyrrolo[2,3-b]pyrazin-7-yl)-6-(thiophen-2-yl)pyrimidin-4-yl)amino)bicyclo[2.2.2]octane-2-carboxylate (91 mg, 0.17 mmol) in THF/MeOH (v/v=5 mL/5 mL) was added a solution of NaOH (35 mg, 0.89 mmol) in water (1 mL), and the mixture was stirred at rt overnight. To the reaction mixture was added water (20 mL), and the mixture was acidified with hydrochloric acid (1 M) to pH about 6. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (72 mg, 83%).

MS (ESI, pos. ion) m/z: 478.9 [M+H]$^+$;
HRMS (ESI, pos. ion) m/z: 479.1676, (C$_{24}$H$_{24}$FN$_6$O$_2$S) [M+H]$^+$ theoretical value:479.1665;
$^1$H NMR (600 MHz, DMSO-d$_6$) δ (ppm): 12.26 (d, J=2.2 Hz, 1H), 8.34 (d, J=2.9 Hz, 1H), 8.19 (s, 1H), 7.88 (d, J=3.2 Hz, 1H), 7.83 (d, J=4.9 Hz, 1H), 7.55 (d, J=6.3 Hz, 1H), 7.30-7.26 (m, 1H), 4.68 (s, 1H), 2.85 (m, 1H), 2.64 (s, 3H), 2.14 (s, 1H), 1.99 (s, 1H), 1.90 (s, 1H), 1.80-1.70 (m, 2H), 1.60-1.35 (m, 5H).

Example 44: (2S,3S)-heptyl 3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate

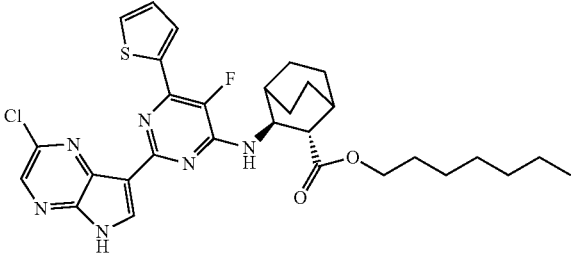 [SMILES: CCCCCCCOC(=O)[C@H]1C2CCC(CC2)[C@@H]1Nc1nc(-c2c[nH]c3ncc(Cl)nc23)nc(-c2cccs2)c1F]

Step 1: (2S,3S)-heptyl 3-((2-bromo-5-fluoro-6-(thiophen-2-yl)pyrimidin-4-yl)amino)bicyclo[2.2.2]octane-2-carboxylate To DMF (10 mL) were added (2S,3S)-3-((2-bromo-5-fluoro-6-(thiophen-2-yl) pyrimidin-4-yl)amino)bicyclo[2.2.2]octane-2-carboxylic acid (625 mg, 1.46 mmol), potassium carbonate (600 mg, 4.39 mmol), 7-bromo-1-heptane (525 mg, 2.93 mmol), and the mixture was stirred at rt overnight. To the reaction mixture was added water (30 mL), and the resulting mixture was extracted with ethyl acetate (30 mL×3). The combined organic layers were washed with saturated brine (50 mL), dried over anhydrous sodium sulfate and filtered. The filtrate was concentrated in vacuo to give the title compound as a white solid (770 mg, 100%).

$^1$H NMR (400 MHz, CDCl$_3$) δ (ppm): 7.83 (d, J=3.7 Hz, 1H), 7.57 (d, J=5.0 Hz, 1H), 7.20-7.16 (m, 1H), 5.31 (s, 1H), 4.54 (s, 1H), 4.23-4.15 (m, 2H), 2.41 (d, J=5.9 Hz, 1H), 2.04 (s, 1H), 1.92 (s, 1H), 1.84 (s, 1H), 1.67 (m, 7H), 1.30 (m, 10H), 0.88 (t, J=6.8 Hz, 3H).

Step 2: (2S,3S)-heptyl 3-((2-(2-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate To 1,4-dioxane (10 mL) were added 2-chloro-7-(4,4,5,5-tetramethyl-1,3,2-dioxaborolan-2-yl)-5-trityl-5H-pyrrolo[2,3-b]pyrazine (740 mg, 0.91 mmol, 65%), $K_2CO_3$ (420 mg, 3.05 mmol), $PdCl_2(dppf)$ (110 mg, 0.03 mmol) and (2S,3S)-heptyl 3-((2-bromo-5-fluoro-6-(thiophen-2-yl)pyrimidin-4-yl) amino)bicyclo[2.2.2]octane-2-carboxylate (400 mg, 0.76 mmol), then $H_2O$ (1 mL) was added into the mixture. The air in the mixture was exchanged with nitrogen by bubbling for 10 min. The mixture in the sealed tub was stirred for 3 h at 115° C. The mixture was filtered to remove the solid impurities, and the solvent was removed. The residue was purified by silica gel column chromatography (PE/EtOAc (v/v)=20/1-10/1) to give the title compound as a white solid (510 mg, 69%).

Step 3: (2S,3S)-heptyl 3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate To a solution of (2S,3S)-heptyl 3-((2-(2-chloro-5-trityl-5H-pyrrolo[2,3-b]pyrazin-7-yl)-5-fluoro-6-(thiophen-2-yl) pyrimidin-4-yl)amino)bicyclo[2.2.2]octane-2-carboxylate (510 mg, 0.60 mmol) in dichloromethane (10 mL) was added $Et_3SiH$ (0.80 mL, 4.76 mmol) and TFA (0.80 mL, 5.40 mmol), and the mixture was stirred at rt overnight. The reaction mixture was added into saturated aqueous sodium bicarbonate (50 mL). The resulting mixture was extracted with dichloromethane (60 mL). The combined organic layers were washed with saturated brine (30 mL), dried over anhydrous sodium sulfate, and filtered. The filtrate was concentrated in vacuo, and the residue was purified by silica gel column chromatography (PE/EtOAc (v/v)=4/1) to give the title compound as a white solid (255 mg, 70%).

MS (ESI, pos. ion) m/z: 598.2 [M+H]$^+$;
HRMS (ESI, pos. ion) m/z: 597.2202, ($C_{30}H_{35}ClFN_6O_2S$)[M+H]$^+$ theoretical value: 508.2228;
$^1$H NMR (600 MHz, $CDCl_3$) δ (ppm): 10.02 (s, 1H), 8.49 (s, 1H), 8.27 (s, 1H), 7.91 (s, 1H), 7.56 (d, J=4.0 Hz, 1H), 7.20 (s, 1H), 5.29 (s, 1H), 4.79 (s, 1H), 4.12 (s, 1H), 3.99 (s, 1H), 2.47 (d, J=4.1 Hz, 1H), 2.18-1.97 (m, 4H), 1.86-1.67 (m, 8H), 1.18 (s, 8H), 0.82 (t, J=6.2 Hz, 3H).

Example 45: (2S,3S)-((ethoxycarbonyl)oxy)methyl 3-((2-(2-chloro-5H-pyrrolo[2,3-b]pyrazin-7-yl)-6-(5-chlorothiophen-2-yl)-5-fluoropyrimidin-4-yl)amino)bicyclo[2.2.2]octane-2-carboxylate

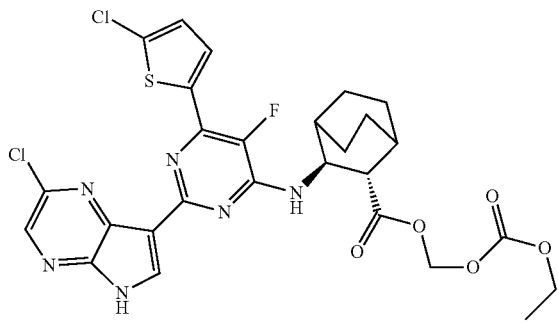 [SMILES: CCOC(=O)OCOC(=O)[C@H]1C2CCC(CC2)[C@@H]1Nc1nc(-c2c[nH]c3ncc(Cl)nc23)nc(-c2ccc(Cl)s2)c1F]

Step 1: (2S,3S)-3-((2-chloro-6-(5-chlorothiophen-2-yl)-5-fluoropyrimidin-4-yl)amino)bicyclo[2.2.2]octane-2-carboxylic Acid To a solution of (2S,3S)-ethyl 3-((2-chloro-6-(5-chlorothiophen-2-yl)-5-fluoro pyrimidin-4-yl)amino)bicyclo [2.2.2]octane-2-carboxylate (1.21 g, 2.72 mmol) in THF/MeOH/$H_2O$ (v/v/v=8 mL/4 mL/4 mL) was added NaOH (0.24 g, 5.45 mmol) in portions. The mixture was stirred at rt overnight. To the reaction mixture was added water (20 mL), and the mixture was acidified with hydrochloric acid (1 M) to pH about 5. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent and give the title compound as a light yellow solid (1.12 g, 98%).

LC-MS (ESI, pos. ion) m/z: 417.8[M+H]$^+$.

Step 2: (2S,3S)-3-((2-bromo-6-(5-chlorothiophen-2-yl)-5-fluoropyrimidin-4-yl)amino)bicyclo[2.2.2]octane-2-carboxylic Acid To a reaction flask was added (2S,3S)-3-((2-chloro-6-(5-chlorothiophen-2-yl)-5-fluoropyrimidin-4-yl)amino)bicyclo [2.2.2]octane-2-carboxylic acid (1.12 g, 2.69 mol) and a solution of hydrobromic acid in acetic acid (15 mL, 90 mmol, 33%), and the mixture was stirred at rt for 1 h. The reaction mixture was added into ice-water (20 mL), and the resulting mixture was extracted with EtOAc (30 mL×3). The combined organic layers were washed with saturated aqueous sodium bicarbonate (20 mL×3) and saturated brine (50 mL), dried over anhydrous $Na_2SO_4$, and filtered. The filtrate was concentrated in vacuo to give the title compound as a light yellow solid (1.1 g, 89%).

MS (ESI, pos. ion) m/z: 461.9 [M+H]$^+$.

Step 3: (2S,3S)-((ethoxycarbonyl)oxy)methyl 3-((2-bromo-6-(5-chlorothiophen-2-yl)-5-fluoropyrimidin-4-yl) amino)bicyclo[2.2.2]octane-2-carboxylate To DMF (10 mL) were added chloromethyl ethyl carbonate (0.66 g, 4.77 mmol), potassium carbonate (1.00 g, 7.16 mmol) and (2S,3S)-3((2-bromo-6-(5-chlorothiophen-2-yl)-5-fluoropyrimidin-4-yl)amino)bicyclo[2.2.2]octane-2-carboxylic acid (1.10 g, 2.39 mmol) and the mixture was stirred at rt overnight. To the reaction mixture was added water (40 mL), and the resulting mixture was extracted with ethyl acetate (30 mL×3). The combined organic layers were washed with saturated brine (30 mL), dried over anhydrous sodium sulfate and filtered. The filtrate was concentrated and the residue was purified by silica gel column chromatography (PE/EtOAc (v/v)=15/1) to give the title compound as a light yellow solid (0.90 g, 67%).

Step 4: (2S,3S)-((ethoxycarbonyl)oxy)methyl 3-((2-(2-chloro-5-trityl-5H-pyrrolo[2,3-b]pyrazin-7-yl)-6-(5-chlorothiophen-2-yl)-5-fluoropyrimidin-4-yl) amino)bicyclo[2.2.2]octane-2-carboxylate To 1,4-dioxane (10 mL) were added 2-chloro-7-(4,4,5,5-tetramethyl-1,3,2-dioxaborolan-2-yl)-5-trityl-5H-pyrrolo[2,3-b]pyrazine (770 mg, 0.96 mmol, 65%), potassium phosphate (442 mg, 3.19 mmol), Pd(dppf)$Cl_2$ (83 mg, 0.10 mmol) and (2S,3S)-((ethoxycarbonyl)oxy)methyl 3-((2-bromo-6-(5-chlorothiophen-2-yl)-5-fluoropyrimidin-4-yl) amino)bicyclo[2.2.2]octane-2-carboxylate (450 mg, 0.80 mmol), then H₂O (1 mL) was added. The mixture was stirred for 12 h at 100° C. under nitrogen protection. The mixture was filtered to remove the solid impuries, and the solvent was removed. The residue was purified by silica gel column chromatography (PE/EtOAc (v/v)=20/1) to give the title compound as a light yellow solid (450 mg, 64%).

Step 5: (2S,3S)-((ethoxycarbonyl)oxy)methyl 3-((2-(2-chloro-5H-pyrrolo[2,3-b]pyrazin-7-yl)-6-(5-chlorothiophen-2-yl)-5-fluoropyrimidin-4-yl) amino) bicyclo[2.2.2]octane-2-carboxylate To a solution of (2S,3S)-((ethoxycarbonyl)oxy)methyl 3-((2-(2-chloro-5-trityl-5H-pyrrolo[2,3-b]pyrazin-7-yl)-6-(5-chlorothiophen-2-yl)-5-fluoropyrimidin-4-yl)amino)bicyclo[2.2.2]octane-2-carboxylate (450 mg, 0.51 mmol) in dichloromethane (10 mL) were added Et₃SiH (0.80 mL, 4.76 mmol) and TFA (0.80 mL, 5.40 mmol), and the mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (100 mL), dried over anhydrous sodium sulfate, and filtered. The filtrate was concentrated in vacuo, and the residue was purified by silica gel column chromatography (PE/EtOAc (v/v)=4/1) to give the title compound as a white solid (262 mg, 80%).

MS (ESI, pos. ion) m/z: 637.2 [M+H]⁺;
HRMS (ESI, pos. ion) m/z: 635.1043, (C₂₆H₃₁ClN₇O₂) [M+H]⁺ theoretical value: 635.1046;
¹H NMR (400 MHz, CDCl₃) δ (ppm): 10.40 (s, 1H), 8.40 (d, J=2.4 Hz, 1H), 8.26 (s, 1H), 7.62 (d, J=3.6 Hz, 1H), 6.98 (d, J=3.8 Hz, 1H), 5.80 (d, J=5.6 Hz, 1H), 5.69 (d, J=5.6 Hz, 1H), 5.33 (d, J=4.5 Hz, 1H), 4.69 (s, 1H), 4.16-4.08 (m, 2H), 2.58 (s, 1H), 2.09 (s, 2H), 1.94 (s, 1H), 1.82 (s, 1H), 1.76-1.56 (m, 6H), 1.17 (s, 3H).

Example 46: (2S,3S)-(5-methyl-2-oxo-1,3-dioxol-4-yl)methyl 3-((2-(2-chloro-5H-pyrrolo[2,3-b]pyrazin-7-yl)-5-fluoro-6-(thiophen-2-yl)pyrimidin-4-yl) amino)bicyclo[2.2.2]octane-2-carboxylate

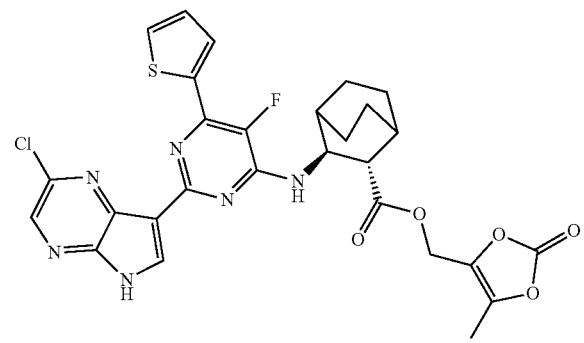 [SMILES: Cc1oc(=O)oc1COC(=O)[C@H]1C2CCC(CC2)[C@@H]1Nc1nc(-c2c[nH]c3ncc(Cl)nc23)nc(-c2cccs2)c1F]

Step 1: (2S,3S)-(5-methyl-2-oxo-1,3-dioxol-4-yl) methyl 3-((2-(2-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate To DMF (10 mL) were added (2S,3S)-3-((2-(2-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylic acid (1.56 g, 2.10 mmol), potassium carbonate (880 mg, 6.31 mmol), 4-(bromomethyl)-5-methyl-1,3-dioxol-2-one (0.82 g, 4.21 mmol), and the mixture was stirred at rt overnight. To the reaction mixture was added water (30 mL), and the resulting mixture was extracted with ethyl acetate (20 mL×3). The combined organic layers were washed with saturated brine (50 mL), dried over anhydrous sodium sulfate and filtered. The filtrate was concentrated in vacuo to give the title compound as a white solid (1.70 g, 95%).

Step 2: (2S,3S)-(5-methyl-2-oxo-1,3-dioxol-4-yl) methyl 3-((2-(2-chloro-5H-pyrrolo[2,3-b]pyrazin-7-yl)-5-fluoro-6-(thiophen-2-yl)pyrimidin-4-yl) amino) bicyclo[2.2.2]octane-2-carboxylate To a solution of (2S,3S)-(5-methyl-2-oxo-1,3-dioxl-4-yl) methyl 3-((2-(2-chloro-5-trityl-5H-pyrrolo[2,3-b]pyrazin-7-yl)-5-fluoro-6-(thiophen-2-yl)pyrimidin-4-yl) amino)bicyclo[2.2.2]octane-2-carboxylate (1.70 g, 2.0 mmol) in dichloromethane (15 mL) were added Et₃SiH (2.00 mL, 9.60 mmol) and TFA (4.00 mL, 5.40 mmol), and the mixture was stirred at rt overnight. The reaction mixture was added into saturated aqueous sodium bicarbonate (50 mL). The resulting mixture was extracted with dichloromethane (60 mL×3). The combined organic layers were washed with saturated brine (30 mL), dried over anhydrous sodium sulfate, and filtered. The filtrate was concentrated in vacuo, and the residue was purified by silica gel column chromatography (PE/EtOAc(v/v)=4/1) to give the title compound as a white solid (300 mg, 25%).

MS (ESI, pos. ion) m/z: 611.2 [M+H]⁺;
HRMS (ESI, pos. ion) m/z: 597.2202, (C₂₄H₂₅ClFN₆O₅S)[M+H]⁺ theoretical value: 597.2215;
¹H NMR (600 MHz, CDCl₃) δ (ppm): 9.77 (s, 1H), 8.47 (d, J=2.8 Hz, 1H), 8.28 (s, 1H), 7.92 (d, J=3.5 Hz, 1H), 7.58 (d, J=5.0 Hz, 1H), 7.23-7.19 (m, 1H), 5.29 (d, J=6.0 Hz, 1H), 4.91 (d, J=13.9 Hz, 1H), 4.82 (t, J=5.8 Hz, 1H), 4.65 (s, 1H), 2.50 (d, J=6.1 Hz, 1H), 2.13 (s, 1H), 2.07 (s, 1H), 2.03 (s, 3H), 1.79-1.67 (m, 8H).

Example 47: 3-((2-(2-chloro-5H-pyrrolo[2,3-b]pyrazin-7-yl)-5-fluoro-6-(thiophen-2-yl)pyrimidin-4-yl)amino)-4-methyl-4-(pyridin-2-yl)pentanoic Acid

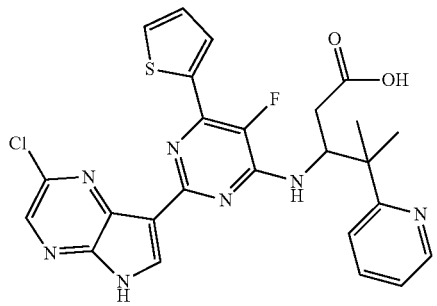 [SMILES: CC(C)(c1ccccn1)C(CC(=O)O)Nc1nc(-c2c[nH]c3ncc(Cl)nc23)nc(-c2cccs2)c1F]

Step 1: 2-methyl-2-(pyridin-2-yl)propanenitrile

To a solution of 2-fluoropyridine (10 g, 103 mmol) and isobutyronitrile (28 g, 412 mmol) in toluene (200 mL) was added potassium bis(trimethylsilyl)amide (160 mL, 1.0 mol/L). The mixture was stirred at 80° C. overnight. The reaction mixture was cooled to rt, and to the reaction mixture was added water (200 mL). The resulting mixture was extracted with ethyl acetate (100 mL×2). The combined organic layers were washed with saturated brine (150 mL), dried over anhydrous sodium sulfate and filtered. The filtrate was concentrated in vacuo and the residue was purified by silica gel column chromatography (PE/EtOAc (v/v)=15/1) to give the title compound as light yellow oil (6.50 g, 43%).

MS (ESI, pos. ion) m/z: 147.2 [M+H]$^+$.

Step 2: (E)-ethyl 3-amino-4-methyl-4-(pyridin-2-yl)pent-2-enoate

To a suspension of zinc powder (15.00 g, 220 mmol) in tetrahydrofuran (150 mL) was added methanesulfonic acid (1.70 g, 18 mmol), and the mixture was heated to reflux and stirred for 30 min under nitrogen protection. Then a solution of 2-methyl-2-(pyridin-2-yl)propanenitrile (6.5 g, 44 mmol) in tetrahydrofuran (50 mL) was added, and a solution of 2-bromoethyl acetate (22 g, 131 mmol) in tetrahydrofuran (50 mL) was added dropwise slowly. After the addition, the mixture was refuxed for 2 h. The reaction mixture was cooled to rt, and saturated aqueous sodium bicarbonate (200 mL) was added to quench the reaction. The resulting mixture was extracted with EtOAc (100 mL×3). The combined organic phases were washed with saturated brine (100 mL), dried over anhydrous sodium sulfate, filtered, and the filtrate was concentrated in vacuo. The residue was purified by silica gel chromatograph (PE/EtOAc (v/v)=15/1) to give the title compound as light yellow oil (7.0 g, 67%).

MS (ESI, pos. ion) m/z: 235.1 [M+H]$^+$.

Step 3: ethyl 3-amino-4-methyl-4-(pyridin-2-yl)pentanoate

To a mixed solvent of ethanol (300 mL) and glacial acetic acid (30 mL) was added (E)-ethyl 3-amino-4-methyl-4-(pyridin-2-yl)pent-2-enoate (7.0 g, 29.9 mmol), then sodium cyanoborohydride (2.25 g, 35.9 mmol) was added. The mixture was stirred at 60° C. overnight under nitrogen protection. The reaction mixture was concentrated in vacuo, and saturated aqueous sodium bicarbonate (300 mL) was added. The resulting mixture was extracted with ethyl acetate (70 mL×3). The combined organic layers were washed with saturated aqueous sodium chloride (70 mL), dried over anhydrous sodium sulfate and filtered. The filtrate was concentrated in vacuo and the residue was purified by silica gel column chromatography (PE/EtOAc (v/v)=2/1) to give the title compound as light yellow oil (7.0 g, 99%).

MS (ESI, pos.ion) m/z: 237.1[M+H]$^+$.

Step 4: ethyl 3-((2-chloro-5-fluoro-6-(thiophen-2-yl)pyrimidin-4-yl)amino)-4-methyl-4-(pyridin-2-yl)pentanoate To a solution of ethyl 3-amino-4-methyl-4-(pyridin-2-yl)pentanoate (2.50 g, 10.4 mmol) and 2,4-dichloro-5-fluoro-6-(thiophen-2-yl)pyrimidine (2.00 g, 8.03 mmol) in THF (20 mL) was added DIPEA (406 mg, 2.94 mmol). The resulting mixture was refluxed overnight. The reaction mixture was diluted with water (40 mL), and the resulting mixture was extracted with EtOAc (40 mL×3). The combined organic layers were washed with saturated brine (50 mL), dried over anhydrous Na$_2$SO$_4$, and filtered. The filtrate was concentrated in vacuo, and the residue was purified by silica gel column chromatography (PE/EA (v/v)=20/1) to give the title compound as a white solid (3.42 g, 94%).

MS (ESI, pos.ion) m/z: 449.3 [M+H]$^+$.

Step 5: ethyl 3-((2-bromo-5-fluoro-6-(thiophen-2-yl)pyrimidin-4-yl)amino)-4-methyl-4-(pyridin-2-yl)pentanoate To a solution of hydrobromic acid in acetic acid (40 mL, 240 mmol, 33%) was added ethyl 3-((2-chloro-5-fluoro-6-(thiophen-2-yl)pyrimidin-4-yl)amino)-4-methyl-4-(pyridin-2-yl) pentanoate (3.40 g, 7.57 mol), and the mixture was stirred at rt overnight. The reaction mixture was added into ice-water (20 mL), and the resulting mixture was extracted with DCM (20 mL×3). The combined organic layers were washed with saturated aqueous sodium bicarbonate (20 mL×3) and saturated brine (20 mL), dried over anhydrous Na$_2$SO$_4$, and filtered. The filtrate was concentrated in vacuo to give the title compound as a light yellow solid (3.30 g, 88%).

MS (ESI, pos. ion) m/z: 495.0 [M+H]$^+$.

Step 6: ethyl 3-((2-(2-chloro-5-trityl-5H-pyrrolo[2,3-b]pyrazin-7-yl)-5-fluoro-6-(thiophen-2-yl)pyrimidin-4-yl)amino)-4-methyl-4-(pyridin-2-yl)pentanoate To a mixed solvent of 1,4-dioxane (5 mL) and H$_2$O (0.5 mL) were added 2-chloro-7-(4,4,5,5-tetramethyl-1,3,2-dioxaborolan-2-yl)-5-trityl-5H-pyrrolo[2,3-b]pyrazine (330 mg, 0.44 mmol, 70%), K$_2$CO$_3$ (230 mg, 1.62 mmol), PdCl$_2$(dppf) (60 mg, 0.08 mmol) and ethyl 3-((2-bromo-5-fluoro-6-(thiophen-2-yl)pyrimidin-4-yl) amino)-4-methyl-4-(pyridin-2-yl)pentanoate (200 mg, 0.40 mmol). The air in the mixture was exchanged with nitrogen by bubbling for 10 min. The mixture in the sealed tub was stirred for 3 h at 115° C. The mixture was filtered to remove the solid impuries, and the solvent was removed. The residue was purified by silica gel column chromatography (PE/EtOAc (v/v)=10/1-5/1) to give the title compound as a white solid (220 mg, 67%).

Step 7: ethyl 3-((2-(2-chloro-5H-pyrrolo[2,3-b]pyrazin-7-yl)-5-fluoro-6-(thiophen-2-yl)pyrimidin-4-yl)amino)-4-methyl-4-(pyridin-2-yl)pentanoate To a solution of ethyl 3-((2-(2-chloro-5-trityl-5H-pyrrolo[2,3-b]pyrazin-7-yl)-5-fluoro-6-(thiophen-2-yl)pyrimidin-4-yl)amino)-4-methyl-4-(pyridin-2-yl)pentanoate (220 mg, 0.27 mmol) in DCM (10 mL) were added Et$_3$SiH (1 mL, 6.26 mmol) and TFA (1.0 mL, 13.46 mmol). The mixture was stirred at rt overnight. The reaction was stopped, and the reaction mixture was added into saturated aqueous sodium bicarbonate (30 mL). The resulting mixture was extracted with dichloromethane (30 mL×3). The combined organic layers were washed with saturated brine (20 mL), dried over anhydrous sodium sulfate, and filtered. The filtrate was concentrated in vacuo, and the residue was purified by silica gel column chromatography (DCM/MeOH (v/v)=10/1) to give the title compound as a white solid (120 mg, 77%).

MS (ESI, pos. ion) m/z: 566.3 [M+H]$^+$.

Step 8: 3-((2-(2-chloro-5H-pyrrolo[2,3-b]pyrazin-7-yl)-5-fluoro-6-(thiophen-2-yl)pyrimidin-4-yl)amino)-4-methyl-4-(pyridin-2-yl)pentanoic Acid To a solution of ethyl 3-((2-(2-chloro-5H-pyrrolo[2,3-b]pyrazin-7-yl)-5-fluoro-6-(thiophen-2-yl)pyrimidin-4-yl)amino)-4-methyl-4-(pyridin-2-yl)pentanoate (120 mg, 0.21 mmol) in a mixed solvent of ethanol (4 mL) and THF(4 mL)

was added a solution of NaOH (42 mg, 1.06 mmol) in water (2 mL). The mixture was stirred at rt for 2 h. The reaction mixture was quenched with water (10 mL), and the mixture was acidified with hydrochloric acid (1 M) to pH about 6. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by column chromatography (DCM/MeOH (v/v)=10/1-5/1) to give the title compound as a white solid (108 mg, 94%).

MS (ESI, pos. ion) m/z: 538.3 [M+H]$^+$;
HRMS (ESI, pos. ion) m/z: 538.1251, (C$_{25}$H$_{22}$ClN$_7$O$_2$S) [M+H]$^+$ theoretical value: 538.1228;
$^1$H NMR (600 MHz, DMSO-d$_6$) δ (ppm): 12.84 (d, J=2.3 Hz, 1H), 11.94 (s, 1H), 8.57 (dd, J=4.4, 1.8 Hz, 2H), 8.41 (s, 1H), 7.90 (d, J=3.4 Hz, 1H), 7.86 (d, J=4.9 Hz, 1H), 7.81 (s, 2H), 7.63 (d, J=8.7 Hz, 1H), 7.29 (dd, J=9.4, 4.7 Hz, 2H), 5.39 (t, J=9.0 Hz, 1H), 2.57-2.53 (m, 1H), 2.23-2.15 (m, 1H), 1.50 (s, 3H), 1.45 (s, 3H).

Example 48: 3-((2-(2-chloro-5H-pyrrolo[2,3-b]pyrazin-7-yl)-5-fluoro-6-(thiophen-2-yl)pyrimidin-4-yl)amino)-4-methyl-4-(thiazol-2-yl)pentanoic Acid

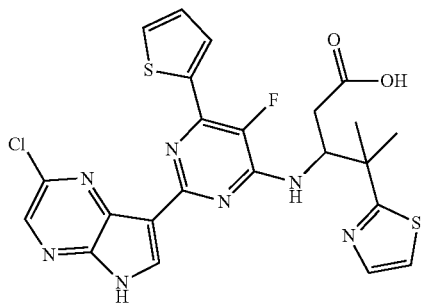 [SMILES: CC(C)(c1nccs1)C(CC(=O)O)Nc1nc(-c2c[nH]c3ncc(Cl)nc23)nc(-c2cccs2)c1F]

Step 1: thiazole-2-carbaldehyde

To a reaction flask were added a solution of n-butyl lithium in cyclohexane (60 mL, 150 mmol, 2.5 mol/L) and anhydrous ethyl ether (100 mL). The mixture was stirred at −78° C. under nitrogen protection, then 2-bromothiazole (20 g, 122 mmol) was added dropwise slowly into the mixture for 1 h. The mixture was heated to 70° C. and stirred for 30 min, then DMF (14.26 g, 195 mmol) was added for 1 h. The mixture was cooled to −40° C. and stirred for 1 h. The reaction mixture was warmed to 0° C. and to the reaction mixture was added HCl (4 M) (100 mL), and the resulting mixture was partitioned. The aqueous layer was adjusted with saturated aqueous potassium carbonate to pH about 7 to 8. The mixture was extracted with ethyl ether (100 mL×3). The combined organic layers were washed with saturated brine (100 mL), dried over anhydrous sodium sulfate and filtered. The filtrate was concentrated in vacuo to give the title compound as brownish red oil (7.0 g, 51%).

MS (ESI, pos. ion) m/z: 114.1 [M+H]$^+$.

Step 2: thiazol-2-ylmethanol

To a 0° C. solution of thiazole-2-carbaldehyde (7.00 g, 61.9 mmol) in anhydrous methanol (140 mL) was added sodium borohydride (4.70 g, 124 mmol), and the mixture was warmed to rt and stirred overnight. To the reaction mixture was added water (200 mL), and the resulting mixture was extracted with ethyl acetate (100 mL×3). The combined organic layers were washed with saturated brine (100 mL), dried over anhydrous sodium sulfate and filtered. The filtrate was concentrated to give the title compound as brown oil (5.80 g, 81%).

MS (ESI, pos. ion) m/z: 116.2 [M+H]$^+$.

Step 3: 2-(chloromethyl)thiazole

To a 0° C. solution of thiazol-2-ylmethanol (5.80 g, 50.4 mmol) in DCM (100 mL) was added slowly thionyl chloride (12.00 g, 101 mmol). After the addition, the mixture was heated to reflux and stirred for 3 h. The reaction mixture was cooled to rt and concentrated in vacuo to give the title compound as brown oil (6.70 g, 100%), which was used in the next step without further purification.

Step 4: 2-(thiazol-2-yl)acetonitrile

To a solution of TBAF in tetrahydrofuran (150 mL, 150 mmol, 1.0 mol/L) was added 2-(chloromethyl)thiazole (5.80 g, 50.4 mmol) and trimethylsilyl cyanide (10.00 g, 100 mmol). The mixture was stirred at rt overnight. The reaction mixture was concentrated in vacuo, and to the residue was added into saturated aqueous sodium bicarbonate (100 mL), and the resulting mixture was extracted with dichloromethane (50 mL×3). The combined organic layers were washed with saturated brine (100 mL), dried over anhydrous sodium sulfate, and filtered. The filtrate was concentrated in vacuo to remove the solvent, and the residue was purified by silica gel column chromatography (DCM/MeOH (v/v)=20/1) to give the title compound as brown oil (2.4 g, 39%).

MS (ESI, pos. ion) m/z: 125.2 [M+H]$^+$.

Step 5: 2-methyl-2-(thiazol-2-yl)propanenitrile

To a reaction flask were added 2-(thiazol-2-yl)acetonitrile (2.40 g, 19 mmol) and tetrahydrofuran (60 mL). The mixture was cooled to 0° C., and potassium tert-butoxide (6.50 g, 58 mmol) and 18-crown ether-6 (1.0 g, 3.8 mmol) were added into the mixture, then iodomethane (4.80 mL, 77 mmol) was added dropwise slowly. After the addition, the mixture was stirred at rt overnight. After the reaction was completed, the reaction mixture was poured into saturated aqeuous ammonium chloride (100 mL), and the resulting mixture was extracted with EtOAc (50 mL×3). The combined organic phases were washed with saturated brine (50 mL), dried over anhydrous sodium sulfate, filtered, and the filtrate was concentrated in vacuo. The residue was purified by silica gel chromatograph (PE/EtOAc (v/v)=8/1) to give the title compound as brown oil (2.0 g, 68%).

MS (ESI, pos. ion) m/z: 153.2 [M+H]$^+$.

Step 6: (E)-ethyl 3-amino-4-methyl-4-(thiazol-2-yl)pent-2-enoate

To a reaction flask were added zinc powder (3.65 g, 55.8 mmol) and tetrahydrofuran (30 mL), then methanesulfonic acid (0.43 g, 4.6 mmol) was added into the mixture under nitrogen protection, and the mixture was heated to reflux and stirred for 30 min. Then a solution of 2-methyl-2-(thiazol-2-yl)propanenitrile (1.70 g, 11.2 mmol) in tetrahydrofuran (50 mL) was added, and then a solution of ethyl 2-bromoacetate (5.60 g, 33.5 mmol) in tetrahydrofuran (10 mL) was added dropwise slowly. After the addition, the mixture was refluxed for 2 h. The reaction mixture was cooled to rt, and saturated aqueous sodium bicarbonate (80 mL) was added to quench the reaction, and the resulting mixture was extracted with EtOAc (50 mL×3). The combined organic phases were washed with saturated brine (50 mL), dried over anhydrous $Na_2SO_4$, filtered, and the filtrate was concentrated in vacuo. The residue was purified by silica gel chromatograph (PE/EtOAc (v/v)=15/1) to give the title compound as light yellow oil (1.60 g, 59%).

MS (ESI, pos. ion) m/z: 241.2 $[M+H]^+$.

Step 7: ethyl 3-amino-4-methyl-4-(thiazol-2-yl)pentanoate

To a mixed solvent of methanol (70 mL) and glacial acetic acid (10 mL) was added (E)-ethyl 3-amino-4-methyl-4-(thiazol-2-yl)pent-2-enoate (1.60 g, 6.66 mmol), then sodium cyanoborohydride (1.05 g, 16.7 mmol) was added. The mixture was stirred at rt overnight under nitrogen protection. The reaction mixture was concentrated in vacuo, and to the residue was added saturated aqueous sodium bicarbonate (100 mL), and the resulting mixture was extracted with ethyl acetate (20 mL×3). The combined organic layers were washed with saturated aqueous sodium chloride (50 mL), dried over anhydrous sodium sulfate and filtered. The filtrate was concentrated in vacuo and the residue was purified by silica gel column chromatography (PE/EtOAc (v/v)=2/1) to give the title compound as light yellow oil (1.56 g, 96%).

MS (ESI, pos. ion) m/z: 243.1 [M+H]+.

Step 8: ethyl 3-((2-chloro-5-fluoro-6-(thiophen-2-yl)pyrimidin-4-yl)amino)-4-methyl-4-(thiazol-2-yl)pentanoate To a solution of ethyl 3-amino-4-methyl-4-(thiazol-2-yl)pentanoate (1.56 g, 6.3 mmol) and 2,4-dichloro-5-fluoro-6-(thiophen-2-yl)pyrimidine (1.20 g, 4.80 mmol) in THF (20 mL) was added DIPEA (1.20 g, 9.6 mmol). The resulting mixture was refluxed overnight. To the reaction mixture was added water (40 mL), and the resulting mixture was extracted with ethyl acetate (20 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=20/1) to give the title compound as a white solid (1.82 g, 83%).

MS (ESI, pos.ion) m/z: 455.2 $[M+H]^+$.

Step 9: ethyl 3-((2-bromo-5-fluoro-6-(thiophen-2-yl)pyrimidin-4-yl)amino)-4-methyl-4-(thiazol-2-yl)pentanoate To a reaction flask were added ethyl 3-((2-chloro-5-fluoro-6-(thiophen-2-yl) pyrimidin-4-yl)amino)-4-methyl-4-(thiazol-2-yl)pentanoate (1.82 g, 4.00 mol) and a solution of hydrobromic acid in acetic acid (20 mL, 109 mmol, 33%). The reaction mixture was stirred at rt for 1 h, then added into ice-water (30 mL), and the resulting mixture was extracted with DCM (20 mL×3). The combined organic layers were washed with saturated aqueous sodium bicarbonate (20 mL×3) and saturated brine (20 mL), dried over anhydrous $Na_2SO_4$, and filtered. The filtrate was concentrated in vacuo to give the title compound as a light yellow solid (1.89 g, 94%).

MS (ESI, pos. ion) m/z:498.9 $[M+H]^+$.

Step 10: ethyl 3-((2-(2-chloro-5-trityl-5H-pyrrolo[2,3-b]pyrazin-7-yl)-5-fluoro-6-(thiophen-2-yl)pyrimidin-4-yl)amino)-4-methyl-4-(thiazol-2-yl)pentanoate To a mixed solvent of 1,4-dioxane (5 mL) and $H_2O$ (0.5 mL) were added 2-chloro-7-(4,4,5,5-tetramethyl-1,3,2-dioxaborolan-2-yl)-5-trityl-5H-pyrrolo[2,3-b]pyrazine (350 mg, 0.44 mmol, 65%), $K_2CO_3$ (230 mg, 1.62 mmol), $PdCl_2$(dppf) (60 mg, 0.08 mmol) and ethyl 3-((2-bromo-5-fluoro-6-(thiophen-2-yl)pyrimidin-4-yl) amino)-4-methyl-4-(thiazol-2-yl)pentanoate (200 mg, 0.40 mmol). The air in the mixture was exchanged with nitrogen by bubbling for 10 min. The mixture in the sealed tub was stirred for 3 h at 115° C. The mixture was filtered to remove the solid impuries, and the solvent was removed. The residue was purified by silica gel column chromatography (PE/EtOAc (v/v)=10/1-5/1) to give the title compound as a white solid (250 mg, 76%).

Step 11: ethyl 3-((2-(2-chloro-5H-pyrrolo[2,3-b]pyrazin-7-yl)-5-fluoro-6-(thiophen-2-yl)pyrimidin-4-yl)amino)-4-methyl-4-(thiazol-2-yl)pentanoate To a solution of ethyl 3-((2-(2-chloro-5-trityl-5H-pyrrolo[2,3-b]pyrazin-7-yl)-5-fluoro-6-(thiophen-2-yl)pyrimidin-4-yl)amino)-4-methyl-4-(thiazol-2-yl)pentanoate (250 mg, 0.30 mmol) in DCM (10 mL) were added $Et_3SiH$ (1 mL, 2.52 mmol) and TFA (1.0 mL, 2.70 mmol). The mixture was stirred at rt overnight. The reaction was stopped, and the reaction mixture was added into saturated aqueous sodium bicarbonate (30 mL). The resulting mixture was extracted with dichloromethane (30 mL×3). The combined organic layers were washed with saturated brine (60 mL), dried over anhydrous sodium sulfate, and filtered. The filtrate was concentrated in vacuo, and the residue was purified by silica gel column chromatography (DCM/MeOH (v/v)=10/1) to give the title compound as a white solid (100 mg, 56%).

MS (ESI, pos. ion) m/z: 572.0 $[M+H]^+$.

Step 12: 3-((2-(2-chloro-5H-pyrrolo[2,3-b]pyrazin-7-yl)-5-fluoro-6-(thiophen-2-yl)pyrimidin-4-yl)amino)-4-methyl-4-(thiazol-2-yl)pentanoic Acid To a solution of ethyl 3-((2-(2-chloro-5H-pyrrolo[2,3-b]pyrazin-7-yl)-5-fluoro-6-(thiophen-2-yl)pyrimidin-4-yl)amino)-4-methyl-4-(thiazol-2-yl)pentanoate (100 mg, 0.17 mmol) in a mixed solvent of ethanol (4 mL) and THF (4 mL) was added a solution of NaOH (34 mg, 0.87 mmol) in water (2 mL) in portions. The mixture was stirred at rt for 2 h. To the reaction mixture was added water (20 mL), and the mixture was acidified with hydrochloric acid (1 M) to pH about 6. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (90 mg, 94%).

MS (ESI, pos. ion) m/z: 544.0 $[M+H]^+$;
HRMS (ESI, pos. ion) m/z: 544.0788, ($C_{23}H_{20}ClN_7O_2S_2$) $[M+H]^+$ theoretical value: 544.0792;
$^1$H NMR (600 MHz, DMSO-$d_6$) δ (ppm): 12.80 (s, 1H), 8.51 (d, J=2.9 Hz, 1H), 8.39 (s, 1H), 7.91 (d, J=3.1 Hz, 1H), 7.87 (d, J=4.9 Hz, 1H), 7.77 (d, J=3.2 Hz, 1H), 7.65 (d, J=3.2 Hz, 1H), 7.56 (d, J=8.8 Hz, 1H), 7.34-7.27 (m, 1H), 5.30 (t, J=8.8 Hz, 1H), 2.60 (dd, J=16.0, 10.9 Hz, 1H), 2.47-2.40 (m, 1H), 1.55 (d, J=14.1 Hz, 6H).

Example 49: (2S,3S)-3-((2-(2-chloro-5H-pyrrolo[2,3-b]pyrazin-7-yl)-5-fluoro-6-(thiazol-2-yl)pyrimidin-4-yl)amino)bicyclo[2.2.2]octane-2-carboxylic Acid

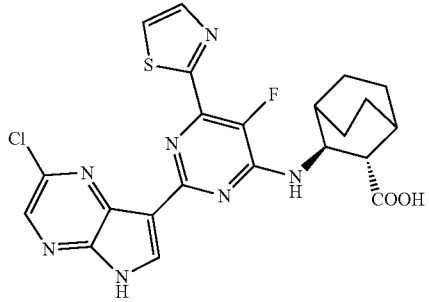 [SMILES: O=C(O)[C@H]1C2CCC(CC2)[C@@H]1Nc1nc(-c2c[nH]c3ncc(Cl)nc23)nc(-c2nccs2)c1F]

Step 1: (2S,3S)-ethyl 3-aminobicyclo[2.2.2]octane-2-carboxylate hydrochloride

The title compound was prepared by the synthetic method disclosed in patent application WO 2015073491.

Step 2: (2S,3S)-ethyl 3-((2,6-dichloro-5-fluoropyrimidin-4-yl)amino)bicyclo[2.2.2]octane-2-carboxylate To DMF (8 mL) were added 2,4,6-trichloro-5-fluoropyrimidine (1.54 g, 7.65 mmol) and (2S,3S)-ethyl 3-aminobicyclo[2.2.2]octane-2-carboxylate hydrochloride (1.51 g, 7.65 mmol), then K$_2$CO$_3$ (2.11 g, 15.30 mmol) was added into the mixture. The mixture was stirred at rt overnight. To the reaction mixture was added water (30 mL), and the resulting mixture was extracted with ethyl acetate (30 mL×3). The combined organic layers were washed with saturated brine (80 mL×2), dried over anhydrous sodium sulfate and filtered. The filtrate was concentrated in vacuo and the residue was purified by silica gel column chromatography (PE/EtOAc (v/v)=5/1) to give the title compound as a light yellow solid (0.69 g, 25%).

MS (ESI, pos. ion) m/z: 362.1 [M+H]$^+$;

$^1$H NMR (400 MHz, CDCl$_3$) δ (ppm): 5.38 (d, J=4.2 Hz, 1H), 4.53 (t, J=5.0 Hz, 1H), 4.22 (q, J=7.1 Hz, 2H), 2.38 (d, J=5.8 Hz, 1H), 2.04 (d, J=2.2 Hz, 1H), 1.89 (s, 1H), 1.80 (m, 1H), 1.61 (m, 4H), 1.47 (m, 1H), 1.28 (t, J=7.1 Hz, 4H).

Step 3: (2S,3S)-ethyl 3-((2-chloro-5-fluoro-6-(trimethylstannyl)pyrimidin-4-yl)amino)bicyclo[2.2.2]octane-2-carboxylate A suspension of (2S,3S)-ethyl 3-((2,6-dichloro-5-fluoropyrimidin-4-yl)amino) bicyclo[2.2.2]octane-2-carboxylate (1.51 g, 4.17 mmol), hexamethylditin (2.05 g, 6.26 mmol), triphenylarsine (0.14 g, 0.44 mmol), and bis(triphenylphosphine)palladium(II) chloride (0.30 g, 0.42 mmol) in 1,4-dioxane (20 mL) was stirred at 85° C. overnight under nitrogen protection. The reaction mixture was filtered through a celite pad, and the filter cake was washed with ethyl acetate (10 mL). The filtrate was concentrated in vacuo to give the title compound as black oil (2.03 g), which was used directly in the next step without further purification.

MS (ESI, pos. ion) m/z: 492.2 [M+H]$^+$.

Step 4: (2S,3S)-ethyl 3-((2-chloro-5-fluoro-6-(thiazol-2-yl)pyrimidin-4-yl)amino)bicyclo[2.2.2]octane-2-carboxylate A suspension of (2S,3S)-ethyl 3-((2-chloro-5-fluoro-6-(trimethylstannyl)pyrimidin-4-yl)amino)bicyclo[2.2.2]octane-2-carboxylate (1.01 g, 2.06 mmol), 2-bromothiazole (0.28 mL, 3.10 mmol), bis(triphenylphosphine)palladium (II) chloride (271 mg, 6.20 mmol), cuprous iodide (79 mg, 0.41 mmol), lithium chloride (271 mg, 6.20 mmol) in 1,4-dioxane (10 mL) was stirred at 90° C. for 6 h under nitrogen protection. The reaction mixture was filtered through a celite pad. The filter cake was washed with ethyl acetate (10 mL×2). The combined filtrates was concentrated in vacuo, and the residue was purified by silica gel column chromatography (PE/EtOAc (v/v)=5/1) to give the title compound as a light yellow solid (362 mg, 43%).

MS (ESI, pos. ion) m/z: 411.2 [M+H]$^+$;

$^1$H NMR (400 MHz, CDCl$_3$) δ (ppm): 8.08 (d, J=3.1 Hz, 1H), 7.59 (d, J=3.2 Hz, 1H), 4.57 (t, J=5.6 Hz, 1H), 4.24 (q, J=7.1 Hz, 2H), 2.43 (d, J=5.9 Hz, 1H), 1.94 (d, J=2.2 Hz, 1H), 1.83 (m, 1H), 1.74-1.68 (m, 4H), 1.60 (m, 2H), 1.50-1.44 (m, 1H), 1.29 (m, 3H).

Step 5: (2S,3S)-ethyl 3-((2-bromo-5-fluoro-6-(thiazol-2-yl)pyrimidin-4-yl)amino)bicyclo[2.2.2]octane-2-carboxylate To a solution of hydrobromic acid in acetic acid (33%, 10 mL) was added (2S,3S)-ethyl 3-((2-chloro-5-fluoro-6-(thiazol-2-yl)pyrimidin-4-yl)amino)bicyclo[2.2.2]octane-2-carboxylate (0.14 g, 0.34 mmol), and the mixture was stirred at rt for 5 h. The reaction mixture was added into ice-water (50 mL), and the resulting mixture was extracted with EtOAc (25 mL×3). The combined organic layers were washed with saturated aqueous sodium bicarbonate (60 mL), dried over anhydrous Na$_2$SO$_4$, and filtered. The filtrate was concentrated in vacuo to give the title compound as light yellow oil (0.15 g, 97%).

MS (ESI, pos. ion) m/z: 455.0 [M+H]$^+$.

Step 6: (2S,3S)-ethyl 3-((2-(2-chloro-5-trityl-5H-pyrrolo[2,3-b]pyrazin-7-yl)-5-fluoro-6-(thiazol-2-yl) pyrimidin-4-yl) amino)bicyclo[2.2.2]octane-2-carboxylate To a mixed solvent of 1,4-dioxane (10 mL) and H$_2$O (0.5 mL) were added 2-chloro-7-(4,4,5,5-tetramethyl-1,3,2-dioxaborolan-2-yl)-5-trityl-5H-pyrrolo[2,3-b]pyrazine (265 mg, 0.33 mmol, 65%), K$_2$CO$_3$(138 mg, 1.00 mmol), PdCl$_2$ (dppf) (74 mg, 0.10 mmol) and (2S,3S)-ethyl 3-((2-bromo-5-fluoro-6-(thiazol-2-yl)pyrimidin-4-yl) amino)bicyclo [2.2.2]octane-2-carboxylate (150 mg, 0.33 mmol). The air in the mixture was exchanged with nitrogen by bubbling for 10 min. Then the mixture was stirred for 3 h at 115° C. by microwave heating. The mixture was filtered to remove the solid impuries, and the filtrate was concentrated to remove the solvent. The residue was purified by silica gel column chromatography (PE/EtOAc (v/v)=10/1) to give the title compound as a yellow solid (120 mg, 47%).

MS (ESI, pos. ion) m/z: 770.0 [M+H]$^+$;

$^1$H NMR (400 MHz, CDCl$_3$) δ (ppm): 8.44 (s, 1H), 8.08 (d, J=3.2 Hz, 1H), 7.96 (s, 1H), 7.59 (d, J=3.2 Hz, 1H), 7.32 (m, 9H), 7.22 (m, 6H), 4.64 (s, 1H), 4.17-4.11 (m, 2H), 2.38 (d, J=7.4 Hz, 1H), 1.95 (s, 1H), 1.71 (d, J=7.7 Hz, 4H), 1.53 (m, 4H), 1.17 (t, J=7.1 Hz, 3H).

Step 7: (2S,3S)-ethyl 3-((2-(2-chloro-5H-pyrrolo[2,3-b]pyrazin-7-yl)-5-fluoro-6-(thiazol-2-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-5-fluoro-6-(thiazol-2-yl)pyrimidin-4-yl) amino)bicyclo[2.2.2]octane-2-carboxylate (120 mg, 0.16 mmol) in dichloromethane (6 mL) were added Et₃SiH (0.30 mL, 1.90 mmol) and TFA (0.14 mL, 1.90 mmol), and the mixture was stirred at rt overnight. The reaction mixture was added into saturated aqueous sodium bicarbonate (30 mL). The resulting mixture was extracted with dichloromethane (30 mL×3). The combined organic layers were washed with saturated brine (80 mL), dried over anhydrous sodium sulfate, and filtered. The filtrate was concentrated in vacuo to remove the solvent, and the residue was purified by silica gel column chromatography (PE/EtOAc (v/v)=2/1) to give the title compound as light yellow oil (61 mg, 74%).

MS (ESI, pos. ion) m/z: 528.1 [M+H]⁺.

Step 8: (2S,3S)-3-((2-(2-chloro-5H-pyrrolo[2,3-b]pyrazin-7-yl)-5-fluoro-6-(thiazol-2-yl)pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-5-fluoro-6-(thiazol-2-yl)pyrimidin-4-yl)amino)bicyclo[2.2.2]octane-2-carboxylate (60 mg, 0.11 mmol) in THF/MeOH/H₂O (v/v/v=2 mL/2 mL/2 mL) was added NaOH (46 mg, 1.15 mmol) in portions. The mixture was stirred at rt overnight. To the reaction mixture was added saturated brine (20 mL), and the mixture was acidified with hydrochloric acid (1 M) to pH about 6. The resulting mixture was extracted with ethyl acetate (20 mL×3). The combined organic layers were washed with saturated brine (50 mL), dried over anhydrous sodium sulfate, and filtered. The filtrate was concentrated in vacuo to remove the solvent, and the residue was purified by preparative thin-layer chromatography (DCM/MeOH (v/v)=20/1) to give the title compound as a light yellow solid (25 mg, 44%).

MS (ESI, pos. ion) m/z: 500.2 [M+H]⁺;
HRMS (ESI, pos. ion) m/z: 500.1078, (C₂₂H₂₀ClFN₇O₂S)[M+H]⁺ theoretical value: 500.1072;
¹H NMR (400 MHz, DMSO-d₆) δ (ppm): 12.80 (s, 1H), 8.53 (s, 1H), 8.38 (s, 1H), 8.12 (d, J=2.7 Hz, 1H), 8.02 (s, 1H), 7.84 (d, J=5.6 Hz, 1H), 4.69 (s, 1H), 2.87 (d, J=6.4 Hz, 1H), 2.09 (s, 1H), 2.00 (m, 2H), 1.75 (m, 2H), 1.57-1.42 (m, 4H).

Example 50: (2S,3S)-3-((2-(2-chloro-5H-pyrrolo[2,3-b]pyrazin-7-yl)-6-(thiophen-3-yl)pyrimidin-4-yl)amino)bicyclo[2.2.2]octane-2-carboxylic Acid

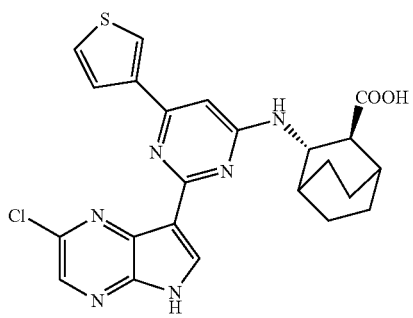 [SMILES: O=C(O)[C@H]1C2CCC(CC2)[C@@H]1Nc1cc(-c2ccsc2)nc(-c2c[nH]c3ncc(Cl)nc23)n1]

Step 1: (2S,3S)-ethyl 3-aminobicyclo[2.2.2]octane-2-carboxylate hydrochloride The title compound was prepared by the synthetic method disclosed in patent application WO 2015073491.

Step 2: 2,4-dichloro-6-(thiophen-3-yl)pyrimidine

To a suspension of thiophen-3-ylboronic acid (100 mg, 0.78 mmol), tetrakis(triphenylphosphine)palladium (90 mg, 0.08 mmol), 2,4,6-trichloropyrimidine (144 mg, 0.79 mmol) in acetonitrile (4 mL) was added aqueous potassium carbonate solution (0.4 M, 4 mL, 1.60 mmol). The resulting mixture was heated to 90° C. and stirred for 2 h. To the reaction mixture was added water (10 mL), and the resulting mixture was extracted with ethyl acetate (10 mL×3). The combined organic layers were washed with saturated brine (20 mL), dried over anhydrous sodium sulfate and filtered. The filtrate was concentrated in vacuo and the residue was purified by silica gel column chromatography (PE) to give the title compound as a white solid (82 mg, 45%).

MS (ESI, pos. ion) m/z: 231.1[M+H]⁺;
¹H NMR (400 MHz, CDCl₃) δ (ppm): 8.27 (dd, J=3.0, 1.2 Hz, 1H), 7.67 (dd, J=5.1, 1.2 Hz, 1H), 7.52 (s, 1H), 7.48 (dd, J=5.1, 3.0 Hz, 1H).

Step 3: (2S,3S)-ethyl 3-((2-chloro-6-(thiophen-3-yl)pyrimidin-4-yl)amino)bicyclo[2.2.2]octane-2-carboxylate To a solution of ethyl 3-aminobicyclo[2.2.2]octane-2-carboxylate hydrochloride (101 mg, 0.43 mmol) and 2,4-dichloro-6-(thiophen-3-yl)pyrimidine (82 mg, 0.35 mmol) in DMF (6 mL) was added potassium carbonate (147 mg, 1.06 mmol), and the mixture was stirred at 60° C. overnight. To the reaction mixture was added water (20 mL), and the resulting mixture was extracted with ethyl acetate (20 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as light yellow oil (100 mg, 72%).

MS (ESI, pos.ion) 392.5 [M+H]⁺;
¹H NMR (400 MHz, CDCl₃) δ (ppm): 8.11 (d, J=2.0 Hz, 1H), 7.60 (d, J=4.8 Hz, 1H), 7.40 (dd, J=5.1, 3.1 Hz, 1H), 6.71 (s, 1H), 5.46 (s, 1H), 4.32 (s, 1H), 4.26-4.16 (m, 2H), 2.37 (d, J=4.4 Hz, 1H), 2.10 (s, 1H), 1.90-1.84 (m, 1H), 1.80-1.61 (m, 8H).

Step 4: (2S,3S)-ethyl 3-((2-bromo-6-(thiophen-3-yl)pyrimidin-4-yl)amino)bicyclo[2.2.2]octane-2-carboxylate To a solution of hydrobromic acid in acetic acid (2 mL, 33%) was added (2S,3S)-ethyl 3-((2-chloro-6-(thiophen-3-yl)pyrimidin-4-yl)amino)bicyclo[2.2.2]octane-2-carboxylate (82 mg, 0.21 mmol), and the mixture was stirred at rt for 1 h. The reaction mixture was added into ice-water (10 mL), and the resulting mixture was extracted with EtOAc (10 mL×3). The combined organic layers were washed with saturated brine (20 mL), dried over anhydrous Na₂SO₄, and filtered. The filtrate was concentrated in vacuo to give the title compound as a brown solid (58 mg, 64%).

MS (ESI, pos.ion) m/z: 436.4 [M+H]⁺.

Step 5: (2S,3S)-ethyl 3-((2-(2-chloro-5-trityl-5H-pyrrolo[2,3-b]pyrazin-7-yl)-6-(thiophen-3-yl)pyrimidin-4-yl)amino)bicyclo[2.2.2]octane-2-carboxylate To a mixed solvent of 1,4-dioxane (8 mL) and H$_2$O (0.5 mL) were added 2-chloro-7-(4,4,5,5-tetramethyl-1,3,2-dioxaborolan-2-yl)-5-trityl-5H-pyrrolo[2,3-b]pyrazine (167 mg, 0.19 mmol, 60%), K$_2$CO$_3$(61 mg, 0.44 mmol), Pd(dppf)Cl$_2$ (24 mg, 0.03 mmol) and (2S,3S)-ethyl 3-((2-bromo-6-(thiophen-3-yl)pyrimidin-4-yl)amino)bicyclo[2.2.2]octane-2-carboxylate (58 mg, 0.15 mmol). The air in the mixture was exchanged with nitrogen by bubbling for 10 min. The mixture in the sealed tub was stirred for 2 h at 110° C. by microwave heating. The mixture was filtered to remove the solid impurity, and the filtrate was concentrated to remove the solvent. The residue was purified by silica gel column chromatography (PE/EtOAc (v/v)=2/1) to give the title compound as light yellow oil (63 mg, 57%).

$^1$H NMR (400 MHz, CDCl$_3$) δ (ppm): 8.56 (s, 1H), 8.07 (d, J=2.0 Hz, 1H), 7.95 (s, 1H), 7.65 (d, J=5.0 Hz, 1H), 7.40 (dd, J=5.0, 3.1 Hz, 1H), 7.34-7.29 (m, 9H), 7.23 (dd, J=6.5, 3.1 Hz, 6H), 6.65 (s, 1H), 5.89 (s, 1H), 4.34 (s, 1H), 4.16 (dd, J=13.4, 6.3 Hz, 2H), 2.45 (s, 1H), 1.94 (s, 1H), 1.56 (m, 9H), 1.22 (t, J=7.1 Hz, 3H).

Step 6: (2S,3S)-ethyl 3-((2-(2-chloro-5H-pyrrolo[2,3-b]pyrazin-7-yl)-6-(thiophen-3-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-6-(thiophen-3-yl)pyrimidin-4-yl)amino)bicyclo[2.2.2]octane-2-carboxylate (63 mg, 0.08 mmol) in dichloromethane (5 mL) were added Et$_3$SiH (0.14 mL, 0.84 mmol) and TFA (0.06 mL, 0.84 mmol), and the mixture was stirred at rt overnight. The reaction mixture was added into saturated aqueous sodium bicarbonate (20 mL). The resulting mixture was extracted with dichloromethane (20 mL×3). The combined organic layers were washed with saturated brine (20 mL), dried over anhydrous sodium sulfate, and filtered. The filtrate was concentrated in vacuo to give the title compound as a yellow solid (42.7 mg, 100%).

MS (ESI, pos. ion) m/z: 509.1 [M+H]$^+$.

Step 7: (2R,3R)-3 (2-chloro-5H-pyrrolo[2,3-b]pyrazin-7-yl)-6-(thiophen-3-yl)pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-6-(thiophen-3-yl)pyrimidin-4-yl)amino)bicyclo[2.2.2]octane-2-carboxylate (42 mg, 0.10 mmol) in THF/MeOH/H$_2$O (v/v/v=5 mL/5 mL/5 mL) was added a solution of NaOH (33 mg, 0.83 mmol) in water (1 mL), and the mixture was stirred at rt overnight. To the reaction mixture was added saturated brine (10 mL), and the mixture was acidified with hydrochloric acid (1 M) to pH about 6. The resulting mixture was extracted with 2-methyltetrahydrofuran (15 mL×3). The combined organic layers were washed with saturated brine (50 mL), dried over anhydrous sodium sulfate, and filtered. The filtrate was concentrated in vacuo to remove the solvent, and the residue was purified by preparative thin-layer chromatography (DCM/MeOH (v/v)=15/1) to give the title compound as a light yellow solid (23 mg, 58%).

MS (ESI, pos. ion) m/z: 481.1 [M+H]$^+$;
HRMS (ESI, pos. ion) m/z: 481.1206, (C$_{23}$H$_{22}$ClN$_6$O$_2$S) [M+H]$^+$ theoretical value: 481.1213;

$^1$H NMR (400 MHz, DMSO-d$_6$) δ (ppm): 8.64 (s, 1H), 8.36 (s, 1H), 8.27 (s, 1H), 7.70-7.66 (m, 1H), 7.48 (s, 1H), 6.70 (s, 1H), 4.57 (s, 1H), 2.04-1.51 (m, 10H).

Example 51: (2S,3S)-3-((2-(3-chloro-5H-pyrrolo[2,3-b]pyrazin-7-yl)-5-fluoro-6-(furan-2-yl)pyrimidin-4-yl)amino)bicyclo[2.2.2]octane-2-carboxylic Acid

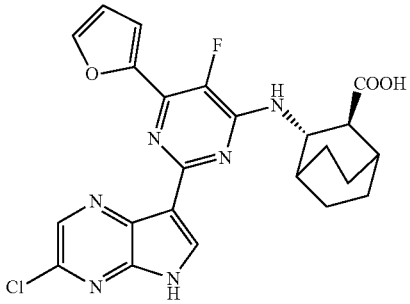 [SMILES: O=C(O)[C@H]1C2CCC(CC2)[C@@H]1Nc1nc(-c2c[nH]c3nc(Cl)cnc23)nc(-c2ccco2)c1F]

Step 1: (2S,3S)-ethyl 3-((2-chloro-5-fluoro-6-(furan-2-yl)pyrimidin-4-yl)amino)bicyclo[2.2.2]octane-2-carboxylate A suspension of (2S,3S)-ethyl 3-((2,6-dichloro-5-fluoropyrimidin-4-yl) amino)bicyclo[2.2.2]octane-2-carboxylate (1.00 g, 2.76 mmol), furan-2-ylboronic acid (0.29 g, 2.62 mmol), Pd(dppf)Cl$_2$ (450 mg, 0.55 mmol), potassium acetate (0.82 g, 8.41 mmol), lithium chloride (271 mg, 6.20 mmol) in a mixed solvent of 1,4-dioxane (1 mL) and water (1 mL) was refluxed for 24 h under nitrogen protection. The reaction mixture was filtered through a celite pad, and the filter cake was washed with ethyl acetate (10 mL). The filtrate was concentrated in vacuo and the residue was purified by silica gel column chromatography (PE/EA (v/v)=20/1) to give the title compound as a light yellow solid (250 mg, 23%).

$^1$H NMR (400 MHz, CDCl$_3$) δ (ppm): 7.66 (s, 1H), 7.19-7.13 (m, 1H), 6.59 (dd, J=3.3, 1.6 Hz, 1H), 5.35 (d, J=3.9 Hz, 1H), 4.54 (s, 1H), 4.24 (q, J=7.2 Hz, 2H), 2.41 (d, J=5.8 Hz, 1H), 1.91 (s, 1H), 1.84 (t, J=11.7 Hz, 1H), 1.68 (d, J=11.6 Hz, 5H), 1.46 (t, J=10.3 Hz, 1H), 1.28 (m, 5H).

Step 2: (2S,3S)-ethyl 3-((2-bromo-5-fluoro-6-(furan-2-yl)pyrimidin-4-yl)amino)bicyclo[2.2.2]octane-2-carboxylate To a solution of hydrobromic acid in acetic acid (33%, 5 mL) was added (2S,3S)-ethyl 3-((2-chloro-5-fluoro-6-(furan-2-yl)pyrimidin-4-yl) amino)bicyclo[2.2.2]octane-2-carboxylate (100 mg, 0.25 mmol), and the mixture was stirred at rt for 4 h. The reaction mixture was added into ice-water (30 mL), and the resulting mixture was extracted with EtOAc (30 mL×3). The combined organic layers were washed with saturated aqueous sodium bicarbonate (60 mL×3), dried over anhydrous Na$_2$SO$_4$, and filtered. The filtrate was concentrated in vacuo to give the title compound as light yellow oil (97 mg, 87%).

MS (ESI, pos. ion) m/z: 440.1 [M+H]$^+$.

Step 3: (2S,3S)-ethyl 3-((2-(3-chloro-5-trityl-5H-pyrrolo[2,3-b]pyrazin-7-yl)-5-fluoro-6-(furan-2-yl)pyrimidin-4-yl)amino)bicyclo[2.2.2]octane-2-carboxylate To a mixed solvent of 1,4-dioxane (3 mL) and H$_2$O (0.5 mL) were added 2-chloro-7-(4,4,5,5-tetramethyl-1,3,2-dioxaborolan-2-yl)-5-trityl-5H-pyrrolo[2,3-b]pyrazine (116 mg, 0.22 mmol), potassium carbonate (70 mg, 0.51 mmol), Pd(dppf)Cl$_2$ (27 mg, 0.03 mmol) and (2S,3S)-ethyl 3-((2-bromo-5-fluoro-6-(furan-2-yl)pyrimidin-4-yl)amino) bicyclo[2.2.2]octane-2-carboxylate (75 mg, 0.17 mmol). The air in the mixture was exchanged with nitrogen by bubbling for 10 min. The mixture in the sealed tub was stirred for 2 h at 110° C. The mixture was filtered to remove the solid impurity, and the filtrate was concentrated to remove the solvent. The residue was purified by silica gel column chromatography (PE/EtOAc (v/v)=2/1) to give the title compound as light yellow oil (100 mg, 78%).

Step 4: (2S,3S)-ethyl 3-((2-(3-chloro-5H-pyrrolo[2,3-b]pyrazin-7-yl)-5-fluoro-6-(furan-2-yl)pyrimidin-4-yl)amino)bicyclo[2.2.2]octane-2-carboxylate To a solution of (2S,3S)-ethyl 3-((2-(3-chloro-5-trityl-5H-pyrrolo[2,3-b]pyrazin-7-yl)-5-fluoro-6-(furan-2-yl)pyrimidin-4-yl)amino)bicyclo[2.2.2]octane-2-carboxylate (100 mg, 0.13 mmol) in dichloromethane (3 mL) was added Et$_3$SiH (0.22 mL, 1.33 mmol) and TFA (0.10 mL, 1.33 mmol), and the mixture was stirred at rt overnight. The reaction mixture was added into saturated aqueous sodium bicarbonate (20 mL). The resulting mixture was extracted with dichloromethane (20 mL×3). The combined organic layers were washed with saturated brine (20 mL), dried over anhydrous sodium sulfate, and filtered. The filtrate was concentrated in vacuo to give the title compound as a yellow solid (42 mg, 62%).

Step 5: ((2S,3S)-3-((2-(3-chloro-5H-pyrrolo[2,3-b]pyrazin-7-yl)-5-fluoro-6-(furan-2-yl)pyrimidin-4-yl)amino)bicyclo[2.2.2]octane-2-carboxylic Acid To a solution of (2S,3S)-ethyl 3-((2-(3-chloro-5H-pyrrolo[2,3-b]pyrazin-7-yl)-5-fluoro-6-(furan-2-yl)pyrimidin-4-yl)amino)bicyclo[2.2.2]octane-2-carboxylate (42 mg, 0.08 mmol) in THF/MeOH/H$_2$O (v/v/v=1 mL/1 mL/1 mL) was added a solution of NaOH (20 mg, 0.50 mmol) in water (1 mL), and the mixture was stirred at rt overnight. To the reaction mixture was added water (20 mL), and the mixture was acidified with hydrochloric acid (1 M) to pH about 6. The resulting mixture was extracted with 2-methyltetrahydrofuran (15 mL×3). The combined organic layers were washed with saturated brine (50 mL), dried over anhydrous sodium sulfate, and filtered. The filtrate was concentrated in vacuo to remove the solvent, and the residue was purified by preparative thin-layer chromatography (DCM/MeOH (v/v)=15/1) to give the title compound as a light yellow solid (26 mg, 98%).

MS (ESI, pos. ion) m/z: 483.6 [M+H]$^+$;
HRMS (ESI, pos. ion) m/z: 483.1355, (C$_{23}$H$_{21}$ClFN$_6$O$_3$) [M+H]$^+$ theoretical value: 483.1348;
$^1$H NMR (400 MHz, DMSO-d$_6$) δ (ppm): 8.59 (s, 1H), 8.45 (s, 1H), 7.99 (s, 1H), 7.58 (s, 1H), 7.23 (s, 1H), 6.75 (s, 1H), 5.33 (s, 1H), 4.64 (s, 1H), 2.67 (s, 1H), 2.33 (s, 2H), 2.03 (m, 8H).

Example 52: (2S,3S)-3-((2-(2-chloro-5H-pyrrolo[2,3-b]pyrazin-7-yl)-6-(1H-imidazol-1-yl)pyrimidin-4-yl)amino)bicyclo[2.2.2]octane-2-carboxylic Acid

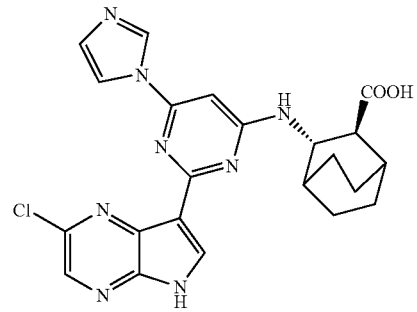 [SMILES: O=C(O)[C@H]1C2CCC(CC2)[C@@H]1Nc1cc(-n2ccnc2)nc(-c2c[nH]c3ncc(Cl)nc23)n1]

Step 1: (2S,3S)-ethyl 3-((2-chloro-6-(1H-imidazol-1-yl)pyrimidin-4-yl)amino)bicyclo[2.2.2]octane-2-carboxylate To toluene (3 mL) were added (2S,3S)-ethyl 3-((2,6-dichloropyrimidin-4-yl)amino) bicyclo[2.2.2]octane-2-carboxylate (88 mg, 0.26 mmol), imidazole (22 mg, 0.32 mmol), potassium carbonate (166 mg, 0.51 mmol), Pd(dba)$_3$ (24 mg, 0.03 mmol) and X-phos (12 mg, 0.02 mmol). The air in the mixture was exchanged with nitrogen by bubbling for 10 min, and then the mixture was heated to 120° C. and stirred for 1 h by microwave heating. The reaction mixture was concentrated in vacuo to remove the solvent, and the residue was purified by silica gel column chromatography (PE/EtOAc (v/v)=1/1) to give the title compound as a white solid (43 mg, 45%).

MS (ESI, pos. ion) m/z: 376.3[M+H]$^+$;
$^1$H NMR (400 MHz, CDCl$_3$) δ (ppm): 8.65 (s, 1H), 7.85 (s, 1H), 7.16 (s, 1H), 6.40 (s, 1H), 6.15 (s, 1H), 4.25-4.11 (m, 2H), 3.49 (s, 1H), 2.44 (s, 1H), 1.96-1.35 (m, 10H), 1.28-1.21 (m, 3H).

Step 2: (2S,3S)-ethyl 3-((2-(2-chloro-5-trityl-5H-pyrrolo[2,3-b]pyrazin-7-yl)-6-(1H-imidazol-1-yl)pyrimidin-4-yl) amino)bicyclo[2.2.2]octane-2-carboxylate To a mixed solvent of 1,4-dioxane (3 mL) and H$_2$O (0.5 mL) were added 2-chloro-7-(4,4,5,5-tetramethyl-1,3,2-dioxaborolan-2-yl)-5-trityl-5H-pyrrolo[2,3-b]pyrazine (300 mg, 0.35 mmol, 60%), potassium carbonate (110 mg, 0.80 mmol), Pd(dppf)Cl$_2$ (35 mg, 0.05 mmol) and (2S,3S)-ethyl 3-((2-chloro-6-(1H-imidazol-1-yl)pyrimidin-4-yl) amino) bicyclo[2.2.2]octane-2-carboxylate (100 mg, 0.27 mmol). The air in the mixture was exchanged with nitrogen by bubbling for 10 min. The mixture was stirred for 2 h at 110° C. by microwave heating. The mixture was filtered to remove the solid impurity, and the filtrate was concentrated to remove the solvent. The residue was purified by silica gel column chromatography (PE/EtOAc (v/v)=2/1) to give the title compound as light yellow oil (141 mg, 72%).

Step 3: (2S,3S)-ethyl 3-((2-(2-chloro-5H-pyrrolo[2,3-b]pyrazin-7-yl)-6-(1H-imidazol-1-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-6-(1H-imidazol-1-yl)pyrimidin-4-yl) amino)bicyclo[2.2.2]octane-2-carboxylate (140 mg, 0.19 mmol) in dichloromethane (5 mL) were added Et₃SiH (0.31 ml, 0.84 mmol) and TFA (0.14 mL, 0.84 mmol), and the mixture was stirred at rt overnight. The reaction mixture was added into saturated aqueous sodium bicarbonate (20 mL). The resulting mixture was extracted with dichloromethane (20 mL×3). The combined organic layers were washed with saturated brine (20 mL), dried over anhydrous sodium sulfate, and filtered. The filtrate was concentrated in vacuo to give the title compound as a yellow solid (93.9 mg, 100%).

MS (ESI, pos. ion) m/z: 493.6[M+H]⁺.

Step 4: (2S,3S)-3-((2-(2-chloro-5H-pyrrolo[2,3-b]pyrazin-7-yl)-6-(1H-imidazol-1-yl)pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-6-(1H-imidazol-1-yl)pyrimidin-4-yl)amino)bicyclo[2.2.2]octane-2-carboxylate (110 mg, 0.22 mmol) in THF/MeOH/H₂O (v/v/v=5 mL/5 mL/5 mL) was added NaOH (89 mg, 2.23 mmol) in portions. The mixture was stirred at rt overnight. To the reaction mixture was added saturated brine (15 mL), and the mixture was acidified with hydrochloric acid (1 M) to pH about 6. The resulting mixture was extracted with 2-methyltetrahydrofuran (15 mL×3). The combined organic layers were washed with saturated brine (50 mL), dried over anhydrous sodium sulfate, and filtered. The filtrate was concentrated in vacuo, and the residue was purified by preparative thin-layer chromatography (DCM/MeOH (v/v)=15/1) to give the title compound as a light yellow solid (100 mg, 96%).

MS (ESI, pos. ion) m/z: 465.1 [M+H]⁺;
HRMS (ESI, pos. ion) m/z: 465.1554, (C₂₂H₂₂ClN₈O₂) [M+H]⁺ theoretical value: 465.1550;
¹H NMR (400 MHz, DMSO-d₆) δ (ppm): 8.88 (s, 1H), 8.66 (s, 1H), 8.44 (s, 1H), 8.13 (d, J=5.8 Hz, 1H), 8.02 (s, 1H), 7.43 (s, 1H), 7.08 (s, 1H), 4.48 (s, 1H), 1.95 (s, 1H), 1.86 (s, 2H), 1.70-1.37 (m, 8H);
¹³C NMR (151 MHz, DMSO-d₆) δ (ppm): 163.87, 156.11, 154.07, 142.18, 141.64, 136.42, 136.28, 135.86, 135.31, 130.12, 129.95, 117.24, 111.86, 99.16, 50.92, 49.96, 45.82, 31.74, 29.54, 29.48, 29.44, 29.32, 29.30, 29.28, 29.20, 29.15, 29.03, 28.65, 28.47, 27.01, 26.02, 25.58, 24.33, 22.55, 21.34, 19.52, 14.41.

Example 53: (2S,3S)-3-((2-(3-chloro-5H-pyrrolo[2,3-b]pyrazin-7-yl)-5-fluoro-6-(thiophen-2-yl)pyrimidin-4-yl)amino)bicyclo[2.2.2]octane-2-carboxylic Acid

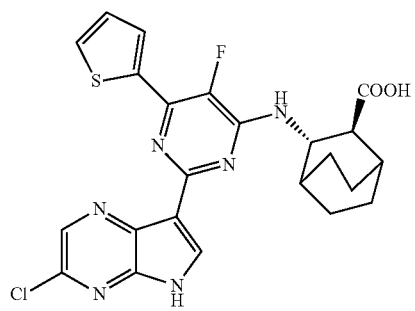 [SMILES: O=C(O)[C@H]1C2CCC(CC2)[C@@H]1Nc1nc(-c2c[nH]c3nc(Cl)cnc23)nc(-c2cccs2)c1F]

Step 1: (2S,3S)-ethyl 3-((2-(3-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate To 1,4-dioxane (3 mL) were added 3-chloro-7-(4,4,5,5-tetramethyl-1,3,2-dioxaborolan-2-yl)-5-trityl-5H-pyrrolo[2,3-b]pyrazine (373 mg, 0.29 mmol, 40%), potassium carbonate (91 mg, 0.66 mmol), Pd(dppf)Cl₂ (35 mg, 0.04 mmol) and (2S,3S)-ethyl 3-((2-bromo-5-fluoro-6-(thiophen-2-yl)pyrimidin-4-yl)amino)bicyclo[2.2.2]octane-2-carboxylate (100 mg, 0.22 mmol), then H₂O (0.5 mL) was added into the mixture. The air in the mixture was exchanged with nitrogen by bubbling for 10 min. The mixture was stirred for 2 h at 110° C. by microwave heating. The mixture was filtered to remove the solid impurity, and the filtrate was concentrated to remove the solvent. The residue was purified by silica gel column chromatography (PE/EtOAc (v/v)=2/1) to give the title compound as light yellow oil (169 mg, 100%).

¹H NMR (400 MHz, DMSO-d₆) δ(ppm): 8.54 (s, 1H), 8.29 (s, 1H), 7.82 (d, J=4.6 Hz, 2H), 7.70 (d, J=6.9 Hz, 1H), 7.36 (dt, J=6.7, 4.6 Hz, 10H), 7.19 (d, J=7.0 Hz, 5H), 4.50 (t, J=7.1 Hz, 1H), 4.03 (dd, J=7.1, 1.9 Hz, 2H), 2.89 (d, J=7.4 Hz, 1H), 1.94 (s, 1H), 1.85 (s, 1H), 1.71 (s, 2H), 1.46 (m), 1.11 (t, J=7.1 Hz, 3H).

Step 2: (2S,3S)-ethyl 3-((2-(3-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate To a solution of (2S,3S)-ethyl 3-((2-(3-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate (169 mg, 0.22 mmol) in dichloromethane (3 mL) were added Et₃SiH (0.35 mL, 2.20 mmol) and trifluoroacetic acid (0.16 mL, 2.20 mmol), and the mixture was stirred at rt overnight. The reaction mixture was added into saturated aqueous sodium bicarbonate (20 mL). The resulting mixture was extracted with dichloromethane (20 mL×3). The combined organic layers were washed with saturated brine (20 mL), dried over anhydrous sodium sulfate, and filtered. The filtrate was concentrated in vacuo to give the title compound as a yellow solid (90 mg, 78%).

Step 3: (2S,3S)-3-((2-(3-chloro-5H-pyrrolo[2,3-b]pyrazin-7-yl)-5-fluoro-6-(thiophen-2-yl)pyrimidin-4-yl)amino)bicyclo[2.2.2]octane-2-carboxylic acid To a solution of (2S,3S)-ethyl 3-((2-(3-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate (90 mg, 0.17 mmol) in THF/MeOH/H₂O (v/v/v=1 mL/1 mL/1 mL) was added NaOH (67 mg, 1.71 mmol), and the mixture was stirred at rt overnight. To the reaction mixture was added saturated brine (20 mL), and the mixture was acidified with hydrochloric acid (1 M) to pH about 6. The resulting mixture was extracted with 2-methyltetrahydrofuran (20 mL×3). The combined organic layers were washed with saturated brine (50 mL), dried over anhydrous sodium sulfate, and filtered. The filtrate was concentrated in vacuo to remove the solvent, and the residue was purified by preparative thin-layer chromatography (DCM/MeOH (v/v)=15/1) to give the title compound as a light yellow solid (66 mg, 77%).

MS (ESI, pos. ion) m/z: 499.0 [M+H]⁺;
HRMS (ESI, pos. ion) m/z: 499.1110, (C₂₃H₂₁ClFN₆O₂S) [M+H]⁺ theoretical value: 499.1119;

¹H NMR (400 MHz, DMSO-d₆) δ (ppm): 8.59 (s, 1H), 8.42 (s, 1H), 7.87 (d, J=3.4 Hz, 1H), 7.84 (d, J=4.9 Hz, 1H), 7.64 (d, J=6.3 Hz, 1H), 7.29-7.25 (m, 1H), 4.63 (t, J=6.4 Hz, 1H), 3.16 (s, 1H), 2.07 (s, 1H), 1.99 (s, 1H), 1.75 (t, J=9.7 Hz, 2H), 1.57-1.32 (m, 6H).

Example 54: (2S,3S)-((ethoxycarbonyl)oxy)methyl 3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate

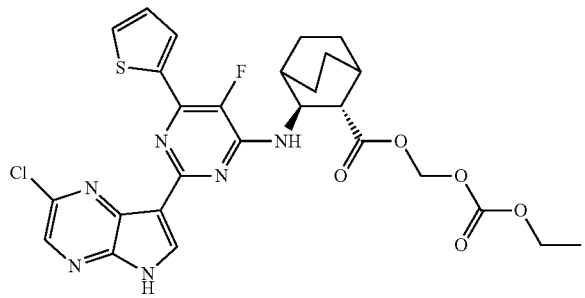 [SMILES: CCOC(=O)OCOC(=O)[C@H]1C2CCC(CC2)[C@@H]1Nc1nc(-c2c[nH]c3ncc(Cl)nc23)nc(-c2cccs2)c1F]

Step 1: (2S,3S)-((ethoxycarbonyl)oxy)methyl 3-((2-bromo-5-fluoro-6-(thiophen-2-yl)pyrimidin-4-yl)amino)bicyclo[2.2.2]octane-2-carboxylate To a solution of (2S,3S)-3-((2-bromo-5-fluoro-6-(thiophen-2-yl)pyrimidin-4-yl)amino)bicyclo[2.2.2]octane-2-carboxylic acid (2.00 g, 4.69 mmol) in DMF (20 mL) were added potassium carbonate (2.02 g, 14.20 mmol) and chloromethyl ethyl carbonate (0.79 g, 5.70 mmol), and the mixture was stirred at rt overnight. To the reaction mixture was added water (50 mL), and the resulting mixture was extracted with ethyl acetate (50 mL×3). The combined organic layers were washed with saturated brine (100 mL×3), dried over anhydrous sodium sulfate and filtered. The filtrate was concentrated in vacuo and the residue was purified by silica gel column chromatography (PE/EtOAc (v/v)=5/1) to give the title compound as a light yellow solid (0.48 g, 69%).

MS (ESI, pos. ion) m/z: 527.7 [M+H]⁺;
¹H NMR (400 MHz, CDCl₃) δ (ppm): 7.84-7.81 (m, 1H), 7.57 (d, J=5.0 Hz, 1H), 7.20-7.14 (m, 1H), 6.02 (d, J=5.7 Hz, 1H), 5.77 (d, J=5.6 Hz, 1H), 4.45 (d, J=5.2 Hz, 1H), 4.24 (q, J=7.1 Hz, 2H), 2.50 (d, J=5.4 Hz, 1H), 2.03 (d, J=2.3 Hz, 1H), 1.91 (d, J=2.4 Hz, 1H), 1.81 (m, 1H), 1.72 (m, 4H), 1.65-1.57 (m, 2H), 1.33 (t, J=7.1 Hz, 3H).

Step 2: (2S,3S)-((ethoxycarbonyl)oxy)methyl 3-((2-(2-chloro-5-trityl-5H-pyrrolo[2,3-b]pyrazin-7-yl)-5-fluoro-6-(thiophen-2-yl)pyrimidin-4-yl) amino)bicyclo[2.2.2]octane-2-carboxylate To a mixed solvent of 1,4-dioxane (20 mL) and H₂O (1 mL) were added 2-chloro-7-(4,4,5,5-tetramethyl-1,3,2-dioxaborolan-2-yl)-5-trityl-5H-pyrrolo[2,3-b]pyrazine (65%, 0.85 g, 1.10 mmol), K₂CO₃ (0.40 g, 2.90 mmol), Pd(dppf)Cl₂ (0.22 g, 0.29 mmol) and (2S,3S)-((ethoxycarbonyl)oxy)methyl 3-((2-bromo-5-fluoro-6-(thiophen-2-yl)pyrimidin-4-yl) amino)bicyclo[2.2.2]octane-2-carboxylate (0.50 g, 0.95 mmol). The air in the mixture was exchanged with nitrogen by bubbling for 10 min. The mixture in the sealed tub was stirred for 4 h at 115° C. The reaction was stopped, and the mixture was filtered through a celite pad to remove the solid impurity. The filtrate was concentrated in vacuo, and the residue was purified by silica gel column chromatography (PE/EtOAc (v/v)=10/1) to give the title compound as a yellow solid (0.69 g, 86%).

Step 3: (2S,3S)-((ethoxycarbonyl)oxy)methyl 3-((2-(2-chloro-5H-pyrrolo[2,3-b]pyrazin-7-yl)-5-fluoro-6-(thiophen-2-yl)pyrimidin-4-yl)amino)bicyclo[2.2.2]octane-2-carboxylate To a solution of (2S,3S)-((ethoxycarbonyl)oxy)methyl 3-((2-(2-chloro-5-trityl-5H-pyrrolo[2,3-b]pyrazin-7-yl)-5-fluoro-6-(thiophen-2-yl)pyrimidin-4-yl) amino)bicyclo[2.2.2]octane-2-carboxylate (0.69 g, 0.82 mmol) in dichloromethane (10 mL) were added Et₃SiH (1.60 mL, 10.00 mmol) and TFA (0.74 mL, 10.00 mmol), and the mixture was stirred at rt overnight. The reaction mixture was added into saturated aqueous sodium bicarbonate (30 mL). The resulting mixture was extracted with dichloromethane (30 mL×3). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=4/1) to give the title compound as a light yellow solid (0.25 g, 51%).

MS (ESI, pos. ion) m/z: 600.8 [M+H]⁺;
HRMS (ESI, pos. ion) m/z: 601.1483, (C₂₇H₂₇ClFN₆O₅S)[M+H]⁺ theoretical value: 601.1436;
¹H NMR (400 MHz, DMSO-d₆) δ (ppm): 10.09 (s, 1H), 8.46 (d, J=2.7 Hz, 1H), 8.28 (s, 1H), 7.93 (d, J=3.1 Hz, 1H), 7.58 (d, J=4.8 Hz, 1H), 7.24-7.17 (m, 1H), 5.80 (d, J=5.6 Hz, 1H), 5.69 (d, J=5.6 Hz, 1H), 4.71 (s, 1H), 4.18-4.08 (m, 2H), 2.60 (s, 1H), 2.09 (s, 1H), 1.92 (s, 1H), 1.81 (m, 1H), 1.76-1.61 (m, 5H), 1.50 (m, 1H), 1.18 (t, J=7.1 Hz, 3H).

Example 55: (2S,3S)-3-((2-(2-chloro-5H-pyrrolo[2,3-b]pyrazin-7-yl)-6-(1H-pyrrol-1-yl)pyrimidin-4-yl)amino)bicyclo[2.2.2]octane-2-carboxylic Acid

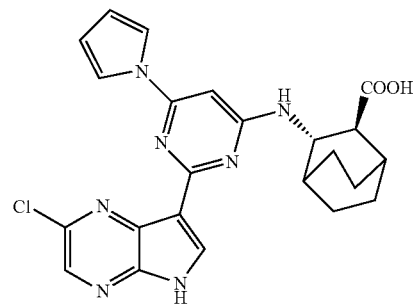 [SMILES: O=C(O)[C@H]1C2CCC(CC2)[C@@H]1Nc1cc(-n2cccc2)nc(-c2c[nH]c3ncc(Cl)nc23)n1]

Step 1: 2,4-dichloro-6-(1H-pyrrol-1-yl)pyrimidine

To a two-neck flask was added sodium hydride (1.43 g, 35.8 mmol, 60%). The air in the mixture was exchanged with nitrogen for three times, then anydrous THF (20 mL) was added into the mixture. The mixture was cooled to 0° C., and pyrrole (2.00 g, 29.8 mmol) was added. The resulting mixture was stirred at this temperature for 1 h, then 2,4,6-trichloropyrimidine (6.01 g, 32.8 mmol) was added. The resulting mixture was stirred at 0° C. overnight. To the reaction mixture was added water (40 mL) to quench the reaction, and the resulting mixture was extracted with ethyl acetate (30 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=10/1) to give the title compound as a white solid (806 mg, 13%).

Step 2: (2S,3S)-ethyl 3-((2-chloro-6-(1H-pyrrol-1-yl)pyrimidin-4-yl)amino)bicyclo[2.2.2]octane-2-carboxylate To DMF (5 mL) were added 2,4-dichloro-6-(1H-pyrrol-1-yl)pyrimidine (800 mg, 3.74 mmol) and (2S,3S)-ethyl 3-aminobicyclo[2.2.2]octane-2-carboxylate hydrochloride (961 mg, 4.11 mmol), then $K_2CO_3$ (1.55 g, 11.2 mmol) was added into the mixture. The mixture was stirred at 50° C. overnight. To the reaction mixture was added water (30 mL), and the resulting mixture was extracted with ethyl acetate (30 mL×2). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as colorless oil (127 mg, 9%).

MS (ESI, pos. ion) m/z: 375.1[M+H]$^+$.

Step 3: (2S,3S)-ethyl 3-((2-(2-chloro-5-trityl-5H-pyrrolo[2,3-b]pyrazin-7-yl)-6-(1H-pyrrol-1-yl)pyrimidin-4-yl)amino)bicyclo[2.2.2]octane-2-carboxylate To a mixed solvent of 1,4-dioxane (3 mL) and water (0.5 mL) were added 2-chloro-7-(4,4,5,5-tetramethyl-1,3,2-dioxaborolan-2-yl)-5-trityl-5H-pyrrolo[2,3-b]pyrazine (361 mg, 0.42 mmol, 60%), potassium carbonate (132 mg, 0.96 mmol), Pd(dppf)Cl$_2$ (52 mg, 0.06 mmol) and ((2S,3S)-ethyl 3-((2-chloro-6-(1H-pyrrol-1-yl)pyrimidin-4-yl)amino) bicyclo[2.2.2]octane-2-carboxylate (120 mg, 0.32 mmol). The air in the mixture was exchanged with nitrogen by bubbling for 10 min. The mixture was stirred for 2 h at 110° C. by microwave heating. The mixture was filtered to remove the solid impurity, and the filtrate was concentrated to remove the solvent. The residue was purified by silica gel column chromatography (PE/EtOAc (v/v)=2/1) to give the title compound as light yellow oil (235 mg, 100%).

Step 4: (2S,3S)-ethyl 3-((2-(2-chloro-5H-pyrrolo[2,3-b]pyrazin-7-yl)-6-(1H-pyrrol-1-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-6-(1H-pyrrol-1-yl)pyrimidin-4-yl) amino)bicyclo[2.2.2]octane-2-carboxylate (185 mg, 0.25 mmol) in dichloromethane (5 mL) was added Et$_3$SiH (0.40 mL, 2.52 mmol) and trifluoroacetic acid (0.19 mL, 2.52 mmol), and the mixture was stirred at rt overnight. The reaction mixture was added into saturated aqueous sodium bicarbonate (20 mL). The resulting mixture was extracted with dichloromethane (20 mL×3). The combined organic layers were washed with saturated brine (20 mL), dried over anhydrous sodium sulfate, and filtered. The filtrate was concentrated in vacuo to give the title compound as a yellow solid (37 mg, 30%).

MS (ESI, pos. ion) m/z: 492.6[M+H]$^+$.

Step 5: (2R,3R)-3-((2-(2-chloro-5H-pyrrolo[2,3-b]pyrazin-7-yl)-6-(1H-pyrrol-1-yl)pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-6-(1H-pyrrol-1-yl)pyrimidin-4-yl)amino)bicyclo[2.2.2]octane-2-carboxylate (37 mg, 0.08 mmol) in THF/MeOH/H$_2$O (v/v/v=1 mL/1 mL/1 mL) was added NaOH (30 mg, 0.80 mmol), and the mixture was stirred at rt overnight. To the reaction mixture was added saturated brine (30 mL), and the mixture was acidified with hydrochloric acid (1 M) to pH about 6. The resulting mixture was extracted with 2-methyltetrahydrofuran (30 mL×3). The combined organic layers were washed with saturated brine (50 mL), dried over anhydrous sodium sulfate, and filtered. The filtrate was concentrated in vacuo to remove the solvent, and the residue was purified by preparative thin-layer chromatography (DCM/MeOH (v/v)=15/1) to give the title compound as a light yellow solid (18 mg, 52%).

MS (ESI, pos. ion) m/z: 464.1 [M+H]$^+$;

HRMS (ESI, pos. ion) m/z: 464.1589, (C$_{23}$H$_{22}$ClN$_6$O$_3$) [M+H]+ theoretical value: 464.1602;

$^1$H NMR (400 MHz, DMSO-d$_6$) δ (ppm): 12.80 (s, 1H), 8.66 (s, 1H), 8.38 (s, 1H), 7.71 (s, 1H), 7.49 (s, 1H), 6.39 (s, 1H), 6.33 (s, 2H), 4.57 (s, 1H), 3.60 (s, 1H), 2.83 (s, 1H), 1.97 (s, 1H), 1.91 (s, 1H), 1.76 (s, 2H), 1.41 (m, 6H).

Example 56: (2S,3S)-3-((5-fluoro-2-(2-fluoro-5H-pyrrolo[2,3-b]pyrazin-7-yl)-6-(thiophen-2-yl)pyrimidin-4-yl)amino)bicyclo[2.2.2]octane-2-carboxylic Acid

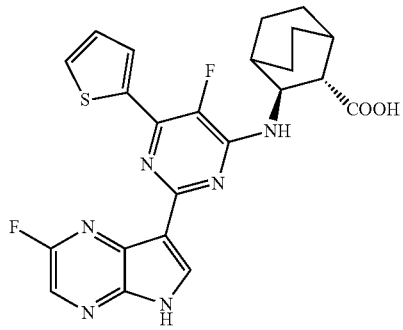 [SMILES: O=C(O)[C@H]1C2CCC(CC2)[C@@H]1Nc1nc(-c2c[nH]c3ncc(F)nc23)nc(-c2cccs2)c1F]

Step 1:
5-bromo-3-((trimethylsilyl)ethynyl)pyrazin-2-amine

To a solution of 3,5-dibromopyrazin-2-amine (2.00 g, 7.91 mmol) in THF (24 mL) were added triethylamine (3.3 mL, 24 mmol), cuprous iodide (151 mg, 0.79 mmol) and Pd(PPh$_3$)$_2$Cl$_2$ (561 mg, 0.79 mmol). The mixture was cooled to −5° C. under nitrogen protection, then trimethylsilylacetylene (1.07 mL, 7.50 mmol) was dropwised slowly into the mixture. After the addition, the mixture was warmed to 0° C. and stirred for 1.5 h. The mixture was concentrated in vacuo to remove the solvent and the residue was purified by silica gel column chromatography (PE/EtOAc (v/v)=5/1) to give the title compound as black oil (42 mg, 94%).

MS (ESI, pos. ion) m/z: 272.00 [M+H]$^+$;

¹H NMR (400 MHz, CDCl₃) δ (ppm): 8.04 (s, 1H), 5.14 (s, 2H), 0.30 (s, 9H).

Step 2: 2-bromo-5-tosyl-5H-pyrrolo[2,3-b]pyrazine

To a 0° C. solution of 5-bromo-3-((trimethylsilyl)ethynyl)pyrazin-2-amine (1.22 g, 4.52 mmol) in anhydrous DMF (10 mL) was added sodium hydride (253 mg, 6.33 mmol, 60%). The mixture was stirred at 0° C. for 15 min, then paratoluensulfonyl chloride (865 mg, 4.51 mmol) was added into the mixture. The resulting mixture was warmed to rt and stirred for 3 h. To the reaction mixture was added ice-water (40 mL) to quench the reaction, and the resulting mixture was extracted with ethyl acetate (30 mL×3). The combined organic layers were washed with saturated brine (60 mL), dried over anhydrous sodium sulfate and filtered. The filtrate was concentrated in vacuo and the residue was purified by silica gel column chromatography (PE/EtOAc (v/v)=10/1) to give the title compound as a yellow solid (624 mg, 39.2%).

Step 3: tert-butyl (5-tosyl-5H-pyrrolo[2,3-b]pyrazin-2-yl)carbamate

To a solution of 2-bromo-5-tosyl-5H-pyrrolo[2,3-b]pyrazine (624 mg, 1.77 mmol) in 1,4-dioxane (10 mL) were added tert-butyl carbamate (311 mg, 2.65 mmol), potassium carbonate (734 mg, 5.31 mmol), xantphos (209 mg, 0.35 mmol) and palladium acetate (41 mg, 0.17 mmol). The mixture was heated to 105° C. and stirred for 2.5 h. The reaction mixture was concentrated in vacuo and the residue was purified by silica gel column chromatography (PE/EtOAc (v/v)=10/1) to give the title compound as a white solid (513 mg, 75%).

Step 4: 5-tosyl-5H-pyrrolo[2,3-b]pyrazin-2-amine

A solution of tert-butyl (5-tosyl-5H-pyrrolo[2,3-b]pyrazin-2-yl)carbamate (513 mg, 1.32 mmol) in phosphoric acid (5 mL, 85.97 mmol) was heated to 70° C. and stirred for 2 h. To the reaction mixture was added saturated aqueous sodium bicarbonate (30 mL), and the resulting mixture was extracted with ethyl acetate (30 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (200 mg, 53%).
MS (ESI, pos. ion) m/z: 289.4 [M+H]⁺.

Step 5: 2-fluoro-5-tosyl-5H-pyrrolo[2,3-b]pyrazine

A suspension of 5-tosyl-5H-pyrrolo[2,3-b]pyrazin-2-amine (50 mg, 0.17 mmol), copper powder (1 mg, 0.02 mmol) in aqueous HBF₄ solution (3 mL, 40%) was stirred at rt for 10 min, then cooled to −5° C., and sodium nitrite (12 mg, 0.2 mmol) was added into the suspension. The mixture was stirred at 0° C. for 15 min, then warmed to rt and stirred for 6 h. The reaction mixture was cooled to 0° C., and adjusted with saturated aqueous sodium carbonate to pH 6. The reaction mixture was extracted with ethyl acetate (30 mL×2). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=10/1) to give the title compound as a white solid (25 mg, 49%).

MS (ESI, pos. ion) m/z: 292.2 [M+H]⁺;
¹H NMR (400 MHz, CDCl₃) δ (ppm): 8.19 (d, J=6.9 Hz, 1H), 8.09-8.03 (m, 3H), 7.34 (d, J=8.1 Hz, 2H), 6.75 (d, J=4.1 Hz, 1H), 2.42 (s, 3H).

Step 6: 2-fluoro-5H-pyrrolo[2,3-b]pyrazine

A solution of 2-fluoro-5-tosyl-5H-pyrrolo[2,3-b]pyrazine (100 mg, 0.34 mmol) in TBAF (0.42 mL, 0.42 mmol, 1 mol/L in THF) was stirred at rt for 1.5 h. The reaction mixture was concentrated in vacuo, and the residue was diluted with saturated aqueous sodium bicarbonate (20 mL). The resulting mixture was extracted with ethyl acetate (20 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (42 mg, 89%).
MS (ESI, pos. ion) m/z: 138.1 [M+H]⁺;
¹H NMR (400 MHz, DMSO-d₆) δ (ppm): 12.31 (s, 1H), 8.20 (d, J=6.9 Hz, 1H), 7.96 (d, J=3.5 Hz, 1H), 6.58 (d, J=3.5 Hz, 1H).

Step 7: 2-fluoro-7-iodo-5H-pyrrolo[2,3-b]pyrazine

To a solution of 2-chloro-5H-pyrrolo[2,3-b]pyrazine (423 mg, 3.09 mmol) in 2-methyltetrahydrofuran (10 mL) was added NIS (787 mg, 3.39 mmol), and the reaction mixture was stirred at rt overnight. Saturated aqueous sodium thiosulfate (50 mL) was added to quench the reaction, and the resulting mixture was partitioned. The aqueous layer was extracted with EtOAc (50 mL×2). The combined organic layers were washed with saturated brine (80 mL), dried over anhydrous Na₂SO₄, filtered, and the filtrate was concentrated in vacuo. The residue was purified by silica gel chromatograph (PE/EtOAc (v/v)=20/1-4/1) to give the title compound as a white solid (814 mg, 100%).
MS (ESI, neg.ion) m/z: 262.1 [M−H]⁻.

Step 8: 2-fluoro-7-iodo-5-trityl-5H-pyrrolo[2,3-b]pyrazine

A solution of 2-fluoro-7-iodo-5H-pyrrolo[2,3-b]pyrazine (834 mg, 3.17 mmol) in DMF (10 mL) was cooled to 0° C., and NaH (152 mg, 3.80 mmol, 60%) was added into the solution. The mixture was stirred at 0° C. for 0.5 h. Then to the mixture was added triphenylchloromethane (972 mg, 3.49 mmol), and the resulting mixture was stirred at rt for 3 h. To the reaction mixture was added water (40 mL) to quench to reaction, and the resulting mixture was extracted with ethyl acetate (30 mL×2). The combined organic layers were washed with saturated brine (20 mL), dried over anhydrous sodium sulfate and filtered. The filtrate was concentrated in vacuo and the residue was purified by silica gel column chromatography (PE/EtOAc (v/v)=1/1) to give the title compound as a white solid (1.6 g, 100%).
¹H NMR (400 MHz, DMSO-d₆) δ (ppm): 8.03 (d, J=7.0 Hz, 1H), 7.72 (s, 1H), 7.32 (dd, J=9.2, 7.1 Hz, 10H), 7.16 (d, J=6.8 Hz, 5H).

Step 9: 2-fluoro-7-(4,4,5,5-tetramethyl-1,3,2-dioxaborolan-2-yl)-5-trityl-5H-pyrrolo[2,3-b]pyrazine A solution of 2-fluoro-7-iodo-5-trityl-5H-pyrrolo[2,3-b]pyrazine (500 mg, 0.99 mmol) and isopropoxyboronic acid pinacol ester (231 mg, 1.24 mmol) in THF (10 mL) was cooled to −27° C., and the mixture was stirred vigorously, then a solution of isopropylmagnesium chloride in tetrahydrofuran (2 M, 0.58 mL) was added dropwise slowly. After the addition, the mixture was continued to stir for 1.5 h. The reaction mixture was added into saturated aqueous sodium carbonate (40 mL), and the mixture was extracted with ethyl acetate (30 mL×3). The combined organic layer was concentrated in vacuo, and the residue was purified by silica gel column chromatography (PE/EtOAc (v/v)=10/1) to give the title compound as a yellow solid (500 mg, 100%).

MS (ESI, pos. ion) m/z: 506.1 [M+H]$^+$.

Step 10: (2S,3S)-ethyl 3-((5-fluoro-2-(2-fluoro-5-trityl-5H-pyrrolo[2,3-b]pyrazin-7-yl)-6-(thiophen-2-yl)pyrimidin-4-yl)amino)bicyclo[2.2.2]octane-2-carboxylate To a mixed solvent of H$_2$O (0.2 mL, 10 mmol) and 1,4-dioxane (2 mL) were added 2-fluoro-7-(4,4,5,5-tetramethyl-1,3,2-dioxaborolan-2-yl)-5-trityl-5H-pyrrolo[2,3-b]pyrazine (1.34 g, 1.33 mmol, 50%), (2S,3S)-ethyl 3-((2-bromo-5-fluoro-6-(thiophen-2-yl) pyrimidin-4-yl)amino) bicyclo[2.2.2]octane-2-carboxylate (500 mg, 1.10 mmol), potassium carbonate (456 mg, 3.30 mmol), Pd(dppf)Cl$_2$ (179 mg, 0.220 mmol). The air in the mixture was exchanged with nitrogen by bubbling for 10 min. The mixture was stirred for 2 h at 110° C. by microwave heating. The reaction mixture was filtered through a celite pad, and the filtrate was concentrated in vacuo. The residue was purified by silica gel column chromatography (n-hexane/EtOAc(v/v)=5/1) to give the title compound as a yellow solid (820 mg, 99%).

$^1$H NMR (400 MHz, DMSO-d$_6$) δ (ppm): 8.32 (s, 1H), 8.02 (d, J=7.5 Hz, 1H), 7.83 (d, J=5.0 Hz, 2H), 7.70 (d, J=6.7 Hz, 1H), 7.35 (dd, J=10.1, 7.2 Hz, 10H), 7.18 (d, J=7.0 Hz, 5H), 4.55 (t, J=7.0 Hz, 1H), 4.06-4.01 (m, 2H), 2.89 (d, J=7.4 Hz, 1H), 1.95 (s, 1H), 1.89 (s, 1H), 1.72 (d, J=7.2 Hz, 2H), 1.49 (m, 6H), 1.12 (t, J=7.1 Hz, 3H).

Step 11: (2S,3S)-ethyl 3-((5-fluoro-2-(2-fluoro-5H-pyrrolo[2,3-b]pyrazin-7-yl)-6-(thiophen-2-yl)pyrimidin-4-yl) amino)bicyclo[2.2.2]octane-2-carboxylate To a solution of (2S,3S)-ethyl 3-((5-fluoro-2-(2-fluoro-5-trityl-5H-pyrrolo[2,3-b]pyrazin-7-yl)-6-(thiophen-2-yl)pyrimidin-4-yl) amino)bicyclo[2.2.2]octane-2-carboxylate (820 mg, 1.09 mmol) in dichloromethane (10 mL) were added Et$_3$SiH (1.74 mL, 10.9 mmol) and trifluoroacetic acid (0.81 mL, 10.9 mmol), and the mixture was stirred at rt overnight. The reaction mixture was added into saturated aqueous sodium bicarbonate (40 mL), and the resulting mixture was extracted with dichloromethane (30 mL×3). The combined organic layers were washed with saturated brine (80 mL), dried over anhydrous sodium sulfate, and filtered. The filtrate was concentrated in vacuo to give the title compound as a yellow solid (460 mg, 83%).

MS (ESI, pos. ion) m/z: 511.3[M+H]$^+$;

$^1$H NMR (400 MHz, CDCl$_3$) δ (ppm): 9.21 (s, 1H), 8.55 (d, J=3.1 Hz, 1H), 8.13 (d, J=7.0 Hz, 1H), 7.95 (d, J=3.6 Hz, 1H), 7.58 (d, J=5.0 Hz, 1H), 7.24-7.19 (m, 1H), 5.29 (d, J=5.7 Hz, 1H), 4.78 (s, 1H), 4.23-4.10 (m, 2H), 2.45 (d, J=5.8 Hz, 1H), 2.10 (s, 1H), 2.06 (s, 1H), 1.94 (d, J=13.4 Hz, 1H), 1.85-1.63 (m, 6H), 1.52 (d, J=13.7 Hz, 1H), 1.15 (t, J=7.1 Hz, 3H).

Step 12: (2S,3S)-3-((5-fluoro-2-(2-fluoro-5H-pyrrolo[2,3-b]pyrazin-7-yl)-6-(thiophen-2-yl)pyrimidin-4-yl)amino)bicyclo[2.2.2]octane-2-carboxylic Acid To a solution of (2S,3S)-ethyl 3-((5-fluoro-2-(2-fluoro-5H-pyrrolo[2,3-b]pyrazin-7-yl)-6-(thiophen-2-yl)pyrimidin-4-yl)amino)bicyclo[2.2.2]octane-2-carboxylate (460 mg, 0.90 mmol) in THF/MeOH/H$_2$O (v/v/v=1/1/1, 3 mL) was added NaOH (360 mg, 9.00 mmol) in portions. The mixture was stirred at rt overnight. To the reaction mixture was added saturated brine (20 mL), and the mixture was acidified with hydrochloric acid (1 M) to pH about 6. The resulting mixture was extracted with 2-methyltetrahydrofuran (15 mL×3). The combined organic layers were washed with saturated brine (50 mL), dried over anhydrous sodium sulfate, and filtered. The filtrate was concentrated in vacuo to remove the solvent, and the residue was purified by preparative thin-layer chromatography (DCM/MeOH (v/v) =15/1) to give the title compound as a light yellow solid (350 mg, 81%).

MS (ESI, pos. ion) m/z: 482.9 [M+H]$^+$;

HRMS (ESI, pos. ion) m/z: 483.1416, (C$_{23}$H$_{21}$F$_2$N$_6$O$_2$S) [M+H]$^+$ theoretical value: 483.1415;

$^1$H NMR (400 MHz, DMSO-d$_6$) δ (ppm): 12.74 (s, 1H), 8.52 (s, 1H), 8.27 (d, J=7.3 Hz, 1H), 7.89 (d, J=3.0 Hz, 1H), 7.84 (d, J=4.9 Hz, 1H), 7.62 (d, J=6.2 Hz, 1H), 7.32-7.24 (m, 1H), 4.65 (d, J=6.3 Hz, 1H), 2.85 (d, J=7.0 Hz, 1H), 2.11 (s, 1H), 1.98 (d, J=14.1 Hz, 2H), 1.84-1.29 (m, 8H);

$^{13}$C NMR (151 MHz, DMSO-d$_6$) δ (ppm): 176.19, 158.21, 156.64, 155.93, 155.88, 152.54, 152.46, 140.90, 140.38, 140.33, 140.29, 138.65, 138.45, 138.41, 134.94, 132.43, 132.33, 130.48, 130.46, 129.72, 129.65, 128.98, 125.03, 124.73, 113.79, 51.36, 48.03, 28.82, 28.49, 25.91, 23.99, 21.67, 19.56.

Example 57: (2S,3S)-3-((6-(5-chlorothiophen-2-yl)-5-fluoro-2-(2-fluoro-5H-pyrrolo[2,3-b]pyrazin-7-yl)pyrimidin-4-yl)amino)bicyclo[2.2.2]octane-2-carboxylic Acid

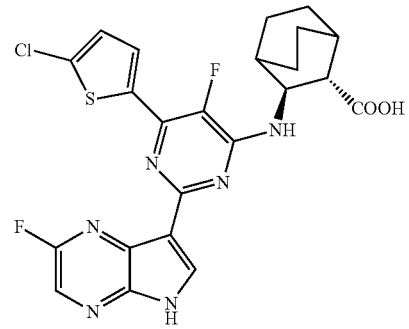 [SMILES: O=C(O)[C@H]1C2CCC(CC2)[C@@H]1Nc1nc(-c2c[nH]c3ncc(F)nc23)nc(-c2ccc(Cl)s2)c1F]

Step 1: (2S,3S)-ethyl 3-((6-(5-chlorothiophen-2-yl)-5-fluoro-2-(2-fluoro-5-trityl-5H-pyrrolo[2,3-b]pyrazin-7-yl)pyrimidin-4-yl)amino)bicyclo[2.2.2]octane-2-carboxylate To a mixed solvent of H$_2$O (0.2 mL) and 1,4-dioxane (10 mL) were added 2-fluoro-7-(4,4,5,5-tetramethyl-1,3,2-dioxaborolan-2-yl)-5-trityl-5H-pyrrolo[2,3-b]pyrazine (1.24 g, 1.23 mmol, 50%), (2S,3S)-ethyl 3-((2-bromo-6-(5-chlorothiophen-2-yl)-5-fluoropyrimidin-4-yl)amino)bicyclo[2.2.2]octane-2-carboxylate (500 mg, 1.02 mmol), potassium carbonate (423 mg, 3.07 mmol) and Pd(dppf)Cl$_2$ (107 mg, 0.20 mmol). The air in the mixture was exchanged with nitrogen by bubbling for 10 min. The mixture was stirred for 2 h at 110° C. by microwave heating. The reaction mixture was filtered through a celite pad, and the filtrate was concentrated in vacuo. The residue was purified by silica gel column chromatography (PE/EtOAc (v/v)=5/1) to give the title compound as a yellow solid (515 mg, 64%).

$^1$H NMR (400 MHz, DMSO-d$_6$) δ (ppm): 8.30 (s, 1H), 8.03 (d, J=7.5 Hz, 1H), 7.78 (d, J=6.9 Hz, 1H), 7.63 (d, J=3.4 Hz, 1H), 7.35 (dd, J=10.7, 7.2 Hz, 10H), 7.28 (d, J=4.1 Hz, 1H), 7.18 (d, J=7.1 Hz, 5H), 4.52 (t, J=7.1 Hz, 1H), 4.04 (m, 2H), 2.89 (d, J=7.3 Hz, 1H), 1.94 (s, 1H), 1.85 (s, 1H), 1.72 (d, J=7.1 Hz, 2H), 1.56-1.39 (m, 6H), 1.12 (t, J=7.1 Hz, 3H).

Step 2: (2S,3S)-ethyl 3-((6-(5-chlorothiophen-2-yl)-5-fluoro-2-(2-fluoro-5H-pyrrolo[2,3-b]pyrazin-7-yl)pyrimidin-4-yl)amino)bicyclo[2.2.2]octane-2-carboxylate To a solution of (2S,3S)-ethyl 3-((6-(5-chlorothiophen-2-yl)-5-fluoro-2-(2-fluoro-5-trityl-5H-pyrrolo[2,3-b]pyrazin-7-yl)pyrimidin-4-yl)amino)bicyclo[2.2.2]octane-2-carboxylate (515 mg, 0.65 mmol) in dichloromethane (10 mL) was added Et$_3$SiH (1.04 mL, 6.54 mmol) and trifluoroacetic acid (0.48 mL, 6.54 mmol), and the mixture was stirred at rt overnight. The reaction mixture was added into saturated aqueous sodium bicarbonate (40 mL), and the resulting mixture was extracted with dichloromethane (30 mL×3). The combined organic layers were washed with saturated brine (60 mL), dried over anhydrous sodium sulfate, and filtered. The filtrate was concentrated in vacuo to give the title compound as a yellow solid (290 mg, 81%).

MS (ESI, pos. ion) m/z: 544.8[M+H]$^+$;

$^1$H NMR (400 MHz, CDCl$_3$) δ (ppm): 9.18 (s, 1H), 8.52 (d, J=3.1 Hz, 1H), 8.13 (d, J=7.0 Hz, 1H), 7.69 (d, J=3.2 Hz, 1H), 7.02 (d, J=4.0 Hz, 1H), 5.27 (d, J=5.2 Hz, 1H), 4.78 (s, 1H), 4.24-4.10 (m, 2H), 2.44 (d, J=5.9 Hz, 1H), 2.10 (s, 1H), 2.06 (s, 1H), 1.94 (d, J=13.6 Hz, 1H), 1.82-1.63 (m, 6H), 1.52 (d, J=13.8 Hz, 1H), 1.16 (t, J=7.1 Hz, 3H).

Step 3: (2S,3S)-3-((6-(5-chlorothiophen-2-yl)-5-fluoro-2-(2-fluoro-5H-pyrrolo[2,3-b]pyrazin-7-yl)pyrimidin-4-yl) amino)bicyclo[2.2.2]octane-2-carboxylic Acid To a solution of (2S,3S)-ethyl 3-((6-(5-chlorothiophen-2-yl)-5-fluoro-2-(2-fluoro-5H-pyrrolo[2,3-b]pyrazin-7-yl)pyrimidin-4-yl)amino)bicyclo[2.2.2]octane-2-carboxylate (290 mg, 0.53 mmol) in THF/MeOH/H$_2$O (v/v/v=1 mL/1 mL/1 mL) was added NaOH (212 mg, 5.32 mmol), and the mixture was stirred at rt overnight. To the reaction mixture was added saturated brine (10 mL), and the mixture was acidified with hydrochloric acid (1 M) to pH about 6. The resulting mixture was extracted with 2-methyltetrahydrofuran (15 mL×3). The combined organic layers were washed with saturated brine (50 mL), dried over anhydrous sodium sulfate, and filtered. The filtrate was concentrated in vacuo to remove the solvent, and the residue was purified by preparative thin-layer chromatography (DCM/MeOH (v/v)=15/1) to give the title compound as a light yellow solid (220 mg, 80%).

MS (ESI, pos. ion) m/z: 517.2 [M+H]$^+$;
HRMS (ESI, pos. ion) m/z: 517.1025, (C$_{23}$H$_{20}$ClF$_2$N$_6$O$_2$S)[M+H]$^+$ theoretical value: 517.1022;

$^1$H NMR (400 MHz, DMSO-d$_6$) δ (ppm): 12.74 (s, 1H), 12.25 (s, 1H), 8.51 (s, 1H), 8.27 (d, J=7.3 Hz, 1H), 7.74-7.64 (m, 2H), 7.29 (d, J=4.0 Hz, 1H), 4.65 (t, J=6.3 Hz, 1H), 2.84 (d, J=7.0 Hz, 1H), 2.09 (s, 1H), 1.97 (d, J=16.1 Hz, 2H), 1.73 (d, J=8.6 Hz, 2H), 1.62-1.32 (m, 6H).

Example 58: (2S,3S)-((ethoxycarbonyl)oxy)methyl 3-((5-fluoro-2-(2-fluoro-5H-pyrrolo[2,3-b]pyrazin-7-yl)-6-(thiophen-2-yl)pyrimidin-4-yl)amino)bicyclo[2.2.2]octane-2-carboxylate

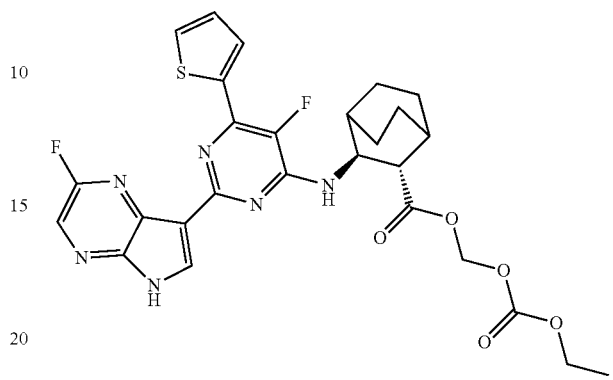

Step 1: (2S,3S)-((ethoxycarbonyl)oxy)methyl 3-((5-fluoro-2-(2-fluoro-5-trityl-5H-pyrrolo[2,3-b]pyrazin-7-yl)-6-(thiophen-2-yl)pyrimidin-4-yl)amino)bicyclo[2.2.2]octane-2-carboxylate To a mixed solvent of H$_2$O (0.2 mL) and 1,4-dioxane (10 mL) were added 2-fluoro-7-(4,4,5,5-tetramethyl-1,3,2-dioxaborolan-2-yl)-5-trityl-5H-pyrrolo[2,3-b]pyrazine (803 mg, 0.79 mmol, 50%), (2S,3S)-((ethoxycarbonyl)oxy)methyl 3-((2-bromo-5-fluoro-6-(thiophen-2-yl)pyrimidin-4-yl)amino)bicyclo[2.2.2]octane-2-carboxylate (400 mg, 0.76 mmol), potassium carbonate (313 mg, 2.27 mmol) and Pd(dppf)Cl$_2$ (123 mg, 0.15 mmol). The air in the mixture was exchanged with nitrogen by bubbling for 10 min. The mixture was stirred for 2 h at 110° C. by microwave heating. The reaction mixture was concentrated in vacuo and the residue was purified by silica gel column chromatography (PE/EtOAc (v/v)=5/1) to give the title compound as a yellow solid (500 mg, 80%).

$^1$H NMR (400 MHz, CD$_3$OD) δ (ppm): 8.50 (s, 1H), 7.92 (d, J=3.7 Hz, 1H), 7.80 (d, J=7.3 Hz, 1H), 7.66 (d, J=5.0 Hz, 1H), 7.37-7.25 (m, 15H), 7.24-7.21 (m, 1H), 5.72 (d, J=5.8 Hz, 1H), 5.66 (d, J=5.8 Hz, 1H), 4.13-4.04 (m, 2H), 2.80 (d, J=7.7 Hz, 1H), 1.92 (s, 1H), 1.82 (s, 2H), 1.67-1.47 (m, 6H), 1.34 (s, 4H), 1.14 (t, J=7.1 Hz, 3H).

Step 2: (2S,3S)-((ethoxycarbonyl)oxy)methyl 3-((5-fluoro-2-(2-fluoro-5H-pyrrolo[2,3-b]pyrazin-7-yl)-6-(thiophen-2-yl)pyrimidin-4-yl)amino)bicyclo[2.2.2]octane-2-carboxylate To a solution of (2S,3S)-((ethoxycarbonyl)oxy)methyl 3-((5-fluoro-2-(2-fluoro-5-trityl-5H-pyrrolo[2,3-b]pyrazin-7-yl)-6-(thiophen-2-yl)pyrimidin-4-yl) amino)bicyclo[2.2.2]octane-2-carboxylate (500 mg, 0.60 mmol) in dichloromethane (10 mL) were added Et$_3$SiH (0.97 mL, 6.05 mmol) and trifluoroacetic acid (0.45 mL, 6.05 mmol), and the mixture was stirred at rt overnight. The reaction mixture was added into saturated aqueous sodium carbonate (30 mL), and the resulting mixture was extracted with dichloromethane (20 mL×3). The combined organic layers were washed with saturated brine (50 mL), dried over anhydrous sodium sulfate, and filtered. The filtrate was concentrated in vacuo to give the title compound as a yellow solid (250 mg, 71%).

MS (ESI, pos. ion) m/z: 584.8[M+H]$^+$;

$^1$H NMR (400 MHz, DMSO-d$_6$) δ (ppm): 12.72 (s, 1H), 8.49 (d, J=2.2 Hz, 1H), 8.27 (d, J=7.2 Hz, 1H), 7.89 (s, 1H), 7.85 (d, J=4.7 Hz, 1H), 7.69 (d, J=6.1 Hz, 1H), 7.28 (d, J=3.9 Hz, 1H), 5.73 (d, J=5.9 Hz, 1H), 5.67 (d, J=6.0 Hz, 1H), 4.69 (s, 1H), 4.07 (d, J=6.8 Hz, 2H), 3.60 (s, 1H), 3.02 (d, J=6.7 Hz, 1H), 2.11 (s, 1H), 1.97 (s, 2H), 1.76 (d, J=3.7 Hz, 2H), 1.56-1.38 (m, 4H), 1.12 (t, J=7.0 Hz, 3H);

$^{13}$C NMR (151 MHz, DMSO-d$_6$) δ (ppm): 173.44, 158.21, 156.64, 155.90, 155.85, 153.66, 152.43, 152.35, 140.90, 140.48, 140.43, 140.38, 138.64, 138.40, 138.35, 134.86, 132.43, 132.33, 130.56, 129.78, 129.71, 129.00, 125.06, 124.76, 113.75, 82.44, 67.49, 64.78, 50.99, 47.79, 28.79, 28.52, 25.69, 25.59, 23.87, 21.31, 19.38, 14.26.

Example 59: (2S,3S)-((ethoxycarbonyl)oxy)methyl 3-((6-(5-chlorothiophen-2-yl)-5-fluoro-2-(2-fluoro-5H-pyrrolo[2,3-b]pyrazin-7-yl)pyrimidin-4-yl)amino)bicyclo[2.2.2]octane-2-carboxylate

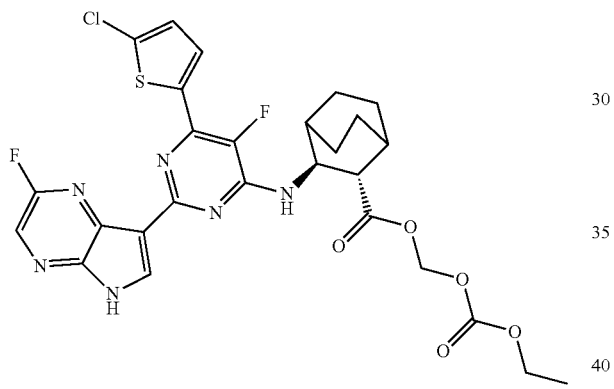

Step 1: (2S,3S)-((ethoxycarbonyl)oxy)methyl 3-((6-(5-chlorothiophen-2-yl)-5-fluoro-2-(2-fluoro-5-trityl-5H-pyrrolo[2,3-b]pyrazin-7-yl)pyrimidin-4-yl)amino)bicyclo[2.2.2]octane-2-carboxylate To a mixed solvent of H$_2$O (0.2 mL) and 1,4-dioxane (10 mL) were added 2-fluoro-7-(4,4,5,5-tetramethyl-1,3,2-dioxaborolan-2-yl)-5-trityl-5H-pyrrolo[2,3-b]pyrazine (685 mg, 0.75 mmol, 55%), (2S,3S)-((ethoxycarbonyl)oxy)methyl 3-((2-bromo-6-(5-chlorothiophen-2-yl)-5-fluoropyrimidin-4-yl)amino)bicyclo[2.2.2]octane-2-carboxylate (420 mg, 0.75 mmol), potassium carbonate (309 mg, 2.24 mmol) and Pd(dppf)Cl$_2$ (121 mg, 0.15 mmol). The air in the mixture was exchanged with nitrogen by bubbling for 10 min. The mixture was stirred for 2 h at 110° C. by microwave heating. The reaction mixture was concentrated in vacuo and the residue was purified by silica gel column chromatography (PE/EtOAc (v/v)=5/1) to give the title compound as a yellow solid (400 mg, 62%).

$^1$H NMR (400 MHz, DMSO-d$_6$) δ (ppm): 8.30 (s, 1H), 8.03 (d, J=7.5 Hz, 1H), 7.83 (d, J=6.7 Hz, 1H), 7.63 (d, J=3.4 Hz, 1H), 7.41-7.31 (m, 10H), 7.28 (d, J=4.1 Hz, 1H), 7.18 (d, J=7.1 Hz, 5H), 5.68 (dd, J=12.7, 6.1 Hz, 2H), 4.50 (t, J=6.9 Hz, 1H), 4.10-4.04 (m, 2H), 3.00 (d, J=7.5 Hz, 1H), 1.95 (s, 1H), 1.86 (s, 1H), 1.72 (d, J=8.7 Hz, 2H), 1.46 (m, 6H), 1.12 (t, J=7.1 Hz, 3H).

Step 2: (2S,3S)-((ethoxycarbonyl)oxy)methyl 3-((6-(5-chlorothiophen-2-yl)-5-fluoro-2-(2-fluoro-5H-pyrrolo[2,3-b]pyrazin-7-yl)pyrimidin-4-yl)amino)bicyclo[2.2.2]octane-2-carboxylate To a solution of ((2S,3S)-((ethoxycarbonyl)oxy)methyl 3-((6-(5-chlorothiophen-2-yl)-5-fluoro-2-(2-fluoro-5-trityl-5H-pyrrolo[2,3-b]pyrazin-7-yl) pyrimidin-4-yl)amino)bicyclo[2.2.2]octane-2-carboxylate (400 mg, 0.46 mmol) in dichloromethane (10 mL) were added Et$_3$SiH (0.74 mL, 4.64 mmol) and trifluoroacetic acid (0.35 mL, 4.64 mmol), and the mixture was stirred at rt overnight. The reaction mixture was added into saturated aqueous sodium carbonate (30 mL), and the resulting mixture was extracted with dichloromethane (30 mL×3). The combined organic layers were washed with saturated brine (60 mL), dried over anhydrous sodium sulfate, and filtered. The filtrate was concentrated in vacuo to give the title compound as a yellow solid (180 mg, 63%).

MS (ESI, pos. ion) m/z: 619.3[M+H]$^+$;

HRMS (ESI, pos. ion) m/z: 619.1371, (C$_{27}$H$_{26}$ClF$_2$N$_6$O$_5$S)[M+H]$^+$ theoretical value: 619.1342;

$^1$H NMR (400 MHz, DMSO-d$_6$) δ (ppm): 12.74 (s, 1H), 8.49 (s, 1H), 8.27 (d, J=7.2 Hz, 1H), 7.76 (d, J=5.9 Hz, 1H), 7.68 (d, J=3.3 Hz, 1H), 7.28 (d, J=3.8 Hz, 1H), 5.75-5.65 (m, 2H), 4.68 (s, 1H), 4.09-4.02 (m, 2H), 3.01 (d, J=6.7 Hz, 1H), 2.09 (s, 1H), 1.97 (d, J=7.0 Hz, 2H), 1.75 (d, J=11.1 Hz, 2H), 1.55-1.38 (m, 4H), 1.12 (t, J=7.0 Hz, 3H).

Example 60: (2S,3S)-3-((2-(2-chloro-5H-pyrrolo[2,3-b]pyrazin-7-yl)-5-fluoro-6-(1H-pyrrol-1-yl)pyrimidin-4-yl)amino)bicyclo[2.2.2]octane-2-carboxylic Acid

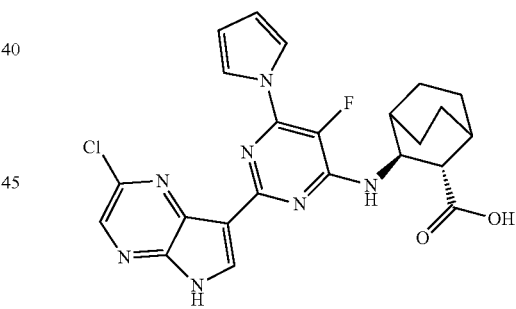

Step 1: 2,6-dichloro-5-fluoropyrimidin-4-amine

To a solution of NH$_3$ in EtOH (50 mL, 100 mmol, 2 mol/L) was added 2,4,6-trichloro-5-fluoropyrimidine (8.00 g, 39.7 mmol). The mixture was stirred at 100° C. for 1.5 h under nitrogen protection. The reaction mixture was concentrated in vacuo and the residue was purified by silica gel column chromatography (PE/EtOAc (v/v)=5/1) to give the title compound as a white solid (6.2 g, 86%).

MS (ESI, pos. ion) m/z: 181.9 [M+H]$^+$.

Step 2: 2-bromo-6-chloro-5-fluoropyrimidin-4-amine

To a solution of hydrobromic acid in acetic acid (1 mL, 1 mol/L) was added 2,6-dichloro-5-fluoropyrimidin-4-amine (100 mg, 0.55 mmol). The mixture was stirred at rt for 1 h. To the reaction mixture was added dropwise saturated aqueous sodium carbonate to pH about 8, and the resulting mixture was extracted with ethyl acetate (20 mL×2). The combined organic layers were washed with saturated brine (30 mL), dried over anhydrous sodium sulfate and filtered. The filtrate was concentrated in vacuo and the residue was purified by silica gel column chromatography (PE/EtOAc (v/v)=1/1) to give the title compound as a white solid (100 mg, 80.369%).

$^1$H NMR (400 MHz, DMSO-$d_6$) δ (ppm): 8.14 (s, 2H).

Step 3: 2-bromo-4-chloro-5-fluoro-6-(1H-pyrrol-1-yl)pyrimidine

To a solution of 2-bromo-6-chloro-5-fluoropyrimidin-4-amine (2.33 g, 10.3 mmol) in glacial acetic acid (10 mL) was added 2,5-dimethoxytetrahydrofuran (1.63 g, 12.3 mmol). The mixture was heated to 100° C. and stirred for 1.5 h. The mixture was concentrated in vacuo and the residue was purified by silica gel column chromatography (PE/EtOAc (v/v)=5/1) to give the title compound as a white solid (42 mg, 74%).

$^1$H NMR (400 MHz, CDCl$_3$) δ (ppm): 7.66 (d, J=1.5 Hz, 2H), 6.49-6.44 (m, 2H).

Step 4: (2S,3S)-ethyl 3-((2-bromo-5-fluoro-6-(1H-pyrrol-1-yl)pyrimidin-4-yl)amino)bicyclo[2.2.2]octane-2-carboxylate To DMF (2 mL) were added 2-bromo-4-chloro-5-fluoro-6-(1H-pyrrol-1-yl)pyrimidine (100 mg, 0.36 mmol) and (2S,3S)-ethyl 3-aminobicyclo[2.2.2]octane-2-carboxylate hydrochloride (78 mg, 10.60 mmol), then potassium carbonate (149 mg, 1.08 mmol) was added into the mixture. The mixture was stirred at 45° C. overnight. To the reaction mixture was added water (30 mL), and the resulting mixture was extracted with ethyl acetate (30 mL×2). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as colorless oil (52 mg, 33%).

MS (ESI, pos. ion) m/z: 439.0 [M+H]$^+$.

Step 5: (2S,3S)-ethyl 3-((2-(2-chloro-5-trityl-5H-pyrrolo[2,3-b]pyrazin-7-yl)-5-fluoro-6-(1H-pyrrol-1-yl)pyrimidin-4-yl)amino)bicyclo[2.2.2]octane-2-carboxylate To a mixed solvent of H$_2$O (0.2 mL, 10 mmol) and 1,4-dioxane (10 mL) were added 2-chloro-7-(4,4,5,5-tetramethyl-1,3,2-dioxaborolan-2-yl)-5-trityl-5H-pyrrolo[2,3-b]pyrazine (917 mg, 1.14 mmol, 65%), (2S,3S)-ethyl 3-((2-bromo-5-fluoro-6-(1H-pyrrol-1-yl) pyrimidin-4-yl)amino)bicyclo[2.2.2]octane-2-carboxylate (500 mg, 1.14 mmol), potassium carbonate (1.61 g, 4.76 mmol), X-phos (109 mg, 0.23 mmol) and Pd$_2$(dba)$_3$ (209 mg, 0.23 mmol). The air in the mixture was exchanged with nitrogen by bubbling for 10 min. The mixture was stirred for 2 h at 110° C. by microwave heating. The reaction mixture was concentrated in vacuo and the residue was purified by silica gel column chromatography (PE/EtOAc (v/v)=5/1) to give the title compound as a yellow solid (360 mg, 42%).

Step 6: (2S,3S)-ethyl 3-((2-(2-chloro-5H-pyrrolo[2,3-b]pyrazin-7-yl)-5-fluoro-6-(1H-pyrrol-1-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-5-fluoro-6-(1H-pyrrol-1-yl)pyrimidin-4-yl) amino)bicyclo[2.2.2]octane-2-carboxylate (660 mg, 0.88 mmol) in dichloromethane (10 mL) were added Et$_3$SiH (1.40 mL, 8.77 mmol) and trifluoroacetic acid (0.65 mL, 8.77 mmol), and the mixture was stirred at rt overnight. The reaction mixture was added into saturated aqueous sodium bicarbonate (30 mL). The resulting mixture was extracted with dichloromethane (30 mL×3). The combined organic layers were washed with saturated brine (20 mL), dried over anhydrous sodium sulfate, and filtered. The filtrate was concentrated in vacuo to give the title compound as a yellow solid (400 mg, 89%).

MS (ESI, pos. ion) m/z: 510.1 [M+H]$^+$.

Step 7: (2S,3S)-3-((2-(2-chloro-5H-pyrrolo[2,3-b]pyrazin-7-yl)-5-fluoro-6-(1H-pyrrol-1-yl) pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-5-fluoro-6-(1H-pyrrol-1-yl)pyrimidin-4-yl) amino)bicyclo[2.2.2]octane-2-carboxylate (400 mg, 0.78 mmol) in THF/MeOH/H$_2$O (v/v/v=1 mL/1 mL/1 mL) was added NaOH (313 mg, 7.84 mmol), and the mixture was stirred at rt overnight. To the reaction mixture was added saturated brine (30 mL), and the mixture was acidified with hydrochloric acid (1 M) to pH about 6. The resulting mixture was extracted with 2-methyltetrahydrofuran (30 mL×3). The combined organic layers were washed with saturated brine (50 mL), dried over anhydrous sodium sulfate, and filtered. The filtrate was concentrated in vacuo to remove the solvent, and the residue was purified by preparative thin-layer chromatography (DCM/MeOH (v/v)=15/1) to give the title compound as a light yellow solid (160 mg, 42%).

MS (ESI, pos. ion) m/z: 482.2 [M+H]$^+$;
HRMS (ESI, pos. ion) m/z: 482.1508, (C$_{23}$H$_{22}$ClFN$_7$O$_2$) [M+H]+ theoretical value: 482.1498;
$^1$H NMR (400 MHz, DMSO-$d_6$) δ (ppm): 12.81 (s, 1H), 12.21 (s, 1H), 8.63 (d, J=2.8 Hz, 1H), 8.39 (s, 1H), 7.76 (s, 2H), 7.65 (d, J=6.1 Hz, 1H), 6.40 (s, 2H), 4.67 (s, 1H), 2.85 (d, J=6.8 Hz, 1H), 2.08 (s, 1H), 1.99 (s, 1H), 1.78-1.70 (m, 2H), 1.56-1.34 (m, 6H).

Example 61: (2S,3S)-3-((2-(3-chloro-5H-pyrrolo[2,3-b]pyrazin-7-yl)-6-(5-chlorothiophen-2-yl)-5-fluoropyrimidin-4-yl)amino)bicyclo[2.2.2]octane-2-carboxylic Acid

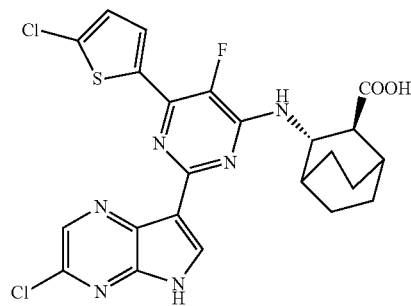 [SMILES: O=C(O)[C@H]1C2CCC(CC2)[C@@H]1Nc1nc(-c2c[nH]c3nc(Cl)cnc23)nc(-c2ccc(Cl)s2)c1F]

Step 1: (2S,3S)-ethyl 3-((2-(3-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate To a mixed solvent of 1,4-dioxane (3 mL) and H$_2$O (0.5 mL) was added 3-chloro-7-(4,4,5,5-tetramethyl-1,3,2-dioxaborolan-2-yl)-5-trityl-5H-pyrrolo[2,3-b]pyrazine (373 mg, 0.29 mmol, 40%), potassium carbonate (91 mg, 0.66 mmol), Pd(dppf)Cl$_2$ (35 mg, 0.04 mmol) and (2S,3S)-ethyl 3-((2-bromo-5-fluoro-6-(thiophen-2-yl)pyrimidin-4-yl)amino) bicyclo[2.2.2]octane-2-carboxylate (100 mg, 0.22 mmol). The air in the mixture was exchanged with nitrogen by bubbling for 10 min. The mixture was stirred for 2 h at 110° C. by microwave heating. The reaction mixture was filtered through a celite pad, and the filtrate was concentrated in vacuo. The residue was purified by silica gel column chromatography (PE/EtOAc (v/v)=2/1) to give the title compound as light yellow oil (169 mg, 100%).

$^1$H NMR (400 MHz, DMSO-d$_6$) δ(ppm): 8.54 (s, 1H), 8.29 (s, 1H), 7.82 (d, J=4.6 Hz, 2H), 7.70 (d, J=6.9 Hz, 1H), 7.36 (dt, J=6.7, 4.6 Hz, 10H), 7.19 (d, J=7.0 Hz, 5H), 4.50 (t, J=7.1 Hz, 1H), 4.03 (dd, J=7.1, 1.9 Hz, 2H), 2.89 (d, J=7.4 Hz, 1H), 1.94 (s, 1H), 1.85 (s, 1H), 1.71 (s, 2H), 1.46 (m), 1.11 (t, J=7.1 Hz, 3H).

Step 2: (2S,3S)-ethyl 3-((2-(3-chloro-5-trityl-5H-pyrrolo[2,3-b]pyrazin-7-yl)-6-(5-chlorothiophen-2-yl)-5-fluoropyrimidin-4-yl)amino)bicyclo[2.2.2]octane-2-carboxylate To a solution of (2S,3S)-ethyl 3-((2-(3-chloro-5-trityl-5H-pyrrolo[2,3-b]pyrazin-7-yl)-5-fluoro-6-(thiophen-2-yl)pyrimidin-4-yl)amino)bicyclo[2.2.2]octane-2-carboxylate (528 mg, 0.69 mmol) in DMF (6 mL) was added NCS (110 mg, 0.82 mmol), and the mixture was stirred at 100° C. overnight. To the reaction mixture was added saturated brine (30 mL), and the resulting mixture was extracted with ethyl acetate (30 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=10/1) to give the title compound as a light yellow solid (98 mg, 18%).

$^1$H NMR (400 MHz, CDCl$_3$) δ(ppm): 8.51 (s, 1H), 8.40 (s, 1H), 7.64 (s, 1H), 7.34-7.30 (m, 10H), 7.24 (m, 5H), 6.99 (d, J=4.0 Hz, 1H), 5.10 (d, J=6.6 Hz, 1H), 4.59 (t, J=6.9 Hz, 1H), 4.06 (m, 2H), 2.37-2.32 (m, 2H), 2.31 (s, 2H), 2.24 (d, J=3.0 Hz, 2H), 2.02 (s, 1H), 1.70 (m, 4H), 1.16 (d, J=7.1 Hz, 3H).

Step 3: (2S,3S)-ethyl 3-((2-(3-chloro-5H-pyrrolo[2,3-b]pyrazin-7-yl)-6-(5-chlorothiophen-2-yl)-5-fluoropyrimidin-4-yl) amino)bicyclo[2.2.2]octane-2-carboxylate To a solution of (2S,3S)-ethyl 3-((2-(3-chloro-5-trityl-5H-pyrrolo[2,3-b]pyrazin-7-yl)-6-(5-chlorothiophen-2-yl)-5-fluoropyrimidin-4-yl)amino)bicyclo[2.2.2]octane-2-carboxylate (98 mg, 0.12 mmol) in dichloromethane (3 mL) were added Et$_3$SiH (142 mg, 1.22 mmol) and trifluoroacetic acid (142 mg, 1.22 mmol), and the mixture was stirred at rt overnight. The reaction mixture was added into saturated aqueous sodium carbonate (30 mL), and the resulting mixture was extracted with dichloromethane (30 mL×3). The combined organic layers were washed with saturated brine (60 mL), dried over anhydrous sodium sulfate, and filtered. The filtrate was concentrated in vacuo to give the title compound as a yellow solid (62 mg, 91%).

MS (ESI, pos. ion) m/z: 561.1[M+H]$^+$.

Step 4: (2S,3S)-3-((2-(3-chloro-5H-pyrrolo[2,3-b]pyrazin-7-yl)-6-(5-chlorothiophen-2-yl)-5-fluoropyrimidin-4-yl) amino)bicyclo[2.2.2]octane-2-carboxylic Acid To a solution of (2S,3S)-ethyl 3-((2-(3-chloro-5H-pyrrolo[2,3-b]pyrazin-7-yl)-6-(5-chlorothiophen-2-yl)-5-fluoropyrimidin-4-yl) amino)bicyclo[2.2.2]octane-2-carboxylate (62 mg, 0.11 mmol) in THF/MeOH/H$_2$O (v/v/v=1 mL/1 mL/1 mL) was added a solution of NaOH (45 mg, 1.10 mmol) in water (1 mL), and the mixture was stirred at rt overnight. To the reaction mixture was added saturated brine (30 mL), and the mixture was acidified with hydrochloric acid (1 M) to pH about 6. The resulting mixture was extracted with 2-methyltetrahydrofuran (30 mL×3). The combined organic layers were washed with saturated brine (50 mL), dried over anhydrous sodium sulfate, and filtered. The filtrate was concentrated in vacuo to remove the solvent, and the residue was purified by preparative thin-layer chromatography (DCM/MeOH (v/v)=15/1) to give the title compound as a light yellow solid (36 mg, 61%).

MS (ESI, pos. ion) m/z: 533.0 [M+H]$^+$;
HRMS (ESI, pos. ion) m/z: 533.0745, (C$_{23}$H$_{20}$Cl$_2$FN$_6$O$_2$S)[M+H]+ theoretical value: 533.0730;
$^1$H NMR (400 MHz, DMSO-d$_6$) δ (ppm): 12.78 (s, 1H), 8.62 (s, 1H), 8.43 (s, 1H), 7.71 (d, J=6.5 Hz, 1H), 7.67 (d, J=3.8 Hz, 1H), 7.28 (d, J=4.0 Hz, 1H), 4.62 (s, 1H), 3.61 (d, J=6.3 Hz, 1H), 2.83 (d, J=7.0 Hz, 1H), 2.05 (s, 1H), 1.99 (s, 1H), 1.74-1.35 (m, 8H).

Example 62: (2S,3S)-3-((2-(2-chloro-5H-pyrrolo[2,3-b]pyrazin-7-yl)-5-fluoro-6-(5-fluorothiophen-2-yl) pyrimidin-4-yl)amino)bicyclo[2.2.2]octane-2-carboxylic Acid

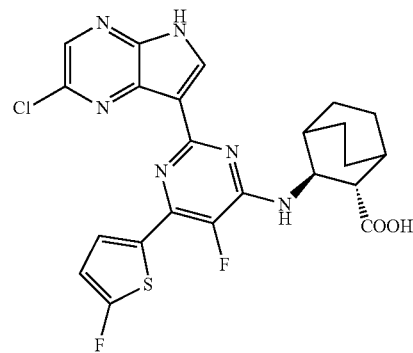 [SMILES: O=C(O)[C@H]1C2CCC(CC2)[C@@H]1Nc1nc(-c2c[nH]c3ncc(Cl)nc23)nc(-c2ccc(F)s2)c1F]

Step 1: (2S,3S)-ethyl 3-aminobicyclo[2.2.2]octane-2-carboxylate hydrochloride The title compound was prepared by the synthetic method disclosed in patent application WO 2015073491.

Step 2: 2,4-dichloro-5-fluoro-6-(5-fluorothiophen-2-yl)pyrimidine

To a solution of 2-fluorothiophene (1.65 g, 16.20 mmol) in anydrous tetrahydrofuran (20 mL) was added n-butyllithium (6.50 mL, 16.20 mmol, 2.5 mol/L) at −15° C., and the mixture was stirred for 1 h at −15° C. Then to the mixture was added dichloro(N,N,N',N'-tetramethylethylenediamine) zinc(II) (1.36 g, 5.33 mmol), and the resulting mixture was stirred for 1 h. Then palladium dichloride (290 mg, 1.62 mmol), triphenylphosphine (850 mg, 3.23 mmol) and 5-fluoro-2,4,6-trichloropyrimidine (3.60 g, 17.80 mmol) were added to the mixture in turn. The resulting mixture was heated to 55° C. under nitrogen protection, and then stirred at this temperature overnight. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a white solid (1.33 g, 31%).

Step 3: (2S,3S)-ethyl 3-((2-chloro-5-fluoro-6-(5-fluorothiophen-2-yl)pyrimidin-4-yl)amino)bicyclo[2.2.2]octane-2-carboxylate To a solution of (2S,3S)-ethyl 3-aminobicyclo[2.2.2]octane-2-carboxylate hydrochloride (1.39 g, 5.94 mmol) and 2,4-dichloro-5-fluoro-6-(5-fluorothiophen-2-yl) pyrimidine (1.32 g, 4.95 mmol) in DMF (30 mL) was added potassium carbonate (1.31 g, 9.91 mmol), and the mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (1.69 g, 79%).

MS (ESI, pos.ion) m/z: 428.2 [M+H]$^+$.

Step 4: (2S,3S)-ethyl 3-((2-bromo-5-fluoro-6-(5-fluorothiophen-2-yl)pyrimidin-4-yl)amino)bicyclo[2.2.2]octane-2-carboxylate To a solution of hydrobromic acid (599 mg, 2.41 mmol) in acetic acid (6 mL) was added (2S,3S)-ethyl 3-((2-chloro-5-fluoro-6-(5-fluorothiophen-2-yl)pyrimidin-4-yl)amino)bicyclo[2.2.2]octane-2-carboxylate (860 mg, 2.01 mmol), and the mixture was stirred at rt for 4 h. The reaction mixture was added into ice-water (40 mL), and the resulting mixture was extracted with EtOAc (30 mL×3). The combined organic layers were washed with saturated aqueous sodium bicarbonate (80 mL) and saturated brine (30 mL), dried over anhydrous Na$_2$SO$_4$, and filtered. The filtrate was concentrated in vacuo to give the title compound as a light yellow solid (922 mg, 97%).

MS (ESI, pos.ion) m/z: 474.1 [M+H]$^+$.

Step 5: (2S,3S)-ethyl 3-((2-(2-chloro-5-trityl-5H-pyrrolo[2,3-b]pyrazin-7-yl)-5-fluoro-6-(5-fluorothiophen-2-yl)pyrimidin-4-yl)amino)bicyclo[2.2.2]octane-2-carboxylate To a mixed solvent of 1,4-dioxane (8 mL) and H$_2$O (1 mL) were added 2-chloro-7-(4,4,5,5-tetramethyl-1,3,2-dioxaborolan-2-yl)-5-trityl-5H-pyrrolo[2,3-b]pyrazine (1.55 g, 2.14 mmol, 60%), K$_2$CO$_3$ (810 mg, 5.84 mmol), PdCl$_2$(dppf) (190 mg, 0.19 mmol) and (2S,3S)-ethyl 3-((2-bromo-5-fluoro-6-(5-fluorothiophen-2-yl)pyrimidin-4-yl)amino)bicyclo[2.2.2]octane-2-carboxylate (920 mg, 1.95 mmol). The air in the mixture was exchanged with nitrogen by bubbling for 10 min. The mixture in the sealed tub was stirred for 3 h at 115° C. The mixture was filtered to remove the solid impuries, and the solvent was removed. The residue was purified by silica gel column chromatography (PE/EtOAc (v/v)=10/1-5/1) to give the title compound as a white solid (1.35 g, 99%).

Step 6: (2S,3S)-ethyl 3-((2-(2-chloro-5H-pyrrolo[2,3-b]pyrazin-7-yl)-5-fluoro-6-(5-fluorothiophen-2-yl)pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-5-fluoro-6-(5-fluorothiophen-2-yl)pyrimidin-4-yl)amino)bicyclo[2.2.2]octane-2-carboxylate (1.35 g, 1.71 mmol) in dichloromethane (6 mL) were added Et$_3$SiH (2.70 mL, 17.10 mmol) and TFA (1.35 mL, 17.10 mmol), and the mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (100 mL), dried over anhydrous sodium sulfate, and filtered. The filtrate was concentrated in vacuo, and the residue was purified by silica gel column chromatography (DCM/MeOH (v/v)=10/1) to give the title compound as a white solid (522 mg, 56%).

MS (ESI, pos. ion) m/z: 545.0 [M+H]$^+$.

Step 7: (2S,3S)-3-((2-(2-chloro-5H-pyrrolo[2,3-b]pyrazin-7-yl)-5-fluoro-6-(5-fluorothiophen-2-yl)pyrimidin-4-yl) amino)bicyclo[2.2.2]octane-2-carboxylic Acid To a solution of (2S,3S)-ethyl 3-((2-(2-chloro-5H-pyrrolo[2,3-b]pyrazin-7-yl)-5-fluoro-6-(5-fluorothiophen-2-yl)pyrimidin-4-yl)amino)bicyclo[2.2.2]octane-2-carboxylate (522 mg, 0.96 mmol) in THF/MeOH (v/v=5 mL/5 mL) was added a solution of NaOH (388 mg, 9.60 mmol) in water (5 mL), and the mixture was stirred at rt overnight. To the reaction mixture was added water (30 mL), and the mixture was acidified with hydrochloric acid (1 M) to pH about 6. The resulting mixture was extracted with EtOAc (30 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (200 mg, 40%).

MS (ESI, pos. ion) m/z: 517.0 [M+H]$^+$;

HRMS (ESI, pos. ion) m/z: 517.1027, (C$_{23}$H$_{20}$F$_2$ClN$_6$O$_2$S)[M+H]$^+$ theoretical value: 517.1025;

$^1$H NMR (600 MHz, DMSO-d$_6$) δ (ppm) 13.17 (s, 1H), 8.54 (s, 1H), 8.49 (s, 1H), 8.33 (s, 1H), 7.38 (s, 1H), 6.82 (d, J=3.0 Hz, 1H), 6.52 (s, 1H), 4.47 (s, 1H), 2.43 (s, 1H), 1.93 (m, 2H), 1.87-1.28 (m, 9H).

Example 63: (2S,3S)-3-((2-(2-chloro-5H-pyrrolo[2,3-b]pyrazin-7-yl)-6-(5-cyanothiophen-2-yl)-5-fluoropyrimidin-4-yl)amino)bicyclo[2.2.2]octane-2-carboxylic acid

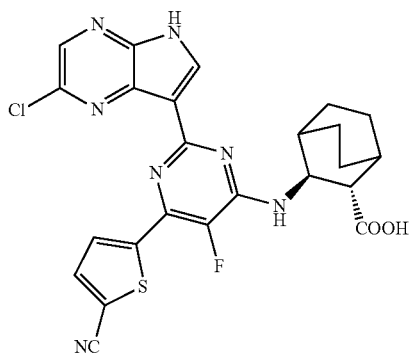 [SMILES: N#Cc1ccc(-c2nc(-c3c[nH]c4ncc(Cl)nc34)nc(N[C@H]3C4CCC(CC4)[C@@H]3C(=O)O)c2F)s1]

Step 1: (2S,3S)-ethyl 3-aminobicyclo[2.2.2]octane-2-carboxylate hydrochloride The title compound was prepared by the synthetic method disclosed in patent application WO 2015073491.

Step 2: (2S,3S)-ethyl 3-((2,6-dichloro-5-fluoropyrimidin-4-yl)amino)bicyclo[2.2.2]octane-2-carboxylate A suspension of 2,4,6-trichloro-5-fluoropyrimidine (2.34 g, 11.70 mmol), (2S,3S)-ethyl 3-aminobicyclo[2.2.2]octane-2-carboxylate hydrochloride (2.48 g, 10.60 mmol) and $K_2CO_3$ (2.95 g, 21.30 mmol) in DMF (5 mL) was stirred at rt overnight. To the reaction mixture was added water (100 mL), and the resulting mixture was extracted with ethyl acetate (80 mL×3). The combined organic layers were washed with saturated brine (150 mL×3), dried over anhydrous sodium sulfate and filtered. The filtrate was concentrated in vacuo and the residue was purified by silica gel column chromatography (PE/EtOAc (v/v)=5/1) to give the title compound as a white solid (2.22 g, 58%).

MS (ESI, pos. ion) m/z: 362.1 [M+H]$^+$.

Step 3: (2S,3S)-ethyl 3-((2-chloro-6-(5-cyanothiophen-2-yl)-5-fluoropyrimidin-4-yl)amino)bicyclo[2.2.2]octane-2-carboxylate To a mixed solvent of 1,4-dioxane (8 mL) and $H_2O$ (1 mL) were added (5-cyanothiophen-2-yl)boronic acid (564 mg, 3.68 mmol), $Na_2CO_3$ (1.06 g, 10.05 mmol), $PdCl_2(PPh_3)_2$ (474 mg, 0.67 mmol) and (2S,3S)-ethyl 3-((2,6-dichloro-5-fluoropyrimidin-4-yl) amino)bicyclo[2.2.2]octane-2-carboxylate (1.21 g, 3.35 mmol). The air in the mixture was exchanged with nitrogen by bubbling for 10 min. The mixture in sealed tub was stirred for 30 min at 140° C. The mixture was filtered to remove the solid impurities, and the solvent was removed. The residue was purified by silica gel column chromatography (PE/EtOAc (v/v)=10/1-5/1) to give the title compound as a white solid (361 mg, 25%).

$^1$H NMR (400 MHz, CDCl$_3$) δ(ppm): 7.79-7.76 (m, 1H), 7.66 (d, J=4.0 Hz, 1H), 5.45 (d, J=5.5 Hz, 1H), 4.56 (t, J=5.4 Hz, 1H), 4.24 (q, J=7.1 Hz, 2H), 2.41 (d, J=5.8 Hz, 1H), 1.92 (s, 1H), 1.85 (s, 1H), 1.70 (m, 8H), 1.30-1.27 (m, 3H).

Step 4: (2S,3S)-ethyl 3-((2-bromo-6-(5-cyanothiophen-2-yl)-5-fluoropyrimidin-4-yl)amino)bicyclo[2.2.2]octane-2-carboxylate To a solution of hydrobromic acid in acetic acid (140 mg, 0.55 mmol, 33%) was added (2S,3S)-ethyl 3-((2-chloro-6-(5-cyanothiophen-2-yl)-5-fluoropyrimidin-4-yl) amino)bicyclo[2.2.2]octane-2-carboxylate (200 mg, 0.46 mmol), and the mixture was stirred at rt for 3 h. The reaction mixture was added into ice-water (40 mL), and the resulting mixture was extracted with EtOAc (40 mL×3). The combined organic layers were washed with saturated aqueous sodium bicarbonate (80 mL) and saturated brine (80 ml), dried over anhydrous $Na_2SO_4$, and filtered. The filtrate was concentrated in vacuo to give the title compound as a light yellow solid (220 mg, 100%).

MS (ESI, pos.ion) m/z: 479.0 [M+H]$^+$.

Step 5: (2S,3S)-ethyl 3-((2-(2-chloro-5-trityl-5H-pyrrolo[2,3-b]pyrazin-7-yl)-6-(5-cyanothiophen-2-yl)-5-fluoropyrimidin-4-yl) amino)bicyclo[2.2.2]octane-2-carboxylate To a mixed solvent of 1,4-dioxane (8 mL) and $H_2O$ (1 mL) was added 2-chloro-7-(4,4,5,5-tetramethyl-1,3,2-dioxaborolan-2-yl)-5-trityl-5H-pyrrolo[2,3-b]pyrazine (474 mg, 0.53 mmol, 60%), $K_2CO_3$(206 mg, 1.43 mmol), PdCl$_2$(dppf) (40 mg, 0.05 mmol) and (2S,3S)-ethyl 3-((2-bromo-6-(5-cyanothiophen-2-yl)-5-fluoropyrimidin-4-yl)amino)bicyclo[2.2.2]octane-2-carboxylate (229 mg, 0.48 mmol). The air in the mixture was exchanged with nitrogen by bubbling for 10 min. The mixture in the sealed tub was stirred for 3 h at 115° C. The mixture was filtered to remove the solid impuries, and the solvent was removed. The residue was purified by silica gel column chromatography (PE/EtOAc (v/v)=10/1-5/1) to give the title compound as a white solid (131 mg, 35%).

$^1$H NMR (400 MHz, CDCl$_3$) δ(ppm): 8.41 (s, 1H), 7.96 (s, 1H), 7.82 (d, J=3.2 Hz, 1H), 7.68 (d, J=4.0 Hz, 1H), 7.38-7.29 (m, 10H), 7.22 (dd, J=6.3, 3.3 Hz, 5H), 5.18 (s, 1H), 4.66 (t, J=7.1 Hz, 1H), 4.12-4.05 (m, 2H), 2.35 (d, J=7.2 Hz, 1H), 2.09 (s, 1H), 1.68 (m, 5H), 1.28 (s, 4H), 1.18 (t, J=7.1 Hz, 3H).

Step 6: (2S,3S)-ethyl 3-((2-(2-chloro-5H-pyrrolo[2,3-b]pyrazin-7-yl)-6-(5-cyanothiophen-2-yl)-5-fluoropyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-6-(5-cyanothiophen-2-yl)-5-fluoropyrimidin-4-yl) amino)bicyclo[2.2.2]octane-2-carboxylate (131 mg, 0.16 mmol) in dichloromethane (6 mL) were added Et$_3$SiH (191 mg, 1.65 mmol) and TFA (191 mg, 1.65 mmol), and the mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (100 mL), dired over anhydrous sodium sulfate, and filtered. The filtrate was concentrated in vacuo, and the residue was purified by silica gel column chromatography (DCM/MeOH (v/v)=10/1) to give the title compound as a white solid (85 mg, 93%).

MS (ESI, pos. ion) m/z: 552.1 [M+H]$^+$.

Step 7: (2S,3S)-3 (2-chloro-5H-pyrrolo[2,3-b]pyrazin-7-yl)-6-(5-cyanothiophen-2-yl)-5-fluoropyrimidin-4-yl) amino)bicyclo[2.2.2]octane-2-carboxylic Acid To a solution of (2S,3S)-ethyl 3-((2-(2-chloro-5H-pyrrolo[2,3-b]pyrazin-7-yl)-6-(5-cyanothiophen-2-yl)-5-fluoropyrimidin-4-yl) amino)bicyclo[2.2.2]octane-2-carboxylate (96 mg, 0.17 mmol) in THF/MeOH (v/v=5 mL/5 mL) was added a solution of LiOH (4 mg, 0.21 mmol) in water (5 mL), and the mixture was stirred at rt overnight. To the reaction mixture was added water (40 mL), and the mixture was acidified with hydrochloric acid (1 M) to pH about 6. The resulting mixture was extracted with EtOAc (30 mL×3). The combined organic layers were washed with saturated brine (50 mL), dried over anhydrous sodium sulfate, and filtered. The filtrate was concentrated in vacuo, and the residue was purified by silica gel column chromatography (DCM/MeOH (v/v)=10/1-5/1) to give the title compound as a white solid (28 mg, 31%).

MS (ESI, pos. ion) m/z: 524.1 [M+H]$^+$;
HRMS (ESI, pos. ion) m/z: 524.1037, ($C_{24}H_{20}FClN_7O_2S$)[M+H]$^+$ theoretical value: 524.1072;
$^1$H NMR (600 MHz, DMSO-$d_6$) δ (ppm): 8.54 (s, 1H), 8.38 (s, 1H), 8.08 (d, J=4.1 Hz, 1H), 7.89 (s, 1H), 7.88 (s, 1H), 4.68 (t, J=6.8 Hz, 1H), 3.59 (d, J=6.6 Hz, 1H), 2.86 (d, J=7.4 Hz, 1H), 2.08 (s, 1H), 2.02 (d, J=12.2 Hz, 3H), 1.78-1.74 (m, 2H), 1.49 (m, 4H).

Example 64: (2S,3S)-3-((5-fluoro-2-(5H-pyrrolo[2,3-b]pyrazin-7-yl)-6-(thiophen-2-yl)pyrimidin-4-yl) amino)bicyclo[2.2.2]octane-2-carboxylic Acid

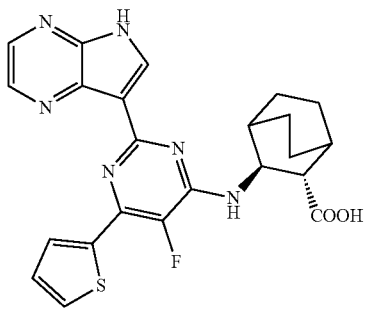 [SMILES: O=C(O)[C@H]1C2CCC(CC2)[C@@H]1Nc1nc(-c2c[nH]c3nccnc23)nc(-c2cccs2)c1F]

Step 1: 7-iodo-5H-pyrrolo[2,3-b]pyrazine

To a solution of 5H-pyrrolo[2,3-b]pyrazine (500 mg, 4.20 mmol) in 2-methyltetrahydrofuran (8 mL) was added NIS (1.13 g, 5.04 mmol), and the reaction mixture was stirred at rt overnight. Saturated aqueous sodium thiosulfate (50 mL) was added to quench the reaction, and the resulting mixture was partitioned. The aqueous layer was extracted with EtOAc (50 mL×2). The combined organic layers were washed with saturated brine (80 mL), dried over anhydrous $Na_2SO_4$, filtered, and the filtrate was concentrated in vacuo. The residue was purified by silica gel chromatograph (PE/EtOAc (v/v)=20/1-4/1) to give the title compound as a yellow solid (965 mg, 94%).

MS (ESI, pos. ion) m/z: 246.0 [M+H]$^+$;
$^1$H NMR (600 MHz, DMSO-$d_6$) δ (ppm) 12.51 (s, 1H), 8.46 (d, J=2.5 Hz, 1H), 8.29 (d, J=2.5 Hz, 1H), 8.11 (d, J=2.5 Hz, 1H).

Step 2: 7-iodo-5-trityl-5H-pyrrolo[2,3-b]pyrazine

To a stirred 0° C. solution of 7-iodo-5H-pyrrolo[2,3-b]pyrazine (937 mg, 3.82 mmol) in DMF (8 mL) was added slowly NaH (60%, 185 mg, 4.59 mmol), then triphenylchloromethane (1.18 g, 4.21 mmol) was added. The resulting mixture was warmed to rt and stirred overnight. The reaction was stopped, and the reaction mixture was added into water (100 mL). The resulting mixture was extracted with ethyl acetate (100 mL×3). The combined organic layers were washed with saturated brine (150 mL×3), dried over anhydrous sodium sulfate, and filtered. The filtrate was concentrated in vacuo, and the residue was purified by silica gel column chromatography (PE/EA (v/v)=20/1) to give the title compound as a light yellow solid (1.55 g, 83%).

$^1$H NMR (400 MHz, CDCl$_3$) δ(ppm): 8.40 (d, J=2.5 Hz, 1H), 7.98 (d, J=2.5 Hz, 1H), 7.65 (s, 1H), 7.34-7.29 (m, 10H), 7.20-7.17 (m, 5H).

Step 3: 7-(4,4,5,5-tetramethyl-1,3,2-dioxaborolan-2-yl)-5-trityl-5H-pyrrolo[2,3-b]pyrazine A solution of 7-iodo-5-trityl-5H-pyrrolo[2,3-b]pyrazine (500 mg, 1.03 mmol) and isopropoxyboronic acid pinacol ester (250 mg, 1.33 mmol) in THF (10 mL) was cooled to −27° C. and stirred under nitrogen protection, then isopropylmagnesium chloride solution (2 M, 0.70 mL) was added dropwise slowly. The reaction was stopped, and the reaction mixture was added into saturated aqueous sodium bicarbonate (100 mL). The resulting mixture was extracted with ethyl acetate (100 mL×3). The combined organic layers were concentrated in vacuo, and the residue was purified by silica gel column chromatography (PE/EtOAc (v/v)=10/1) to give the title compound as a yellow solid (383 mg, 77%).

MS (ESI, pos. ion) m/z: 488.3 [M+H]$^+$.

Step 4: (2S,3S)-ethyl 3-((5-fluoro-6-(thiophen-2-yl)-2-(5-trityl-5H-pyrrolo[2,3-b]pyrazin-7-yl)pyrimidin-4-yl)amino)bicyclo[2.2.2]octane-2-carboxylate To a mixed solvent of 1,4-dioxane (8 mL) and H$_2$O (1 mL) were added 7-(4,4,5,5-tetramethyl-1,3,2-dioxaborolan-2-yl)-5-trityl-5H-pyrrolo[2,3-b]pyrazine (118 mg, 0.29 mmol), potassium carbonate (91 mg, 0.66 mmol), PdCl$_2$ (dppf) (35 mg, 0.04 mmol) and (2S,8S)-ethyl 3-((2-bromo-5-fluoro-6-(thiophen-2-yl)pyrimidin-4-yl)amino)bicyclo[2.2.2]octane-2-carboxylate (100 mg, 0.22 mmol). The air in the mixture was exchanged with nitrogen by bubbling for 10 min. The mixture was stirred for 2 h at 110° C. by microwave heating. The mixture was filtered through a celite pad. The filtrate was concentrated in vacuo, and the residue was purified by silica gel column chromatography (PE/EtOAc (v/v)=10/1-5/1) to give the title compound as a white solid (137 mg, 85%).

$^1$H NMR (400 MHz, CDCl$_3$) δ (ppm): 8.53 (d, J=2.5 Hz, 1H), 8.42 (s, 1H), 7.97 (d, J=2.4 Hz, 1H), 7.92 (d, J=2.7 Hz, 1H), 7.55 (d, J=4.2 Hz, 1H), 7.32-7.29 (m, 10H), 7.24 (dd, J=6.9, 2.9 Hz, 6H), 5.10 (d, J=5.9 Hz, 1H), 4.59 (t, J=7.2 Hz, 1H), 4.18-4.08 (m, 2H), 2.34 (d, J=7.4 Hz, 1H), 2.04 (s, 1H), 1.74-1.62 (m, 9H), 1.16 (t, J=7.1 Hz, 3H).

Step 5: (2S,3S)-ethyl 3-((5-fluoro-2-(5H-pyrrolo[2,3-b]pyrazin-7-yl)-6-(thiophen-2-yl)pyrimidin-4-yl) amino)bicyclo[2.2.2]octane-2-carboxylate To a solution of (2S,3S)-ethyl 3-((5-fluoro-6-(thiophen-2-yl)-2-(5-trityl-5H-pyrrolo[2,3-b]pyrazin-7-yl)pyrimidin- 4-yl)amino)bicyclo[2.2.2]octane-2-carboxylate (188 mg, 0.26 mmol) in dichloromethane (5 mL) were added Et₃SiH (0.41 mL, 2.56 mmol) and TFA (0.19 mL, 2.56 mmol), and the mixture was stirred at rt overnight. The reaction was stopped, and the reaction mixture was added into saturated aqueous sodium bicarbonate (50 mL). The resulting mixture was extracted with dichloromethane (60 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (126 mg, 100%).

MS (ESI, pos. ion) m/z: 493.1 [M+H]⁺.

Step 6: (2S,3S)-3-((5-fluoro-2-(5H-pyrrolo[2,3-b]pyrazin-7-yl)-6-(thiophen-2-yl)pyrimidin-4-yl)amino)bicyclo[2.2.2]octane-2-carboxylic Acid To a solution of (2S,3S)-ethyl 3-((5-fluoro-2-(5H-pyrrolo[2,3-b]pyrazin-7-yl)-6-(thiophen-2-yl)pyrimidin-4-yl)amino)bicyclo[2.2.2]octane-2-carboxylate (180 mg, 0.37 mmol) in THF/MeOH (v/v=5 mL/5 mL) was added a solution of NaOH (146 mg, 3.65 mmol) in water (2 mL), and the mixture was stirred at rt overnight. To the reaction mixture was added water (30 mL), and the mixture was acidified with hydrochloric acid (1 M) to pH about 6. The resulting mixture was extracted with EtOAc (30 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a yellow solid (58 mg, 34%).

MS (ESI, pos. ion) m/z: 465.1 [M+H]⁺;
HRMS (ESI, pos. ion) m/z: 465.1495, ($C_{23}H_{22}FN_6O_2S$) [M+H]⁺ theoretical value: 465.1509;
¹H NMR (400 MHz, DMSO-$d_6$) δ (ppm): 12.58 (s, 1H), 8.55 (d, J=2.4 Hz, 1H), 8.40 (s, 1H), 8.29 (d, J=2.4 Hz, 1H), 7.88 (d, J=3.4 Hz, 1H), 7.83 (d, J=5.0 Hz, 1H), 7.60 (d, J=6.3 Hz, 1H), 7.31-7.25 (m, 1H), 4.65 (t, J=6.4 Hz, 1H), 2.83 (d, J=6.6 Hz, 1H), 2.09 (s, 1H), 2.00 (s, 1H), 1.82-1.29 (m, 8H);
¹³C NMR (151 MHz, DMSO-$d_6$) δ (ppm): 156.39, 156.34, 152.48, 152.41, 142.35, 140.42, 140.30, 140.25, 139.88, 138.68, 138.56, 138.51, 137.52, 137.28, 133.39, 130.40, 130.37, 129.63, 129.56, 128.93, 114.29, 51.45, 48.19, 28.86, 28.57, 25.95, 24.12, 21.73, 19.59.

Example 65: (2S,3S)-3-((2-(2-chloro-5H-pyrrolo[2,3-b]pyrazin-7-yl)-7-(1,3-difluoropropan-2-yl)-7H-pyrrolo[2,3-d]pyrimidin-4-yl)amino)bicyclo[2.2.2]octane-2-carboxylic Acid

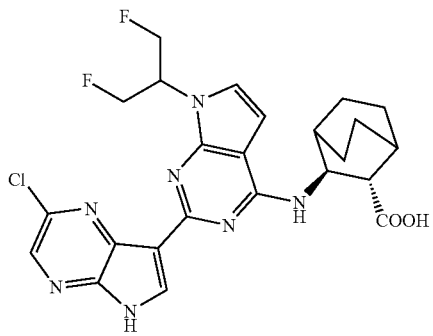 [SMILES: O=C(O)[C@H]1C2CCC(CC2)[C@@H]1Nc1nc(-c2c[nH]c3ncc(Cl)nc23)nc2c1ccn2C(CF)CF]

Step 1: 2,4-dichloro-7-(1,3-difluoropropan-2-yl)-7H-pyrrolo[2,3-d]pyrimidine

To DCM (30 mL) were added 2,4-dichloro-7H-pyrrolo[2,3-d]pyrimidine (1.00 g, 5.32 mmol), triphenylphosphine (2.09 g, 7.98 mmol) and 1,3-difluoropropan-2-ol (0.62 g, 6.38 mmol). The mixture was cooled to 0° C., then DIAD (1.61 g, 7.98 mmol) was dropwised slowly into the mixture. After the addition, the resulting mixture was warmed to rt and stirred overnight. To the reaction mixture was added water (50 mL), and the resulting mixture was extracted with DCM (50 mL×3). The combined organic layers were washed with saturated brine (100 mL), dried over anhydrous sodium sulfate and filtered. The filtrate was concentrated in vacuo and the residue was purified by silica gel column chromatography (PE/EtOAc (v/v)=100/1) to give the title compound as a white solid (1.08 g, 76%).

MS (ESI, pos. ion) m/z: 266.1 [M+H]⁺.

Step 2: (2S,3S)-ethyl 3-((2-chloro-7-(1,3-difluoropropan-2-yl)-7H-pyrrolo[2,3-d]pyrimidin-4-yl)amino)bicyclo[2.2.2]octane-2-carboxylate To DMF (20 mL) were added 2,4-dichloro-7-(1,3-difluoropropan-2-yl)-7H-pyrrolo[2,3-d]pyrimidine (1.08 g, 4.06 mmol), potassium carbonate (1.68 g, 12.20 mmol), (2S,3S)-ethyl 3-aminobicyclo[2.2.2]octane-2-carboxylate hydrochloride (1.24 g, 5.28 mmol). The mixture was stirred at 80° C. for 24 h. After the reaction was completed, to the reaction mixture was added water (30 mL), and the resulting mixture was extracted with ethyl acetate (30 mL×3). The combined organic layers were washed with saturated brine (20 mL), dried over anhydrous sodium sulfate and filtered. The filtrate was concentrated in vacuo and the residue was purified by silica gel column chromatography (PE/EtOAc (v/v)=20/1) to give the title compound as a white solid (1.62 g, 93%).

MS (ESI, pos. ion) m/z: 427.1 [M+H]⁺.

Step 3: (2S,3S)-ethyl 3-((2-bromo-7-(1,3-difluoropropan-2-yl)-7H-pyrrolo[2,3-d]pyrimidin-4-yl)amino)bicyclo[2.2.2]octane-2-carboxylate To a solution of hydrobromic acid in acetic acid (10 mL, 40 mmol, 33%) was added (2S,3S)-ethyl 3-((2-chloro-7-(1,3-difluoropropan-2-yl)-7H-pyrrolo[2,3-d]pyrimidin-4-yl)amino) bicyclo[2.2.2]octane-2-carboxylate (320 mg, 0.75 mmol), and the mixture was stirred at rt for 2 h. The reaction mixture was added into ice-water (20 mL), and the resulting mixture was extracted with EtOAc (30 mL×3). The combined organic layers were washed with saturated aqueous sodium bicarbonate (20 mL×3) and saturated brine (50 mL), dried over anhydrous $Na_2SO_4$, and filtered. The filtrate was concentrated in vacuo to remove the solvent and give the title compound as a light yellow solid (316 mg, 89%).

Step 4: (2S,3S)-ethyl 3-((2-(2-chloro-5-trityl-5H-pyrrolo[2,3-b]pyrazin-7-yl)-7-(1,3-difluoropropan-2-yl)-7H-pyrrolo[2,3-d]pyrimidin-4-yl)amino)bicyclo[2.2.2]octane-2-carboxylate To a mixed solvent of 1,4-dioxane (6 mL) and $H_2O$ (0.6 mL) were added 2-chloro-7-(4,4,5,5-tetramethyl-1,3,2-dioxaborolan-2-yl)-5-trityl-5H-pyrrolo[2,3-b]pyrazine (700 mg, 0.80 mmol, 60%), potassium carbonate (370 mg, 2.68 mmol), Pd(dppf)Cl₂ (98 mg, 0.13 mmol) and (2S,3S)-ethyl 3-((2-bromo-7-(1,3-difluoropropan-2-yl)-7H-pyrrolo[2,3-d]pyrimidin-4-yl)amino)bicyclo[2.2.2]octane-2-carboxylate (316 mg, 0.67 mmol). The air in the mixture was exchanged with nitrogen by bubbling for 10 min. The mixture in the sealed tub was stirred for 2 h at 120° C. The mixture was filtered through a celite pad to remove the solid impurity. The filtrate was concentrated in vacuo, and the residue was purified by silica gel column chromatography (PE/EtOAc (v/v)=10/1) to give the title compound as a light yellow solid (350 mg, 66%).

Step 5: (2S,3S)-ethyl 3-((2-(2-chloro-5H-pyrrolo[2,3-b]pyrazin-7-yl)-7-(1,3-difluoropropan-2-yl)-7H-pyrrolo[2,3-d]pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-7-(1,3-difluoropropan-2-yl)-7H-pyrrolo[2,3-d]pyrimidin-4-yl) amino)bicyclo[2.2.2]octane-2-carboxylate (350 mg, 0.44 mmol) in dichloromethane (10 mL) were added trimethylsilylacetylene (0.73 g, 6.26 mmol) and trifluoroacetic acid (1.53 g, 13.46 mmol), and the mixture was stirred at rt overnight. To the reaction mixture was added saturated aqueous potassium carbonate to pH about 7 to 8, and the resulting mixture was extracted with dichloromethane (20 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=4/1) to give the title compound as a light yellow solid (250 mg, 99%).

Step 6: (2S,3S)-3-((2-(2-chloro-5H-pyrrolo[2,3-b]pyrazin-7-yl)-7-(1,3-difluoropropan-2-yl)-7H-pyrrolo[2,3-d]pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl)-7-(1,3-difluoropropan-2-yl)-7H-pyrrolo[2,3-d]pyrimidin-4-yl)amino)bicyclo[2.2.2]octane-2-carboxylate (240 mg, 0.44 mmol) in THF/MeOH (v/v=8 mL/4 mL) were added a solution of NaOH (55 mg, 1.31 mmol) in water (2 mL), and the mixture was stirred at rt overnight. To the reaction mixture was added water (30 mL), and the mixture was adjusted with hydrochloric acid (1 M) to pH about 6 to 7. The resulting mixture was extracted with EtOAc (30 mL×3). The combined organic layers were washed with saturated brine (80 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (60 mg, 26%).

LC-MS (ESI, pos. ion) m/z: 516.3[M+H]$^+$;

HRMS (ESI, pos. ion) m/z: 516.1736, ($C_{24}H_{25}ClF_2N_7O_2$) [M+H]$^+$ theoretical value: 516.1726;

$^1$H NMR (400 MHz, DMSO-d$_6$) δ (ppm): 12.60 (s, 1H), 8.52 (s, 1H), 8.34 (s, 1H), 7.31 (d, J=6.4 Hz, 1H), 7.25 (d, J=3.1 Hz, 1H), 6.70 (d, J=2.8 Hz, 1H), 5.34-5.25 (m, 1H), 5.17-5.10 (m, 1H), 5.06-4.99 (m, 2H), 4.92 (s, 1H), 4.74 (s, 1H), 2.68 (d, J=6.4 Hz, 1H), 2.14 (s, 1H), 2.02-1.89 (m, 3H), 1.74 (m, 2H), 1.64-1.48 (m, 4H).

Example 66: (2S,3S)-3-((2-(2-chloro-5H-pyrrolo[2,3-b]pyrazin-7-yl)-7-isobutyl-7H-pyrrolo[2,3-d]pyrimidin-4-yl)amino)bicyclo[2.2.2]octane-2-carboxylic Acid

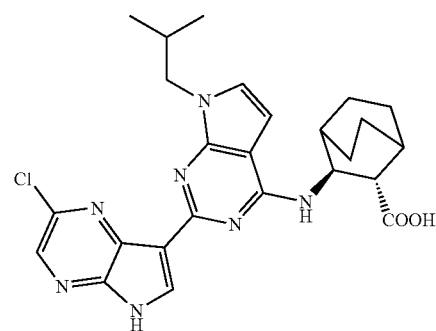 [SMILES: CC(C)Cn1ccc2c(N[C@H]3C4CCC(CC4)[C@@H]3C(=O)O)nc(-c3c[nH]c4ncc(Cl)nc34)nc21]

Step 1: 2,4-dichloro-7-isobutyl-7H-pyrrolo[2,3-d]pyrimidine 2,4-Dichloro-7H-pyrrolo[2,3-d]pyrimidine (1.00 g, 5.32 mmol) was dissolved in DMF (20 mL). The solution was cooled to 0° C., and sodium hydride (0.43 g, 10.60 mmol, 60%) was added into the solution. The mixture was stirred at 0° C. for 0.5 h, then isobutyl iodide (1.47 g, 7.98 mmol) was added dropwise slowly into the mixture. After the addition, the mixture was warmed to rt and stirred for 3 h. The reaction mixture was added into hydrochloric acid (1 M, 100 mL), and the resulting mixture was extracted with ethyl acetate (50 mL×3). The combined organic layers were washed with saturated brine (100 mL), dried over anhydrous sodium sulfate and filtered. The filtrate was concentrated in vacuo and the residue was purified by silica gel column chromatography (PE/EtOAc (v/v)=30/1) to give the title compound as a white solid (0.70 g, 53%).

MS (ESI, pos. ion) m/z: 244.1 [M+H]$^+$.

Step 2: (2S,3S)-ethyl 3-((2-chloro-7-isobutyl-7H-pyrrolo[2,3-d]pyrimidin-4-yl)amino)bicyclo[2.2.2]octane-2-carboxylate To DMF (15 mL) were added 2,4-dichloro-7-isobutyl-7H-pyrrolo[2,3-d]pyrimidine (0.70 g, 2.86 mmol), potassium carbonate (1.20 g, 8.60 mmol), (2S,3S)-ethyl 3-aminobicyclo[2.2.2]octane-2-carboxylate hydrochloride (0.87 g, 3.73 mmol), and the mixture was stirred at 80° C. for 24 h. To the reaction mixture was added water (40 mL), and the resulting mixture was extracted with ethyl acetate (40 mL×3). The combined organic layers were washed with saturated brine (100 mL), dried over anhydrous sodium sulfate and filtered. The filtrate was concentrated in vacuo and the residue was purified by silica gel column chromatography (PE/EtOAc (v/v)=15/1) to give the title compound as a pale solid (1.10 g, 94%).

MS (ESI, pos. ion) m/z: 405.1 [M+H]$^+$.

Step 3: (2S,3S)-ethyl 3-((2-bromo-7-isobutyl-7H-pyrrolo[2,3-d]pyrimidin-4-yl)amino)bicyclo[2.2.2]octane-2-carboxylate To a solution of hydrobromic acid in acetic acid (10 mL, 60 mmol, 33%) was added (2S,3S)-ethyl 3-((2-chloro-7- isobutyl-7H-pyrrolo[2,3-d]pyrimidin-4-yl)amino)bicyclo[2.2.2]octane-2-carboxylate (239 mg, 0.59 mmol), and the mixture was stirred at rt for 1 h. The reaction mixture was added into ice-water (30 mL), and the resulting mixture was extracted with EtOAc (30 mL×3). The combined organic layers were washed with saturated aqueous sodium bicarbonate (80 mL) and saturated brine (80 mL), dried over anhydrous $Na_2SO_4$, and concentrated in vacuo to give the title compound as a light yellow solid (213 mg, 95%).

MS (ESI, pos. ion) m/z: 451.2 [M+H]$^+$.

Step 4: (2S,3S)-ethyl 3-((2-(2-chloro-5-trityl-5H-pyrrolo[2,3-b]pyrazin-7-yl)-7-isobutyl-7H-pyrrolo[2,3-d]pyrimidin-4-yl) amino)bicyclo[2.2.2]octane-2-carboxylate To a mixed solvent of 1,4-dioxane (6 mL) and $H_2O$ (0.6 mL) was added 2-chloro-7-(4,4,5,5-tetramethyl-1,3,2-dioxaborolan-2-yl)-5-trityl-5H-pyrrolo[2,3-b]pyrazine (488 mg, 0.56 mmol, 60%), potassium carbonate (260 mg, 1.89 mmol), Pd(dppf)Cl$_2$ (70 mg, 0.95 mmol) and (2S,3S)-ethyl 3-((2-bromo-7-isobutyl-7H-pyrrolo[2,3-d]pyrimidin-4-yl)amino) bicyclo[2.2.2]octane-2-carboxylate (200 mg, 0.49 mmol). The air in the mixture was exchanged with nitrogen by bubbling for 10 min. The mixture in the sealed tub was stirred for 2 h at 120° C. The mixture was filtered to remove the solid impuries, and the solvent was removed. The residue was purified by silica gel column chromatography (PE/EtOAc (v/v)=10/1) to give the title compound as a light yellow solid (270 mg, 74%).

Step 5: (2S,3S)-ethyl 3-((2-(2-chloro-5H-pyrrolo[2,3-b]pyrazin-7-yl)-7-isobutyl-7H-pyrrolo[2,3-d]pyrimidin-4-yl)amino)bicyclo[2.2.2]octane-2-carboxylate To a solution of (2S,3S)-ethyl 3-((2-(2-chloro-5-trityl-5H-pyrrolo[2,3-b]pyrazin-7-yl)-7-isobutyl-7H-pyrrolo[2,3-d]pyrimidin-4-yl) amino)bicyclo[2.2.2]octane-2-carboxylate (270 mg, 0.35 mmol) in dichoromethane (10 mL) were added trimethylsilylacetylene (0.73 g, 6.26 mmol) and trifluoroacetic acid (1.53 g, 13.46 mmol), and the mixture was stirred at rt overnight. The reaction mixture was adjusted with saturated aqueous potassium carbonate to pH about 7 to 8. The resulting mixture was extracted with dichloromethane (30 mL×3). The combined organic layers were washed with saturated brine (20 mL), dried over anhydrous sodium sulfate, and filtered. The filtrate was concentrated in vacuo to remove the solvent, and the residue was purified by silica gel column chromatography (PE/EtOAc (v/v)=4/1) to give a light yellow solid (144 mg, 78%).

MS (ESI, pos. ion) m/z: 522.3[M+H]$^+$.

Step 6: (2S,3S)-3-((2-(2-chloro-5H-pyrrolo[2,3-b]pyrazin-7-yl)-7-isobutyl-7H-pyrrolo[2,3-d]pyrimidin-4-yl)amino)bicyclo[2.2.2]octane-2-carboxylic Acid To a solution of (2S,3S)-ethyl 3-((2-(2-chloro-5H-pyrrolo[2,3-b]pyrazin-7-yl) 7-isobutyl-7H-pyrrolo[2,3-d]pyrimidin-4-yl)amino)bicyclo[2.2.2]octane-2-carboxylate (144 mg, 0.27 mmol) in THF/MeOH (v/v=8 mL/4 mL) was added a solution of NaOH (110 mg, 2.70 mmol) in water (2 mL), and the mixture was stirred at rt overnight. To the reaction mixture was added water (30 mL), and the mixture was acidified with hydrochloric acid (1 M) to pH about 6. The resulting mixture was extracted with EtOAc (30 mL×3). The combined organic layers were washed with saturated brine (80 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (120 mg, 88%).

MS (ESI, pos. ion) m/z: 494.1[M+H]$^+$;
HRMS (ESI, pos. ion) m/z: 494.2077, ($C_{25}H_{29}ClN_7O_2$) [M+H]$^+$ theoretical value: 494.2071;
$^1$H NMR (400 MHz, DMSO-d$_6$) δ (ppm): 12.64 (s, 1H), 12.27 (s, 1H), 8.52 (s, 1H), 8.36 (s, 1H), 7.14 (s, 1H), 6.68 (s, 1H), 4.72 (s, 1H), 4.02 (d, J=6.3 Hz, 2H), 2.73 (s, 1H), 2.34-2.25 (m, 1H), 2.14 (s, 1H), 2.05-1.90 (m, 3H), 1.78 (m, 3H), 1.57 (m, 3H), 0.89 (dd, J=5.7, 3.1 Hz, 6H).

EXAMPLES OF BIOLOGICAL ASSAY

Using parts of the compounds of the invention as examples, the inventors have detected antiviral and cytotoxicity activities of the compounds of the invention and pharmacokinetic properties in the following examples.

Example A: Cytopathic Effect Assay (CPE Assay)

Detection the inhibitory effect of the compound of the invention and control compound A (Compound A was prepared according to the synthetic method disclosed in WO 2015073491) against cytopathic effect (CPE) caused by virus H1N1 A/Weiss/43 on cellular level in vitro.

Control compound A

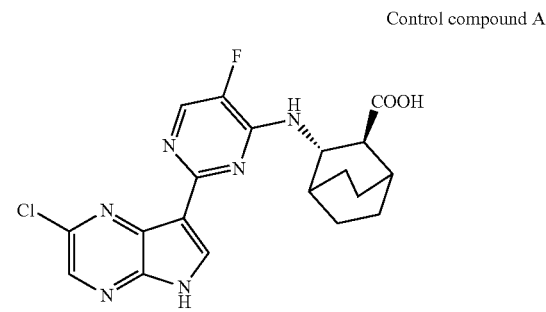 [SMILES: O=C(O)[C@H]1C2CCC(CC2)[C@@H]1Nc1nc(-c2c[nH]c3ncc(Cl)nc23)ncc1F]

Scheme: MDCK cells (Madin-Daby canine kidney cells) were seeded in a 384-well plate with 2000 cells per well and cultured at 37° C. under 5% $CO_2$ condition overnight. Next day, cell culture medium was replenished with fresh medium containing relevant concentrations of test compounds and virus H1N1 A/Weiss/43 at a multiplicity of infection to yield 80-95% CPE (or the titer was 1 TCID90/well). The top final concentration of the test compounds were 50 μM and then diluted by 3-fold serially for a total of 8 concentrations at 50 nM, 16.67 nM, 5.56 nM, 1.85 nM, 0.62 nM, 0.21 nM, 0.069 nM, 0.023 nM. The test condition of cytotoxicity test group was the same as described above, except that the cell culture medium of cytotoxicity test group didn't contain influenza virus. A virus control group without drug and a no virus infected cell control group without drug were set at the same time. Each group was set in duplicate, and incubated at 37° C. under 5% $CO_2$ condition for 5 days. The cell activity was detected by using CCK-8 kits, and the data were used for calculating the antiviral effect and cytotoxicity against virus-infected cell of the compound. Data were analyzed by using GraphPad Prism software, and the CPE inhibition ratio and cell survival ratio were calculated. $EC_{50}$ and $CC_{50}$ values were obtained according to the curve fitting.

CPE inhibition ratio=(absorbance of dosing well–absorbance of virus control well)/(absorbance of cell control well–absorbance of virus control well)×100%

Cell survival ratio=(absorbance of dosing well–absorbance of medium control well)/(absorbance of cell control well–absorbance of medium control well)×100%

Table 1 shows inhibitory activities of parts of compounds in the invention against influenza virus (A/Weiss/43 (H1N1)).

TABLE 1

Inhibitory acitivities of parts of compounds in the invention aganist influenza virus (A/Weiss/43(H1N1))

| Example Number | $EC_{50}$ (nM) |
|---|---|
| Compound A | 33.22 |
| Example 1 | 3.89 |
| Example 3 | 0.672 |
| Example 4 | 0.116 |
| Example 5 | 3.519 |
| Example 6 | 0.398 |
| Example 8 | 0.394 |
| Example 12 | 2.54 |
| Example 13 | 0.017 |
| Example 15 | 0.76 |
| Example 20 | 0.192 |
| Example 27 | 0.024 |
| Example 29 | 0.013 |
| Example 33 | 0.01 |
| Example 39 | 1.218 |
| Example 49 | 0.521 |
| Example 55 | 0.68 |
| Example 62 | 0.011 |
| Example 63 | 0.079 |
| Example 64 | 0.887 |
| Example 66 | 0.274 |

Table 1 shows that compounds of the invention have good anti-influenza virus activity.

Example B: Pharmacokinetic Evaluation after Administering a Certain Amount of the Compound of the Invention by Intravenous or Oral Pharmacokinetic characteristics of the compound of the invention and control compound A (Compound A was prepared according to the synthetic method disclosed in WO 2015073491) in SD rat were evaluated. The compounds disclosed herein were administered in form of a saline solution containing 5% DMSO, 5% Kolliphor HS 15 and 90% Saline. For intravenous administration (iv), the animals were administered with a dose of 1 mg/kg, and blood samples (0.3 mL) were collected at the time points of 0.083, 0.25, 0.5, 1.0, 2.0, 5.0, 7.0 and 24 h after drug administration, then each blood sample was processed to separate plasma by centrifugation at 3000 rpm or 4000 rpm for 10 minutes. For oral administration (po), the animals were administered with a dose of 5 mg/kg, and blood samples (0.3 mL) were collected at the time points of 0.25, 0.5, 1.0, 2.0, 5.0, 7.0 and 24 h after drug administration, then each blood sample was processed to separate plasma by centrifugation at 3000 rpm or 4000 rpm for 10 minutes. Plasma samples were collected and stored at −20° C. or −70° C. until LC/MS/MS analysis.

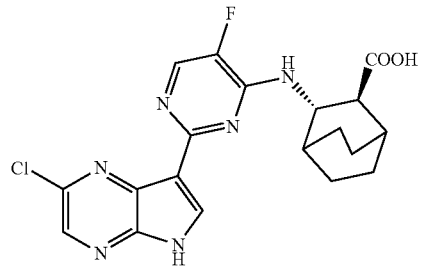

Control compound A

TABLE 2

Pharmacokinetic data of parts of the compounds in the invention in vivo of SD rats

| Test compound | Administration route | dosage mg/kg | $AUC_{last}$ hr * ng/mL | $AUC_{INF}$ hr * ng/mL | CL L/h/Kg |
|---|---|---|---|---|---|
| Control compound A | iv | 1 | 894 | 894 | 18.7 |
|  | po | 5 | 2880 | 2910 | N/A |
| Example 7a | iv | 1 | 3220 | 3260 | 5.11 |
|  | po | 5 | 9840 | 9950 | N/A |
| Example 8 | iv | 1 | 1540 | 1550 | 11.2 |
|  | po | 5 | 5420 | 5440 | N/A |
| Example 13 | iv | 1 | 9900 | 10100 | 1.67 |
|  | po | 5 | 27400 | 29000 | N/A |
| Example 27 | iv | 1 | 1960 | 1960 | 8.62 |
|  | po | 5 | 7170 | 7250 | N/A |
| Example 29 | iv | 1 | 4830 | 4980 | 3.38 |
|  | po | 5 | 23700 | 23800 | N/A |
| Example 49 | iv | 1 | 3940 | 3950 | 4.29 |
|  | po | 5 | 3500 | 3550 | N/A |
| Example 53 | iv | 1 | 3670 | 3740 | 4.45 |
|  | po | 5 | 17700 | 18000 | N/A |
| Example 62 | iv | 1 | 5390 | 5510 | 3.04 |
|  | po | 5 | 24400 | 25000 | N/A |
| Example 65 | iv | 1 | 2370 | 2390 | 7.23 |
|  | po | 5 | 6150 | 6170 | N/A |
| Example 66 | iv | 1 | 3470 | 3480 | 4.95 |
|  | po | 5 | 12500 | 12600 | N/A |

Notes:
$AUC_{last}$—AUC of 0 to 24 h;
$AUC_{INF}$—AUC of 0 to infinite time.

Table 2 shows that $AUC_{last}$ and $AUC_{INF}$ of the compounds of the invention in SD rats are higher for both intravenous administration and oral administration compared to control compound A. It indicates that the compounds of the invention have high exposure level and good absorption, and the compounds of the invention have better pharmacokinetic properties compared to control compound A.

Example C: Cytopathic Effect Assay (CPE Assay)

Detection of the inhibitory effect of the compound of the invention and control compound JNJ-872 against cytopathic effect (CPE) caused by virus Influenza B virus-B/Lee/40 on cellular level in vitro.

Experimental procedure: MDCK cells (Madin-Daby canine kidney cells) were seeded in a 384-well plate with 6000 cells per well and cultured at 37° C. under 5% $CO_2$ condition overnight. Next day, cell culture medium was exchanged with fresh medium containing relevant concentrations of test compounds and virus Influenza B virus-B/Lee/40 (the titer was 30 TCID50/well). The highest tested concentration of the compounds were 50 µM and then the compounds were diluted by 3-fold serially for a total of 11 concentrations. A cytotoxicity test group was set under the same experimental condition as described above, except that the cell culture medium of cytotoxicity test group didn't contain influenza virus; while a virus control group without drug and a no virus infecting cell control group without drug were set at the same time. Each group was set in duplicate, and incubated at 37° C. under 5% $CO_2$ condition for 3 days. The cell activity was detected by using Promega CellTiter Cell Viability kits, and the data were used for calculating the antiviral effect and cytotoxicity against virus-infected cell of the compound. Data were analyzed by using GraphPad Prism software, and the CPE inhibition ratio and Cell survival ratio were calculated. $EC_{50}$ value was obtained according to the curve fitting.

CPE inhibition ratio=(average detection value of dosing well−average detection value of virus control well)/(average detection value of cell control well−average detection value of virus control well)×100%

Cell survival ratio=average detection value of dosing well/average detection value of cell control well×100%

Control compound JNJ-872

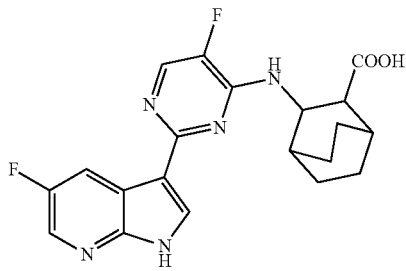

Table 3 shows inhibitory activities of parts of compounds in the invention against influenza virus (Influenza B virus-B/Lee/40)).

TABLE 3

Inhibitory acitivities of parts of compounds in the invention aganist influenza virus (Influenza B virus-B/Lee/40))

| Example Number | $EC_{50}$ (μM) |
| --- | --- |
| JNJ-872 | >50 |
| Example 20 | 1.615 |
| Example 60 | 26.42 |

Table 3 shows that compounds of the invention had good anti-influenza B virus activity.

Reference throughout this specification to "an embodiment," "some embodiments", "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example, "in an example", "in a specific example" or "in some examples" in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments or examples have been shown and described, it would be appreciated by those skilled in the art that the above embodiments or examples cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a tautomer, an N-oxide, a solvate, or a pharmaceutically acceptable salt thereof,

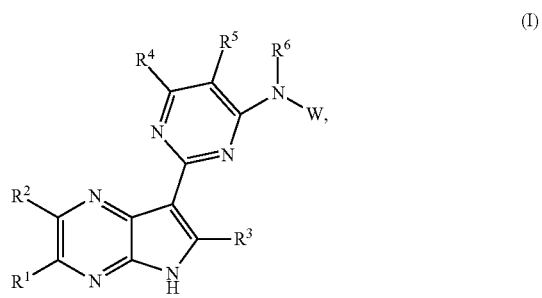

(I)

wherein
each of $R^1$, $R^2$ and $R^3$ is independently H, D, F, Cl, Br, CN, $NO_2$, —C(=O)$R^a$, —C(=O)$OR^b$, —C(=O)$NR^cR^d$, $OR^b$, —$NR^cR^d$, $R^bO$—$C_{1-4}$ alkylene, $R^dR^cN$—$C_{1-4}$ alkylene, $C_{1-6}$ alkyl, $C_{2-6}$ alkenyl or $C_{2-6}$ alkynyl; or, $R^1$ and $R^2$, together with the carbon atoms to which they are attached, form a $C_{3-6}$ carbocyclic ring, 5- to 6-membered heterocyclic ring, $C_{6-10}$ aromatic ring or 5- to 6-membered heteroaromatic ring, and wherein each of $C_{1-6}$ alkyl, $C_{2-6}$ alkenyl, $C_{2-6}$ alkynyl, $C_{3-6}$ carbocyclic ring, 5- to 6-membered heterocyclic ring, $C_{6-10}$ aromatic ring and 5- to 6-membered heteroaromatic ring is independently unsubstituted or substituted with 1, 2, 3 or 4 substituents independently selected from D, F, Cl, Br, CN, $OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

$R^4$ is $OR^b$, —$NR^cR^d$, $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl or (5- to 16-membered heteroaryl)-$C_{1-4}$ alkylene, and wherein each of $C_{2-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl and (5- to 16-membered heteroaryl)-$C_{1-4}$ alkylene is independently unsubstituted or substituted with 1, 2, 3, 4 or 5 R';

$R^5$ is H, D, F, Cl, Br, CN, $NO_2$, —C(=O)$R^a$, —C(=O)$OR^b$, —C(=O)$NR^cR^d$, $OR^b$, —$NR^cR^d$, $R^bO$—$C_{1-4}$ alkylene, $R^dR^cN$—$C_{1-4}$ alkylene, $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3, 4 or 5 R';

or, $R^4$ and $R^5$, together with the carbon atoms to which they are attached, form a $C_{3-12}$ carbocyclic ring, 3- to 12-membered heterocyclic ring, $C_{6-10}$ aromatic ring or 5- to 10-membered heteroaromatic ring, and wherein each of $C_{3-12}$ carbocyclic ring, 3- to 12-membered heterocyclic ring, $C_{6-10}$ aromatic ring and 5- to 10-membered heteroaromatic ring is independently unsubstituted or substituted with 1, 2, 3, 4 or 5 R';

each R' is independently D, F, Cl, Br, CN, $NO_2$, $OR^b$, —$NR^cR^d$, $R^bO$—$C_{1-4}$ alkylene, $R^dR^cN$—$C_{1-4}$ alkylene, $R^a$—C(=O)—O—$C_{1-4}$ alkylene-O—$C_{1-4}$ alkylene, $R^bO$—C(=O)—O—$C_{1-4}$ alkylene —O—$C_{1-4}$ alkylene, —C(=O)$R^a$, —C(=O)$OR^b$, —C(=O)$NR^cR^d$, $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3 or 4 substituents independently selected from D, F, Cl, Br, CN, $NO_2$, $OR^b$, —$NR^cR^d$, $C_{1-6}$ alkyl, $C_{1-6}$ haloalkyl, $R^bO$—$C_{1-4}$ alkylene or $R^dR^cN$—$C_{1-4}$ alkylene;

$R^6$ is H, D or $C_{1-6}$ alkyl, and wherein $C_{1-6}$ alkyl is optionally substituted with 1, 2, 3 or 4 substituents independently selected from D, F, Cl, Br, CN, $NO_2$ or $OR^b$;

W is $C_{1-8}$ alkyl, $C_{3-12}$ carbocyclyl or 3- to 12-membered heterocyclyl, and wherein each of $C_{1-8}$ alkyl, $C_{3-12}$ carbocyclyl and 3- to 12-membered heterocyclyl is independently unsubstituted or substituted with 1, 2, 3 or 4 $R^w$;

each $R^w$ is independently D, F, Cl, Br, CN, $NO_2$, =O, —C(=O)$R^a$, —C(=O)$OR^b$, —C(=O)—O—$C_{1-4}$ alkylene-O—C(=O)—$OR^b$, —C(=O)$NR^cR^d$, —$NR^eC$(=O)$R^a$, —$NR^eC$(=O)$NR^cR^d$, —S(=O)$_2R^f$, —S(=O)$_2NR^e$(=O)$R^a$, —S(=O)$_2NR^cR^d$, $(R^bO)_2$P(=O)—$C_{0-2}$ alkylene, $OR^b$, $R^bO$—$C_{1-2}$ alkylene, $R^dR^cN$—$C_{1-2}$ alkylene, $C_{1-6}$ alkyl, 5- to 6-membered heteroaryl or 5- to 6-membered heterocyclyl, and wherein each of $C_{1-6}$ alkyl, 5- to 6-membered heteroaryl and 5- to 6-membered heterocyclyl is independently unsubstituted or substituted with 1, 2, 3 or 4 substituents independently selected from D, F, Cl, Br, CN, $N_3$, =O, $NO_2$, $OR^b$, $C_{1-6}$ alkyl or $C_{1-6}$ haloalkyl;

each $R^a$, $R^b$, $R^c$, $R^d$, $R^e$ and $R^f$ is independently H, D, hydroxy, $C_{1-6}$ haloalkyl, $C_{1-6}$ alkyl, n-heptyl, $C_{1-6}$ alkoxy, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-6}$ alkyl, n-heptyl, $C_{1-6}$ alkoxy, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino;

or, $R^c$ and $R^d$, together with the nitrogen atom to which they are attached, form 3- to 8-membered heterocyclyl or 5- to 8-membered heteroaryl, and wherein each of 3- to 8-membered heterocyclyl and 5- to 8-membered heteroaryl is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino.

2. The compound of claim 1 having Formula (II),

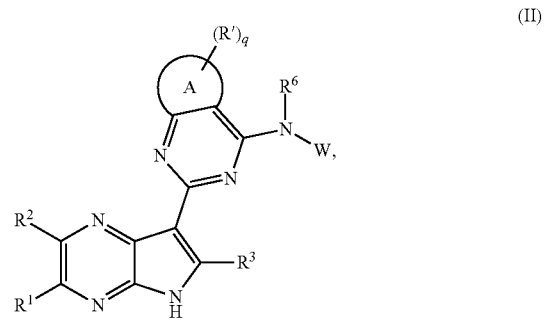

(II)

wherein A is a $C_{3-12}$ carbocyclic ring, 3- to 12-membered heterocyclic ring, $C_{6-10}$ aromatic ring or 5- to 10-membered heteroaromatic ring; and q is 0, 1, 2, 3, 4 or 5.

3. The compound of claim 2, wherein A is a $C_{3-6}$ carbocyclic ring, 3- to 6-membered heterocyclic ring, $C_{6-10}$ aromatic ring or 5- to 6-membered heteroaromatic ring.

4. The compound of claim 2, wherein A is a $C_{3-6}$ carbocyclic ring, 3- to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline.

5. The compound of claim 1, wherein $R^4$ is $OR^b$, —$NR^cR^d$, $C_{2-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 8-membered heterocyclyl, (5- to 8-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{2-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 8-membered heterocyclyl, (5- to 8-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3, 4 or 5 R';

$R^5$ is H, D, F, Cl, Br, CN, $NO_2$, —C(=O)$R^a$, —C(=O)$OR^b$, —C(=O)$NR^cR^d$, $OR^b$, —$NR^cR^d$, $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with 1, 2, 3, 4 or 5 R';

or, $R^4$ and $R^5$, together with the carbon atoms to which they are attached, form a $C_{3-6}$ carbocyclic ring, 3- to 6-membered heterocyclic ring, $C_{6-10}$ aromatic ring or 5- to 6-membered heteroaromatic ring, and wherein each of $C_{3-6}$ carbocyclic ring, 3- to 6-membered heterocyclic ring, $C_{6-10}$ aromatic ring and 5- to 6-membered heteroaromatic ring is independently unsubstituted or substituted with 1, 2, 3, 4 or 5 R'.

6. The compound of claim 1, wherein $R^4$ is $OR^b$, —$NR^cR^d$, ethynyl, propinyl, $C_{3-6}$ carbocyclyl, pyrrolidinyl, pyrazolidinyl, imidazolidinyl, tetrahydrofuryl, tetrahydrothienyl, tetrahydropyranyl, tetrahydrothiopyranyl, tetrahydroisoquinolyl, piperidinyl, morpholinyl, thiomorpholinyl, piperazinyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thiadiazolyl, thienyl, benzothienyl, pyrazinyl, pyridazinyl, pyrimidinyl, indolyl, purinyl, quinolyl, isoquinolyl, phenoxathiinyl,

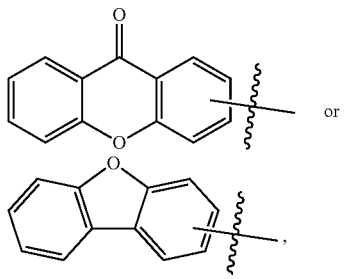 or and wherein each of ethynyl, propinyl, $C_{3-6}$ carbocyclyl, pyrrolidinyl, pyrazolidinyl, imidazolidinyl, tetrahydrofuryl, tetrahydrothienyl, tetrahydropyranyl, tetrahydrothiopyranyl, tetrahydroisoquinolyl, piperidinyl, morpholinyl, thiomorpholinyl, piperazinyl, phenyl, naphthyl, furyl, benzofuryl, pyrrolyl, pyridyl, pyrazolyl, imdazolyl, benzimdazolyl, triazolyl, tetrazolyl, oxazolyl, oxadiazolyl, 1,3,5-triazinyl, thiazolyl, thiadiazolyl, thienyl, benzothienyl, pyrazinyl, pyridazinyl, pyrimidinyl, indolyl, purinyl, quinolyl, isoquinolyl, phenoxathiinyl,

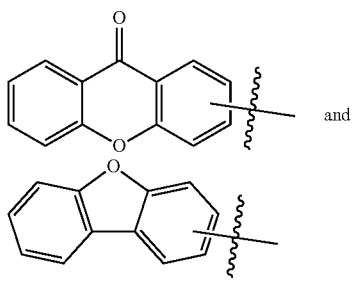 and is independently unsubstituted or substituted with 1, 2, 3, 4 or 5 R';

$R^5$ is H, D, F, Cl, Br, CN, $NO_2$, methyl, ethyl or i-propyl;

or, $R^4$ and $R^5$, together with the carbon atoms to which they are attached, form a $C_{3-6}$ carbocyclic ring, 3- to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline, and wherein each of $C_{3-6}$ carbocyclic ring, 3- to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline and isoquinoline is independently unsubstituted or substituted with 1, 2, 3, 4 or 5 R'.

7. The compound of claim 1, wherein each of $R^1$, $R^2$ and $R^3$ is independently H, D, F, Cl, Br, CN, $NO_2$, —C(═O)$R^a$, —C(═O)$OR^b$, —C(═O)$NR^cR^d$, $OR^b$, —$NR^cR^d$, methyl, ethyl, n-propyl or i-propyl; or, $R^1$ and $R^2$, together with the carbon atoms to which they are attached, form a $C_{5-6}$ carbocyclic ring, 5- to 6-membered heterocyclic ring, benzene ring or 5- to 6-membered heteroaromatic ring, and wherein each of methyl, ethyl, n-propyl, i-propyl, $C_{5-6}$ carbocyclic ring, 5- to 6-membered heterocyclic ring, benzene ring and 5- to 6-membered heteroaromatic ring is independently unsubstituted or substituted with 1, 2, 3 or 4 substituents independently selected from D, F, Cl, Br, CN, $OR^b$, —$NR^cR^d$ or $C_{1-3}$ haloalkyl.

8. The compound of claim 1, wherein each R' is independently D, F, Cl, Br, CN, $NO_2$, $OR^b$, —$NR^cR^d$, $R^a$—C(═O)—O—$C_{1-2}$ alkylene-O—$C_{1-2}$ alkylene, $R^bO$—C(═O)—O—$C_{1-2}$ alkylene-O—$C_{1-2}$ alkylene, —C(═O)$R^a$, —C(═O)$OR^b$, —C(═O)$NR^cR^d$, $C_{1-9}$ alkyl, $C_{1-3}$ haloalkyl, $C_{3-6}$ cycloalkyl, 5- to 6-membered heterocyclyl, phenyl, pheny-$C_{1-2}$ alkylene or 5- to 10-membered heteroaryl, and wherein each of $C_{1-9}$ alkyl, $C_{1-3}$ haloalkyl, $C_{3-6}$ cycloalkyl, 5- to 6-membered heterocyclyl, phenyl, pheny-$C_{1-2}$ alkylene and 5- to 10-membered heteroaryl is independently unsubstituted or substituted with 1, 2, 3 or 4 substituents independently selected from D, F, Cl, Br, CN, $NO_2$, $OR^b$, —$NR^cR^d$, methyl, ethyl, n-propyl or i-propyl.

9. The compound of claim 1, wherein each R' is independently D, F, Cl, Br, CN, $NO_2$, $OR^b$, —$NR^cR^d$,

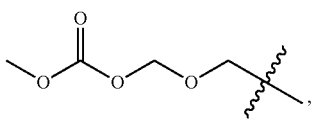,

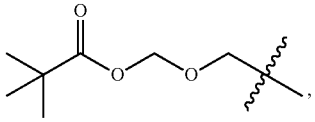,

—C(═O)$R^a$, —C(═O)$OR^b$, —C(═O)$NR^cR^d$, methyl, ethyl, n-propyl, i-propyl, n-butyl, i-butyl, t-butyl, trifluoromethyl, difluoromethyl, monofluoromethyl, 2,2-difluoroethyl, 1,2-difluoroethyl, trifluoroethyl, 1-fluoroethyl, 2-fluoroethyl, cyclopropyl, tetrahydrofuranyl, tetrahydrothienyl, tetrahydropyranyl, tetrahydrothiapyranyl, piperidyl, morpholinyl, thiomorpholinyl, piperazinyl, phenyl, phenyl-$C_{1-2}$ alkylene, furyl, benzofuranyl, pyrrolyl, pyridinyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl or pyrimidinyl, and wherein methyl, ethyl, n-propyl, i-propyl, n-butyl, i-butyl, t-butyl, difluoromethyl, monofluoromethyl, 2,2-difluoroethyl, 1,2-difluoroethyl, trifluoroethyl, 1-fluoroethyl, 2-fluoroethyl, cyclopropyl, tetrahydrofuranyl, tetrahydrothienyl, tetrahydropyranyl, tetrahydrothiapyranyl, piperidyl, morpholinyl, thiomorpholinyl, piperazinyl, phenyl, phenyl-$C_{1-2}$ alkylene, furyl, benzofuranyl, pyrrolyl, pyridinyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl and pyrimidinyl is independently unsubstituted or substituted with 1, 2, 3 or 4 substituents independently selected from D, F, Cl, Br, CN, NO$_2$, OH, —NH$_2$, methyl, ethyl, n-propyl or i-propyl.

10. The compound of claim 1, wherein $R^6$ is H, D, CF$_3$, methyl, ethyl, n-propyl or i-propyl.

11. The compound of claim 1, wherein W is $C_{1-6}$ alkyl, $C_{5-8}$ carbocyclyl or 5- to 8-membered heterocyclyl, and wherein each of $C_{1-6}$ alkyl, $C_{5-8}$ carbocyclyl and 5- to 8-membered heterocyclyl is independently unsubstituted or substituted with 1, 2, 3 or 4 $R^w$.

12. The compound of claim 1, wherein $R^w$ is D, F, Cl, Br, CN, NO$_2$, =O, —C(=O)OCH$_3$, —C(=O)OCH$_2$CH$_3$, —C(=O)OCH$_2$CH$_2$CH$_2$CH$_3$, —C(=O)O(CH$_2$)$_6$CH$_3$, —C(=O)OH,

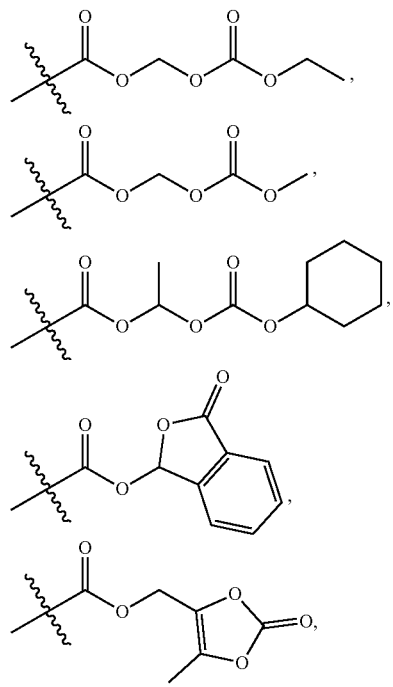

—C(=O)NR$^c$R$^d$, —NHC(=O)R$^a$, —NHC(=O)NR$^c$R$^d$, —S(=O)$_2$R$^f$, —S(=O)$_2$NHC(=O)R$^a$, —S(=O)$_2$NR$^c$R$^d$, (R$^b$O)$_2$P(=O)—C$_{0-2}$ alkylene, OR$^b$, methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl, pyrimidyl or 5- to 6-membered heterocyclyl, and wherein each of methyl, ethyl, n-propyl, i-propyl, furyl, pyrrolyl, pyridyl, pyrazolyl, imdazolyl, triazolyl, tetrazolyl, oxazolyl, oxadiazolyl, 1,3, 5-triazinyl, thiazolyl, thienyl, pyrazinyl, pyridazinyl, pyrimidyl and 5- to 6-membered heterocyclyl is independently unsubstituted or substituted with 1, 2, 3 or 4 substituents independently selected from D, F, Cl, Br, CN, N$_3$, =O, NO$_2$, —OCH$_3$, $C_{1-3}$ alkyl or $C_{1-3}$ haloalkyl.

13. The compound of claim 1, wherein each R$^a$, R$^b$, R$^c$, R$^d$, R$^e$ and R$^f$ is independently H, D, hydroxy, trifluoromethyl, methyl, ethyl, i-propyl, n-propyl, n-butyl, t-butyl, n-pentyl, n-hexyl, n-heptyl, methoxy, ethoxy, $C_{3-6}$ carbocyclyl, 5- to 6-membered heterocyclyl, phenyl, 5- to 10-membered heteroaryl or (5- to 10-membered heteroaryl)-$C_{1-4}$ alkylene, and wherein each of methyl, ethyl, i-propyl, n-propyl, n-butyl, t-butyl, n-pentyl, n-hexyl, n-heptyl, methoxy, ethoxy, $C_{3-6}$ carbocyclyl, 5- to 6-membered heterocyclyl, phenyl, 5- to 10-membered heteroaryl and (5- to 10-membered heteroaryl)-$C_{1-4}$ alkylene is independently unsubstituted or substituted with 1, 2, 3 or 4 substituents independently selected from D, F, Cl, CN, OH, NH$_2$, $C_{1-3}$ alkyl, $C_{1-3}$ haloalkyl or methoxy;

or, R$^c$ and R$^d$, together with the nitrogen atom to which they are attached, form 5- to 6-membered heterocyclyl or 5- to 6-membered heteroaryl, and wherein each of 5- to 6-membered heterocyclyl and 5- to 6-membered heteroaryl is independently unsubstituted or substituted with 1, 2, 3 or 4 substituents independently selected from D, F, Cl, CN, OH, NH$_2$, $C_{1-3}$ alkyl, $C_{1-3}$ haloalkyl or methoxy.

14. The compound of claim 1, wherein W is one of the following sub-formulae:

(W-1)

(W-2)

(W-3)

(W-4)

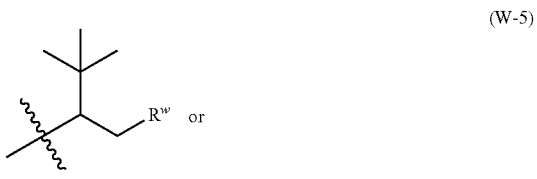
(W-5)

-continued
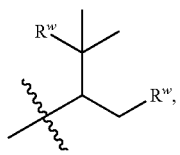
(W-6)
wherein n is 0, 1, 2, 3 or 4.
15. The compound of claim 1 having Formula (III), (IV), (V), (VI), (VII), (VIII), (IX) or (X):
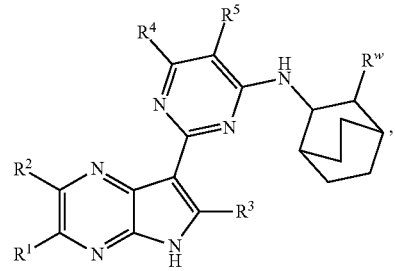
(III)
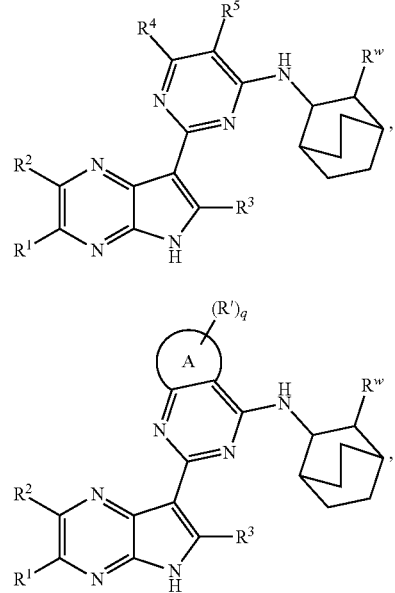
(IV)
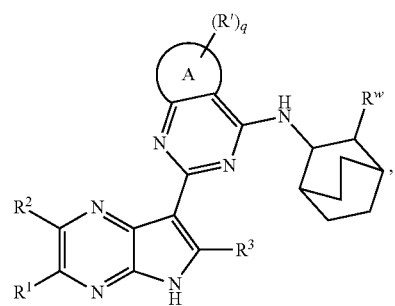
(V)
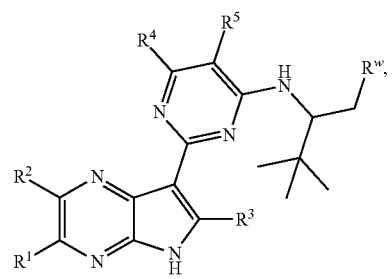
(VI)
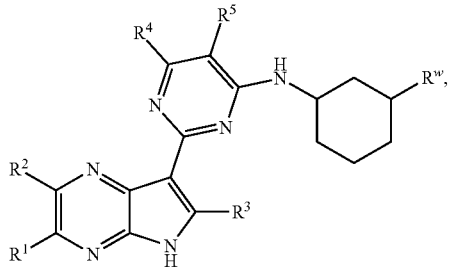
(VII)
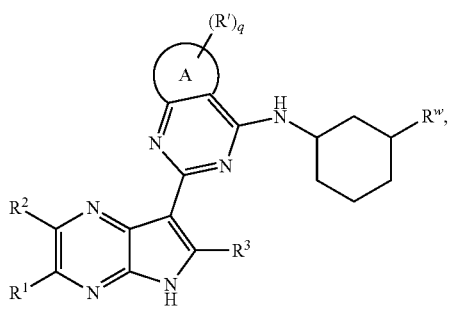
(VIII)
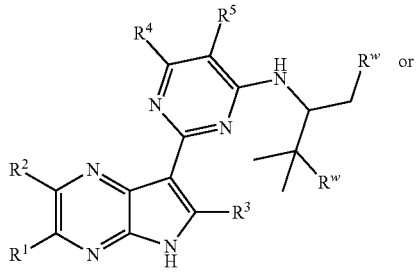
(IX)
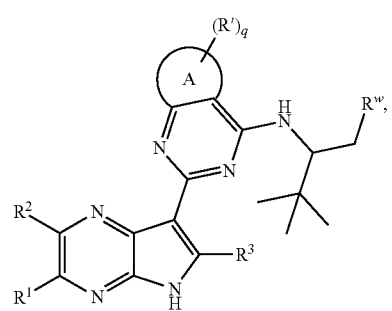
(X)
wherein A is a $C_{3-12}$ carbocyclic ring, 3- to 12-membered heterocyclic ring, $C_{6-10}$ aromatic ring or 5- to 10-membered heteroaromatic ring; and
q is 0, 1, 2, 3, 4 or 5.
16. The compound of claim 15 having Formula (XI), (XII), (XIII) or (XIV):

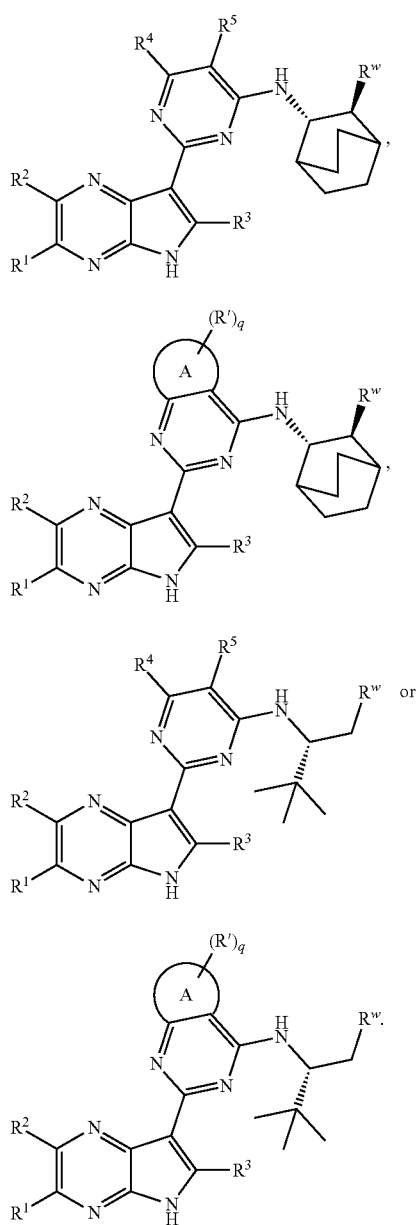
17. The compound of claim 1 having one of the following structures:
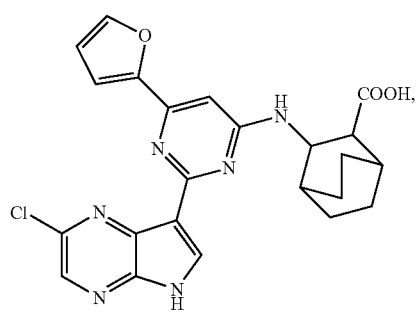
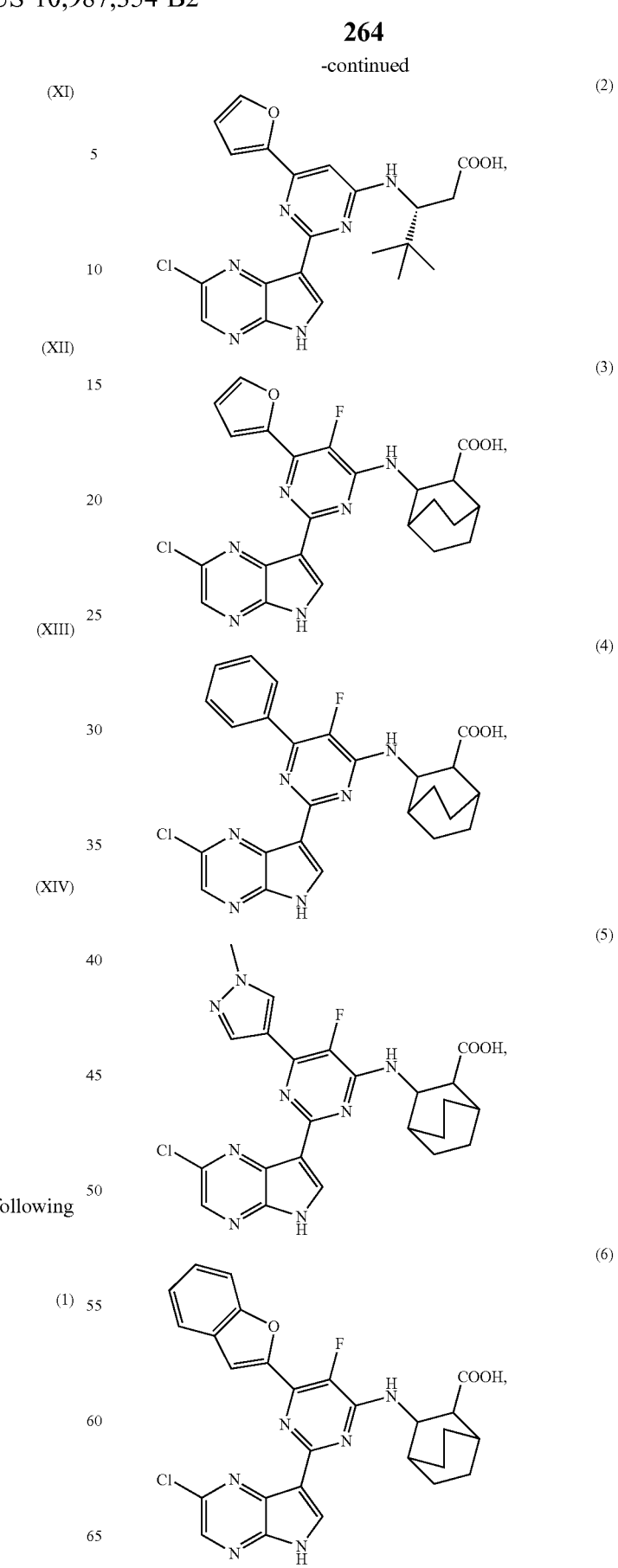

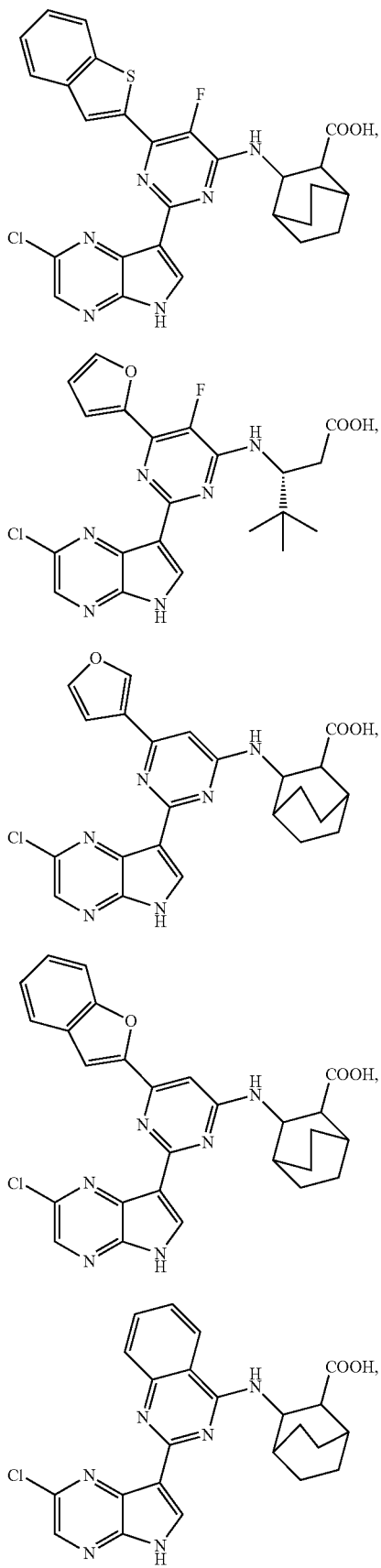
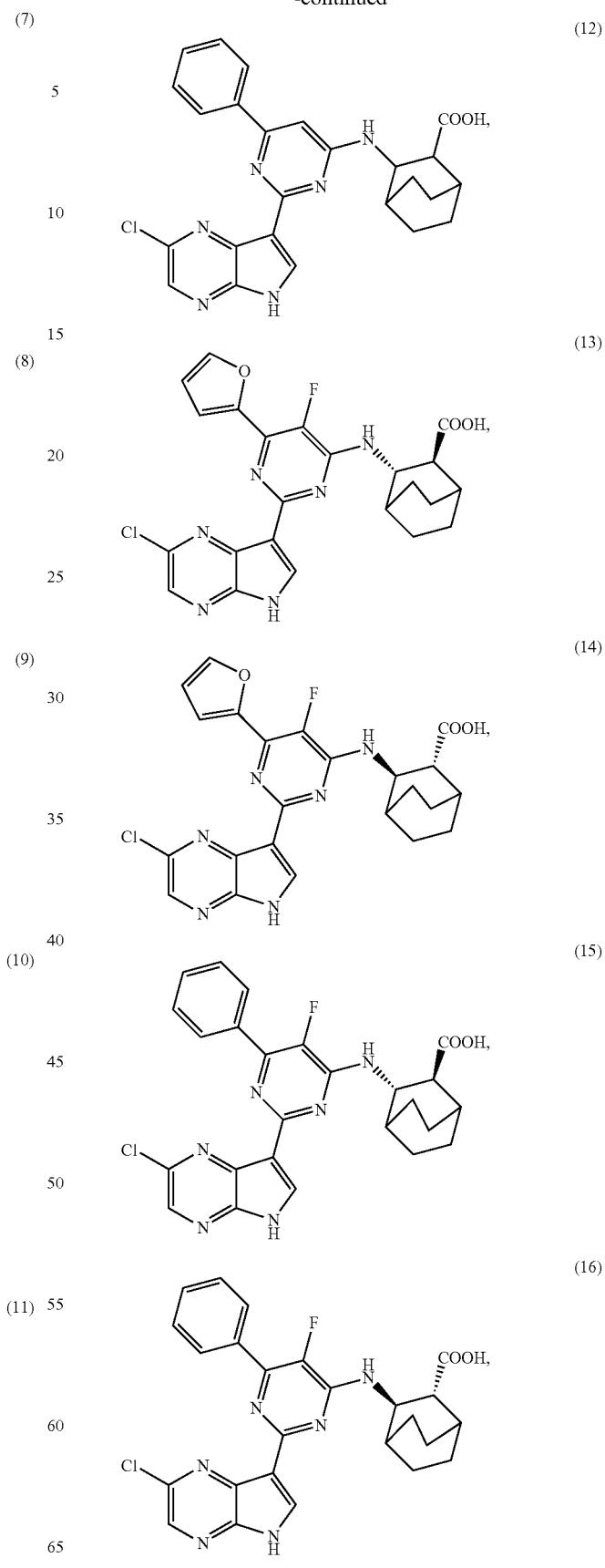

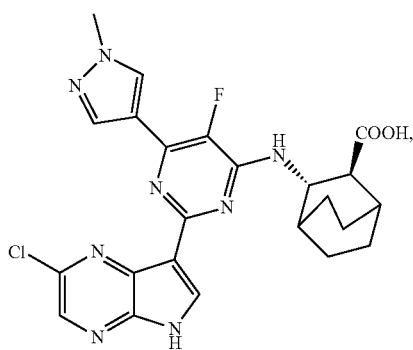
(17)
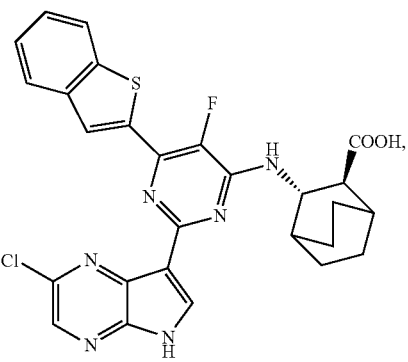
(21)
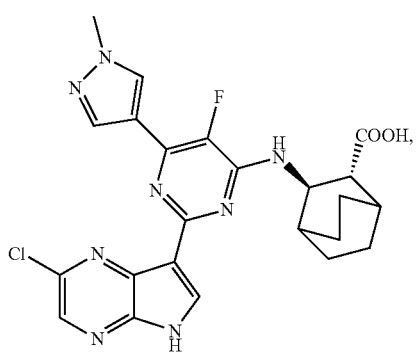
(18)
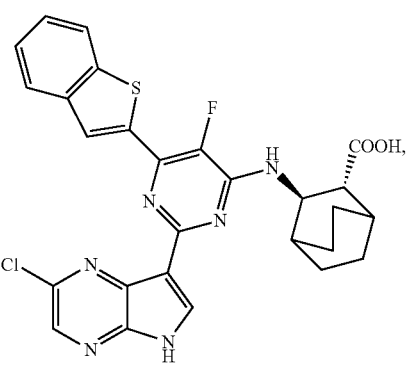
(22)
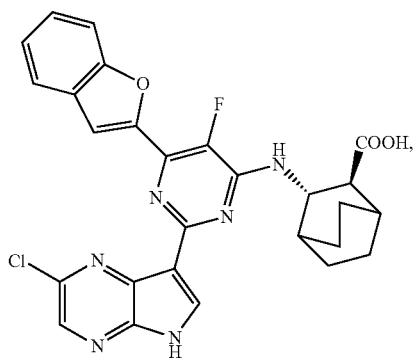
(19)
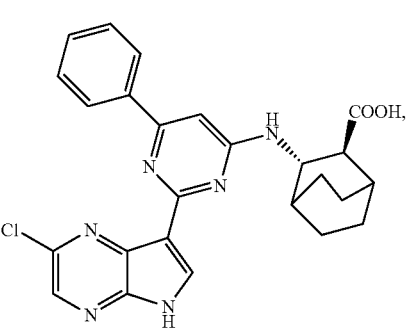
(23)
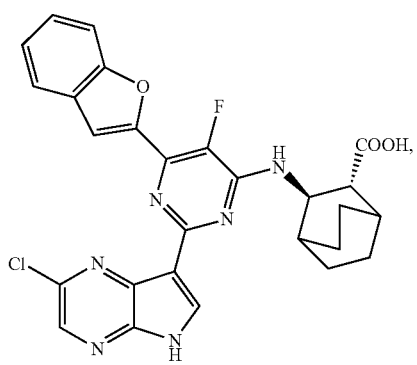
(20)
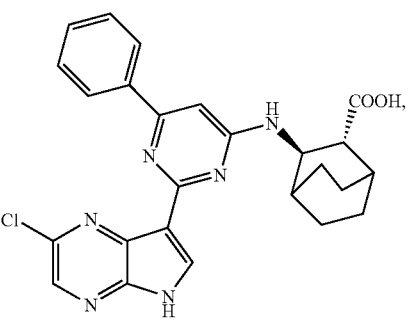
(24)

-continued
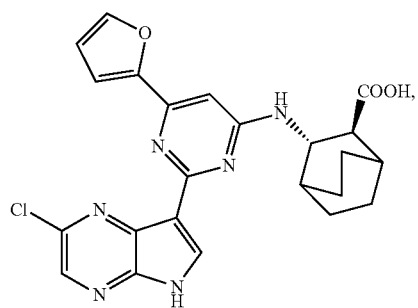 (25)
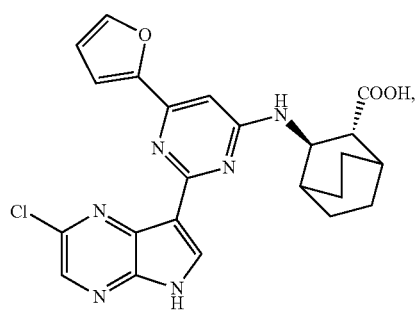 (26)
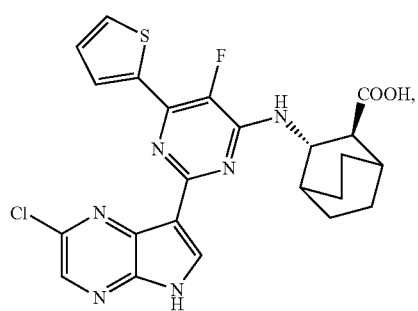 (27)
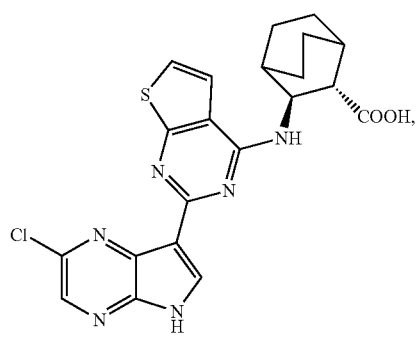 (28)
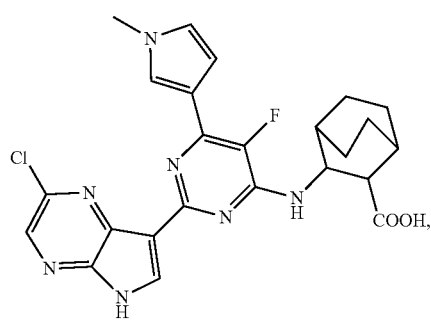 (29)
-continued
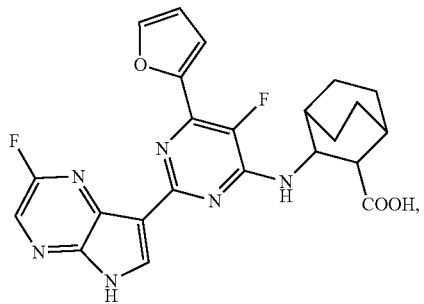 (30)
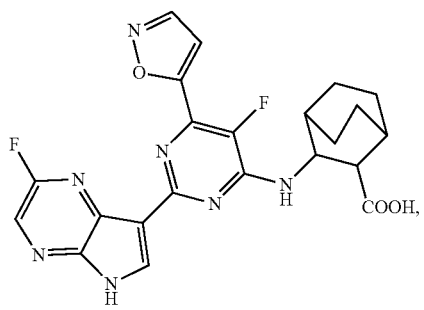 (31)
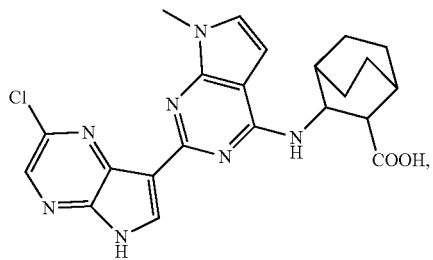 (32)
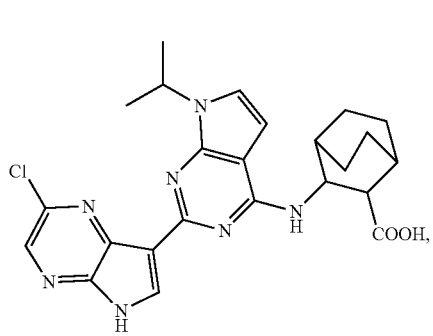 (33)
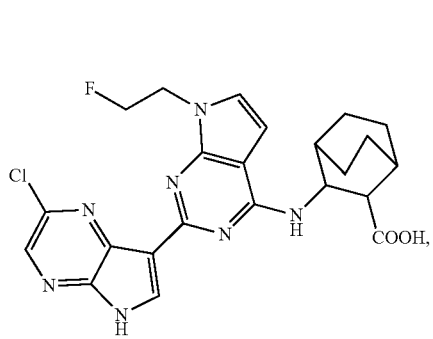 (34)

(35) 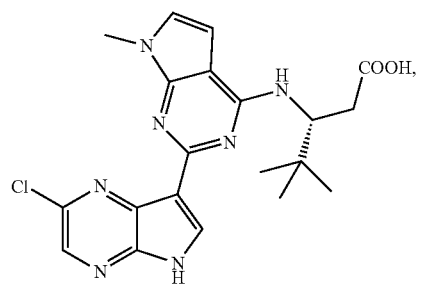
(36) 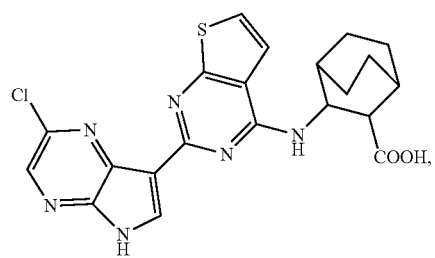
(37) 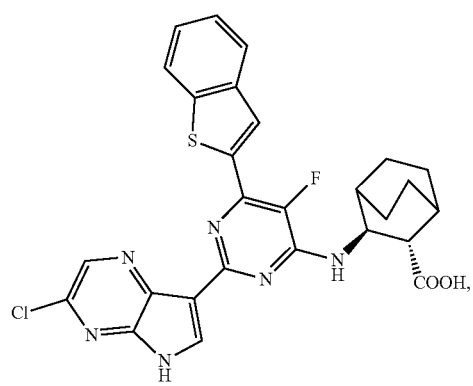
(38) 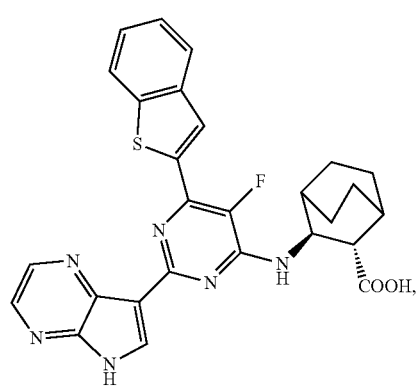
(39) 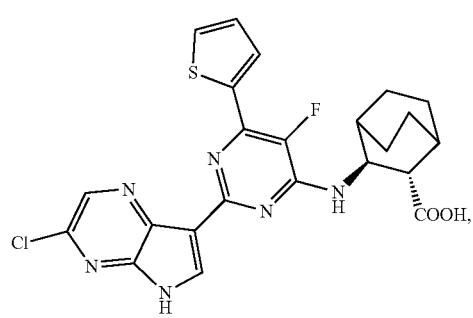
(40) 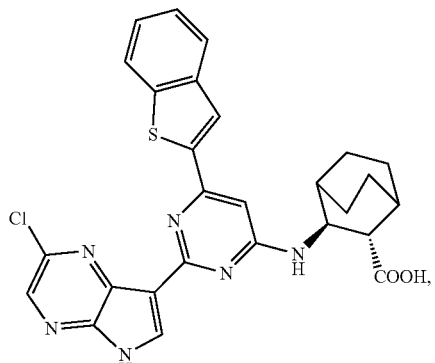
(41) 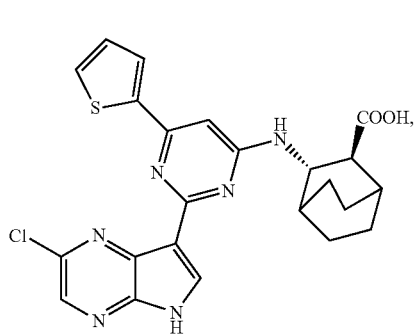
(42) 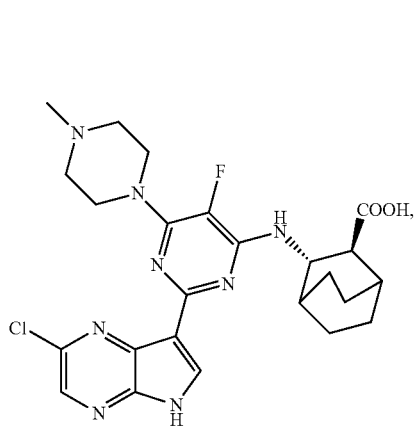
(43) 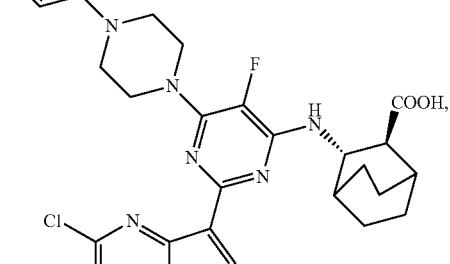

(44) 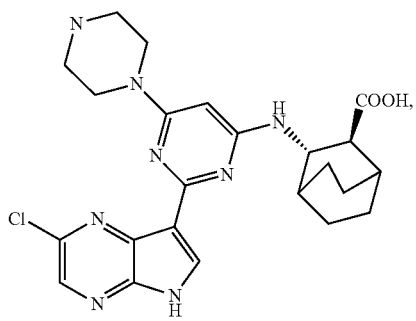
(45) 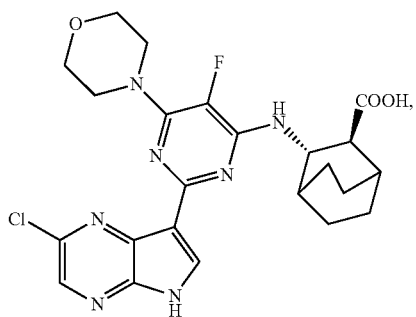
(46) 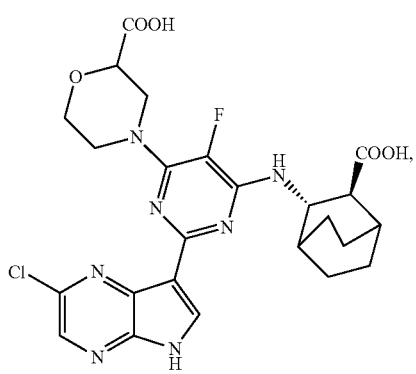
(47) 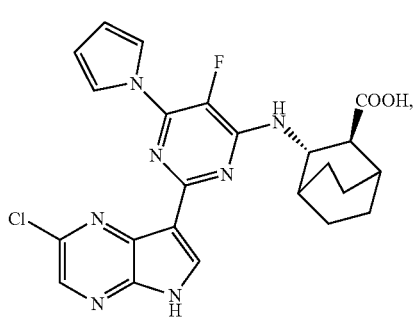
(48) 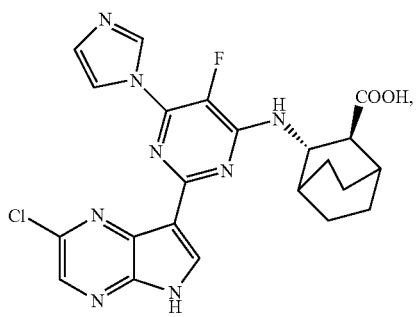
(49) 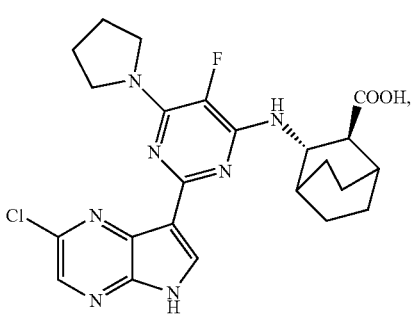
(50) 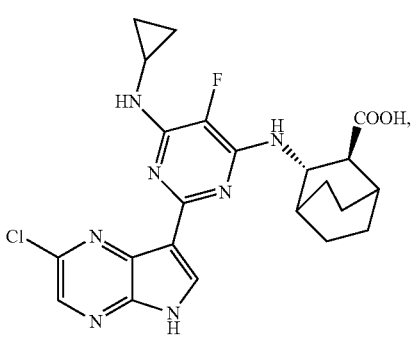
(51) 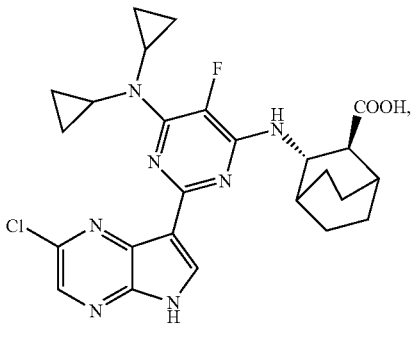
(52) 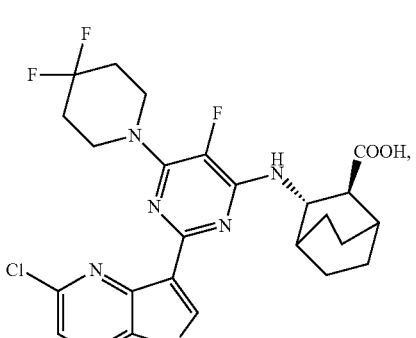

(53)
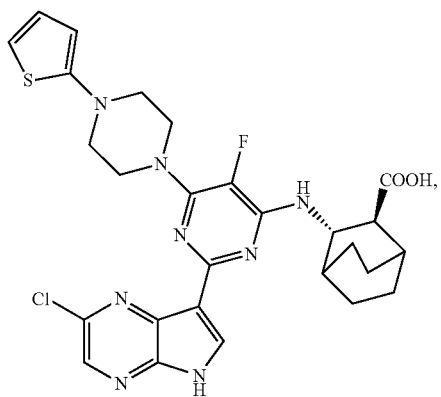
(54)
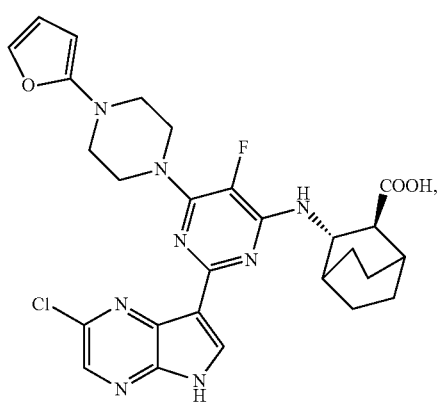
(55)
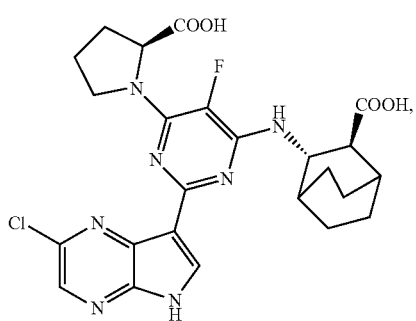
(56)
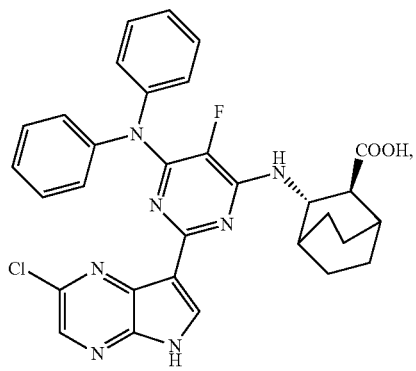
(57)
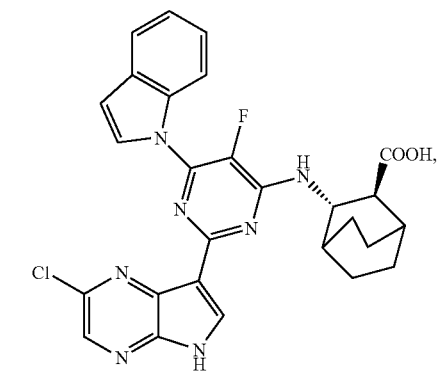
(58)
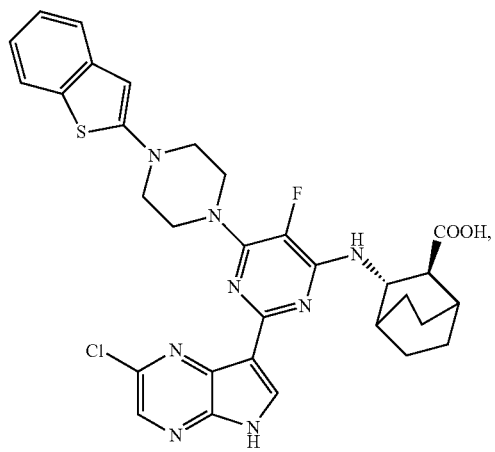
(59)
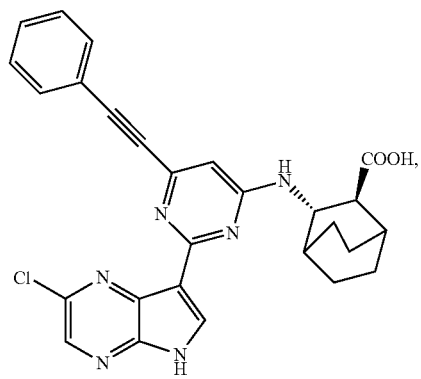
(60)
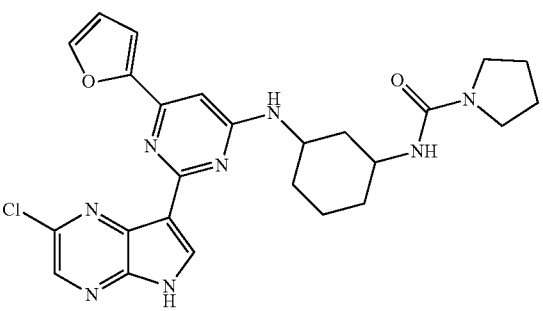

-continued
(61)
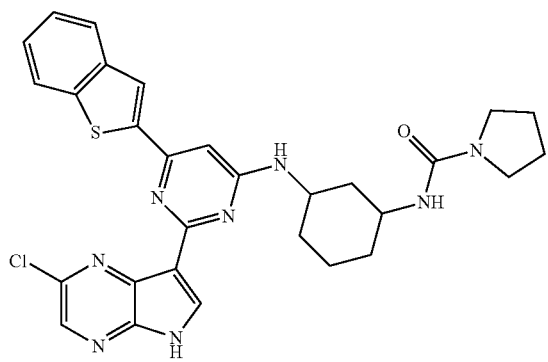
(62)
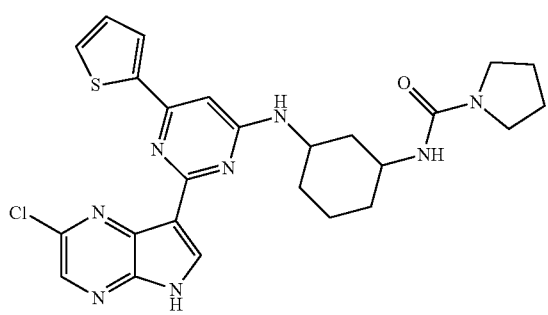
(63)
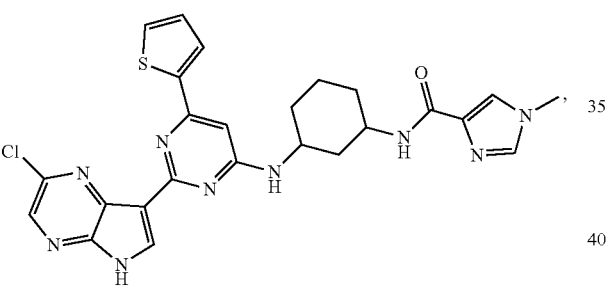
(64)
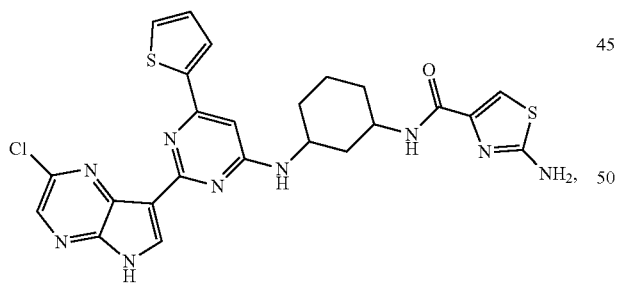
(65)
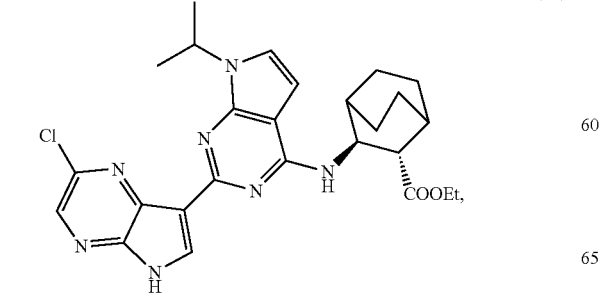
-continued
(66)
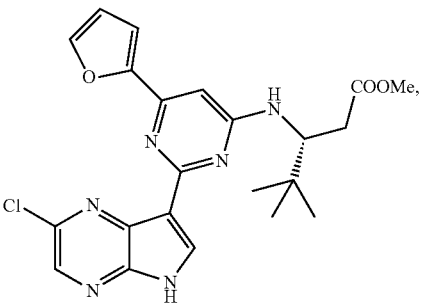
(67)
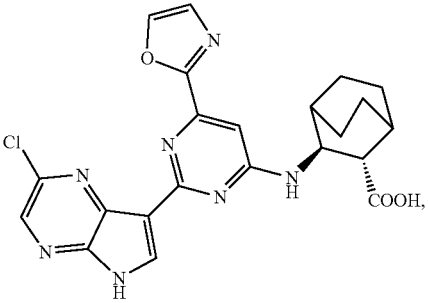
(68)
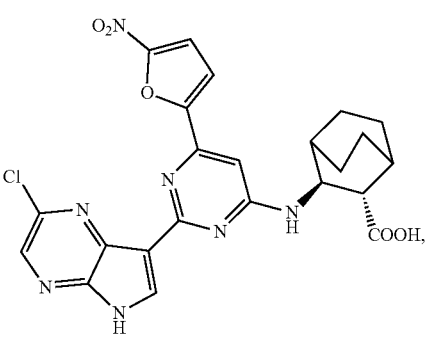
(69)
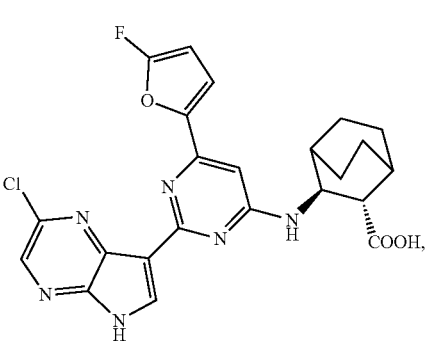
(70)
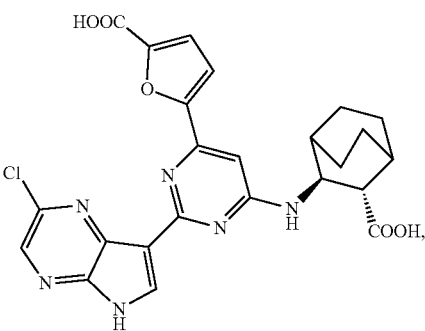

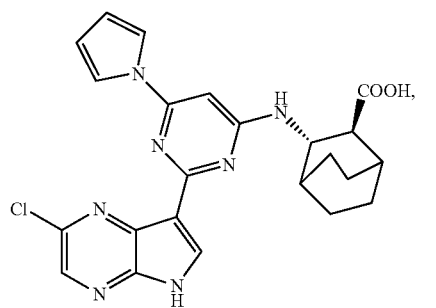
(71)
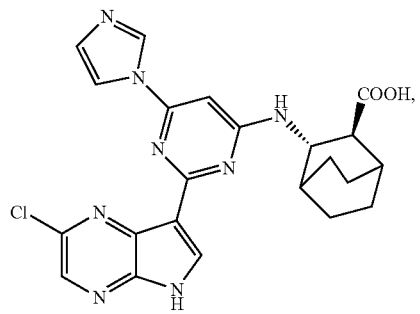
(72)
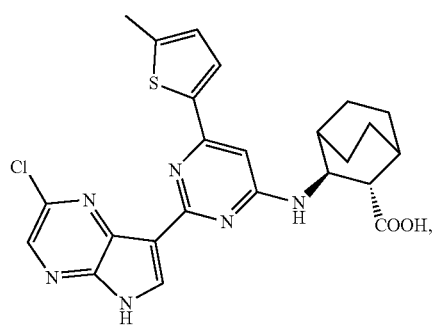
(73)
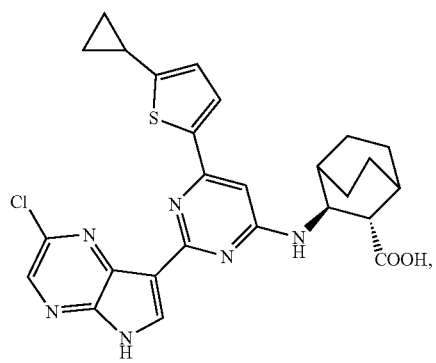
(74)
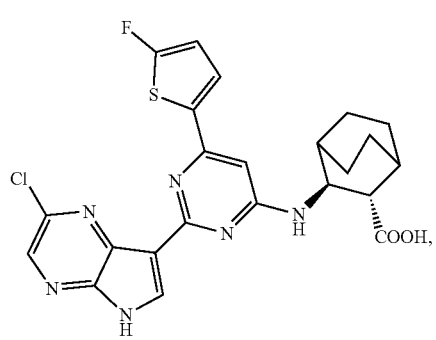
(75)
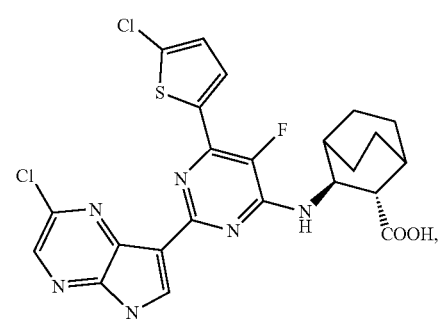
(76)
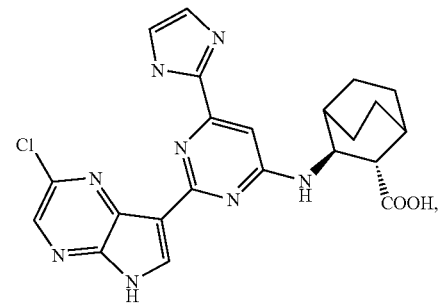
(77)
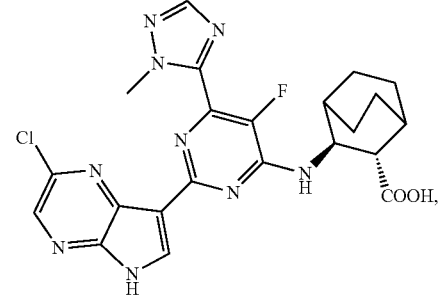
(78)
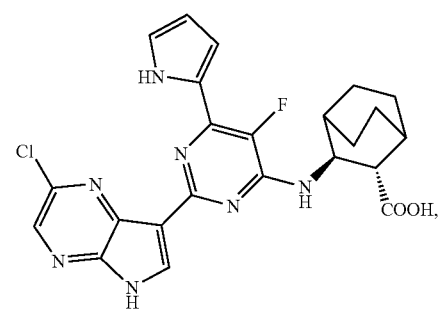
(79)
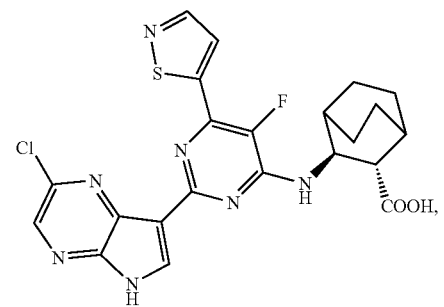
(80)

(81)
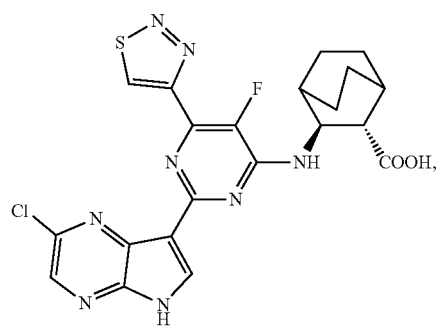
(82)
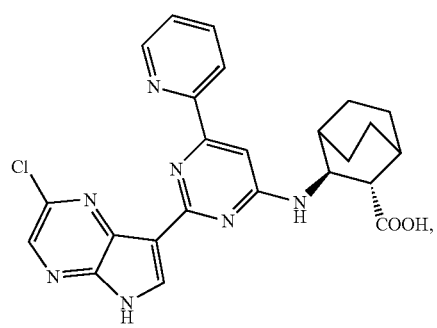
(83)
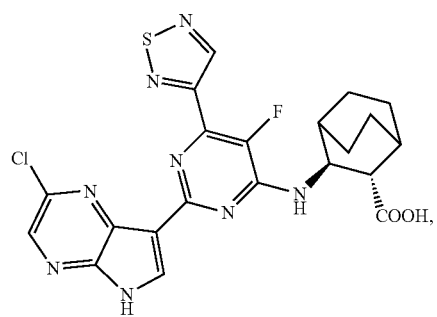
(84)
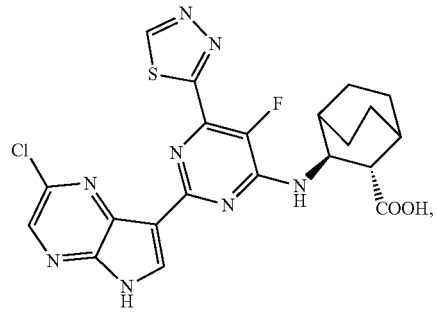
(85)
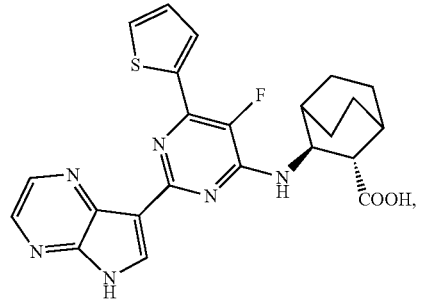
(86)
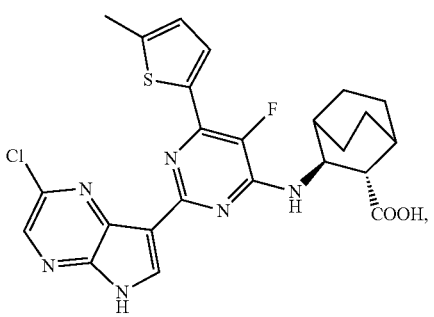
(87)
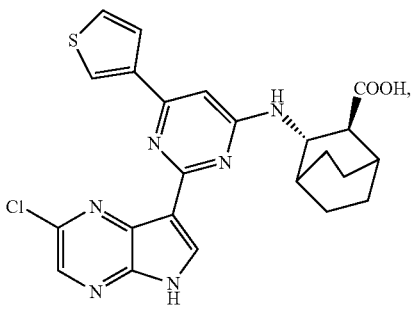
(88)
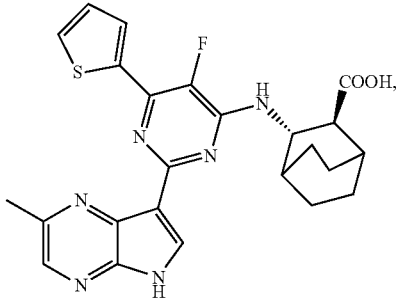
(89)
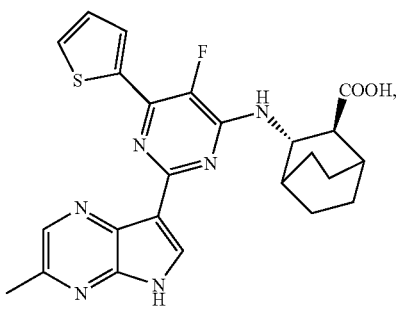
(90)
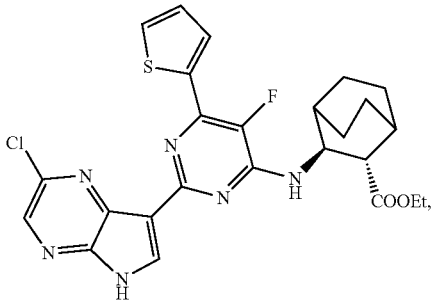

(91)
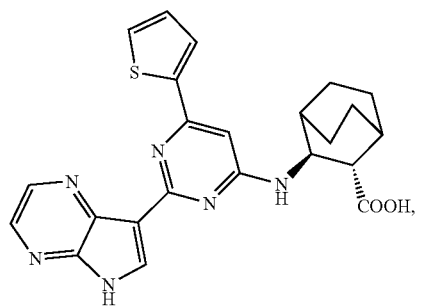
(92)
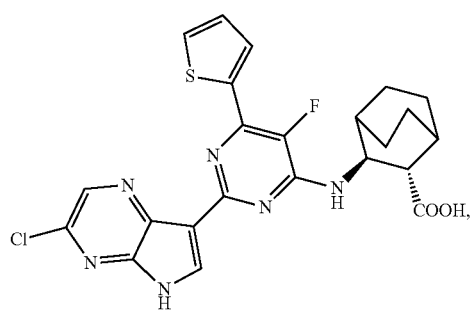
(93)
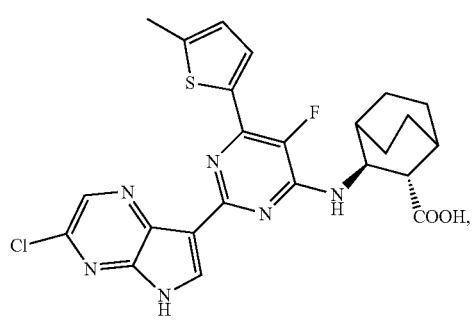
(94)
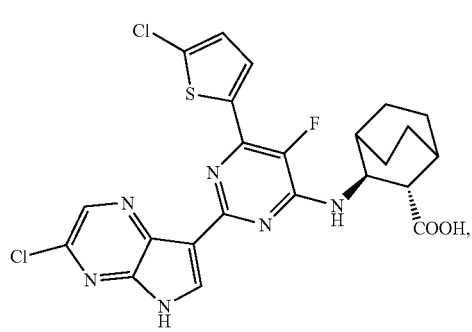
(95)
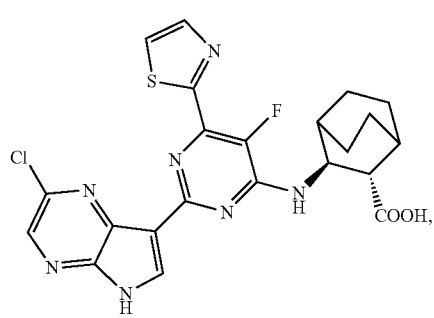
(96)
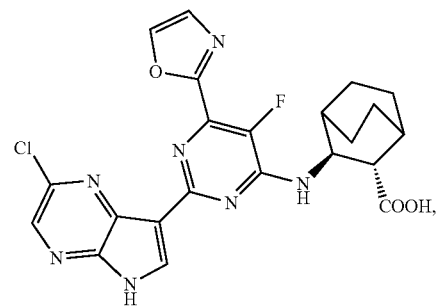
(97)
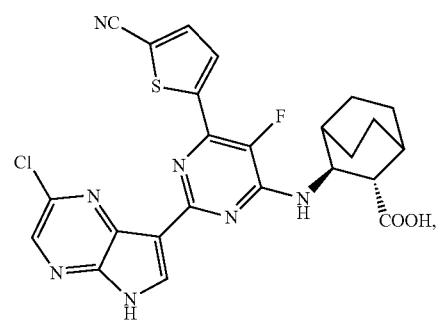
(98)
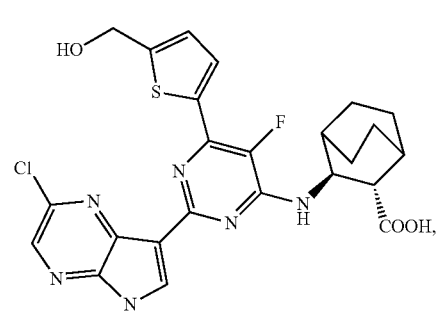
(99)
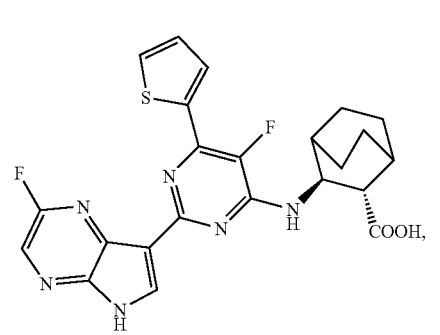
(100)
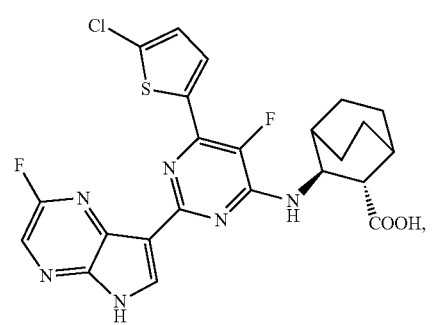

(101)
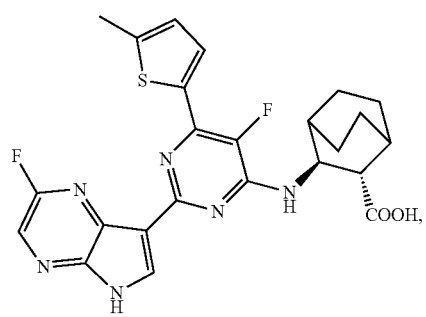
(102)
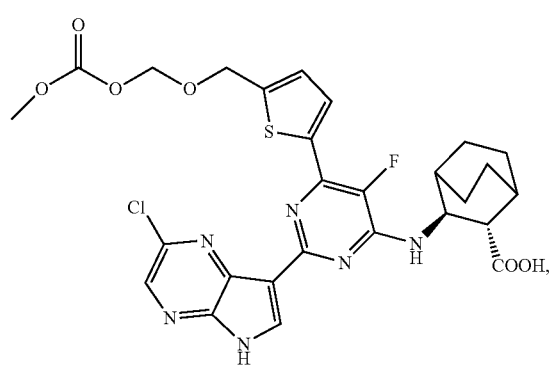
(103)
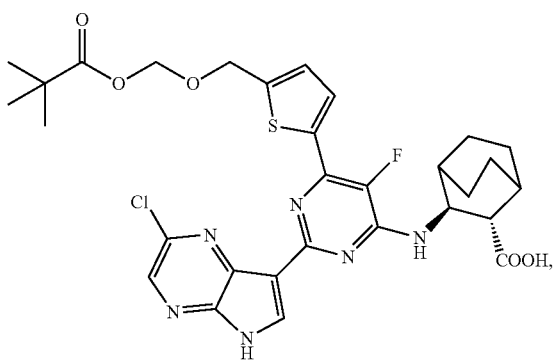
(104)
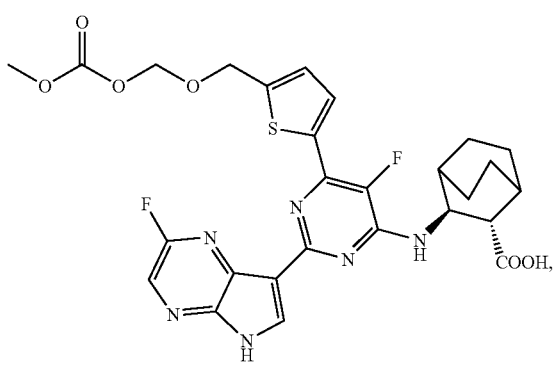
(105)
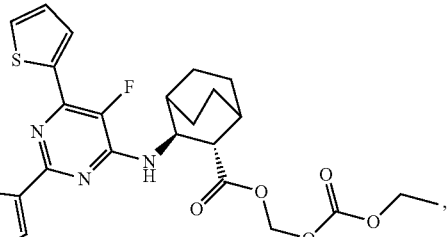
(106)
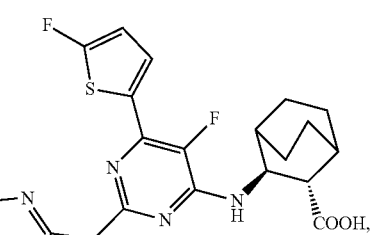
(107)
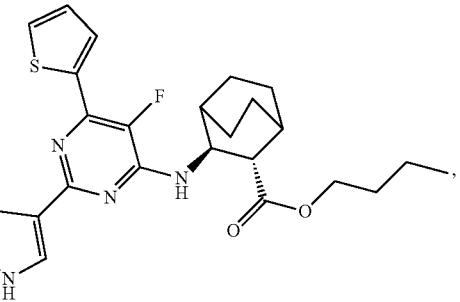
(108)
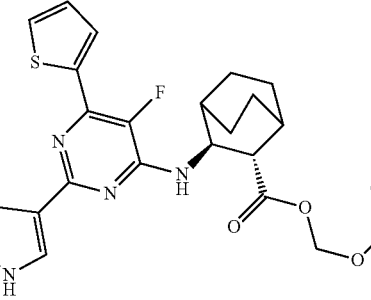
(109)
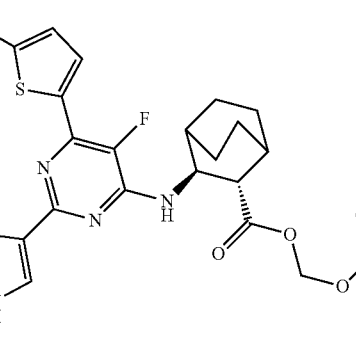

-continued
(110)
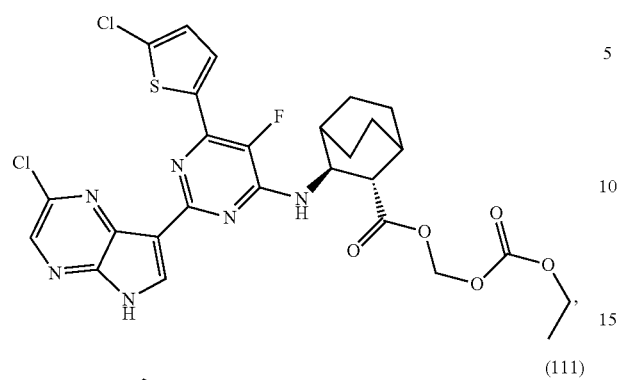
(111)
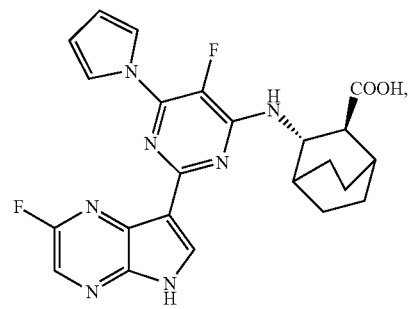
(112)
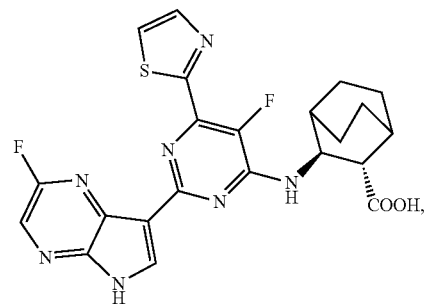
(113)
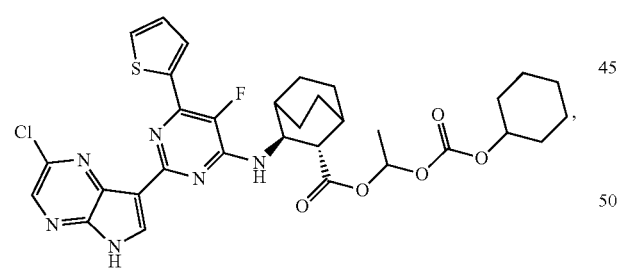
(114)
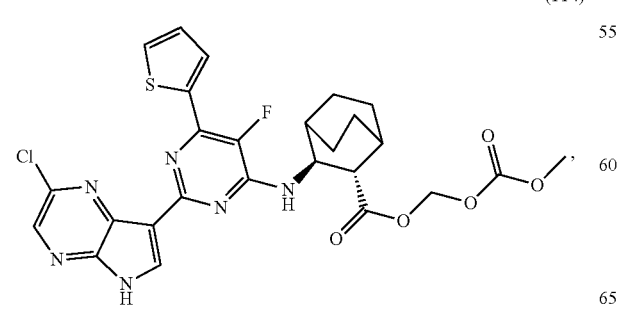
-continued
(115)
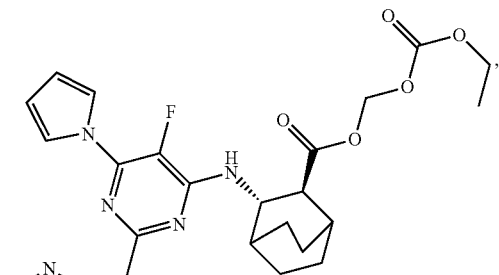
(116)
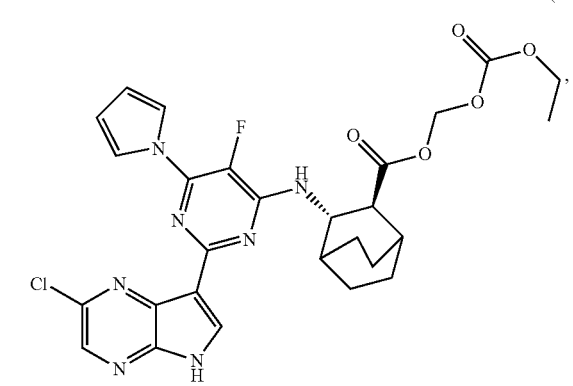
(117)
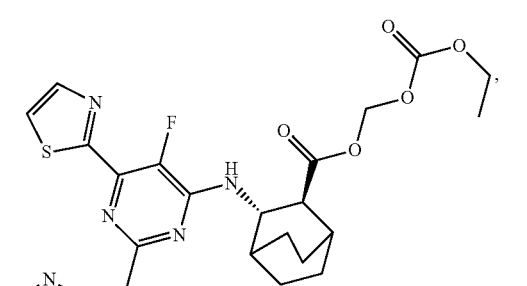
(118)
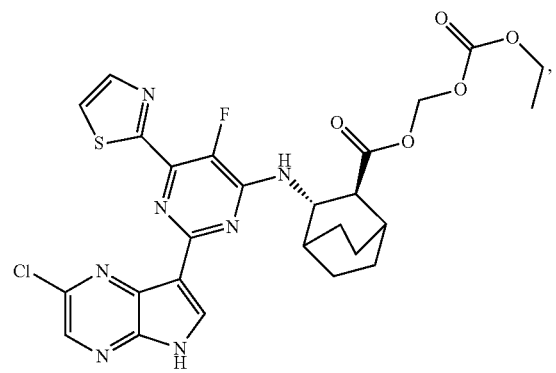

(119)
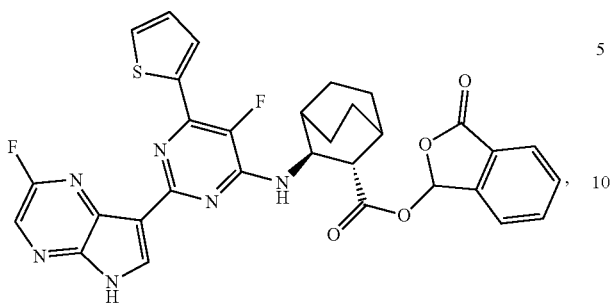
(120)
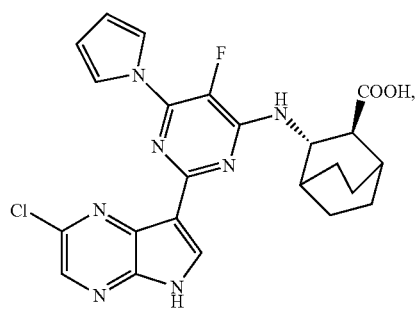
(121)
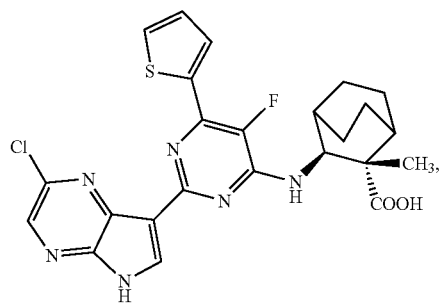
(122)
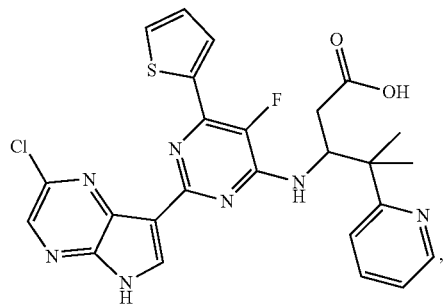
(123)
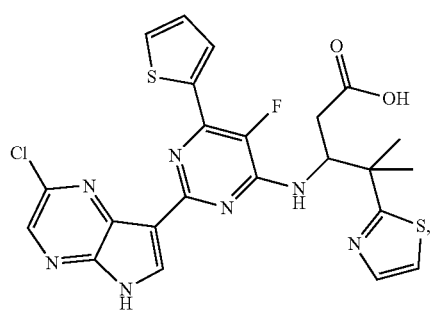
(124)
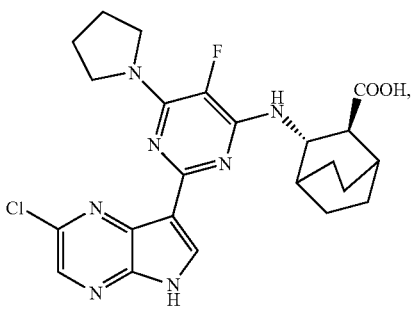
(125)
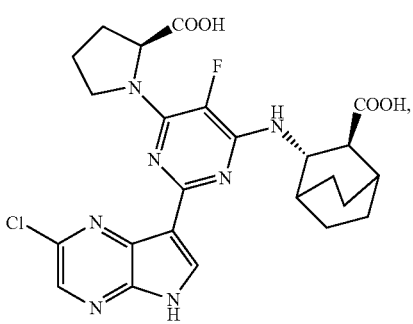
(126)
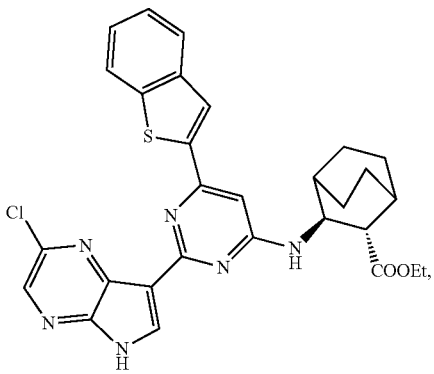
(127)
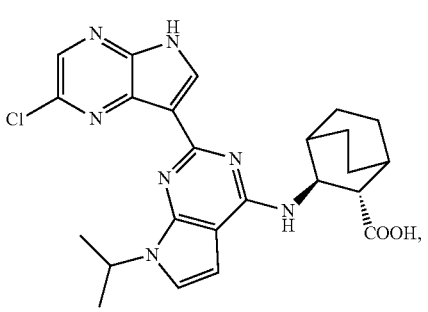
(128)
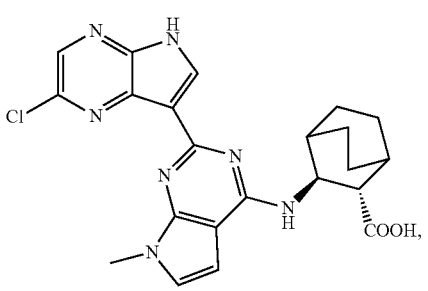

-continued
(129)
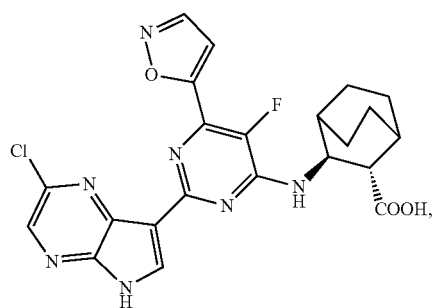
(130)
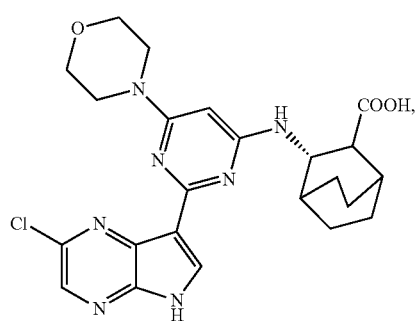
(131)
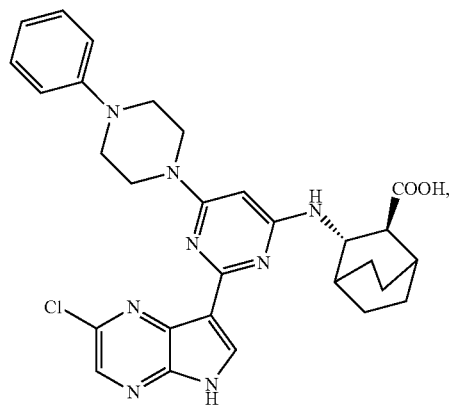
(132)
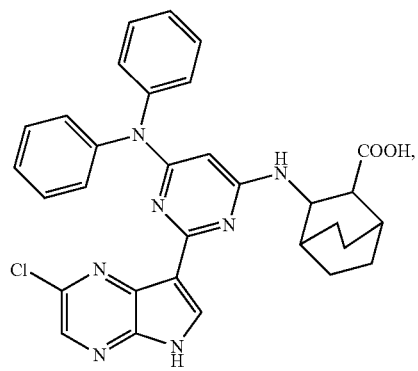
-continued
(133)
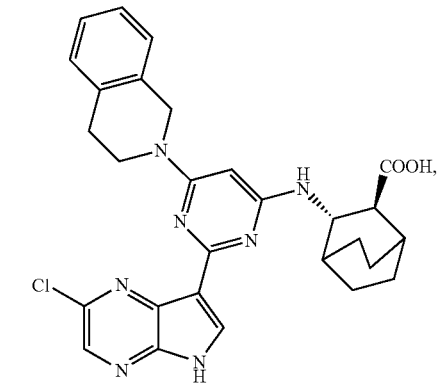
(134)
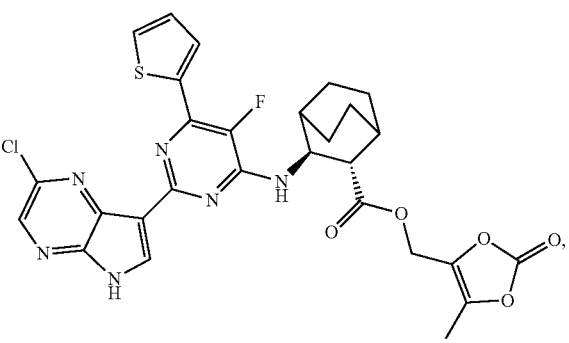
(135)
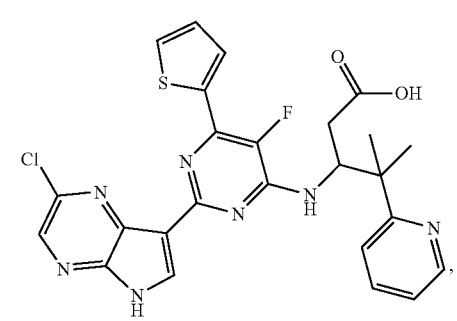
(136)
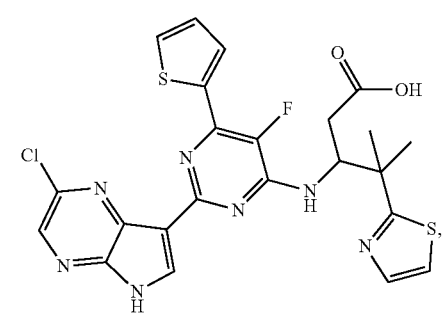

-continued (137)

(138)

(139)

(140)

(141)

-continued (142)

(143)

(144) or (145)

(144)
(145)

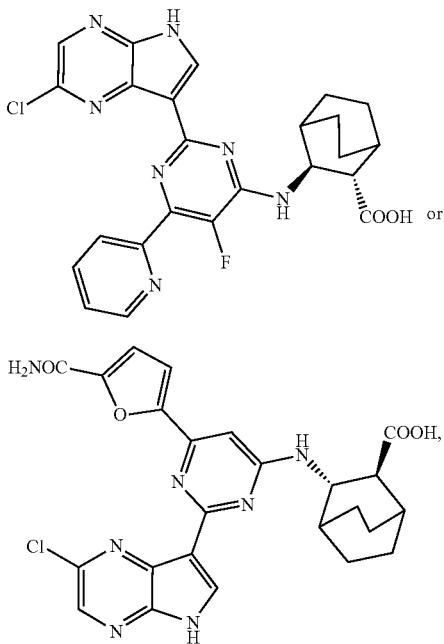

or a stereoisomer, a tautomer, an N-oxide, a solvate, or a pharmaceutically acceptable salt thereof.

18. A pharmaceutical composition comprising an effective amount of the compound of claim 1, and a pharmaceutically acceptable carrier, excipient, vehicle or a combination thereof.

19. The pharmaceutical composition of claim 18 further comprising one or more therapeutic agents, and wherein the therapeutic agent is an anti-influenza virus agent or anti-influenza virus vaccine.

20. The pharmaceutical composition of claim 19, wherein the therapeutic agent is amantadine, rimantadine, oseltamivir, zanamivir, peramivir, laninamivir, laninamivir octanoate hydrate, favipiravir, umifenovir, ribavirin, stachyflin, 5-[2-(1H-imidazol-5-yl)ethylamino]-5-oxopentanoic acid, fludase, (R)-3-((5-fluoro-2-(5-fluoro-1H-pyrrolo[2,3-b]pyridin-3-yl)-pyrimidin-4-yl)amino)-4,4-dimethyl pentanoic acid, pimodivir, baloxavir marboxil, an influenza vaccine or a combination thereof.

21. A method of preventing, managing, treating or lessening a disorder or disease caused by a virus infection in a subject, comprising administering to the subject a therapeutically effective amount of the compound of claim 1, wherein the virus infection is influenza virus infection.

22. A method of inhibiting influenza virus RNA polymerase in a subject, comprising administering to the subject a therapeutically effective amount of the compound of claim 1.

23. A method of preventing, managing, treating or lessening a disorder or disease caused by a virus infection in a subject, comprising administering to the subject a therapeutically effective amount of the pharmaceutical composition of claim 18, wherein the virus infection is influenza virus infection.

24. A method of inhibiting influenza virus RNA polymerase in a subject, comprising administering to the subject a therapeutically effective amount of the pharmaceutical composition of 18.

* * * * *